US009428509B2

(12) United States Patent
Calabrese et al.

(10) Patent No.: US 9,428,509 B2
(45) Date of Patent: *Aug. 30, 2016

(54) SUBSTITUTED PYRROLOPYRIMIDINE COMPOUNDS, COMPOSITIONS THEREOF, AND METHODS OF TREATMENT THEREWITH

(71) Applicant: Signal Pharmaceutical LLC, San Diego, CA (US)

(72) Inventors: Andrew Antony Calabrese, San Diego, CA (US); Brandon Jeffy, San Diego, CA (US); Dale Robinson, Carlsbad, CA (US); Dan Zhu, San Diego, CA (US); Dehua Huang, San Diego, CA (US); Jan Elsner, San Diego, CA (US); John Boylan, Bedminster, NJ (US); Lida Tehrani, San Diego, CA (US); Mark A. Nagy, Carlsbad, CA (US); Raj Kumar Raheja, Poway, CA (US); Paul Erdman, San Diego, CA (US); Rama K. Narla, San Diego, CA (US); Roy L. Harris, San Diego, CA (US); Tam Minh Tran, San Diego, CA (US); Jennifer Riggs, Cardiff, CA (US); Yuhong Ning, San Diego, CA (US); Shuichan Xu, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/155,485

(22) Filed: Jan. 15, 2014

(65) Prior Publication Data
US 2014/0200206 A1 Jul. 17, 2014

Related U.S. Application Data

(60) Provisional application No. 61/753,259, filed on Jan. 16, 2013.

(51) Int. Cl.
*C07D 487/04* (2006.01)
*A61K 31/519* (2006.01)
*A61P 35/04* (2006.01)
*C07D 471/04* (2006.01)

(52) U.S. Cl.
CPC ........... *C07D 487/04* (2013.01); *C07D 471/04* (2013.01)

(58) Field of Classification Search
CPC .......................... C07D 487/04; A61K 31/519
See application file for complete search history.

(56) References Cited

U.S. PATENT DOCUMENTS

| 3,507,866 | A | 4/1970 | Jones et al. |
| 3,567,725 | A | 3/1971 | Grabowki et al. |
| 4,294,836 | A | 10/1981 | Lesher et al. |
| 4,294,837 | A | 10/1981 | Lesher et al. |
| 4,309,537 | A | 1/1982 | Lesher et al. |
| 4,317,909 | A | 3/1982 | Lesher et al. |
| 4,898,872 | A | 2/1990 | Campbell et al. |
| 4,963,561 | A | 10/1990 | Lesher et al. |
| 5,424,311 | A | 6/1995 | Billhardt-Troughton |
| 5,869,659 | A | 2/1999 | Stolle et al. |
| 6,031,105 | A | 2/2000 | Wright |
| 6,093,728 | A | 7/2000 | McMahon et al. |
| 6,372,740 | B1 | 4/2002 | Murata et al. |
| 6,566,367 | B2 | 5/2003 | Bakthavatchalam et al. |
| 6,855,723 | B2 | 2/2005 | McMahon et al. |
| 7,968,556 | B2 | 6/2011 | Mortensen et al. |
| 7,981,893 | B2 | 7/2011 | Mortensen et al. |
| 8,110,578 | B2 | 2/2012 | Perrin-Ninkovic et al. |
| 8,372,976 | B2 | 2/2013 | Mortensen et al. |
| 8,383,634 | B2 | 2/2013 | Mortensen et al. |
| 2003/0036652 | A1 | 2/2003 | Bakthavatchalam et al. |
| 2003/0162968 | A1 | 8/2003 | Ciriillo et al. |
| 2004/0023921 | A1 | 2/2004 | Hong et al. |

(Continued)

FOREIGN PATENT DOCUMENTS

| CA | 2 458 699 A1 | 3/2003 |
| DE | 262 026 | 11/1988 |

(Continued)

OTHER PUBLICATIONS

U.S. Appl. No. 13/689,972, filed Nov. 30, 2012, Asaaf et al.

(Continued)

*Primary Examiner* — Susanna Moore
(74) *Attorney, Agent, or Firm* — Jones Day

(57) ABSTRACT

Provided herein are Pyrrolopyrimidine Compounds having the following structure:

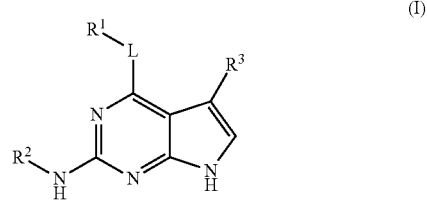

(I)

wherein $R^1$, $R^2$, $R^3$, and L are as defined herein, compositions comprising an effective amount of a Pyrrolopyrimidine Compound, and methods for treating or preventing breast cancer, more particularly triple negative breast cancer, comprising administering an effective amount of such Pyrrolopyrimidine Compounds to a subject in need thereof.

32 Claims, No Drawings

(56) References Cited

U.S. PATENT DOCUMENTS

| | | |
|---|---|---|
| 2004/0063658 A1 | 4/2004 | Roberts et al. |
| 2004/0097485 A1 | 5/2004 | Burkitt et al. |
| 2004/0213757 A1 | 10/2004 | Zhu et al. |
| 2005/0009737 A1 | 1/2005 | Clark |
| 2006/0004014 A1 | 1/2006 | Hoffmann et al. |
| 2006/0106022 A1 | 5/2006 | Liu et al. |
| 2006/0135511 A1 | 6/2006 | Burgey |
| 2006/0142269 A1 | 6/2006 | Dykes |
| 2008/0214580 A1 | 9/2008 | Neagu et al. |
| 2009/0069289 A1 | 3/2009 | Neagu et al. |
| 2009/0163545 A1 | 6/2009 | Goldfarb |
| 2009/0281075 A1 | 11/2009 | Roughton et al. |
| 2010/0144738 A1 | 6/2010 | Bornmann et al. |
| 2010/0249122 A1 | 9/2010 | Kalman |
| 2011/0137028 A1 | 6/2011 | Harris et al. |
| 2011/0257167 A1 | 10/2011 | Chopra et al. |
| 2012/0028972 A1 | 2/2012 | Wong |
| 2012/0059164 A1 | 3/2012 | Perrin-Ninkovic et al. |
| 2012/0071658 A1 | 3/2012 | Perrin-Ninkovic et al. |
| 2013/0079324 A1* | 3/2013 | Cheng et al. ............ 514/210.18 |

FOREIGN PATENT DOCUMENTS

| | | |
|---|---|---|
| EP | 0 385 850 | 9/1990 |
| JP | 63275582 | 5/1987 |
| JP | 2001048882 | 2/2001 |
| JP | 2002100363 | 4/2002 |
| JP | 2002167387 | 6/2002 |
| WO | WO 99/16438 | 4/1999 |
| WO | WO 99/28320 | 6/1999 |
| WO | WO 00/73306 | 12/2000 |
| WO | WO 02/48152 | 6/2002 |
| WO | WO 02/076954 | 10/2002 |
| WO | WO 03/032989 | 4/2003 |
| WO | WO 03/093290 | 11/2003 |
| WO | WO 2004/042002 | 5/2004 |
| WO | WO 2004/065378 | 8/2004 |
| WO | WO 2004/076454 | 9/2004 |
| WO | WO 2004/085409 | 10/2004 |
| WO | WO 2005/003147 | 1/2005 |
| WO | WO 2006/050076 | 5/2005 |
| WO | WO 2005/120511 | 12/2005 |
| WO | WO 2006/001266 | 1/2006 |
| WO | WO 2006/030031 | 3/2006 |
| WO | WO 2006/036883 | 4/2006 |
| WO | WO 2006/045828 | 5/2006 |
| WO | WO 2006/065703 | 6/2006 |
| WO | WO 2006/087530 | 8/2006 |
| WO | WO 2006/091737 | 8/2006 |
| WO | WO 2006/108103 | 10/2006 |
| WO | WO 2008/016669 | 2/2008 |
| WO | WO 2008/051493 | 5/2008 |
| WO | WO 2008/051494 | 5/2008 |
| WO | WO 2009/126926 | 10/2009 |
| WO | WO 2009/131687 | 10/2009 |
| WO | WO 2010/062571 | 6/2010 |
| WO | WO 2010/068483 | 6/2010 |
| WO | WO 2011/097333 | 8/2011 |
| WO | WO 2013/042006 | 3/2013 |
| WO | WO 2014/025486 | 2/2014 |

OTHER PUBLICATIONS

U.S. Appl. No. 13/701,224, filed Mar. 5, 2013, Ning et al.
U.S. Appl. No. 13/654,441, filed Oct. 18, 2012, Xu et al.
U.S. Appl. No. 13/773,686, filed Feb. 22, 2013, Xu et al.
U.S. Appl. No. 13/803,061, filed Mar. 14, 2013, Xu et al.
U.S. Appl. No. 13/803,317, filed Mar. 14, 2013, Xu et al.
U.S. Appl. No. 13/803,323, filed Mar. 14, 2013, Xu et al.
U.S. Appl. No. 14/155,498, filed Jan. 15, 2014, Calabrese et al.
U.S. Appl. No. 14/055,985, filed Oct. 17, 2013, Mortensen et al.
U.S. Appl. No. 14/055,995, filed Oct. 17, 2013, Xu et al.
Barlin, "Purine analogs as amplifiers of phleomycin. VII. Some 1H-inidazo[4,5-b]pyrazines and related compound," Australian Journal of Chemistry, vol. 35, pp. 2299-2306 (1982).

Beresnev et al., "Interaction of 5-methoxy-1,2,4-traizines with uras as a new route to 6-azapurines," Medeleev Commu., vol. 2, pp. 58-59 (2000).
Bergmann et al., "2-Phenylpurines, their chemical and enzumological reactivity," J. Chem Org., pp. 3729-3735 (1963).
Booth et al., "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemstry, vol. pp. 2119-2126 (1992).
Booth et al., "Synthesis of [1α, 2β,3α-2,3-bis(benzyloxymethyl)cyclobutl]imidazol-5-amines: important precursors to cyclobut-A derivatives," J. Chem Society, Perkin Tranactions 1: Organic and Bio-Organic Chemistry, vol. 6, pp. 669-675 (1995).
Booth et al., "The Reactions of Diaminomaleonitrile with Isocyanates and Either Aldehydes or Ketones Revisited," J. Org Chem, vol. 66, pp. 8436-8441 (2001).
Booth, et al., "Synthesis of 4- and 5-Disubstituted 1-Benzylimidazoles, Important Precursors of Purine Analogs," J. of Heterocyclic of Chemistry, vol. 31(2), pp. 345-350 (1994).
Chupakhin et al., "A simple one pot synthesis of condensed 1,2,4-triazines by using the tandem $A_N$-$S_N ipso$ and $S_N^H$—$S_N ipso$ reactions," J. of Heterocyclic Chemistry, vol. 38(4), pp. 901-907 (2001).
Cohen, "The role of protein phosphorylation in human health and disease," Eur. J. Biochem, vol. 268, pp. 5001-5010 (2001).
Cohen, P. "Protein kinases—the major drug targets of the twenty-first century?" Nature Reviews/Drug Discovery, vol. 1, pp. 309-315 (2002).
Coish, et al., "Small molecule inhibitors of IKK kinase activity," Expert Opin. Ther. Patents, vol. 16(1), pp. 1-12 (2006).
Costa et al., "Aspects of mTOR biology and the use of mTOR inhibitors in non-Hodgkin's lymphoma," Cancer Treatment Reviews, Saunders, US, vol. 33(1), pp. 78-84 (2007).
Crofts et al., "Metabolism of 2-amino-1-methyl-6-phenylimidazo[4,5-b]pyridine (PhIP) by human cytochrome P4501B1," Carcinogenesis, vol. 18(9), pp. 1793-1798 (1997).
Dang et al., "Efficient synthesis of purines and purine nucelosides via an inverse electron demand diels-alder reaction," J. Am Chem Soc., vol. 121(24), pp. 5833-5834 (1999).
Database Caplus Online Chemical Abstracts Service, Columbus, Ohio, Database Accession No. 1951:49974 (XP-002472261) (1951).
Database Caplus Online Chemical Abstracts Service, Columbus, Ohio, Database Accession No. 1978:433195 (XP-002472262) (1978).
Database Caplus Online Chemical Abstracts Service, Columbus, Ohio, Database Accession No. 1966:26849 (XP-002472263) (1965).
Dornow et al., "Synthese von2-Oxy-imidazolo-(5',4':2,3)-pyridinen)", Arch Pharm. vol. 290, pp. 20-31 (1957) (w/English language abstract).
Dorwald F. Zaragoza, "Side Reactions in Organic Synthesis: A Guide to Successful Synthesis Design," Weinheim: Wiley-VCH Verlag GmbH & Co. KgaA, Preface. (2005).
Dzierba et al., "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47(23), pp. 5783-5790 (2004).
EPO Supplementary European Search Report dated Feb. 8, 2013 issued in connection with PCT/US2010/053678.
Fabbro et al., "Protein kinases as targets for anticancer agents: from inhibitors touseful drugs," Pharmacology & Therapeutics, vol. 93, pp. 79-98 (2002).
Farhadi et al., "The role of protein kinase C isoforms in modulating injury and repair of the intestinal barrier," J. Pharm Exp. Ther., vol. 316(1), pp. 1-7 (2006).
Frandsen et al., "Reaction of the N2-acetoxy derivative of 2-amino-1-methyl-6-phenylimidazo[4,5,b]pyridine . . . ," Carcinogenesis, vol. 13(4), pp. 629-635 (1992).
Frost et al., "AKT activity regulates the ability of mTOR inhibitors to prevent angiogenesis and VEGF expression in multiple myeloma cells," Oncogene, vol. 26(16), pp. 2255-2262 (2007).

(56) References Cited

OTHER PUBLICATIONS

Georgakis and Younes, "From rapi nui to rapamycin: targeting PI3K/Akt/mTOR for cancer therapy," Expert Rev. Anticancer Ther., vol. 6(1), 131-140 (2006).
Hamad, "A new synthesis of 4-cyano-1,3-dihydro-2-oxo-2H-imidazole-5-($N^1$-tosyl)carboxamide: Reactive precursor for thiopurine analogues," J of Heterocyclic Chemistry, vol. 38(4), pp. 939-944 (2001).
http://www.sigmaaldrich.com/catalog/product/ALDRICH/678740?lang=en&region=US, last accessed Nov. 1, 2012.
http://www.sigmaaldrich.com/catalog/product/ALDRICH/701602?lang=en&region=US#, last accessed Nov. 1, 2012.
http://lwww.sigmaaldrich.com/catalog/product/aldrich/697230?lang=en&region=US, last accessed Nov. 1, 2012.
http://lwww.sigmaaldrich.com/chemistry/chemical-synthesis/technology-spotlights/catalysisapplicationguide.html, last accessed Nov. 1, 2012.
Irie et al., "Toward the development of new medicinal leads with selectivity for protein kinase C isozymes," The Chemical Record, vol. 5, pp. 185-195 (2005).
Itoh et al., "A novel practical synthesis of C-2-arylpurines," Advanced Synthesis & Catalysis, vol. 346, pp. 1859-1867 (2004).
Gulati et al. "Involvement of mTORC1 and mTORC2 in regulation of glioblastoma multiforme growth and motility," International Journal of Oncology, vol. 35(4) (2009), abstract.
Jones et al., "6-Substituted-5-chloro-1,3-dihydro-2H-imidazo(4,5-b)pyrazin-2-ones with hypotensive activity," J. Med. Chem., vol. 16(5), pp. 537-542 (1973).
Jordan, V.C., Nature Reviews: Drug Discover, vol. 2, p. 205 (2003).
Kazaoka et al., "Synthesis of 6-substituted 9-benzyl-8-hydroxypurines with potential interferon-indcuing activity," Chemical & Pharmaceutical Bulletin, vol. 51(5), pp. 608-611 (2003).
Killday et al., "Microxine, a new cdc2 kinase inhibitor from the Australian marine sponge *Microxina* species," J. of Natural Products, vol. 64(4), pp. 525-526 (2001).
Minehan et al., "Molecular recognition of DNA by Hoechst Benzimidazoles: Exploring beyond theopyrrole-imidazole-hydroxypyrrole polyamide-pairing code," Helvitica Chima Acta, vol. 83(9), pp. 2197-2213 (2000).
Mortensen et al., "Discovery and SAR exploration of a novel series of imidazo[4,5-] pyrazin-2-ones as potent and selective mTOR kinase inhibitors," Bioorganic & Medicinal Chemistry Letters, Pergamon, Elsevier Science, GB, vol. 21(22), pp. 6793-6799 (2011).
Nagashima et al., "Solution-Phase parallel synthesis of an N-Alkylated dihydropteridinone library from fluorous amino acids," J of Comb. Chemistry, vol. 6(6), pp. 942-949 (2004).
Park et al., "A novel mechanism of TRAF signaling revealed by structural and functional analyses of the TRADD-TRAF2 interaction," Cell, vol. 101, pp. 777-787 (2000).
Patani et al., "Bioisosterim: A rational approach in drug design," Chemical Reviews, vol. 96, pp. 3147-3176 (1996).
Registry File Document for RN 863501-03-5, 863502-39-0 (Sep. 20, 2005).
Seela et al., "Product Class 17: Purines," Science of Synthesis, vol. 16, pp. 945-1108 (2004).
Singh et al., 1994, "Novel cAMP PDE III Inhibitors: Imidazo[4,5-b]pyridin-2(3H)-ones and Thiazolo[4,5-b]pyridin-2(3h)-ones and Their Analogs," J. Med. Chem, vol. 37(2):248-254.
Sridhar et al., "Protein Kinasesas Therapeutic Targets," Pharm. Research, vol. 17(11), pp. 1345-1353 (2000).
Office Action mailed Jun. 11, 2009 for U.S. Appl. No. 11/975,652.
Office Action mailed Sep. 2, 2009 for U.S. Appl. No. 11/975,652.
Final Office Action mailed Feb. 2, 2010 for U.S. Appl. No. 11/975,652.
Office Action mailed May 12, 2010 for U.S. Appl. No. 11/975,652.
Final Office Action mailed Sep. 30, 2010 for U.S. Appl. No. 11/975,652.
PCT International Search Report dated Mar. 29, 2010 issued in connection with PCT/US2009/062143.
PCT Written Opinion of the International Searching Authority dated Mar. 29, 2010.
Office Action mailed Nov. 10, 2010 for U.S. Appl. No. 12/605,791.
PCT IPRP with Written Opinion of the International Searching Authority dated May 12, 2011 in connection with PCT /US2009/062143.
Office Action mailed Jan. 19, 2011 for U.S. Appl. No. 12/605,791.
Final Office Action mailed May 10, 2011 for U.S. Appl. No. 12/605,791.
Advisory Action mailed Aug. 17, 2011 for U.S. Appl. No. 12/605,791.
Advisory Action mailed Sep. 14, 2011 for U.S. Appl. No. 2/605,791.
PCT International Search Report dated Dec. 27, 2010 issued in connection with PCT/US2010/053678.
PCT Written Opinion dated Dec. 27, 2010 in connection with PCT/US/10/53678.
Office Action mailed Feb. 28, 2012 for U.S. Appl. No. 12/910,920.
PCT IPRP dated May 10, 2012 issued in connection with PCT/US2010/053678.
Office Action mailed Jun. 28, 2012 for U.S. Appl. No. 12/910,920.
Final Office Action mailed Nov. 6, 2012 for U.S. Appl. No. 12/910,920.
Office Action mailed Apr. 2, 2012 for U.S. Appl. No. 13/295,513.
Office Action mailed Aug. 27, 2012 for U.S. Appl. No. 13/295,513.
PCT Partial International Search dated Feb. 21, 2013 issued in connection with PCT/US2012/060723.
PCT International Search Report dated Feb. 13, 2013 issued in connection with PCT/US2012/067172.
PCT Written Opinion dated Feb. 13, 2013 issued in connection with PCT/US/2012/067172.
Vippagunta et al., Advanced Drug Delivery Reviews, vol. 48, pp. 3-26 (2001).
Wallace, "Palladium-catalyzed synthesis of quinoxaline derivatives," Tetrahedron, vol. 64, pp. 9675-9684 (2008).
Westover et al., "Synthesis and antiviral activity of certain 9-β-D-Riofuranoaylpurine-6-carboxamides," J.Med. Chem., vol. 24(8), pp. 941-946 (1981).
Wolff, Manfred E., Ed. Burger's Medicinal Chemistry and Drug Discovery—Fifth Edition, New York: John Wiley & Sons, vol. 1, pp. 975-976 (1996).
Yoneda et al., "A transformation of 7-azapteridines into 6-azapurines (Imidazo[4,5-e]-as-triazines)," Heterocycles, vol. 4(9), pp. 1503-1508 (1976).
Yoneda et al., "Synthesis of imadazo[4,5-e]-as-triazine (6-Azapurine) Deriviatives," Chem & Pharm Bulletin, vol. 26(10), pp. 3154-3160 (1978).
Zaki et al., "The synthesis of imidazol[4,5-d]pyridines from a substituted imidazole and acyl or sulfonyl acetonitrile," Tetrahedron, vol. 63(18), pp. 3745-3753 (2007).
PCT Partial International Search dated Nov. 15, 2012 issued in connection with PCT/US2012/049281.
PCT International Search Report dated Jan. 11, 2013 issued in connection with PCT/US2012/049281.
PCT Written Opinion dated Feb. 13, 2013 issued in connection with PCT/US2012/049281.
Yuan et al., "Targeting tumorigenesis: development and use of mTOR inhibitors in cancer therapy," Journal of Hematology & Oncology, vol. 2(1), p. 45 (2009).
Carretero et al., "Integrative Genomic and Proteomic Analyses Identify Targets for Lkb1-Deficient Metastatic Lung Tumors," Cancer Cell, vol. 17(6), pp. 547-559 (2010).
Gao et al., "LKB1 in lung cancerigenesis: a serine/threonine kinase as tumor suppressor," Protein & Cell, vol. 2(2), pp. 99-107 (2011).
Gao et al., "LKB1 inhibits lung cancer progression through lysyl oxidase and extracellular matrix remodeling," Proceedings of the National Academy of Sciences, vol. 107(44), pp. 18892-18897 (2010).
Inge et al., " Expression of LKB1 tumor suppressor in non-small cell lung cancer determines sensitivity to 2-deoxyglucose," Journal of Thoracic and Cardiovascular Surgery, vol. 137(3), pp. 580-58 (2009).
Wingo et al., "Somatic LKB1 Mutations Promote Cervical Cancer Progression," PLOS ONE, vol. 4(4), pp. 5137-5138 (2009).

(56) References Cited

OTHER PUBLICATIONS

Shaw et al., "The LKB1 tumor suppressor negatively regulates mTOR signaling," Cancer Cell, vol. 6(1), pp. 91-99 (2004).
Huang et al., "Genetic and epigenetic silencing of SCARA5 may contribute to human hepatocellular carcinoma by activating FAK signaling," Journal of Clinical Investigation, vol. 120(1), pp. 223-241 (2010).
Brenner et al., "Mechanistic Rationale for Inhibition of Poly(ADP-Ribose) Polymerase in ETS Gene Fusion-Positive Prostate Cancer," Cancer Cell, vol. 19, pp. 664-678 (2011).
Brenner et al., "PARP-1 Inhibition as a Targeted Strategy to Treat Ewing's Sarcoma," Cancer Res vol. 72, pp. 1608-1613 (2012).
Dey et al., "Preclinical efficacy of a dual PI3K-mTOR inhibitor, BEZ235 in triple negative breast cancer," European Journal of Cancer, vol. 47, No. Suppl. 4, Oct. 2011, p. 517.
Johnston, "Are we missing the mTOR target in breast cancer?," Breast Cancer Research and Treatment, Kluwer Academic Publishers, Bolivia, vol. 128, No. 3, Oct. 16, 2010, pp. 607-611.
Lehmann et al., "Identification of human triple-negative breast cancer subtypes and preclinical models for selection of targeted therapies," The Journal of Clinical Investigation, Jul. 2011, vol. 121, No. 7, Jul. 2011, pp. 2750-2767.
Liu et al., "Combinatorial Effects of Lapatinib and Rapamycin in Triple-Negative Breast Cancer Cells," Molecular Cancer Therapeutics, vol. 10, No. 8, Aug. 1, 2011, pp. 1460-1469.
Lori Berk et al., "Analysis of the pharmacodynamic activity of the mTOR inhibitor ridaforolimus (AP23573, MK-8669) in a phase 1 clinical trial," Cancer Chemotherapy and Pharmacology, Springer, Berlin, Germany, vol. 69, No. 5, Jan. 10, 2012, pp. 1369-1377.
Macaskill et al., "The mammalian target of rapamycin inhibitor everolimus (RAD001) in early breast cancer: results of a pre-operative study," Breast Cancer Research and Treatment, Kluwer Academic Publishers, Bolivia, vol. 128, No. 3, Oct. 13, 2010, pp. 725-734.
Sanchez et al., "Preclinical modeling of combined phosphatidylinositol-3-kinase inhibition with endocrine therapy for estrogen receptor-positive breast cancer," Breast Cancer Research, Current Science, London, United Kingdom, vol. 13, No. 2, Mar. 1, 2011, p. R21.
Toft et al., "Minireview: Basal-Like Breast Cancer: From Molecular Profiles to Targeted Therapies," Molecular Endocrinology, vol. 25, No. 2, Feb. 1, 2011, pp. 199-211.
Zeng et al., "Treating triple-negative breast cancer by a combination of rapamycin and cyclophosphamide: An in vivo bioluminescence imaging study," European Journal of Cancer, Pergamon Press, Oxford, United Kingdom, vol. 46, No. 6, Apr. 1, 2010, pp. 1132-1143.
Zhao et al., "The effect of mTOR inhibition alone or combined with MEK inhibitors on brain metastasis: an in vivo analysis in triple-negative breast cancer models," Breast Cancer Research and Treatment, Kluwer Academic Publishers, Bolivia, vol. 131, No. 2, Mar. 11, 2011, pp. 425-436.

\* cited by examiner

SUBSTITUTED PYRROLOPYRIMIDINE COMPOUNDS, COMPOSITIONS THEREOF, AND METHODS OF TREATMENT THEREWITH

This application claims the benefit of U.S. Provisional Application No. 61/753,259, filed Jan. 16, 2013, the entire contents of which are incorporated herein by reference.

FIELD

Provided herein are certain pyrrolopyrimidine compounds, compositions comprising an effective amount of such compounds, and methods for treating or preventing breast cancer, more particularly triple negative breast cancer, comprising administering an effective amount of such pyrrolopyrimidine compounds to a subject in need thereof.

BACKGROUND

Each year more than 1.3 million new cases of breast cancer are diagnosed worldwide. In spite of advances in prevention, surgical resection, chemotherapy and targeted therapy in the past decade, it is estimated that approximately 450,000 women will die of this disease globally each year. Triple negative breast cancer (TNBC) is a subtype that encompasses a heterogeneous subset of tumors that share three defining characteristics: lack of estrogen receptor (ER) and progesterone receptor (PR), and lack of human epidermal growth factor receptor 2 (HER2) overexpression. The majority of TNBCs are of high histologic grade, with more than 90% of TNBC reported to be of invasive ductal histology. Those tumors also account for a large proportion of metastatic breast cancers. Currently, standard chemotherapy remains the cornerstone of treatment for patients with TNBC in the preoperative and adjuvant settings. However, TNBC tumors have a high risk of relapse, irrespective of grade and stage. Even though TNBC accounts for only 15% to 20% of breast cancer, it is responsible for a disproportionate number of breast cancer deaths, due to the lack of effective agents. Therefore, TNBC remains a major challenge to physicians and patients. The search for effective therapies for this disease is a major focus for drug discovery and development efforts.

Citation or identification of any reference in Section 2 of this application is not to be construed as an admission that the reference is prior art to the present application.

SUMMARY

Provided herein are compounds having the following formula (I):

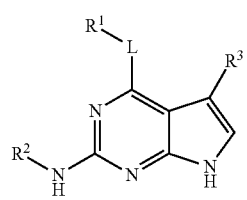

(I)

and pharmaceutically acceptable salts, tautomers, stereoisomers, enantiomers, and isotopologues thereof, wherein $R^1$, $R^2$, $R^3$, and L are as defined herein.

A compound of formula (I) or a pharmaceutically acceptable salt, tautomer, stereoisomer, enantiomer, or isotopologue thereof (each being referred to herein as an "Pyrrolopyrimidine Compound") is useful for treating or preventing breast cancer, in particular, triple negative breast cancer (TNBC).

In one aspect, provided herein are Pyrrolopyrimidine Compounds as described in the instant disclosure, such as, for example, in Table 1.

In one aspect, provided herein are pharmaceutical compositions comprising an effective amount of a Pyrrolopyrimidine Compound as described herein, and a pharmaceutically acceptable carrier, excipient or vehicle. In some embodiments the pharmaceutical composition is suitable for parenteral administration.

In one aspect, provided herein are methods for treating or preventing breast cancer, in particular triple negative breast cancer (TNBC), comprising administering to a subject in need thereof an effective amount of a Pyrrolopyrimidine Compound as described herein. In another aspect, provided herein are methods for treating or preventing breast cancer, in particular triple negative breast cancer (TNBC), comprising administering to a subject in need thereof an effective amount of a Pyrrolopyrimidine Compound as described herein and a pharmaceutically acceptable carrier, excipient or vehicle.

In another aspect provided herein are methods for preparing Pyrrolopyrimidine Compounds as described herein.

The present embodiments can be understood more fully by reference to the detailed description and examples, which are intended to exemplify non-limiting embodiments.

DETAILED DESCRIPTION

Definitions

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or 2 to 4 carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. Examples of unsaturated alkyl groups include, but are not limited to, vinyl, allyl, —CH=CH(CH₃), —CH=C(CH₃)₂, —C(CH₃)=CH₂, —C(CH₃)=CH(CH₃), —C(CH₂CH₃)=CH₂, —C≡CH, —C≡C(CH₃), —C≡C(CH₂CH₃), —CH₂C≡CH, —CH₂C≡C(CH₃) and —CH₂C≡C(CH₂CH₃), among others. An alkyl group can be substituted or unsubstituted. When the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; B(OH)₂, or O(alkyl)aminocarbonyl.

A "cycloalkyl" group is a saturated, or partially saturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1] pentyl, bicyclo[2.1.1]hexyl, bicyclo[2.2.1]heptyl, bicyclo [2.2.2]octyl, adamantyl and the like. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d] oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1 (2H)-onyl), tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-one or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4] dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo[d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indolyl-2-onyl or isoindolin-1-onyl), indolinyl, isoindolyl, isoindolinyl, azaindolyl (pyrrolopyridyl or 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (i.e., benzo[d]oxazolyl), benzothiazolyl, benzothiadiazolyl, benzo[1,3]dioxolyl, pyrazolopyridyl (for example, 1H-pyrazolo[3,4-b]pyridyl, 1H-pyrazolo[4,3-b]pyridyl), imidazopyridyl (e.g., azabenzimidazolyl or 1H-imidazo[4,5-b]pyridyl), triazolopyridyl, isoxazolopyridyl, purinyl, xanthinyl, adeninyl, guaninyl, quinolinyl, isoquinolinyl (e.g., 3,4-dihydroisoquinolin-1(2H)-onyl), quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

A "cycloalkylalkyl" group is a radical of the formula: -alkyl-cycloalkyl, wherein alkyl and cycloalkyl are as defined above. Substituted cycloalkylalkyl groups may be substituted at the alkyl, the cycloalkyl, or both the alkyl and the cycloalkyl portions of the group. Representative cycloalkylalkyl groups include but are not limited to methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopentyl, propylcyclohexyl and the like.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

An "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocylylalkyl groups include but are not limited to 4-ethyl-morpholinyl, 4-propylmorpholinyl, furan-2-yl methyl, furan-3-yl methyl, pyridin-3-yl methyl, tetrahydrofuran-2-yl ethyl, and indol-2-yl propyl.

A "halogen" is chloro, iodo, bromo, or fluoro.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amine" group is a radical of the formula: —NH$_2$.

A "hydroxyl amine" group is a radical of the formula: —N(R$^\#$)OH or —NHOH, wherein R$^\#$ is a substituted or unsubstituted alkyl, cycloalkyl, aryl, aralkyl, heterocyclyl or heterocyclylalkyl group as defined herein.

An "alkoxyamine" group is a radical of the formula: —N(R$^\#$)O-alkyl or —NHO-alkyl, wherein R$^\#$ is as defined above.

An "aralkoxyamine" group is a radical of the formula: —N(R$^\#$)O-aryl or —NHO-aryl, wherein R$^\#$ is as defined above.

An "alkylamine" group is a radical of the formula: —NH-alkyl or —N(alkyl), wherein each alkyl is independently as defined above.

An "aminocarbonyl" group is a radical of the formula: —C(=O)N(R$^\#$)$_2$, —C(=O)NH(R$^\#$) or —C(=O)NH$_2$, wherein each R$^\#$ is as defined above.

An "acylamino" group is a radical of the formula: —NHC(=O)(R$^\#$) or —N(alkyl)C(=O)(R$^\#$), wherein each alkyl and R$^\#$ are independently as defined above.

An "O(alkyl)aminocarbonyl" group is a radical of the formula: —O(alkyl)C(=O)N(R$^\#$)$_2$, —O(alkyl)C(=O)NH(R$^\#$) or —O(alkyl)C(=O)NH$_2$, wherein each R$^\#$ is independently as defined above.

An "N-oxide" group is a radical of the formula: —N$^+$—O$^-$.

A "carboxy" group is a radical of the formula: —C(=O)OH.

A "ketone" group is a radical of the formula: —C(=O)(R$^\#$), wherein R$^\#$ is as defined above.

An "aldehyde" group is a radical of the formula: —CH(=O).

An "ester" group is a radical of the formula: —C(=O)O(R$^\#$) or —OC(=O)(R$^\#$), wherein R$^\#$ is as defined above.

A "urea" group is a radical of the formula: —N(alkyl)C(=O)N(R$^\#$)$_2$, —N(alkyl)C(=O)NH(R$^\#$), —N(alkyl)C(=O)NH$_2$, —NHC(=O)N(R$^\#$)$_2$, —NHC(=O)NH(R$^\#$), or —NHC(=O)NH$_2^\#$, wherein each alkyl and R$^\#$ are independently as defined above.

An "imine" group is a radical of the formula: —N=C(R$^\#$)$_2$ or —C(R$^\#$)=N(R$^\#$), wherein each R$^\#$ is independently as defined above.

An "imide" group is a radical of the formula: —C(=O)N(R#)C(=O)(R$^\#$) or —N((C=O)(R$^\#$))$_2$, wherein each R$^\#$ is independently as defined above.

A "urethane" group is a radical of the formula: —OC(=O)N(R$^\#$)$_2$, —OC(=O)NH(R$^\#$), —N(R$^\#$)C(=O)O(R$^\#$), or —NHC(=O)O(R$^\#$), wherein each R$^\#$ is independently as defined above.

An "amidine" group is a radical of the formula: —C(=N(R$^\#$))N(R$^\#$)$_2$, —C(=N(R$^\#$))NH(R$^\#$), —C(=N(R$^\#$))NH$_2$, —C(=NH)N(R$^\#$)$_2$, —C(=NH)NH(R$^\#$), —C(=NH)NH$_2$, —N=C(R$^\#$)N(R$^\#$)$_2$, —N=C(R$^\#$)NH(R$^\#$), —N=C(R$^\#$)NH$_2$, —N(R$^\#$)C(R$^\#$)=N(R$^\#$), —NHC(R$^\#$)=N(R$^\#$), —N(R$^\#$)C(R$^\#$)=NH, or —NHC(R$^\#$)=NH, wherein each R$^\#$ is independently as defined above.

A "guanidine" group is a radical of the formula: —N(R$^\#$)C(=N(R$^\#$))N(R$^\#$)$_2$, —NHC(=N(R$^\#$))N(R$^\#$)$_2$, —N(R$^\#$)C(=NH)N(R$^\#$)$_2$, —N(R$^\#$)C(=N(R$^\#$))NH(R$^\#$), —N(R$^\#$)C(=N(R$^\#$))NH$_2$, —NHC(=NH)N(R$^\#$)$_2$, —NHC(=N(R$^\#$))NH(R$^\#$), —NHC(=N(R$^\#$))NH$_2$, —NHC(=NH)NH(R$^\#$), —NHC(=NH)NH$_2$, —N=C(N(R$^\#$)$_2$)$_2$, —N=C(NH(R$^\#$))$_2$, or —N=C(NH$_2$)$_2$, wherein each R$^\#$ is independently as defined above.

A "enamine" group is a radical of the formula: —N(R$^\#$)C(R$^\#$)=C(R$^\#$)$_2$, —NHC(R$^\#$)=C(R$^\#$)$_2$, —C(N(R$^\#$)$_2$)=C(R$^\#$)$_2$, —C(NH(R$^\#$))=C(R$^\#$)$_2$, —C(NH$_2$)=C(R$^\#$)$_2$, —C(R$^\#$)=C(R$^\#$)(N(R$^\#$)$_2$), —C(R$^\#$)=C(R$^\#$)(NH(R$^\#$)) or —C(R$^\#$)=C(R$^\#$)(NH$_2$), wherein each R$^\#$ is independently as defined above.

An "oxime" group is a radical of the formula: —C(=NO(R$^\#$))(R$^\#$), —C(=NOH)(R$^\#$), —CH(=NO(R$^\#$)), or —CH(=NOH), wherein each R$^\#$ is independently as defined above.

A "hydrazide" group is a radical of the formula: —C(=O)N(R$^\#$)N(R$^\#$)$_2$, —C(=O)NHN(R$^\#$)$_2$, —C(=O)N(R$^\#$)NH(R$^\#$), —C(=O)N(R$^\#$)NH$_2$, —C(=O)NHNH(R$^\#$)$_2$, or —C(=O)NHNH$_2$, wherein each R$^\#$ is independently as defined above.

A "hydrazine" group is a radical of the formula: —N(R$^\#$)N(R$^\#$)$_2$, —NHN(R$^\#$)$_2$, —N(R$^\#$)NH(R$^\#$), —N(R$^\#$)NH$_2$, —NHNH(R$^\#$)$_2$, or —NHNH$_2$, wherein each R$^\#$ is independently as defined above.

A "hydrazone" group is a radical of the formula: —C(=N—N(R$^\#$)$_2$)(R$^\#$)$_2$, —C(=N—NH(R$^\#$))(R$^\#$)$_2$, —C(=N—NH$_2$)(R$^\#$)$_2$, —N(R$^\#$)(N=C(R$^\#$)$_2$), or —NH(N=C(R$^\#$)$_2$), wherein each R$^\#$ is independently as defined above.

An "azide" group is a radical of the formula: —N$_3$.

An "isocyanate" group is a radical of the formula: —N=C=O.

An "isothiocyanate" group is a radical of the formula: —N=C=S.

A "cyanate" group is a radical of the formula: —OCN.

A "thiocyanate" group is a radical of the formula: —SCN.

A "thioether" group is a radical of the formula; —S(R$^\#$), wherein R$^\#$ is as defined above.

A "thiocarbonyl" group is a radical of the formula: —C(=S)(R$^\#$), wherein R$^\#$ is as defined above.

A "sulfinyl" group is a radical of the formula: —S(=O)(R$^\#$), wherein R$^\#$ is as defined above.

A "sulfone" group is a radical of the formula: —S(=O)$_2$(R$^\#$), wherein R$^\#$ is as defined above.

A "sulfonylamino" group is a radical of the formula: —NHSO$_2$(R$^\#$) or —N(alkyl)SO$_2$(R$^\#$), wherein each alkyl and R$^\#$ are defined above.

A "sulfonamide" group is a radical of the formula: —S(=O)$_2$N(R$^\#$)$_2$, or —S(=O)$_2$NH(R$^\#$), or —S(=O)$_2$NH$_2$, wherein each R$^\#$ is independently as defined above.

A "phosphonate" group is a radical of the formula: —P(=O)(O(R$^\#$))$_2$, —P(=O)(OH)$_2$, —OP(=O)(O(R$^\#$))(R$^\#$), or —OP(=O)(OH)(R$^\#$), wherein each R$^\#$ is independently as defined above.

A "phosphine" group is a radical of the formula: —P(R$^\#$)$_2$, wherein each R$^\#$ is independently as defined above.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amine; alkylamine; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidyl, benzimidazolyl, benzothiophenyl, or benzofuranyl)aryloxy; aralkyloxy; heterocyclyloxy; and heterocyclyl alkoxy.

As used herein, the term "Pyrrolopyrimidine Compound" refers to compounds of formula (I), as well as to further embodiments provided herein. In one embodiment, a "Pyrrolopyrimidine Compound" is a compound set forth in Table 1. The term "Pyrrolopyrimidine Compound" includes pharmaceutically acceptable salts, tautomers, stereoisomers, enantiomers and isotopologues of the compounds provided herein.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "stereoisomer" or "stereomerically pure" means one stereoisomer of a Pyrrolopyrimidine Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Pyrrolopyrimidine Compounds can have chiral centers and can occur as racemates, individual enantiomers or diastereomers, and mixtures thereof. All such isomeric forms are included within the embodiments disclosed herein, including mixtures thereof.

The use of stereomerically pure forms of such Pyrrolopyrimidine Compounds, as well as the use of mixtures of those forms, are encompassed by the embodiments disclosed herein. For example, mixtures comprising equal or unequal amounts of the enantiomers of a particular Pyrrolopyrimidine Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Pyrrolopyrimidine Compounds can include E and Z isomers, or a mixture thereof, and cis and trans isomers or a mixture thereof. In certain embodiments, the Pyrrolopyrimidine Compounds are isolated as either the E or Z isomer. In other embodiments, the Pyrrolopyrimidine Compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

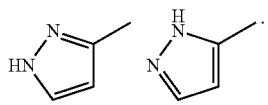

As readily understood by one skilled in the art, a wide variety of functional groups and other structures may exhibit tautomerism and all tautomers of compounds of formula (I) are within the scope of the present invention.

It should also be noted the Pyrrolopyrimidine Compounds can contain unnatural proportions of atomic isotopes at one or more of the atoms. For example, the compounds may be radiolabeled with radioactive isotopes, such as for example tritium ($^3$H), iodine-125 ($^{125}$I), sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., breast cancer therapeutic agents, research reagents, e.g., binding assay reagents, and diagnostic agents, e.g., in vivo imaging agents. All isotopic variations of the Pyrrolopyrimidine Compounds as described herein, whether radioactive or not, are intended to be encompassed within the scope of the embodiments provided herein. In some embodiments, there are provided isotopologues of the Pyrrolopyrimidine Compounds, for example, the isotopologues are deuterium, carbon-13, or nitrogen-15 enriched Pyrrolopyrimidine Compounds.

It should be noted that if there is a discrepancy between a depicted structure and a name for that structure, the depicted structure is to be accorded more weight.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is breast cancer, in particular, triple negative breast cancer (TNBC). In some embodiments, "treating" means an alleviation, in whole or in part, of breast cancer, or symptoms associated with breast cancer, in particular, triple negative breast cancer (TNBC), or a slowing, or halting of further progression or worsening of those symptoms.

"Preventing" as used herein, means a method of delaying and/or precluding the onset, recurrence or spread, in whole or in part, of breast cancer, in particular, triple negative breast cancer (TNBC); barring a subject from acquiring breast cancer, in particular, triple negative breast cancer (TNBC); or reducing a subject's risk of acquiring breast cancer, in particular, triple negative breast cancer (TNBC).

The term "effective amount" in connection with a Pyrrolopyrimidine Compound means an amount capable of treating or preventing breast cancer, in particular, triple negative breast cancer (TNBC), or symptoms thereof, as disclosed herein. The effective amount of Pyrrolopyrimidine Compound, for example in a pharmaceutical composition, may be at a level that will exercise the desired effect; for example, about 0.005 mg/kg of a subject's body weight to about 100 mg/kg of a patient's body weight in unit dosage for parenteral administration. As will be apparent to those skilled in the art, it is to be expected that the effective amount of a Pyrrolopyrimidine Compound disclosed herein may vary depending on the severity of the indication being treated.

The terms "patient" and "subject" as used herein include an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having breast cancer, in particular, triple negative breast cancer (TNBC), or symptoms thereof. In one embodiment, a patient is a human having histologically or cytologically-confirmed triple negative breast cancer, including subjects who have progressed on (or not been able to tolerate) standard anticancer therapy or for whom no standard anticancer therapy exists.

As used herein, and unless otherwise specified, the terms "cancer" refers to or describes the physiological condition in mammals that is typically characterized by unregulated cell growth. Examples of breast cancer include, but are not limited to, triple negative breast cancer.

"Triple negative breast cancer" as used herein, means breast cancer that does not express the proteins corresponding to the estrogen receptor (ER)— and progesterone receptor (PR), and that does not overexpress the human epidermal growth factor receptor 2 (Her2/neu) protein.

Pyrrolopyrimidine Compounds

Provided herein are compounds having the following formula (I):

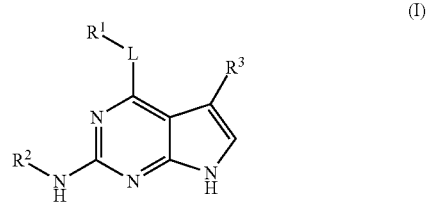

(I)

and pharmaceutically acceptable salts, tautomers, stereoisomers, enantiomers, and isotopologues thereof, wherein:

$R^1$ is substituted or unsubstituted $C_{1-8}$ alkyl, substituted or unsubstituted $C_{3-8}$ cycloalkyl, or substituted or unsubstituted non-aromatic heterocyclyl;

$R^2$ is substituted or unsubstituted aryl, or substituted or unsubstituted heteroaryl;

$R^3$ is substituted or unsubstituted heterocyclyl or substituted or unsubstituted aryl, and L is NH or O;

provided that when L is NH, $R^3$ is not pyridyl.

Provided herein are compounds having the following formula (I):

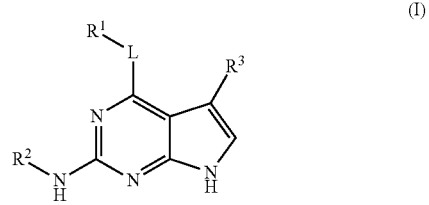

(I)

and pharmaceutically acceptable salts, tautomers, stereoisomers, enantiomers, and isotopologues thereof, wherein:

$R^1$ is substituted or unsubstituted $C_{1-8}$ alkyl, substituted or unsubstituted $C_{3-8}$ cycloalkyl, or substituted or unsubstituted non-aromatic heterocyclyl;

$R^2$ is substituted or unsubstituted aryl, or substituted or unsubstituted heteroaryl;

$R^3$ is substituted or unsubstituted heterocyclyl or substituted or unsubstituted aryl, and L is NH or O;

provided $R^3$ is not pyridyl when L is NH or when $R^2$ is pyrazolyl; and the compound is not N-methyl-N-[trans-3-[[5-(1-methyl-1H-pyrazol-4-yl)-2-[(1-methyl-1Hpyrazol-4-yl)amino]-7H-pyrrolo[2,3-d]pyrimidin-4-yl]oxy]cyclobutyl]-2-propenamide; or N-methyl-N-[trans-3-[[5-(1-methyl-1H-pyrazol-3-yl)-2-[(1-methyl-1Hpyrazol-4-yl)amino]-7H-pyrrolo[2,3-d]pyrimidin-4-yl]oxy]cyclobutyl]-2-propenamide.
The compound as described herein is not a compound selected from:
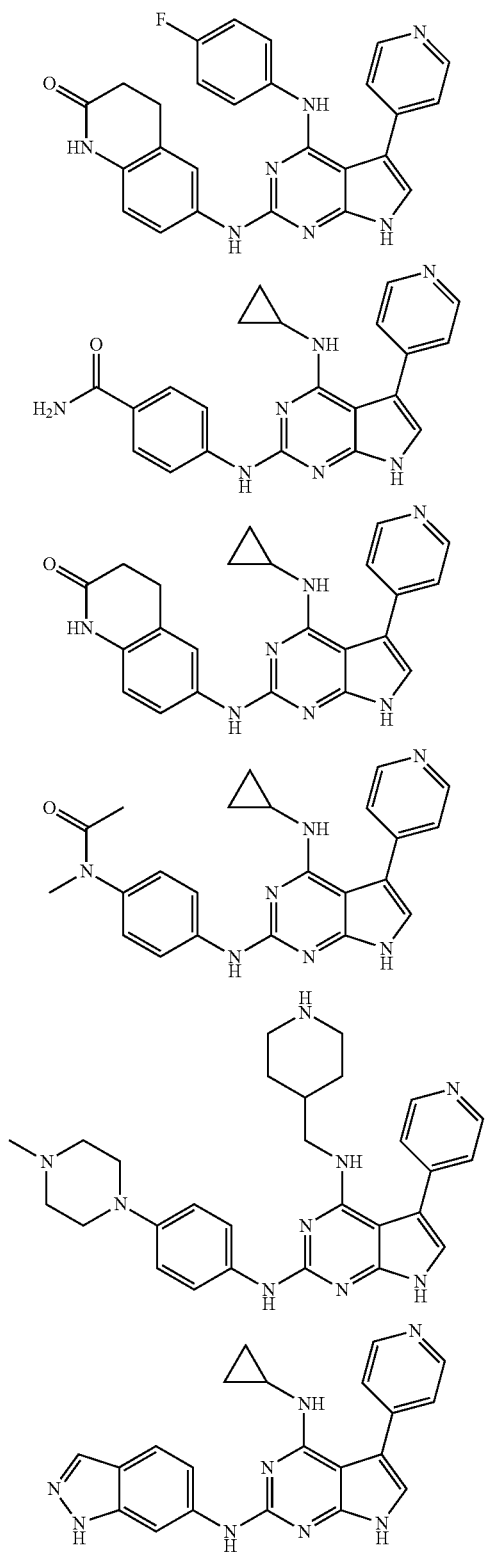
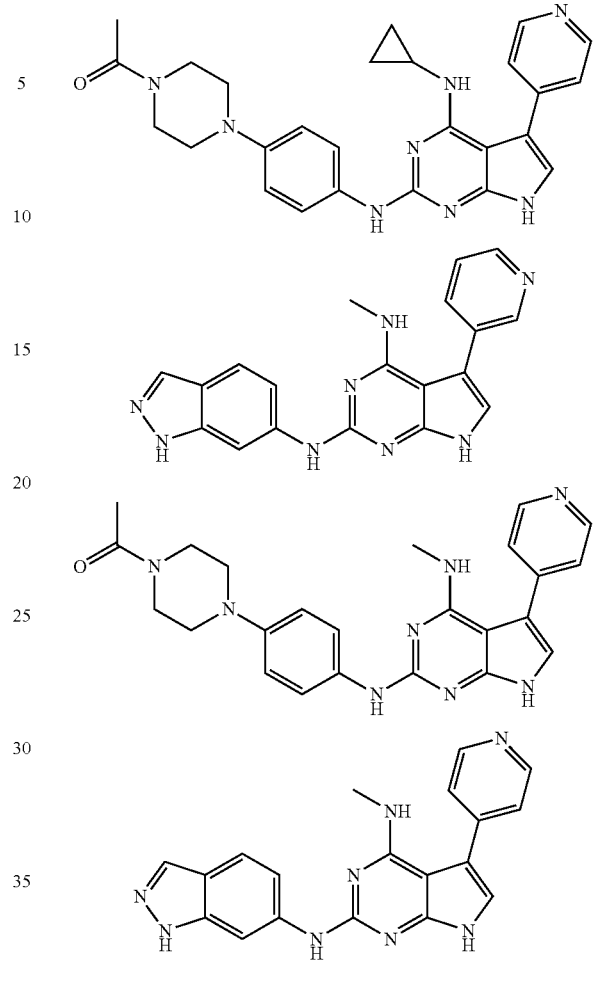
As described herein, the compound is not
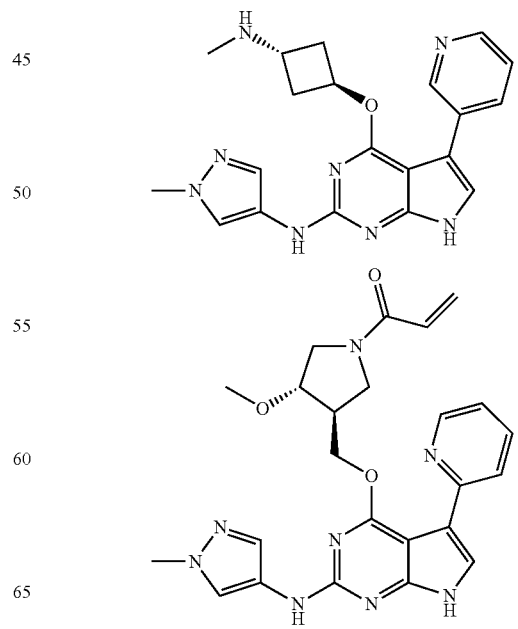

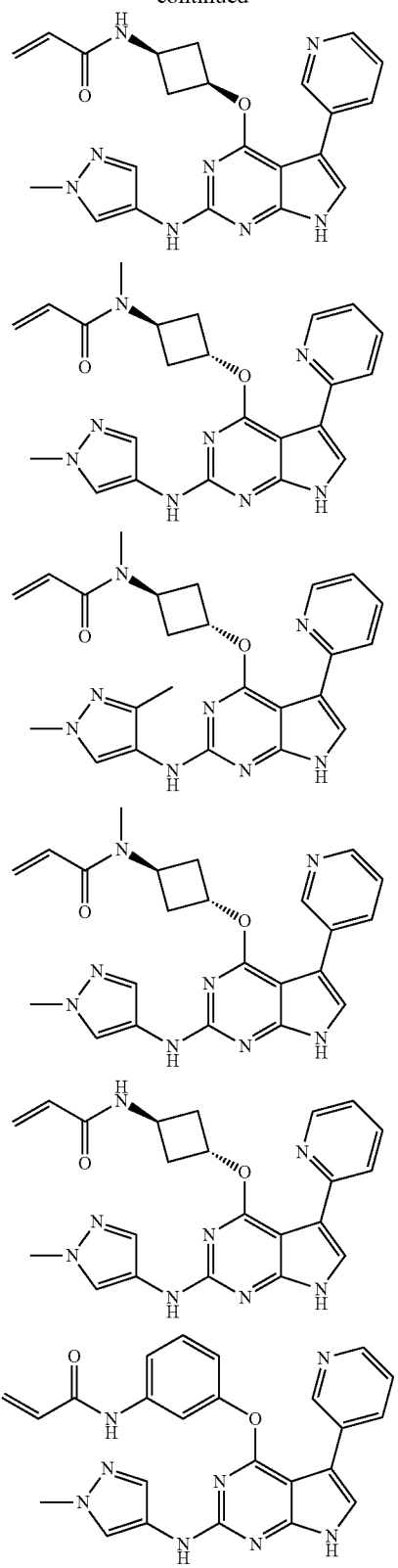

In one embodiment, the compound is not N-methyl-N-[trans-3-[[5-(1-methyl-1H-pyrazol-4-yl)-2-[(1-methyl-1Hpyrazol-4-yl)amino]-7H-pyrrolo[2,3-d]pyrimidin-4-yl]oxy]cyclobutyl]-2-propenamide (also named N-methyl-N-((1r,3r)-3-((5-(1-methyl-1H-pyrazol-4-yl)-2-((1-methyl-1H-pyrazol-4-yl)amino)-7H-pyrrolo[2,3-d]pyrimidin-4-yl)oxy)cyclobutyl)acrylamide)

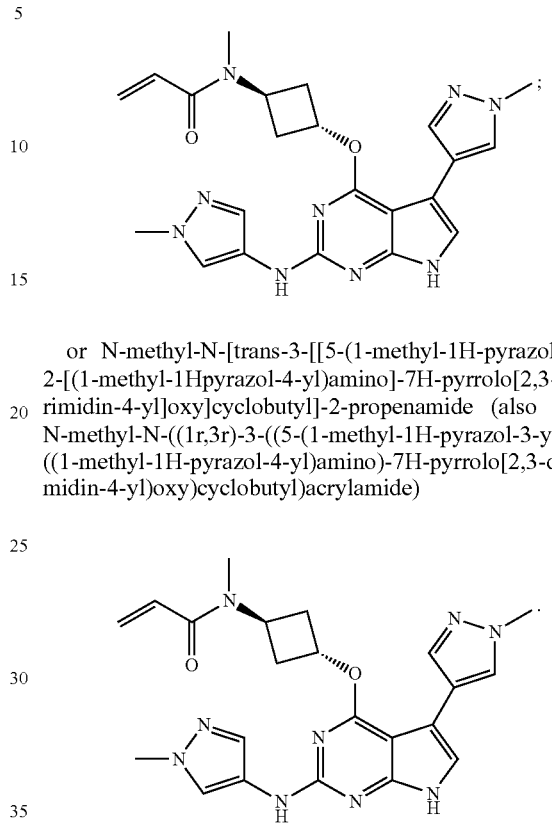

or N-methyl-N-[trans-3-[[5-(1-methyl-1H-pyrazol-3-yl)-2-[(1-methyl-1Hpyrazol-4-yl)amino]-7H-pyrrolo[2,3-d]pyrimidin-4-yl]oxy]cyclobutyl]-2-propenamide (also named N-methyl-N-((1r,3r)-3-((5-(1-methyl-1H-pyrazol-3-yl)-2-((1-methyl-1H-pyrazol-4-yl)amino)-7H-pyrrolo[2,3-d]pyrimidin-4-yl)oxy)cyclobutyl)acrylamide)

In yet another embodiment, the compound is not

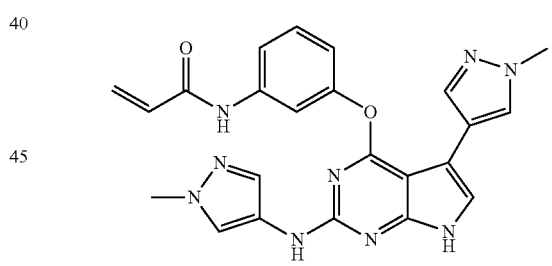

In one embodiment, provided herein are compounds of formula (I), wherein L is O.

In some embodiments of compounds of formula (I), $R^1$ is substituted or unsubstituted alkyl, for example, $R^1$ is substituted or unsubstituted methyl, ethyl, propyl, isopropyl, n-butyl, sec-butyl, tert-butyl, n-pentyl, sec-pentyl, tert-pentyl, or 2,2-dimethylpropyl. In some embodiments, $R^1$ is substituted or unsubstituted methyl, ethyl, isopropyl, sec-butyl, t-butyl, or 2,2-dimethylpropyl. In some embodiments of formula (I), wherein $R^1$ is alkyl, the alkyl is substituted with one or more —OR or —$NR_2$, wherein each R is independently —H or substituted or unsubstituted $(C_{1-4})$alkyl. For example $R^1$ is —$CH_2CH_2OH$, —$CH_2CH_2OCH_3$, or —$CH_2CH_2NHCH_3$. In other embodiments of compounds of formula (I), $R^1$ is substituted or unsubstituted $C_{3-8}$ cycloalkyl, for example, $R^1$ is substituted or unsubstituted cyclopropyl, cyclobutyl, cyclopentyl, cyclohexyl, or cycloheptyl. In some such embodiments, the cycloalkyl is substituted with one or more —CN, halogen, —OR or a substituted or unsubstituted $C_{1-3}$ alkyl, wherein each R is independently —H or substituted or unsubstituted $(C_{1-4})$alkyl. For example, in some embodiments the cycloalkyl is substituted with one or more —CN, —F, —OH, or —$CH_3$. In some other embodiments of compounds of formula (I), $R^1$ is substituted or unsubstituted non-aromatic heterocyclyl, for example, $R^1$ is substituted or unsubstituted oxetanyl, tetrahydrofuranyl, tetrahydropyranyl, or piperidinyl.

In some other embodiments of compounds of formula (I), $R^1$ is substituted or unsubstituted $C_{1-8}$ alkyl,

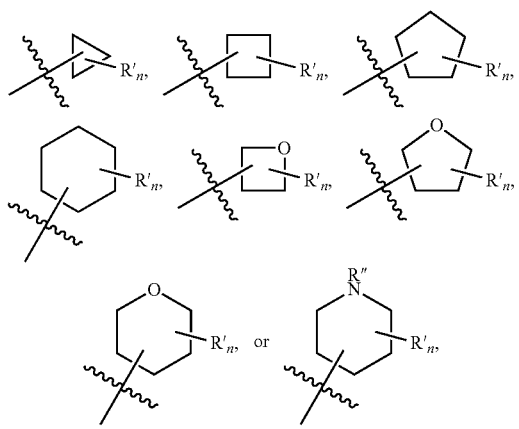

wherein each R' is independently —CN, halogen, —OR or $C_{1-3}$ alkyl;

R" is —H or $C_{1-3}$ alkyl;

each R is independently —H or substituted or unsubstituted $(C_{1-4})$alkyl; and n is 0-2.

In some such embodiments, $R^1$ is substituted or unsubstituted methyl, ethyl, isopropyl, sec-butyl, t-butyl, or 2,2-dimethylpropyl,

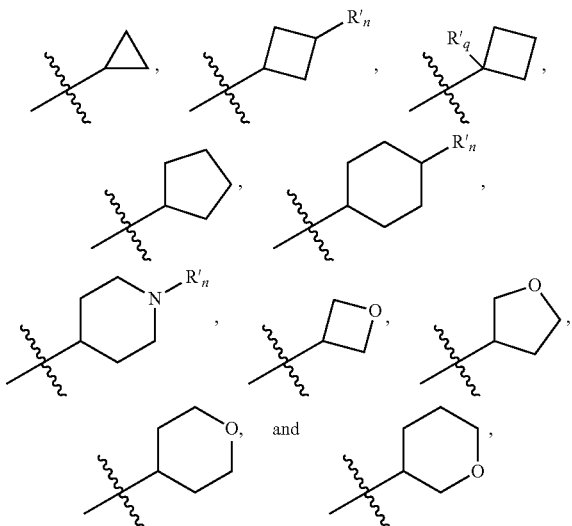

and R' is —CN, —F, —OH, or —$CH_3$;

R" is —$CH_3$;

n is 0, 1 or 2; and q is 0 or 1.

Also provided herein are compounds of formula (I), wherein $R^2$ is substituted phenyl. In some such embodiments, $R^2$ is phenyl, substituted with one or more substituted or unsubstituted $C_1$-6 alkyl, halogen, —CN, —$OR^5$, —C(=O)$NR^5_2$, —C(=O)(substituted or unsubstituted heterocyclyl), —C(=O)(substituted or unsubstituted heterocyclylalkyl), —NHC(=O)$R^5$, —$SO_2NR^5_2$, or substituted or unsubstituted heteroaryl, wherein each $R^5$ is independently —H, substituted or unsubstituted alkyl, substituted or unsubstituted cycloalkyl, substituted or unsubstituted heterocyclyl, or substituted or unsubstituted heterocyclylalkyl. For example, $R^2$ is phenyl, substituted with one or more —($C_{1-3}$ alkyl), —($C_{1-3}$ alkyl)$NR_2$, —$CF_3$, —Cl, —F, —CN, —$OCH_3$, —$OCF_3$, —C(=O)$NR_2$, —C(=O)NR(substituted or unsubstituted cycloalkyl), —C(=O)NR$(CH_2)_{0-2}CR_2(CH_2)_{0-2}OR$, —C(=O)NR$(CH_2)_{0-2}CR_2(CH_2)_{0-2}NR_2$, —C(=O)NR$(CH_2)_{0-2}CR_2(CH_2)_{0-2}$C(=O)$NR_2$, —C(=O)N(substituted or unsubstituted cycloalkyl)$(CH_2)_{0-2}OR$, —C(=O)NR$(CH_2)_{0-3}$(substituted or unsubstituted heterocyclyl), —C(=O)$(CH_2)_{0-3}$(substituted or unsubstituted heterocyclyl), —C(=NR)$NR_2$, —NRC(=O)R, —$SO_2NR_2$, —$SO_2R$, or substituted or unsubstituted heterocyclyl, wherein each R is independently —H or substituted or unsubstituted $(C_{1-4})$alkyl. In some such embodiments, each R is independently —H or —$CH_3$.

In some embodiments of compounds of formula (I), $R^2$ is phenyl, substituted with one or more —$CH_3$, —$CH_2CH_3$, —$CH_2CH_2CH_3$, —$CH(CH_3)_2$, —$CH_2NH_2$, —$CF_3$, —Cl, —F, —CN, —$OCH_3$, —$OCF_3$, —C(=O)$NH_2$, —C(=O)$NHCH_3$, —C(=O)$N(CH_3)_2$, —C(=O)$NC(CH_3)_3$, —C(=O)$NHCH_2CH_2F$, —C(=O)$NHCH_2CHF_2$, —C(=O)$NHCH_2CF_3$, —C(=O)$NHCH_2CF_2CH_3$, —C(=O)$NHCH_2CN$, —C(=O)$N(CH_3)CH_2CN$, —C(=O)$NHCH_2CH_2CN$, —C(=O)$N(CH_3)CH_2CH_2CN$, —C(=O)NH-cyclobutyl, —C(=O)NH-(hydroxy-cyclobutyl), —C(=O)NH-cyclopentyl, —C(=O)NH-(hydroxyl-cyclopentyl), —C(=O)$NHCH_2CH_2OH$, —C(=O)$NHCH_2CH_2OCH_3$, —C(=O)$N(CH_3)CH_2CH_2OH$, —C(=O)$N(CH_3)CH_2CH_2OCH_3$, —C(=O)$NHCH_2CH_2CH_2OH$, —C(=O)$N(CH_3)CH_2CH_2CH_2OH$, —C(=O)$N(CH_3)CH_2CH_2CH_2OCH_3$, —C(=O)$NHCH(CH_3)OH$, —C(=O)$NHCH_2C(CH_3)_2OH$, —C(=O)$NHCH(CH_3)CH_2OH$, —C(=O)$NHC(CH_3)_2CH_2OH$, —C(=O)$NHCH_2CH_2NH_2$, —C(=O)$NHCH_2CH_2NH(CH_3)$, —C(=O)$NHCH_2CH_2N(CH_3)_2$, —C(=O)$NHCH_2C(=O)NH_2$, —C(=O)$N(CH_3)CH_2C(=O)NH_2$, —C(=O)$NHCH_2CH_2C(=O)NH_2$, —C(=O)$N(CH_3)CH_2CH_2C(=O)NH_2$, —C(=O)N(cyclopropyl)$CH_2CH_2OH$, —C(=O)NH-oxetanyl, —C(=O)$N(CH_3)$-oxetanyl, —C(=O)NH-(methyl-oxetanyl), —C(=O)NH-azetidinyl, —C(=O)NH-(methylazetidinyl), —C(=O)NH-(1-acetylazetidinyl), —C(=O)NH-pyrrolidyl, —C(=O)NH-piperidyl, —C(=O)NH-tetrahydrofuranyl, —C(=O)$N(CH_3)$-tetrahydrofuranyl, —C(=O)NH-tetrahydropyranyl, —C(=O)$N(CH_3)$-tetrahydropyranyl, —C(=O)$NHCH_2$-oxetanyl, —C(=O)$N(CH_3)CH_2$-oxetanyl, —C(=O)$NHCH_2$-(methyl-oxetanyl), —C(=O)$N(CH_3)CH_2$-(methyl-oxetanyl), —C(=O)$NHCH_2$-tetrahydrofuranyl, —C(=O)$NHCH_2$-tetrahydropyranyl, —C(=O)$NHCH_2$-dioxanyl, —C(=O)aziridinyl, —C(=O)(methyl-aziridinyl), —C(=O)(dimethyl-aziridinyl), —C(=O)(hydroxymethyl-aziridinyl), —C(=O)azetidinyl, —C(=O)pyrrolidinyl, —C(=O)(hydroxyl-pyrrolidinyl), —C(=O)(hydroxyl, methoxypyrrolidinyl), —C(=O)(dimethoxypyrrolidinyl), —C(=O)morpholinyl, —C(=O)piperazinyl, —C(=O)

(methylpiperazinyl), —C(=O)(hydroxy-piperidyl), —C(=O)(fluoropiperidinyl), —(C=O)(methoxy-piperidyl), —C(=NH)NH$_2$, —NHC(=O)CH$_3$, —SO$_2$NHCH$_3$, —SO$_2$CH$_3$, or substituted or unsubstituted pyrazolyl. In some other embodiments, R$^2$ is phenyl, substituted with one or more —CH$_3$, —CH$_2$CH$_3$, —CH$_2$CH$_2$CH$_3$, —CH(CH$_3$)$_2$, —CH$_2$NH$_2$, —CF$_3$, —Cl, —F, —CN, —OCH$_3$, —OCF$_3$, —C(=O)NH$_2$, —C(=O)NHCH$_3$, —C(=O)N(CH$_3$)$_2$, —C(=O)NC(CH$_3$)$_3$, —C(=O)NHCH$_2$CH$_2$F, —C(=O)NHCH$_2$CF$_2$CH$_3$, —C(=O)N(CH$_3$)CH$_2$CN, —C(=O)N(CH$_3$)CH$_2$CH$_2$CN, —C(=O)NH-(3-hydroxy-cyclobutyl), —C(=O)NH-cyclopentyl, —C(=O)NH-(2-hydroxycyclopentyl), —C(=O)NHCH$_2$CH$_2$OH, —C(=O)NHCH$_2$CH$_2$OCH$_3$, —C(=O)N(CH$_3$)CH$_2$CH$_2$OH, —C(=O)N(CH$_3$)CH$_2$CH$_2$OCH$_3$, —C(=O)NHCH$_2$CH$_2$CH$_2$OH, —C(=O)N(CH$_3$)CH$_2$CH$_2$CH$_2$OH, —C(=O)NHCH$_2$CH(CH$_3$)OH, —C(=O)NHCH$_2$C(CH$_3$)$_2$OH, —C(=O)NHCH(CH$_3$)CH$_2$OH, —C(=O)NHC(CH$_3$)$_2$CH$_2$OH, —C(=O)NHCH$_2$CH$_2$NH$_2$, —C(=O)NHCH$_2$CH$_2$NH(CH$_3$), —C(=O)NHCH$_2$CH$_2$N(CH$_3$)$_2$, —C(=O)N(CH$_3$)CH$_2$C(=O)NH$_2$, —C(=O)N(CH$_3$)CH$_2$CH$_2$C(=O)NH$_2$, —C(=O)N(cyclopropyl)CH$_2$CH$_2$OH, —C(=O)NH-oxetanyl, —C(=O)N(CH$_3$)-oxetanyl, —C(=O)NH-(3-methyl-oxetanyl), —C(=O)NH-(1-methylazetidinyl), —C(=O)NH-(1-acetylazetidinyl), —C(=O)NH-piperidyl, —C(=O)NH-tetrahydrofuranyl, —C(=O)NH-tetrahydropyranyl, —C(=O)N(CH$_3$)-tetrahydropyranyl, —C(=O)NHCH$_2$-oxetanyl, —C(=O)N(CH$_3$)CH$_2$-(3-methyl-oxetanyl), —C(=O)NHCH$_2$-tetrahydrofuranyl, —C(=O)NHCH$_2$-tetrahydropyranyl, —C(=O)NHCH$_2$-dioxanyl, —C(=O)aziridinyl, —C(=O)(2-methyl-aziridinyl), —C(=O)(2,2-dimethyl-aziridinyl), —C(=O)(2-(hydroxymethyl)aziridinyl), —C(=O)azetidinyl, —C(=O)pyrrolidinyl, —C(=O)(3-hydroxy-4-methoxypyrrolidinyl), —C(=O)(3,4-dimethoxypyrrolidinyl), —C(=O)morpholinyl, —C(=O)piperazinyl, —C(=O)(4-methylpiperazinyl), —C(=O)(4-hydroxy-piperidyl), —C(=O)(4,4-difluoropiperidinyl), —(C=O)(4-methoxy-piperidyl), —C(=NH)NH$_2$, —NHC(=O)CH$_3$, —SO$_2$NHCH$_3$, —SO$_2$CH$_3$, or substituted or unsubstituted pyrazolyl.

In some embodiments of compounds of formula (I), R$^2$ is substituted or unsubstituted pyrazolyl, substituted or unsubstituted pyridyl, substituted or unsubstituted indazolyl or substituted or unsubstituted isoindolinone. In some such embodiments, R$^2$ is substituted with one or more halogen, substituted or unsubstituted (C$_{1-4}$)alkyl, —OR, —C(=O)NR$_2$, or substituted or unsubstituted heterocyclyl, wherein each R is independently —H or substituted or unsubstituted (C$_{1-4}$)alkyl. For example, R$^2$ is pyrazolyl substituted with one or more —Cl, —CH$_3$, —CH$_2$CH$_3$, —CH(CH$_3$)$_2$, —CH$_2$CH$_2$OCH$_3$, —CH$_2$C(CH$_3$)$_2$OH, or tetrahydropyranyl. Alternatively, R$^2$ is pyridyl, substituted with one or more —OCH$_3$, C(=O)NHCH$_3$, or tetrahydropyranyl. In yet other embodiments, R$^2$ is indazolyl or isoindolinone, substituted with one or more —CH$_3$.

In some such embodiments of R$^2$, R$^1$ is substituted or unsubstituted C$_{1-8}$ alkyl,

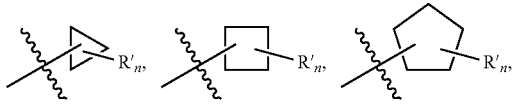

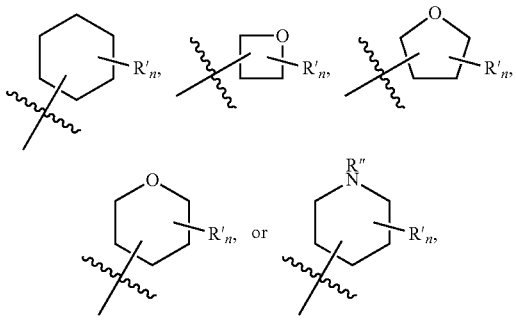

wherein each R' is independently —OR or C$_{1-3}$ alkyl;

R" is —H or C$_{1-3}$ alkyl;

each R is independently —H or substituted or unsubstituted (C$_{1-4}$)alkyl; and n is 0-2.

In yet other embodiments of compounds of formula (I), R$^3$ is substituted or unsubstituted heterocyclyl, for example, substituted or unsubstituted pyrazolyl, oxazolyl, isoxazolyl, oxadiazolyl, pyridyl, pyridazinyl, pyrimidyl, pyrazinyl, benztriazolyl, indazolyl, indolyl, benzoxazolyl, benzisoxazolyl, benzthiazolyl, benzoxazolonyl, benzoxadiazolyl, benzimidazolyl, or quinolyl. In some such embodiments, the heterocyclyl is substituted with one or more substituents selected from substituted or unsubstituted (C$_{1-4}$)alkyl, halogen, —OR, —CN, —NR$_2$, —C(=O)NR$_2$, —NRC(=O)R, or substituted or unsubstituted triazolyl, wherein each R is independently —H or substituted or unsubstituted (C$_{1-4}$) alkyl. For example, the heterocyclyl is substituted with one or more substituents selected from —CH$_3$, —CH(CH$_3$)$_2$, —F, —Cl, —OH, —OCH$_3$, —OCH$_2$CH$_3$, —CN, —NH$_2$, —NHCH$_3$, —N(CH$_3$)$_2$, —C(=O)NH(CH$_3$), —NHC(=O)CH$_3$, or substituted or unsubstituted triazolyl. In some such embodiments, the pyrazolyl is substituted with one or more —CH$_3$, or —Cl. In others, the pyridyl is substituted with one or more —CH$_3$, —F, —Cl, —OH, —OCH$_3$, —OCH$_2$CH$_3$, —CN, —NH$_2$, —NHCH$_3$, —N(CH$_3$)$_2$, —C(=O)NH(CH$_3$), or —NHC(=O)CH$_3$. In still others, the benzoxazolyl is substituted with one or more —CH$_3$, —CH(CH$_3$)$_2$, —F or —OCH$_2$CH$_3$.

In other embodiments of compounds of formula (I), R$^3$ is substituted or unsubstituted aryl, for example, R$^3$ is substituted or unsubstituted phenyl. In some such embodiments, the phenyl is substituted with one or more substituents selected from substituted or unsubstituted C$_{1-4}$ alkyl, halogen, —CN, —OR, —NR$_2$, —NRSO$_2$R', —NR(C=O)NR$_2$, —NR(C=O)R', —COOR, —(C=O)NR$_2$, —C(=NH)NR$_2$, —SO$_2$R', or substituted or unsubstituted heteroaryl, wherein each R is independently —H or substituted or unsubstituted (C$_{1-4}$)alkyl, and R' is C$_{1-3}$ alkyl. In yet other embodiments, the phenyl is substituted with one or more substituents selected from —CH$_3$, —CH$_2$OH, —CH(OH)CH$_3$, —C(CH$_3$)$_2$OH, —CN, —F, —Cl, —OH, —OCH$_3$, —NH$_2$, —N(CH$_3$)$_2$, —NHSO$_2$CH$_3$, —NH(C=O)NH$_2$, —NH(C=O)CH$_3$, —COOCH$_3$, —(C=O)NHCH$_3$, —C(=N)NH$_2$, —SO$_2$CH$_3$, substituted or unsubstituted triazolyl, substituted or unsubstituted pyrazolyl, or substituted or unsubstituted imidazolyl.

In some such embodiments of $R^3$, $R^1$ is substituted or unsubstituted $C_{1-8}$ alkyl,

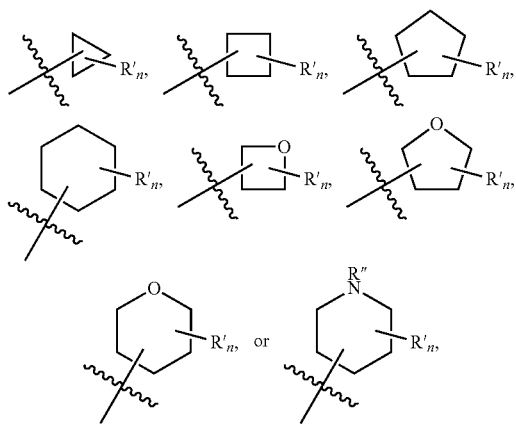

wherein
each R' is independently —OR or $C_{1-3}$ alkyl;
R" is —H or $C_{1-3}$ alkyl;
each R is independently —H or substituted or unsubstituted $(C_{1-4})$alkyl; and
n is 0-2.

In some such embodiments, $R^2$ is phenyl, substituted with one or more —$(C_{1-3}$ alkyl), —$(C_{1-3}$ alkyl)$NR_2$, —$CF_3$, —Cl, —F, —CN, —$OCH_3$, —$OCF_3$, —C(=O)$NR_2$, —C(=O)NR (substituted or unsubstituted cycloalkyl), —C(=O)NR$(CH_2)_{0-2}CR_2(CH_2)_{0-2}$OR, —C(=O)NR$(CH_2)_{0-2}$ $CR_2(CH_2)_{0-2}NR_2$, —C(=O)NR$(CH_2)_{0-2}CR_2(CH_2)_{0-2}$C(=O)$NR_2$, —C(=O)N (substituted or unsubstituted cycloalkyl) $(CH_2)_{0-2}$OR, —C(=O)NR$(CH_2)_{0-3}$ (substituted or unsubstituted heterocyclyl), —C(=O)$(CH_2)_{0-3}$ (substituted or unsubstituted heterocyclyl), —C(=NR)$NR_2$, —NRC(=O)R, —$SO_2NR_2$, —$SO_2$R, or substituted or unsubstituted heterocyclyl, wherein each R is independently —H or substituted or unsubstituted $(C_{1-4})$alkyl.

Further embodiments provided herein include combinations of one or more of the particular embodiments set forth above.

In other embodiments, the compound at a concentration of 10 μM inhibits triple negative breast cancer cell proliferation by at least about 50%.

In some embodiments of compounds of formula (I), the compound is selected from Table 1, or a pharmaceutically acceptable salt, tautomer, stereoisomer, enantiomer, or isotopologue thereof. In some embodiments, provided herein is a compound from Table 1 with activity level B, or a pharmaceutically acceptable salt, tautomer, stereoisomer, enantiomer, or isotopologue thereof. In other embodiments, provided herein is a compound from Table 1 with activity level C, or a pharmaceutically acceptable salt, tautomer, stereoisomer, enantiomer, or isotopologue thereof. In yet other embodiments, provided herein is a compound from Table 1 with activity level D, or a pharmaceutically acceptable salt, tautomer, stereoisomer, enantiomer, or isotopologue thereof.

Pyrrolopyrimidine Compounds set forth in Table 1 were tested in breast cancer cell proliferation assays described herein and were found to have activity as anti-breast cancer agents. In one embodiment, the Pyrrolopyrimidine Compound is a compound as described herein, wherein the compound at a concentration of 10 μM inhibits breast cancer cell proliferation, for example triple negative breast cancer cell proliferation, by at least about 50% or more.

Methods for Making Pyrrolopyrimidine Compounds

The Pyrrolopyrimidine Compounds described herein can be made using conventional organic syntheses and commercially available starting materials. By way of example and not limitation, Pyrrolopyrimidine Compounds of formula (I) can be prepared as outlined in Schemes 1, 2 and 3, shown below, as well as in the examples set forth herein. It should be noted that one skilled in the art can modify the procedures set forth in the illustrative schemes and examples to arrive at the desired product.

Scheme 1

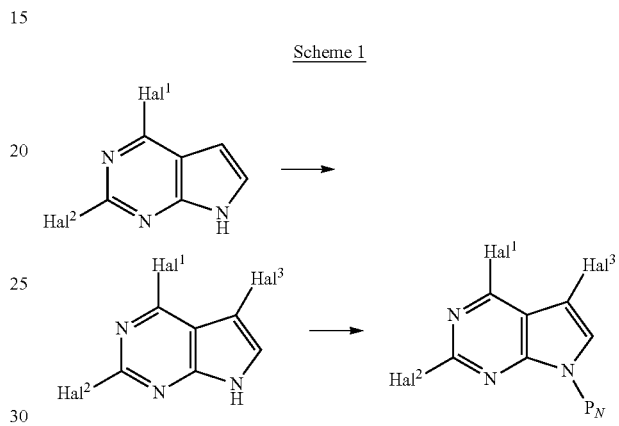

Appropriately derivatized pyrrolopyrimidine starting materials, wherein $Hal^1$, $Hal^2$ and $Hal^3$ are each halogen (for example $Hal^1$ is —Cl, $Hal^2$ is —Cl, and $Hal^3$ is —I or —Br), and $P_N$ is a protecting group (for example SEM, Boc, Trityl, Tosyl, Benzyl, 4-methoxybenzyl, 2,4-dimethoxybenzyl, or THP), can be prepared as shown in Scheme 1. $Hal^3$ (either I or Br) was introduced by treatment of the dihalogenated pyrrolo[2,3-d]pyrimidine with N-halosuccinimide (i.e. iodo- or bromosuccinimide, respectively) in a solvent, such as, for example, DCM. Subsequently, the pyrrole nitrogen group can optionally be protected with a protecting group $P_N$, such as, for example, SEM (for example by treatment with SEM-chloride in the presence of a base such as sodium hydride in a solvent such as DMF or THF), Boc (for example by treatment with Boc-anhydride in the presence of a base such as sodium hydride, TEA, or DIEA in a solvent such as DCM, acetonitrile, THF, NMP, or DMF, optionally in the presence of DMAP), Trityl (for example by treatment with trityl chloride in the presence of a base such as sodium hydride, TEA, or DIEA in a solvent such as DCM, THF, NMP, or DMF), Tosyl (for example by treatment with tosyl chloride in the presence of a base such as sodium hydride, TEA, or DIEA in a solvent such as DCM, THF, NMP, or DMF), Benzyl (for example by treatment with benzyl bromide in the presence of a base such as sodium hydride, TEA, or DIEA in a solvent such as DCM, THF or DMF), 4-Methoxybenzyl (for example by treatment with 4-methoxybenzyl bromide in the presence of a base such as sodium hydride, TEA, or DIEA in a solvent such as DCM, THF or DMF), 2,4-Dimethoxybenzyl (for example by treatment with 4-methoxybenzyl bromide in the presence of a base such as sodium hydride, TEA, or DIEA in a solvent such as DCM, THF or DMF), or THP (for example by treatment with 3,4-dihydro-2H-pyran in the presence of a catalytic amount of methane sulfonic acid or p-toluene sulfonic acid in a solvent such as DCM, THF, or 1,4-dioxane).

Scheme 2

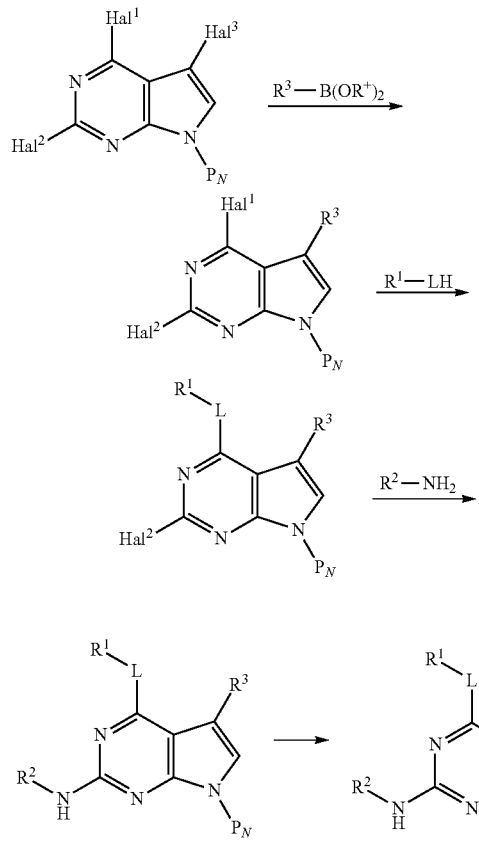

As shown in Scheme 2, compounds of formula (I), wherein L, $R^1$, $R^2$ and $R^3$ are as defined herein, can be prepared starting from the derivatized, optionally protected (that is, the protecting group $P_N$ as defined above can be present or absent, wherein when $P_N$ is absent, it is replaced by hydrogen), pyrrolo[2,3-d]pyrimidine, prepared above, by treatment with the appropriate boronic acid or borate ester $R^3$—$B(OR^+)_2$ (wherein $R^+$ is —H, lower alkyl, or together with the boron atom and the atoms to which they are attached, form a cyclic boronate), in the presence of a palladium catalyst (such as, for example, tetrakis(triphenylphosphine) palladium(0) or dichloro[1,1'-bis(diphenylphosphino)ferrocene]palladium(II) dichloromethane), in a solvent (such as 1,4-dioxane/water) and a base (such as sodium carbonate, potassium carbonate, or potassium phosphate), at elevated temperature (for example, 60° C.-100° C.). Typical reaction conditions and reagents can be found herein. The resulting compound is treated with $R^1$-LH, in a solvent (for example 1,4-dioxane or DMSO), in the presence of a base (for example, sodium tert-butoxide, sodium hydride, or potassium carbonate), optionally at elevated temperature (for example, 20° C.-90° C. The $R^2$ substituent is then introduced by treatment with the amine $R^2NH_2$, in the presence of a palladium catalyst (for example, tris(dibenzylideneacetone)dipalladium(0) or palladium(II)acetate), a ligand (for example, 4,5-bis(diphenylphosphino)-9,9-dimethylxanthene, or [1,1'-binaphthalene]-2,2'-diylbis[diphenyl]-rac-2,2'-bis(diphenylphosphino)-1,1'-binaphthyl phosphine), a base (for example, cesium carbonate, sodium tert-butoxide, potassium tert-butoxide or sodium carbonate), at elevated temperature (for example, 100° C.-150° C.).

When $P_N$ is present, deprotection affords compounds of formula (I). For example, when $P_N$ is Boc, deprotection is achieved by, for example, treatment with an acid such TFA or HCl, in a solvent such as DCM or THF; when $P_N$ is SEM, deprotection is achieved by, for example, treatment with TFA in DCM to give the hemiaminal, then treatment with aqueous ammonium hydroxide, in a solvent, for example methanol, ethanol, or 1,4-dioxane, or treatment with tetrabutylammonium fluoride, in a solvent, for example, methanol or 1,4-dioxane; when $P_N$ is trityl, deprotection is achieved by, for example, treatment with an acid such TFA or HCl, in a solvent such as DCM or THF; when $P_N$ is tosyl, deprotection is achieved by, for example, treatment with a base such as sodium hydroxide or potassium hydroxide, in a solvent such as water or methanol; when $P_N$ is benzyl, deprotection is achieved by, for example, treatment with palladium on carbon (10%) in the presence of a hydrogen atmosphere, in a solvent such as methanol, ethanol or ethyl acetate; when $P_N$ is 4-methoxybenzyl, deprotection is achieved by, for example, treatment with an acid such TFA, neat or in a solvent such as DCM or THF; when $P_N$ is 2,4-dimethoxybenzyl, deprotection is achieved by, for example, treatment with an acid such TFA, neat or in a solvent such as DCM or THF; or when $P_N$ is THP, deprotection is achieved by, for example, treatment with an acid such TFA or HCl, in a solvent such as DCM, THF, or 1,4-dioxane.

Alternatively, the order of side-chain introduction can be changed, with incorporation of $R^1$-L first, followed by introduction of $R^3$ and $R^2$, and finally deprotection, using the methods described above, to afford compounds of formula (I).

Scheme 3

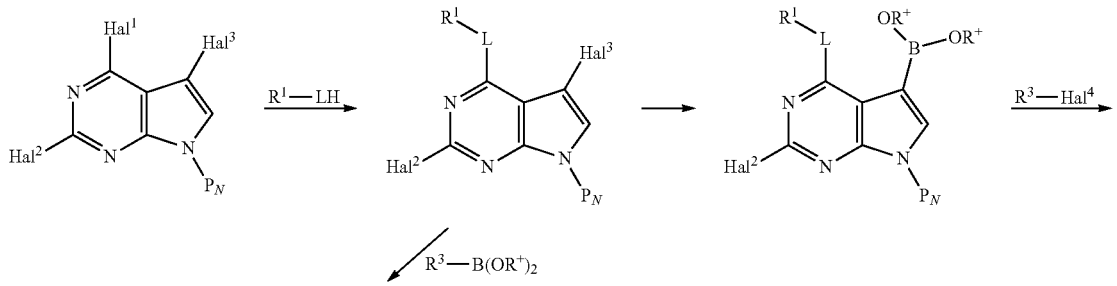

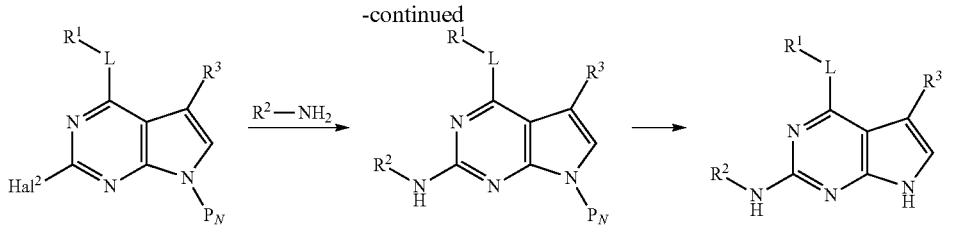

A third approach is shown in Scheme 3. The derivatized, optionally protected (that is, the protecting group $P_N$ as defined above can be present or absent, wherein when $P_N$ is absent, it is replaced by hydrogen), pyrrolo[2,3-d]pyrimidine is, as before, treated with $R^1$-LH, to introduce the L-$R^1$ substituent. Subsequently, treatment with a strong base (for example, n-butyl lithium) and a borate (for example, $B(OR^+)_3$, wherein $R^+$ is a lower alkyl such as methyl), forms the pyrrolo[2,3-d]pyrimidine boronate derivative, wherein $R^+$ is —H. Alternatively, the pyrrolo[2,3-d]pyrimidine boronic ester can be formed by treatment with a boronate (for example, $[B(OR^+)_2]_2$, wherein $R^+$ together with the boron atom and the atoms to which they are attached, forms a cyclic boronate, for example, 4,4,4',4',5,5,5',5'-octamethyl-2,2'-bi(1,3,2-dioxaborolane) in the presence of a palladium catalyst (for example tetrakis(triphenylphosphine) palladium(0) or dichloro[1,1'-bis(diphenyl-phosphino)ferrocene]palladium(II) dichloromethane) and a base, such as potassium acetate in a solvent, such as 1,4-dioxane or DMF. Introduction of the $R^3$ side-chain is accomplished by treatment with $R^3$-$Hal^4$ (wherein $Hal^4$ is —Br, —I or —Cl) in the presence of a palladium catalyst (such as, for example, tetrakis(triphenylphosphine) palladium(0) or dichloro[1,1'-bis(diphenyl-phosphino)ferrocene]palladium(II) dichloromethane), in a solvent (such as, for example, 1,4-dioxane/water) and a base (such as sodium carbonate, potassium carbonate, or potassium phosphate), at elevated temperature (for example, 60° C.-100° C.). Alternatively, $R^3$ is introduced, as before, by treatment of the $Hal^3$ containing intermediate with the appropriate boronic acid or borate ester, in the presence of a palladium catalyst (such as, for example, tetrakis(triphenylphosphine) palladium(0) or dichloro[1,1'-bis(diphenyl-phosphino)ferrocene]palladium(II) dichloromethane), in a solvent (such as 1,4-dioxane/water) and a base (such as sodium carbonate, potassium carbonate, or potassium phosphate), at elevated temperature (for example, 60° C.-100° C.). Compounds of formula (I) are obtained as before by the methods described above, by treatment with $R^2$—$NH_2$ and optionally deprotection.

In one aspect, provided herein are methods for preparing a compound of formula (I):

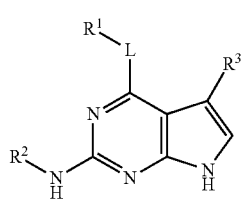

the methods comprising deprotecting a compound of formula (Ia)

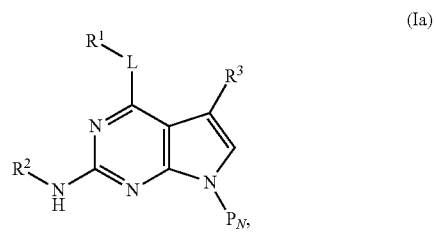

by treatment with
a. when $P_N$ is Boc, an acid;
b. when $P_N$ is SEM, an acid followed by ammonium hydroxide; or tetrabutylammonium fluoride;
c. when $P_N$ is trityl, an acid;
d. when $P_N$ is tosyl, a base;
e. when $P_N$ is benzyl, hydrogen gas in the presence of Pd/C;
f. when $P_N$ is 4-methoxybenzyl, an acid;
g. when $P_N$ is 2,4-dimethoxybenzyl, an acid;
h. when $P_N$ is THP, an acid;
optionally in a solvent, under conditions suitable to provide a compound of formula (I), wherein:
$R^1$ is substituted or unsubstituted $C_{1-8}$ alkyl, substituted or unsubstituted $C_{3-8}$ cycloalkyl, or substituted or unsubstituted non-aromatic heterocyclyl;
$R^2$ is substituted or unsubstituted aryl, or substituted or unsubstituted heteroaryl;
$R^3$ is substituted or unsubstituted heterocyclyl or substituted or unsubstituted aryl, and
L is NH or O.

In one embodiment, when L is NH, $R^3$ is not pyridyl. In another, $R^3$ is not pyridyl when L is NH or when $R^2$ is pyrazolyl. In yet another, the compound is not N-methyl-N-[trans-3-[[5-(1-methyl-1H-pyrazol-4-yl)-2-[(1-methyl-1Hpyrazol-4-yl)amino]-7H-pyrrolo[2,3-d]pyrimidin-4-yl]oxy]cyclobutyl]-2-propenamide; or N-methyl-N-[trans-3-[[5-(1-methyl-1H-pyrazol-3-yl)-2-[(1-methyl-1Hpyrazol-4-yl)amino]-7H-pyrrolo[2,3-d]pyrimidin-4-yl]oxy]cyclobutyl]-2-propenamide.

In one embodiment, when $P_N$ is Boc, the acid is TFA or HCl and the solvent is DCM or THF. In another embodiment, when $P_N$ is SEM, the acid is TFA and the solvent is methanol, ethanol, or 1,4-dioxane. In another embodiment, when $P_N$ is trityl, the acid is TFA or HCl, and the solvent is DCM or THF. In yet another embodiment, when $P_N$ is tosyl, the base is sodium hydroxide or potassium hydroxide, and the solvent is water or methanol. In some embodiments, when $P_N$ is benzyl, the solvent is methanol, ethanol or ethyl acetate. In other embodiments, when $P_N$ is 4-methoxybenzyl, the acid is TFA, and the solvent is DCM or THF. In yet other embodiments, when $P_N$ is 2,4-dimethoxybenzyl, the acid is TFA, and the solvent is DCM or THF. In other embodiments, when $P_N$ is THP, the acid is TFA or HCl, and the solvent is DCM, THF, or 1,4-dioxane.

In some embodiments, the methods further comprise preparing a compound of formula (Ia):

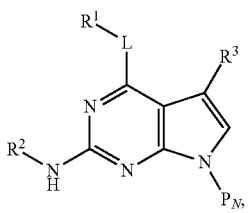

(Ia)

the methods comprising contacting a compound of formula (Ib)

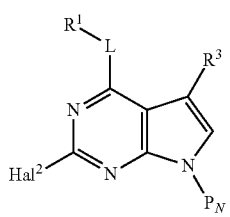

(Ib)

wherein $Hal^2$ is halogen, with an amine $R^2NH_2$, in a solvent, in the presence of a catalyst, a ligand and a base, under conditions suitable to provide a compound of formula (Ia).

In one embodiment, $Hal^2$ is —Cl. In some embodiments, the solvent is 1,4-dioxane. In another embodiment, the catalyst is tris(dibenzylideneacetone)dipalladium(0) or palladium(II)acetate. In some embodiments, the ligand is 4,5-bis(diphenylphosphino)-9,9-dimethylxanthene, or [1,1'-binaphthalene]-2,2'-diylbis[diphenyl]-rac-2,2'-bis(diphenylphosphino)-1,1'-binaphthyl phosphine. In some embodiments, the base is cesium carbonate, sodium tert-butoxide, potassium tert-butoxide or sodium carbonate. In some embodiments, the contacting is performed at elevated temperature, for example, between about 100° C. to about 150° C.

In some embodiments, the methods further comprise preparing a compound of formula (Ib)

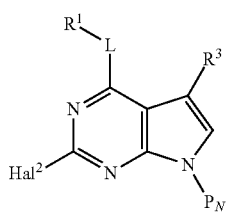

(Ib)

the methods comprising contacting a compound of formula (Ic)

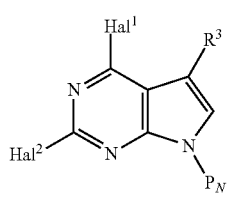

(Ic)

wherein $Hal^1$ is a halogen, with $R^1LH$, in a solvent, in the presence of a base, under conditions suitable to provide a compound of formula (Ib).

In one embodiment, $Hal^1$ is —Cl. In one embodiment, the solvent is 1,4-dioxane or DMSO. In some embodiments, the base is sodium tert-butoxide, sodium hydride, or potassium carbonate. In one embodiment, the contacting is performed at elevated temperature, for example, between about 20° C. and about 90° C.

In some embodiments, the methods further comprise preparing a compound of formula (Ic)

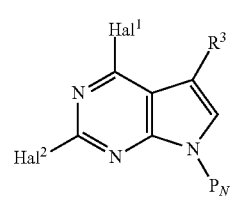

(Ic)

the methods comprising contacting a compound of formula (Id)

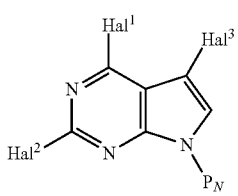

(Id)

wherein $Hal^3$ is a halogen, with a boronic acid or borate ester $R^3$—$B(OR^+)_2$, wherein $R^+$ is —H, lower alkyl, or together with the boron atom and the atoms to which they are attached, form a cyclic boronate, in a solvent, in the presence of a catalyst and a base, under conditions suitable to provide a compound of formula (Ic).

In some embodiments, $Hal^3$ is —I or —Br. In some embodiments of $R^3$—$B(OR^+)_2$, $R^+$ is —H or —$(C(CH_3)_2$—$C(CH_3)_2$—. In one embodiment, the catalyst is tetrakis(triphenylphosphine) palladium(0) or dichloro[1,1'-bis(diphenylphosphino)ferrocene]palladium(II) dichloromethane. In some embodiments, the solvent is 1,4-dioxane/water. In some other embodiments, the base is sodium carbonate, potassium carbonate, or potassium phosphate. In some embodiments, the contacting is performed at elevated temperature, for example, between about 60° C. to about 100° C.

In some other embodiments, the methods further comprise preparing a compound of formula (Ib)

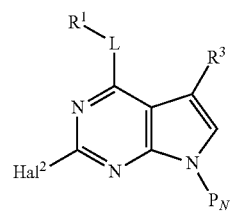

(Ib)

the methods comprising contacting a compound of formula (Ie)

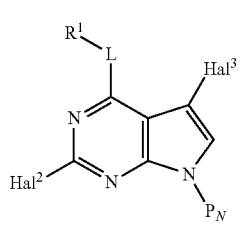

wherein Hal³ is a halogen, with a boronic acid or borate ester R³—B(OR⁺)₂, wherein R⁺ is H, lower alkyl, or together with the boron atom and the atoms to which they are attached, form a cyclic boronate, in a solvent, in the presence of a catalyst and a base, under conditions suitable to provide a compound of formula (Ib).

In some embodiments, Hal³ is —I or —Br. In some embodiments of R³—B(OR⁺)₂, R⁺ is —H or —(C(CH₃)₂—C(CH₃)₂—. In one embodiment, the catalyst is tetrakis(triphenylphosphine) palladium(0) or dichloro[1,1'-bis(diphenylphosphino)ferrocene]palladium(II) dichloromethane. In some embodiments, the solvent is 1,4-dioxane/water. In some other embodiments, the base is sodium carbonate, potassium carbonate, or potassium phosphate. In some embodiments, the contacting is performed at elevated temperature, for example, between about 60° C. to about 100° C.

In some other embodiments, the methods further comprise preparing a compound of formula (Ie)

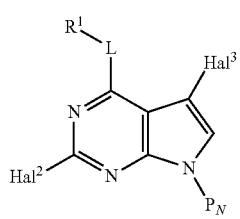

the methods comprising contacting a compound of formula (Id)

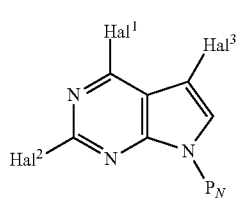

wherein Hal¹ is a halogen, with R¹LH, in a solvent, in the presence of a base, under conditions suitable to provide a compound of formula (Ie).

In one embodiment, Hal¹ is —Cl. In one embodiment, the solvent is 1,4-dioxane or DMSO. In some embodiments, the base is sodium tert-butoxide, sodium hydride, or potassium carbonate. In one embodiment, the contacting is performed at elevated temperature, for example, between about 20° C. and about 90° C.

In some embodiments, the methods further comprise preparing a compound of formula (Id)

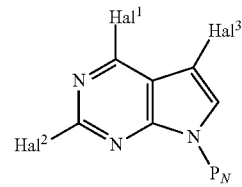

the methods comprising protecting a compound of formula (If)

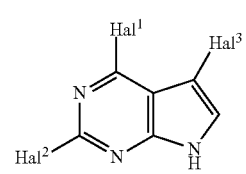

wherein P_N is a protecting group, in a solvent, in the presence of a base, under conditions suitable to provide a compound of formula (Id).

In one embodiment, wherein P_N is Boc, protection is performed by treatment with Boc-anhydride, the base is sodium hydride, TEA, or DIEA and the solvent is DCM, acetonitrile, THF, NMP, or DMF. In another embodiment, wherein P_N is SEM, protection is performed by treatment with SEM-chloride, the base is sodium hydride and the solvent is DMF or THF. In another embodiment, wherein P_N is trityl, protection is performed by treatment with trityl chloride, the base is sodium hydride, TEA, or DIEA and the solvent is DCM, THF, NMP, or DMF. In another embodiment, wherein P_N is tosyl, protection is performed by treatment with tosyl chloride, the base is sodium hydride, TEA, or DIEA and the solvent is DCM, THF, NMP, or DMF. In yet another embodiment, wherein P_N is benzyl, protection is performed by treatment with benzyl bromide, the base is sodium hydride, TEA, or DIEA and the solvent is DCM, THF, or DMF. In some embodiments, wherein P_N is 4-methoxybenzyl, protection is performed by treatment with 4-methoxybenzyl bromide, the base is sodium hydride, TEA, or DIEA and the solvent is DCM, THF, or DMF. In another embodiment, wherein P_N is 2,4-dimethoxybenzyl, protection is performed by treatment with 2,4-dimethoxybenzyl bromide, the base is sodium hydride, TEA, or DIEA and the solvent is DCM, THF, or DMF.

In some embodiments, the methods further comprise preparing a compound of formula (If)

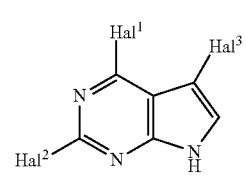

the method comprising contacting a compound of formula (Ig)

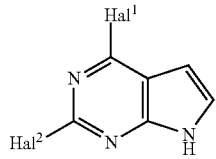

(Ig)

with a N-halosuccinimide, in a solvent, in the presence of a base, under conditions suitable to provide a compound of formula (If).

In some embodiments, the N-halosuccinimide is iodosuccinimide or bromosuccinimide. In other embodiments, the solvent is DCM.

In some embodiments, the methods further comprise preparing a compound of formula (Ib)

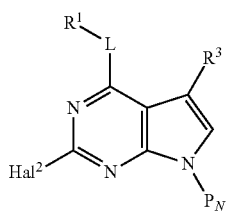

(Ib)

the methods comprising contacting a compound of formula (Ih)

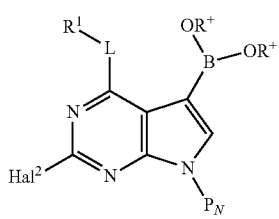

(Ih)

wherein $R^+$ is —H, or together with the boron atom and the atoms to which they are attached, forms a cyclic boronate, with $R^3$-$Hal^4$, in a solvent, in the presence of a palladium catalyst and a base, under conditions suitable to provide a compound of formula (Ib).

In some embodiments, $Hal^4$ is —Br, —I or —Cl. In some embodiments, $R^+$ is —H or —$C(CH_3)_2$—$C(CH_3)_2$—. In one embodiment, the catalyst is tetrakis(triphenylphosphine) palladium(0) or dichloro[1,1'-bis(diphenyl-phosphino)ferrocene]palladium(II) dichloromethane. In some embodiments, the solvent is 1,4-dioxane/water. In some other embodiments, the base is sodium carbonate, potassium carbonate, or potassium phosphate. In some embodiments, the contacting is performed at elevated temperature, for example, between about 60° C. to about 100° C.

In some embodiments, the methods further comprise preparing a compound of formula (Ih)

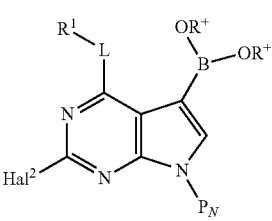

(Ih)

the methods comprising contacting a compound of formula (Ie)

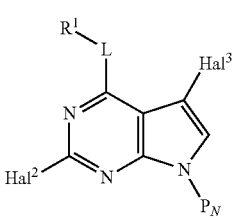

(Ie)

wherein $Hal^3$ is —I or —Br, and $R^+$ is —H, or together with the boron atom and the atoms to which they are attached, forms a cyclic boronate;
  a. with $B(OR^+)_3$, wherein $R^+$ is a lower alkyl, in the presence of a strong base; or
  b. with $[B(OR^+)_2]_2$, wherein $R^+$ together with the boron atom and the atoms to which they are attached, forms a cyclic boronate, in the presence of a palladium catalyst and a base;
in a solvent, under conditions suitable to provide a compound of formula (Ih).

In some embodiments, $Hal^4$ is —Br, —I or —Cl. In some embodiments of formula (Ih), $R^+$ is —H or —$C(CH_3)_2$—$C(CH_3)_2$—. In some embodiments of $B(OR^+)_3$, $R^+$ is methyl. In some such embodiments, the strong base is n-butyl lithium. In some embodiments of $[B(OR^+)_2]_2$, $R^+$ is —$C(CH_3)_2$—$C(CH_3)_2$—. In one embodiment, the catalyst is tetrakis(triphenylphosphine) palladium(0) or dichloro[1,1'-bis(diphenyl-phosphino)ferrocene]palladium(II) dichloromethane. In some embodiments, the solvent is 1,4-dioxane/water or DMF. In some other embodiments, the base is potassium acetate.

It should be noted that one skilled in the art would know how to modify the procedures set forth in the illustrative schemes and examples to arrive at the desired products.

Methods of Use

The Pyrrolopyrimidine Compounds have utility as pharmaceuticals to treat, prevent or improve breast cancer in animals or humans. Accordingly, provided herein are uses of the Pyrrolopyrimidine Compounds, including the treatment or prevention of those breast cancers set forth below. The methods provided herein comprise the administration of an effective amount of one or more Pyrrolopyrimidine Compound(s) to a subject in need thereof.

In another aspect provided herein are methods for treating or preventing breast cancer, comprising administering to a subject in need thereof an effective amount of a Pyrrolopyrimidine Compound, as described herein. In some embodiments, the breast cancer is triple negative breast cancer.

Pharmaceutical Compositions and Routes of Administration

The Pyrrolopyrimidine Compounds can be administered to a subject parenterally in the conventional form of preparations, such as injections, suspensions, solutions and emulsions. Suitable vehicles that can be used to provide intravenous formulations of a Pyrrolopyrimidine Compound are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. An intravenous formulation can be prepared by reconstituting a Pyrrolopyrimidine Compound with such a suitable liquid vehicle. A desired concentration of the intravenous formulation can be obtained by reconstituting an appropriate amount of a Pyrrolopyrimidine Compound with an appropriate volume of liquid vehicle. A desired concentration of the intravenous formulation provides a therapeutically effective amount of a Pyrrolopyrimidine Compound to the patient in need of the intravenous formulation and maintains a therapeutically effective level of a Pyrrolopyrimidine Compound in the patient. The dose which is therapeutically effective will depend on the rate at which the intravenous formulation is delivered to the patient and the concentration of the intravenous formulation.

The effective amount of the Pyrrolopyrimidine Compound in the pharmaceutical composition may be at a level that will exercise the desired effect; for example, about 0.005 mg/kg of a subject's body weight to about 100 mg/kg of a subject's body weight in unit dosage for parenteral administration.

The dose of a Pyrrolopyrimidine Compound to be administered to a subject is rather widely variable and can be subject to the judgment of a health-care practitioner. In general, the Pyrrolopyrimidine Compounds can be administered one to seven times a week, once every two weeks, once every three weeks or once every four weeks in a dose of about 0.005 mg/kg of a subject's body weight to about 10 mg/kg of a subject's body weight in a subject, but the above dosage may be properly varied depending on the age, body weight and medical condition of the subject and the type of administration. In one embodiment, the dose is about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per week. In others, one dose is given two, three or four times per week. In still others, one dose is given per two weeks, per three weeks or per four weeks. In any given case, the amount of the Pyrrolopyrimidine Compound administered will depend on such factors as the solubility of the active component, the formulation used and the route of administration.

In another embodiment, provided herein are methods for the treatment or prevention of a disease or disorder comprising the administration of about 0.375 mg/dose to about 750 mg/dose, about 0.75 mg/dose to about 375 mg/dose, about 3.75 mg/dose to about 75 mg/dose, about 7.5 mg/dose to about 55 mg/dose or about 18 mg/dose to about 37 mg/dose of a Pyrrolopyrimidine Compound to a subject in need thereof.

In another embodiment, provided herein are methods for the treatment or prevention of a disease or disorder comprising the administration of about 1 mg/dose to about 1200 mg/dose, about 10 mg/dose to about 1200 mg/dose, about 100 mg/dose to about 1200 mg/dose, about 400 mg/dose to about 1200 mg/dose, about 600 mg/dose to about 1200 mg/dose, about 400 mg/dose to about 800 mg/dose or about 600 mg/dose to about 800 mg/dose of a Pyrrolopyrimidine Compound to a subject in need thereof. In a particular embodiment, the methods disclosed herein comprise the administration of 400 mg/dose, 600 mg/dose or 800 mg/dose of a Pyrrolopyrimidine Compound to a subject in need thereof.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of a Pyrrolopyrimidine Compound.

In a particular embodiment, provided herein are unit dosage formulations comprising about 100 mg or 400 mg of a Pyrrolopyrimidine Compound.

In another embodiment, provided herein are unit dosage formulations that comprise 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a Pyrrolopyrimidine Compound.

A Pyrrolopyrimidine Compound can be administered once, twice, three, four or more times daily. In a particular embodiment, doses of 600 mg or less are administered as a once daily dose and doses of more than 600 mg are administered twice daily in an amount equal to one half of the total daily dose.

In another embodiment, provided herein are compositions comprising an effective amount of a Pyrrolopyrimidine Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of solutions, parenteral solutions, and suspensions and the like. Compositions can be formulated to contain a single dose, or a convenient fraction of a single dose, in a dosage unit, which may be a single vial or convenient volume of a liquid. In one embodiment, the solutions are prepared from water-soluble salts, such as the hydrochloride salt. In general, all of the compositions are prepared according to known methods in pharmaceutical chemistry.

The effect of the Pyrrolopyrimidine Compound can be delayed or prolonged by proper formulation. The parenteral preparations can be made long-acting, by dissolving or suspending the Pyrrolopyrimidine Compound in oily or emulsified vehicles that allow it to disperse slowly in the serum.

EXAMPLES

The following Examples are presented by way of illustration, not limitation. Compounds are named using the automatic name generating tool provided in Chemdraw Ultra 9.0 (Cambridgesoft), which generates systematic names for chemical structures, with support for the Cahn-Ingold-Prelog rules for stereochemistry. One skilled in the art can modify the procedures set forth in the illustrative examples to arrive at the desired products.

Abbreviations used:

| | |
|---|---|
| Ac | Acetyl |
| Dba | Dibenzylideneacetone |
| DCM | Dichloromethane |
| DEA | Diethylamine |
| DIEA | N,N-Diisopropylethylamine |
| DMA | N,N-Dimethylacetamide |
| DMF | N,N-Dimethylformamide |
| DMSO | Dimethylsulfoxide |
| EDC | Ethyl-(N',N'-dimethylamino)propylcarbodiimide hydrochloride |
| ESI | Electrospray ionization |
| EtOH | Ethanol |
| HATU | O-(7-azabenzotriazol-1-yl)-N,N,N',N'-tetramethyluronium hexafluorophosphate |
| HOBt | 1-Hydroxybenzotriazole |
| HPLC | High performance liquid chromatography |
| HTRF | Homogeneous time resolved fluorescence |
| LCMS | Liquid chromatography mass spectrometry |
| mCPBA | Meta-chloroperoxybenzoic acid |
| MeOH | Methanol |
| MS | Mass spectrometry |
| NMP | N-methylpyrrolidone |
| NMR | Nuclear magnetic resonance |
| Rac-BINAP | [1,1'-binaphthalene]-2,2'-diylbis[diphenyl]-rac-2,2'-Bis(diphenylphosphino)-1,1'-binaphthyl phosphine |
| SEM | 2-(trimethylsilyl)ethoxymethyl |
| SFC | Supercritical fluid chromatography |
| TBTU | O-benzotriazol-1-yl-N,N,N',N'-tetra-methyluronium tetrafluoroborate |
| TEA | Triethylamine |
| TFA | Trifluoroacetic acid |
| THF | Tetrahydrofuran |
| TLC | Thin layer chromatography |
| Xantphos | 4,5-Bis(diphenylphosphino)-9,9-dimethylxanthene |

Compound Synthesis

General Procedure A. Deprotection of SEM Group.

The SEM protected pyrrolo[2,3-d]pyrimidine derivative was treated with a solution of TFA (5-500 equiv) in DCM (1-5 times the volume of TFA) The mixture was stirred for 1-24 h at room temperature. The solvent was removed under reduced pressure and the residue was stirred with aqueous ammonium hydroxide (10-30% solution, 2-100 equiv) in MeOH or 1,4-dioxane (1-5 times the volume of ammonium hydroxide solution) with or without DCM (0.5-2.5 times the volume of MeOH) for 1-24 h at room temperature to 60° C. In cases where the compound contained aqueous acid sensitive functionalities, the residue was treated with an excess of methanolic ammonia (2-7 N) prior to addition of the aqueous ammonium hydroxide. The final product was either collected by filtration or purified using standard techniques.

Example 1

2,4-Dichloro-5-iodo-7-((2-(trimethylsilyl)ethoxy)methyl)-7H-pyrrolo[2,3-d]pyrimidine

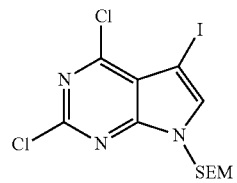 [SMILES: C[Si](C)(C)CCOCn1cc(I)c2c(Cl)nc(Cl)nc21]

2,4-Dichloro-5-iodo-7H-pyrrolo[2,3-d]pyrimidine

A 50-L jacketed reactor was charged with 2,4-dichloro-7H-pyrrolo[2,3-d]pyrimidine (950 g, 5053 mmol) and DCM (16 L). The resulting tan suspension was cooled to 16° C., and N-iodosuccinimide (1598 g, 7104 mmol) was added portionwise over 20 min. The reaction mixture was stirred at room temperature for 16 h, after which time TLC analysis (2:1 hexane/ethyl acetate) indicated complete reaction. The resulting precipitate was filtered, washed with DCM (3×1.5 L), and dried under reduced pressure at 40° C. for 64 h to afford 1447 g (Yield: 91%) of target compound as a beige solid. MS (ESI) m/z 314.0 [M+1]+.

2,4-Dichloro-5-iodo-7-((2-(trimethylsilyl)ethoxy)methyl)-7H-pyrrolo[2,3-d]pyrimidine A 50-L jacketed reactor was flushed with nitrogen and charged with 2,4-dichloro-5-iodo-7H-pyrrolo[2,3-d]pyrimidine (1437 g, 4578 mmol), anhydrous DMF (5.75 L) and SEM-Cl (1145 g, 6867 mmol). The reaction solution was cooled to 0-5° C. and treated with sodium hydride (60% dispersion in mineral oil, 275 g, 6867 mmol) portion wise over 2 h. The mixture was allowed to warm to room temperature over 1 h, after which time TLC analysis indicated complete reaction. The reaction mixture was treated with saturated aqueous NH$_4$Cl (4.5 L), diluted with water (14 L), and stirred at room temperature for 16 h to give a brown precipitate. The precipitate was filtered and washed with water (3×3 L) and hexane (2×3 L) to give 2065 g of a crude brown solid. The crude solid was dissolved in DCM (3 L), and the solution was filtered to remove insoluble material and concentrated to a solid. The solid was triturated twice from MeOH/water (4 L, 5:1) and dried under reduced pressure at 45° C. for 64 h to afford 1100 g (Yield: 54%) of the title compound as a beige solid. $^1$H NMR (500 MHz, DMSO-d$_6$) δ ppm 8.14 (s, 1H), 5.54 (s, 2H), 3.52 (t, J=7.94 Hz, 2H), 0.84 (t, J=7.94 Hz, 2H), −0.08 (s, 9H). MS (ESI) m/z 443.9 [M+1]+.

Example 2

4-(4-(Cyclopentylamino)-5-(4-hydroxyphenyl)-7h-pyrrolo[2,3-d]pyrimidin-2-ylamino)-3-methoxy-n-methylbenzamide

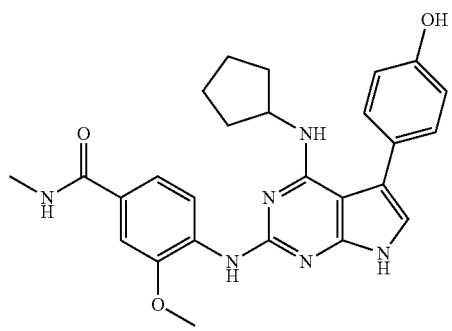 [SMILES: CNC(=O)c1ccc(Nc2nc(NC3CCCC3)c3c(-c4ccc(O)cc4)c[nH]c3n2)c(OC)c1]

2-Chloro-N-cyclopentyl-5-iodo-7-((2-(trimethylsilyl)ethoxy)methyl)-7H-pyrrolo[2,3-d]pyrimidin-4-amine 2,4-Dichloro-5-iodo-7-((2-(trimethylsilyl)ethoxy)methyl)-7H-pyrrolo[2,3-d]pyrimidine (1 equiv), cyclopentanamine (1 equiv), sodium tert-butoxide (7.5 equiv), and 1,4-dioxane (0.28 M) were combined in a sealable vessel with a stir bar. The resulting mixture was put under nitrogen atmosphere, sealed, stirred vigorously, and heated at 70° C. After cooling to room temperature, the reaction mixture was loaded directly onto a silica gel column and purified using flash chromatography (Biotage) (0-20% ethyl acetate in hexane) to give the title compound (94% yield) as a yellow solid. MS (ESI) m/z 493.2 [M+1]$^+$.

4-(2-Chloro-4-(cyclopentylamino)-7-((2-(trimethylsilyl)ethoxy)methyl)-7H-pyrrolo[2,3-d]pyrimidin-5-yl)phenol 2-Chloro-N-cyclopentyl-5-iodo-7-((2-(trimethylsilyl)ethoxy)methyl)-7H-pyrrolo[2,3-d]pyrimidin-4-amine (1 equiv), 4-hydroxyphenylboronic acid (1 equiv), potassium carbonate (2.5 equiv) and tetrakis(triphenylphosphine)palladium(0) (0.2 equiv), suspended in 1,4-dioxane/water, and flushed with nitrogen, were stirred at 100° C. for 16 h. The reaction mixture was loaded directly onto a silica gel column and purified using 5-100% ethyl acetate in hexane. Fractions containing desired product were combined and volatile organics were removed under reduced pressure to give 4-(2-chloro-4-(cyclopentylamino)-7-((2-(trimethylsilyl)ethoxy)methyl)-7H-pyrrolo[2,3-d]pyrimidin-5-yl)phenol (32.2% yield) as a yellow solid. MS (ESI) m/z 459.3 [M+1]$^+$.

4-(4-(Cyclopentylamino)-5-(4-hydroxyphenyl)-7-((2-(trimethylsilyl)ethoxy)methyl)-7H-pyrrolo[2,3-d]pyrimidin-2-ylamino)-3-methoxy-N-methylbenzamide A mixture of 4-(2-chloro-4-(cyclopentylamino)-7-((2-(trimethylsilyl)ethoxy)methyl)-7H-pyrrolo[2,3-d]pyrimidin-5-yl)phenol (1 equiv), 4-amino-3-methoxy-N-methylbenzamide (1 equiv), potassium carbonate (2.5 equiv), (9,9-dimethyl-9H-xanthene-4,5-diyl)bis(diphenylphosphine) (0.2 equiv), and tris(dibenzylideneacetone)-dipalladium (0.2 equiv) in 1,4-dioxane (0.13 M) was purged with nitrogen and sealed. The reaction mixture was heated to 130° C. for 1.5 h. The reaction was filtered and solvents were removed under reduced pressure. The reaction mixture was loaded directly onto a silica gel column and purified using 15-100% ethyl acetate in hexane, followed by 100% ethyl acetate. Fractions containing desired product were combined and volatile organic solvents were removed under reduced pressure to give the title compound (29.2% yield) as a brown oil. MS (ESI) m/z 603.5 [M+1]$^+$.

4-(4-(Cyclopentylamino)-5-(4-hydroxyphenyl)-7H-pyrrolo[2,3-d]pyrimidin-2-ylamino)-3-methoxy-N-methylbenzamide

[4-(4-(Cyclopentylamino)-5-(4-hydroxyphenyl)-7-((2-(trimethylsilyl)ethoxy)methyl)-7H-pyrrolo[2,3-d]pyrimidin-2-ylamino)-3-methoxy-N-methylbenzamide was deprotected according to General Procedure A. The solvent was removed under reduced pressure and the residue was purified to give the desired product (46.4% yield). $^1$H NMR (400 MHz, DMSO-d$_6$) δ ppm 11.34 (d, J=2.34 Hz, 1H) 9.54 (s, 1H) 8.74 (d, J=8.98 Hz, 1H) 8.28 (d, J=4.30 Hz, 1H) 7.45-7.51 (m, 2H) 7.44 (s, 1H) 7.25 (d, J=8.20 Hz, 2H) 6.79-6.93 (m, 3H) 5.14 (d, J=7.03 Hz, 1H) 4.32-4.51 (m, 1H) 3.96 (s, 3H) 2.79 (d, J=4.29 Hz, 3H) 1.95 (br. s., 2H) 1.47-1.67 (m, 4H) 1.37 (d, 2H). MS (ESI) m/z 473.2 [M+1]$^+$.

Example 3

4-((4-(Cyclopentyloxy)-5-(2-methylbenzo[d]oxazol-6-yl)-7H-pyrrolo[2,3-d]pyrimidin-2-yl)amino)-3-methoxy-N-methylbenzamide

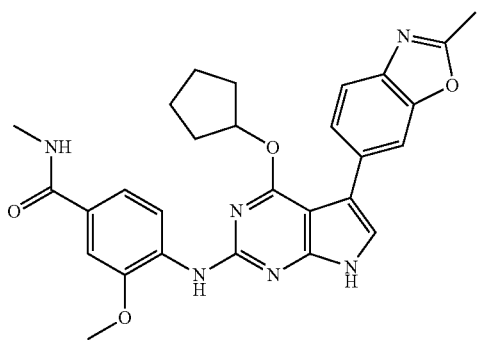 [SMILES: CNC(=O)c1ccc(Nc2nc(OC3CCCC3)c3c(-c4ccc5nc(C)oc5c4)c[nH]c3n2)c(OC)c1]

2-Methyl-6-(4,4,5,5-tetramethyl-1,3,2-dioxaborolan-2-yl)benzo[d]oxazole

A suspension of 6-bromo-2-methylbenzo[d]oxazole (1 equiv), bis(pinacolato)diboron (2 equiv), potassium acetate (3 equiv) in 1,4-dioxane was degassed with argon for 10 min. Then, 1,1'-bis(diphenylphosphino)ferrocene palladium (II) chloride dichloromethane adduct (0.05 equiv) was added and the solution was further degassed with argon for 10 min. The reaction mixture was heated at 110° C. overnight. The reaction mixture was cooled to room temperature, the solvent was removed under reduced pressure and the crude product was purified by column chromatography (silica gel 100-200 mesh 0-10% ethyl acetate in n-hexane as eluent) to give the title compound. (Yield: 34%), MS (ESI) m/z 260 [M+1]$^1$.

4-Amino-3-methoxy-N-methylbenzamide

To a solution of 4-amino-3-methoxybenzoic acid (1 equiv) in N—N-dimethylformamide (0.6 M) was added sodium bicarbonate (9.7 equiv), HATU (2 equiv) and methyl amine hydrochloride (10 equiv). The reaction mixture was stirred at room temperature overnight. The reaction mixture was poured on water and extracted with ethyl acetate. The organic layer was dried over sodium sulfate and concentrated under reduced pressure. The crude product was purified by column chromatography (silica gel 100-200 mesh, 0-10% MeOH in DCM as eluent) to give the title compound. (Yield: 63%). MS (ESI) m/z 181 [M+1]$^1$.

6-(2,4-Dichloro-7-((2-(trimethylsilyl)ethoxy)methyl)-7H-pyrrolo[2,3-d]pyrimidin-5-yl)-2-methylbenzo[d]oxazole 2-Methyl-6-(4,4,5,5-tetramethyl-1,3,2-dioxaborolan-2-yl)benzo[d]oxazole (1 equiv), 2,4-dichloro-5-iodo-7-((2-(trimethylsilyl)ethoxy)methyl)-7H-pyrrolo[2,3-d]pyrimidine (1 equiv), sodium carbonate (3 equiv) and [1,1'-bis(diphenylphosphino)ferrocene]-dichloropalladium(II) complex with dichloromethane (0.04 equiv) were combined in a 5:1 mixture of 1,4-dioxane and water (0.27 M). The mixture was heated to 85° C. for 1.5 h. The crude product was purified on silica gel (0-10% ethyl acetate in petroleum ether) to give an impure brown oil. The product was purified on silica gel (0-20% ethyl acetate in petroleum ether) to give the title compound (58% yield) as a white solid. $^1$H NMR (400 MHz, DMSO-$d_6$) δ ppm 7.70 (d, J=8 Hz, 1H), 7.62 (s, 1H), 7.44 (m, 2H), 5.68 (s, 2H), 3.65 (m, 2H), 2.69 (s, 3H), 0.99 (m, 2H), 0.05 (s, 9H). MS (ESI) m/z 449.0 [M+1]$^+$.

6-(2-Chloro-4-(cyclopentyloxy)-7-((2-(trimethylsilyl)ethoxy)methyl)-7H-pyrrolo[2,3-d]pyrimidin-5-yl)-2-methylbenzo[d]oxazole A solution of 6-(2,4-dichloro-7-((2-(trimethylsilyl)ethoxy)methyl)-7H-pyrrolo[2,3-d]pyrimidin-5-yl)-2-methylbenzo[d]oxazole (1 equiv), cyclopentanol (1.1 equiv), and sodium tert-butoxide (1 equiv) in 1,4-dioxane (0.22 M) was taken in a sealable flask. The reaction mixture was put under a nitrogen atmosphere, the sealable flask was sealed and the mixture was stirred at 70° C. for 3 h. The mixture was cooled to room temperature and concentrated to afford an oil, which was suspended in DCM and loaded onto a silica column (packed with hexane). The column was eluted with 0-30% ethyl acetate in hexane. The fractions containing product were combined and concentrated to dryness to give the target product as a light yellow oil (Yield: 88%) that solidified upon standing. MS (ESI) m/z 499.4 [M+1]$^+$.

4-((4-(Cyclopentyloxy)-5-(2-methylbenzo[d]oxazol-6-yl)-7-((2-(trimethylsilyl)ethoxy)methyl)-7H-pyrrolo[2,3-d]pyrimidin-2-yl)amino)-3-methoxy-N-methylbenzamide A mixture of 6-(2-chloro-4-(cyclopentyloxy)-7-((2-(trimethylsilyl)ethoxy)methyl)-7H-pyrrolo[2,3-d]pyrimidin-5-yl)-2-methylbenzo[d]oxazole (1 equiv), 4-amino-3-methoxy-N-methylbenzamide (1 equiv), and cesium carbonate (3 equiv) in 1,4-dioxane (0.1 M) was degassed with N$_2$ for 10 min. Then Pd(OAc)$_2$ (0.2 equiv), and BINAP (0.4 equiv) were added to this mixture. The mixture was stirred at 110° C. for 6 h. The mixture was cooled to room temperature, filtered and concentrated to a dark residue. The residue was dissolved in DCM and loaded onto a silica column (packed with DCM). The column was eluted with 0-10% MeOH in DCM. The fractions containing product were combined and concentrated to dryness to give the target product as a light yellow solid. The orange solid was dissolved in DCM and loaded onto a silica column (packed with DCM). The column was eluted with 0-5% MeOH in DCM carefully. The fractions containing pure product were combined and concentrated to dryness to give the target compound as a light yellow solid (Yield: 61%). MS (ESI) m/z 643.2 [M+1]$^+$.

4-((4-(Cyclopentyloxy)-5-(2-methylbenzo[d]oxazol-6-yl)-7H-pyrrolo[2,3-d]pyrimidin-2-yl)amino)-3-methoxy-N-methylbenzamide 4-((4-(Cyclopentyloxy)-5-(2-methylbenzo[d]oxazol-6-yl)-7-((2-(trimethylsilyl)ethoxy)methyl)-7H-pyrrolo[2,3-d]pyrimidin-2-yl)amino)-3-methoxy-N-methylbenzamide was deprotected according to General Procedure A. The mixture was then concentrated to dryness and the residue was purified. (Yield: 44%). $^1$H NMR (400 MHz, METHANOL-$d_4$) δ ppm 8.73 (d, J=9.37 Hz, 1H), 7.82-7.86 (m, 1H), 7.57-7.63 (m, 1H), 7.48-7.53 (m, 1H), 7.41-7.47 (m, 2H), 7.13 (d, J=0.78 Hz, 1H), 5.64-5.71 (m, 1H), 3.98 (s, 3H), 2.90 (s, 3H), 2.61 (s, 3H), 1.96 (d, J=6.25 Hz, 2H), 1.83-1.92 (m, 2H), 1.60-1.77 (m, 4H); MS (ESI) m/z 512.9 [M+1]$^+$.

Example 4

4-(4-(Cyclopentyloxy)-5-(4-(methylcarbamoyl)phenyl)-7H-pyrrolo[2,3-d]pyrimidin-2-ylamino)-3-methoxy-N-methylbenzamide

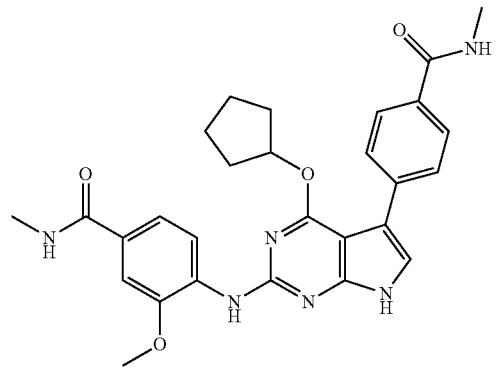

4-(2-Chloro-4-(cyclopentyloxy)-7-((2-(trimethylsilyl)ethoxy)methyl)-7H-pyrrolo[2,3-d]pyrimidin-5-yl)-N-methylbenzamide 2-Chloro-4-(cyclopentyloxy)-5-iodo-7-((2-(trimethylsilyl)ethoxy)methyl)-7H-pyrrolo[2,3-d]pyrimidine (1 equiv) and (4-(methylcarbamoyl)phenyl)boronic acid (1.3 equiv) were combined in 1,4-dioxane (0.3 M). Sodium carbonate (3 equiv), dissolved in water (3.6 M), was added to the reaction mixture, followed by addition of [1,1'-bis(diphenylphosphino)ferrocene]-dichloropalladium(II), complex with dichloromethane (0.1 equiv). Nitrogen gas was bubbled through the reaction mixture for 2 min then reaction was heated at 90° C. for 3 h. The solvent was removed under reduced pressure and the product was purified by silica gel chromatography (Biotage, 0-80% ethyl acetate in hexane over 2.2 L). The fractions containing the desired product were combined and evaporated under reduced pressure to give the title compound (62.5% yield) as an orange solid. MS (ESI) m/z 501.4 [M+1]$^+$.

4-((4-(Cyclopentyloxy)-5-(4-(methylcarbamoyl)phenyl)-7-((2-(trimethylsilyl)ethoxy)methyl)-7H-pyrrolo[2,3-d]pyrimidin-2-yl)amino)-3-methoxy-N-methylbenzamide 4-(2-Chloro-4-(cyclopentyloxy)-7-((2-(trimethylsilyl)ethoxy)-methyl)-7H-pyrrolo[2,3-d]pyrimidin-5-yl)-N-methylbenzamide 1 equiv), 4-amino-3-methoxy-N-methylbenzamide (1.2 equiv), 2,2'-bis(diphenylphosphino)-1,1'-binaphthyl (binap) (0.2 equiv), cesium carbonate (5 equiv) and palladium(II) acetate (0.1 equiv) were combined in a sealed tube along with 1,4-dioxane (0.14 M). Nitrogen gas was bubbled through the reaction mixture for 2 min, the reaction vessel was sealed and heated in an oil bath at 110° C. for 4 h. The solvent was removed under reduced pressure and the crude material was stirred in DCM. The solids were filtered off and the filtrate was loaded directly onto a silica gel column. The product was purified by silica gel chromatography (Biotage, 20-100% ethyl acetate in hexane over 400 mL, 100% ethyl acetate for 200 mL, 0-10% MeOH in ethyl acetate over 600 mL then held at 10% MeOH in ethyl acetate for 500 mL). The fractions containing the desired product were combined and evaporated under reduced pressure to give the title compound (67.1% yield) as a tan solid. MS (ESI) m/z 645.6 [M+1]$^+$.

4-((4-(Cyclopentyloxy)-5-(4-(methylcarbamoyl) phenyl)-7H-pyrrolo[2,3-d]pyrimidin-2-yl)amino)-3-methoxy-N-methylbenzamide 4-((4-(Cyclopentyloxy)-5-(4-(methylcarbamoyl)phenyl)-7-((2-(trimethylsilyl)ethoxy)methyl)-7H-pyrrolo[2,3-d]pyrimidin-2-yl)amino)-3-methoxy-N-methylbenzamide was deprotected according to General Procedure A. The solvent was evaporated under reduced pressure and the residue was purified to give the title compound (56.3% yield). $^1$H NMR (400 MHz, DMSO-d$_6$) δ ppm 1.60-1.78 (m, 4H) 1.78-1.90 (m, 2H) 1.93-2.07 (m, 2H) 2.74-2.85 (m, 6H) 3.97 (s, 3H) 5.64-5.75 (m, 1H) 7.46 (d, J=2.34 Hz, 1H) 7.49-7.55 (m, 2H) 7.74 (s, 1H) 7.76-7.88 (m, 4H) 8.29-8.35 (m, 1H) 8.43 (q, J=4.43 Hz, 1H) 8.63 (d, J=8.98 Hz, 1H) 11.91 (d, J=1.95 Hz, 1H); MS (ESI) m/z 515.0 [M+1]$^+$.

Example 5

3-Chloro-4-(4-methoxy-5-(2-methyl-1H-benzo[d]imidazol-5-yl)-7H-pyrrolo[2,3-d]pyrimidin-2-ylamino)-N,N-dimethylbenzamide

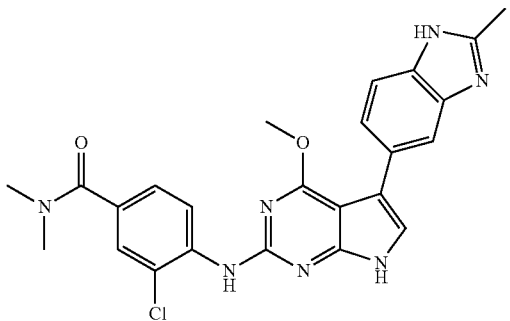

tert-Butyl 4-(4,4,5,5-tetramethyl-1,3,2-dioxaborolan-2-yl)-1,2-phenylenedicarbamate To a degassed mixture of tert-butyl 4-(4,4,5,5-tetramethyl-1,3,2-dioxaborolan-2-yl)-1,2-phenylenedicarbamate (1 equiv), 4,4,4',4',5,5,5',5'-octamethyl-2,2'-bi(1,3,2-dioxaborolane) (1.5 equiv) and potassium acetate (3 equiv) in 1,4-dioxane (0.13 M) was added [1,1'-bis(diphenylphosphino)ferrocene]palladium(II) chloride (0.1 equiv). The mixture was heated under reflux for 3 h. Filtration and concentration gave the crude product, which was purified by silica gel column chromatography (10% ethyl acetate in petroleum ether) to afford the title compound (82% yield). MS (ESI) m/z 435.2 [M+1]$^+$.

tert-Butyl 4-(2-chloro-4-methoxy-7-((2-(trimethylsilyl)ethoxy)methyl)-7H-pyrrolo[2,3-d]pyrimidin-5-yl)-1,2-phenylenedicarbamate To a degassed mixture of tert-butyl 4-(4,4,5,5-tetramethyl-1,3,2-dioxaborolan-2-yl)-1,2-phenylenedicarbamate (1 equiv), 2-chloro-5-iodo-4-methoxy-7-(2-trimethylsilanyl-ethoxymethyl)-7H-pyrrolo[2,3-d]pyrimidine (1.2 equiv) and tripotassium phosphate trihydrate (3 equiv) in 1,4-dioxane and water (10:1, 0.034 M) was added tetrakis (triphenylphosphine)palladium (0.2 equiv). The mixture was heated under reflux for 3 h. Filtration and concentration gave the crude product, which was purified by silica gel column chromatography (10% ethyl acetate in petroleum ether) to afford the title compound (59% yield). MS (ESI) m/z 620.2 [M+1]$^+$.

4-Amino-3-chloro-N,N-dimethylbenzamide

To a solution of 4-amino-3-chlorobenzoic acid (1 equiv) in DCM (0.12 M) was added N-(3-dimethylaminopropyl)-N'-ethylcarbodiimide hydrochloride (1.2 equiv), 1-hydroxybenzotriazole (1.2 equiv), triethylamine (4 equiv) and dimethylamine hydrochloride (2 equiv) sequentially. The mixture was stirred at room temperature overnight. After the reaction was complete, as monitored by LCMS, the mixture was diluted with a mixture of isopropanol in chloroform (30%), washed with water and dried over anhydrous sodium sulfate. The organic phase was concentrated and the residue obtained was recrystallized in the mixture of hexane and ethyl acetate (10%) to afford the desired product (Yield: 59.6%) as a light brown solid. MS (ESI) m/z 199.1 [M+1]$^+$.

tert-Butyl 4-(2-(2-chloro-4-(dimethylcarbamoyl) phenylamino)-4-methoxy-7-((2-(trimethylsilyl) ethoxy)methyl)-7H-pyrrolo[2,3-d]pyrimidin-5-yl)-1,2-phenylenedicarbamate To a degassed mixture of tert-butyl 4-(2-chloro-4-methoxy-7-((2-(trimethylsilyl)ethoxy)methyl)-7H-pyrrolo[2,3-d]pyrimidin-5-yl)-1,2-phenylenedicarbamate (1 equiv), 4-amino-3-chloro-N,N-dimethylbenzamide (1.3 equiv) and cesium carbonate (3 equiv) in 1,4-dioxane (0.06 M) was added palladium (II) trifluoroacetate (0.3 equiv) and 4,5-bis (diphenyl phosphino)-9,9-dimethylxanthene (0.6 equiv). The resulting reaction mixture was refluxed at 90° C. overnight. The reaction mixture was filtered and concentrated; the crude product was purified by silica gel column chromatography (10% ethyl acetate in petroleum ether) to afford the title compound (33% yield). MS (ESI) m/z 782.4 [M+1]$^+$.

3-Chloro-4-(5-(3,4-diaminophenyl)-4-methoxy-7-((2-(trimethylsilyl)ethoxy)methyl)-7H-pyrrolo[2,3-d]pyrimidin-2-ylamino)-N,N-dimethylbenzamide tert-Butyl 4-(2-(2-chloro-4-(dimethylcarbamoyl)phenylamino)-4-methoxy-7-((2-(trimethylsilyl)ethoxy)methyl)-7H-pyrrolo[2,3-d]pyrimidin-5-yl)-1,2-phenylenedicarbamate (1 equiv) was dissolved in methanolic hydrochloric acid (1N, 7.8 equiv) and stirred at 0° C. overnight. After the reaction was complete, the mixture was basified at 0° C. with aqueous ammonia to pH=7-8 and the aqueous layer was extracted with DCM. The combined organic layers were washed with brine, dried over anhydrous sodium sulfate and filtered. Concentration under reduced pressure gave the crude product, which was purified by silica gel column chromatography (10% ethyl acetate in petroleum ether) to afford the title compound (78% yield). MS (ESI) m/z 582.3 [M+1]$^+$.

3-Chloro-4-(4-methoxy-5-(2-methyl-1H-benzo[d]imidazol-5-yl)-7-((2-(trimethylsilyl)ethoxy)methyl)-7H-pyrrolo[2,3-d]pyrimidin-2-ylamino)-N,N-dimethylbenzamide 3-Chloro-4-(5-(3,4-diaminophenyl)-4-methoxy-7-((2-(trimethylsilyl)ethoxy)methyl)-7H-pyrrolo[2,3-d]pyrimidin-2-ylamino)-N,N-dimethylbenzamide (1 equiv) was dissolved in acetic acid (40 equiv) and stirred at 115° C. for 3 h. After the reaction was complete, the solvent was removed under high vacuum. The residue was purified by silica gel column chromatography (10% ethyl acetate in petroleum ether) to afford the title compound (73% yield). MS (ESI) m/z 606.2[M+1]+.

3-Chloro-4-(4-methoxy-5-(2-methyl-1H-benzo[d]imidazol-5-yl)-7H-pyrrolo[2,3-d]pyrimidin-2-ylamino)-N,N-dimethylbenzamide 3-Chloro-4-(4-methoxy-5-(2-methyl-1H-benzo[d]imidazol-5-yl)-7-((2-(trimethylsilyl)ethoxy)methyl)-7H-pyrrolo[2,3-d]pyrimidin-2-ylamino)-N,N-dimethylbenzamide was deprotected according to General Procedure A. Concentration and purification gave the desired product (46% yield); $^1$H NMR (400 MHz, METHANOL-$d_4$) δ ppm 8.86 (d, J=8.8 Hz, 1H), 7.79 (s, 1H), 7.55-7.43 (m, 4H), 7.13 (s, 1H), 4.08 (s, 3H), 3.09 (s, 6H), 2.59 (s, 3H); MS (ESI) m/z 476.1 [M+1]+

Example 6

N,N,3-Trimethyl-4-((5-(pyridin-4-yl)-4-((tetrahydro-2H-pyran-4-yl)amino)-7H-pyrrolo[2,3-d]pyrimidin-2-yl)amino)benzamide

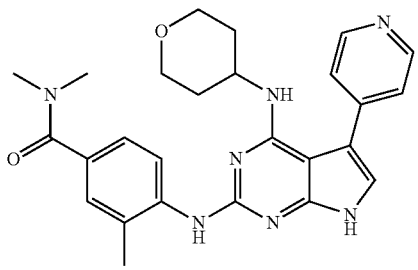 [SMILES: Cc1cc(C(=O)N(C)C)ccc1Nc1nc(NC2CCOCC2)c2c(-c3ccncc3)c[nH]c2n1]

2,4-Dichloro-5-(pyridin-4-yl)-7-((2-(trimethylsilyl)ethoxy)methyl)-7H-pyrrolo[2,3-d]pyrimidine To a degassed mixture of 2,4-dichloro-5-iodo-7-((2-(trimethylsilyl)ethoxy)methyl)-7H-pyrrolo[2,3-d]pyrimidine (1 equiv), pyridin-4-ylboronic acid (1.1 equiv) and tripotassium phosphate trihydrate (3 equiv) in a 9:1 mixture of 1,4-dioxane and water (0.33 M) was added palladium 1,1-bis(diphenylphosphino)-ferrocene dichloride (0.2 equiv). The reaction mixture was stirred at 100° C. for 2 h. After the reaction was complete, the reaction mixture was cooled to room temperature and concentrated. The residue was purified by silica gel chromatography (0-30% ethyl acetate in petroleum ether) to afford the desired product (40% yield) as a red solid. MS (ESI) m/z 395.1 [M+1]+.

2-Chloro-5-(pyridin-4-yl)-N-(tetrahydro-2H-pyran-4-yl)-7-((2-(trimethylsilyl)ethoxy)methyl)-7H-pyrrolo[2,3-d]pyrimidin-4-amine To a solution of 2,4-dichloro-5-(pyridin-4-yl)-7-((2-(trimethylsilyl)ethoxy)methyl)-7H-pyrrolo[2,3-d]pyrimidine (1 equiv) in 1,4-dioxane (0.4 M) in a sealable vessel was added tetrahydro-2H-pyran-4-amine hydrochloride (1.5 equiv) and triethylamine (3 equiv). The resulting mixture was heated at 120° C. for 2 h under nitrogen atmosphere. After the reaction was complete, the reaction mixture was cooled to room temperature and concentrated. The residue was purified by silica gel chromatography (0-30% ethyl acetate in petroleum ether) to afford the desired product (34% yield) as a yellow solid. MS (ESI) m/z 460.2 [M+1]+.

N,N,3-Trimethyl-4-((5-(pyridin-4-yl)-4-((tetrahydro-2H-pyran-4-yl)amino)-7-((2-(trimethylsilyl)ethoxy)methyl)-7H-pyrrolo[2,3-d]pyrimidin-2-yl)amino)benzamide To a degassed mixture of 2-chloro-5-(pyridin-4-yl)-N-(tetrahydro-2H-pyran-4-yl)-7-((2-(trimethylsilyl)ethoxy)methyl)-7H-pyrrolo[2,3-d]pyrimidin-4-amine (1 equiv), 4-amino-N,N,3-trimethylbenzamide (1.2 equiv) and cesium carbonate (3 equiv) in 1,4-dioxane (0.2 M) was added palladium acetate (0.3 equiv) and 2,2'-bis-diphenylphosphanyl-[1,1']binaphthalenyl (0.6 equiv). The reaction was stirred at 110° C. for 2 hours. After the reaction was complete, the reaction mixture was cooled to room temperature and concentrated. The residue was purified by silica gel chromatography (0-2% DCM in MeOH) to afford the desired product (35% yield) as a yellow solid. MS (ESI) m/z 602.3 [M+1]+.

N,N,3-Trimethyl-4-((5-(pyridin-4-yl)-4-((tetrahydro-2H-pyran-4-yl)amino)-7H-pyrrolo[2,3-d]pyrimidin-2-yl)amino)benzamide N,N,3-Trimethyl-4-(5-(pyridin-4-yl)-4-((tetrahydro-2H-pyran-4-yl)amino)-7-((2-(trimethylsilyl)ethoxy)methyl)-7H-pyrrolo[2,3-d]pyrimidin-2-yl)amino)benzamide was deprotected according to general procedure A. The resulting mixture was concentrated and the residue was purified to afford the title compound (40% yield). $^1$H NMR (400 MHz, CHLOROFORM-$d_1$) δ ppm 9.28 (s, 1H), 8.67 (d, J=5.6 Hz, 2H), 8.33 (d, J=8.4 Hz, 1H), 7.39 (d, J=5.6 Hz, 2H), 7.32-7.28 (m, 2H), 6.76 (s, 1H), 6.68 (s, 1H), 4.85 (d, J=7.2 Hz, 1H), 4.40-4.30 (m, 1H), 3.97-3.92 (m, 2H), 3.58-3.52 (m, 2H), 3.06 (s, 6H), 2.38 (s, 3H), 2.07-2.02 (m, 2H), 1.51-1.42 (m, 2H); MS (ESI) m/z 472.2 [M+1]+.

Example 7

4-((4-(Cyclopentyloxy)-5-(2-methylbenzo[d]oxazol-6-yl)-7H-pyrrolo[2,3-d]pyrimidin-2-yl)amino)-N-(2-hydroxyethyl)-3-methoxybenzamide

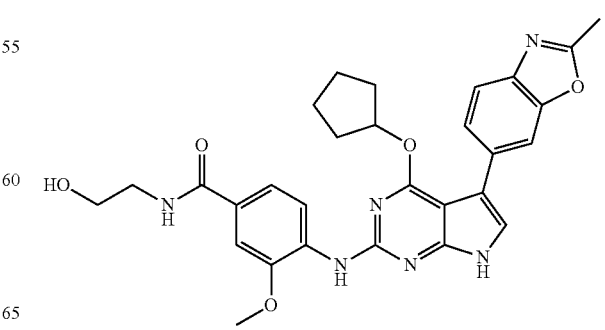

2-Chloro-4-(cyclopentyloxy)-5-iodo-7-((2-(trimethylsilyl)ethoxy)methyl)-7H-pyrrolo[2,3-d]pyrimidine To a solution of cyclopentanol (1 equiv) in anhydrous THF (0.22 M) was added sodium hydride (60% in mineral oil, 1.3 equiv) at 0° C. under nitrogen. After the resulting reaction mixture was stirred at room temperature for 30 min, 2,4-dichloro-5-iodo-7-((2-(trimethylsilyl)ethoxy)methyl)-7H-pyrrolo[2,3-d]pyrimidine (0.67 equiv) was added. The reaction was stirred at room temperature for 4 h and quenched with saturated aqueous ammonium chloride solution. The aqueous layer was extracted with ethyl acetate. The combined organic layers were washed with brine, dried over anhydrous sodium sulfate and filtered. Concentration under vacuum gave the crude product, which was purified by silica gel column chromatography (5% ethyl acetate in petroleum ether) to afford the title compound (46% yield). MS (ESI) m/z 493.2. [M+1]$^+$.

6-(2-Chloro-4-(cyclopentyloxy)-7-((2-(trimethylsilyl)ethoxy)methyl)-7H-pyrrolo[2,3-d]pyrimidin-5-yl)-2-methylbenzo[d]oxazole To a mixture of 2-chloro-4-(cyclopentyloxy)-5-iodo-7-((2-(trimethylsilyl)ethoxy)methyl)-7H-pyrrolo[2,3-d]pyrimidine (1 equiv), 2-methyl-6-(4,4,5,5-tetramethyl-[1,3,2]dioxaborolan-2-yl)-benzooxazole (1 equiv), tripotassium phosphate trihydrorate (3 equiv) in 1,4-dioxane and water (8:1, 0.5 M) was added 1,1-bis(diphenylphosphion)ferrocene palladium dichloride (0.1 equiv). The mixture was refluxed at 90° C. for 2 h. Filtration and concentration gave the crude product, which was purified by silica gel column chromatography (20% ethyl acetate in petroleum ether) to afford the title compound (42% yield). MS (ESI) m/z 498.2 [M+1]$^+$.

4-Amino-N-(2-hydroxyethyl)-3-methoxybenzamide

To a solution of 4-amino-3-methoxybenzoic acid (1 equiv) in anhydrous DCM (0.6 M) was added triethylamine (4 equiv), N-(3-dimethylaminopropyl)-N'-ethylcarbodiimide hydrochloride (1.2 equiv) and 2-aminoethanol (2 equiv) portionwise. The mixture was stirred at room temperature overnight. After the reaction was complete, as monitored by LCMS, the mixture was diluted with a mixture of isopropanol in chloroform (30%), washed with water and dried over anhydrous sodium sulfate. The organic phase was concentrated and purified by silica column to give the title compound as a white solid (17% yield). $^1$H NMR (400 MHz, DMSO-d$_6$) δ ppm 8.05-8.02 (t, J=5.6 Hz, 1H), 7.32-7.27 (m, 1H), 6.60 (d, J=8.0 Hz, 1H), 5.21 (brs, 2H), 4.69 (t, J=5.6 Hz, 1H), 3.80 (s, 3H), 3.50-3.46 (m, 2H), 2.34-3.27 (m, 2H). MS (ESI) m/z 211.1 [M+1]$^+$.

4-((4-(Cyclopentyloxy)-5-(2-methylbenzo[d]oxazol-6-yl)-7-((2-(trimethylsilyl)ethoxy)methyl)-7H-pyrrolo[2,3-d]pyrimidin-2-yl)amino)-N-(2-hydroxyethyl)-3-methoxybenzamide To a degassed mixture of 6-(2-chloro-4-(cyclopentyloxy)-7-((2-(trimethylsilyl)ethoxy)methyl)-7H-pyrrolo[2,3-d]pyrimidin-5-yl)-2-methylbenzo[d]oxazole (1 equiv), 4-amino-N-(2-hydroxyethyl)-3-methoxybenzamide (1.2 equiv) and cesium carbonate (5 equiv) in 1,4-dioxane (0.14 M) was added palladium acetate (0.1 equiv) and 2,2'-bis-diphenylphosphanyl-[1,1']binaphthalenyl (0.2 equiv). The mixture was stirred at 120° C. overnight. The reaction was cooled to room temperature and filtered. The filtrate was concentrated and the residue obtained was purified by preparative thin layer chromatography (8% MeOH in DCM) to afford the title compound (30% yield). MS (ESI) m/z 673.1 [M+1]$^+$.

4-((4-(Cyclopentyloxy)-5-(2-methylbenzo[d]oxazol-6-yl)-7H-pyrrolo[2,3-d]pyrimidin-2-yl)amino)-N-(2-hydroxyethyl)-3-methoxybenzamide 4-((4-(Cyclopentyloxy)-5-(2-methylbenzo[d]oxazol-6-yl)-7-((2-(trimethylsilyl)ethoxy)methyl)-7H-pyrrolo[2,3-d]pyrimidin-2-yl)amino)-N-(2-hydroxyethyl)-3-methoxybenzamide was deprotected according to General Procedure A. The resulting mixture was concentrated and purified to afford the title compound (38% yield); $^1$H NMR (400 MHz, METHANOL-d$_4$) δ ppm 8.76-8.74 (m, 1H), 7.855 (s, 1H), 7.63-7.61 (m, 1H), 7.53-7.49 (m, 3H), 7.15 (s, 1H), 7.05 (s, 1H), 5.57-5.69 (brs, 1H), 4.01 (s, 3H), 3.75-3.73 (m, 2H), 3.53-3.51 (m, 2H), 2.64 (s, 3H), 2.01-1.87 (m, 4H), 1.77-1.65 (m, 4H); MS (ESI) m/z 543.2 [M+1]$^+$.

Example 8

N,N,3-Trimethyl-4-((5-(1-methyl-1H-pyrazol-4-yl)-4-((tetrahydro-2H-pyran-4-yl)oxy)-7H-pyrrolo[2,3-d]pyrimidin-2-yl)amino)benzamide

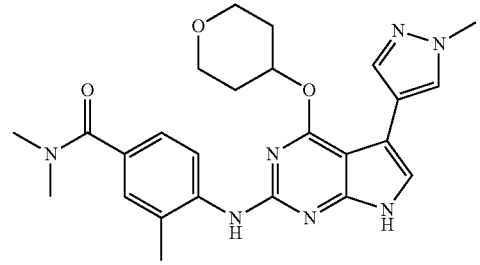

2-Chloro-5-iodo-4-((tetrahydro-2H-pyran-4-yl)oxy)-7-((2-(trimethylsilyl)ethoxy)methyl)-7H-pyrrolo[2,3-d]pyrimidine 2,4-Dichloro-5-iodo-7-((2-(trimethylsilyl)ethoxy)methyl)-7H-pyrrolo[2,3-d]pyrimidine (1 equiv), tetrahydro-2H-pyran-4-ol (1.05 equiv), sodium tert-butoxide (1.05 equiv) and 1,4-dioxane (0.56 M) were combined and heated at 70° C. for 5 h. The reaction mixture was concentrated and extracted with ethyl acetate/H$_2$O. The organic layers were combined, evaporated under reduced pressure and purified by silica-gel chromatography (0-50% hexane:ethyl acetate over 800 mL) followed by 5-15% (DCM:MeOH over 800 mL). Pure fractions were combined, evaporated under reduced pressure and dried under high vacuum to give the title compound (86% yield) as a yellow oil. $^1$H NMR (400 MHz, METHANOL-d$_4$) δ ppm 7.57 (s, 1H), 5.62-5.70 (m, 1H), 5.59 (s, 2H), 4.11-4.19 (m, 2H), 3.74-3.82 (m, 2H), 3.62 (d, J=8.20 Hz, 2H), 2.15-2.24 (m, 2H), 1.91-2.01 (m, 2H), 0.90-0.98 (m, 2H), 0.00 (s, 9H); MS (ESI) m/z 510.2 [M+1]$^+$.

2-Chloro-5-(1-methyl-1H-pyrazol-4-yl)-4-((tetrahydro-2H-pyran-4-yl)oxy)-7-((2-(trimethylsilyl)ethoxy)methyl)-7H-pyrrolo[2,3-d]pyrimidine To a degassed mixture of 2-chloro-5-iodo-4-((tetrahydro-2H-pyran-4-yl)oxy)-7-((2-(trimethylsilyl)ethoxy)methyl)-

7H-pyrrolo[2,3-d]pyrimidine (1 equiv), 1-methyl-4-(4,4,5,5-tetramethyl-1,3,2-dioxaborolan-2-yl)-1H-pyrazole (1.1 equiv) and potassium phosphate tribasic trihydrate (3 equiv) in a 10:1 mixture of 1,4-dioxane and water (0.09 M)) was added palladium 1,1-bis(diphenylphosphion)ferrocene dichloride (0.2 equiv). The mixture was stirred at 110° C. for 2 h. The suspension was cooled to room temperature and filtered. The filtrate was concentrated and the residue obtained was purified by silica gel chromatography (20% ethyl acetate in petroleum ether) to afford the title compound (88% yield). MS (ESI) m/z=464.1 [M+1]$^+$.

N,N,3-Trimethyl-4-((5-(1-methyl-1H-pyrazol-4-yl)-4-((tetrahydro-2H-pyran-4-yl)oxy)-7-((2-(trimethylsilyl)ethoxy)methyl)-7H-pyrrolo[2,3-d]pyrimidin-2-yl)amino)benzamide To a degassed mixture of 2-chloro-5-(1-methyl-1H-pyrazol-4-yl)-4-((tetrahydro-2H-pyran-4-yl)oxy)-7-((2-(trimethylsilyl)ethoxy)methyl)-7H-pyrrolo[2,3-d]pyrimidine (1 equiv), 4-amino-N,N,3-trimethylbenzamide (1 equiv) and cesium carbonate (3 equiv) in 1.4-dioxane (0.086 M) were added palladium acetate (0.3 equiv) and 2,2'-bis-diphenylphosphanyl-[1,1']binaphthalenyl (0.6 equiv). The mixture was stirred at 110° C. for 2 h. The reaction was cooled to room temperature and filtered. The filtrate was concentrated and the residue obtained was purified by preparative thin layer chromatography (3.3% MeOH in DCM) to afford the title compound (76% yield). MS (ESI) m/z 606.1 [M+1]$^+$.

N,N,3-Trimethyl-4-((5-(1-methyl-1H-pyrazol-4-yl)-4-((tetrahydro-2H-pyran-4-yl)oxy)-7H-pyrrolo[2,3-d]pyrimidin-2-yl)amino)benzamide N,N,3-Trimethyl-4-((5-(1-methyl-1H-pyrazol-4-yl)-4-((tetrahydro-2H-pyran-4-yl)oxy)-7-((2-(trimethylsilyl)ethoxy)methyl)-7H-pyrrolo[2,3-d]pyrimidin-2-yl)amino)benzamide was deprotected according to General Procedure A. The resulting mixture was concentrated and purified to afford the title compound (12% yield). $^1$H NMR (400 MHz, CHLOROFORM-d$_1$) δ ppm 8.75 (s, 1H), 8.31-8.29 (d, J=8.4 Hz, 1H), 7.76-7.75 (d, J=6.0 Hz, 2H), 7.32-7.29 (m, 2H), 6.87-6.86 (d, J=2.4 Hz, 1H), 6.69 (s, 1H), 5.52-5.48 (m, 1H), 4.02-3.97 (m, 2H), 3.94 (s, 3H), 3.66-3.60 (m, 2H), 3.07 (s, 6H), 12.37 (s, 2H), 2.21-2.16 (m, 2H), 1.96-1.87 (m, 2H); MS (ESI) m/z 476.2 [M+1]$^+$.

Example 9

3-Methoxy-N-methyl-4-((5-(pyridin-4-yl)-4-((tetrahydro-2H-pyran-4-yl)oxy)-7H-pyrrolo[2,3-d]pyrimidin-2-yl)amino)benzamide

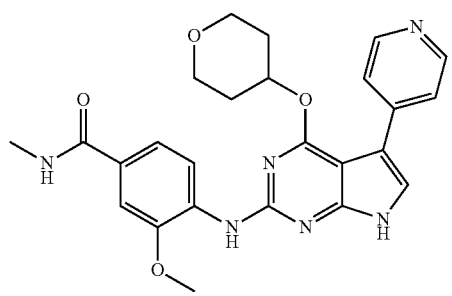 [SMILES: CNC(=O)c1ccc(Nc2nc(OC3CCOCC3)c3c(-c4ccncc4)c[nH]c3n2)c(OC)c1]

2-Chloro-5-(pyridin-4-yl)-4-((tetrahydro-2H-pyran-4-yl)oxy)-7-((2-(trimethylsilyl)ethoxy)methyl)-7H-pyrrolo[2,3-d]pyrimidine To a solution of 2-chloro-5-iodo-4-((tetrahydro-2H-pyran-4-yl)oxy)-7-((2-(trimethylsilyl)ethoxy)methyl)-7H-pyrrolo[2,3-d]pyrimidine (1 equiv), pyridin-4-ylboronic acid (1.1 equiv), tetrakis(triphenylphosphine)-palladium(0) (0.1 equiv) in a 5:1 mixture of 1,4-dioxane and water (0.17 M) was added sodium carbonate (2.1 equiv). The reaction was stirred at 75° C. for 3 h. The reaction mixture was quenched with saturated aqueous sodium chloride and then washed with ethyl acetate. The organic phase was combined and washed with saturated aqueous sodium chloride. The organic layer was dried (magnesium sulfate), filtered, and concentrated. The crude product was purified by silica gel column chromatography (0-90%) ethyl acetate (with 10% 1N ammonia in MeOH) in hexane) to give the title compound (50.5% yield) as a yellow oil. $^1$H NMR (400 MHz, DMSO-d$_6$) δ ppm −0.06 (s, 9H) 0.82-0.91 (m, 2H) 1.74 (dtd, J=12.74, 8.37, 8.37, 3.71 Hz, 2H) 2.01-2.16 (m, 2H) 3.50-3.63 (m, 4H) 3.69-3.83 (m, 2H) 5.50 (tt, J=7.91, 3.81 Hz, 1H) 5.59 (s, 2H) 7.72 (d, J=6.25 Hz, 2H) 8.12 (s, 1H) 8.60 (d, J=6.25 Hz, 2H); MS (ESI) m/z 461.0 [M+1]$^+$.

3-Methoxy-N-methyl-4-((5-(pyridin-4-yl)-4-((tetrahydro-2H-pyran-4-yl)oxy)-7-((2-(trimethylsilyl)ethoxy)methyl)-7H-pyrrolo[2,3-d]pyrimidin-2-yl)amino)benzamide To a solution of 2-chloro-5-(pyridin-4-yl)-4-((tetrahydro-2H-pyran-4-yl)oxy)-7-((2-(trimethylsilyl)ethoxy)methyl)-7H-pyrrolo[2,3-d]pyrimidine (1 equiv), (9,9-dimethyl-9H-xanthene-4,5-diyl)bis(diphenylphosphine) (0.2 equiv), tris(dibenzylideneacetone)dipalladium(0) (0.1 equiv), 4-amino-3-methoxy-N-methylbenzamide (1.1 equiv) in 1,4-dioxane (0.1 M) was added cesium carbonate (3 equiv). The reaction mixtures were heated, with microwave irradiation, in a microwave reactor at 150° C. for 2 h. The reaction mixture was quenched with saturated aqueous sodium chloride and then washed with ethyl acetate. The organic phase was combined and washed with saturated aqueous sodium chloride. The organic layer was dried (magnesium sulfate), filtered, and concentrated. The crude was purified by silica gel column chromatography (0-90%) ethyl acetate (with 10% 1N ammonia in MeOH) in hexane) to give the title compound (49.1%% yield) as yellow solid. $^1$H NMR (400 MHz, DMSO-d$_6$) δ ppm −0.11 (s, 9H) 0.85-0.93 (m, 2H) 1.68-1.82 (m, 2H) 2.06-2.18 (m, 2H) 2.79 (d, J=4.30 Hz, 3H) 3.51-3.66 (m, 4H) 3.77-3.86 (m, 2H) 3.96 (s, 3H) 5.47-5.55 (m, 1H) 5.56 (s, 2H) 7.50-7.57 (m, 2H) 7.71-7.76 (m, 2H) 7.83 (s, 1H) 7.92 (s, 1H) 8.34 (q, J=4.43 Hz, 1H) 8.52-8.60 (m, 3H); MS (ESI) m/z 605.6 [M+1]$^+$.

3-Methoxy-N-methyl-4-((5-(pyridin-4-yl)-4-((tetrahydro-2H-pyran-4-yl)oxy)-7H-pyrrolo[2,3-d]pyrimidin-2-yl)amino)benzamide 3-Methoxy-N-methyl-4-((5-(pyridin-4-yl)-4-((tetrahydro-2H-pyran-4-yl)oxy)-7-((2-(trimethylsilyl)ethoxy)methyl)-7H-pyrrolo[2,3-d]pyrimidin-2-yl)amino)benzamide was deprotected according to General Procedure A. The crude product was purified to afford the title compound (25.3% yield). $^1$H NMR (400 MHz, DMSO-d$_6$) δ ppm 1.72 (dtd, J=12.84, 8.52, 8.52, 4.10 Hz, 2H) 2.08 (d, J=10.15 Hz, 2H) 2.75 (d, J=4.69 Hz, 3H) 3.54 (ddd, J=11.52, 8.59, 2.93 Hz, 2H) 3.71-3.84 (m, 2H) 5.47 (dt, J=8.30, 4.25 Hz, 1H)

7.40-7.52 (m, 2H) 7.61 (d, J=2.34 Hz, 1H) 7.66-7.74 (m, 2H) 7.77 (s, 1H) 8.29 (d, J=4.30 Hz, 1H) 8.42-8.57 (m, 3H) 12.05 (s, 1H); MS (ESI) m/z 475.5 [M+1]⁺.

Example 10

4-(4-Isopropoxy-5-(2-methylbenzo[d]oxazol-6-yl)-7H-pyrrolo[2,3-d]pyrimidin-2-ylamino)-3-methoxy-N-methylbenzamide

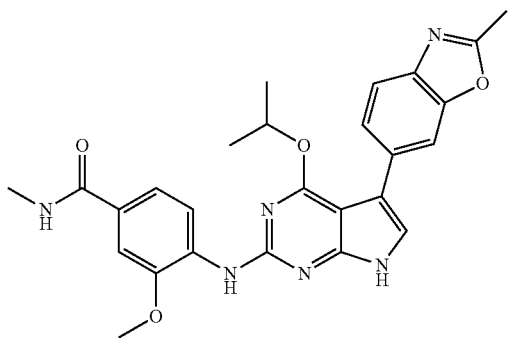

6-(2-Chloro-4-isopropoxy-7-((2-(trimethylsilyl)ethoxy)methyl)-7H-pyrrolo[2,3-d]pyrimidin-5-yl)-2-methylbenzo[d]oxazole 6-(2,4-Dichloro-7-((2-(trimethylsilyl)ethoxy)methyl)-7H-pyrrolo[2,3-d]pyrimidin-5-yl)-2-methylbenzo[d]oxazole (1 equiv), propan-2-ol (1.1 equiv), sodium tert-butoxide (1.1 equiv), and 1,4-dioxane (0.1 M) were combined and the resulting mixture was allowed to stir at 70° C. for several hours. The reaction was cooled and concentrated to an oil under reduced pressure that was purified by silica gel chromatography (0-30% ethyl acetate/hexane) to afford the title compound (101% yield) that was used without further purification. MS (ESI) m/z 473.3 [M+1]⁺.

4-(4-Isopropoxy-5-(2-methylbenzo[d]oxazol-6-yl)-7-((2-(trimethylsilyl)ethoxy)methyl)-7H-pyrrolo[2,3-d]pyrimidin-2-ylamino)-3-methoxy-N-methylbenzamide 6-(2-Chloro-4-isopropoxy-7-((2-(trimethylsilyl)ethoxy)methyl)-7H-pyrrolo[2,3-d]pyrimidin-5-yl)-2-methylbenzo[d]oxazole (1 equiv), 4-amino-3-methoxy-N-methylbenzamide (1.2 equiv), palladium acetate (0.1 equiv), 2,2'-bis(diphenylphosphino)-1,1'-binaphthalene (0.2 equiv), cesium carbonate (5 equiv), and 1,4-dioxane (0.14 M) were combined and allowed to stir at 110° C. for 4 h and then cool to ambient temperature overnight. The reaction mixture was diluted with ethyl acetate and filtered through a pre-wetted (with ethyl acetate) bed of Celite. The filtrate was concentrated to an oil under reduced pressure that was purified by silica gel chromatography (0-70% ethyl acetate with 10% MeOH/hexane) to afford the title compound (82% yield). MS (ESI) m/z 617.5 [M+1]⁺.

4-(4-Isopropoxy-5-(2-methylbenzo[d]oxazol-6-yl)-7H-pyrrolo[2,3-d]pyrimidin-2-ylamino)-3-methoxy-N-methylbenzamide 4-((4-Isopropoxy-5-(2-methylbenzo[d]oxazol-6-yl)-7-((2-(trimethylsilyl)ethoxy)methyl)-7H-pyrrolo[2,3-d]pyrimidin-2-yl)amino)-3-methoxy-N-methylbenzamide was deprotected according to General Procedure A. The reaction mixture was concentrated and purified to afford the title (86% yield). ¹H NMR (400 MHz, DMSO-d₆) δ ppm 11.77-11.95 (m, 1H), 8.53-8.69 (m, 1H), 8.27-8.37 (m, 1H), 7.94-8.00 (m, 1H), 7.70-7.75 (m, 1H), 7.65-7.70 (m, 1H), 7.57-7.64 (m, 1H), 7.47-7.55 (m, 2H), 7.34-7.43 (m, 1H), 5.46-5.58 (m, 1H), 3.97 (s, 3H), 2.75-2.83 (m, 3H), 2.62 (s, 3H), 1.38 (d, J=6.25 Hz, 6H); MS (ESI) m/z 487.4 [M+1]⁺.

Example 11

(S)—N,3-Dimethyl-4-((5-(2-methylbenzo[d]oxazol-6-yl)-4-((tetrahydrofuran-3-yl)oxy)-7H-pyrrolo[2,3-d]pyrimidin-2-yl)amino)benzamide

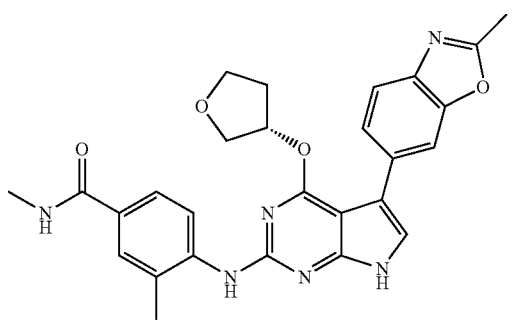

6-(2,4-Dichloro-7-((2-(trimethylsilyl)ethoxy)methyl)-7H-pyrrolo[2,3-d]pyrimidin-5-yl)-2-methylbenzo[d]oxazole To a solution of 2,4-dichloro-5-iodo-7-((2-(trimethylsilyl)ethoxy)methyl)-7H-pyrrolo[2,3-d]pyrimidine (1 equiv), 2-methyl-6-(4,4,5,5-tetramethyl-1,3,2-dioxaborolan-2-yl)benzo[d]oxazole (1 equiv), [1,1'-bis(diphenylphosphino)ferrocene]dichloropalladium(II), complex with DCM (0.1 equiv) in a 3:1 mixture of 1,4-dioxane and water (0.2 M) was added sodium carbonate (3 equiv). The reaction was stirred at 85° C. for 15 h. The reaction mixture was quenched with saturated aqueous sodium chloride and then extracted with ethyl acetate. The organic phase was combined and washed with saturated aqueous sodium chloride. The organic layer was dried (magnesium sulfate), filtered, and concentrated. The crude was purified by silica gel column chromatography (0-50% ethyl acetate in hexane) to give the title compound (72.0% yield) as a brown oil ¹H NMR (400 MHz, DMSO-d₆) δ ppm −0.06 (s, 9H) 0.83-0.92 (m, 2H) 2.64 (s, 3H) 3.55-3.65 (m, 2H) 5.65 (s, 2H) 7.47 (dd, J=8.00, 1.76 Hz, 1H) 7.72 (d, J=8.20 Hz, 1H) 7.79-7.83 (m, 1H) 8.05 (s, 1H); MS (ESI) m/z 449.5 [M+1]⁺.

(S)-6-(2-Chloro-4-((tetrahydrofuran-3-yl)oxy)-7-((2-(trimethylsilyl)ethoxy)methyl)-7H-pyrrolo[2,3-d]pyrimidin-5-yl)-2-methylbenzo[d]oxazole To a solution of 6-(2,4-dichloro-7-((2-(trimethylsilyl)ethoxy)methyl)-7H-pyrrolo[2,3-d]pyrimidin-5-yl)-2-methylbenzo[d]oxazole (1 equiv), (S)-tetrahydrofuran-3-ol (1.1 equiv) in 1,4-dioxane (0.2 M) was added sodium tert-butoxide (1.1 equiv). The reaction was stirred at 75° C. for 5 h. The reaction mixture was quenched with saturated aqueous sodium chloride and then washed with ethyl acetate. The organic phase was combined and washed with saturated aqueous sodium chloride. The organic layer was dried (magnesium sulfate), filtered, and concentrated. The crude was purified by silica gel column chromatography (0-90%) ethyl acetate in hexane) to give the title compound (90% yield) as yellow solid; $^1$H NMR (400 MHz, DMSO-d$_6$) δ ppm −0.07 (s, 9H) 0.84-0.90 (m, 2H) 1.99-2.10 (m, 1H) 2.26 (dtd, J=13.96, 8.25, 8.25, 6.25 Hz, 1H) 2.63 (s, 3H) 3.53-3.62 (m, 2H) 3.73-3.81 (m, 2H) 3.84 (d, J=10.54 Hz, 1H) 3.93 (dd, J=10.54, 4.30 Hz, 1H) 5.57 (s, 2H) 5.72-5.80 (m, 1H) 7.59-7.64 (m, 1H) 7.66 (d, J=8.59 Hz, 1H) 7.89 (s, 1H) 7.91 (d, J=0.78 Hz, 1H); MS (ESI) m/z 501.1 [M+1]$^+$.

4-Amino-N,3-dimethylbenzamide

To a solution of 4-amino-3-methylbenzoic acid (1 equiv), N$^1$-((ethylimino)methylene)-N$^3$,N$^3$-dimethylpropane-1,3-diamine hydrochloride (1.2 equiv), methanamine hydrochloride (1.2 equiv) in DMF (1.3 M) was added sodium hydrogencarbonate (2 equiv). The reaction was stirred at 25° C. for 15 h. The reaction mixture was quenched with saturated aqueous sodium chloride and then washed with ethyl acetate. The organic phase was combined and washed with saturated aqueous sodium chloride. The organic layer was dried (anhydrous magnesium sulfate), filtered, and concentrated. The crude product was purified by silica gel column chromatography (0-90% ethyl acetate (with 10% 1N ammonia in MeOH) in hexane). Concentration of the desired fractions afforded the title compound (18.4% yield) as a yellow solid. $^1$H NMR (400 MHz, DMSO-d$_6$) δ ppm 2.06 (s, 3H) 2.71 (d, J=4.69 Hz, 3H) 5.33 (s, 2H) 6.56 (d, J=8.59 Hz, 1H) 7.41 (dd, J=8.39, 2.15 Hz, 1H) 7.45 (s, 1H) 7.87-7.99 (m, 1H); MS (ESI) m/z 165.4 [M+1]$^+$.

(S)—N,3-Dimethyl-4-((5-(2-methylbenzo[d]oxazol-6-yl)-4-((tetrahydrofuran-3-yl)oxy)-7-((2-(trimethylsilyl)ethoxy)methyl)-7H-pyrrolo[2,3-d]pyrimidin-2-yl)amino)benzamide To a solution of (S)-6-(2-chloro-4-((tetrahydrofuran-3-yl)oxy)-7-((2-(trimethylsilyl)ethoxy)methyl)-7H-pyrrolo[2,3-d]pyrimidin-5-yl)-2-methylbenzo[d]oxazole (1 equiv), 4-amino-N,3-dimethylbenzamide (1 equiv), tris(dibenzylideneacetone)dipalladium(0) (0.1 equiv), xantphos (0.2 equiv) in 1,4-dioxane (0.1 M) was added cesium carbonate (1.4 equiv). The reaction was heated, under microwave irradiation, in a microwave reactor at 150° C. for 2 h. The reaction mixture was quenched with saturated aqueous sodium chloride and then washed with ethyl acetate. The organic phase was combined and washed with saturated aqueous sodium chloride. The organic layer was dried (magnesium sulfate), filtered, and concentrated. The crude was purified by silica gel column chromatography (20-80% ethyl acetate, with 10% 1N ammonia in MeOH in hexane). Concentration of the desired fractions afforded the title compound (63.6% yield) as a yellow solid; MS (ESI) m/z 629.4 [M+1]$^+$.

(S)—N,3-Dimethyl-4-((5-(2-methylbenzo[d]oxazol-6-yl)-4-((tetrahydrofuran-3-yl)oxy)-7H-pyrrolo[2,3-d]pyrimidin-2-yl)amino)benzamide (S)—N,3-Dimethyl-4-((5-(2-methylbenzo[d]oxazol-6-yl)-4-((tetrahydrofuran-3-yl)oxy)-7-((2-(trimethylsilyl)ethoxy)methyl)-7H-pyrrolo[2,3-d]pyrimidin-2-yl)amino)benzamide was deprotected according to general procedure A. The crude product was purified to afford the title compound (41.0% yield). $^1$H NMR (400 MHz, DMSO-d$_6$) δ ppm 1.98-2.10 (m, 1H) 2.17-2.30 (m, 1H) 2.33 (s, 3H) 2.62 (s, 3H) 2.78 (d, J=4.30 Hz, 3H) 3.75-3.88 (m, 3H) 3.90-3.99 (m, 1H) 5.69 (br. s., 1H) 7.34 (s, 1H) 7.56-7.63 (m, 1H) 7.63-7.69 (m, 2H) 7.70 (s, 1H) 7.90 (d, J=8.20 Hz, 1H) 7.93 (s, 1H) 8.28 (d, J=4.69 Hz, 1H) 8.32 (s, 1H) 11.71 (s, 1H). mp 273-274° C.; MS (ESI) m/z 499.6 [M+1]$^+$.

Example 12

(S)-3-Chloro-N-methyl-4-((5-(2-methylbenzo[d]oxazol-6-yl)-4-((tetrahydrofuran-3-yl)oxy)-7H-pyrrolo[2,3-d]pyrimidin-2-yl)amino)benzamide

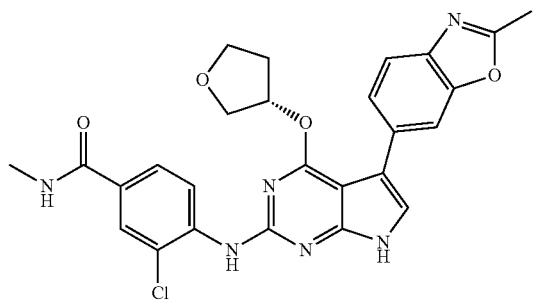

4-Amino-3-chloro-N-methylbenzamide

The solution of 4-amino-3-chlorobenzoic acid (1 equiv), EDCI (1.2 equiv), methylamine hydrochloride (1.2 equiv) in DMF (1.5 M) was added sodium bicarbonate (1 equiv). The reaction was stirred at 25° C. for 15 h. The reaction mixture was quenched with saturated aqueous sodium chloride and then extracted with ethyl acetate. The organic phase was combined and washed with saturated aqueous sodium chloride. The organic layer was dried (anhydrous magnesium sulfate), filtered, and concentrated. The crude product was purified by silica gel column chromatography (0-90% ethyl acetate (with 10% 1N ammonia in MeOH) in hexane). Concentration of the desired fractions afforded the title compound (89% yield) as colorless oil; $^1$H NMR (400 MHz, DMSO-d$_6$) δ ppm 2.67 (d, J=4.29 Hz, 3H) 5.81 (s, 2H) 6.72 (d, J=8.59 Hz, 1H) 7.49 (dd, J=8.39, 2.15 Hz, 1H) 7.67 (d, J=1.95 Hz, 1H) 8.08 (d, J=4.29 Hz, 1H); MS (ESI) m/z 185.0 [M+1]$^+$.

(S)-3-Chloro-N-methyl-4-((5-(2-methylbenzo[d]oxazol-6-yl)-4-((tetrahydrofuran-3-yl)oxy)-7-((2-(trimethylsilyl)ethoxy)methyl)-7H-pyrrolo[2,3-d]pyrimidin-2-yl)amino)benzamide To a solution of (S)-6-(2-chloro-4-((tetrahydrofuran-3-yl)oxy)-7-((2-(trimethylsilyl)ethoxy)-methyl)-7H-pyrrolo[2,3-d]pyrimidin-5-yl)-2-methylbenzo[d]oxazole (1 equiv), 4-amino-3-chloro-N-methylbenzamide (1.2 equiv), tris(dibenzylideneacetone)dipalladium(0) (0.1 equiv), xantphos (0.2 equiv) in 1,4-dioxane (0.1 M) was added cesium carbonate (1.4 equiv). The reaction was heated, under microwave irradiation, in a microwave reactor at 150° C. for 2 h. The reaction mixture was quenched with saturated aqueous sodium chloride and then washed with ethyl acetate. The organic phase was combined and washed with saturated aqueous sodium chloride. The organic layer was dried (anhydrous magnesium sulfate), filtered, and concentrated. The crude was purified by silica gel column chromatography (20-80% ethyl acetate (with 10% 1N ammonia in MeOH) in hexane). Concentration of the desired fractions under reduced pressure afforded the title compound (64.7% yield) as yellow solid; MS (ESI) m/z 649.6 [M+1]+.

(S)-3-Chloro-N-methyl-4-((5-(2-methylbenzo[d]oxazol-6-yl)-4-((tetrahydrofuran-3-yl)oxy)-7H-pyrrolo[2,3-d]pyrimidin-2-yl)amino)benzamide (S)-3-Chloro-N-methyl-4-((5-(2-methylbenzo[d]oxazol-6-yl)-4-((tetrahydrofuran-3-yl)oxy)-7-((2-(trimethylsilyl)ethoxy)methyl)-7H-pyrrolo[2,3-d]pyrimidin-2-yl)amino)benzamide was deprotected according to General Procedure A. The crude product was purified to afford the title compound (19.66% yield). $^1$H NMR (400 MHz, DMSO-$d_6$) δ ppm 2.01-2.15 (m, 1H) 2.18-2.33 (m, 1H) 2.63 (s, 3H) 2.79 (d, J=4.69 Hz, 3H) 3.72-3.90 (m, 3H) 3.92-4.00 (m, 1H) 5.68-5.79 (m, 1H) 7.43 (d, J=2.34 Hz, 1H) 7.61 (d, J=8.20 Hz, 1H) 7.66 (dd, J=8.20, 1.56 Hz, 1H) 7.84 (dd, J=8.59, 1.95 Hz, 1H) 7.97 (d, J=1.95 Hz, 1H) 7.94 (d, J=1.56 Hz, 1H) 8.25 (s, 1H) 8.39 (d, J=8.59 Hz, 1H) 8.46 (q, J=4.56 Hz, 1H) 11.91 (d, J=1.95 Hz, 1H); MS (ESI) m/z 519.5 [M+1]+.

Example 13

3-Methoxy-4-((4-(2-methoxyethoxy)-5-(2-methylbenzo[d]oxazol-6-yl)-7H-pyrrolo[2,3-d]pyrimidin-2-yl)amino)-N-methylbenzamide

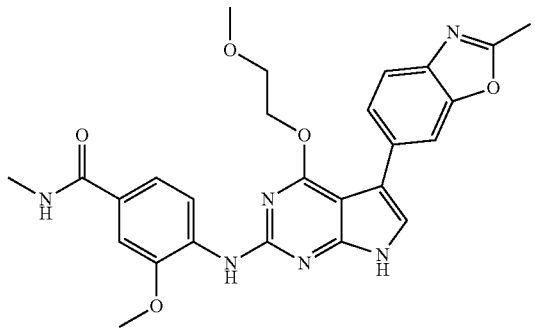

2-Chloro-5-iodo-4-(2-methoxyethoxy)-7-((2-(trimethylsilyl)ethoxy)methyl)-7H-pyrrolo[2,3-d]pyrimidine To a solution of 2,4-dichloro-5-iodo-7-((2-(trimethylsilyl)ethoxy)methyl)-7H-pyrrolo[2,3-c]pyrimidine (1 equiv) in 1,4-dioxane (0.08 M) 2-methoxyethanol (1 equiv) and sodium t-butoxide (1.04 equiv) were added. The resulting reaction mixture was allowed to stir at room temperature overnight. The reaction mixture was diluted with water and the compound was extracted with ethyl acetate. The organic layer was separated, dried over sodium sulfate and concentrated under reduced pressure. The crude product was purified by column chromatography (neutral silica gel 100-200 mesh, 0-1.5% MeOH in DCM as eluent) to afford the title compound (74% yield). MS (ESI) m/z 484 [M+1]+.

6-(2-Chloro-4-(2-methoxyethoxy)-7-((2-(trimethylsilyl)ethoxy)methyl)-7H-pyrrolo[2,3-d]pyrimidin-5-yl)-2-methylbenzo[d]oxazole A solution of 2-chloro-5-iodo-4-(2-methoxyethoxy)-7-((2-(trimethylsilyl)ethoxy)methyl)-7H-pyrrolo[2,3-c]pyrimidine (1 equiv), 2-methyl-6-(4,4,5,5-tetramethyl-1,3,2-dioxaborolan-2-yl)benzo[d]oxazole (1 equiv) and sodium carbonate (2 equiv) in 1,4-dioxane:water (3:1, 0.05 M) was degassed with argon for 10 min. Tetrakis(triphenylphosphine)palladium(0) (0.1 equiv) was added and the solution was further degassed with argon for 10 min. The reaction mixture was heated at 75° C. overnight. The reaction mixture was cooled to room temperature and the solvent was evaporated under reduced pressure. The reaction mixture was diluted with water and the compound was extracted in ethyl acetate. The organic layer was separated, dried over sodium sulfate, and purified by column chromatography (neutral silica gel 100-200 mesh, 0-3% MeOH in DCM as eluent) to afford the title compound (76% yield). MS (ESI) m/z 489 [M+1]+.

3-Methoxy-4-((4-(2-methoxyethoxy)-5-(2-methylbenzo[d]oxazol-6-yl)-7-((2-(trimethylsilyl)ethoxy)methyl)-7H-pyrrolo[2,3-d]pyrimidin-2-yl)amino)-N-methylbenzamide A mixture of 6-(2-chloro-4-(2-methoxyethoxy)-7-((2-(trimethylsilyl)ethoxy)methyl)-7H-pyrrolo[2,3-c]pyrimidin-5-yl)-2-methylbenzo[d]oxazole (1 equiv), 4-amino-3-methoxy-N-methylbenzamide (1.1 equiv), cesium carbonate (2 equiv), xantphos (0.2 equiv) in dry 1,4-dioxane (0.04 M) was degassed with argon for 15 min. Tris(dibenzylideneacetone)dipalladium(0) (0.1 equiv) was added and the solution was further degassed with argon for 10 min. The reaction mixture was heated at 150° C. for 30 min. The reaction mixture was concentrated under reduced pressure. The crude product was purified by column chromatography (neutral silica gel 100-200 mesh, 0-5% MeOH in DCM as eluent) to afford the title compound (74% yield). MS (ESI) m/z 633 [M+1]+.

3-Methoxy-4-((4-(2-methoxyethoxy)-5-(2-methylbenzo[d]oxazol-6-yl)-7H-pyrrolo[2,3-d]pyrimidin-2-yl)amino)-N-methylbenzamide 3-Methoxy-4-((4-(2-methoxyethoxy)-5-(2-methylbenzo[d]oxazol-6-yl)-7-((2-(trimethylsilyl)ethoxy)methyl)-7H-pyrrolo[2,3-d]pyrimidin-2-yl)amino)-N-methylbenzamide was deprotected according to general procedure A. The solvent was removed under reduced pressure and the residue was purified to afford the title compound (19% yield). $^1$H NMR (400 MHz, DMSO-$d_6$) δ ppm 11.9 (s, 1H), 8.61 (d, J=8.8 Hz, 1H), 8.30 (m, 1H), 8.03 (d, J=1.6 Hz, 1H), 7.76 (s, 1H), 7.70 (dd, J=8.3, 1.7 Hz, 1H), 7.59 (d, J=8.3 Hz, 1H), 7.51 (m, 2H), 7.42 (d, J=2.5 Hz, 1H), 4.60 (m, 2H), 3.97 (s, 3H), 3.72 (m, 2H), 3.33 (s, 3H), 2.80 (d, J=4.5 Hz, 3H), 2.62 (s, 3H); MS (ESI) m/z 503 [M+1]+.

Example 14

3-Methoxy-4-((5-(2-methoxypyridin-4-yl)-4-((tetrahydro-2H-pyran-4-yl)oxy)-7H-pyrrolo[2,3-d]pyrimidin-2-yl)amino)-N-methylbenzamide

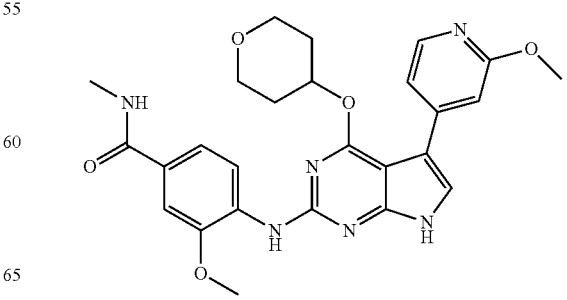

(2-Methoxypyridin-4-yl)boronate

To a solution of 4-bromo-2-methoxypyridine (1 equiv) in anhydrous THF (0.2 M) was added a solution of butyllithium in hexane (1.1 equiv) dropwise at −78° C. Then the solution was stirred at this temperature for 3 minutes. After that, trimethyl borate (2 equiv) was added at −78° C. The reaction mixture was allowed to warm up to room temperature and stirred for another 10 minutes. The solution was quenched with crushed ice and the pH was adjusted with 0.5 N hydrogen chloride solution to pH=7. The solution was concentrated and the crude product was washed with water and cooled ether to give the title compound (66% yield). MS (ESI) m/z 152.1 [M−1]$^-$.

2-Chloro-5-iodo-4-((tetrahydro-2H-pyran-4-yl)oxy)-7-((2-(trimethylsilyl)ethoxy)methyl)-7H-pyrrolo[2,3-d]pyrimidine To a suspension of sodium hydride (1 equiv) in dry THF (0.42 M) under nitrogen atmosphere was added tetrahydro-2H-pyran-4-ol (1 equiv) at 0° C. The reaction mixture was stirred at room temperature for 30 min before a solution of 2,4-dichloro-5-iodo-7-((2-(trimethylsilyl)ethoxy)methyl)-7H-pyrrolo[2,3-d]pyrimidine (0.67 equiv) in dry THF (0.75 M) was added at 0° C. The mixture was stirred at 0° C. for 1 h. The reaction was monitored by thin layer chromatography. Upon completion, the reaction mixture was quenched with water and extracted with ethyl acetate. The organic layers were combined, washed with brine, dried over sodium sulfate, filtered and concentrated. The crude product was purified by silica gel flash column chromatography (5% ethyl acetate in petroleum ether) to afford the title compound as a yellowish oil (84% yield). MS (ESI) m/z 510.1 [M+1]$^+$.

2-Chloro-5-(2-methoxypyridin-4-yl)-4-((tetrahydro-2H-pyran-4-yl)oxy)-7-((2-(trimethylsilyl)ethoxy)methyl)-7H-pyrrolo[2,3-d]pyrimidine To a degassed mixture of 2-chloro-5-iodo-4-((tetrahydro-2H-pyran-4-yl)oxy)-7-((2-(trimethylsilyl)ethoxy)methyl)-7H-pyrrolo[2,3-d]pyrimidine (1 equiv), (2-methoxypyridin-4-yl)boronic acid (2 equiv) and tripotassium phosphate trihydrate (3 equiv) in a 9:1 mixture of 1,4-dioxane and water (0.1 M) was added palladium 1,1-bis(diphenylphosphion)ferrocene dichloride (0.2 equiv). The reaction mixture was stirred at 80° C. for 1.5 h. After the reaction was complete, the reaction mixture was cooled to room temperature and concentrated. The residue was purified by silica gel chromatography (15% ethyl acetate in petroleum ether) to afford the title compound (71% yield) as a white powder. MS (ESI) m/z 491.3 [M+1]$^+$.

3-Methoxy-4-((5-(2-methoxypyridin-4-yl)-4-((tetrahydro-2H-pyran-4-yl)oxy)-7-((2-(trimethylsilyl)ethoxy)methyl)-7H-pyrrolo[2,3-d]pyrimidin-2-yl)amino)-N-methylbenzamide To a degassed mixture of 2-chloro-5-(2-methoxypyridin-4-yl)-4-((tetrahydro-2H-pyran-4-yl)oxy)-7-((2-(trimethylsilyl)ethoxy)methyl)-7H-pyrrolo[2,3-d]pyrimidine (1 equiv), 4-amino-3-methoxy-N-methylbenzamide (1.1 equiv) and cesium carbonate (3 equiv) in 1,4-dioxane (0.175 M) was added palladium acetate (0.3 equiv) and 2,2'-bis-diphenylphosphanyl-[1,1']binaphthalenyl (0.6 equiv). The reaction was stirred at 100° C. for 2 h. After the reaction was complete, the reaction mixture was cooled to room temperature, filtered and concentrated to afford the crude product (95% yield, crude) as a brown solid which was used in the next step without further purification. MS (ESI) m/z 635.3 [M+1]$^+$.

3-Methoxy-4-((5-(2-methoxypyridin-4-yl)-4-((tetrahydro-2H-pyran-4-yl)oxy)-7H-pyrrolo[2,3-d]pyrimidin-2-yl)amino)-N-methylbenzamide 3-Methoxy-4-((5-(2-methoxypyridin-4-yl)-4-((tetrahydro-2H-pyran-4-yl)oxy)-7-((2-(trimethylsilyl)ethoxy)methyl)-7H-pyrrolo[2,3-d]pyrimidin-2-yl)amino)-N-methylbenzamide was deprotected according to General Procedure A. The solution was concentrated and the crude product was purified to give the title compound as a off-white powder (65.7% yield over two steps). $^1$H NMR (400 MHz, CHLOROFORM-d$_1$) δ ppm 9.19 (s, 1H), 8.59-8.57 (d, J=8.8 Hz 1H), 8.14-8.13 (d, J=7.2 Hz, 1H), 7.67 (s, 1H), 7.47-4.46 (d, J=1.6 Hz, 1H), 7.28-7.27 (d, J=1.6 Hz, 1H), 7.18-7.17 (d, J=7.2 Hz, 1H), 7.15 (s, 1H), 7.12-7.11 (d, J=2.0 Hz, 1H), 6.20-6.18 (m, 1H), 5.59-5.55 (m, 1H), 3.99-3.98 (d, J=3.2 Hz, 6H), 3.98-3.91 (m, 2H), 3.70-3.64 (m, 2H), 3.02-3.00 (d, J=4.8 Hz, 3H), 2.17-2.11 (m, 2H), 1.97-1.88 (m, 2H); MS (ESI) m/z 505.3 [M+1]$^+$.

Example 15A 4-((4-(((1r,4r)-4-Hydroxy-4-methylcyclohexyl)oxy)-5-(2-methylbenzo[d]oxazol-6-yl)-7H-pyrrolo[2,3-d]pyrimidin-2-yl)amino)-N,3-dimethylbenzamide

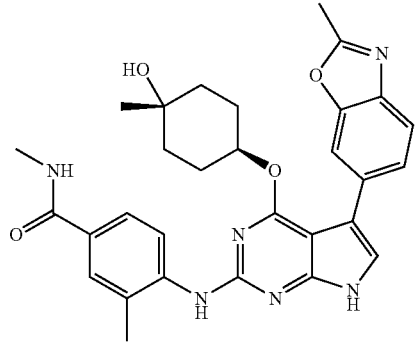 [SMILES: CNC(=O)c1ccc(Nc2nc(O[C@H]3CC[C@](C)(O)CC3)c3c(-c4ccc5nc(C)oc5c4)c[nH]c3n2)c(C)c1]

Example 15B 4-((4-(((1s,4s)-4-Hydroxy-4-methylcyclohexyl)oxy)-5-(2-methylbenzo[d]oxazol-6-yl)-7H-pyrrolo[2,3-d]pyrimidin-2-yl)amino)-N,3-dimethylbenzamide

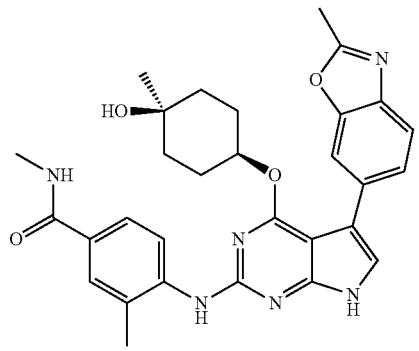 [SMILES: CNC(=O)c1ccc(Nc2nc(O[C@H]3CC[C@@](C)(O)CC3)c3c(-c4ccc5nc(C)oc5c4)c[nH]c3n2)c(C)c1]

8-Methyl-1,4-dioxaspiro[4.5]decan-8-ol

To a cooled (−78° C.) solution of 1,4-dioxaspiro[4.5]decan-8-one (1 equiv) in THF (0.64 M) was added a solution of methylmagnesium bromide (1.8 equiv, 3 mol/L in ether) dropwise under nitrogen atmosphere. The resulting mixture was stirred at −78° C. for 20 minutes, then warmed to −30° C. for 30 minutes and then stirred at 0° C. for 30 minutes. After the reaction was complete, the resulting mixture was quenched with saturated aqueous ammonia chloride solution and extracted with ethyl acetate. The organic layers were combined, washed with brine, dried over sodium sulfate, filtered and concentrated to afford the title compound as a white solid (92% yield), which was used in the next step without further purification. $^1$H NMR (300 MHz, CHLOROFORM-$d_1$) δ ppm 4.00-3.91 (m, 4H), 1.95-1.80 (m, 3H), 1.77-1.67 (m, 4H), 1.59-1.58 (m, 1H), 1.27 (s, 3H), 1.17 (s, 1H).

4-Hydroxy-4-methylcyclohexanone

To a solution of 8-methyl-1,4-dioxaspiro[4.5]decan-8-ol (1 equiv) in a 2:1 mixture of acetone and water (0.38 M) was added pyridinium p-toluenesulfonate (0.2 equiv). The resulting mixture was refluxed for 8 h. After the reaction was complete, the reaction mixture was cooled to room temperature and concentrated. The residue was purified by silica gel chromatography (0-30% ethyl acetate in petroleum ether) to afford the title compound (86% yield) as a yellow solid. $^1$H NMR (400 MHz, CHLOROFORM-$d_1$) δ ppm 3.96-3.93 (m, 2H), 2.27-2.25 (m, 1H), 2.25-2.22 (m, 1H), 2.01-1.94 (m, 2H), 1.90-1.82 (m, 2H), 1.38 (s, 3H).

1-Methylcyclohexane-1,4-diol

To a cooled (0° C.) solution of 4-hydroxy-4-methylcyclohexanone (1 equiv) in MeOH (0.5 M) was added sodium borohydride (2 equiv). The resulting mixture was stirred at room temperature overnight. After the reaction was complete, the resulting mixture was quenched with water and extracted with ethyl acetate. The organic layers were combined, washed with brine (20 mL), dried over sodium sulfate, filtered and concentrated. The crude product was purified by silica gel flash column chromatography (0-10% DCM in MeOH) to afford the title compound as a white solid (87% yield, cis/trans mixture). $^1$H NMR (300 MHz, DMSO-$d_6$) δ ppm 4.34-4.32 (d, J=4.5 Hz, 1H), 4.29-4.27 (d, J=3.6 Hz, 0.45H), 4.12-4.06 (m, 0.47H), 4.00 (s, 0.39H), 3.97 (s, 1H), 3.82 (s, 0.48H), 3.55-3.50 (m, 0.47H), 3.20-3.17 (d, J=7.5 Hz, 1H), 1.76-1.62 (m, 1H), 1.60-1.40 (m, 8H), 1.35-1.20 (m, 4H), 1.07 (s, 1.5H), 1.05 (s, 3H).

4-((2-Chloro-5-iodo-7-((2-(trimethylsilyl)ethoxy)methyl)-7H-pyrrolo[2,3-d]pyrimidin-4-yl)oxy)-1-methylcyclohexanol To a suspension of sodium hydride (60% in mineral oil, 1.36 equiv) in dry THF (0.68 M) under nitrogen atmosphere was added 1-methylcyclohexane-1,4-diol (1 equiv). The reaction mixture was stirred at room temperature for 30 min before a solution of 2,4-dichloro-5-iodo-7-((2-(trimethylsilyl)ethoxy)methyl)-7H-pyrrolo[2,3-d]pyrimidine (0.9 equiv,) in dry THF (0.45 M) was added. The mixture was stirred at room temperature for 2 h. The reaction was monitored by thin layer chromatography. Upon completion, the reaction mixture was quenched with water and extracted with ethyl acetate. The organic layers were combined, washed with brine (20 mL), dried over sodium sulfate, filtered and concentrated. The crude product was purified by silica gel flash column chromatography (0-30% ethyl acetate in petroleum ether) to afford the title compound as a white solid (78% yield). MS (ESI) m/z 538.4 [M+1]$^+$.

4-((2-Chloro-5-(2-methylbenzo[d]oxazol-6-yl)-7-((2-(trimethylsilyl)ethoxy)-methyl)-7H-pyrrolo[2,3-d]pyrimidin-4-yl)oxy)-1-methylcyclohexanol To a degassed mixture of 4-((2-chloro-5-iodo-7-((2-(trimethylsilyl)ethoxy)methyl)-7H-pyrrolo[2,3-d]pyrimidin-4-yl)oxy)-1-methylcyclohexanol (1 equiv), 2-methyl-6-(4,4,5,5-tetramethyl-1,3,2-dioxaborolan-2-yl)benzo[d]oxazole (1.2 equiv) and tripotassium phosphate trihydrate (3 equiv) in a 9:1 mixture of 1,4-dioxane and water (0.18 M) was added palladium 1,1-bis(diphenylphosphion)ferrocene dichloride (0.1 equiv). The reaction mixture was stirred at 70° C. for 3 h. After the reaction was completed, the reaction mixture was cooled to room temperature and concentrated. The residue was purified by silica gel chromatography (0-2% DCM in MeOH) to afford the title compound (95% yield) as a red oil. MS (ESI) m/z 543.2 [M+1]$^+$.

4-((4-((4-Hydroxy-4-methylcyclohexyl)oxy)-5-(2-methylbenzo[d]oxazol-6-yl)-7-((2-(trimethylsilyl)ethoxy)methyl)-7H-pyrrolo[2,3-d]pyrimidin-2-yl)amino)-$N_3$,3-dimethylbenzamide To a degassed mixture of 4-((2-chloro-5-(2-methylbenzo[d]oxazol-6-yl)-7-((2-(trimethylsilyl)ethoxy)methyl)-7H-pyrrolo[2,3-d]pyrimidin-4-yl)oxy)-1-methylcyclohexanol (1 equiv), 4-amino-N,3-dimethylbenzamide (1.1 equiv) and cesium carbonate (3 equiv) in 1,4-dioxane (0.17 M) was added palladium acetate (0.1 equiv) and 2,2'-bis-diphenylphosphanyl-[1,1']binaphthalenyl (0.2 equiv). The reaction was stirred at 100° C. for 2 h. After the reaction was complete, the reaction mixture was cooled to room temperature and concentrated. The residue was purified by silica gel chromatography (0-2% DCM in MeOH) to afford the title compound 100% yield) as a red oil. MS (ESI) m/z 671.2 [M+1]$^+$.

4-((4-(((1r,4r)-4-Hydroxy-4-methylcyclohexyl)oxy)-5-(2-methylbenzo[d]oxazol-6-yl)-7H-pyrrolo[2,3-d]pyrimidin-2-yl)amino)-N,3-dimethylbenzamide and 4-((4-(((1s,4s)-4-hydroxy-4-methylcyclohexyl)oxy)-5-(2-methylbenzo[d]oxazol-6-yl)-7H-pyrrolo[2,3-d]pyrimidin-2-yl)amino)-N,3-dimethylbenzamide 4-((4-((4-Hydroxy-4-methylcyclohexyl)oxy)-5-(2-methylbenzo[d]oxazol-6-yl)-7-((2-(trimethylsilyl)ethoxy)methyl)-7H-pyrrolo[2,3-d]pyrimidin-2-yl)amino)-N,3-dimethylbenzamide was deprotected according to General Procedure A. The resulting mixture was concentrated and the residue was purified to afford the racemic product (33% yield), which was separated by chiral HPLC (30% EtOH in hexane) to give 4-((4-(((1r,4r)-4-hydroxy-4-methylcyclohexyl)oxy)-5-(2-methylbenzo[d]oxazol-6-yl)-7H-pyrrolo[2,3-d]pyrimidin-2-yl)amino)-N,3-dimethylbenzamide (10% yield) and 4-((4-(((1s,4s)-4-hydroxy-4-methylcyclohexyl)oxy)-5-(2-methylbenzo[d]oxazol-6-yl)-7H-pyrrolo[2,3-d]pyrimidin-2-yl)amino)-N,3-dimethylbenzamide (31% yield).

4-((4-(((1r,4r)-4-Hydroxy-4-methylcyclohexyl)oxy)-5-(2-methylbenzo[d]oxazol-6-yl)-7H-pyrrolo[2,3-d]pyrimidin-2-yl)amino)-N,3-dimethylbenzamide $^1$H NMR (400 MHz, DMSO-$d_6$) δ ppm 11.63 (d, J=2.0 Hz, 1H), 8.26-8.22 (m, 2H), 7.94-7.89 (m, 2H), 7.69-7.56

(m, 4H), 7.26 (d, J=2.4 Hz, 1H), 5.53 (brs, 1H), 4.09 (s, 1H), 2.77 (d, J=4.8 Hz, 3H), 2.60 (s, 3H), 2.33 (s, 3H), 1.96-1.88 (m, 2H), 1.69-1.64 (m, 2H), 1.48-1.41 (m, 2H), 1.35-1.31 (m, 2H), 0.99 (s, 3H); MS (ESI) m/z 541.2 [M+1]$^+$; Purity: 98.3% (214 nm), 97.0% (254 nm); Conditions for Chiral HPLC: Column: Chiralpak IC, 5 μm, 0.46 cm I.D.*25 cm L; Injection: 10 μL; Mobile Phase: hexane:EtOH=70:30; Flow: 1.0 mL/min; 230 nm; T=30° C.

4-((4-(((1s,4s)-4-Hydroxy-4-methylcyclohexyl)oxy)-5-(2-methylbenzo[d]oxazol-6-yl)-7H-pyrrolo[2,3-d]pyrimidin-2-yl)amino)-N,3-dimethylbenzamide $^1$H NMR (400 MHz, DMSO-d$_6$) δ ppm 11.64 (d, J=1.6 Hz, 1H), 8.26-8.24 (m, 1H), 8.18 (m, 1H), 7.97-7.95 (m, 2H), 7.70-7.58 (m, 4H), 7.31 (d, J=2.4 Hz, 1H), 5.19-5.15 (m, 1H), 4.17 (s, 1H), 2.78 (d, J=4.8 Hz, 3H), 2.62 (s, 3H), 2.33 (s, 3H), 1.91-1.75 (m, 4H), 1.64-1.61 (m, 2H), 1.43-1.36 (m, 2H), 1.14 (s, 3H); MS (ESI) m/z 541.2 [M+1]$^+$; Purity: 99.2% (214 nm), 98.0% (254 nm); Conditions for Chiral HPLC: Column: Chiralpak IC, 5 μm, 0.46 cm I.D.*25 cm L; Injection: 10 μL; Mobile Phase: Hexane:EtOH=70:30; Flow: 1.0 mL/min; 230 nm; T=30° C.

Example 16

4-((4-(Cyclopentyloxy)-5-(2-methylbenzo[d]oxazol-6-yl)-7H-pyrrolo[2,3-d]pyrimidine-2-yl)amino)-3-methoxy-N-(oxetan-3-yl)benzamide

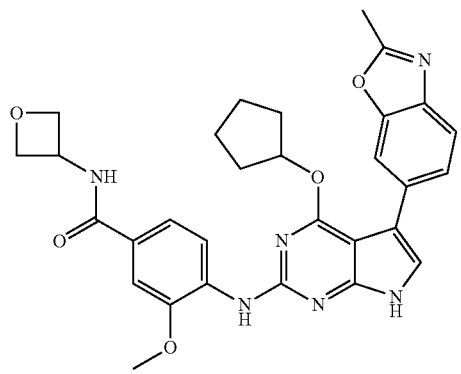 [SMILES: COc1cc(C(=O)NC2COC2)ccc1Nc1nc(OC2CCCC2)c2c(-c3ccc4nc(C)oc4c3)c[nH]c2n1]

4-Amino-3-methoxy-N-(oxetan-3-yl)benzamide

To a solution of 4-amino-3-methoxybenzoic acid (1 equiv) in DCM (0.1 M) was added HOBt (1.2 equiv), EDC (1.2 equiv) and DIEA (4 equiv). Oxetan-3-amine (1.2 equiv) was added and the reaction mixture was stirred at room temperature overnight. The mixture was extracted with ethyl acetate and the organic layer was dried over sodium sulfate. The solids were filtered off, the filtrate was concentrated and the product was purified by silica gel chromatography to afford the title compound (53% yield) as a yellow solid. MS (ESI) m/z 223.1 [M+1]$^+$.

4-((4-(Cyclopentyloxy)-5-(2-methylbenzo[d]oxazol-6-yl)-7-((2-(trimethylsilyl)ethoxy)methyl)-7H-pyrrolo[2,3-d]pyrimidin-2-yl)amino)-3-methoxy-N-(oxetan-3-yl)benzamide To a degassed mixture of 6-(2-chloro-4-(cyclopentyloxy)-7-((2-(trimethylsilyl)ethoxy)methyl)-7H-pyrrolo[2,3- d]pyrimidin-5-yl)-2-methylbenzo[d]oxazole (1 equiv), 4-amino-3-methoxy-N-(oxetan-3-yl)benzamide (1.2 equiv) and cesium carbonate (3 equiv) in 1,4-dioxane (0.1 M) was added palladium acetate (0.2 equiv) and 2,2'-bis-diphenyl-phosphanyl-[1,1']binaphthalenyl (0.2 equiv). The reaction was stirred at 100° C. for 2 h. The reaction mixture was cooled to room temperature, and concentrated. The residue was purified by silica gel chromatography (0-5% DCM in MeOH) to afford the title compound (crude) as a yellow solid which was used in the next step without further purification. MS (ESI) m/z 686.1 [M+1]$^+$.

4-((4-(Cyclopentyloxy)-5-(2-methylbenzo[d]oxazol-6-yl)-7H-pyrrolo[2,3-d]pyrimidine-2-yl)amino)-3-methoxy-N-(oxetan-3-yl)benzamide 4-((4-(Cyclopentyloxy)-5-(2-methylbenzo[d]oxazol-6-yl)-7-((2-(trimethylsilyl)ethoxy)methyl)-7H-pyrrolo[2,3-d]pyrimidin-2-yl)amino)-3-methoxy-N-(oxetan-3-yl)benzamide was deprotected according to General Procedure A. The solution was concentrated and the crude material was purified to give the title compound (45% over two steps). $^1$H NMR (400 MHz, DMSO-d$_6$): δ ppm 11.88 (s, 1H), 8.69-8.67 (d, J=8.0 Hz, 1H), 7.93 (s, 1H), 7.77 (s, 1H), 7.66-7.58 (m, 2H), 7.51-7.45 (m, 2H), 7.39 (s, 1H), 5.70-5.67 (m, 1H), 4.86-4.83 (m, 1H), 4.44-4.41 (m, 1H), 4.29-4.22 (m, 2H), 3.96 (s, 3H), 3.62-3.58 (m, 1H), 3.48-3.42 (m, 1H), 2.62 (s, 3H), 1.98-1.95 (m, 2H), 1.83-1.78 (m, 2H), 1.75-1.63 (m, 4H). MS (ESI) m/z 555.3 [M+1]$^+$.

Example 17

Aziridin-1-yl(4-((4-(cyclopentyloxy)-5-(2-methylbenzo[d]oxazol-6-yl)-7H-pyrrolo[2,3-d]pyrimidin-2-yl)amino)-3-methoxyphenyl)methanone

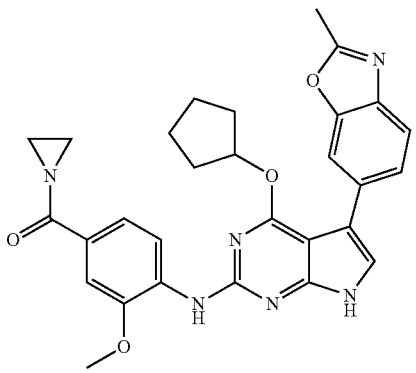 [SMILES: COc1cc(C(=O)N2CC2)ccc1Nc1nc(OC2CCCC2)c2c(-c3ccc4nc(C)oc4c3)c[nH]c2n1]

Aziridin-1-yl(3-methoxy-4-nitrophenyl)methanone

To a solution of 3-methoxy-4-nitrobenzoic acid (1 equiv) in toluene (0.21 M) was added triphenyl phosphine (1.5 equiv), carbon tetrabromide (1.6 equiv), TEA (2 equiv) and 2-aminoethanol (0.7 equiv). Then the resulting mixture was stirred at 80° C. for 1 h. The reaction mixture was filtered, the filtrate was concentrated and the crude was purified by reverse phase HPLC (10%-95% acetonitrile in water) to give the title compound (34% yield) as a yellow solid. MS (ESI) m/z 223.1 [M+1]$^+$.

(4-Amino-3-methoxyphenyl)(aziridin-1-yl)methanone

To a solution of aziridin-1-yl(3-methoxy-4-nitrophenyl) methanone (1 equiv) in MeOH (0.24 M) was added 10% palladium on carbon (25% by weight). The reaction mixture was stirred at 50° C. under hydrogen atmosphere (50 Psi) overnight then filtered through celite. The filtrate was concentrated and the residue was purified by silica gel chromatography (50% ethyl acetate in petroleum ether) to afford the title compound (33% yield) as a yellow solid. MS (ESI) m/z 193.1 [M+1]$^+$.

Aziridin-1-yl(4-((4-(cyclopentyloxy)-5-(2-methyl-benzo[d]oxazol-6-yl)-7-((2-(trimethylsilyl)ethoxy) methyl)-7H-pyrrolo[2,3-d]pyrimidin-2-yl)amino)-3-methoxyphenyl)methanone To a degassed mixture of 6-(2-chloro-4-(cyclopentyloxy)-7-((2-(trimethylsilyl)ethoxy)methyl)-7H-pyrrolo[2,3-d]pyrimidin-5-yl)-2-methylbenzo[d]oxazole (1 equiv), (4-amino-3-methoxyphenyl)(aziridin-1-yl)methanone (1.2 equiv) and cesium carbonate (3 equiv) in 1,4-dioxane (0.1 M) was added palladium acetate (0.2 equiv) and 2,2'-bis-diphenylphosphanyl-[1,1']binaphthalenyl (0.2 equiv). The reaction was stirred at 100° C. for 2 h. The reaction mixture was concentrated and the residue was purified by silica gel chromatography (0-10% DCM in MeOH) to afford the title compound (crude) as a yellow solid. The material was used in next step without further purification. MS (ESI) m/z 655.1 [M+1]$^+$.

Aziridin-1-yl(4-((4-(cyclopentyloxy)-5-(2-methyl-benzo[d]oxazol-6-yl)-7H-pyrrolo[2,3-d]pyrimidin-2-yl)amino)-3-methoxyphenyl)methanone Aziridin-1-yl(4-((4-(cyclopentyloxy)-5-(2-methylbenzo[d]oxazol-6-yl)-7-((2-(trimethylsilyl)ethoxy)methyl)-7H-pyrrolo[2,3-d]pyrimidin-2-yl)amino)-3-methoxyphenyl) methanone was deprotected according to General Procedure A. The solution was concentrated and the product was purified to give the title compound (18% over two steps). $^1$H NMR (400 MHz, DMSO-d$_6$) δ ppm 8.78 (s, 1H), 8.73-8.71 (m, 1H), 7.82 (s, 1H), 7.71 (s, 1H), 7.62-7.59 (m, 3H), 7.51 (m, 1H), 6.99-6.98 (m, 1H), 5.73-5.70 (m, 1H), 4.47-4.42 (m, 2H), 4.09-4.04 (m, 2H), 3.99 (s, 3H), 2.66 (s, 3H), 2.00-1.91 (m, 4H), 1.76-1.63 (m, 4H); MS (ESI) m/z 525.3 [M+1]$^+$.

Example 18

4-((4-Cyclobutoxy-5-(4-(methylcarbamoyl)phenyl)-7H-pyrrolo[2,3-d]pyrimidin-2-yl)amino)-3-methoxy-N-(oxetan-3-yl)benzamide

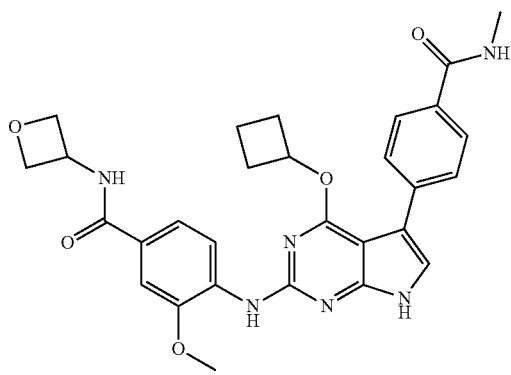 [SMILES: CNC(=O)c1ccc(-c2c[nH]c3nc(Nc4ccc(C(=O)NC5COC5)cc4OC)nc(OC4CCC4)c23)cc1]

2-Chloro-4-cyclobutoxy-5-iodo-7-((2-(trimethylsilyl)ethoxy)-methyl)-7H-pyrrolo[2,3-d]pyrimidine To a suspension of sodium hydride (2 equiv, 60% in mineral oil) in dry THF (0.44 M) under nitrogen atmosphere was added a solution of cyclobutanol (1.05 equiv) in dry THF (1.4 M) at 0° C. The reaction mixture was stirred at room temperature for 30 minutes before 2,4-dichloro-5-iodo-7-((2-(trimethylsilyl)ethoxy)-methyl)-7H-pyrrolo[2,3-d]pyrimidine (1 equiv) in dry THF (0.33 M) was added and the resulting reaction mixture was stirred at 30° C. for 1 h. The reaction mixture was quenched with saturated aqueous ammonium chloride solution. The organic solvent was removed under reduced pressure and the resulting aqueous layer was extracted with ethyl acetate. The combined organic layers were washed with brine, dried over anhydrous sodium sulfate and filtered. The filtrate was evaporated under reduced pressure. The crude obtained was purified by flash column chromatography on silica gel (5% ethyl acetate in petroleum ether) to afford the title compound (95% yield) as a white solid. MS (ESI) m/z 479.2 [M+1]$^+$.

4-(2-Chloro-4-cyclobutoxy-7-((2-(trimethylsilyl) ethoxy)methyl)-7H-pyrrolo[2,3-d]pyrimidin-5-yl)-N-methylbenzamide To a degassed mixture of 2-chloro-4-cyclobutoxy-5-iodo-7-((2-(trimethylsilyl)ethoxy)methyl)-7H-pyrrolo[2,3-d]pyrimidine (1 equiv), N-methyl-4-(4,4,5,5-tetramethyl-1,3,2-dioxaborolan-2-yl)benzamide (1.2 equiv) and tripotassium phosphate trihydrate (3 equiv) in a 9:1 mixture of 1,4-dioxane and water (0.1 M) was added palladium 1,1-bis (diphenylphosphino)ferrocene dichloride (0.1 equiv). The reaction mixture was stirred at 80° C. for 2 h. After the reaction was completed, the reaction mixture was cooled to room temperature and concentrated. The residue was purified by silica gel chromatography (0-30% ethyl acetate in petroleum ether) to afford the title compound (67% yield) as a yellow solid. MS (ESI) m/z 487.2 [M+1]$^+$.

4-Amino-3-methoxy-N-(oxetan-3-yl)benzamide

To a solution of 4-amino-3-methoxybenzoic acid (1 equiv) in DCM (0.11 M) was added HOBT (1.2 equiv), EDC (1.2 equiv) and DIEA (4 equiv). Oxetan-3-amine (1.2 equiv) was added then the reaction mixture was stirred at room temperature overnight. The mixture was extracted with ethyl acetate then the organic layer was dried over sodium sulfate The solids were filtered off, the filtrate was concentrated and the product was purified by silica gel chromatography (5% DCM in MeOH) to afford the title compound (53% yield) as a yellow solid. MS (ESI) m/z 223.1 [M+1]$^+$

4-((4-Cyclobutoxy-5-(4-(methylcarbamoyl)phenyl)-7-((2-(trimethylsilyl)ethoxy)methyl)-7H-pyrrolo[2,3-d]pyrimidin-2-yl)amino)-3-methoxy-N-(oxetan-3-yl) benzamide To a degassed mixture of 4-(2-chloro-4-cyclobutoxy-7-((2-(trimethylsilyl)ethoxy)methyl)-7H-pyrrolo[2,3-d]pyrimidin-5-yl)-N-methylbenzamide (1 equiv), 4-amino-3-methoxy-N-(oxetan-3-yl)benzamide (1.1 equiv) and cesium carbonate (3 equiv) in 1,4-dioxane (0.09 M) was added palladium acetate (0.1 equiv) and 2,2'-bis-diphenylphosphanyl-[1,1']binaphthalenyl (0.3 equiv). The reaction was stirred at 100° C. for 2 h. The reaction mixture was cooled to room temperature, and concentrated. The residue was purified by silica gel chromatography (0-5% DCM in MeOH) to afford the title compound (crude) as a yellow solid which was used in the next step without further purification. MS (ESI) m/z 673.1 [M+1]+.

4-((4-Cyclobutoxy-5-(4-(methylcarbamoyl)phenyl)-7H-pyrrolo[2,3-d]pyrimidin-2-yl)amino)-3-methoxy-N-(oxetan-3-yl)benzamide 4-((4-Cyclobutoxy-5-(4-(methylcarbamoyl)phenyl)-7-((2-(trimethylsilyl)ethoxy)methyl)-7H-pyrrolo[2,3-d]pyrimidin-2-yl)amino)-3-methoxy-N-(oxetan-3-yl)benzamide was deprotected according to General Procedure A. The resulting mixture was concentrated and the residue was purified to afford the title compound (40% over two steps). $^1$H NMR (400 MHz, DMSO-d$_6$) δ ppm 11.97 (s, 1H), 8.67 (d, J=8.4 Hz, 1H), 8.43 (d, J=4.4 Hz, 1H), 7.88-7.79 (m, 5H), 7.55-7.49 (m, 3H), 5.44-5.38 (m, 1H), 4.92 (s, 1H), 4.53-4.47 (m, 1H), 4.32 (s, 2H), 3.94 (s, 3H), 3.63-3.57 (m, 1H), 3.51-3.45 (m, 1H), 2.81 (d, J=4 Hz, 3H), 2.50 (s, 2H), 2.20-2.11 (m, 2H), 1.89-1.70 (m, 2H); MS (ESI) m/z 543.3 [M+1]+.

Example 19

4-(4-Cyclopropoxy-5-(2-methylbenzo[d]oxazol-6-yl)-7H-pyrrolo[2,3-d]pyrimidin-2-ylamino)-3-methoxy-N-methylbenzamide

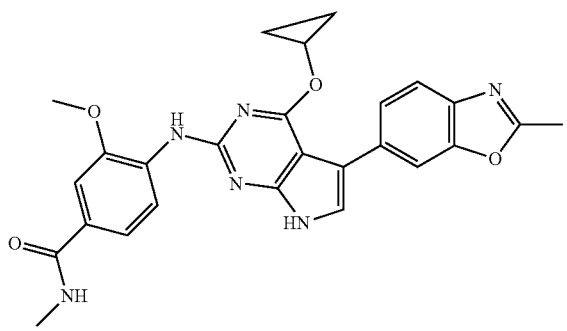 [SMILES: CNC(=O)c1ccc(Nc2nc(OC3CC3)c3c(-c4ccc5nc(C)oc5c4)c[nH]c3n2)c(OC)c1]

Cyclopropanol

A solution of aqueous hydrogen peroxide (30%, 84 equiv) was added drop-wise to a stirring solution of cyclopropylboronic acid (1 equiv) in aqueous 10% sodium hydroxide (1 equiv) at 0° C. The resulting mixture was stirred at 0° C. for 1 h. The reaction mixture was quenched with saturated aqueous sodium thiosulfate pentahydrate and extracted with diethyl ether. The combined organic were dried over sodium sulfate, filtered, and concentrated in vacuo at 0° C. to give cyclopropanol (43% yield) as clear oil. $^1$H NMR (400 MHz, CHLOROFORM-d$_1$) δ ppm 3.49-3.53 (m, 1H) 2.22 (br. s., 1H) 0.52-0.60 (m, 2H) 0.42-0.52 (m, 2H).

6-(2-Chloro-4-cyclopropoxy-7-((2-(trimethylsilyl)ethoxy)methyl)-7H-pyrrolo[2,3-d]pyrimidin-5-yl)-2-methylbenzo[d]oxazole 6-(2,4-Dichloro-7-((2-(trimethylsilyl)ethoxy)methyl)-7H-pyrrolo[2,3-d]pyrimidin-5-yl)-2-methylbenzo[d]oxazole (1 equiv), cyclopropanol (2 equiv), sodium tert-butoxide (2 equiv), 1,4-dioxane (0.03 M) were combined and stirred at 25° C. The reaction mixture was loaded directly onto a silica gel column and purified using flash chromatography (0-50% ethyl acetate in hexane) column, to give the title compound (80% yield) as clear oil. MS (ESI) m/z 471.5 [M+1]+.

4-(4-Cyclopropoxy-5-(2-methylbenzo[d]oxazol-6-yl)-7-((2-(trimethylsilyl)ethoxy)methyl)-7H-pyrrolo[2,3-d]pyrimidin-2-ylamino)-3-methoxy-N-methylbenzamide A mixture of 6-(2-chloro-4-cyclopropoxy-7-((2-(trimethylsilyl)-ethoxy)methyl)-7H-pyrrolo[2,3-d]pyrimidin-5-yl)-2-methylbenzo[d]oxazole (1 equiv), 4-amino-3-methoxy-N-methylbenzamide (2 equiv), potassium carbonate (3.5 equiv), (9,9-dimethyl-9H-xanthene-4,5-diyl)bis(diphenylphosphine) (0.23 equiv), tris(dibenzylideneacetone)dipalladium (0.23 equiv) in 1,4-dioxane (0.085 M) was purged with nitrogen and sealed. The reaction mixture was heated to 140° C. for 1.5 h. After cooling to room temperature the reaction mixture was purified using flash chromatography (0-100% ethyl acetate in hexane then 0-20% MeOH in DCM) eluted with 17% MeOH in DCM to give the title compound (57.5% yield) as brown oil. MS (ESI) m/z 615.4 [M+1]+.

4-(4-Cyclopropoxy-5-(2-methylbenzo[d]oxazol-6-yl)-7H-pyrrolo[2,3-d]pyrimidin-2-ylamino)-3-methoxy-N-methylbenzamide 4-(4-Cyclopropoxy-5-(2-methylbenzo[d]oxazol-6-yl)-7-((2-(trimethylsilyl)ethoxy)methyl)-7H-pyrrolo[2,3-d]pyrimidin-2-ylamino)-3-methoxy-N-methylbenzamide was deprotected according to General Procedure A. The solvent was removed under reduced pressure, and the residue was purified to afford the title compound (67.7% yield). $^1$H NMR (500 MHz, DMSO-d$_6$) δ ppm 11.90 (s, 1H) 8.73 (d, J=8.83 Hz, 1H) 8.31 (d, J=4.73 Hz, 1H) 7.85 (s, 1H) 7.77 (s, 1H) 7.57-7.64 (m, 2H) 7.50-7.55 (m, 2H) 7.41 (s, 1H) 4.50-4.58 (m, J=6.19, 6.19, 3.07, 2.84 Hz, 1H) 3.98 (s, 3H) 2.80 (d, J=4.41 Hz, 3H) 2.63 (s, 3H) 0.88 (d, J=6.94 Hz, 2H) 0.76-0.82 (m, 2H). MS (ESI) m/z 485.2 [M+1]+.

Example 20

5-(2-((4-(Dimethylcarbamoyl)-2-methylphenyl)amino)-4-((tetrahydro-2H-pyran-4-yl)oxy)-7H-pyrrolo[2,3-d]pyrimidin-5-yl)-N-methylpicolinamide

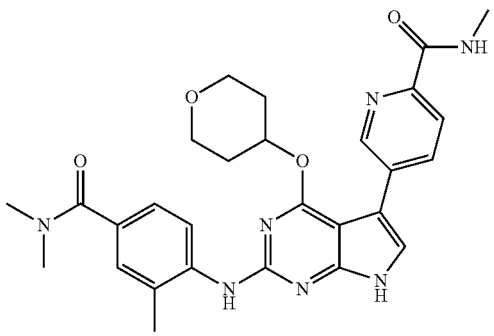

5-(2-Chloro-4-(tetrahydro-2H-pyran-4-yloxy)-7-((2-(trimethylsilyl)ethoxy)methyl)-7H-pyrrolo[2,3-d]pyrimidin-5-yl)-N-methylpicolinamide 2-Chloro-5-iodo-4-(tetrahydro-2H-pyran-4-yloxy)-7-((2-(trimethylsilyl)ethoxy)methyl)-7H-pyrrolo[2,3-d]pyrimidine (1 equiv), N-methyl-5-(4,4,5,5-tetramethyl-1,3,2-dioxaborolan-2-yl)picolinamide (1 equiv), 1′-bis(diphenylphosphino)-ferrocene]dichloropalladium(II) complex with dichloromethane (0.1 equiv), sodium carbonate (3 equiv) were suspended in a 3:1 mixture of 1,4-dioxane and water (0.09 M) were combined in a sealed reaction vessel. The resulting solution was flushed with nitrogen and stirred at 85° C. for 2 h. After cooling to room temperature the reaction mixture was loaded directly onto a silica-gel column and purified using flash chromatography (0-55% ethyl acetate in hexane). Fractions were combined, concentrated and the residue dried under high vacuum to give the title compound (61% yield) as a brown semi solid. MS (ESI) m/z 519.1 [M+1]$^+$.

5-(2-(4-(Dimethylcarbamoyl)-2-methylphenylamino)-4-(tetrahydro-2H-pyran-4-yloxy)-7H-pyrrolo[2,3-d]pyrimidin-5-yl)-N-methylpicolinamide 5-(2-Chloro-4-(tetrahydro-2H-pyran-4-yloxy)-7-((2-(trimethylsilyl)ethoxy)methyl)-7H-pyrrolo[2,3-d]pyrimidin-5-yl)-N-methylpicolinamide (1 equiv), 4-amino-N,N,3-trimethylbenzamide (1 equiv), (9,9-dimethyl-9H-xanthene-4,5-diyl)bis(diphenylphosphine) (0.2 equiv), cesium carbonate (2 equiv), tris(dibenzylideneacetone)dipalladium (0) (0.1 equiv) and 1,4-dioxane (0.2 M) were combined in a microwave vial and irradiated heated at 150° C. for 30 min. The mixture was concentrated and purified by flash chromatography 0-55% (hexane:ethyl acetate—800 mL), followed by 5-15% B (DCM:MeOH—800 mL) in the same run. Fractions were combined, concentrated and the compound was deprotected according to General Procedure A. The reaction mixture was concentrated and purified to give the title compound (21% yield). $^1$H NMR (400 MHz, METHANOL-d$_4$) δ ppm 8.92 (d, J=1.95 Hz, 1H), 8.20 (dd, J=7.81, 1.56 Hz, 1H), 8.07 (dd, J=16.59, 8.39 Hz, 2H), 7.22-7.31 (m, 3H), 5.49 (s, 1H), 3.78-3.88 (m, 2H), 3.52-3.61 (m, 2H), 3.07 (s, 6H), 2.96 (s, 3H), 2.35 (s, 3H), 2.08 (d, J=13.28 Hz, 2H), 1.73-1.84 (m, 2H). MS (ESI) m/z 530.0 [M+1]$^+$.

Example 21

6-Methoxy-N-methyl-5-((5-(2-methylbenzo[d]oxazol-6-yl)-4-((tetrahydro-2H-pyran-4-yl)oxy)-7H-pyrrolo[2,3-d]pyrimidin-2-yl)amino)picolinamide

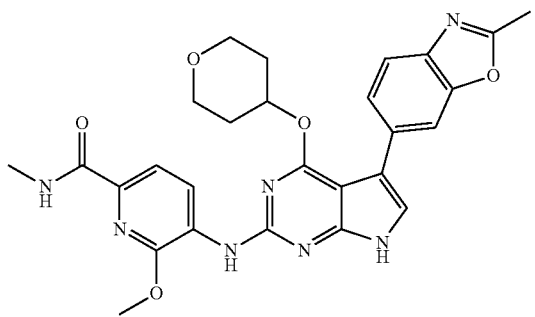

6-Methoxy-N-methyl-5-nitropicolinamide

The suspension of 6-methoxy-5-nitropicolinic acid (1 equiv), methylamine hydrochloride (2 equiv), sodium bicarbonate (2 equiv), HATU (2 equiv) in DMSO (1 M) was stirred at 25° C. for 15 h. The reaction mixture was quenched with saturated aqueous sodium chloride and then washed with ethyl acetate. The organic phase was combined and washed with saturated aqueous sodium bicarbonate. The organic layer was dried (anhydrous sodium sulfate), filtered, and concentrated. The crude product was purified by silica gel column chromatography (0-90% ethyl acetate (with 1% 1N ammonia in MeOH) in hexane). Concentration of the desired fractions under reduced pressure afforded the title compound (85%) as a yellow solid. $^1$H NMR (500 MHz, DMSO-d$_6$) δ ppm 2.86 (d, J=4.73 Hz, 3H) 4.17 (s, 3H) 7.77 (dd, J=8.04, 0.79 Hz, 1H) 8.54-8.60 (m, 1H) 8.77 (m, J=4.10 Hz, 1H); MS (ESI) m/z 212.2 [M+1]$^+$.

5-Amino-6-methoxy-N-methylpicolinamide

The solution of 6-methoxy-N-methyl-5-nitropicolinamide (1 equiv) in MeOH (0.43 M) was stirred with palladium on carbon 10% w/w (10% by mass) under hydrogen (45 psi) for 1 h. The reaction mixture was filtered over Celite and concentrated. The crude product was purified by silica gel column chromatography (20-90% ethyl acetate (with 1% 1N ammonia in MeOH) in hexane). Concentration of the desired fractions under reduced pressure afforded the title compound (97%) as a white solid. $^1$H NMR (400 MHz, DMSO-d$_6$) δ ppm 2.73 (d, J=4.69 Hz, 3H) 3.91 (s, 3H) 5.49 (br. s., 2H) 6.83 (d, J=7.81 Hz, 1H) 7.35 (d, J=7.81 Hz, 1H) 8.05 (q, J=4.82 Hz, 1H); MS (ESI) m/z 182.3 [M+1]$^+$.

6-Methoxy-N-methyl-5-((5-(2-methylbenzo[d]oxazol-6-yl)-4-((tetrahydro-2H-pyran-4-yl)oxy)-7-((2-(trimethylsilyl)ethoxy)methyl)-7H-pyrrolo[2,3-d]pyrimidin-2-yl)amino)picolinamide The solution of 6-(2-chloro-4-((tetrahydro-2H-pyran-4-yl)oxy)-7-((2-(trimethylsilyl)ethoxy)methyl)-7H-pyrrolo[2,3-d]pyrimidin-5-yl)-2-methylbenzo[d]oxazole (1 equiv), 5-amino-6-methoxy-N-methylpicolinamide (1.05 equiv), xantphos (0.2 equiv), tris(dibenzylideneacetone)dipalladium (0) (0.1 equiv) in 1,4-dioxane (0.16 M) was added cesium carbonate (1.4 equiv). The reaction mixture was stirred at 150° C. for 2 h under microwave irradiation. The reaction was filtered, and concentrated. The crude was purified using silica gel chromatography (0-90% ethyl acetate (with 10% 1N ammonia in MeOH) in hexane) to give the title compound (82% yield) as yellow solid. $^1$H NMR (400 MHz, DMSO-d$_6$) δ ppm −0.11 (s, 9H) 0.84-0.93 (m, 2H) 1.63-1.76 (m, 2H) 2.03-2.16 (m, 2H) 2.64 (s, 3H) 2.84 (d, J=4.69 Hz, 3H) 3.49-3.65 (m, 4H) 3.70-3.80 (m, 2H) 4.12 (s, 3H) 5.52-5.55 (m, 1H) 5.58 (s, 2H) 7.60 (s, 1H) 7.65 (d, J=1.17 Hz, 2H) 7.70 (d, J=8.20 Hz, 1H) 7.91-7.99 (m, 1H) 8.03 (s, 1H) 8.41 (q, J=4.69 Hz, 1H) 8.91 (d, J=7.81 Hz, 1H); MS (ESI) m/z 660.5 [M+1]$^+$.

6-Methoxy-N-methyl-5-((5-(2-methylbenzo[d]oxazol-6-yl)-4-((tetrahydro-2H-pyran-4-yl)oxy)-7H-pyrrolo[2,3-d]pyrimidin-2-yl)amino)picolinamide 6-Methoxy-N-methyl-5-((5-(2-methylbenzo[d]oxazol-6-yl)-4-((tetrahydro-2H-pyran-4-yl)oxy)-7-((2-(trimethylsilyl)ethoxy)methyl)-7H-pyrrolo[2,3-d]pyrimidin-2-yl)amino)picolinamide was deprotected according to General Procedure A. The crude product was purified to afford the title compound (38.8%). ¹H NMR (400 MHz, DMSO-$d_6$) δ ppm 1.70 (dtd, J=12.49, 8.20, 8.20, 3.90 Hz, 2H) 2.02-2.16 (m, 2H) 2.63 (s, 3H) 2.84 (d, J=4.69 Hz, 3H) 3.56 (ddd, J=11.52, 8.00, 3.12 Hz, 2H) 3.71-3.81 (m, 2H) 4.12 (s, 3H) 5.53 (tt, J=7.76, 4.15 Hz, 1H) 7.43 (d, J=2.34 Hz, 1H) 7.62 (d, J=1.00 Hz, 1H) 7.65-7.71 (m, 2H) 7.92 (s, 1H) 7.96 (dd, J=1.56, 0.78 Hz, 1H) 8.41 (q, J=4.69 Hz, 1H) 8.86 (d, J=8.20 Hz, 1H) 11.95 (d, J=2.34 Hz, 1H); MS (ESI) m/z 530.6 [M+1]⁺.

Example 22

4-(5-(4-(1H-imidazol-2-yl)phenyl)-4-isopropoxy-7H-pyrrolo[2,3-d]pyrimidin-2-ylamino)-3-methoxy-N-methylbenzamide

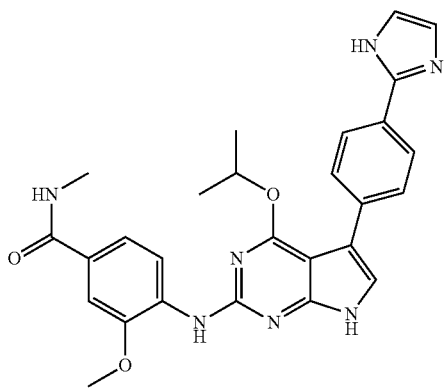 [SMILES: CNC(=O)c1ccc(Nc2nc(OC(C)C)c3c(-c4ccc(-c5ncc[nH]5)cc4)c[nH]c3n2)c(OC)c1]

2-(4-Bromophenyl)-1-((2-(trimethylsilyl)ethoxy)methyl)-1H-imidazole

To a solution of 2-(4-bromophenyl)-1H-imidazole (1 equiv) in DMF (0.47 M) was added sodium hydride (3 equiv, 60% in mineral oil) at 0° C. under nitrogen. After the resulting reaction mixture was stirred at 0° C. for 15 min, (2-(chloromethoxy)-ethyl)trimethylsilane (1.1 equiv) was added. Then the mixture was stirred at room temperature for 3 h and quenched with saturated aqueous ammonium chloride solution. The aqueous layer was extracted with DCM. The combined organic layers were washed with brine, dried over anhydrous sodium sulfate and filtered. Concentration under vacuum gave the crude product, which was purified by silica gel column chromatography (25% ethyl acetate in petroleum ether) to afford the title compound (80% yield). MS (ESI) m/z 354.2 [M+1]⁺.

2-(4-(4,4,5,5-Tetramethyl-1,3,2-dioxaborolan-2-yl)phenyl)-1-((2-(trimethylsilyl)ethoxy)methyl)-1H-imidazole To a solution of 2-(4-bromophenyl)-1-((2-(trimethylsilyl)ethoxy)methyl)-1H-imidazole (1 equiv) in 1,4-dioxane (0.33 M) were added 4,4,4',4',5,5,5',5'-octamethyl-2,2'-bi(1,3,2-dioxaborolane) (1.5 equiv), potassium acetate (3 equiv) and palladium 1,1-bis(diphenyl phosphion)ferrocene dichloride (0.15 equiv). The reaction mixture was stirred at 100° C. for 2 h. After the reaction was complete, the reaction mixture was cooled to room temperature and concentrated. The residue was purified by silica gel chromatography (0-50% ethyl acetate in petroleum ether) to afford the title compound (83% yield) as a yellow oil. MS (ESI) m/z 401.2 [M+1]⁺.

2-Chloro-5-iodo-4-isopropoxy-7-((2-(trimethylsilyl)ethoxy)methyl)-7H-pyrrolo[2,3-d]pyrimidine To a suspension of sodium hydride (1 equiv, 60% in mineral oil) in dry THF (0.9 M) under nitrogen atmosphere was added propan-2-ol (0.52 equiv). The reaction mixture was stirred at room temperature for 30 min before a solution of 2,4-dichloro-5-iodo-7-((2-(trimethylsilyl)ethoxy)methyl)-7H-pyrrolo[2,3-d]pyrimidine (0.5 equiv) in dry THF (0.45 M) was added. The mixture was stirred at room temperature for 1 h. The reaction was monitored by thin layer chromatography. Upon completion, the reaction mixture was quenched with water and extracted with ethyl acetate. The organic layers were combined, washed with brine, dried over sodium sulfate, filtered and concentrated. The crude product was purified by silica gel flash column chromatography (0-10% ethyl acetate in petroleum ether) to afford the title compound as a yellow oil (81% yield). MS (ESI) m/z 468.2 [M+1]⁺.

2-Chloro-4-isopropoxy-7-((2-(trimethylsilyl)ethoxy)methyl)-5-(4-(1-((2-(trimethylsilyl)ethoxy)methyl)-1H-imidazol-2-yl)phenyl)-7H-pyrrolo[2,3-d]pyrimidine To a degassed mixture of 2-chloro-5-iodo-4-isopropoxy-7-((2-(trimethylsilyl)ethoxy)methyl)-7H-pyrrolo[2,3-d]pyrimidine (1 equiv), (4,5,5-trimethyl-2-(4-(1-((2-(trimethylsilyl)ethoxy)methyl)-1H-imidazol-2-yl)phenyl)-1,3,2-dioxaborolan-4-yl)methylium (1.2 equiv) and tripotassium phosphate trihydrate (3 equiv) in a 9:1 mixture of 1,4-dioxane and water (0.09 M) was added palladium 1,1-bis(diphenylphosphion)-ferrocene dichloride (0.2 equiv). The reaction mixture was stirred at 100° C. for 2 h. After the reaction was complete, the reaction mixture was cooled to room temperature and concentrated. The residue was purified by silica gel chromatography (0-20% ethyl acetate in petroleum ether) to afford the title compound (82% yield) as a red solid. MS (ESI) m/z 614.2 [M+1]⁺.

4-((4-Isopropoxy-7-((2-(trimethylsilyl)ethoxy)methyl)-5-(4-(1-((2-(trimethylsilyl)ethoxy)methyl)-1H-imidazol-2-yl)phenyl)-7H-pyrrolo[2,3-d]pyrimidin-2-yl)amino)-3-methoxy-N-methylbenzamide To a degassed mixture of 2-chloro-4-isopropoxy-7-((2-(trimethylsilyl)ethoxy)methyl)-5-(4-(1-((2-(trimethylsilyl)ethoxy)methyl)-1H-imidazol-2-yl)phenyl)-7H-pyrrolo[2,3-d]pyrimidine (1 equiv), 4-amino-3-methoxybenzamide (1.2 equiv) and cesium carbonate (3.0 equiv) in 1,4-dioxane (0.07 M) was added palladium acetate (0.1 equiv) and 2,2'-bis-diphenylphosphanyl-[1,1']binaphthalenyl (0.3 equiv). The reaction was stirred at 100° C. for 3 h. After the reaction was complete, the reaction mixture was cooled to room temperature and concentrated. The residue was purified by silica gel chromatography (0-2% DCM in MeOH) to afford the crude title compound (60% yield) as a yellow solid. MS (ESI) m/z 758.2 [M+1]⁺.

4-(5-(4-(1H-imidazol-2-yl)phenyl)-4-isopropoxy-7H-pyrrolo[2,3-d]pyrimidin-2-ylamino)-3-methoxy-N-methylbenzamide 4-((4-Isopropoxy-7-((2-(trimethylsilyl)ethoxy)methyl)-5-(4-(1-((2-(trimethylsilyl)ethoxy)methyl)-1H-imidazol-2-yl)phenyl)-7H-pyrrolo[2,3-d]pyrimidin-2-yl)amino)-3-methoxy-N-methylbenzamide was deprotected according to General Procedure A. The resulting mixture was concentrated and the residue was purified to afford the title compound (13% yield). $^1$H NMR (400 MHz, DMSO-$d_6$) δ ppm 12.52 (brs, 1H), 11.85 (s, 1H), 8.62 (d, J=8 Hz, 1H), 8.31 (s, 1H), 7.93 (d, J=8 Hz, 2H), 7.80 (d, J=12 Hz, 2H), 7.72 (s, 1H), 7.52 (d, J=8 Hz, 2H), 7.41 (s, 1H), 7.14 (s, 1H), 5.57-5.50 (m, 1H), 3.97 (s, 3H), 2.80 (d, J=4.8 Hz, 3H), 1.41 (d, J=8 Hz, 6H); MS (ESI) m/z 498.2 [M+1]$^+$.

Example 23

N-(5-Chloro-1-(2-methoxyethyl)-1H-pyrazol-4-yl)-4-(cyclopentyloxy)-5-(2-methylbenzo[d]oxazol-6-yl)-7H-pyrrolo[2,3-d]pyrimidin-2-amine

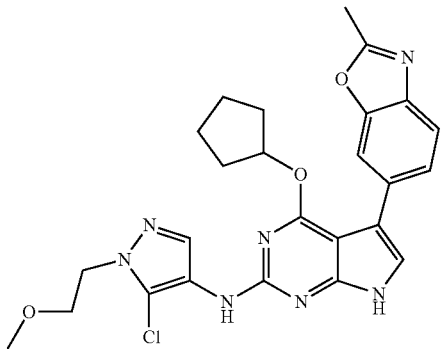 [SMILES: COCCn1ncc(Nc2nc(OC3CCCC3)c3c(-c4ccc5nc(C)oc5c4)c[nH]c3n2)c1Cl]

1-(2-Methoxyethyl)-4-nitro-1H-pyrazole

A mixture of 4-nitro-1H-pyrazole (1 equiv), 1-bromo-2-methoxyethane (1.05 equiv), potassium carbonate (1.5 equiv) and acetonitrile (0.44 M) was stirred and heated to 60° C. for 6 h. The resultant mixture was evaporated and the residue was purified by flash chromatography (2.5% MeOH in DCM) to afford the desired product as a yellow solid (76% yield). $^1$H NMR (400 MHz, CHLOROFORM-$d_1$) δ ppm 8.25 (s, 1H), 8.08 (s, 1H), 4.34-4.31 (t, J=4.8 Hz, 2H), 3.77-3.74 (t, J=4.8 Hz, 2H), 3.37 (s, 3H).

5-Chloro-1-(2-methoxyethyl)-4-nitro-1H-pyrazole

To a solution of 1-(2-methoxyethyl)-4-nitro-1H-pyrazole (1 equiv) in THF (0.5 M) was added dropwise lithium bis(trimethylsilyl)amide (2.7 equiv) in THF (1.0 M) at −78° C. The reaction was stirred at −78° C. for 30 min before the addition of hexachloroethane (1.5 equiv) in THF (1.84 M). The reaction was stirred at −78° C. for 2.5 h before warming to room temperature. The reaction was diluted with brine and extracted with ethyl acetate. The combined extracts were washed with brine, dried over sodium sulfate, filtered and concentrated. The crude product was purified by flash chromatography (10-20% ethyl acetate in petroleum ether) to afford the desired product as a yellow solid (83% yield). $^1$H NMR (400 MHz, CHLOROFORM-$d_1$) δ ppm 8.13 (s, 1H), 8.08 (s, 1H), 4.31-4.28 (t, J=4.2 Hz, 2H), 3.74-3.72 (t, J=5.36 Hz, 2H), 3.37 (s, 3H).

5-Chloro-1-(2-methoxyethyl)-1H-pyrazol-4-amine

To a suspension of 5-chloro-1-(2-methoxyethyl)-4-nitro-1H-pyrazole (1 equiv) and iron dust (3 equiv) in water (0.51 M) was added acetic acid (2.6 equiv). The mixture was heated to 90° C. for 1.5 h, then cooled to room temperature. The reaction was quenched by addition of solid sodium bicarbonate and treated with ethyl acetate with continuous stirring. The mixture was filtered and the solid was rinsed with ethyl acetate. The combined filtrate was dried over sodium sulfate and concentrated. The crude product was purified by silica gel chromatography (1.5% MeOH in DCM) to provide the desired product (69% yield) as a brown oil. MS (ESI) m/z 176 [M+H]$^+$.

N-(5-Chloro-1-(2-methoxyethyl)-1H-pyrazol-4-yl)-4-(cyclopentyloxy)-5-(2-methylbenzo[d]oxazol-6-yl)-7-((2-(trimethylsilyl)ethoxy)methyl)-7H-pyrrolo[2,3-d]pyrimidin-2-amine To a degassed mixture of 6-(2-chloro-4-(cyclopentyloxy)-7-((2-(trimethylsilyl)ethoxy)methyl)-7H-pyrrolo[2,3-d]pyrimidin-5-yl)-2-methylbenzo[d]oxazole (1 equiv), 5-chloro-1-(2-methoxyethyl)-1H-pyrazol-4-amine (1.5 equiv) and cesium carbonate (3 equiv) in 1,4-dioxane (0.06 M) was added palladium acetate (0.1 equiv) and 2,2'-bis-diphenylphosphanyl-[1,1']binaphthalenyl (0.2 equiv). The reaction was stirred at 100° C. for 2 h. Upon completion, the reaction mixture was cooled to room temperature, and concentrated. The residue was purified by silica gel chromatography (1-2% MeOH in DCM) to afford the desired product (60% yield, crude) as a yellow solid which was used in next step without further purification. MS (ESI) m/z 638.2 [M+H]$^+$.

N-(5-Chloro-1-(2-methoxyethyl)-1H-pyrazol-4-yl)-4-(cyclopentyloxy)-5-(2-methylbenzo[d]oxazol-6-yl)-7H-pyrrolo[2,3-d]pyrimidin-2-amine N-(5-chloro-1-(2-methoxyethyl)-1H-pyrazol-4-yl)-4-(cyclopentyloxy)-5-(2-methylbenzo[d]oxazol-6-yl)-7-((2-(trimethylsilyl)ethoxy)methyl)-7H-pyrrolo[2,3-d]pyrimidin-2-amine was deprotected according to General Procedure A. The crude product was purified to give the desired product (20% yield). $^1$H NMR (400 MHz, DMSO-$d_6$) δ ppm 7.92 (s, 1H), 7.77 (s, 1H), 7.53 (d, J=8.4 Hz, 1H), 7.43 (d, J=8.0 Hz, 1H), 6.98 (s, 1H), 5.56 (s, 1H), 5.24-4.21 (t, J=5.2 Hz, 2H), 3.68-3.66 (t, J=4.2 Hz, 1H), 3.32 (s, 3H), 2.55 (s, 3H), 1.86-1.72 (m, 4H), 1.65-1.53 (m, 4H). MS (ESI) m/z 508.2 [M+H]$^+$.

Example 24

1-(5-Chloro-4-((4-(cyclopentyloxy)-5-(2-methylbenzo[d]oxazol-6-yl)-7H-pyrrolo[2,3-d]pyrimidin-2-yl)amino)-1H-pyrazol-1-yl)-2-methylpropan-2-ol

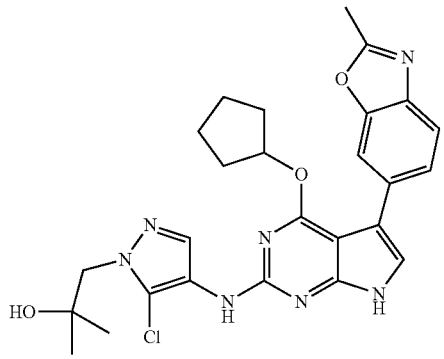 [SMILES: Cc1nc2ccc(-c3c[nH]c4nc(Nc5cnn(CC(C)(C)O)c5Cl)nc(OC5CCCC5)c34)cc2o1]

2-Methyl-1-(4-nitro-1H-pyrazol-1-yl)propan-2-ol

To a solution of 4-nitro-1H-pyrazole (1 equiv) in acetonitrile (1 M) was added 1,8-diazabicycloundec-7ene (2 equiv) and 1,2-epoxy-2-methylpropane (3.2 equiv). The reaction mixture was stirred at 60° C. for 20 h. The solvent was removed under reduced pressure and the residue was dissolved in ethyl acetate. The organic solution was washed with HCl (1 N), water and brine, dried over anhydrous sodium sulfate, filtered and concentrated in vacuo to give the title compound which was directly used in the next step without further purification (73% yield). $^1$H NMR (400 MHz, CHLOROFORM-$d_1$) δ ppm 8.26 (s, 1H), 8.09 (s, 1H), 4.13 (s, 2H), 2.64 (s, 1H) 1.24 (s, 6H). MS (ESI) m/z 186.2 [M+H]$^+$.

1-(2-Methyl-2-((trimethylsilyl)oxy)propyl)-4-nitro-1H-pyrazole

To a solution of 2-methyl-1-(4-nitro-1H-pyrazol-1-yl)propan-2-ol (1 equiv) in dry DMF (0.18 M) was added trimethylsilyl chloride (1.26 equiv) at 0° C. and imidazole (2.55 equiv) under an atmosphere of nitrogen. The resulting mixture was stirred at room temperature for 4 h and then diluted with ethyl acetate. The organic solution was washed with water and brine, dried over sodium sulfate and concentrated under reduced pressure to afford the title compound as a yellow oil (75.5% yield). $^1$H NMR (400 MHz, CHLOROFORM-$d_1$) δ ppm (9.06 (bs, 1H), 7.91 (s, 1H), 4.13 (s, 3H), 3.79 (s, 2H), 1.70 (s, 9H), 1.68 (s, 6H). MS (ESI) m/z 258.1 [M+H]$^+$.

5-Chloro-1-(2-methyl-2-((trimethylsilyl)oxy)propyl)-4-nitro-1H-pyrazole

A solution of 1-(2-methyl-2-((trimethylsilyl)oxy)propyl)-4-nitro-1H-pyrazole (1 equiv) in THF (0.41 M) was cooled into −78° C., followed by addition of lithium bis(trimethylsilyl)amide (2.6 equiv). After 1 h, hexachloroethane (1.5 equiv) was added. The reaction mixture was stirred at −78° C. for 2 h then the mixture was quenched with saturated aqueous ammonium chloride solution. The mixture was extracted with ethyl acetate and the organic layer was dried over sodium sulfate, filtered and concentrated. The product was purified by silica gel flash chromatography (15% ethyl acetate in petroleum ether) to afford the title compound as a colorless oil (80.1% yield). $^1$H NMR (400 MHz, CHLOROFORM-$d_1$) δ ppm 8.12 (s, 1H), 4.06 (s, 2H), 1.51 (s, 6H), 0.01 (s, 9H). MS (ESI) m/z 292.1 [M+H]$^+$.

1-(4-Amino-5-chloro-1H-pyrazol-1-yl)-2-methylpropan-2-ol

To a solution of 5-chloro-1-(2-methyl-2-((trimethylsilyl)oxy)propyl)-4-nitro-1H-pyrazole (1 equiv) in EtOH (0.13 M) was added iron powder (5.2 equiv) and ammonium chloride (14.3 equiv). The mixture was heated to reflux for 24 h and then filtered through celite. The filtrate was concentrated and dissolved in ethyl acetate. The organic solution was washed with aqueous sodium bicarbonate and brine, dried over sodium sulfate, filtered and concentrated. The product was purified by reverse phase silica gel chromatography (5-95% acetonitrile in water) to afford the title compound as an oil (90% yield). $^1$H NMR (400 MHz, CHLOROFORM-$d_1$) δ ppm 7.27 (s, 1H), 4.06 (s, 1H), 3.99 (s, 2H), 2.95 (bs, 2H), 1.67 (s, 1H), 1.77 (s, 6H). MS (ESI) m/z 190.1 [M+H]$^+$.

1-(5-Chloro-4-((4-(cyclopentyloxy)-5-(2-methylbenzo[d]oxazol-6-yl)-7-((2-(trimethylsilyl)ethoxy)methyl)-7H-pyrrolo[2,3-d]pyrimidin-2-yl)amino)-1H-pyrazol-1-yl)-2-methylpropan-2-ol To a degassed mixture of 1-(4-amino-5-chloro-1H-pyrazol-1-yl)-2-methylpropan-2-ol (1 equiv), 6-(2-chloro-4-(cyclopentyloxy)-7-((2-(trimethylsilyl)ethoxy)methyl)-7H-pyrrolo[2,3-d]pyrimidin-5-yl)-2-methylbenzo[d]oxazole (1.01 equiv) and 2,2'-bis-diphenylphosphanyl-[1,1']binaphthalenyl (0.1 equiv) in 1,4-dioxane (0.08 M) was added palladium acetate (0.1 equiv) and cesium carbonate (3 equiv). The reaction was stirred at 100° C. for 2 h. Upon completion, the reaction mixture was cooled to room temperature and concentrated to give the title compound which was used directly in next step without further purification (97% yield). MS (ESI) m/z 652.2 [M+H]$^+$.

1-(5-Chloro-4-{[4-cyclopentyloxy-5-(2-methylbenzoxazol-6-yl)pyrrolo[2,3-d]pyrimidin-2-yl]amino}pyrazolyl)-2-methylpropan-2-ol To a solution of tetra-(n-butyl)ammonium fluoride in THF (1 M, 7.8 equiv) was added 1-(5-chloro-4-((4-(cyclopentyloxy)-5-(2-methylbenzo[d]oxazol-6-yl)-7-((2-(trimethylsilyl)ethoxy)-methyl)-7H-pyrrolo[2,3-d]pyrimidin-2-yl)amino)-1H-pyrazol-1-yl)-2-methylpropan-2-ol (1 equiv). The resulting mixture was heated at 90° C. for 16 h and then quenched by addition of calcium carbonate (13.0 equiv). The mixture was filtered. The filtrate was concentrated to give the crude product which was purified to afford the title compound (15.6% yield). $^1$H NMR (400 MHz, METHANOL-$d_4$) δ ppm 8.10 (s, 1H), 7.95 (s, 1H), 7.71-7.69 (m, 1H), 7.62-7.60 (m, 1H), 7.15 (s, 1H), 5.76 (m, 1H), 4.21 (s, 2H), 2.72 (s, 3H), 2.03-1.70 (m, 8H), 1.25 (s, 6H). MS (ESI) m/z 522.3 [M+H]$^+$.

Example 25

4-((4-Cyclobutoxy-5-(4-(methylcarbamoyl)phenyl)-7H-pyrrolo[2,3-d]pyrimidin-2-yl)amino)-3-methoxy-N-(1-methylazetidin-3-yl)benzamide

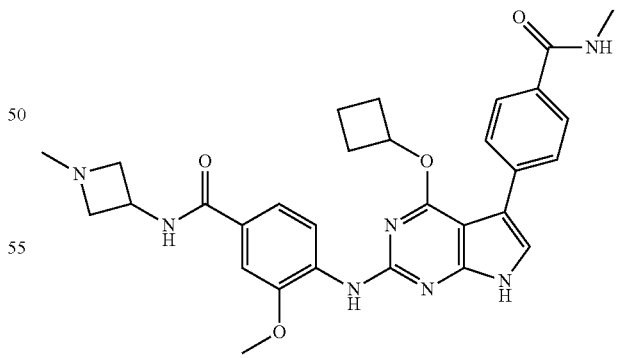

3-Methoxy-N-(1-methylazetidin-3-yl)-4-nitrobenzamide

To a solution of 1-methylazetidin-3-amine (1 equiv) in dry DCM (0.13 M) was added triethylamine (1.8 equiv). A solution of 3-methoxy-4-nitrobenzoyl chloride (0.91 equiv)

in dry DCM was added and the reaction was stirred at room temperature for 5 min. The mixture was then concentrated and purified by silica gel chromatography (5% MeOH in DCM) to afford the title compound (46.4% yield) as a yellow solid. MS (ESI) m/z 266.1 [M+H]$^+$.

4-Amino-3-methoxy-N-(1-methylazetidin-3-yl)benzamide

A mixture of 3-methoxy-N-(1-methylazetidin-3-yl)-4-nitrobenzamide (1 equiv) and 10% palladium on carbon was stirred in a mixture of MeOH/THF under a hydrogen atmosphere. The mixture was stirred at 50° C. for 2 h. The reaction mixture was filtered and the filtrate was evaporated under reduced pressure to give the desired product (99% yield) as a white solid. MS (ESI) m/z 236.1 [M+H]$^+$.

4-(2-Chloro-4-cyclobutoxy-7-((2-(trimethylsilyl) ethoxy)methyl)-7H-pyrrolo[2,3-d]pyrimidin-5-yl)- N-methylbenzamide To a degassed mixture of 2-chloro-4-cyclobutoxy-5-iodo-7-((2-(trimethylsilyl)ethoxy)methyl)-7H-pyrrolo[2,3-d]pyrimidine (1 equiv), N-methyl-4-(4,4,5,5-tetramethyl-1,3,2-dioxaborolan-2-yl)benzamide (1.1 equiv) and tripotassium phosphate trihydrorate (3.0 equiv) in a 9:1 mixture of 1,4-dioxane and water (0.125 M) was added palladium 1,1-bis(diphenylphosphion)ferrocene dicholoride (0.1 equiv). The reaction mixture was stirred at 80° C. for 4 h. After the reaction was completed, the reaction mixture was cooled to room temperature and concentrated. The residue was purified by silica gel chromatography (1% MeOH in DCM) to afford the desired product (65.7% yield) as a yellow solid. MS (ESI) m/z 487.2 [M+H]$^+$.

4-((4-Cyclobutoxy-5-(4-(methylcarbamoyl)phenyl)- 7-((2-(trimethylsilyl)ethoxy)methyl)-7H-pyrrolo[2,3- d]pyrimidin-2-yl)amino)-3-methoxy-N-(1-methyl- azetidin-3-yl)benzamide To a degassed mixture of 4-(2-chloro-4-cyclobutoxy-7-((2-(trimethylsilyl)ethoxy)methyl)-7H-pyrrolo[2,3-d]pyrimidin-5-yl)-N-methylbenzamide (1 equiv), 4-amino-3-methoxy-N-(1-methylazetidin-3-yl)benzamide (1.2 equiv) and cesium carbonate (3 equiv) in 1,4-dioxane (0.1 M) was added palladium acetate (0.1 equiv) and 2,2'-bis-diphenylphosphanyl-[1,1']binaphthalenyl (0.2 equiv). The reaction was stirred at 100° C. for 2 h. After the reaction was completed, the reaction mixture was cooled to room temperature and concentrated. The residue was purified by silica gel chromatography (10% MeOH in DCM) to afford the desired product (73% yield) as a yellow solid. MS (ESI) m/z 686.4 [M+H]$^+$.

4-((4-Cyclobutoxy-5-(4-(methylcarbamoyl)phenyl)- 7H-pyrrolo[2,3-d]pyrimidin-2-yl)amino)-3-methoxy- N-(1-methylazetidin-3-yl)benzamide 4-((4-Cyclobutoxy-5-(4-(methylcarbamoyl)phenyl)-7-((2-(trimethylsilyl)ethoxy)methyl)-7H-pyrrolo[2,3-d]pyrimidin-2-yl)amino)-3-methoxy-N-(1-methylazetidin-3-yl)benzamide (1 equiv) was deprotected according to General Procedure A. Standard work-up provided the title compound (52.5% yield). $^1$H NMR (400 MHz, DMSO-d$_6$) δ ppm 11.93 (s, 1H), 8.64-8.60 (m, 2H), 8.44-8.42 (d, J=4.4 Hz, 1H), 7.87-7.82 (m, 4H), 7.75 (s, 1H), 7.58-7.48 (m 3H), 5.42-5.39 (m, 1H), 4.54-4.12 (m, 1H), 3.98 (s, 3H), 3.58-3.55 (m, 2H), 3.01-2.94 (m, 2H), 2.81-2.80 (d, J=4 Hz, 3H), 2.50 (s, 2H), 2.27 (s, 3H), 2.19-2.14 (m, 2H), 1.87-1.85 (m, 1H), 1.77-1.73 (m, 1H). MS (ESI) m/z 556.3 [M+H]$^+$.

Example 26

3-Methoxy-4-((5-(2-methylbenzo[d]oxazol-6-yl)-4- (1-methylcyclobutoxy)-7H-pyrrolo[2,3-d]pyrimidin- 2-yl)amino)-N-(oxetan-3-yl)benzamide

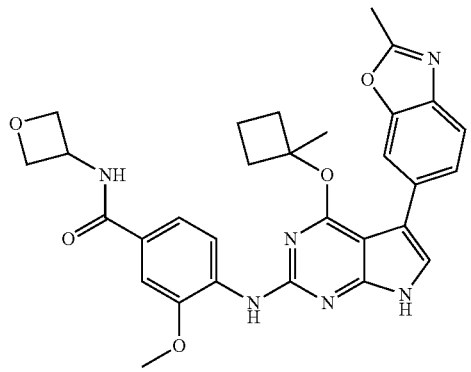 [SMILES: COc1cc(C(=O)NC2COC2)ccc1Nc1nc(OC2(C)CCC2)c2c(-c3ccc4nc(C)oc4c3)c[nH]c2n1]

2-Chloro-5-iodo-4-(1-methylcyclobutoxy)-7-((2- (trimethylsilyl)ethoxy)methyl)-7H-pyrrolo[2,3-d] pyrimidine To a suspension of sodium hydride (60% in mineral oil, 2.0 equiv) in dry THF (0.45 M) under a nitrogen atmosphere was added a solution of 1-methylcyclobutanol (1.2 equiv) in dry THF (0.27 M) at 0° C. The reaction mixture was stirred at 30° C. for 30 min before a solution of 2,4-dichloro-5-iodo-7-((2-(trimethylsilyl)ethoxy)methyl)-7H-pyrrolo[2,3-d]pyrimidine (1 equiv) in dry THF (0.23 M) was added and the resulting reaction mixture was heated at 60° C. for 2 h. After the reaction was completed, the reaction mixture was quenched with saturated aqueous ammonium chloride solution. The organic solvent was removed under vacuum and the aqueous layer was extracted with ethyl acetate. The combined organic layers were washed with brine, dried over anhydrous sodium sulfate and filtered. The filtrate was evaporated under reduced pressure. The product was purified by silica gel chromatography (2% ethyl acetate in petroleum ether) to afford the title compound (77% yield) as a yellow oil. MS (ESI) m/z 494.2 [M+H]$^+$.

6-(2-Chloro-4-(1-methylcyclobutoxy)-7-((2-(trim- ethylsilyl)-ethoxy)methyl)-7H-pyrrolo[2,3-d]pyrimi- din-5-yl)-2-methylbenzo[d]oxazole To a degassed mixture of 2-chloro-5-iodo-4-(1-methylcyclobutoxy)-7-((2-(trimethylsilyl)ethoxy)methyl)-7H-pyrrolo[2,3-d]pyrimidine (1 equiv), 2-methyl-6-(4,4,5,5-tetramethyl-1,3,2-dioxaborolan-2-yl)benzo[d]oxazole (1.1 equiv) and tripotassium phosphate trihydrorate (3.0 equiv) in a 9:1 mixture of 1,4-dioxane and water (0.45 M) was added palladium 1,1-bis(diphenylphosphion)-ferrocene dicholoride (0.1 equiv). The reaction mixture was stirred at 70° C. for 2 h. The reaction mixture was cooled to room temperature and concentrated. The residue was purified by silica gel chromatography (0-25% ethyl acetate in petroleum ether) to afford the title compound (49% yield) as a yellow solid. MS (ESI) m/z 499.2 [M+H]⁺.

3-Methoxy-4-((5-(2-methylbenzo[d]oxazol-6-yl)-4-(1-methylcyclobutoxy)-7-((2-(trimethylsilyl)ethoxy)methyl)-7H-pyrrolo[2,3-d]pyrimidin-2-yl)amino)-N-(oxetan-3-yl)benzamide To a degassed mixture of 6-(2-chloro-4-(1-methylcyclobutoxy)-7-((2-(trimethylsilyl)ethoxy)methyl)-7H-pyrrolo[2,3-d]pyrimidin-5-yl)-2-methylbenzo[d]oxazole (1 equiv), 4-amino-3-methoxy-N-(oxetan-3-yl)benzamide (1.1 equiv) and cesium carbonate (3 equiv) in 1,4-dioxane (0.22 M) was added palladium acetate (0.1 equiv) and 2,2'-bis-diphenylphosphanyl-[1,1']binaphthalenyl (0.2 equiv). The reaction was stirred at 100° C. for 2 h. After the reaction was completed, the reaction mixture was cooled to room temperature, and concentrated. The residue was purified by silica gel chromatography (0-2% DCM in MeOH) to afford the title compound (99% yield) as a yellow solid which was used without further purification. MS (ESI) m/z 685.2 [M+H]⁺.

3-Methoxy-4-((5-(2-methylbenzo[d]oxazol-6-yl)-4-(1-methylcyclobutoxy)-7H-pyrrolo[2,3-d]pyrimidin-2-yl)amino)-N-(oxetan-3-yl)benzamide A mixture of 3-methoxy-4-((5-(2-methylbenzo[d]oxazol-6-yl)-4-(1-methylcyclobutoxy)-7-((2-(trimethylsilyl)ethoxy)methyl)-7H-pyrrolo[2,3-d]pyrimidin-2-yl)amino)-N-(oxetan-3-yl)benzamide (1 equiv) in THF (0.1 M) in a sealed tube was added a solution of tetrabutylammonium fluoride in THF (1 M, 10 equiv). The resulting mixture was heated at 90° C. for 16 h. The reaction mixture was cooled to room temperature and concentrated. The residue was purified to afford the title compound (17% yield over two steps). ¹H NMR (400 MHz, DMSO-d₆) δ ppm 11.82 (s, 1H), 8.97 (d, J=6.4 Hz, 1H), 8.58 (d, J=8.0 Hz, 1H), 7.97 (d, J=0.8 Hz, 1H), 7.68-7.54 (m, 5H), 7.38 (d, J=2.4 Hz, 1H), 5.06-5.00 (m, 1H), 4.79 (t, J=7.0 Hz, 2H), 4.62 (t, J=6.4 Hz, 2H), 3.98 (s, 3H), 2.62 (s, 3H), 2.49-2.43 (m, 2H), 2.32-2.27 (m, 2H), 1.87-1.78 (m, 2H), 1.75 (s, 3H). MS (ESI) m/z 555.3 [M+H]⁺.

Example 27

(R)-(4-((4-(Cyclopentyloxy)-5-(2-methylbenzo[d]oxazol-6-yl)-7H-pyrrolo[2,3-d]pyrimidin-2-yl)amino)-3-methoxyphenyl)(2-(hydroxymethyl)aziridin-1-yl)methanone

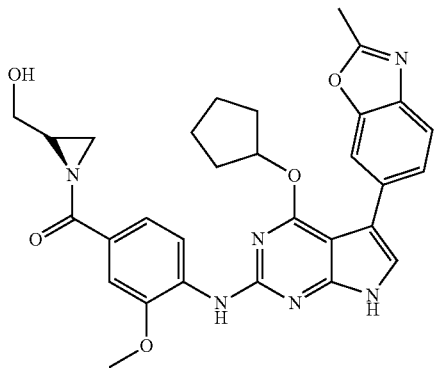

N-(2-Hydroxy-1-hydroxymethyl-ethyl)-3-methoxy-4-nitrobenzamide

To a mixture of 2-amino-propane-1,3-diol (1 equiv) in 1,4-dioxane (0.062 M) was added DIEA (2 equiv) and a solution of 3-methoxy-4-nitrobenzoyl chloride (1 equiv) in 1,4-dioxane (1.86 M) dropwise at room temperature. The resulting mixture was stirred at room temperature for 15 min. The solution was concentrated and the crude material was triturated in a 5:1 mixture of water:DCM (0.5 M), filtered, and dried to afford the title compound the solid (85% yield) that was used in the next step without further purification. MS (ESI) m/z 271.1 [M+H]⁺.

Methanesulfonic acid 1-(3-methoxy-4-nitrobenzoyl)-aziridin-2-ylmethyl ester

To a stirring solution of N-(2-Hydroxy-1-hydroxymethyl-ethyl)-3-methoxy-4-nitrobenzamide (1 equiv) in THF (0.16 M) was added DIEA (3 equiv) and methanesulfonyl chloride (2.5 equiv) dropwise at 0° C. The mixture was stirred at room temperature for 30 min. Water was added and the mixture was extracted with ethyl acetate. The combined organic layers were dried over anhydrous sodium sulfate, filtered and concentrated to afford methanesulfonic acid 3-methanesulfonyloxy-2-(3-methoxy-4-nitro-benzoylamino)-propyl, which was used without further purification and dissolved in THF (0.23 M). To the resulting solution was added sodium hydride (2 equiv) at 0° C. The resulting mixture was stirred at 50° C. for 2 h. The mixture was quenched with a saturated ammonium chloride and concentrated. The residue was triturated in diethyl ether (0.32 M) to afford the title compound (77% yield). MS (ESI) m/z 331.0 [M+H]⁺.

(R)-(2-(Hydroxymethyl)aziridin-1-yl)-(3-methoxy-4-nitrophenyl)-methanone and (S)-(2-(Hydroxymethyl)aziridin-1-yl)-(3-methoxy-4-nitrophenyl)-methanone To a solution of methanesulfonic acid 1-(3-methoxy-4-nitrobenzoyl)-aziridin-2-ylmethyl ester (1 equiv.) in DMSO (0.13 M) was added potassium acetate (15.8 equiv). The mixture was stirred at 100° C. for 16 h. After the reaction was completed, MeOH (0.052 M) and sodium hydroxide (2.1 equiv) were added. Then the mixture was stirred for another hour at room temperature. The resulting solution was concentrated and the residue was poured into water extracted with ethyl acetate. The combined organic layer was dried over anhydrous sodium sulfate, filtered and concentrated under reduced pressure. The title compound was purified by silica gel chromatography (2-5% MeOH in DCM) to afford the desired product (83% yield) as a yellow solid. MS (ESI) m/z 252.1 [M+H]⁺.

After chiral HPLC separation, (R)-(2-(Hydroxymethyl)aziridin-1-yl)-(3-methoxy-4-nitrophenyl)-methanone (37% yield) and (S)-(2-(Hydroxymethyl)aziridin-1-yl)-(3-methoxy-4-nitrophenyl)-methanone (37% yield) were obtained. (Stereochemistry was determined by resynthesis using stereoselectively prepared intermediates)

(R)-(4-Amino-3-methoxyphenyl)(2-(hydroxymethyl)aziridin-1-yl)methanone

To a solution of (R)-(2-(hydroxymethyl)aziridin-1-yl)(3-methoxy-4-nitrophenyl)methanone (1 equiv) in MeOH (0.12 M) was added 10% palladium on charcoal (67 weight %). The reaction mixture was stirred at 50° C. under hydrogen atmosphere (50 psi) overnight and then filtered through celite. The filtrate was concentrated and the residue was purified by silica gel chromatography (0-10% DCM in MeOH) to afford the desired product (92% yield) as a white solid. MS (ESI) m/z 223.2 [M+H]+.

(R)-(4-((4-(Cyclopentyloxy)-5-(2-methylbenzo[d]oxazol-6-yl)-7-((2-(trimethylsilyl)ethoxy)methyl)-7H-pyrrolo[2,3-d]pyrimidin-2-yl)amino)-3-methoxyphenyl)(2-(hydroxymethyl)aziridin-1-yl)methanone To a degassed mixture of 6-(2-chloro-4-(cyclopentyloxy)-7-((2-(trimethylsilyl)ethoxy)methyl)-7H-pyrrolo[2,3-d]pyrimidin-5-yl)-2-methylbenzo[d]oxazole (1 equiv), (R)-(4-amino-3-methoxyphenyl)(2-(hydroxymethyl)aziridin-1-yl)methanone (1.2 equiv) and cesium carbonate (3 equiv) in 1,4-dioxane (0.15 M) was added palladium acetate (0.3 equiv) and 2,2'-bis-diphenylphosphanyl-[1,1']binaphthalenyl (0.2 equiv). The reaction was stirred at 100° C. for 1 h. After the reaction was completed, the reaction mixture was cooled to room temperature and concentrated. The residue was purified by silica gel chromatography (2% MeOH in DCM) to afford the desired product (80% yield) as a white powder. MS (ESI) m/z 685.2 [M+H]+.

(R)-(4-((4-(Cyclopentyloxy)-5-(2-methylbenzo[d]oxazol-6-yl)-7H-pyrrolo[2,3-d]pyrimidin-2-yl)amino)-3-methoxyphenyl)(2-(hydroxymethyl)aziridin-1-yl)methanone (R)-(4-((4-(Cyclopentyloxy)-5-(2-methylbenzo[d]oxazol-6-yl)-7-((2-(trimethylsilyl)ethoxy)methyl)-7H-pyrrolo[2,3-d]pyrimidin-2-yl)amino)-3-methoxyphenyl)(2-(hydroxymethyl)aziridin-1-yl)methanone (1 equiv) was deprotected according to General Procedure A. The crude product was purified to afford the title compound (45% yield). $^1$H NMR (400 MHz, CHLOROFORM-d$_1$) δ ppm 9.09 (s, 1H), 8.68 (dd, J=15.5, 8.5 Hz, 1H), 7.81 (s, 1H), 7.72 (s, 1H), 7.64-7.50 (m, 3H), 7.39 (s, 1H), 6.99 (d, J=1.9 Hz, 1H), 5.75-5.59 (m, 1H), 4.59-4.28 (m, 3H), 4.11-4.02 (m, 1H), 3.98-3.87 (s, 3H), 3.69 (dd, J=11.4, 2.9 Hz, 1H), 2.66 (s, 3H), 2.06-1.82 (m, 4H), 1.80-1.52 (m, 4H). MS (ESI) m/z 555.3 [M+H]+.

Example 28

(R)-(4-(4-(Cyclopentyloxy)-5-(2-methylbenzo[d]oxazol-6-yl)-7H-pyrrolo[2,3-d]pyrimidin-2-ylamino)-3-methoxyphenyl)(2-methylaziridin-1-yl)methanone

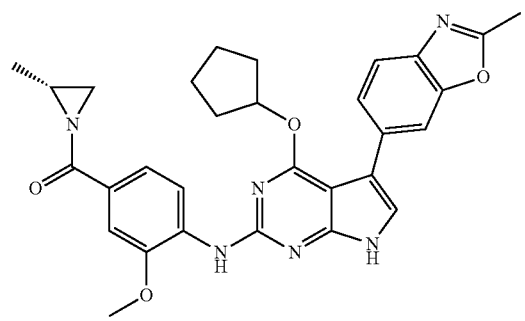

(R)-2-(3-Methoxy-4-nitrobenzamido)propyl methanesulfonate

To a solution of (R)—N-(1-hydroxypropan-2-yl)-3-methoxy-4-nitrobenzamide (1 equiv) in dry THF (0.2 M) was added trimethylamine (1.5 equiv) followed by addition of methanesulfonyl chloride (1.5 equiv). The reaction was stirred at room temperature overnight. The reaction mixture was washed with water (0.6 M) and brine (0.6 M) sequentially. The aqueous was extracted with ethyl acetate (0.23 M). The combined organic phase was dried over magnesium sulfate and filtered. The filtrate was concentrated. The crude material was purified by silica gel chromatography (20% ethyl acetate in petroleum ether) to afford the desired compound (62% yield). MS (ESI) m/z 253.1 [M+H]+.

(R)-(3-Methoxy-4-nitrophenyl)(2-methylaziridin-1-yl)methanone

To a solution of (R)-2-(3-methoxy-4-nitrobenzamido)propyl methanesulfonate (1 equiv) in THF (0.14 M) was added sodium hydride (4 equiv, 60% in mineral oil). The mixture was stirred at 60° C. for 5 h. The reaction was quenched with aqueous ammonium chloride, diluted with ethyl acetate (0.16 M), and then washed with water (0.27 M) and brine (0.27 M). The aqueous layer was extracted with ethyl acetate (0.16 M). The combined organic phase was dried over magnesium sulfate and filtered. The filtrate was concentrated. The crude compound was purified by silica gel chromatography (15% ethyl acetate in petroleum ether) to afford the desired compound (71% yield). MS (ESI) m/z 235.1 [M+H]+.

(R)-(4-Amino-3-methoxyphenyl)(2-methylaziridin-1-yl)methanone

To a solution of (R)-(3-methoxy-4-nitrophenyl)(2-methylaziridin-1-yl)methanone (1 equiv) in MeOH (0.22 M) was added 10% palladium on carbon (18 weight %). The reaction was stirred at room temperature for 1 h under hydrogen. The mixture was filtered through a pad of celite and concentrated to give the desired product (94% yield) as a white solid. MS (ESI) m/z 207.1 [M+H]+.

(R)-(4-(4-(Cyclopentyloxy)-5-(2-methylbenzo[d]oxazol-6-yl)-7-((2-(trimethylsilyl)ethoxy)methyl)-7H-pyrrolo[2,3-d]pyrimidin-2-ylamino)-3-methoxyphenyl)(2-methylaziridin-1-yl)methanone To a degassed mixture of 2-chloro-4-cyclopentyloxy-5-(2-methyl-benzooxazol-6-yl)-7-(2-trimethylsilanyl-ethoxymethyl)-7H-pyrrolo[2,3-d]pyrimidine (1 equiv), (R)-(4-amino-3-methoxyphenyl)(2-methylaziridin-1-yl)methanone (1.2 equiv) and cesium carbonate (2 equiv) in 1,4-dioxane (0.05M) were added palladium acetate (0.2 equiv) and 2,2'-bis-diphenylphosphanyl-[1,1']binaphthalenyl (0.4 equiv). The reaction mixture was refluxed at 110° C. for 1 h. The reaction mixture was filtered, concentrated under reduced pressure, and the crude product was purified by preparative thin layer chromatography (5% MeOH in DCM) to afford the desired product (75% yield). MS (ESI) m/z 669.1 [M+H]+.

(R)-(4-(4-(Cyclopentyloxy)-5-(2-methylbenzo[d]oxazol-6-yl)-7H-pyrrolo[2,3-d]pyrimidin-2-ylamino)-3-methoxyphenyl)(2-methylaziridin-1-yl)methanone (R)-(4-(4-(cyclopentyloxy)-5-(2-methylbenzo[d]oxazol-6-yl)-7-((2-(trimethylsilyl)ethoxy)methyl)-7H-pyrrolo[2,3-d]pyrimidin-2-ylamino)-3-methoxyphenyl)(2-methylaziridin-1-yl)methanone (1 equiv) was deprotected according to General Procedure A. The crude product was purified to afford the title compound (33% yield). $^1$H NMR (400 MHz, METHANOL-d$_4$) δ ppm 8.62 (d, J=8.0 Hz, 1H), 7.74 (s, 1H), 7.52 (d, J=8.0 Hz, 1H), 7.48-7.34 (m, 3H), 7.05 (s, 1H), 5.55 (br. s, 1H), 4.47 (d, J=8.4 Hz, 1H), 4.36-4.18 (m, 1H), 3.93 (m, 1H), 3.89 (s, 3H), 3.25 (s, 3H), 2.55 (s, 3H), 1.89 (m, 2H), 1.84-1.74 (m, 2H), 1.62 (m, 4H), 1.26 (d, J=6.4 Hz, 3H). MS (ESI) m/z 539.3 [M+H]$^+$.

Example 29

N-(5-Chloro-1-(tetrahydro-2H-pyran-4-yl)-1H-pyrazol-4-yl)-4-(cyclopentyloxy)-5-(2-methylbenzo[d]oxazol-6-yl)-7H-pyrrolo[2,3-d]pyrimidin-2-amine

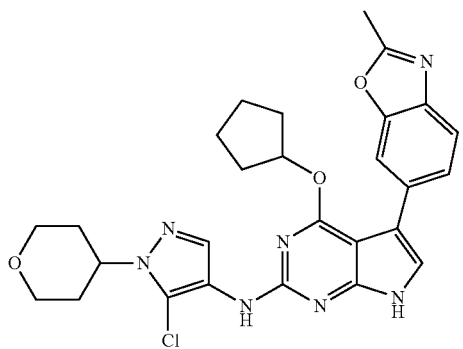 [SMILES: Cc1nc2ccc(-c3c[nH]c4nc(Nc5cnn(C6CCOCC6)c5Cl)nc(OC5CCCC5)c34)cc2o1]

4-Nitro-1-(tetrahydro-2H-pyran-4-yl)-1H-pyrazole

To a stirred solution of tetrahydro-2H-pyran-4-ol (1 equiv), 4-nitro-1H-pyrazole (1 equiv) and triphenylphosphine (1.2 equiv) in THF (1.0 M) was added diisopropyl azodicarboxylate (1.5 equiv) in THF (2.0 M) at 0° C. The mixture was stirred at room temperature overnight. The crude product was purified by silica gel chromatography (2.5% MeOH in DCM) to afford the desired product (23% yield) as a white solid. MS (ESI) m/z 198.1 [M+H]$^+$.

5-Chloro-4-nitro-1-(tetrahydro-2H-pyran-4-yl)-1H-pyrazole

To a solution of 4-nitro-1-(tetrahydro-2H-pyran-4-yl)-1H-pyrazole (1 equiv) in THF (0.5 M) was added dropwise a 1.0M solution of lithium bis(trimethylsilyl)amide (14 equiv) in THF at −78° C. The reaction was stirred at −78° C. for 30 min before hexachloroethane (1.5 equiv) in THF (1.15 M) was added. The reaction was stirred at −78° C. for 2.5 h then warmed to room temperature. The reaction was diluted with brine (0.23 M) and extracted with ethyl acetate. The combined extracts were washed with brine, dried over sodium sulfate, filtered and concentrated. The crude product was purified by silica gel chromatography (10-20% ethyl acetate in petroleum ether) to afford the desired product (81% yield) as a white solid. MS (ESI) m/z 232.1 [M+H]$^+$.

5-Chloro-1-(tetrahydro-2H-pyran-4-yl)-1H-pyrazol-4-amine

To a suspension of 5-chloro-4-nitro-1-(tetrahydro-2H-pyran-4-yl)-1H-pyrazole (1 equiv) and iron dust (3 equiv) in water (0.35 M) was added acetic acid (3.54 M). The mixture was heated to 90° C. for 1.5 h then cooled to room temperature. The reaction was quenched by addition of solid sodium bicarbonate and treated with ethyl acetate (0.06M) with continuous stirring. The mixture was filtered and the filter cake was rinsed with ethyl acetate. The combined filtrate was dried over sodium sulfate and concentrated under reduced pressure. The crude product was purified by silica gel chromatography (1.5% MeOH in DCM) to provide the desired product (52% yield) as a brown oil. MS (ESI) m/z 202.1 [M+H]$^+$.

N-(5-Chloro-1-(tetrahydro-2H-pyran-4-yl)-1H-pyrazol-4-yl)-4-(cyclopentyloxy)-5-(2-methylbenzo[d]oxazol-6-yl)-7-((2-(trimethylsilyl)ethoxy)-methyl)-7H-pyrrolo[2,3-d]pyrimidin-2-amine To a degassed mixture of 6-(2-chloro-4-(cyclopentyloxy)-7-((2-(trimethylsilyl)ethoxy)methyl)-7H-pyrrolo[2,3-d]pyrimidin-5-yl)-2-methylbenzo[d]oxazole (1 equiv), 5-chloro-1-(tetrahydro-2H-pyran-4-yl)-1H-pyrazol-4-amine (1.2 equiv), and cesium carbonate (2 equiv) in 1,4-dioxane (0.05M), was added palladium acetate (0.1 equiv) and 2,2'-bis-diphenyl-phosphanyl-[1,1']binaphthalenyl (0.3 equiv). The reaction was stirred at 100° C. for 2 h. Upon completion, the reaction mixture was cooled to room temperature and concentrated. The residue was purified by silica gel chromatography (1-2% MeOH in DCM) to afford the desired product as a yellow solid which was used in next step without further purification. MS (ESI) m/z 664.2 [M+H]$^+$.

N-(5-Chloro-1-(tetrahydro-2H-pyran-4-yl)-1H-pyrazol-4-yl)-4-(cyclopentyloxy)-5-(2-methylbenzo[d]oxazol-6-yl)-7H-pyrrolo[2,3-d]pyrimidin-2-amine N-(5-Chloro-1-(tetrahydro-2H-pyran-4-yl)-1H-pyrazol-4-yl)-4-(cyclopentyloxy)-5-(2-methylbenzo[d]oxazol-6-yl)-7-((2-(trimethylsilyl)ethoxy)methyl)-7H-pyrrolo[2,3-d]pyrimidin-2-amin (1 equiv) was deprotected according to General Procedure A. The product was purified to give the desired product (21% over two steps). $^1$H NMR (400 MHz, METHANOL-d$_4$) δ ppm 7.82 (s, 1H), 7.66 (s, 1H), 7.42 (d, J=8.4 Hz, 1H), 7.32 (d, J=8.4 Hz, 1H), 6.87 (s, 1H), 5.46-5.44 (m, 1H), 4.42-4.36 (m, 1H), 3.90-3.86 (m, 2H), 3.42-3.37 (t, J=11.2 Hz, 2H), 2.44 (s, 3H), 2.05-1.95 (m, 2H), 1.75-1.62 (m, 6H), 1.54-1.42 (m, 4H). MS (ESI) m/z 534.3 [M+H]$^+$.

Example 30

N-(5-Chloro-1-isopropyl-1H-pyrazol-4-yl)-4-(cyclopentyloxy)-5-(2-methylbenzo[d]oxazol-6-yl)-7H-pyrrolo[2,3-d]pyrimidin-2-amine

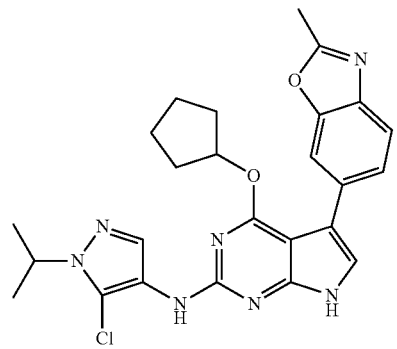 [SMILES: Cc1nc2ccc(-c3c[nH]c4nc(Nc5cnn(C(C)C)c5Cl)nc(OC5CCCC5)c34)cc2o1]

5-Chloro-1-isopropyl-4-nitro-1H-pyrazole

To a solution of 1-isopropyl-4-nitro-1H-pyrazole (1 equiv) in THF (0.65 M) was added dropwise a 1.0 M solution of lithium bis(trimethylsilyl)amide (2.6 equiv) in THF at −78° C. The reaction was stirred at −78° C. for 30 min before the addition of hexachloroethane (1.5 equiv) in THF (1.63 M). The reaction was stirred at −78° C. for 2.5 h then warmed to room temperature. The reaction was diluted with brine and extracted with ethyl acetate. The combined extracts were washed with brine, dried over sodium sulfate, filtered and concentrated. The crude product was purified by silica gel chromatography (10-20% ethyl acetate in petroleum ether) to afford the desired product (84% yield) as a white solid. MS (ESI) m/z 190.1 [M+H]$^+$.

5-Chloro-1-isopropyl-1H-pyrazol-4-amine

To a suspension of 5-chloro-1-isopropyl-4-nitro-1H-pyrazole (1 equiv) and iron dust (3 equiv) in EtOH (0.26 M) was added ammonium chloride (3 equiv). The mixture was heated to 80° C. for 20 h then cooled to room temperature. The reaction was quenched with solid sodium bicarbonate and treated with ethyl acetate (0.09 M) with continuous stirring. The mixture was filtered and the filter cake was rinsed with ethyl acetate. The combined filtrate was dried over sodium sulfate and concentrated under reduced pressure. The crude product was purified by silica gel chromatography (1.5% MeOH in DCM) to provide the desired product (76% yield) as a brown oil. MS (ESI) m/z 160.1 [M+H]$^+$.

N-(5-Chloro-1-isopropyl-1H-pyrazol-4-yl)-4-(cyclopentyloxy)-5-(2-methylbenzo[d]oxazol-6-yl)-7-((2-(trimethylsilyl)ethoxy)methyl)-7H-pyrrolo[2,3-d]pyrimidin-2-amine To a degassed mixture of 6-(2-chloro-4-(cyclopentyloxy)-7-((2-(trimethylsilyl)ethoxy)methyl)-7H-pyrrolo[2,3-d]pyrimidin-5-yl)-2-methylbenzo[d]oxazole (1 equiv), 5-chloro-1-isopropyl-1H-pyrazol-4-amine (1.3 equiv) and cesium carbonate (3 equiv) in 1,4-dioxane (0.06 M) was added palladium acetate (0.1 equiv) and 2,2'-bis-diphenylphosphanyl-[1,1']binaphthalenyl (0.3 equiv). The reaction was stirred at 100° C. for 2 h. Upon completion, the reaction mixture was cooled to room temperature, and concentrated. The residue was purified by silica gel chromatography (1-2% MeOH in DCM) to afford the desired product as a yellow solid, which was used in next step without further purification. MS (ESI) m/z 622.2 [M+H]$^+$.

N-(5-Chloro-1-isopropyl-1H-pyrazol-4-yl)-4-(cyclopentyloxy)-5-(2-methylbenzo[d]oxazol-6-yl)-7H-pyrrolo[2,3-d]pyrimidin-2-amine N-(5-Chloro-1-isopropyl-1H-pyrazol-4-yl)-4-(cyclopentyloxy)-5-(2-methylbenzo[d]oxazol-6-yl)-7-((2-(trimethylsilyl)ethoxy)methyl)-7H-pyrrolo[2,3-d]pyrimidin-2-amine (1 equiv) was deprotected according to General Procedure A. The product was purified to give the desired product (22% over two steps). $^1$H NMR (300 MHz, DMSO-d$_6$) δ ppm 8.23 (s, 1H), 7.90 (s, 1H), 7.79 (s, 1H), 7.68-7.46 (m, 2H), 7.24 (s, 1H), 5.70-5.45 (m, 1H), 4.74-4.52 (m, 1H), 2.61 (s, 3H), 1.98-1.81 (m, 2H), 1.77-1.58 (m, 6H), 1.40 (d, J=6.60 Hz, 6H). MS (ESI) m/z 492.2 [M+H]$^+$.

Example 31

N-(5-Chloro-1-ethyl-1H-pyrazol-4-yl)-4-(cyclopentyloxy)-5-(2-methylbenzo[d]oxazol-6-yl)-7H-pyrrolo[2,3-d]pyrimidin-2-amine

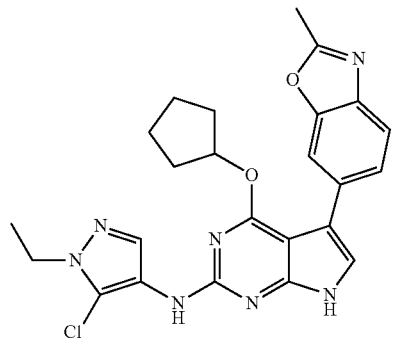 [SMILES: CCn1ncc(Nc2nc(OC3CCCC3)c3c(-c4ccc5nc(C)oc5c4)c[nH]c3n2)c1Cl]

5-Chloro-1-ethyl-4-nitro-1H-pyrazole

To a suspension of sodium hydride (1 equiv, 60% in mineral oil) in DMF (0.64 M) under nitrogen atmosphere was added a solution of 4-nitro-1H-pyrazole (0.83 equiv) in DMF (3.2 M) at 0° C. The reaction mixture was stirred at room temperature for 30 min before a solution of iodoethane (1 equiv) in DMF (3.2 M) was added. The mixture was stirred at room temperature for 2 h. Saturated aqueous ammonium chloride solution (0.32 M) was added, and the solvent was removed under reduced pressure to give the crude product, which was purified by silica gel column chromatography (25% ethyl acetate in petroleum ether) to give the desire product (82.2% yield) as white solid. MS (ESI) m/z 142.0 [M+H]$^+$.

1-Ethyl-4-nitro-1H-pyrazole

To a solution of 5-chloro-1-ethyl-4-nitro-1H pyrazole (1 equiv) in THF (0.6 M) was added dropwise a 1.0 M solution of lithium bis(trimethylsilyl)amide (2.6 equiv) at −78° C. The reaction mixture was stirred at −78° C. for 30 min before the addition of hexachloroethane (1.5 equiv) in THF (1.2 M). The mixture was stirred at −78° C. for 2.5 h then warmed to room temperature. The reaction was diluted with brine (1.8 M) and extracted with ethyl acetate. The combined extracts were washed with brine, dried over sodium sulfate, filtered and concentrated. The crude product was purified by silica gel chromatography (10-15% ethyl acetate in petroleum ether) to afford the desired product as a white solid (88.2% yield). MS (ESI) m/z 176.0 [M+H]$^+$.

5-Chloro-1-ethyl-1H-pyrazol-4-amine

To a suspension of 1-ethyl-4-nitro-1H pyrazole (1 equiv) and iron dust (5 equiv) in EtOH (0.285 M) was added ammonium chloride (10 equiv). The mixture was heated to 80° C. for 20 h then cooled to room temperature. The solvent was removed under reduced pressure to give crude material that was purified by silica gel chromatography (1.5% MeOH in DCM) to provide the desired product (30% yield) as a yellow oil. MS (ESI) m/z 146.0 [M+H]$^+$.

N-(5-Chloro-1-ethyl-1H-pyrazol-4-yl)-4-(cyclopentyloxy)-5-(2-methylbenzo[d]oxazol-6-yl)-7-((2-(trimethylsilyl)ethoxy)methyl)-7H-pyrrolo[2,3-d]pyrimidin-2-amine To a degassed mixture of 6-(2-chloro-4-(cyclopentyloxy)-7-((2-(trimethylsilyl)thoxy)methyl)-7H-pyrrolo[2,3-d]pyrimidin-5-yl)-2-methylbenzo[d]oxazole (1 equiv), 5-chloro-1-ethyl-1H-pyrazol-4-amine (1 equiv) and cesium carbonate (3 equiv) in 1,4-dioxane (0.2 M) was added palladium acetate (0.1 equiv) and 2,2'-bis-diphenylphosphanyl-[1,1'] binaphthalenyl (0.3 equiv). The reaction was stirred at 100° C. for 2 h. Upon completion, the reaction mixture was cooled to room temperature, and concentrated. The residue was purified by silica gel chromatography (15% ethyl acetate in petroleum ether) to afford the desired product (65.2% yield) as a yellow solid. MS (ESI) m/z 608.2 [M+H]$^+$.

N-(5-Chloro-1-ethyl-1H-pyrazol-4-yl)-4-(cyclopentyloxy)-5-(2-methylbenzo[d]oxazol-6-yl)-7H-pyrrolo[2,3-d]pyrimidin-2-amine N-(5-Chloro-1-ethyl-1H-pyrazol-4 yl)-4-(cyclopentyloxy)-5-(2-methylbenzo[d]oxazol-6-yl)-7-((2-(trimethylsilyl)ethoxy)methyl)-7H-pyrrolo[2,3-d]pyrimidin-2-amine (1 equiv) dissolved in 1 M tetrabutylammonium fluoride in THF (6.3 equiv). The mixture was stirred at 80° C. for 12 h. After cooling to room temperature, the reaction was diluted with THF (0.063 M) and cesium carbonate (5 equiv) was added. The solids were filtered and the filtrate was dried over sodium sulfate and concentrated. The crude product was purified to give the desired compound (19.7% yield). $^1$H NMR (400 MHz, CHLOROFORM-d$_1$) δ ppm 8.81 (br. s, 1H), 8.13 (s, 1H), 7.81 (s, 1H), 7.62-7.56 (m, 2H), 6.91 (s, 1H), 6.30 (s, 1H), 5.68-5.65 (m, 1H), 4.18 (q, J=7.2 Hz, 2H), 2.66 (s, 3H), 1.95-1.87 (m, 4H), 1.74-1.68 (m, 2H), 1.43 (t, J=7.2 Hz, 3H). MS (ESI) m/z 478.2 [M+H]$^+$.

Example 32

4-((4-(3-Cyanocyclobutoxy)-5-(4-(methylcarbamoyl)phenyl)-7H-pyrrolo[2,3-d]pyrimidin-2-yl)amino)-3-methoxy-N-(oxetan-3-yl)benzamide

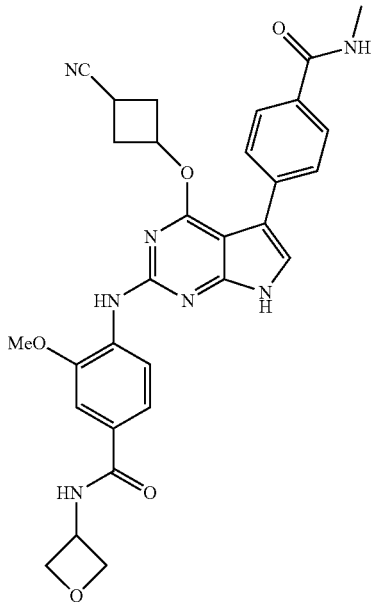 [SMILES: CNC(=O)c1ccc(-c2c[nH]c3nc(Nc4ccc(C(=O)NC5COC5)cc4OC)nc(OC4CC(C#N)C4)c23)cc1]

3-((2-Chloro-5-iodo-7-((2-(trimethylsilyl)ethoxy)methyl)-7H-pyrrolo[2,3-d]pyrimidin-4-yl)oxy)cyclobutanecarbonitrile 2,4-Dichloro-5-iodo-7-((2-(trimethylsilyl)ethoxy)methyl)-7H-pyrrolo[2,3-d]pyrimidine (1 equiv), 3-hydroxycyclobutanecarbonitrile (1.1 equiv), sodium 2-methylpropan-2-olate (1.2 equiv) and 1,4-dioxane (0.14 M) were combined in a sealable vessel with a stir bar. The resulting mixture was put under nitrogen atmosphere, sealed, stirred vigorously, and heated at 70° C. for 16 h. After cooling to room temperature, the reaction mixture was purified using silica gel chromatography (0 to 50% ethyl acetate in hexane) to give the title compound (77% yield). MS (ESI) m/z 505.0 [M+H]$^+$.

4-(2-Chloro-4-(3-cyanocyclobutoxy)-7-((2-(trimethylsilyl)ethoxy)-methyl)-7H-pyrrolo[2,3-d]pyrimidin-5-yl)-N-methylbenzamide 3-((2-Chloro-5-iodo-7-((2-(trimethylsilyl)ethoxy)methyl)-7H-pyrrolo[2,3-d]pyrimidin-4-yl)oxy)cyclobutanecarbonitrile (1 equiv), N-methyl-4-(4,4,5,5-tetramethyl-1,3,2-dioxaborolan-2-yl)benzamide (1.15 equiv), sodium carbonate (3 equiv) and [1,1'-bisdiphenylphosphino)ferrocene]-dichloropalladium(II), complex with dichloromethane (0.1 equiv) suspended in 1,4-dioxane/water, and flushed with nitrogen, were stirred at 85° C. for 2 h. The reaction mixture was purified using silica gel chromatography (0 to 100% ethyl acetate in hexane) to give the title compound (50% yield). MS (ESI) m/z 512.3 [M+H]$^+$.

4-((4-(3-Cyanocyclobutoxy)-5-(4-(methylcarbamoyl)phenyl)-7-((2-(trimethylsilyl)ethoxy)methyl)-7H-pyrrolo[2,3-d]pyrimidin-2-yl)amino)-3-methoxy-N-(oxetan-3-yl)benzamide A mixture of 4-(2-chloro-4-(3-cyanocyclobutoxy)-7-((2-(trimethylsilyl)ethoxy)methyl)-7H-pyrrolo[2,3-d]pyrimidin-5-yl)-N-methylbenzamide (1 equiv), 4-amino-3-methoxy-N-(oxetan-3-yl)benzamide (1.2 equiv), 2,2'-Bis(diphenylphosphino)-1,1'-binapthalene (0.2 equiv), cesium carbonate (5 equiv), and palladium acetate (0.1 equiv) in 1,4-dioxane (0.2 M) was purged with nitrogen and sealed. The reaction mixture was heated to 110° C. for 2 h. The reaction was filtered and solvents were removed under reduced pressure. The reaction mixture was purified using silica gel chromatography (0 to 100% ethyl acetate in hexane) to give the title compound (55% yield). MS (ESI) m/z 698.4 [M+H]$^+$.

4-((4-(3-Cyanocyclobutoxy)-5-(4-(methylcarbamoyl)phenyl)-7H-pyrrolo[2,3-d]pyrimidin-2-yl)amino)-3-methoxy-N-(oxetan-3-yl)benzamide 4-((4-(3-Cyanocyclobutoxy)-5-(4-(methylcarbamoyl)phenyl)-7-((2-(trimethylsilyl)ethoxy)methyl)-7H-pyrrolo[2,3-d]pyrimidin-2-yl)amino)-3-methoxy-N-(oxetan-3-yl)benzamide was deprotected according to General Procedure A. The solvent was removed under reduced pressure and the residue was purified to give the desired product (78% yield). $^1$H NMR (400 MHz, DMSO-d$_6$) δ ppm 2.44-2.46 (m, 1H) 2.81 (br. s., 3H) 2.97 (br. s., 2H) 3.23 (d, J=8.78 Hz, 1H) 3.46 (br. s., 1H) 3.60 (br. s., 1H) 3.95 (br. s., 3H) 4.26 (d, J=6.59 Hz, 2H) 4.44 (br. s., 1H) 4.84 (br. s., 1H) 5.32 (d, J=7.14 Hz, 1H) 7.42-7.58 (m, 3H) 7.75-7.92 (m, 5H) 8.42 (br. s., 1H) 8.59 (d, J=8.23 Hz, 1H) 11.99 (br. s., 1H). MS (ESI) m/z 567.9 [M+H]$^+$.

Example 33

4-((4-(Cyclopentyloxy)-5-(4-fluoro-2-methylbenzo[d]oxazol-6-yl)-7H-pyrrolo[2,3-d]pyrimidin-2-yl)amino)-3-methoxy-N-methylbenzamide

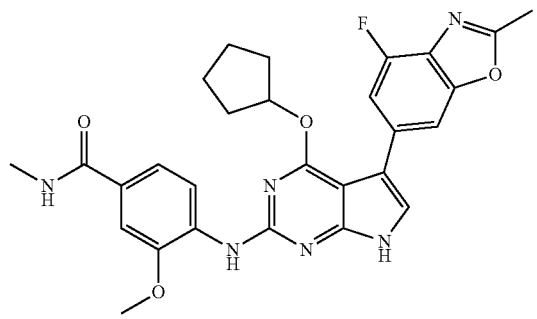

4-Bromo-2-fluoro-6-methoxyaniline hydrobromide

A solution of 2-fluoro-6-methoxyaniline (1 equiv) in acetic acid (0.7 M) was cooled to 5° C. A mixture of bromine (0.9 equiv) in acetic acid (0.7 M) was slowly added. The reaction mixture was stirred for 2 h at 5° C. The resulting solid was filtered, washed with ether, and dried to give the title compound (90% yield). $^1$H NMR (500 MHz, DMSO-$d_6$) δ ppm 3.84 (s, 3H) 6.79 (br. s., 2H) 6.97 (s, 1H) 7.06 (d, J=10.09 Hz, 1H). MS (ESI) m/z 219.9 [M+H]$^+$.

2-Amino-5-bromo-3-fluorophenol

To a suspension of 4-bromo-2-fluoro-6-methoxyaniline hydrobromide (1 equiv) in DCM (0.3 M) was added boron tribromide (2 equiv) in DCM at 0° C. The reaction mixture was stirred at room temperature for 2 h. After quenching, the reaction mixture was diluted with DCM then purified by silica gel chromatography (0 to 100% ethyl acetate in hexane) to give the title compound (92% yield). MS (ESI) m/z 205.9 [M+H]$^+$.

6-Bromo-4-fluoro-2-methylbenzo[d]oxazole

A mixture of 2-amino-5-bromo-3-fluorophenol (1 equiv), ytterbium(iii) trifluoromethanesulfonate (0.01 equiv), and trimethyl orthoacetate (1.2 equiv) in EtOH (1.3 M) was heated to 90° C. for 2 h. The reaction mixture was filtered through celite and washed with EtOH. The residual filtrate was concentrated in vacuo, then saturated aqueous sodium bicarbonate added and extracted with ethyl acetate. The combined organic layers were dried over sodium sulfate, filtered, and concentrated in vacuo. The residue was purified using silica gel chromatography (0 to 60% ethyl acetate in hexane) to afford the title compound (73% yield). MS (ESI) m/z 232.2 [M+H]$^+$.

6-(2-Chloro-4-(cyclopentyloxy)-7-((2-(trimethylsilyl)ethoxy)methyl)-7H-pyrrolo[2,3-d]pyrimidin-5-yl)-4-fluoro-2-methylbenzo[d]oxazole (2-Chloro-4-(cyclopentyloxy)-7-((2-(trimethylsilyl)ethoxy)methyl)-7H-pyrrolo[2,3-d]pyrimidin-5-yl)boronic acid (1 equiv), 6-bromo-4-fluoro-2-methylbenzo[d]oxazole (1.1 equiv), sodium carbonate (3 equiv) and [1,1'-Bisdiphenylphosphino)ferrocene]-dichloropalladium(II), complex with dichloromethane (0.1 equiv) were suspended in 1,4-dioxane/water, flushed with nitrogen, and stirred at 90° C. for 2 h. The reaction mixture was purified by silica gel chromatography (0 to 60% ethyl acetate in hexane) to give the title compound (72% yield). MS (ESI) m/z 517.3 [M+H]$^+$.

4-((4-(Cyclopentyloxy)-5-(4-fluoro-2-methylbenzo[d]oxazol-6-yl)-7-((2-(trimethylsilyl)ethoxy)methyl)-7H-pyrrolo[2,3-d]pyrimidin-2-yl)amino)-3-methoxy-N-methylbenzamide A mixture of 6-(2-chloro-4-(cyclopentyloxy)-7-((2-(trimethylsilyl)ethoxy)methyl)-7H-pyrrolo[2,3-d]pyrimidin-5-yl)-4-fluoro-2-methylbenzo[d]oxazole (1 equiv), 4-amino-3-methoxy-N-methylbenzamide (1.2 equiv), brettphos (0.15 equiv), cesium carbonate (3 equiv), and dicyclohexyl(2',6'-diisopropoxy-[1,1'-biphenyl]-2-yl)phosphine (0.15 equiv) in 1,4-dioxane (0.2 M) was purged with nitrogen and sealed. The reaction mixture was heated to 110° C. for 2 h. The reaction was filtered and solvents were removed under reduced pressure. The reaction mixture was purified using silica gel chromatography (0 to 100% ethyl acetate in hexane) to give the title compound (63% yield). MS (ESI) m/z 661.5 [M+H]$^+$.

4-((4-(Cyclopentyloxy)-5-(4-fluoro-2-methylbenzo[d]oxazol-6-yl)-7H-pyrrolo[2,3-d]pyrimidin-2-yl)amino)-3-methoxy-N-methylbenzamide 4-((4-(Cyclopentyloxy)-5-(4-fluoro-2-methylbenzo[d]oxazol-6-yl)-7-((2-(trimethylsilyl)ethoxy)methyl)-7H-pyrrolo[2,3-d]pyrimidin-2-yl)amino)-3-methoxy-N-methylbenzamide was deprotected according to General Procedure A. The solvent was removed under reduced pressure and the residue was purified to give the desired product (65% yield). $^1$H NMR (400 MHz, DMSO-$d_6$) δ ppm 1.62-1.77 (m, 4H) 1.86 (br. s., 2H) 1.96-2.04 (m, 2H) 2.64 (s, 3H) 2.80 (d, J=4.10 Hz, 3H) 3.96 (s, 3H) 5.70 (br. s., 1H) 7.48-7.54 (m, 3H) 7.59 (d, J=11.66 Hz, 1H) 7.74 (s, 1H) 7.84 (s, 1H) 8.31 (d, J=4.41 Hz, 1H) 8.62 (d, J=8.83 Hz, 1H) 11.93 (br. s., 1H); MS (ESI) m/z 531.3 [M+H]$^+$.

Example 34

N-Methyl-4-(2-((1-methyl-1H-pyrazol-5-yl)amino)-4-((tetrahydro-2H-pyran-4-yl)oxy)-7H-pyrrolo[2,3-d]pyrimidin-5-yl)benzamide

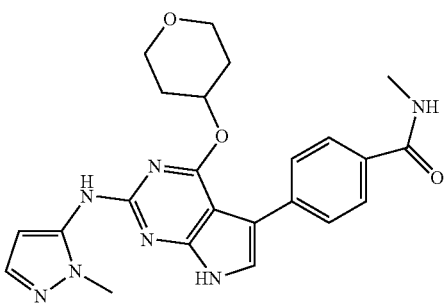 [SMILES: CNC(=O)c1ccc(-c2c[nH]c3nc(Nc4ccnn4C)nc(OC4CCOCC4)c23)cc1]

4-(2,4-Dichloro-7-((2-(trimethylsilyl)ethoxy)methyl)-7H-pyrrolo[2,3-d]pyrimidin-5-yl)-N-methylbenzamide 2,4-Dichloro-5-iodo-7-((2-(trimethylsilyl)ethoxy)methyl)-7H-pyrrolo[2,3-d]pyrimidine (1 equiv), (4-(methylcarbamoyl)phenyl)boronic acid (1.2 equiv), sodium carbonate (3 equiv) and [1,1'-bis(diphenylphosphino)ferrocene]-dichloropalladium(II) complex with dichloromethane (0.1 equiv) were combined in a 5:1 mixture of 1,4-dioxane and water (0.27 M). The mixture was heated to 90° C. for 3 h. The crude product was purified on silica gel (0-100% ethyl acetate in hexane) to give the title compound (68% yield) an orange solid. MS (ESI) m/z 451.2 [M]$^+$.

4-(2-Chloro-4-((tetrahydro-2H-pyran-4-yl)oxy)-7-((2-(trimethylsilyl)ethoxy)methyl)-7H-pyrrolo[2,3-d]pyrimidin-5-yl)-N-methylbenzamide A solution of 4-(2,4-dichloro-7-((2-(trimethylsilyl)ethoxy)methyl)-7H-pyrrolo[2,3-d]pyrimidin-5-yl)-N-methylbenzamide (1 equiv), tetrahydro-2H-pyran-4-ol (1.1 equiv), and sodium tert-butoxide (1.2 equiv) in 1,4-dioxane (0.22 M) were combined in a sealable flask. The reaction mixture was put under a nitrogen atmosphere, the sealable flask was sealed, and the mixture was stirred at 70° C. for 16 h. The mixture was cooled to room temperature and concentrated to afford an oil, which was suspended in DCM and purified using flash chromatography (0-50% ethyl acetate in hexane) to afford the desired product (89% yield) as a clear oil. MS (ESI) m/z 517.5 [M+1]$^+$.

N-Methyl-4-(2-((1-methyl-1H-pyrazol-5-yl)amino)-4-((tetrahydro-2H-pyran-4-yl)oxy)-7-((2-(trimethylsilyl)ethoxy)methyl)-7H-pyrrolo[2,3-d]pyrimidin-5-yl)benzamide A mixture of 4-(2-chloro-4-((tetrahydro-2H-pyran-4-yl)oxy)-7-((2-(trimethylsilyl)ethoxy)methyl)-7H-pyrrolo[2,3-d]pyrimidin-5-yl)-N-methylbenzamide (1 equiv), 1-methyl-1H-pyrazol-5-amine (1 equiv), and cesium carbonate (3 equiv) in 1,4-dioxane (0.1 M) was degassed with N$_2$ for 10 min. Then (9,9-dimethyl-9H-xanthene-4,5-diyl)bis(diphenylphosphine) (0.2 equiv), tris(dibenzylideneacetone)dipalladium(0) (0.1 equiv), were added to this mixture. The mixture was stirred at 140° C. for 1.5 h. After cooling to room temperature the reaction mixture was purified using flash chromatography (0-100% ethyl acetate in hexane then 0-20% MeOH in DCM) to give the title compound (39.4% yield) as an off white solid. MS (ESI) m/z 578.5 [M+1]$^+$.

N-Methyl-4-(2-((1-methyl-1H-pyrazol-5-yl)amino)-4-((tetrahydro-2H-pyran-4-yl)oxy)-7H-pyrrolo[2,3-d]pyrimidin-5-yl)benzamide N-Methyl-4-(2-((1-methyl-1H-pyrazol-5-yl)amino)-4-((tetrahydro-2H-pyran-4-yl)oxy)-7-((2-(trimethylsilyl)ethoxy)methyl)-7H-pyrrolo[2,3-d]pyrimidin-5-yl)benzamide was deprotected according to General Procedure A. The crude product was purified to afford the title compound (88% yield). 1H NMR (500 MHz, DMSO-d$_6$) δ ppm 11.78 (br. s., 1H) 8.92 (d, 1H) 8.41 (d, 1H) 7.85 (d, 2H) 7.80 (d, 2H) 7.34 (d, J=1.89 Hz, 2H) 6.23 (s, 1H) 5.30-5.56 (m, 1H) 3.74-3.89 (m, 2H) 3.69 (d, 3H) 3.43-3.58 (m, 2H) 2.81 (s, 3H) 2.02-2.13 (m, 2H) 1.70 (br. s., 2H). MS (ESI) m/z 448.3 [M+1]$^+$.

Example 35

4-((4-(3,3-Difluorocyclobutoxy)-5-(4-(methylcarbamoyl)phenyl)-7H-pyrrolo[2,3-d]pyrimidin-2-yl)amino)-3-methoxy-N-(oxetan-3-yl)benzamide

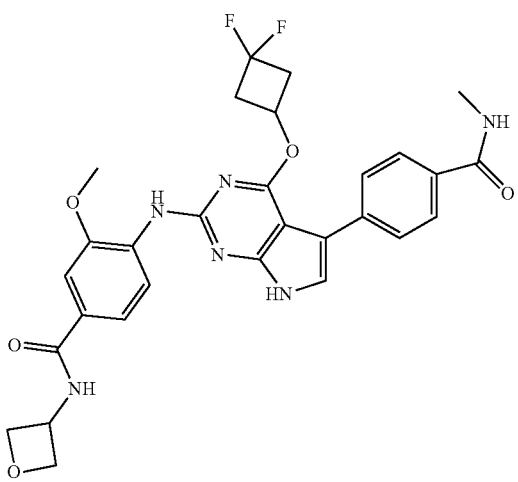 [SMILES: CNC(=O)c1ccc(-c2c[nH]c3nc(Nc4ccc(C(=O)NC5COC5)cc4OC)nc(OC4CC(F)(F)C4)c23)cc1]

4-(2-Chloro-4-(3,3-difluorocyclobutoxy)-7-((2-(trimethylsilyl)ethoxy)-methyl)-7H-pyrrolo[2,3-d]pyrimidin-5-yl)-N-methylbenzamide A solution of 4-(2,4-dichloro-7-((2-(trimethylsilyl)ethoxy)methyl)-7H-pyrrolo[2,3-d]pyrimidin-5-yl)-N-methylbenzamide (1 equiv), 3,3-difluorocyclobutan-1-ol (1.1 equiv), and sodium tert-butoxide (1.2 equiv) in 1,4-dioxane (0.22 M) were combined in a sealable flask. The reaction mixture was put under a nitrogen atmosphere, the sealable flask was sealed, and the mixture was stirred at 70° C. for 16 h. The mixture was cooled to room temperature and concentrated to afford an oil, which was suspended in DCM and purified using silica gel chromatography (0-50% ethyl acetate in hexane) to afford the title product (64.1% yield) as a clear oil. MS (ESI) m/z 523.4 [M+1]$^+$.

4-((4-(3,3-Difluorocyclobutoxy)-5-(4-(methylcarbamoyl)phenyl)-7-((2-(trimethylsilyl)ethoxy)methyl)-7H-pyrrolo[2,3-d]pyrimidin-2-yl)amino)-3-methoxy-N-(oxetan-3-yl)benzamide A mixture of 4-(2-chloro-4-(3,3-difluorocyclobutoxy)-7-((2-(trimethylsilyl)ethoxy)methyl)-7H-pyrrolo[2,3-d]pyrimidin-5-yl)-N-methylbenzamide (1 equiv), 4-amino-3-methoxy-N-(oxetan-3-yl)benzamide (1 equiv), and cesium carbonate (3 equiv) in 1,4-dioxane (0.1 M) was degassed with N$_2$ for 10 min. Then (9,9-dimethyl-9H-xanthene-4,5-diyl)bis(diphenylphosphine) (0.2 equiv), tris(dibenzylideneacetone)dipalladium(0) (0.1 equiv), were added to this mixture. The mixture was stirred at 140° C. for 1.5 h. After cooling to room temperature, the reaction mixture was purified using silica gel chromatography (0-100% ethyl acetate in hexane then 0-20% MeOH in DCM) to afford the title compound (78.3% yield). MS (ESI) m/z 709.4 [M+1]$^+$.

4-((4-(3,3-Difluorocyclobutoxy)-5-(4-(methylcarbamoyl)phenyl)-7H-pyrrolo[2,3-d]pyrimidin-2-yl)amino)-3-methoxy-N-(oxetan-3-yl)benzamide Tetrabutylammonium fluoride (5 equiv) was added to a stirred solution of 4-((4-(3,3-difluorocyclobutoxy)-5-(4-

(methylcarbamoyl)phenyl)-7-((2-(trimethylsilyl)ethoxy) methyl)-7H-pyrrolo[2,3-d]pyrimidin-2-yl)amino)-3-methoxy-N-(oxetan-3-yl)benzamide (1 equiv) in THF (20 mL). The resulting mixture was capped and stirred at 50° C. for 16 h. The crude product was purified to afford the title compound (53.9% yield). 1H NMR (500 MHz, DMSO-d$_6$) δ ppm 11.99 (s, 1H) 8.97 (d, J=6.62 Hz, 1H) 8.57 (d, 1H) 8.41 (d, J=4.41 Hz, 1H) 7.87 (d, J=10.09 Hz, 2H) 7.81 (d, 2H) 7.60 (d, 1H) 7.57-7.62 (m, 1H) 7.50 (d, J=2.21 Hz, 1H) 5.31-5.43 (m, 1H) 4.99-5.09 (m, 1H) 4.81 (t, J=6.94 Hz, 2H) 4.63 (t, J=6.31 Hz, 2H) 3.99 (s, 3H) 3.25 (br. s., 2H) 2.73-2.90 (m, 5H). MS (ESI) m/z 579.0 [M+1]$^+$.

Example 36

4-(4-Cyclobutoxy-2-((1,3-dimethyl-1H-pyrazol-4-yl) amino)-7H-pyrrolo[2,3-d]pyrimidin-5-yl)-N-methyl-benzamide

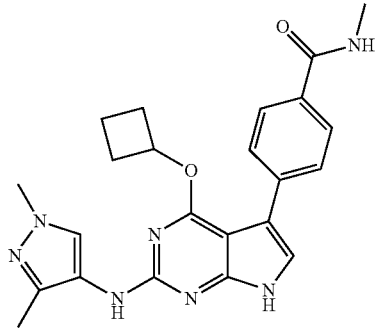 [SMILES: CNC(=O)c1ccc(-c2c[nH]c3nc(Nc4cn(C)nc4C)nc(OC4CCC4)c23)cc1]

4-(4-Cyclobutoxy-2-((1,3-dimethyl-1H-pyrazol-4-yl) amino)-7-((2-(trimethylsilyl)ethoxy)methyl)-7H-pyrrolo[2,3-d]pyrimidin-5-yl)-N-methylbenzamide To a degassed mixture of 4-(2-chloro-4-cyclobutoxy-7-((2-(trimethylsilyl)ethoxy)methyl)-7H-pyrrolo[2,3-d]pyrimidin-5-yl)-N-methylbenzamide (1 equiv), 1,3-dimethyl-1H-pyrazol-4-amine (1 equiv) and sodium tert-butoxide (2 equiv) in 1,4-dioxane (0.15 M) was added chloro[2-(dicyclohexylphosphino)-3,6-dimethoxy-2',4',6'-tri-1-propyl-1,1'-biphenyl][2-(2-aminoethyl)phenyl]palladium(II), (0.06 equiv) and dicyclohexyl(2',6'-diisopropoxy-[1,1'-biphenyl]-2-yl)phosphine (0.06 equiv). The reaction was stirred at 100° C. for 16 h. The reaction mixture was cooled to room temperature, and concentrated. The residue was purified by silica gel chromatography (0-5% MeOH in DCM) to afford the title compound (37% yield). MS (ESI) m/z 562.3 [M+1]$^+$.

4-(4-Cyclobutoxy-2-((1,3-dimethyl-1H-pyrazol-4-yl) amino)-7H-pyrrolo[2,3-d]pyrimidin-5-yl)-N-methyl-benzamide 4-(4-Cyclobutoxy-2-((1,3-dimethyl-1H-pyrazol-4-yl) amino)-7-((2-(trimethylsilyl)ethoxy)methyl)-7H-pyrrolo[2, 3-d]pyrimidin-5-yl)-N-methylbenzamide was deprotected according to General Procedure A. The resulting mixture was concentrated and the residue was purified to afford the title compound (77% yield). 1H NMR (400 MHz, DMSO-d$_6$) δ ppm 11.56 (br. s., 1H), 8.39 (d, J=4.73 Hz, 1H), 8.12 (s, 1H), 7.81 (q, J=8.51 Hz, 5H), 7.28 (s, 1H), 3.74 (s, 3H), 2.80 (d, J=4.41 Hz, 3H), 2.42 (br. s., 2H), 2.06-2.15 (m, 5H), 1.82 (q, J=10.09 Hz, 1H), 1.61-1.71 (m, 1H). MS (ESI) m/z 432.5 [M+1]$^+$.

Example 37

4-(2-((5-Chloro-1-methyl-1H-pyrazol-4-yl)amino)-4-cyclobutoxy-7H-pyrrolo[2,3-d]pyrimidin-5-yl)-N-methylbenzamide

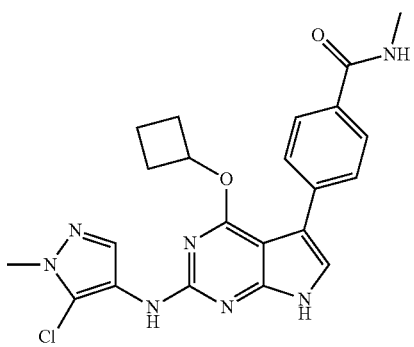

4-(2-((5-Chloro-1-methyl-1H-pyrazol-4-yl)amino)-4-cyclobutoxy-7-((2-(trimethylsilyl)ethoxy)methyl)-7H-pyrrolo[2,3-d]pyrimidin-5-yl)-N-methylbenzamide To a degassed mixture of 4-(2-chloro-4-cyclobutoxy-7-((2-(trimethylsilyl)ethoxy)methyl)-7H-pyrrolo[2,3-d]pyrimidin-5-yl)-N-methylbenzamide (1 equiv), 5-chloro-1-methyl-1H-pyrazol-4-amine hydrochloride (1 equiv) and cesium carbonate (5 equiv) in 1,4-dioxane (0.09 M) was added tris(dibenzylideneacetone)dipalladium(0) (0.1 equiv) and (dicyclohexyl(2',4',6'-triisopropyl-[1,1'-biphenyl]-2-yl) phosphine) (0.2 equiv). The reaction was stirred at 100° C. for 16 h. The reaction mixture was cooled to room temperature, and concentrated. The residue was purified by silica gel chromatography (0-5% MeOH in DCM) to afford the title compound (23% yield). MS (ESI) m/z 582.4 [M]$^+$.

4-(2-((5-Chloro-1-methyl-1H-pyrazol-4-yl)amino)-4-cyclobutoxy-7H-pyrrolo[2,3-d]pyrimidin-5-yl)-N-methylbenzamide 4-(2-((5-Chloro-1-methyl-1H-pyrazol-4-yl)amino)-4-cyclobutoxy-7-((2-(trimethylsilyl)ethoxy)methyl)-7H-pyrrolo [2,3-d]pyrimidin-5-yl)-N-methylbenzamide was deprotected according to General Procedure A. The resulting mixture was concentrated and the residue was purified to afford the title compound (88% yield). $^1$H NMR (400 MHz, DMSO-d$_6$) δ ppm 11.65 (s, 1H), 8.39 (d, J=4.94 Hz, 1H), 8.25 (s, 1H), 7.81-7.85 (m, 2H), 7.77-7.80 (m, 2H), 7.72 (s, 1H), 7.30 (d, J=2.74 Hz, 1H), 5.25-5.31 (m, 1H), 3.80 (s, 3H), 2.80 (d, J=4.39 Hz, 3H), 2.42 (br. s., 1H), 2.05-2.14 (m, 2H), 1.81 (d, J=10.43 Hz, 1H), 1.60-1.68 (m, 1H); MS (ESI) m/z 452.2 [M+1]$^+$.

Example 38

3-Chloro-4-((4-(cyclopentyloxy)-5-(2-methylbenzo[d]oxazol-6-yl)-7H-pyrrolo[2,3-d]pyrimidin-2-yl)amino)-N-methylbenzamide

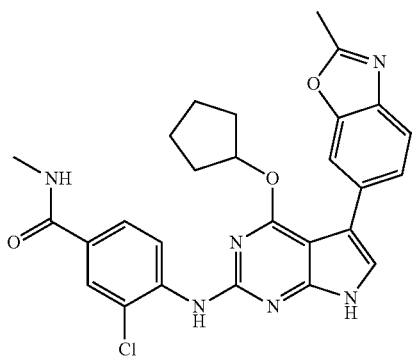 [SMILES: CNC(=O)c1ccc(Nc2nc(OC3CCCC3)c3c(-c4ccc5nc(C)oc5c4)c[nH]c3n2)c(Cl)c1]

3-Chloro-4-((4-(cyclopentyloxy)-5-(2-methylbenzo[d]oxazol-6-yl)-7-((2-(trimethylsilyl)ethoxy)methyl)-7H-pyrrolo[2,3-d]pyrimidin-2-yl)amino)-N-methylbenzamide To a degassed mixture of 6-(2-chloro-4-(cyclopentyloxy)-7-((2-(trimethylsilyl)ethoxy)methyl)-7H-pyrrolo[2,3-d]pyrimidin-5-yl)-2-methylbenzo[d]oxazole (1 equiv), 4-amino-3-chloro-N-methylbenzamide (1 equiv) and cesium carbonate (3 equiv) in 1,4-dioxane (0.1 M) was added palladium acetate (0.2 equiv) and 2,2'-bis-diphenylphosphanyl-[1,1']binaphthalenyl (0.2 equiv). The reaction was stirred at 100° C. for 4 h. The reaction mixture was cooled to room temperature, and concentrated. The residue was purified by silica gel chromatography (0-5% MeOH in DCM) to afford the title compound (65% yield). MS (ESI) m/z 648.2 [M+1]$^+$.

3-Chloro-4-((4-(cyclopentyloxy)-5-(2-methylbenzo[d]oxazol-6-yl)-7H-pyrrolo[2,3-d]pyrimidin-2-yl)amino)-N-methylbenzamide 3-Chloro-4-((4-(cyclopentyloxy)-5-(2-methylbenzo[d]oxazol-6-yl)-7-((2-(trimethylsilyl)ethoxy)methyl)-7H-pyrrolo[2,3-d]pyrimidin-2-yl)amino)-N-methylbenzamide was deprotected according to General Procedure A. The solution was concentrated and the crude material was purified to give the title compound (64% yield). $^1$H NMR (400 MHz, DMSO-d$_6$) δ ppm 11.87 (s, 1H), 8.43-8.50 (m, 2H), 8.15 (s, 1H), 7.97 (d, J=1.95 Hz, 1H), 7.94 (d, J=1.17 Hz, 1H), 7.83 (dd, J=8.59, 1.95 Hz, 1H), 7.64-7.67 (m, 1H), 7.58-7.62 (m, 1H), 7.41 (d, J=2.34 Hz, 1H), 5.66 (tt, J=5.52, 2.69 Hz, 1H), 2.79 (d, J=4.30 Hz, 3H), 2.62 (s, 3H), 1.90-2.00 (m, 2H), 1.77-1.86 (m, 2H), 1.58-1.74 (m, 4H). MS (ESI) m/z 517.6 [M+1]$^+$.

Example 39A (S)—N,N,3-Trimethyl-4-((5-(2-methylbenzo[d]oxazol-6-yl)-4-((tetrahydrofuran-3-yl)oxy)-7H-pyrrolo[2,3-d]pyrimidin-2-yl)amino)benzamide

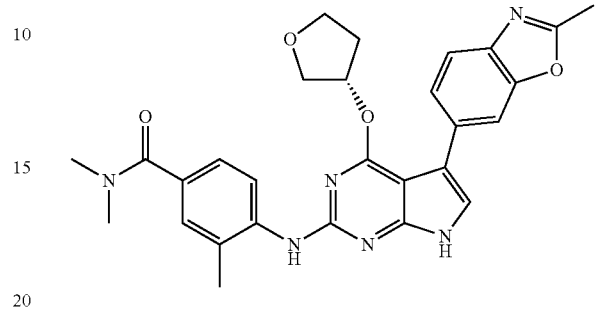

Example 39B (R)—N,N,3-Trimethyl-4-((5-(2-methylbenzo[d]oxazol-6-yl)-4-((tetrahydrofuran-3-yl)oxy)-7H-pyrrolo[2,3-d]pyrimidin-2-yl)amino)benzamide 6-(2-Chloro-4-((tetrahydrofuran-3-yl)oxy)-7-((2-(trimethylsilyl)ethoxy)-methyl)-7H-pyrrolo[2,3-d]pyrimidin-5-yl)-2-methylbenzo[d]oxazole To a suspension of sodium hydride (1.2 equiv, 60% by weight in mineral oil) in THF (0.3 M) under nitrogen atmosphere was added tetrahydrofuran-3-ol (1.5 equiv) in THF (0.6 M) at 0° C. The resulting reaction mixture was stirred at 0° C. for 20 min. A solution of 6-(2,4-dichloro-7-((2-(trimethylsilyl)ethoxy)methyl)-7H-pyrrolo[2,3-d]pyrimidin-5-yl)-2-methylbenzo[d]oxazole (1 equiv) in THF (0.6 M) was added and the resulting reaction mixture was stirred at room temperature for 3 h. The reaction mixture was quenched with saturated aqueous ammonium chloride solution (0.6 M) and the organic solvents were removed under reduced pressure. The resulting residue was diluted with water and extracted with ethyl acetate. The combined organic layers were washed with brine, dried over anhydrous sodium sulfate, and filtered. The filtrate was evaporated under reduced pressure and the crude product was purified by silica gel chromatography (15% ethyl acetate in petroleum ether) to afford the title compound (83% yield). MS (ESI) m/z 501.1 [M+H]$^+$.

N,N,3-Trimethyl-4-((5-(2-methylbenzo[d]oxazol-6-yl)-4-((tetrahydrofuran-3-yl)oxy)-7-((2-(trimethylsilyl)ethoxy)methyl)-7H-pyrrolo[2,3-d]pyrimidin-2-yl)amino)benzamide To a suspension of 6-(2-chloro-4-((tetrahydrofuran-3-yl)oxy)-7-((2-(trimethylsilyl)ethoxy)methyl)-7H-pyrrolo[2,3-d]pyrimidin-5-yl)-2-methylbenzo[d]oxazole (1 equiv) in 1,4-dioxane (0.24 M) was added 4-amino-N,N,3-trimethylbenzamide (1 equiv), cesium carbonate (3 equiv), palladium acetate (0.3 equiv) and 2,2'-bis-diphenylphosphanyl-[1,1'] binaphthalene (0.6 equiv). The resulting reaction mixture was refluxed at 110° C. for 3 h. The reaction mixture was filtered and concentrated under reduced pressure. The crude product was purified by silica gel chromatography (5% MeOH in DCM) to afford the title compound (72% yield). MS (ESI) m/z 643.1 [M+H]$^+$.

(R)—N,N,3-Trimethyl-4-((5-(2-methylbenzo[d]oxazol-6-yl)-4-((tetrahydrofuran-3-yl)oxy)-7H-pyrrolo[2,3-d]pyrimidin-2-yl)amino)benzamide and (S)—N,N,3-Trimethyl-4-((5-(2-methylbenzo[d]oxazol-6-yl)-4-((tetrahydrofuran-3-yl)oxy)-7H-pyrrolo[2,3-d]pyrimidin-2-yl)amino)benzamide A solution of N,N,3-trimethyl-4-((5-(2-methylbenzo[d]oxazol-6-yl)-4-((tetrahydrofuran-3-yl)oxy)-7-((2-(trimethylsilyl)ethoxy)methyl)-7H-pyrrolo[2,3-d]pyrimidin-2-yl)amino)benzamide was deprotected according to General Procedure A. The mixture was concentrated to dryness and the residue was purified to afford the racemic products (90% yield), which were separated by standard chiral separation methods to afford the title compounds. Stereochemistry was determined based on analytical characterization of similar compounds described herein.

(S)—N,N,3-Trimethyl-4-((5-(2-methylbenzo[d]oxazol-6-yl)-4-((tetrahydrofuran-3-yl)oxy)-7H-pyrrolo[2,3-d]pyrimidin-2-yl)amino)benzamide $^1$H NMR (400 MHz, CHLOROFORM-d$_1$) δ ppm 8.99 (s, 1H), 8.30-8.23 (m, 1H), 7.79 (s, 1H), 7.60-7.54 (m, 1H), 7.33-7.32 (m, 2H), 6.93-6.92 (m, 1H), 6.73 (s, 1H), 5.76-5.73 (m, 1H), 4.12-4.10 (m, 1H), 4.00-3.97 (m, 1H), 3.94-3.90 (m, 2H), 3.06 (m, 6H), 2.67 (s, 3H), 2.37 (s, 3H), 2.25-2.14 (m, 2H), 1.88-1.83 (m, 2H). MS (ESI) m/z 513.2 [M+H]$^+$. Conditions for Chiral HPLC: Column: CHIRALCEL OJ-H, 5 μm, 0.46 cm I.D.×15 cm L; Injection: 2 μL; Mobile phase: MeOH:acetonitrile:diethylamine=80:20:0.1; Flow rate: 1.0 mL/min; 254 nm; T=30° C. Retention time: 3.03 min. e.e=99.9%.

(R)—N,N,3-Trimethyl-4-((5-(2-methylbenzo[d]oxazol-6-yl)-4-((tetrahydrofuran-3-yl)oxy)-7H-pyrrolo[2,3-d]pyrimidin-2-yl)amino)benzamide $^1$H NMR (400 MHz, CHLOROFORM-d$_1$) δ ppm 8.90 (s, 1H), 8.30-8.28 (m, 1H), 7.79 (s, 1H), 7.62-7.54 (m, 2H), 7.33-7.32 (m, 2H), 6.94 (s, 1H), 6.73 (s, 1H), 5.76-5.73 (m, 1H), 4.12-4.08 (m, 1H), 4.00-3.99 (m, 1H), 3.97-3.90 (m, 2H), 3.07 (m, 6H), 2.66 (s, 3H), 2.37 (s, 3H), 2.23-2.16 (m, 2H). MS (ESI) m/z 513.2 [M+H]$^+$. Conditions for Chiral HPLC: Column: CHIRALCEL OJ-H, 5 μm, 0.46 cm I.D.×15 cm L; Injection: 2 μL; Mobile phase: MeOH:acetonitrile:diethylamine=80:20:0.1; Flow rate: 1.0 mL/min; 254 nm; T=30° C. Retention time: 4.64 min; e.e=100%.

ASSAYS

Cell Assays

Cell Titer Glo Proliferation Assay.

Triple negative breast cancer cell line CAL51 was purchased from DSMZ. Breast cancer cell lines MDA-MB-231, MDA-MB-468, BT-474, MDA-MB-361 and ZR-75-30 cells were purchased from the American Tissue Culture Collection. Allcell lines were maintained in growth media consisting of 90% high glucose Dulbecco's Modified Eagle Medium or RPMI1640 (Invitrogen), 10% fetal bovine serum (Hyclone), and 2 mM L-glutamine (Invitrogen). All cells were cultured at 37° C. in 95% air and 5% CO$_2$. Cells were plated at a density of 3,000 (CAL51, MDA-MB-231 and MDA-MB-468), or 10,000 (BT-474, MDA-MB-361 and ZR-75-30) cells per well in a 96-well plate in 100 μL of growth media. After overnight culture, compound stock (30 mM) was diluted serially in DMSO, further diluted in growth media, and was added to each well as a 10× concentrated solution in a volume of 11 μL, mixed, and allowed to incubate with cells. The compound vehicle (DMSO) was maintained at a final concentration of 0.2% in all wells. After 72 h, 100 μL of Cell Titer Glo solution (Promega) was added to each well of the 96-well plate. The plate was placed on a shaker for 2 minutes. After 10 minutes incubation, the luminescence signal was detected with Envision microplate reader (Perkin Elmer). The IC$_{50}$ values were calculated as the concentration of compound at which the level of luminescence signal was reduced to 50% of the signal window. Table 1 shows the effect of Pyrrolopyrimidine compounds on CAL51 cell proliferation. Certain compounds of Table 1 affect the proliferation of MDA-MB-231, MDA-MB-468, BT-474, MDA-MB-361 and/or ZR-75-30 cells with an IC$_{50}$ value ranging from 0.01-10 μM.

NucView 488 Caspase 3 Apoptosis Assay

Triple negative breast cancer cell line CAL51 was purchased from DSMZ. Breast cancer cell lines MDA-MB-231, MDA-MB-468, BT-474, MDA-MB-361 and ZR-75-30 cells were purchased from the American Tissue Culture Collection. All cell lines were maintained in growth media consisting of 90% high glucose Dulbecco's Modified Eagle Medium or RPMI1640 (Invitrogen), 10% fetal bovine serum (Hyclone), and 2 mM L-glutamine (Invitrogen). All cells were cultured at 37° C. in 95% air and 5% CO$_2$. Cells were plated at a density of 3,000 (CAL51, MDA-MB-231 and MDA-MB-468), or 10,000 (BT-474, MDA-MB-361 and ZR-75-30) cells per well in a 96-well Flat Bottom plates (Perkin Elmer View Plate) in 100 μL of growth media. After overnight culture, compound stock (30 mM) was diluted serially in DMSO, further diluted in growth media, and was added to each well as a 10× concentrated solution in a volume of 11 μL, mixed, and allowed to incubate with cells. The compound vehicle (DMSO) was maintained at a final concentration of 0.2% in all wells. Two hours after compound addition, NucView 488 substrate (Biotium) was diluted 1:50 with PBS (Invitrogen) and 10 μL of the diluted substrate was added to each well. Plates were placed in the IncuCyte-FLR instrument (Essen Biosciences) and fluorescence readings were taken every 2 h, starting at 2 h post compound treatment and up to 72 h. The fold of apoptosis was calculated as the ratio of fluorescence signal between each compound treated well and DMSO treated well. For example certain compounds of Table 1 induced 2-10 fold apoptosis in the CAL51 cell line.

Animal Models

Breast Cancer Xenograft Model.

For xenograft model studies human breast cancer cell lines were injected into SCID (severe combined immunodeficiency) mice. Breast cancer cell lines were propagated in culture in vitro. Tumor bearing animals were generated by injecting precisely determined numbers of cells into mice. Following inoculation of animals, the tumors were allowed to grow to a certain size prior to randomization. The mice bearing xenograft tumors ranging between 100 and 400 mm$^3$ were pooled together and randomized into various treatment groups. Primary tumorgrafts were propagated in vivo. Tumor fragments from donor mice were implanted into small numbers of mice for maintenance, or larger numbers of mice for study initiation. A typical efficacy study design involved administering one or more compounds at various dose levels to tumor-bearing mice. Additionally, reference chemotherapeutic agents (positive control) and negative controls were similarly administered and maintained. Routes of administration can include subcutaneous (SC), intraperitoneal (IP), intravenous (IV), intramuscular (IM) and oral (PO). Tumor measurements and body weights were taken over the course of the study and morbidity and mortality were recorded. Necropsy, histopathology, and PCR can also be performed to enhance understanding of disease and drug action.

Some of the typical human breast cancer cell lines that were or can be used in the above xenograft models are: the MDA-MB-231, CAL-51, BT-474, MCF7, MDA-MB-435, and T-47D cell lines.

For a typical xenograft study, SCID mice bearing tumors were randomized and dosed with compounds ranging from, for example, 100 mg/kg to 0.1 mg/kg with different dose scheduling, including, but not limited to, qd, q2d, q3d, q5d, q7d and bid. The compounds were formulated in various types of formulation. Some of the formulations include but not limiting to CMC-Tween (0.5% CMC/0.25% Tween), NPS (n-methylpyrrolidone, PEG, Saline), ESPS (Ethanol, PEG, Solutol, Saline), NSPS (n-methylpyrrolidone, PEG, Solutol, saline) and delivered orally, intraperitoneally or intravenously. The mice were dosed for 2-4 weeks. Tumors were measured twice a week using calipers and tumor volumes were calculated using the formula of $W^2 \times L/2$. Example Xenograft models tested included CAL-51 and MDA-MB-231.

In this breast cancer model, Pyrrolopyrimidine Compounds have, or are expected to have, an $ED_{50}$ value of <100 mg/kg, with some compounds having an $ED_{50}$ of <10 mg/kg and others an $ED_{50}$ of <1 mg/kg.

Activity Tables

Each of the compounds in Table 1 was tested in one or more of the cell assays and was found to have activity therein, with all of the compounds having an $IC_{50}$ below 10 μM in the assay, with some compounds having an $IC_{50}$ below 100 nM (activity level D), some an $IC_{50}$ between 100 nM and 400 nM (activity level C), some an $IC_{50}$ between 400 nM and 1 μM (activity level B), and others having an $IC_{50}$ between 1 μM and 10 μM (activity level A).

TABLE 1

| Cmpd No. | Structure | Name | Obs. MH$^+$ | Act. Level |
|---|---|---|---|---|
| 1 | 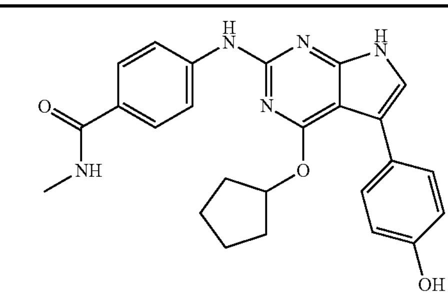 | 4-(4-(cyclopentyloxy)-5-(4-hydroxyphenyl)-7H-pyrrolo[2,3-d]pyrimidin-2-ylamino)-N-methylbenzamide | 444.4 | D |
| 2 | 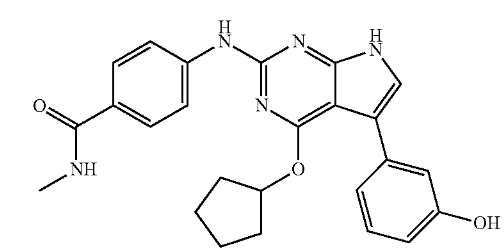 [SMILES: CNC(=O)c1ccc(Nc2nc(OC3CCCC3)c3c(-c4cccc(O)c4)c[nH]c3n2)cc1] | 4-(4-(cyclopentyloxy)-5-(3-hydroxyphenyl)-7H-pyrrolo[2,3-d]pyrimidin-2-ylamino)-N-methylbenzamide | 444.2 | D |
| 3 | 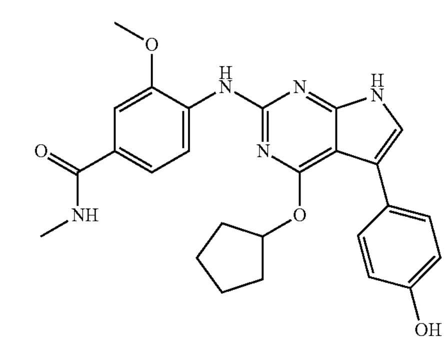 [SMILES: CNC(=O)c1ccc(Nc2nc(OC3CCCC3)c3c(-c4ccc(O)cc4)c[nH]c3n2)c(OC)c1] | 4-(4-(cyclopentyloxy)-5-(4-hydroxyphenyl)-7H-pyrrolo[2,3-d]pyrimidin-2-ylamino)-3-methoxy-N-methylbenzamide | 474.2 | D |

TABLE 1-continued

| Cmpd No. | Structure | Name | Obs. MH⁺ | Act. Level |
|---|---|---|---|---|
| 4 | 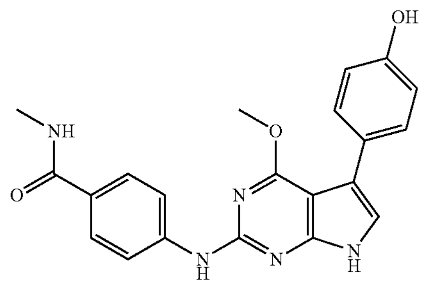 [SMILES: CNC(=O)c1ccc(Nc2nc(OC)c3c(-c4ccc(O)cc4)c[nH]c3n2)cc1] | 4-(5-(4-hydroxyphenyl)-4-methoxy-7H-pyrrolo[2,3-d]pyrimidin-2-ylamino)-N-methylbenzamide | 390.1 | D |
| 5 | 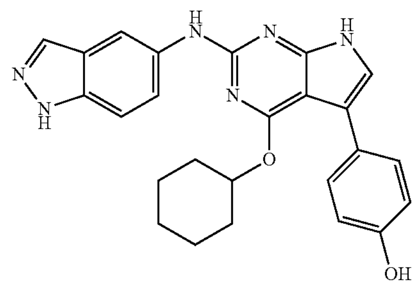 [SMILES: Oc1ccc(-c2c[nH]c3nc(Nc4ccc5[nH]ncc5c4)nc(OC4CCCCC4)c23)cc1] | 4-(2-(1H-indazol-5-ylamino)-4-(cyclohexyloxy)-7H-pyrrolo[2,3-d]pyrimidin-5-yl)phenol | 441.1 | D |
| 6 | 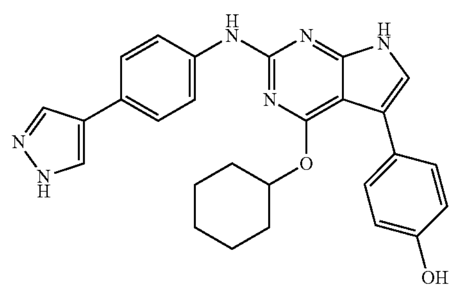 [SMILES: Oc1ccc(-c2c[nH]c3nc(Nc4ccc(-c5cn[nH]c5)cc4)nc(OC4CCCCC4)c23)cc1] | 4-(2-(4-(1H-pyrazol-4-yl)phenylamino)-4-(cyclohexyloxy)-7H-pyrrolo[2,3-d]pyrimidin-5-yl)phenol | 467.2 | D |
| 7 | 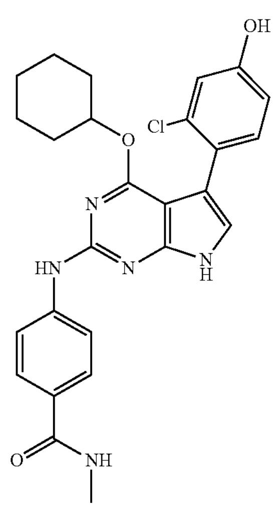 [SMILES: CNC(=O)c1ccc(Nc2nc(OC3CCCCC3)c3c(-c4ccc(O)cc4Cl)c[nH]c3n2)cc1] | 4-(5-(2-chloro-4-hydroxyphenyl)-4-(cyclohexyloxy)-7H-pyrrolo[2,3-d]pyrimidin-2-ylamino)-N-methylbenzamide | 492.3 | C |

TABLE 1-continued

| Cmpd No. | Structure | Name | Obs. MH+ | Act. Level |
|---|---|---|---|---|
| 8 | 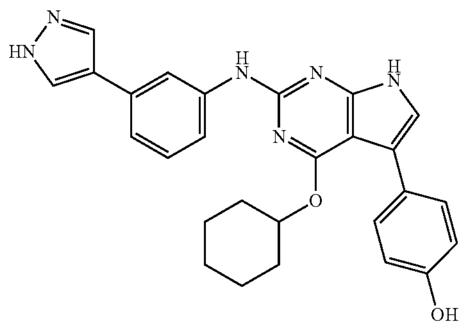 [SMILES: Oc1ccc(-c2c[nH]c3nc(Nc4cccc(-c5cn[nH]c5)c4)nc(OC4CCCCC4)c23)cc1] | 4-(2-(3-(1H-pyrazol-4-yl)phenylamino)-4-(cyclohexyloxy)-7H-pyrrolo[2,3-d]pyrimidin-5-yl)phenol | 467.1 | D |
| 9 | 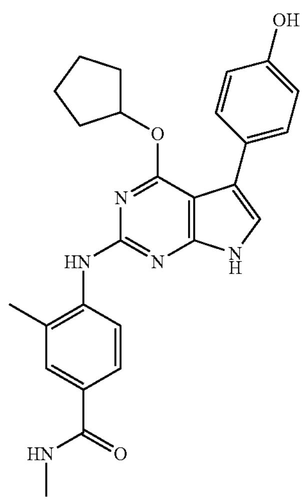 [SMILES: CNC(=O)c1ccc(Nc2nc(OC3CCCC3)c3c(-c4ccc(O)cc4)c[nH]c3n2)c(C)c1] | 4-(4-(cyclopentyloxy)-5-(4-hydroxyphenyl)-7H-pyrrolo[2,3-d]pyrimidin-2-ylamino)-N,3-dimethylbenzamide | 458.7 | D |
| 10 | 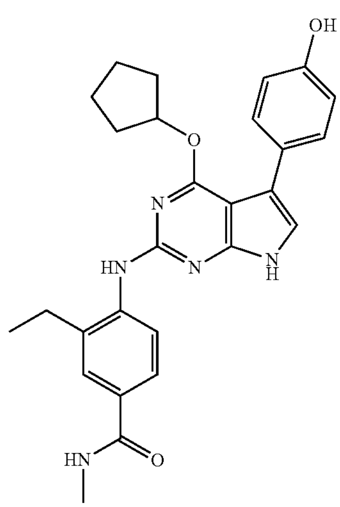 [SMILES: CCc1cc(C(=O)NC)ccc1Nc1nc(OC2CCCC2)c2c(-c3ccc(O)cc3)c[nH]c2n1] | 4-(4-(cyclopentyloxy)-5-(4-hydroxyphenyl)-7H-pyrrolo[2,3-d]pyrimidin-2-ylamino)-3-ethyl-N-methylbenzamide | 472.7 | C |

TABLE 1-continued

| Cmpd No. | Structure | Name | Obs. MH+ | Act. Level |
|---|---|---|---|---|
| 11 | 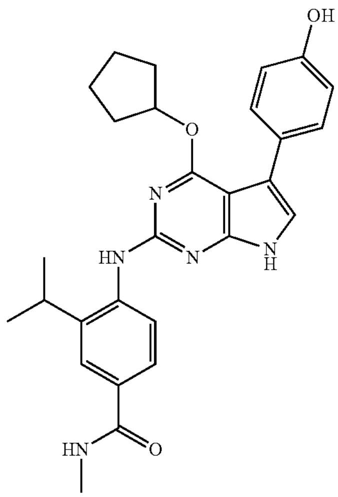 [SMILES: CNC(=O)c1ccc(Nc2nc(OC3CCCC3)c3c(-c4ccc(O)cc4)c[nH]c3n2)c(C(C)C)c1] | 4-(4-(cyclopentyloxy)-5-(4-hydroxyphenyl)-7H-pyrrolo[2,3-d]pyrimidin-2-ylamino)-3-isopropyl-N-methylbenzamide | 486.2 | D |
| 12 | 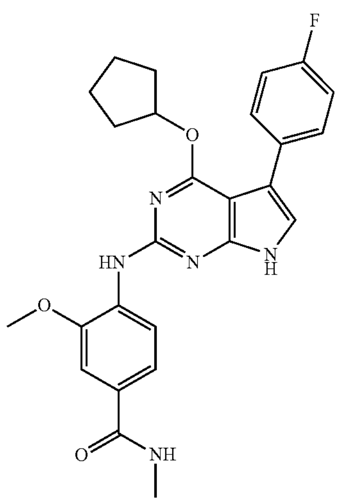 [SMILES: CNC(=O)c1ccc(Nc2nc(OC3CCCC3)c3c(-c4ccc(F)cc4)c[nH]c3n2)c(OC)c1] | 4-(4-(cyclopentyloxy)-5-(4-fluorophenyl)-7H-pyrrolo[2,3-d]pyrimidin-2-ylamino)-3-methoxy-N-methylbenzamide | 476.1 | B |
| 13 | 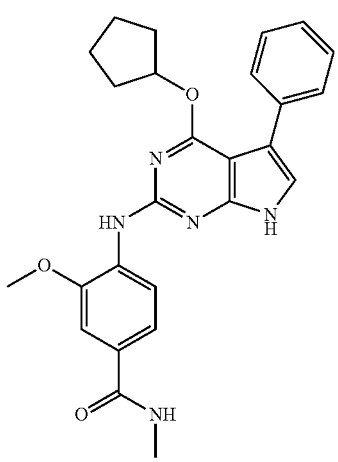 [SMILES: CNC(=O)c1ccc(Nc2nc(OC3CCCC3)c3c(-c4ccccc4)c[nH]c3n2)c(OC)c1] | 4-(4-(cyclopentyloxy)-5-phenyl-7H-pyrrolo[2,3-d]pyrimidin-2-ylamino)-3-methoxy-N-methylbenzamide | 458 | B |

TABLE 1-continued

| Cmpd No. | Structure | Name | Obs. MH+ | Act. Level |
|---|---|---|---|---|
| 14 | 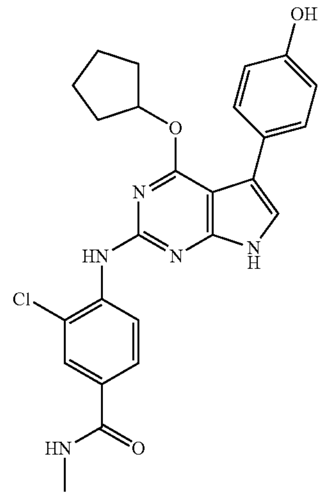 [SMILES: CNC(=O)c1ccc(Nc2nc(OC3CCCC3)c3c(-c4ccc(O)cc4)c[nH]c3n2)c(Cl)c1] | 3-chloro-4-(4-(cyclopentyloxy)-5-(4-hydroxyphenyl)-7H-pyrrolo[2,3-d]pyrimidin-2-ylamino)-N-methylbenzamide | 478.6 | D |
| 15 | 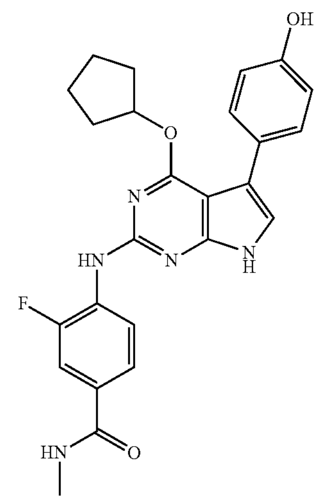 [SMILES: CNC(=O)c1ccc(Nc2nc(OC3CCCC3)c3c(-c4ccc(O)cc4)c[nH]c3n2)c(F)c1] | 4-(4-(cyclopentyloxy)-5-(4-hydroxyphenyl)-7H-pyrrolo[2,3-d]pyrimidin-2-ylamino)-3-fluoro-N-methylbenzamide | 462.6 | D |
| 16 | 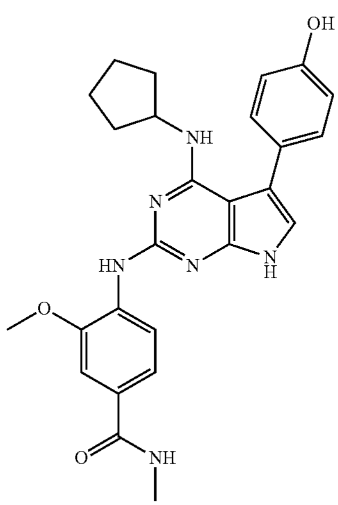 [SMILES: CNC(=O)c1ccc(Nc2nc(NC3CCCC3)c3c(-c4ccc(O)cc4)c[nH]c3n2)c(OC)c1] | 4-(4-(cyclopentylamino)-5-(4-hydroxyphenyl)-7H-pyrrolo[2,3-d]pyrimidin-2-ylamino)-3-methoxy-N-methylbenzamide | 473.1 | D |

TABLE 1-continued

| Cmpd No. | Structure | Name | Obs. MH+ | Act. Level |
|---|---|---|---|---|
| 17 | 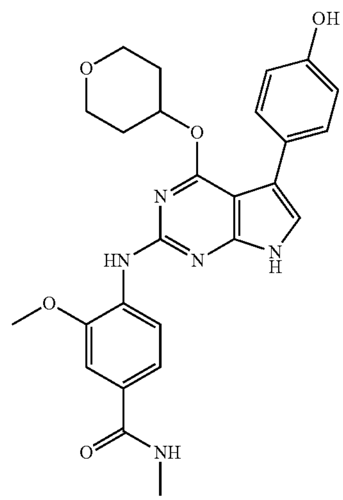 [SMILES: CNC(=O)c1ccc(Nc2nc(OC3CCOCC3)c3c(-c4ccc(O)cc4)c[nH]c3n2)c(OC)c1] | 4-(5-(4-hydroxyphenyl)-4-(tetrahydro-2H-pyran-4-yloxy)-7H-pyrrolo[2,3-d]pyrimidin-2-ylamino)-3-methoxy-N-methylbenzamide | 490 | D |
| 18 | 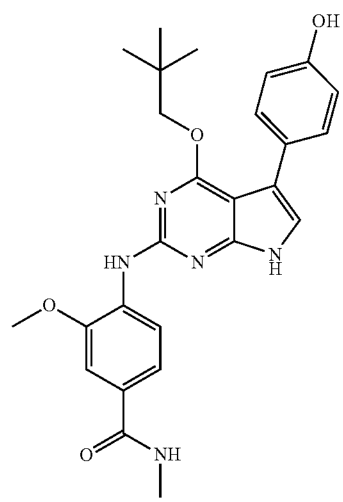 [SMILES: CNC(=O)c1ccc(Nc2nc(OCC(C)(C)C)c3c(-c4ccc(O)cc4)c[nH]c3n2)c(OC)c1] | 4-(5-(4-hydroxyphenyl)-4-(neopentyloxy)-7H-pyrrolo[2,3-d]pyrimidin-2-ylamino)-3-methoxy-N-methylbenzamide | 476.2 | D |
| 19 | 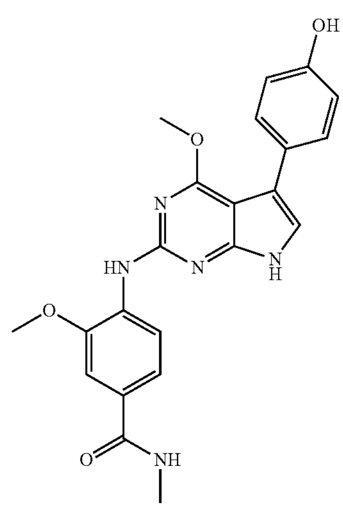 [SMILES: CNC(=O)c1ccc(Nc2nc(OC)c3c(-c4ccc(O)cc4)c[nH]c3n2)c(OC)c1] | 4-(5-(4-hydroxyphenyl)-4-methoxy-7H-pyrrolo[2,3-d]pyrimidin-2-ylamino)-3-methoxy-N-methylbenzamide | 420.1 | D |

TABLE 1-continued

| Cmpd No. | Structure | Name | Obs. MH+ | Act. Level |
|---|---|---|---|---|
| 20 | 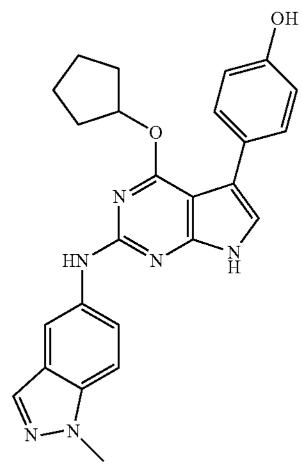 [SMILES: Cn1ncc2cc(Nc3nc(OC4CCCC4)c4c(-c5ccc(O)cc5)c[nH]c4n3)ccc21] | 4-(4-(cyclopentyloxy)-2-(1-methyl-1H-indazol-5-ylamino)-7H-pyrrolo[2,3-d]pyrimidin-5-yl)phenol | 441.2 | D |
| 21 | 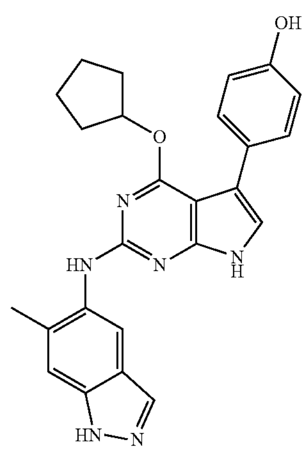 [SMILES: Cc1cc2[nH]ncc2cc1Nc1nc(OC2CCCC2)c2c(-c3ccc(O)cc3)c[nH]c2n1] | 4-(4-(cyclopentyloxy)-2-(6-methyl-1H-indazol-5-ylamino)-7H-pyrrolo[2,3-d]pyrimidin-5-yl)phenol | 441.2 | D |
| 22 | 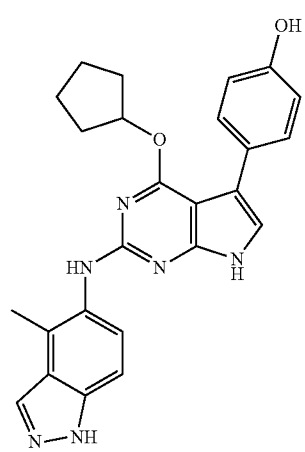 [SMILES: Cc1c(Nc2nc(OC3CCCC3)c3c(-c4ccc(O)cc4)c[nH]c3n2)ccc2[nH]ncc12] | 4-(4-(cyclopentyloxy)-2-(4-methyl-1H-indazol-5-ylamino)-7H-pyrrolo[2,3-d]pyrimidin-5-yl)phenol | 441.1 | D |

TABLE 1-continued

| Cmpd No. | Structure | Name | Obs. MH+ | Act. Level |
|---|---|---|---|---|
| 23 | 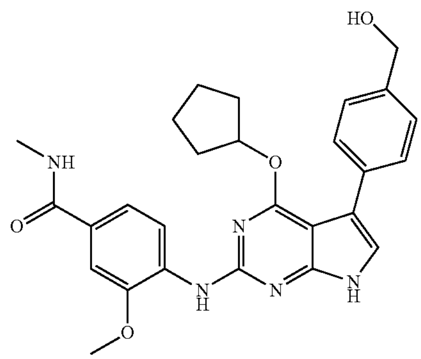 [SMILES: CNC(=O)c1ccc(Nc2nc(OC3CCCC3)c3c(-c4ccc(CO)cc4)c[nH]c3n2)c(OC)c1] | 4-(4-(cyclopentyloxy)-5-(4-(hydroxymethyl)phenyl)-7H-pyrrolo[2,3-d]pyrimidin-2-ylamino)-3-methoxy-N-methylbenzamide | 488.3 | C |
| 24 | 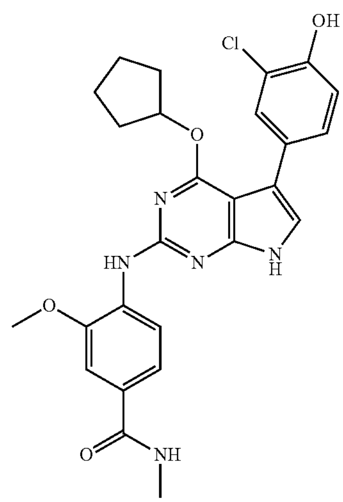 [SMILES: CNC(=O)c1ccc(Nc2nc(OC3CCCC3)c3c(-c4ccc(O)c(Cl)c4)c[nH]c3n2)c(OC)c1] | 4-(5-(3-chloro-4-hydroxyphenyl)-4-(cyclopentyloxy)-7H-pyrrolo[2,3-d]pyrimidin-2-ylamino)-3-methoxy-N-methylbenzamide | 508.2 | D |
| 25 | 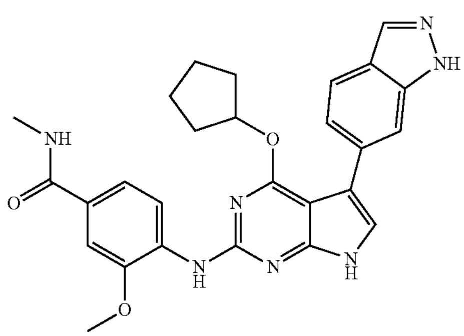 [SMILES: CNC(=O)c1ccc(Nc2nc(OC3CCCC3)c3c(-c4ccc5cn[nH]c5c4)c[nH]c3n2)c(OC)c1] | 4-(4-(cyclopentyloxy)-5-(1H-indazol-6-yl)-7H-pyrrolo[2,3-d]pyrimidin-2-ylamino)-3-methoxy-N-methylbenzamide | 498.2 | C |
| 26 | 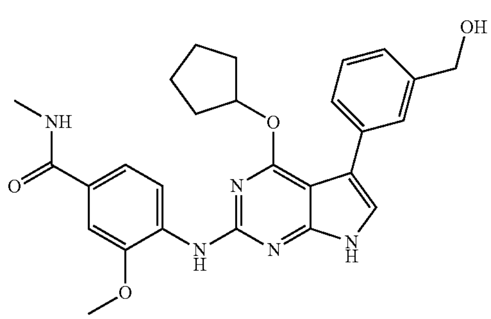 [SMILES: CNC(=O)c1ccc(Nc2nc(OC3CCCC3)c3c(-c4cccc(CO)c4)c[nH]c3n2)c(OC)c1] | 4-(4-(cyclopentyloxy)-5-(3-(hydroxymethyl)phenyl)-7H-pyrrolo[2,3-d]pyrimidin-2-ylamino)-3-methoxy-N-methylbenzamide | 488.2 | D |

TABLE 1-continued

| Cmpd No. | Structure | Name | Obs. MH$^+$ | Act. Level |
|---|---|---|---|---|
| 27 | 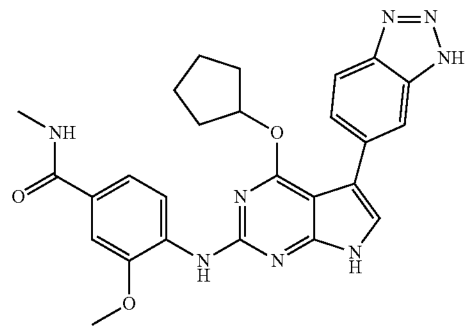 [SMILES: CNC(=O)c1ccc(Nc2nc(OC3CCCC3)c3c(-c4ccc5nn[nH]c5c4)c[nH]c3n2)c(OC)c1] | 4-(5-(1H-benzo[d][1,2,3]triazol-6-yl)-4-(cyclopentyloxy)-7H-pyrrolo[2,3-d]pyrimidin-2-ylamino)-3-methoxy-N-methylbenzamide | 499.2 | D |
| 28 | 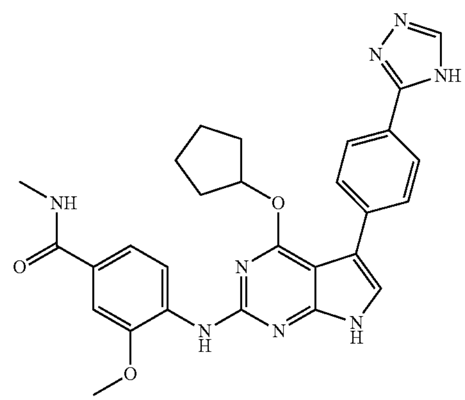 [SMILES: CNC(=O)c1ccc(Nc2nc(OC3CCCC3)c3c(-c4ccc(-c5nnc[nH]5)cc4)c[nH]c3n2)c(OC)c1] | 4-(5-(4-(4H-1,2,4-triazol-3-yl)phenyl)-4-(cyclopentyloxy)-7H-pyrrolo[2,3-d]pyrimidin-2-ylamino)-3-methoxy-N-methylbenzamide | 525.3 | D |
| 29 | 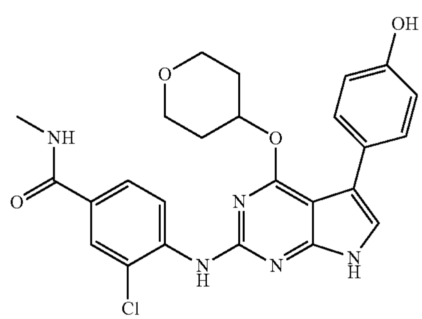 [SMILES: CNC(=O)c1ccc(Nc2nc(OC3CCOCC3)c3c(-c4ccc(O)cc4)c[nH]c3n2)c(Cl)c1] | 3-chloro-4-(5-(4-hydroxyphenyl)-4-(tetrahydro-2H-pyran-4-yloxy)-7H-pyrrolo[2,3-d]pyrimidin-2-ylamino)-N-methylbenzamide | 494.1 | D |
| 30 | 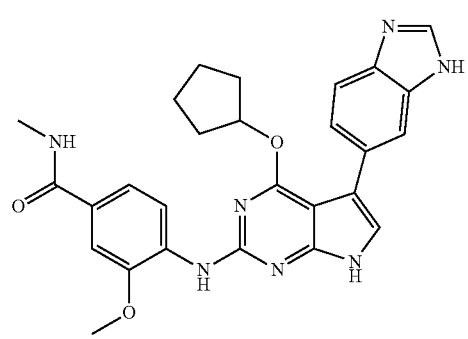 [SMILES: CNC(=O)c1ccc(Nc2nc(OC3CCCC3)c3c(-c4ccc5nc[nH]c5c4)c[nH]c3n2)c(OC)c1] | 4-(5-(1H-benzo[d]imidazol-6-yl)-4-(cyclopentyloxy)-7H-pyrrolo[2,3-d]pyrimidin-2-ylamino)-3-methoxy-N-methylbenzamide | 498.2 | D |

TABLE 1-continued

| Cmpd No. | Structure | Name | Obs. MH+ | Act. Level |
|---|---|---|---|---|
| 31 | 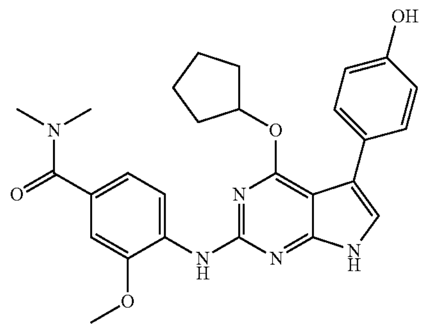 [SMILES: COc1cc(C(=O)N(C)C)ccc1Nc1nc(OC2CCCC2)c2c(-c3ccc(O)cc3)c[nH]c2n1] | 4-(4-(cyclopentyloxy)-5-(4-hydroxyphenyl)-7H-pyrrolo[2,3-d]pyrimidin-2-ylamino)-3-methoxy-N,N-dimethylbenzamide | 488.2 | D |
| 32 | 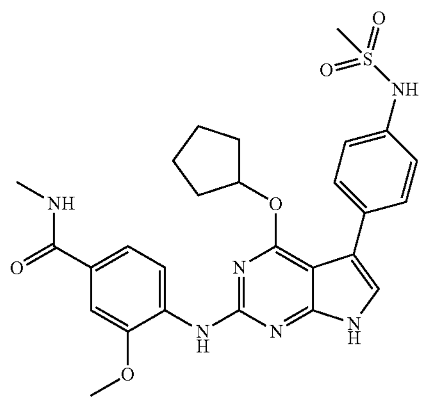 [SMILES: CNC(=O)c1ccc(Nc2nc(OC3CCCC3)c3c(-c4ccc(NS(C)(=O)=O)cc4)c[nH]c3n2)c(OC)c1] | 4-(4-(cyclopentyloxy)-5-(4-(methylsulfonamido)phenyl)-7H-pyrrolo[2,3-d]pyrimidin-2-ylamino)-3-methoxy-N-methylbenzamide | 551.2 | D |
| 33 | 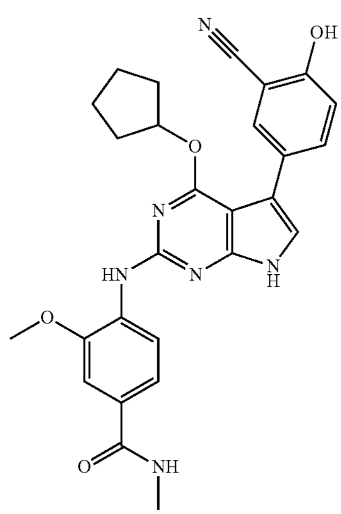 [SMILES: CNC(=O)c1ccc(Nc2nc(OC3CCCC3)c3c(-c4ccc(O)c(C#N)c4)c[nH]c3n2)c(OC)c1] | 4-(5-(3-cyano-4-hydroxyphenyl)-4-(cyclopentyloxy)-7H-pyrrolo[2,3-d]pyrimidin-2-ylamino)-3-methoxy-N-methylbenzamide | 499.3 | D |

TABLE 1-continued

| Cmpd No. | Structure | Name | Obs. MH+ | Act. Level |
|---|---|---|---|---|
| 34 | 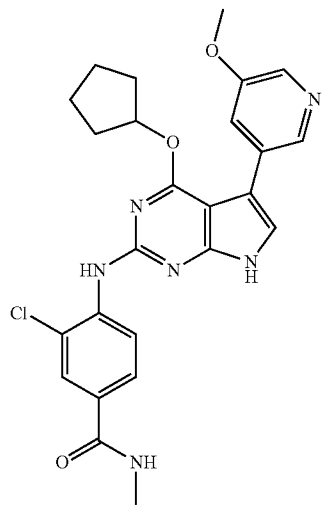 [SMILES: CNC(=O)c1ccc(Nc2nc(OC3CCCC3)c3c(-c4cncc(OC)c4)c[nH]c3n2)c(Cl)c1] | 3-chloro-4-(4-(cyclopentyloxy)-5-(5-methoxypyridin-3-yl)-7H-pyrrolo[2,3-d]pyrimidin-2-ylamino)-N-methylbenzamide | 493.2 | C |
| 35 | 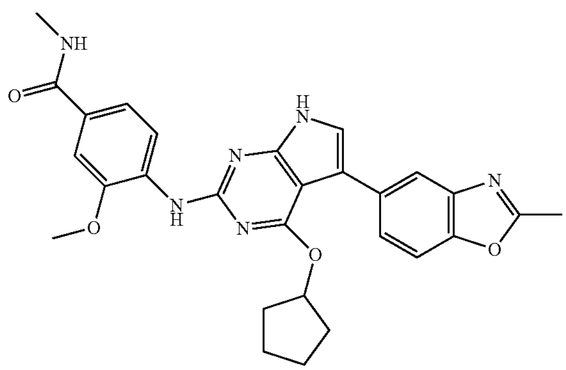 [SMILES: CNC(=O)c1ccc(Nc2nc(OC3CCCC3)c3c(-c4ccc5oc(C)nc5c4)c[nH]c3n2)c(OC)c1] | 4-(4-(cyclopentyloxy)-5-(2-methylbenzo[d]oxazol-5-yl)-7H-pyrrolo[2,3-d]pyrimidin-2-ylamino)-3-methoxy-N-methylbenzamide | 513.2 | A |
| 36 | 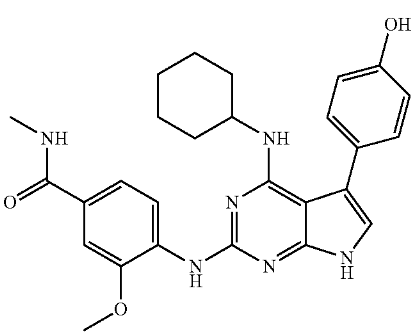 [SMILES: CNC(=O)c1ccc(Nc2nc(NC3CCCCC3)c3c(-c4ccc(O)cc4)c[nH]c3n2)c(OC)c1] | 4-(4-(cyclohexylamino)-5-(4-hydroxyphenyl)-7H-pyrrolo[2,3-d]pyrimidin-2-ylamino)-3-methoxy-N-methylbenzamide | 487.3 | D |
| 37 | 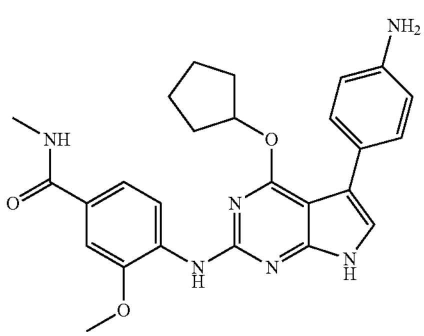 [SMILES: CNC(=O)c1ccc(Nc2nc(OC3CCCC3)c3c(-c4ccc(N)cc4)c[nH]c3n2)c(OC)c1] | 4-(5-(4-aminophenyl)-4-(cyclopentyloxy)-7H-pyrrolo[2,3-d]pyrimidin-2-ylamino)-3-methoxy-N-methylbenzamide | 473.3 | D |

TABLE 1-continued

| Cmpd No. | Structure | Name | Obs. MH+ | Act. Level |
|---|---|---|---|---|
| 38 | 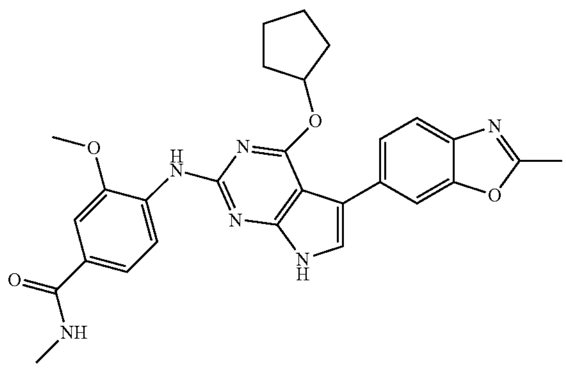 [SMILES: CNC(=O)c1ccc(Nc2nc(OC3CCCC3)c3c(-c4ccc5nc(C)oc5c4)c[nH]c3n2)c(OC)c1] | 4-(4-(cyclopentyloxy)-5-(2-methylbenzo[d]oxazol-6-yl)-7H-pyrrolo[2,3-d]pyrimidin-2-ylamino)-3-methoxy-N-methylbenzamide | 513 | D |
| 39 | 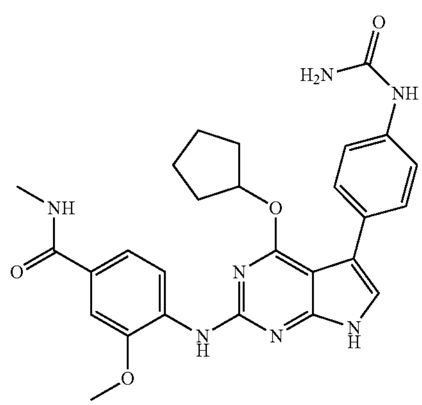 [SMILES: CNC(=O)c1ccc(Nc2nc(OC3CCCC3)c3c(-c4ccc(NC(N)=O)cc4)c[nH]c3n2)c(OC)c1] | 4-(4-(cyclopentyloxy)-5-(4-ureidophenyl)-7H-pyrrolo[2,3-d]pyrimidin-2-ylamino)-3-methoxy-N-methylbenzamide | 516.2 | D |
| 40 | 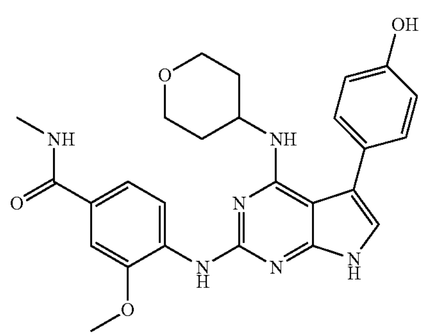 [SMILES: CNC(=O)c1ccc(Nc2nc(NC3CCOCC3)c3c(-c4ccc(O)cc4)c[nH]c3n2)c(OC)c1] | 4-(5-(4-hydroxyphenyl)-4-(tetrahydro-2H-pyran-4-ylamino)-7H-pyrrolo[2,3-d]pyrimidin-2-ylamino)-3-methoxy-N-methylbenzamide | 489.2 | D |
| 41 | 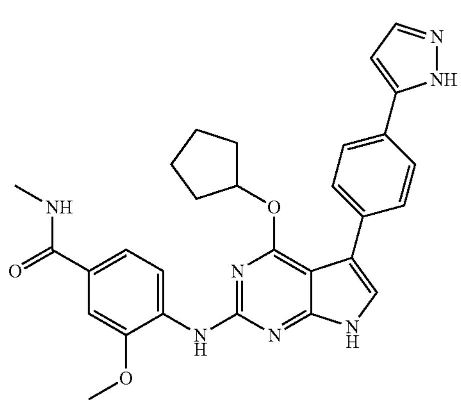 [SMILES: CNC(=O)c1ccc(Nc2nc(OC3CCCC3)c3c(-c4ccc(-c5ccn[nH]5)cc4)c[nH]c3n2)c(OC)c1] | 4-(5-(4-(1H-pyrazol-5-yl)phenyl)-4-(cyclopentyloxy)-7H-pyrrolo[2,3-d]pyrimidin-2-ylamino)-3-methoxy-N-methylbenzamide | 524.2 | C |

TABLE 1-continued

| Cmpd No. | Structure | Name | Obs. MH+ | Act. Level |
|---|---|---|---|---|
| 42 | 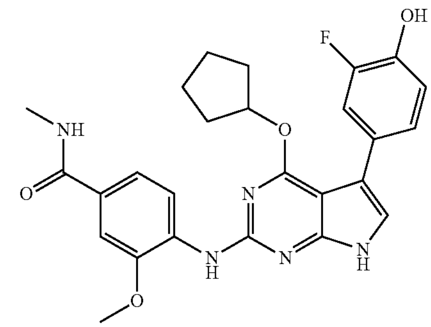 [SMILES: CNC(=O)c1ccc(Nc2nc(OC3CCCC3)c3c(-c4ccc(O)c(F)c4)c[nH]c3n2)c(OC)c1] | 4-(4-(cyclopentyloxy)-5-(3-fluoro-4-hydroxyphenyl)-7H-pyrrolo[2,3-d]pyrimidin-2-ylamino)-3-methoxy-N-methylbenzamide | 492.2 | D |
| 43 | 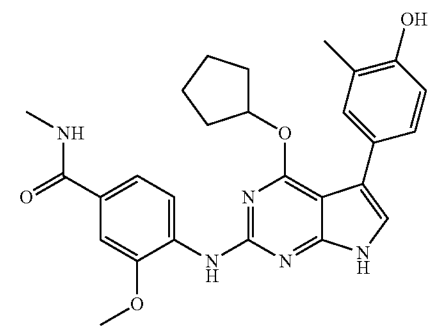 [SMILES: CNC(=O)c1ccc(Nc2nc(OC3CCCC3)c3c(-c4ccc(O)c(C)c4)c[nH]c3n2)c(OC)c1] | 4-(4-(cyclopentyloxy)-5-(4-hydroxy-3-methylphenyl)-7H-pyrrolo[2,3-d]pyrimidin-2-ylamino)-3-methoxy-N-methylbenzamide | 488.2 | D |
| 44 | 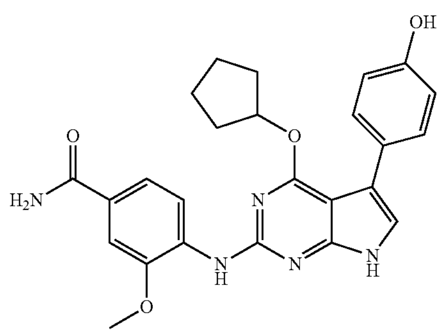 [SMILES: COc1cc(C(N)=O)ccc1Nc1nc(OC2CCCC2)c2c(-c3ccc(O)cc3)c[nH]c2n1] | 4-(4-(cyclopentyloxy)-5-(4-hydroxyphenyl)-7H-pyrrolo[2,3-d]pyrimidin-2-ylamino)-3-methoxybenzamide | 460.2 | D |
| 45 | 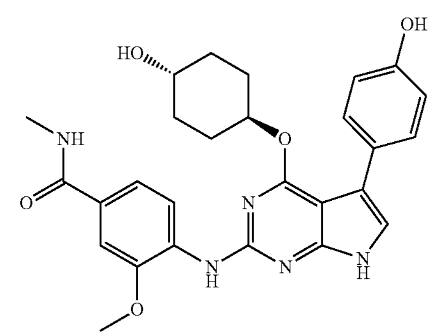 [SMILES: CNC(=O)c1ccc(Nc2nc(O[C@H]3CC[C@H](O)CC3)c3c(-c4ccc(O)cc4)c[nH]c3n2)c(OC)c1] | 4-(4-((1r,4r)-4-hydroxycyclohexyloxy)-5-(4-hydroxyphenyl)-7H-pyrrolo[2,3-d]pyrimidin-2-ylamino)-3-methoxy-N-methylbenzamide | 504.2 | D |

TABLE 1-continued

| Cmpd No. | Structure | Name | Obs. MH+ | Act. Level |
|---|---|---|---|---|
| 46 | 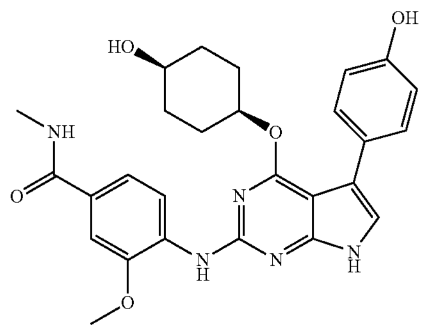 [SMILES: CNC(=O)c1ccc(Nc2nc(O[C@H]3CC[C@@H](O)CC3)c3c(-c4ccc(O)cc4)c[nH]c3n2)c(OC)c1] | 4-(4-((1s,4s)-4-hydroxycyclohexyloxy)-5-(4-hydroxyphenyl)-7H-pyrrolo[2,3-d]pyrimidin-2-ylamino)-3-methoxy-N-methylbenzamide | 504.2 | D |
| 47 | 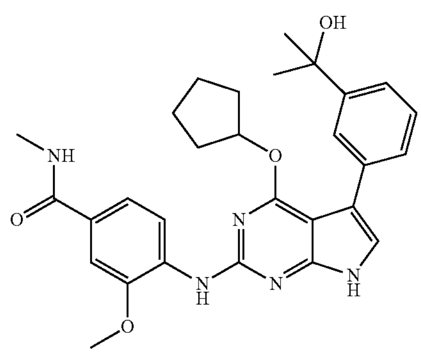 [SMILES: CNC(=O)c1ccc(Nc2nc(OC3CCCC3)c3c(-c4cccc(C(C)(C)O)c4)c[nH]c3n2)c(OC)c1] | 4-(4-(cyclopentyloxy)-5-(3-(2-hydroxypropan-2-yl)phenyl)-7H-pyrrolo[2,3-d]pyrimidin-2-ylamino)-3-methoxy-N-methylbenzamide | 516.2 | B |
| 48 | 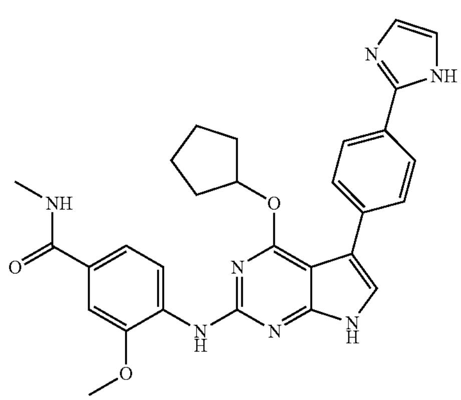 [SMILES: CNC(=O)c1ccc(Nc2nc(OC3CCCC3)c3c(-c4ccc(-c5ncc[nH]5)cc4)c[nH]c3n2)c(OC)c1] | 4-(5-(4-(1H-imidazol-2-yl)phenyl)-4-(cyclopentyloxy)-7H-pyrrolo[2,3-d]pyrimidin-2-ylamino)-3-methoxy-N-methylbenzamide | 524.2 | D |
| 49 | 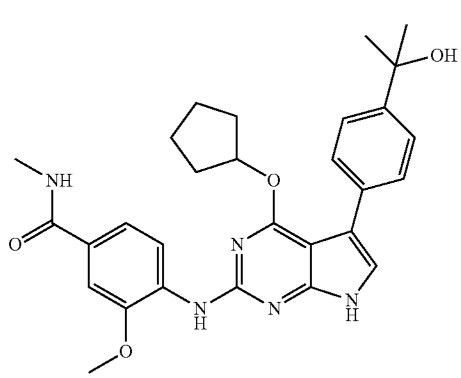 [SMILES: CNC(=O)c1ccc(Nc2nc(OC3CCCC3)c3c(-c4ccc(C(C)(C)O)cc4)c[nH]c3n2)c(OC)c1] | 4-(4-(cyclopentyloxy)-5-(4-(2-hydroxypropan-2-yl)phenyl)-7H-pyrrolo[2,3-d]pyrimidin-2-ylamino)-3-methoxy-N-methylbenzamide | 516.2 | C |

TABLE 1-continued

| Cmpd No. | Structure | Name | Obs. MH+ | Act. Level |
|---|---|---|---|---|
| 50 | 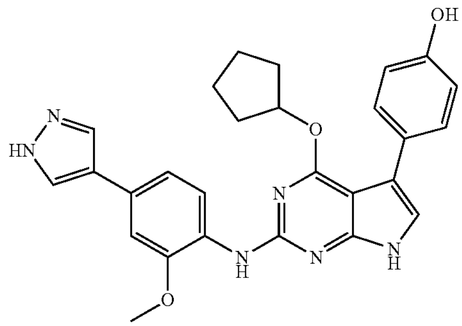 [SMILES: COc1cc(-c2cn[nH]c2)ccc1Nc1nc(OC2CCCC2)c2c(-c3ccc(O)cc3)c[nH]c2n1] | 4-(4-(cyclopentyloxy)-2-(2-methoxy-4-(1H-pyrazol-4-yl)phenylamino)-7H-pyrrolo[2,3-d]pyrimidin-5-yl)phenol | 483.2 | D |
| 51 | 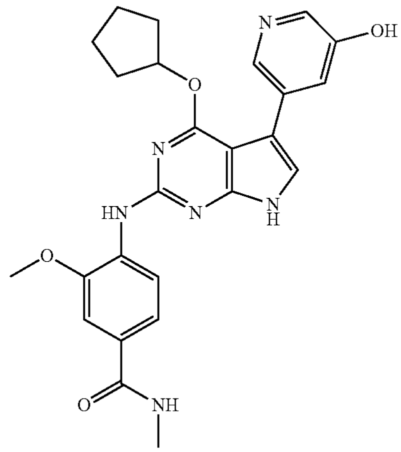 [SMILES: CNC(=O)c1ccc(Nc2nc(OC3CCCC3)c3c(-c4cncc(O)c4)c[nH]c3n2)c(OC)c1] | 4-(4-(cyclopentyloxy)-5-(5-hydroxypyridin-3-yl)-7H-pyrrolo[2,3-d]pyrimidin-2-ylamino)-3-methoxy-N-methylbenzamide | 475.3 | D |
| 52 | 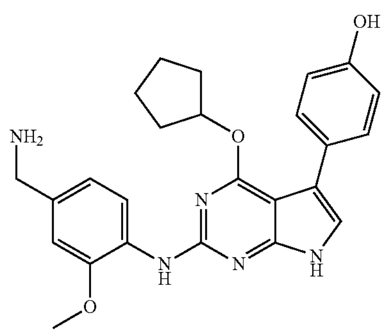 [SMILES: COc1cc(CN)ccc1Nc1nc(OC2CCCC2)c2c(-c3ccc(O)cc3)c[nH]c2n1] | 4-(2-(4-(aminomethyl)-2-methoxyphenylamino)-4-(cyclopentyloxy)-7H-pyrrolo[2,3-d]pyrimidin-5-yl)phenol | 446.2 | C |
| 53 | 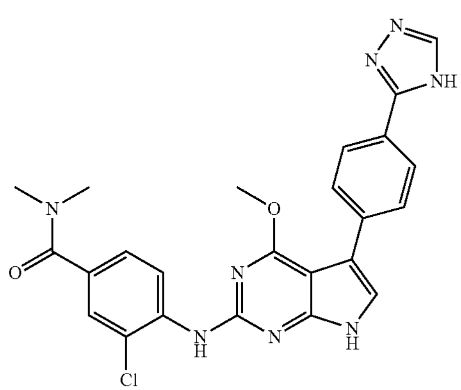 [SMILES: COc1nc(Nc2ccc(C(=O)N(C)C)cc2Cl)nc2[nH]cc(-c3ccc(-c4nnc[nH]4)cc3)c12] | 4-(5-(4-(4H-1,2,4-triazol-3-yl)phenyl)-4-methoxy-7H-pyrrolo[2,3-d]pyrimidin-2-ylamino)-3-chloro-N,N-dimethylbenzamide | 489.1 | C |

TABLE 1-continued

| Cmpd No. | Structure | Name | Obs. MH+ | Act. Level |
|---|---|---|---|---|
| 54 | 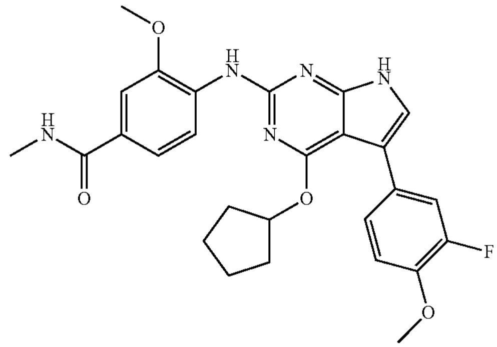 [SMILES: CNC(=O)c1ccc(Nc2nc(OC3CCCC3)c3c(-c4ccc(OC)c(F)c4)c[nH]c3n2)c(OC)c1] | 4-(4-(cyclopentyloxy)-5-(3-fluoro-4-methoxyphenyl)-7H-pyrrolo[2,3-d]pyrimidin-2-ylamino)-3-methoxy-N-methylbenzamide | 506.2 | C |
| 55 | 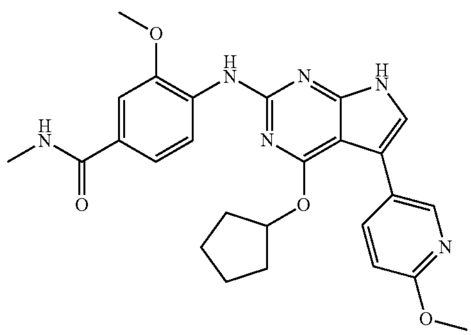 | 4-(4-(cyclopentyloxy)-5-(6-methoxypyridin-3-yl)-7H-pyrrolo[2,3-d]pyrimidin-2-ylamino)-3-methoxy-N-methylbenzamide | 489.4 | C |
| 56 | 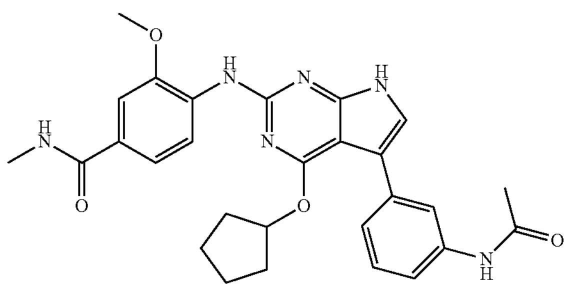 [SMILES: CNC(=O)c1ccc(Nc2nc(OC3CCCC3)c3c(-c4cccc(NC(C)=O)c4)c[nH]c3n2)c(OC)c1] | 4-(5-(3-acetamidophenyl)-4-(cyclopentyloxy)-7H-pyrrolo[2,3-d]pyrimidin-2-ylamino)-3-methoxy-N-methylbenzamide | 515.2 | D |
| 57 | 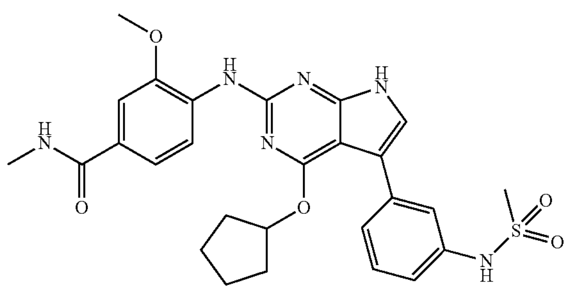 [SMILES: CNC(=O)c1ccc(Nc2nc(OC3CCCC3)c3c(-c4cccc(NS(C)(=O)=O)c4)c[nH]c3n2)c(OC)c1] | 4-(4-(cyclopentyloxy)-5-(3-(methylsulfonamido)phenyl)-7H-pyrrolo[2,3-d]pyrimidin-2-ylamino)-3-methoxy-N-methylbenzamide | 551.2 | C |
| 58 | 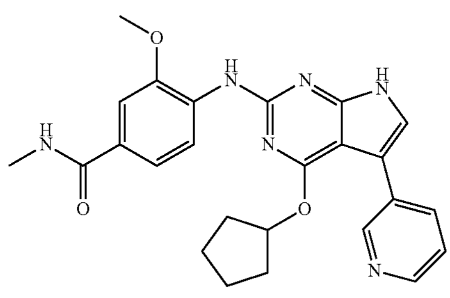 [SMILES: CNC(=O)c1ccc(Nc2nc(OC3CCCC3)c3c(-c4cccnc4)c[nH]c3n2)c(OC)c1] | 4-(4-(cyclopentyloxy)-5-(pyridin-3-yl)-7H-pyrrolo[2,3-d]pyrimidin-2-ylamino)-3-methoxy-N-methylbenzamide | 459.4 | D |

TABLE 1-continued

| Cmpd No. | Structure | Name | Obs. MH+ | Act. Level |
|---|---|---|---|---|
| 59 | 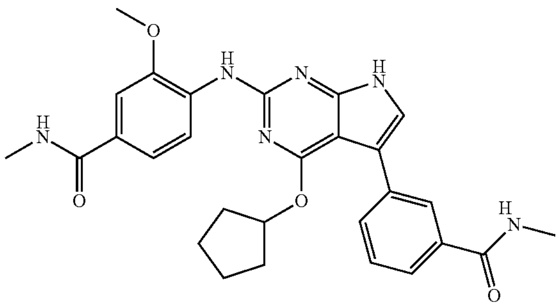 | 4-(4-(cyclopentyloxy)-5-(3-(methylcarbamoyl)phenyl)-7H-pyrrolo[2,3-d]pyrimidin-2-ylamino)-3-methoxy-N-methylbenzamide | 515.2 | C |
| 60 | 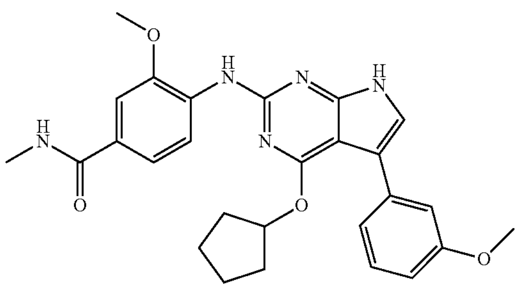 | 4-(4-(cyclopentyloxy)-5-(3-methoxyphenyl)-7H-pyrrolo[2,3-d]pyrimidin-2-ylamino)-3-methoxy-N-methylbenzamide | 488.4 | C |
| 61 | 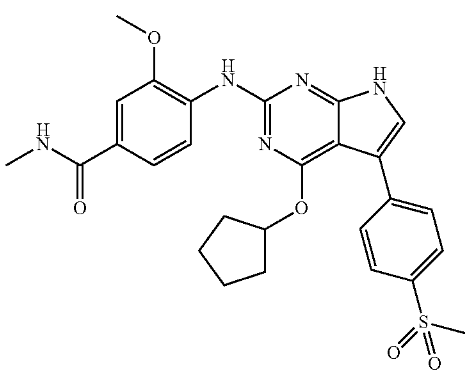 | 4-(4-(cyclopentyloxy)-5-(4-(methylsulfonyl)phenyl)-7H-pyrrolo[2,3-d]pyrimidin-2-ylamino)-3-methoxy-N-methylbenzamide | 536.4 | D |
| 62 | 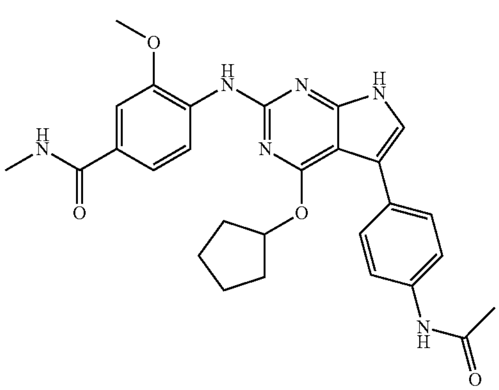 [SMILES: CNC(=O)c1ccc(Nc2nc(OC3CCCC3)c3c(-c4ccc(NC(C)=O)cc4)c[nH]c3n2)c(OC)c1] | 4-(5-(4-acetamidophenyl)-4-(cyclopentyloxy)-7H-pyrrolo[2,3-d]pyrimidin-2-ylamino)-3-methoxy-N-methylbenzamide | 515.2 | D |

TABLE 1-continued

| Cmpd No. | Structure | Name | Obs. MH+ | Act. Level |
|---|---|---|---|---|
| 63 | 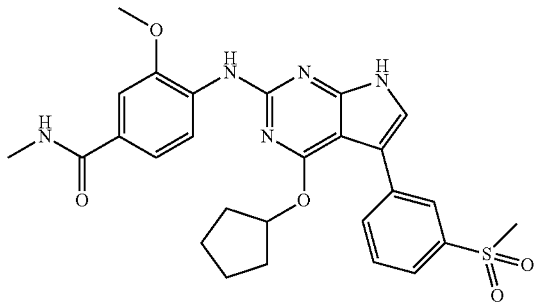 [SMILES: CNC(=O)c1ccc(Nc2nc(OC3CCCC3)c3c(-c4cccc(S(C)(=O)=O)c4)c[nH]c3n2)c(OC)c1] | 4-(4-(cyclopentyloxy)-5-(3-(methylsulfonyl)phenyl)-7H-pyrrolo[2,3-d]pyrimidin-2-ylamino)-3-methoxy-N-methylbenzamide | 536.2 | D |
| 64 | 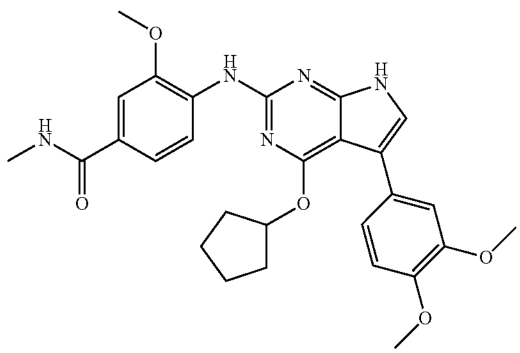 | 4-(4-(cyclopentyloxy)-5-(3,4-dimethoxyphenyl)-7H-pyrrolo[2,3-d]pyrimidin-2-ylamino)-3-methoxy-N-methylbenzamide | 518.4 | C |
| 65 | 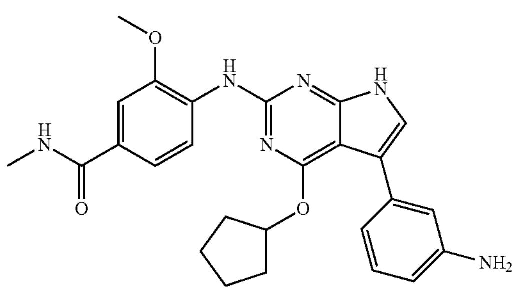 [SMILES: CNC(=O)c1ccc(Nc2nc(OC3CCCC3)c3c(-c4cccc(N)c4)c[nH]c3n2)c(OC)c1] | 4-(5-(3-aminophenyl)-4-(cyclopentyloxy)-7H-pyrrolo[2,3-d]pyrimidin-2-ylamino)-3-methoxy-N-methylbenzamide | 473.4 | D |
| 66 | 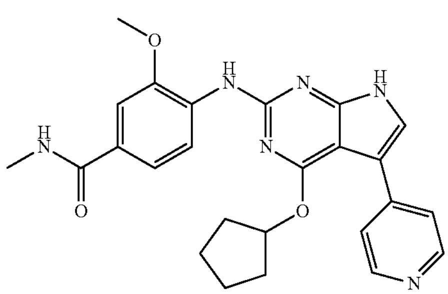 [SMILES: CNC(=O)c1ccc(Nc2nc(OC3CCCC3)c3c(-c4ccncc4)c[nH]c3n2)c(OC)c1] | 4-(4-(cyclopentyloxy)-5-(pyridin-4-yl)-7H-pyrrolo[2,3-d]pyrimidin-2-ylamino)-3-methoxy-N-methylbenzamide | 459.4 | D |

TABLE 1-continued

| Cmpd No. | Structure | Name | Obs. MH+ | Act. Level |
|---|---|---|---|---|
| 67 | 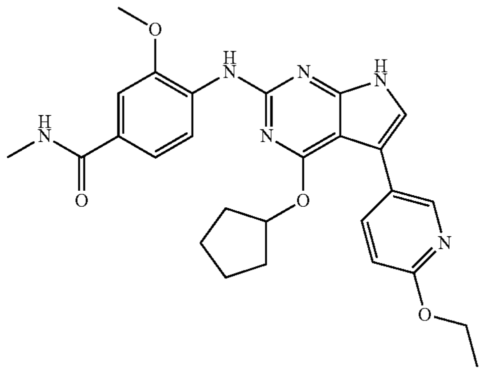 [SMILES: CCOc1ccc(-c2c[nH]c3nc(Nc4ccc(C(=O)NC)cc4OC)nc(OC4CCCC4)c23)cn1] | 4-(4-(cyclopentyloxy)-5-(6-ethoxypyridin-3-yl)-7H-pyrrolo[2,3-d]pyrimidin-2-ylamino)-3-methoxy-N-methylbenzamide | 503.6 | C |
| 68 | 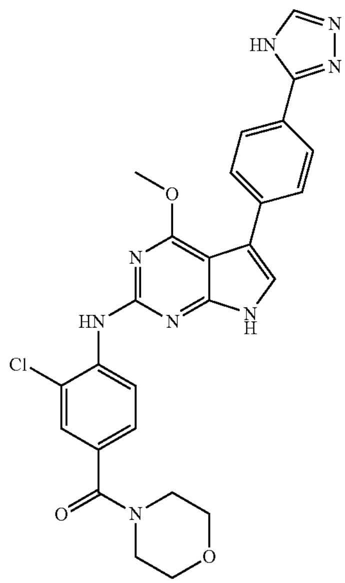 [SMILES: COc1nc(Nc2ccc(C(=O)N3CCOCC3)cc2Cl)nc2[nH]cc(-c3ccc(-c4nnc[nH]4)cc3)c12] | (4-(5-(4-(4H-1,2,4-triazol-3-yl)phenyl)-4-methoxy-7H-pyrrolo[2,3-d]pyrimidin-2-ylamino)-3-chlorophenyl)(morpholino)-methanone | 531.2 | C |
| 69 | 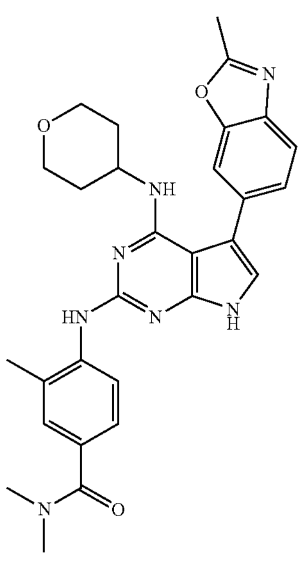 [SMILES: Cc1nc2ccc(-c3c[nH]c4nc(Nc5ccc(C(=O)N(C)C)cc5C)nc(NC5CCOCC5)c34)cc2o1] | N,N,3-trimethyl-4-(5-(2-methylbenzo[d]oxazol-6-yl)-4-(tetrahydro-2H-pyran-4-ylamino)-7H-pyrrolo[2,3-d]pyrimidin-2-ylamino)benzamide | 526.6 | C |

| Cmpd No. | Structure | Name | Obs. MH+ | Act. Level |
|---|---|---|---|---|
| 70 | 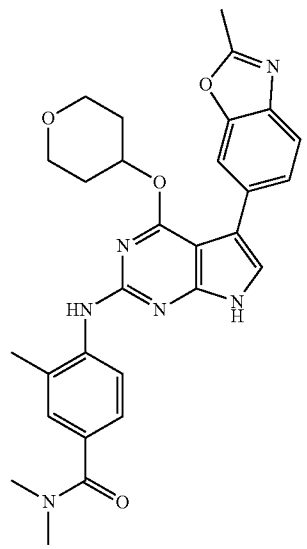 [SMILES: Cc1nc2ccc(-c3c[nH]c4nc(Nc5ccc(C(=O)N(C)C)cc5C)nc(OC5CCOCC5)c34)cc2o1] | N,N,3-trimethyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide | 527.6 | C |
| 71 | 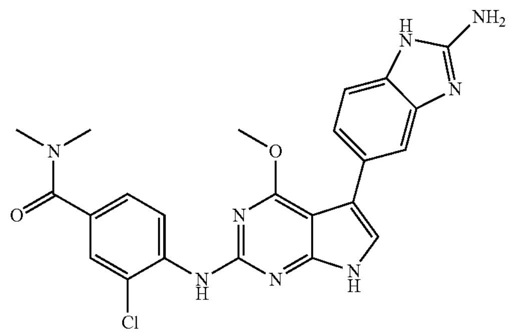 [SMILES: COc1nc(Nc2ccc(C(=O)N(C)C)cc2Cl)nc2[nH]cc(-c3ccc4[nH]c(N)nc4c3)c12] | 4-(5-(2-amino-1H-benzo[d]imidazol-5-yl)-4-methoxy-7H-pyrrolo[2,3-d]pyrimidin-2-ylamino)-3-chloro-N,N-dimethylbenzamide | 477.1 | C |
| 72 | 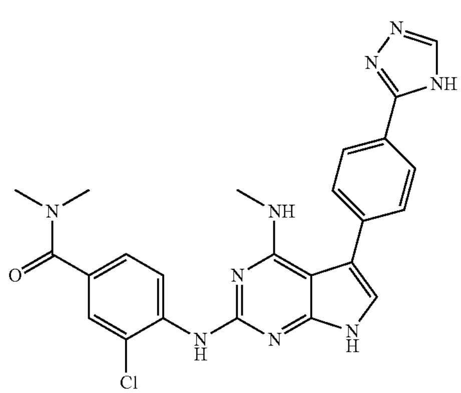 [SMILES: CNc1nc(Nc2ccc(C(=O)N(C)C)cc2Cl)nc2[nH]cc(-c3ccc(-c4nnc[nH]4)cc3)c12] | 4-(5-(4-(4H-1,2,4-triazol-3-yl)phenyl)-4-(methylamino)-7H-pyrrolo[2,3-d]pyrimidin-2-ylamino)-3-chloro-N,N-dimethylbenzamide | 488.2 | B |

TABLE 1-continued

| Cmpd No. | Structure | Name | Obs. MH+ | Act. Level |
|---|---|---|---|---|
| 73 | 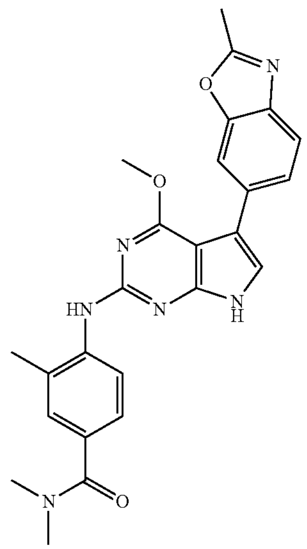 [SMILES: COc1nc(Nc2ccc(C(=O)N(C)C)cc2C)nc2[nH]cc(-c3ccc4nc(C)oc4c3)c12] | 4-(4-methoxy-5-(2-methylbenzo[d]oxazol-6-yl)-7H-pyrrolo[2,3-d]pyrimidin-2-ylamino)-N,N,3-trimethylbenzamide | 457.5 | A |
| 74 | 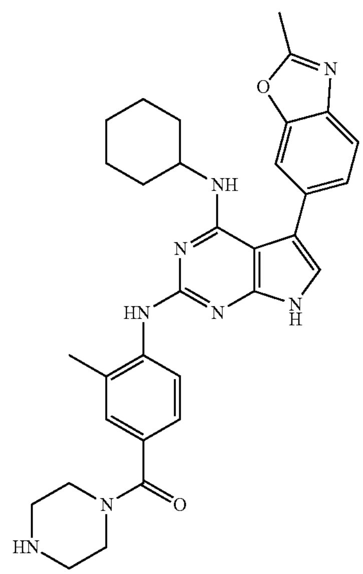 [SMILES: Cc1nc2ccc(-c3c[nH]c4nc(Nc5ccc(C(=O)N6CCNCC6)cc5C)nc(NC5CCCCC5)c34)cc2o1] | (3-methyl-4-(5-(2-methylbenzo[d]oxazol-6-yl)-4-(tetrahydro-2H-pyran-4-ylamino)-7H-pyrrolo[2,3-d]pyrimidin-2-ylamino)phenyl)(piperazin-1-yl)methanone | 567.5 | C |
| 75 | 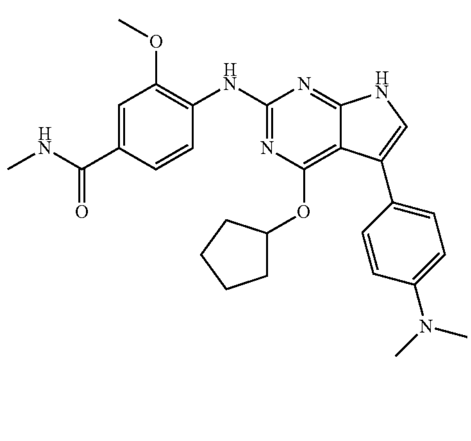 | 4-(4-(cyclopentyloxy)-5-(4-(dimethylamino)phenyl)-7H-pyrrolo[2,3-d]pyrimidin-2-ylamino)-3-methoxy-N-methylbenzamide | 501.4 | D |

TABLE 1-continued

| Cmpd No. | Structure | Name | Obs. MH+ | Act. Level |
|---|---|---|---|---|
| 76 | 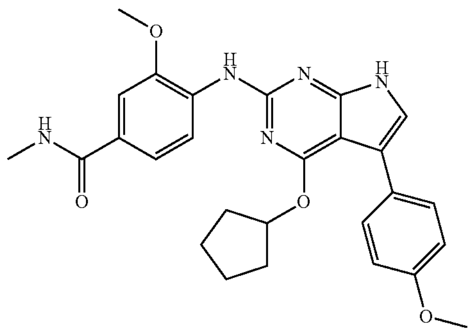 | 4-(4-(cyclopentyloxy)-5-(4-methoxyphenyl)-7H-pyrrolo[2,3-d]pyrimidin-2-ylamino)-3-methoxy-N-methylbenzamide | 488.4 | D |
| 77 | 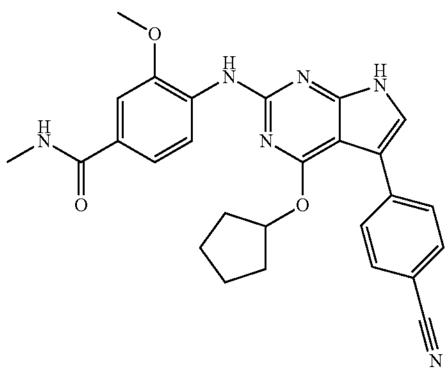 [SMILES: CNC(=O)c1ccc(Nc2nc(OC3CCCC3)c3c(-c4ccc(C#N)cc4)c[nH]c3n2)c(OC)c1] | 4-(5-(4-cyanophenyl)-4-(cyclopentyloxy)-7H-pyrrolo[2,3-d]pyrimidin-2-ylamino)-3-methoxy-N-methylbenzamide | 483.2 | A |
| 78 | 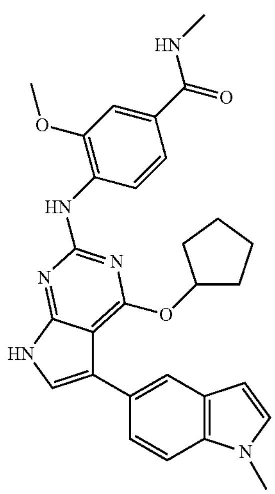 [SMILES: CNC(=O)c1ccc(Nc2nc(OC3CCCC3)c3c(-c4ccc5c(ccn5C)c4)c[nH]c3n2)c(OC)c1] | 4-(4-(cyclopentyloxy)-5-(1-methyl-1H-indol-5-yl)-7H-pyrrolo[2,3-d]pyrimidin-2-ylamino)-3-methoxy-N-methylbenzamide | 511.4 | A |
| 79 | 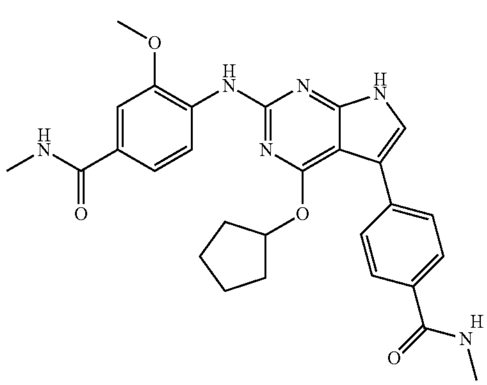 | 4-(4-(cyclopentyloxy)-5-(4-(methylcarbamoyl)phenyl)-7H-pyrrolo[2,3-d]pyrimidin-2-ylamino)-3-methoxy-N-methylbenzamide | 515 | D |

TABLE 1-continued

| Cmpd No. | Structure | Name | Obs. MH+ | Act. Level |
|---|---|---|---|---|
| 80 | 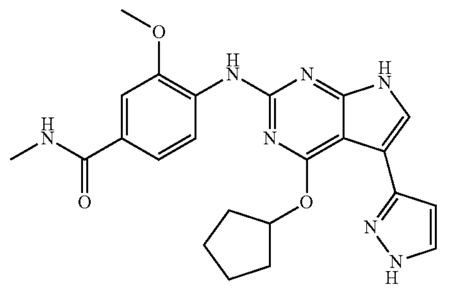 | 4-(4-(cyclopentyloxy)-5-(1H-pyrazol-3-yl)-7H-pyrrolo[2,3-d]pyrimidin-2-ylamino)-3-methoxy-N-methylbenzamide | 448.2 | D |
| 81 | 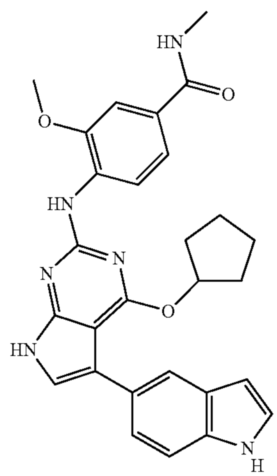 | 4-(4-(cyclopentyloxy)-5-(1H-indol-5-yl)-7H-pyrrolo[2,3-d]pyrimidin-2-ylamino)-3-methoxy-N-methylbenzamide | 497.2 | B |
| 82 | 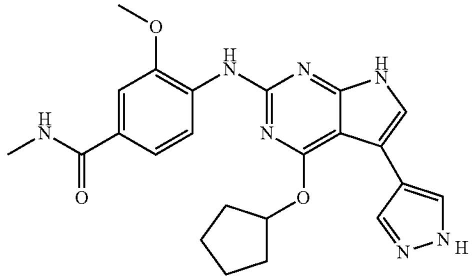 | 4-(4-(cyclopentyloxy)-5-(1H-pyrazol-4-yl)-7H-pyrrolo[2,3-d]pyrimidin-2-ylamino)-3-methoxy-N-methylbenzamide | 448.2 | D |
| 83 | 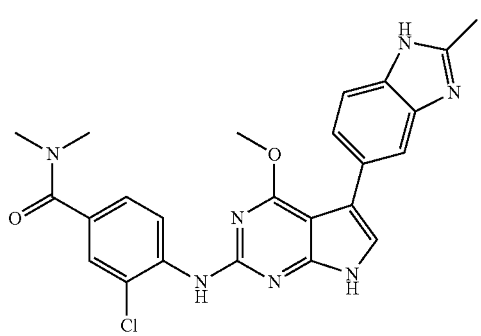 [SMILES: COc1nc(Nc2ccc(C(=O)N(C)C)cc2Cl)nc2[nH]cc(-c3ccc4[nH]c(C)nc4c3)c12] | 3-chloro-4-(4-methoxy-5-(2-methyl-1H-benzo[d]imidazol-5-yl)-7H-pyrrolo[2,3-d]pyrimidin-2-ylamino)-N,N-dimethylbenzamide | 476.1 | D |

TABLE 1-continued

| Cmpd No. | Structure | Name | Obs. MH+ | Act. Level |
|---|---|---|---|---|
| 84 | 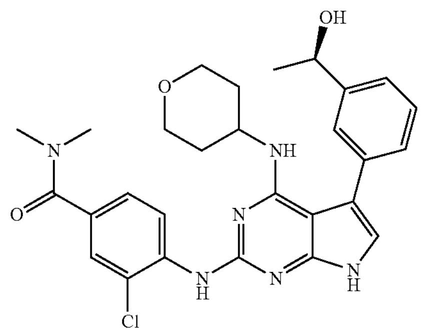 [SMILES: C[C@@H](O)c1cccc(-c2c[nH]c3nc(Nc4ccc(C(=O)N(C)C)cc4Cl)nc(NC4CCOCC4)c23)c1] | (R)-3-chloro-4-(5-(3-(1-hydroxyethyl)phenyl)-4-(tetrahydro-2H-pyran-4-ylamino)-7H-pyrrolo[2,3-d]pyrimidin-2-ylamino)-N,N-dimethylbenzamide | 535.2 | C |
| 85 | 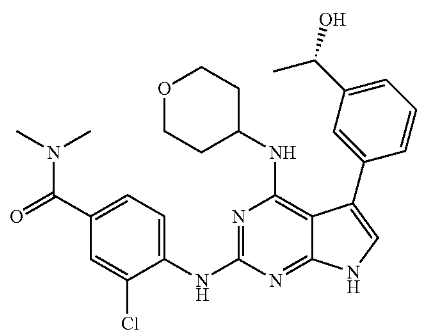 [SMILES: C[C@H](O)c1cccc(-c2c[nH]c3nc(Nc4ccc(C(=O)N(C)C)cc4Cl)nc(NC4CCOCC4)c23)c1] | (S)-3-chloro-4-(5-(3-(1-hydroxyethyl)phenyl)-4-(tetrahydro-2H-pyran-4-ylamino)-7H-pyrrolo[2,3-d]pyrimidin-2-ylamino)-N,N-dimethylbenzamide | 535.3 | D |
| 86 | 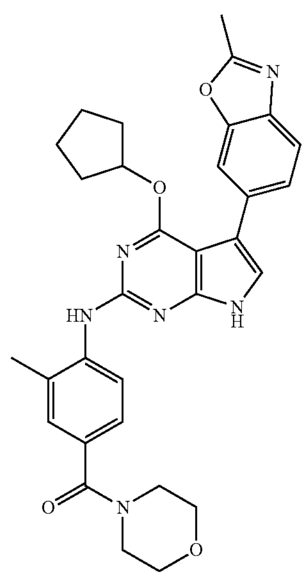 [SMILES: Cc1nc2ccc(-c3c[nH]c4nc(Nc5ccc(C(=O)N6CCOCC6)cc5C)nc(OC5CCCC5)c34)cc2o1] | (4-(4-(cyclopentyloxy)-5-(2-methylbenzo[d]oxazol-6-yl)-7H-pyrrolo[2,3-d]pyrimidin-2-ylamino)-3-methyl-phenyl)(morpholino)methanone | 552.9 | C |
| 87 | 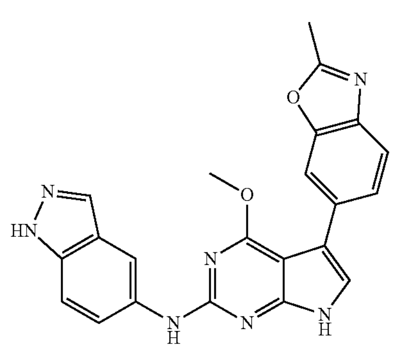 [SMILES: COc1nc(Nc2ccc3[nH]ncc3c2)nc2[nH]cc(-c3ccc4nc(C)oc4c3)c12] | N-(1H-indazol-5-yl)-4-methoxy-5-(2-methylbenzo[d]oxazol-6-yl)-7H-pyrrolo[2,3-d]pyrimidin-2-amine | 412.1 | C |

TABLE 1-continued

| Cmpd No. | Structure | Name | Obs. MH+ | Act. Level |
|---|---|---|---|---|
| 88 | 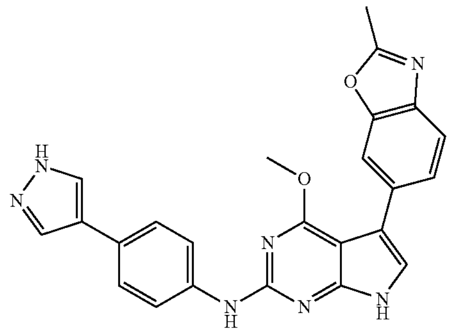 [SMILES: COc1nc(Nc2ccc(-c3cn[nH]c3)cc2)nc2[nH]cc(-c3ccc4nc(C)oc4c3)c12] | N-(4-(1H-pyrazol-4-yl)phenyl)-4-methoxy-5-(2-methylbenzo[d]oxazol-6-yl)-7H-pyrrolo[2,3-d]pyrimidin-2-amine | 438.1 | C |
| 89 | 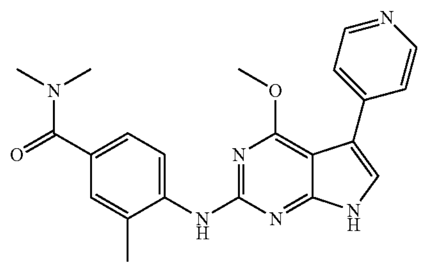 [SMILES: COc1nc(Nc2ccc(C(=O)N(C)C)cc2C)nc2[nH]cc(-c3ccncc3)c12] | 4-(4-methoxy-5-(pyridin-4-yl)-7H-pyrrolo[2,3-d]pyrimidin-2-ylamino)-N,N,3-trimethylbenzamide | 403.1 | C |
| 90 | 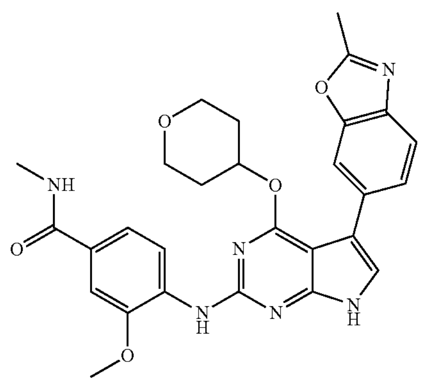 [SMILES: CNC(=O)c1ccc(Nc2nc(OC3CCOCC3)c3c(-c4ccc5nc(C)oc5c4)c[nH]c3n2)c(OC)c1] | 3-methoxy-N-methyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide | 529 | D |
| 91 | 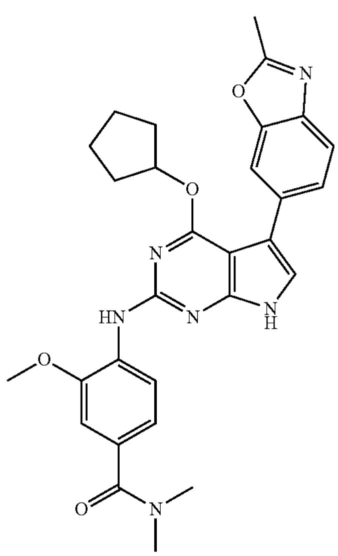 [SMILES: COc1cc(C(=O)N(C)C)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N,N-dimethylbenzamide | 527.5 | C |

TABLE 1-continued

| Cmpd No. | Structure | Name | Obs. MH$^+$ | Act. Level |
|---|---|---|---|---|
| 92 | 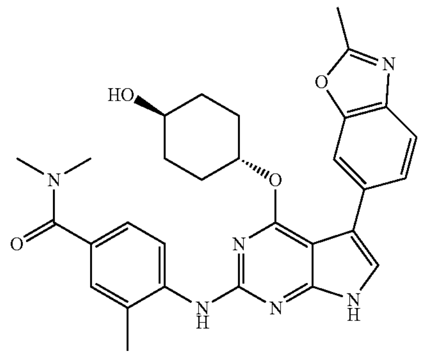 [SMILES: Cc1nc2ccc(-c3c[nH]c4nc(Nc5ccc(C(=O)N(C)C)cc5C)nc(O[C@H]5CC[C@H](O)CC5)c34)cc2o1] | 4-(4-((1r,4r)-4-hydroxycyclohexyloxy)-5-(2-methylbenzo[d]oxazol-6-yl)-7H-pyrrolo[2,3-d]pyrimidin-2-ylamino)-N,N,3-trimethylbenzamide | 541.2 | D |
| 93 | 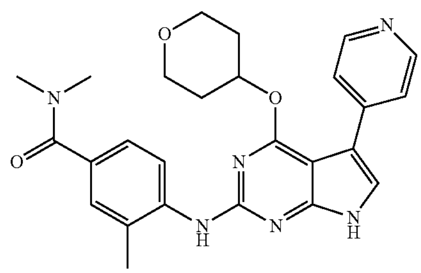 [SMILES: Cc1cc(C(=O)N(C)C)ccc1Nc1nc(OC2CCOCC2)c2c(-c3ccncc3)c[nH]c2n1] | N,N,3-trimethyl-4-(5-(pyridin-4-yl)-4-(tetrahydro-2H-pyran-4-yloxy)-7H-pyrrolo[2,3-d]pyrimidin-2-ylamino)benzamide | 473.2 | D |
| 94 | 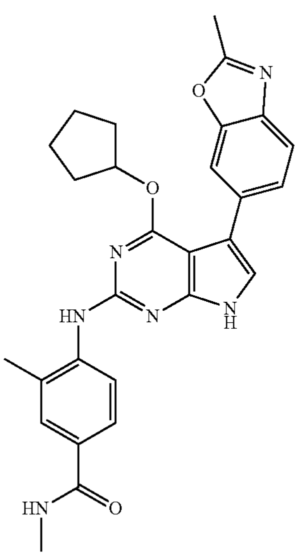 [SMILES: CNC(=O)c1ccc(Nc2nc(OC3CCCC3)c3c(-c4ccc5nc(C)oc5c4)c[nH]c3n2)c(C)c1] | 4-(4-(cyclopentyloxy)-5-(2-methylbenzo[d]oxazol-6-yl)-7H-pyrrolo[2,3-d]pyrimidin-2-ylamino)-N,3-dimethylbenzamide | 497 | B |

TABLE 1-continued

| Cmpd No. | Structure | Name | Obs. MH+ | Act. Level |
|---|---|---|---|---|
| 95 | 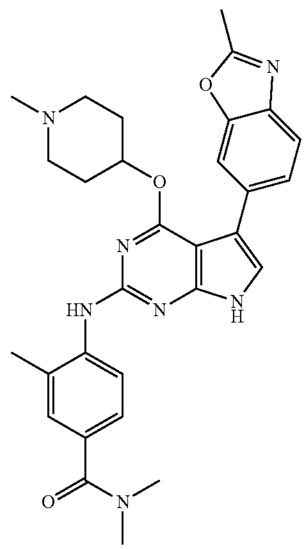 [SMILES: Cc1nc2ccc(-c3c[nH]c4nc(Nc5ccc(C(=O)N(C)C)cc5C)nc(OC5CCN(C)CC5)c34)cc2o1] | N,N,3-trimethyl-4-(5-(2-methylbenzo[d]oxazol-6-yl)-4-(1-methylpiperidin-4-yloxy)-7H-pyrrolo[2,3-d]pyrimidin-2-ylamino)benzamide | 540 | B |
| 96 | 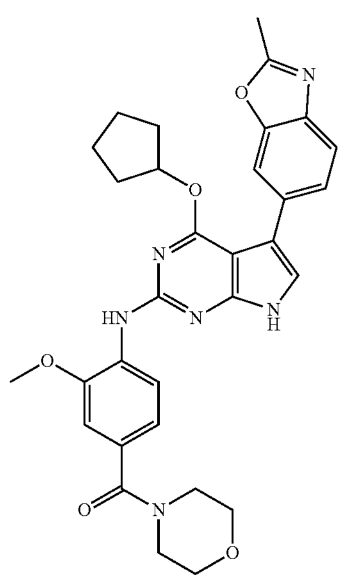 [SMILES: COc1cc(C(=O)N2CCOCC2)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)(morpholino)methanone | 569.3 | B |

TABLE 1-continued

| Cmpd No. | Structure | Name | Obs. MH+ | Act. Level |
|---|---|---|---|---|
| 97 | 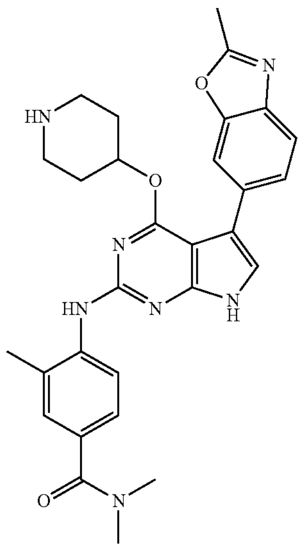 [SMILES: Cc1nc2ccc(-c3c[nH]c4nc(Nc5ccc(C(=O)N(C)C)cc5C)nc(OC5CCNCC5)c34)cc2o1] | N,N,3-trimethyl-4-(5-(2-methylbenzo[d]oxazol-6-yl)-4-(piperidin-4-yloxy)-7H-pyrrolo[2,3-d]pyrimidin-2-ylamino)benzamide | 525.9 | A |
| 98 | 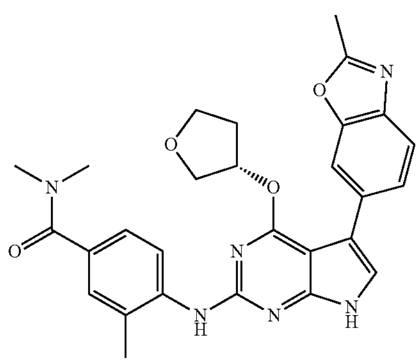 [SMILES: Cc1nc2ccc(-c3c[nH]c4nc(Nc5ccc(C(=O)N(C)C)cc5C)nc(O[C@H]5CCOC5)c34)cc2o1] | (S)-N,N,3-trimethyl-4-(5-(2-methylbenzo[d]oxazol-6-yl)-4-(tetrahydrofuran-3-yloxy)-7H-pyrrolo[2,3-d]pyrimidin-2-ylamino)benzamide | 513.2 | D |
| 99 | 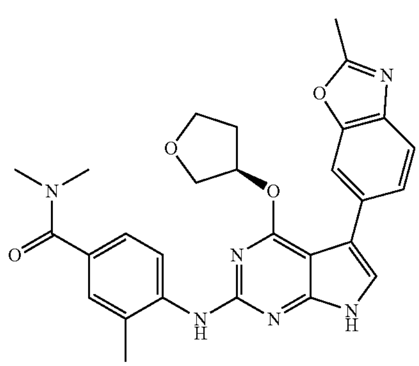 [SMILES: Cc1nc2ccc(-c3c[nH]c4nc(Nc5ccc(C(=O)N(C)C)cc5C)nc(O[C@@H]5CCOC5)c34)cc2o1] | (R)-N,N,3-trimethyl-4-(5-(2-methylbenzo[d]oxazol-6-yl)-4-(tetrahydrofuran-3-yloxy)-7H-pyrrolo[2,3-d]pyrimidin-2-ylamino)benzamide | 513.2 | D |

TABLE 1-continued

| Cmpd No. | Structure | Name | Obs. MH+ | Act. Level |
|---|---|---|---|---|
| 100 | 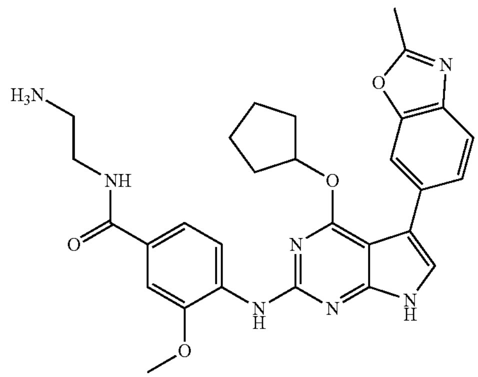 [SMILES: COc1cc(C(=O)NCCN)ccc1Nc1nc(OC2CCCC2)c2c(-c3ccc4nc(C)oc4c3)c[nH]c2n1] | N-(2-aminoethyl)-4-(4-(cyclopentyloxy)-5-(2-methylbenzo[d]oxazol-6-yl)-7H-pyrrolo[2,3-d]pyrimidin-2-ylamino)-3-methoxybenzamide | 542.2 | D |
| 101 | 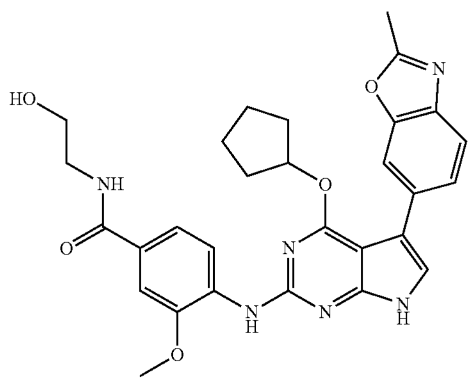 [SMILES: COc1cc(C(=O)NCCO)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-(2-hydroxyethyl)-3-methoxybenzamide | 543.2 | D |
| 102 | 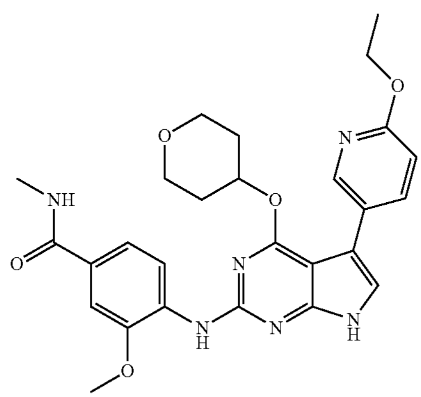 [SMILES: CCOc1ccc(-c2c[nH]c3nc(Nc4ccc(C(=O)NC)cc4OC)nc(OC4CCOCC4)c23)cn1] | 4-(5-(6-ethoxypyridin-3-yl)-4-(tetrahydro-2H-pyran-4-yloxy)-7H-pyrrolo[2,3-d]pyrimidin-2-ylamino)-3-methoxy-N-methylbenzamide | 519.5 | C |
| 103 | 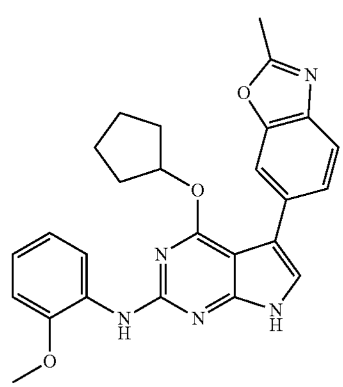 [SMILES: COc1ccccc1Nc1nc(OC2CCCC2)c2c(-c3ccc4nc(C)oc4c3)c[nH]c2n1] | 4-(cyclopentyloxy)-N-(2-methoxyphenyl)-5-(2-methylbenzo[d]oxazol-6-yl)-7H-pyrrolo[2,3-d]pyrimidin-2-amine | 456.2 | C |

TABLE 1-continued

| Cmpd No. | Structure | Name | Obs. MH+ | Act. Level |
|---|---|---|---|---|
| 104 | 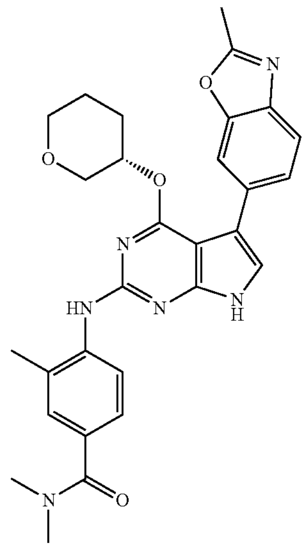 [SMILES: Cc1nc2ccc(-c3c[nH]c4nc(Nc5ccc(C(=O)N(C)C)cc5C)nc(O[C@H]5CCCOC5)c34)cc2o1] | (S)-N,N,3-trimethyl-4-(5-(2-methylbenzo[d]oxazol-6-yl)-4-(tetrahydro-2H-pyran-3-yloxy)-7H-pyrrolo[2,3-d]pyrimidin-2-ylamino)benzamide | 527 | D |
| 105 | 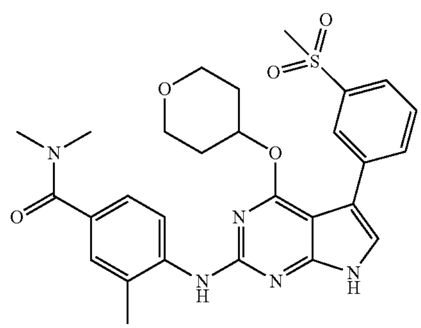 [SMILES: Cc1cc(C(=O)N(C)C)ccc1Nc1nc(OC2CCOCC2)c2c(-c3cccc(S(C)(=O)=O)c3)c[nH]c2n1] | N,N,3-trimethyl-4-(5-(3-(methylsulfonyl)phenyl)-4-(tetrahydro-2H-pyran-4-yloxy)-7H-pyrrolo[2,3-d]pyrimidin-2-ylamino)benzamide | 550.2 | D |
| 106 | 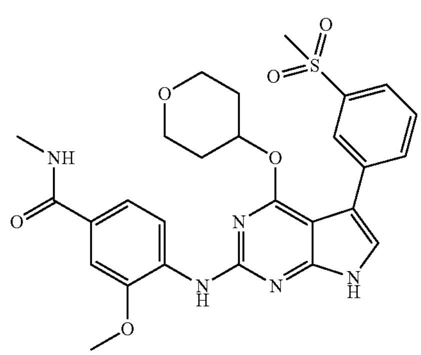 [SMILES: CNC(=O)c1ccc(Nc2nc(OC3CCOCC3)c3c(-c4cccc(S(C)(=O)=O)c4)c[nH]c3n2)c(OC)c1] | 3-methoxy-N-methyl-4-(5-(3-(methylsulfonyl)phenyl)-4-(tetrahydro-2H-pyran-4-yloxy)-7H-pyrrolo[2,3-d]pyrimidin-2-ylamino)benzamide | 552.2 | D |

| Cmpd No. | Structure | Name | Obs. MH+ | Act. Level |
|---|---|---|---|---|
| 107 | 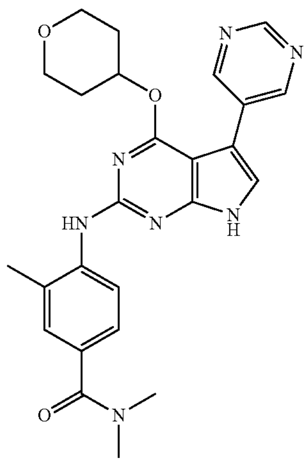 [SMILES: Cc1cc(C(=O)N(C)C)ccc1Nc1nc(OC2CCOCC2)c2c(-c3cncnc3)c[nH]c2n1] | N,N,3-trimethyl-4-(5-(pyrimidin-5-yl)-4-(tetrahydro-2H-pyran-4-yloxy)-7H-pyrrolo[2,3-d]pyrimidin-2-ylamino)benzamide | 474 | C |
| 108 | 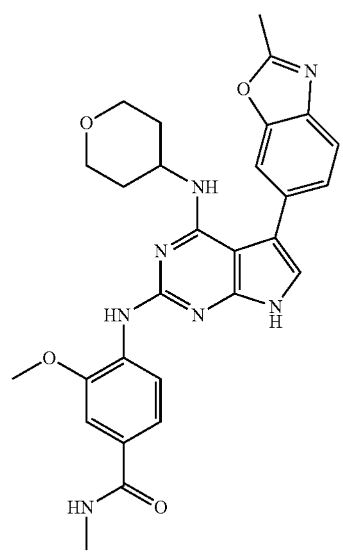 | 3-methoxy-N-methyl-4-(5-(2-methylbenzo[d]oxazol-6-yl)-4-(tetrahydro-2H-pyran-4-ylamino)-7H-pyrrolo[2,3-d]pyrimidin-2-ylamino)benzamide | 527.8 | B |
| 109 | 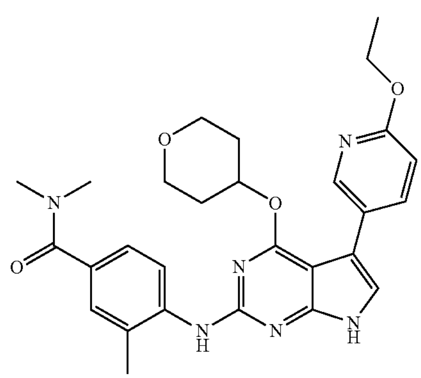 [SMILES: CCOc1ccc(-c2c[nH]c3nc(Nc4ccc(C(=O)N(C)C)cc4C)nc(OC4CCOCC4)c23)cn1] | 4-(5-(6-ethoxypyridin-3-yl)-4-(tetrahydro-2H-pyran-4-yloxy)-7H-pyrrolo[2,3-d]pyrimidin-2-ylamino)-N,N,3-trimethylbenzamide | 517.3 | D |

TABLE 1-continued

| Cmpd No. | Structure | Name | Obs. MH+ | Act. Level |
|---|---|---|---|---|
| 110 | 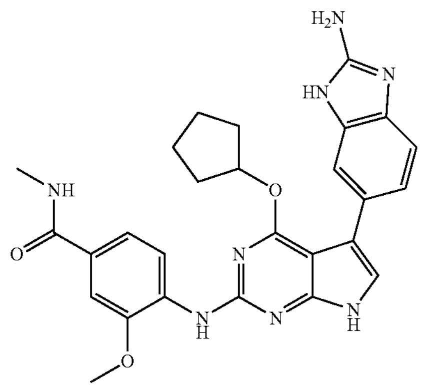 [SMILES: CNC(=O)c1ccc(Nc2nc(OC3CCCC3)c3c(-c4ccc5nc(N)[nH]c5c4)c[nH]c3n2)c(OC)c1] | 4-(5-(2-amino-1H-benzo[d]imidazol-6-yl)-4-(cyclopentyloxy)-7H-pyrrolo[2,3-d]pyrimidin-2-ylamino)-3-methoxy-N-methylbenzamide | 513.2 | D |
| 111 | 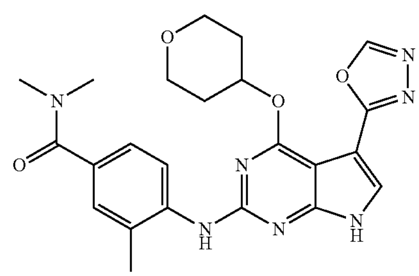 [SMILES: Cc1cc(C(=O)N(C)C)ccc1Nc1nc(OC2CCOCC2)c2c(-c3nnco3)c[nH]c2n1] | 4-(5-(1,3,4-oxadiazol-2-yl)-4-(tetrahydro-2H-pyran-4-yloxy)-7H-pyrrolo[2,3-d]pyrimidin-2-ylamino)-N,N,3-trimethylbenzamide | 464.2 | A |
| 112 | 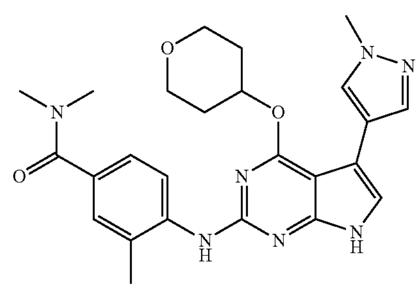 [SMILES: Cc1cc(C(=O)N(C)C)ccc1Nc1nc(OC2CCOCC2)c2c(-c3cnn(C)c3)c[nH]c2n1] | N,N,3-trimethyl-4-(5-(1-methyl-1H-pyrazol-4-yl)-4-(tetrahydro-2H-pyran-4-yloxy)-7H-pyrrolo[2,3-d]pyrimidin-2-ylamino)benzamide | 476.2 | D |
| 113 | 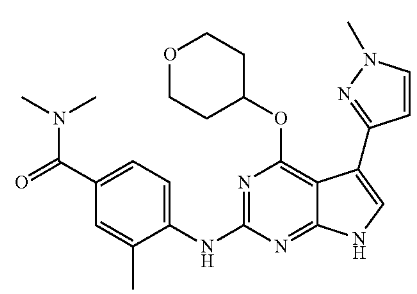 [SMILES: Cc1cc(C(=O)N(C)C)ccc1Nc1nc(OC2CCOCC2)c2c(-c3ccn(C)n3)c[nH]c2n1] | N,N,3-trimethyl-4-(5-(1-methyl-1H-pyrazol-3-yl)-4-(tetrahydro-2H-pyran-4-yloxy)-7H-pyrrolo[2,3-d]pyrimidin-2-ylamino)benzamide | 476.2 | B |

| Cmpd No. | Structure | Name | Obs. MH+ | Act. Level |
|---|---|---|---|---|
| 114 | 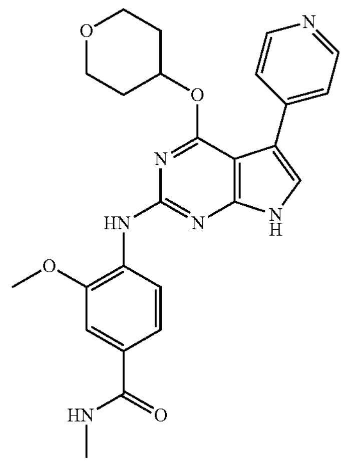 | 3-methoxy-N-methyl-4-(5-(pyridin-4-yl)-4-(tetrahydro-2H-pyran-4-yloxy)-7H-pyrrolo[2,3-d]pyrimidin-2-ylamino)benzamide | 475.5 | D |
| 115 | 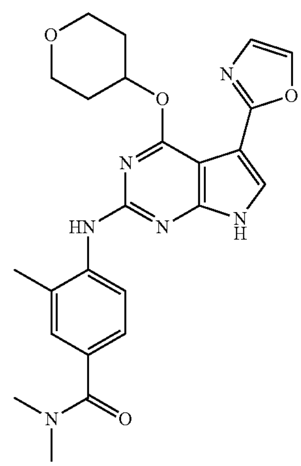 [SMILES: Cc1cc(C(=O)N(C)C)ccc1Nc1nc(OC2CCOCC2)c2c(-c3ncco3)c[nH]c2n1] | N,N,3-trimethyl-4-(5-(oxazol-2-yl)-4-(tetrahydro-2H-pyran-4-yloxy)-7H-pyrrolo[2,3-d]pyrimidin-2-ylamino)benzamide | 463.2 | B |
| 116 | 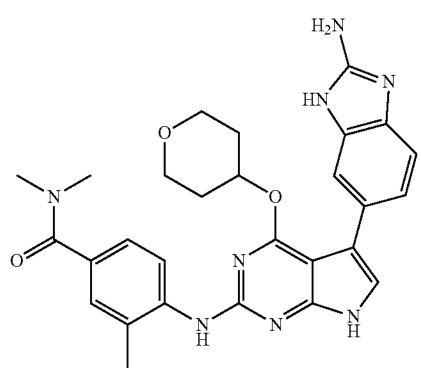 [SMILES: Cc1cc(C(=O)N(C)C)ccc1Nc1nc(OC2CCOCC2)c2c(-c3ccc4nc(N)[nH]c4c3)c[nH]c2n1] | 4-(5-(2-amino-1H-benzo[d]imidazol-6-yl)-4-(tetrahydro-2H-pyran-4-yloxy)-7H-pyrrolo[2,3-d]pyrimidin-2-ylamino)-N,N,3-trimethylbenzamide | 527.2 | D |
| 117 | 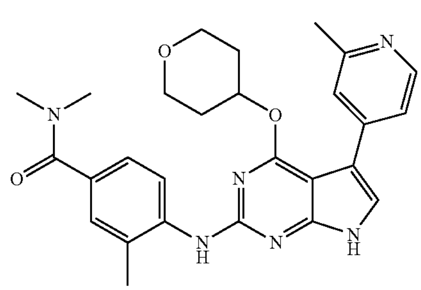 [SMILES: Cc1cc(-c2c[nH]c3nc(Nc4ccc(C(=O)N(C)C)cc4C)nc(OC4CCOCC4)c23)ccn1] | N,N,3-trimethyl-4-(5-(2-methylpyridin-4-yl)-4-(tetrahydro-2H-pyran-4-yloxy)-7H-pyrrolo[2,3-d]pyrimidin-2-ylamino)benzamide | 487.2 | D |

TABLE 1-continued

| Cmpd No. | Structure | Name | Obs. MH+ | Act. Level |
|---|---|---|---|---|
| 118 | 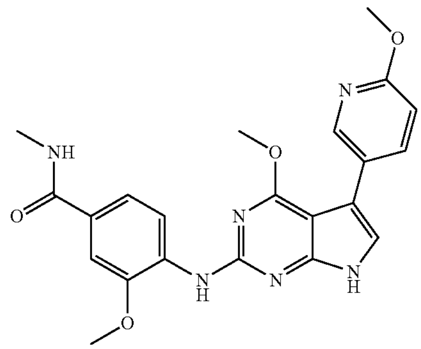 [SMILES: CNC(=O)c1ccc(Nc2nc(OC)c3c(-c4ccc(OC)nc4)c[nH]c3n2)c(OC)c1] | 3-methoxy-4-(4-methoxy-5-(6-methoxypyridin-3-yl)-7H-pyrrolo[2,3-d]pyrimidin-2-ylamino)-N-methylbenzamide | 435.2 | C |
| 119 | 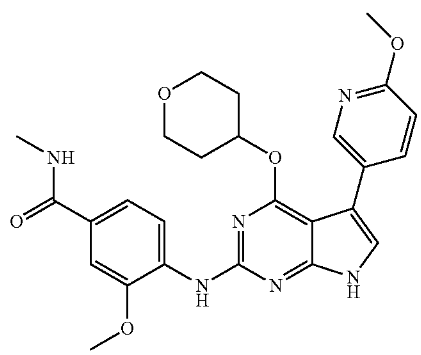 [SMILES: CNC(=O)c1ccc(Nc2nc(OC3CCOCC3)c3c(-c4ccc(OC)nc4)c[nH]c3n2)c(OC)c1] | 3-methoxy-4-(5-(6-methoxypyridin-3-yl)-4-(tetrahydro-2H-pyran-4-yloxy)-7H-pyrrolo[2,3-d]pyrimidin-2-ylamino)-N-methylbenzamide | 505.2 | D |
| 120 | 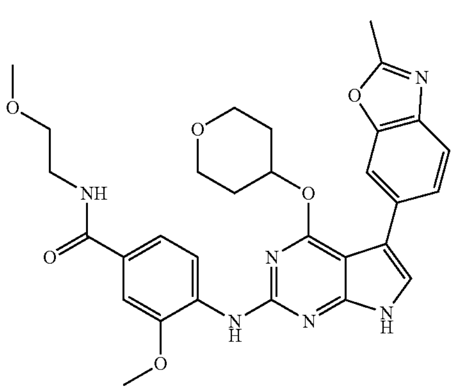 [SMILES: COCCNC(=O)c1ccc(Nc2nc(OC3CCOCC3)c3c(-c4ccc5nc(C)oc5c4)c[nH]c3n2)c(OC)c1] | 3-methoxy-N-(2-methoxyethyl)-4-(5-(2-methylbenzo[d]oxazol-6-yl)-4-(tetrahydro-2H-pyran-4-yloxy)-7H-pyrrolo[2,3-d]pyrimidin-2-ylamino)benzamide | 573.2 | D |

TABLE 1-continued

| Cmpd No. | Structure | Name | Obs. MH+ | Act. Level |
|---|---|---|---|---|
| 121 | 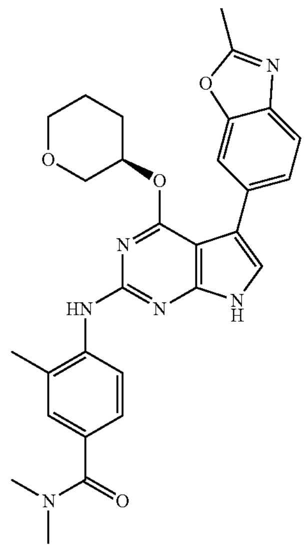 [SMILES: Cc1nc2ccc(-c3c[nH]c4nc(Nc5ccc(C(=O)N(C)C)cc5C)nc(O[C@@H]5CCCOC5)c34)cc2o1] | (R)-N,N,3-trimethyl-4-(5-(2-methylbenzo[d]oxazol-6-yl)-4-(tetrahydro-2H-pyran-3-yloxy)-7H-pyrrolo[2,3-d]pyrimidin-2-ylamino)benzamide | 527 | |
| 122 | 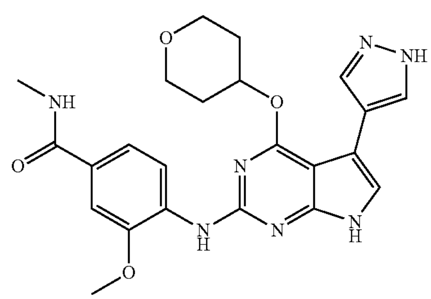 [SMILES: CNC(=O)c1ccc(Nc2nc(OC3CCOCC3)c3c(-c4cn[nH]c4)c[nH]c3n2)c(OC)c1] | 4-(5-(1H-pyrazol-4-yl)-4-(tetrahydro-2H-pyran-4-yloxy)-7H-pyrrolo[2,3-d]pyrimidin-2-ylamino)-3-methoxy-N-methylbenzamide | 464.1 | D |
| 123 | 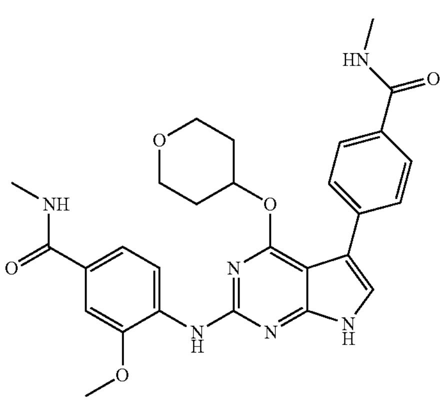 [SMILES: CNC(=O)c1ccc(-c2c[nH]c3nc(Nc4ccc(C(=O)NC)cc4OC)nc(OC4CCOCC4)c23)cc1] | 3-methoxy-N-methyl-4-(5-(4-(methylcarbamoyl)phenyl)-4-(tetrahydro-2H-pyran-4-yloxy)-7H-pyrrolo[2,3-d]pyrimidin-2-ylamino)benzamide | 531.3 | D |

TABLE 1-continued

| Cmpd No. | Structure | Name | Obs. MH+ | Act. Level |
|---|---|---|---|---|
| 124 | 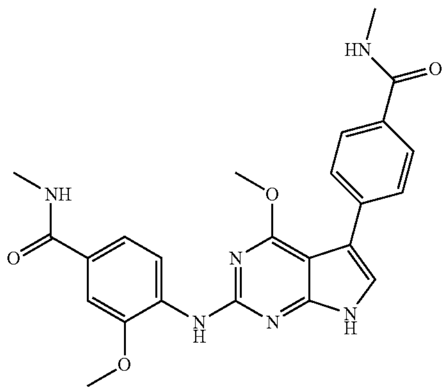 [SMILES: CNC(=O)c1ccc(-c2c[nH]c3nc(Nc4ccc(C(=O)NC)cc4OC)nc(OC)c23)cc1] | 3-methoxy-4-(4-methoxy-5-(4-(methylcarbamoyl)phenyl)-7H-pyrrolo[2,3-d]pyrimidin-2-ylamino)-N-methylbenzamide | 461.2 | C |
| 125 | 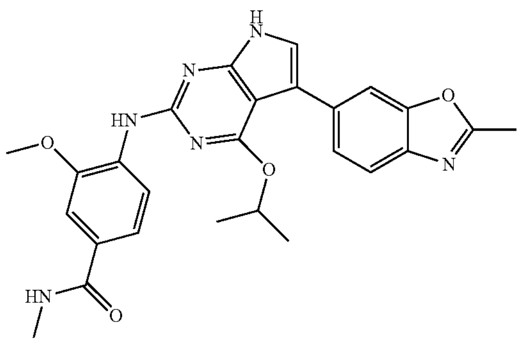 | 4-(4-isopropoxy-5-(2-methylbenzo[d]oxazol-6-yl)-7H-pyrrolo[2,3-d]pyrimidin-2-ylamino)-3-methoxy-N-methylbenzamide | 487 | D |
| 126 | 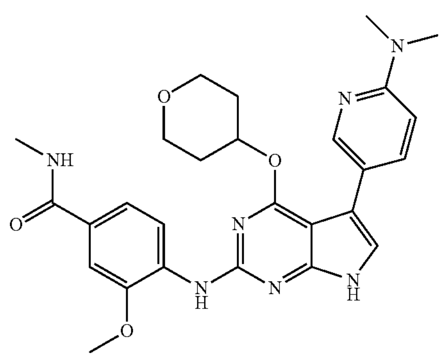 [SMILES: CNC(=O)c1ccc(Nc2nc(OC3CCOCC3)c3c(-c4ccc(N(C)C)nc4)c[nH]c3n2)c(OC)c1] | 4-(5-(6-(dimethylamino)pyridin-3-yl)-4-(tetrahydro-2H-pyran-4-yloxy)-7H-pyrrolo[2,3-d]pyrimidin-2-ylamino)-3-methoxy-N-methylbenzamide | 518.2 | B |
| 127 | 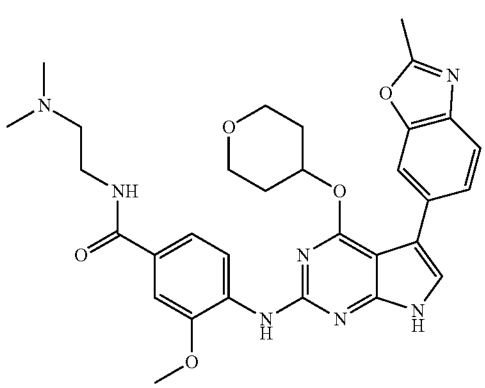 [SMILES: COc1cc(C(=O)NCCN(C)C)ccc1Nc1nc(OC2CCOCC2)c2c(-c3ccc4nc(C)oc4c3)c[nH]c2n1] | N-(2-(dimethylamino)ethyl)-3-methoxy-4-(5-(2-methylbenzo[d]oxazol-6-yl)-4-(tetrahydro-2H-pyran-4-yloxy)-7H-pyrrolo[2,3-d]pyrimidin-2-ylamino)benzamide | 586.2 | D |

TABLE 1-continued

| Cmpd No. | Structure | Name | Obs. MH+ | Act. Level |
|---|---|---|---|---|
| 128 | 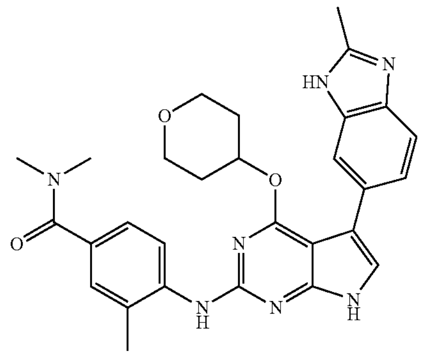 [SMILES: Cc1nc2ccc(-c3c[nH]c4nc(Nc5ccc(C(=O)N(C)C)cc5C)nc(OC5CCOCC5)c34)cc2[nH]1] | N,N,3-trimethyl-4-(5-(2-methyl-1H-benzo[d]imidazol-6-yl)-4-(tetrahydro-2H-pyran-4-yloxy)-7H-pyrrolo[2,3-d]pyrimidin-2-ylamino)benzamide | 526.2 | D |
| 129 | 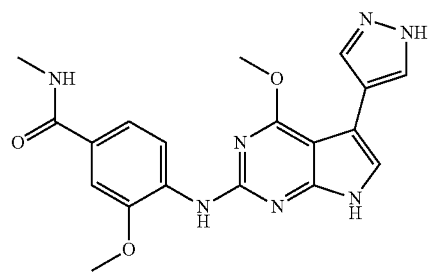 [SMILES: CNC(=O)c1ccc(Nc2nc(OC)c3c(-c4cn[nH]c4)c[nH]c3n2)c(OC)c1] | 3-methoxy-4-(4-methoxy-5-(1H-pyrazol-4-yl)-7H-pyrrolo[2,3-d]pyrimidin-2-ylamino)-N-methylbenzamide | 394.1 | C |
| 130 | 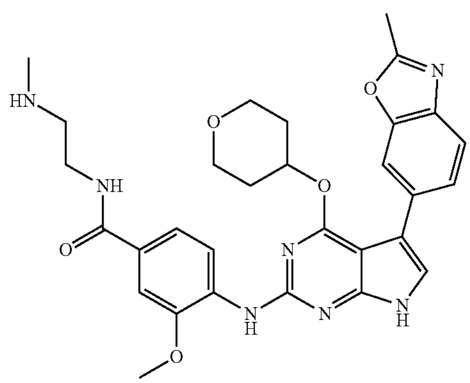 [SMILES: CNCCNC(=O)c1ccc(Nc2nc(OC3CCOCC3)c3c(-c4ccc5nc(C)oc5c4)c[nH]c3n2)c(OC)c1] | 3-methoxy-N-(2-(methylamino)ethyl)-4-(5-(2-methylbenzo[d]oxazol-6-yl)-4-(tetrahydro-2H-pyran-4-yloxy)-7H-pyrrolo[2,3-d]pyrimidin-2-ylamino)benzamide | 572.3 | C |
| 131 | 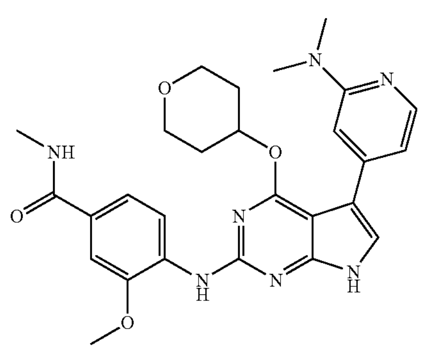 [SMILES: CNC(=O)c1ccc(Nc2nc(OC3CCOCC3)c3c(-c4ccnc(N(C)C)c4)c[nH]c3n2)c(OC)c1] | 4-(5-(2-(dimethylamino)pyridin-4-yl)-4-(tetrahydro-2H-pyran-4-yloxy)-7H-pyrrolo[2,3-d]pyrimidin-2-ylamino)-3-methoxy-N-methylbenzamide | 518.2 | D |

TABLE 1-continued
| Cmpd No. | Structure | Name | Obs. MH+ | Act. Level |
|---|---|---|---|---|
| 132 | 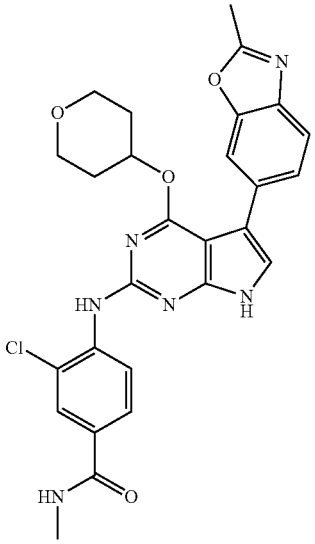 [SMILES: CNC(=O)c1ccc(Nc2nc(OC3CCOCC3)c3c(-c4ccc5nc(C)oc5c4)c[nH]c3n2)c(Cl)c1] | 3-chloro-N-methyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide | 532.8 | B |
| 133 | 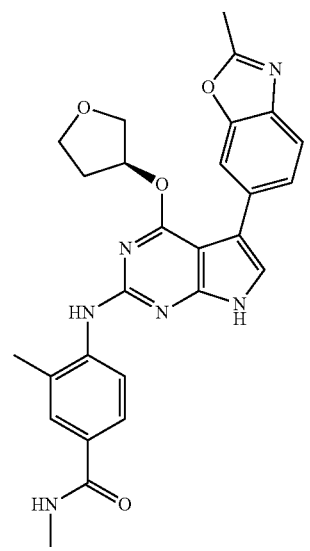 [SMILES: CNC(=O)c1ccc(Nc2nc(O[C@H]3CCOC3)c3c(-c4ccc5nc(C)oc5c4)c[nH]c3n2)c(C)c1] | (S)-N,3-dimethyl-4-(5-(2-methylbenzo[d]oxazol-6-yl)-4-(tetrahydrofuran-3-yloxy)-7H-pyrrolo[2,3-d]pyrimidin-2-ylamino)benzamide | 499.6 | D |

TABLE 1-continued

| Cmpd No. | Structure | Name | Obs. MH+ | Act. Level |
|---|---|---|---|---|
| 134 | 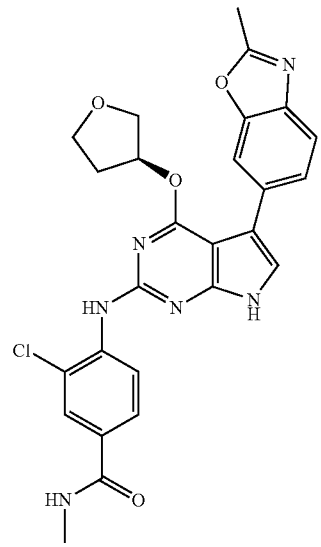 [SMILES: CNC(=O)c1ccc(Nc2nc(O[C@H]3CCOC3)c3c(-c4ccc5nc(C)oc5c4)c[nH]c3n2)c(Cl)c1] | (S)-3-chloro-N-methyl-4-(5-(2-methylbenzo[d]oxazol-6-yl)-4-(tetrahydrofuran-3-yloxy)-7H-pyrrolo[2,3-d]pyrimidin-2-ylamino)benzamide | 519.5 | D |
| 135 | 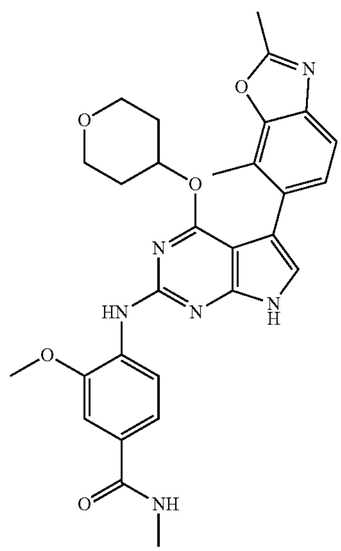 [SMILES: CNC(=O)c1ccc(Nc2nc(OC3CCOCC3)c3c(-c4ccc5nc(C)oc5c4C)c[nH]c3n2)c(OC)c1] | 4-(5-(2,7-dimethylbenzo[d]oxazol-6-yl)-4-(tetrahydro-2H-pyran-4-yloxy)-7H-pyrrolo[2,3-d]pyrimidin-2-ylamino)-3-methoxy-N-methylbenzamide | 542.9 | A |
| 136 | 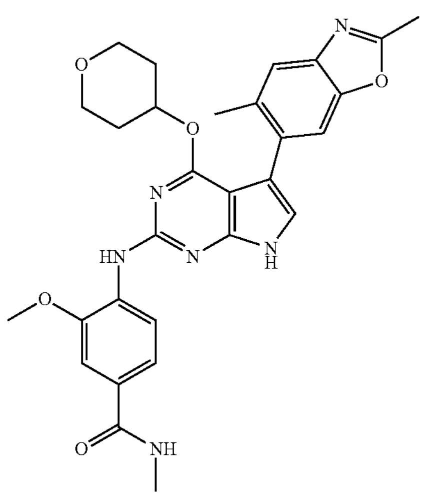 | 4-(5-(2,5-dimethylbenzo[d]oxazol-6-yl)-4-(tetrahydro-2H-pyran-4-yloxy)-7H-pyrrolo[2,3-d]pyrimidin-2-ylamino)-3-methoxy-N-methylbenzamide | 542.9 | A |

TABLE 1-continued

| Cmpd No. | Structure | Name | Obs. MH+ | Act. Level |
|---|---|---|---|---|
| 137 | 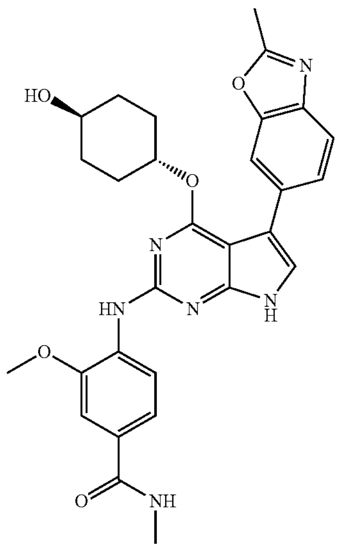 [SMILES: CNC(=O)c1ccc(Nc2nc(O[C@H]3CC[C@H](O)CC3)c3c(-c4ccc5nc(C)oc5c4)c[nH]c3n2)c(OC)c1] | 4-(4-((1r,4r)-4-hydroxycyclohexyloxy)-5-(2-methylbenzo[d]oxazol-6-yl)-7H-pyrrolo[2,3-d]pyrimidin-2-ylamino)-3-methoxy-N-methylbenzamide | 543.2 | D |
| 138 | 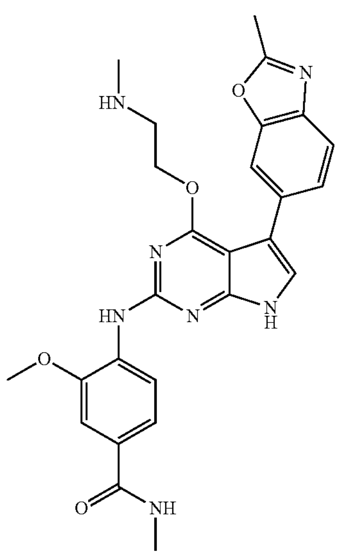 [SMILES: CNCCOc1nc(Nc2ccc(C(=O)NC)cc2OC)nc2[nH]cc(-c3ccc4nc(C)oc4c3)c12] | 3-methoxy-N-methyl-4-(4-(2-(methylamino)ethoxy)-5-(2-methylbenzo[d]oxazol-6-yl)-7H-pyrrolo[2,3-d]pyrimidin-2-ylamino)benzamide | 502.2 | A |

TABLE 1-continued

| Cmpd No. | Structure | Name | Obs. MH+ | Act. Level |
|---|---|---|---|---|
| 139 | 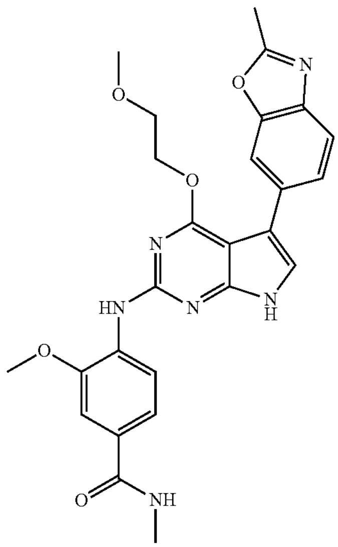 [SMILES: CNC(=O)c1ccc(Nc2nc(OCCOC)c3c(-c4ccc5nc(C)oc5c4)c[nH]c3n2)c(OC)c1] | 3-methoxy-4-(4-(2-methoxyethoxy)-5-(2-methylbenzo[d]oxazol-6-yl)-7H-pyrrolo[2,3-d]pyrimidin-2-ylamino)-N-methylbenzamide | 503.2 | D |
| 140 | 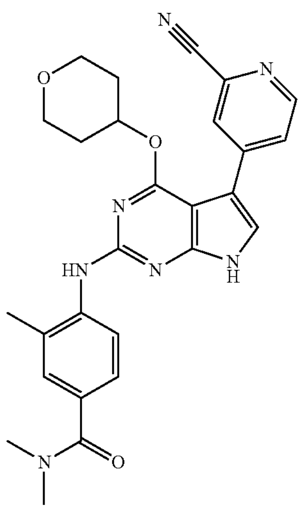 [SMILES: Cc1cc(C(=O)N(C)C)ccc1Nc1nc(OC2CCOCC2)c2c(-c3ccnc(C#N)c3)c[nH]c2n1] | 4-(5-(2-cyanopyridin-4-yl)-4-(tetrahydro-2H-pyran-4-yloxy)-7H-pyrrolo[2,3-d]pyrimidin-2-ylamino)-N,N,3-trimethylbenzamide | 497.9 | C |
| 141 | 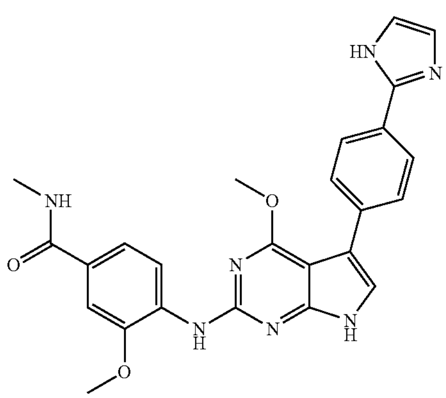 [SMILES: CNC(=O)c1ccc(Nc2nc(OC)c3c(-c4ccc(-c5ncc[nH]5)cc4)c[nH]c3n2)c(OC)c1] | 4-(5-(4-(1H-imidazol-2-yl)phenyl)-4-methoxy-7H-pyrrolo[2,3-d]pyrimidin-2-ylamino)-3-methoxy-N-methylbenzamide | 470.1 | C |

TABLE 1-continued

| Cmpd No. | Structure | Name | Obs. MH+ | Act. Level |
|---|---|---|---|---|
| 142 | 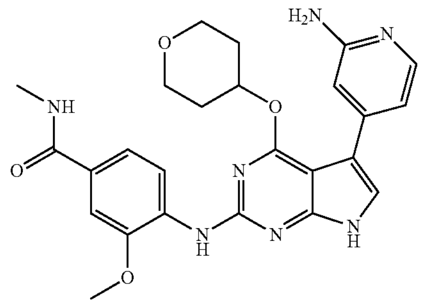 [SMILES: CNC(=O)c1ccc(Nc2nc(OC3CCOCC3)c3c(-c4ccnc(N)c4)c[nH]c3n2)c(OC)c1] | 4-(5-(2-aminopyridin-4-yl)-4-(tetrahydro-2H-pyran-4-yloxy)-7H-pyrrolo[2,3-d]pyrimidin-2-ylamino)-3-methoxy-N-methylbenzamide | 490.2 | D |
| 143 | 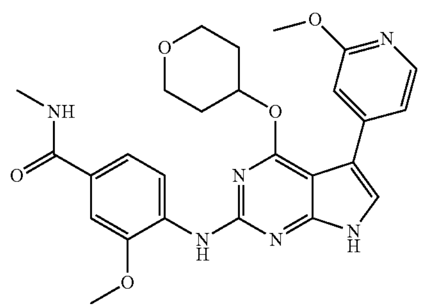 [SMILES: CNC(=O)c1ccc(Nc2nc(OC3CCOCC3)c3c(-c4ccnc(OC)c4)c[nH]c3n2)c(OC)c1] | 3-methoxy-4-(5-(2-methoxypyridin-4-yl)-4-(tetrahydro-2H-pyran-4-yloxy)-7H-pyrrolo[2,3-d]pyrimidin-2-ylamino)-N-methylbenzamide | 505.3 | D |
| 144 | 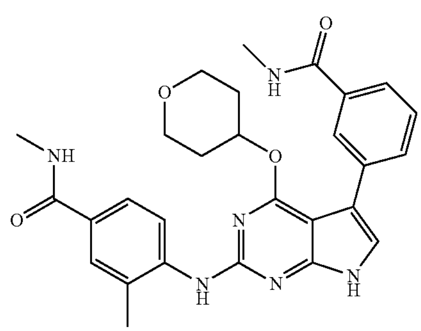 [SMILES: CNC(=O)c1cccc(-c2c[nH]c3nc(Nc4ccc(C(=O)NC)cc4C)nc(OC4CCOCC4)c23)c1] | N,3-dimethyl-4-(5-(3-(methylcarbamoyl)phenyl)-4-(tetrahydro-2H-pyran-4-yloxy)-7H-pyrrolo[2,3-d]pyrimidin-2-ylamino)benzamide | 515.2 | A |
| 145 | 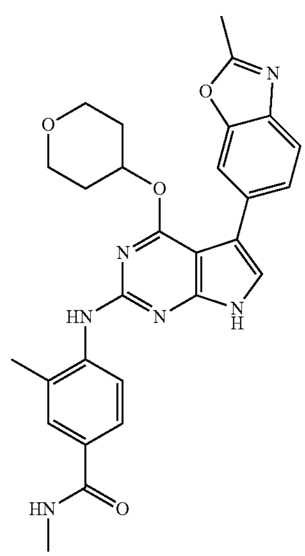 [SMILES: CNC(=O)c1ccc(Nc2nc(OC3CCOCC3)c3c(-c4ccc5nc(C)oc5c4)c[nH]c3n2)c(C)c1] | N,3-dimethyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide | 512.9 | B |

TABLE 1-continued

| Cmpd No. | Structure | Name | Obs. MH+ | Act. Level |
|---|---|---|---|---|
| 146 | 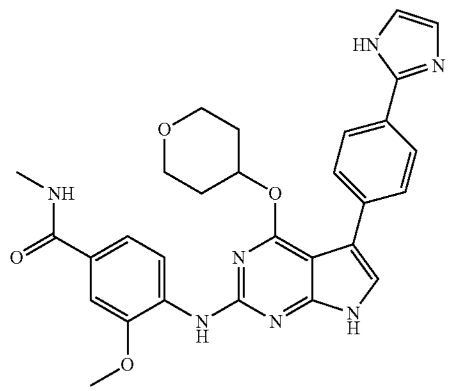 [SMILES: CNC(=O)c1ccc(Nc2nc(OC3CCOCC3)c3c(-c4ccc(-c5ncc[nH]5)cc4)c[nH]c3n2)c(OC)c1] | 4-(5-(4-(1H-imidazol-2-yl)phenyl)-4-(tetrahydro-2H-pyran-4-yloxy)-7H-pyrrolo[2,3-d]pyrimidin-2-ylamino)-3-methoxy-N-methylbenzamide | 540.2 | D |
| 147 | 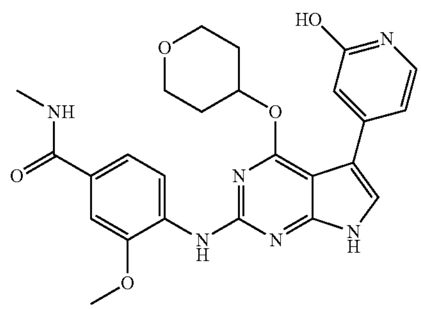 [SMILES: CNC(=O)c1ccc(Nc2nc(OC3CCOCC3)c3c(-c4ccnc(O)c4)c[nH]c3n2)c(OC)c1] | 4-(5-(2-hydroxypyridin-4-yl)-4-(tetrahydro-2H-pyran-4-yloxy)-7H-pyrrolo[2,3-d]pyrimidin-2-ylamino)-3-methoxy-N-methylbenzamide | 491.1 | C |
| 148 | 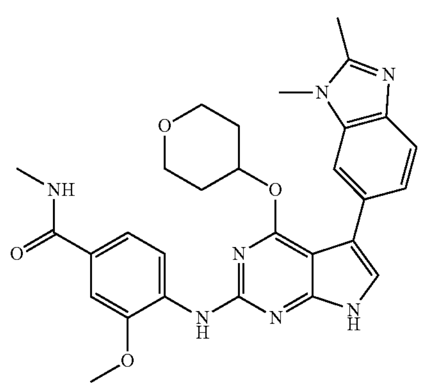 [SMILES: CNC(=O)c1ccc(Nc2nc(OC3CCOCC3)c3c(-c4ccc5nc(C)n(C)c5c4)c[nH]c3n2)c(OC)c1] | 4-(5-(1,2-dimethyl-1H-benzo[d]imidazol-6-yl)-4-(tetrahydro-2H-pyran-4-yloxy)-7H-pyrrolo[2,3-d]pyrimidin-2-ylamino)-3-methoxy-N-methylbenzamide | 542.2 | D |
| 149 | 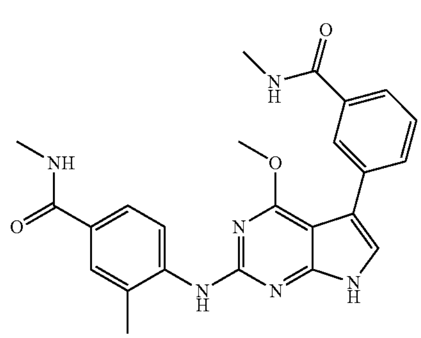 [SMILES: CNC(=O)c1cccc(-c2c[nH]c3nc(Nc4ccc(C(=O)NC)cc4C)nc(OC)c23)c1] | 4-(4-methoxy-5-(3-(methylcarbamoyl)phenyl)-7H-pyrrolo[2,3-d]pyrimidin-2-ylamino)-N,3-dimethylbenzamide | 445.2 | A |

TABLE 1-continued

| Cmpd No. | Structure | Name | Obs. MH+ | Act. Level |
|---|---|---|---|---|
| 150 | 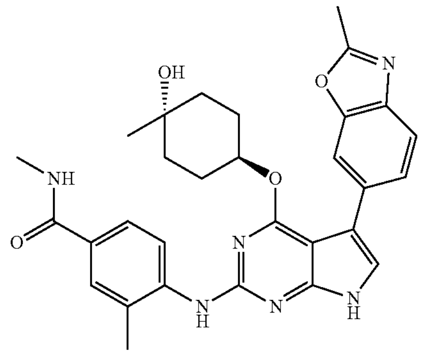 [SMILES: CNC(=O)c1ccc(Nc2nc(O[C@H]3CC[C@](C)(O)CC3)c3c(-c4ccc5nc(C)oc5c4)c[nH]c3n2)c(C)c1] | 4-(4-((1r,4r)-4-hydroxy-4-methylcyclohexyloxy)-5-(2-methylbenzo[d]oxazol-6-yl)-7H-pyrrolo[2,3-d]pyrimidin-2-ylamino)-N,3-dimethylbenzamide | 541.2 | D |
| 151 | 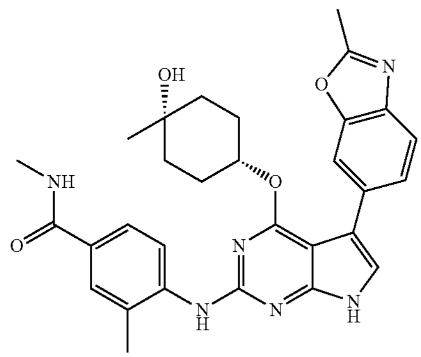 [SMILES: CNC(=O)c1ccc(Nc2nc(O[C@H]3CC[C@@](C)(O)CC3)c3c(-c4ccc5nc(C)oc5c4)c[nH]c3n2)c(C)c1] | 4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-N,3-dimethylbenzamide | 541.2 | D |
| 152 | 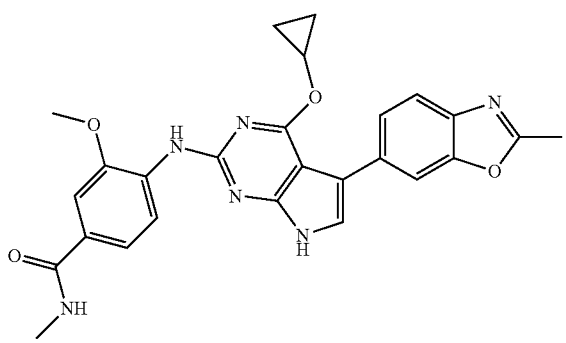 [SMILES: CNC(=O)c1ccc(Nc2nc(OC3CC3)c3c(-c4ccc5nc(C)oc5c4)c[nH]c3n2)c(OC)c1] | 4-(4-cyclopropoxy-5-(2-methylbenzo[d]oxazol-6-yl)-7H-pyrrolo[2,3-d]pyrimidin-2-ylamino)-3-methoxy-N-methylbenzamide | 485 | D |
| 153 | 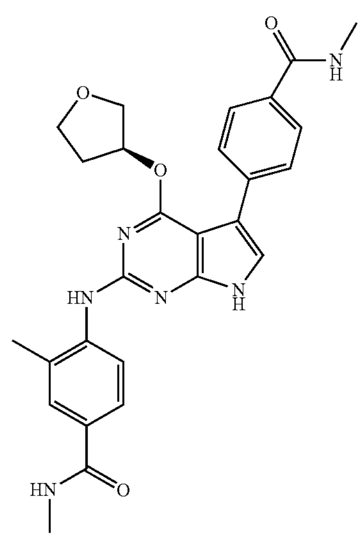 | (S)-N,3-dimethyl-4-(5-(4-(methylcarbamoyl)phenyl)-4-(tetrahydrofuran-3-yloxy)-7H-pyrrolo[2,3-d]pyrimidin-2-ylamino)benzamide | 500.9 | D |

TABLE 1-continued

| Cmpd No. | Structure | Name | Obs. MH+ | Act. Level |
|---|---|---|---|---|
| 154 | 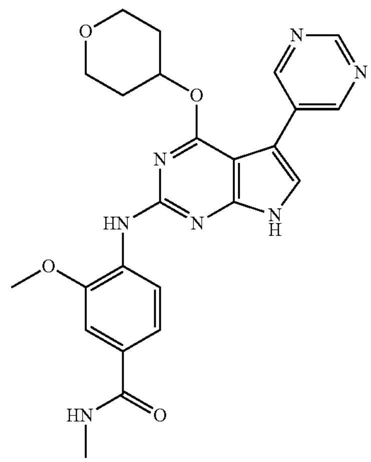 [SMILES: CNC(=O)c1ccc(Nc2nc(OC3CCOCC3)c3c(-c4cncnc4)c[nH]c3n2)c(OC)c1] | 3-methoxy-N-methyl-4-(5-(pyrimidin-5-yl)-4-(tetrahydro-2H-pyran-4-yloxy)-7H-pyrrolo[2,3-d]pyrimidin-2-ylamino)benzamide | 476.6 | C |
| 155 | 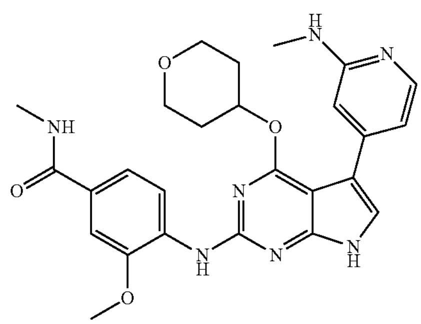 [SMILES: CNC(=O)c1ccc(Nc2nc(OC3CCOCC3)c3c(-c4ccnc(NC)c4)c[nH]c3n2)c(OC)c1] | 3-methoxy-N-methyl-4-(5-(2-(methylamino)pyridin-4-yl)-4-(tetrahydro-2H-pyran-4-yloxy)-7H-pyrrolo[2,3-d]pyrimidin-2-ylamino)benzamide | 504.2 | D |
| 156 | 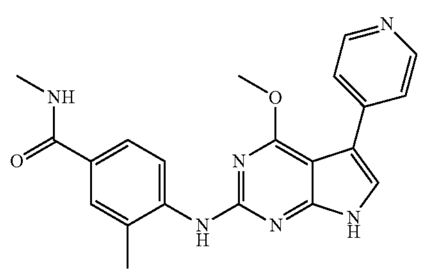 [SMILES: CNC(=O)c1ccc(Nc2nc(OC)c3c(-c4ccncc4)c[nH]c3n2)c(C)c1] | 4-(4-methoxy-5-(pyridin-4-yl)-7H-pyrrolo[2,3-d]pyrimidin-2-ylamino)-N,3-dimethylbenzamide | 389.2 | C |
| 157 | 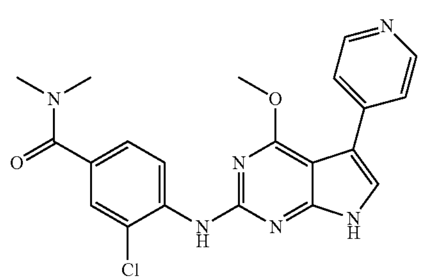 [SMILES: COc1nc(Nc2ccc(C(=O)N(C)C)cc2Cl)nc2[nH]cc(-c3ccncc3)c12] | 3-chloro-4-(4-methoxy-5-(pyridin-4-yl)-7H-pyrrolo[2,3-d]pyrimidin-2-ylamino)-N,N-dimethylbenzamide | 423.1 | C |

TABLE 1-continued

| Cmpd No. | Structure | Name | Obs. MH+ | Act. Level |
|---|---|---|---|---|
| 158 | 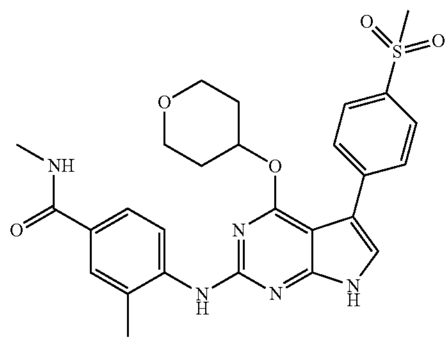 [SMILES: CNC(=O)c1ccc(Nc2nc(OC3CCOCC3)c3c(-c4ccc(S(C)(=O)=O)cc4)c[nH]c3n2)c(C)c1] | N,3-dimethyl-4-(5-(4-(methylsulfonyl)phenyl)-4-(tetrahydro-2H-pyran-4-yloxy)-7H-pyrrolo[2,3-d]pyrimidin-2-ylamino)benzamide | 536.1 | B |
| 159 | 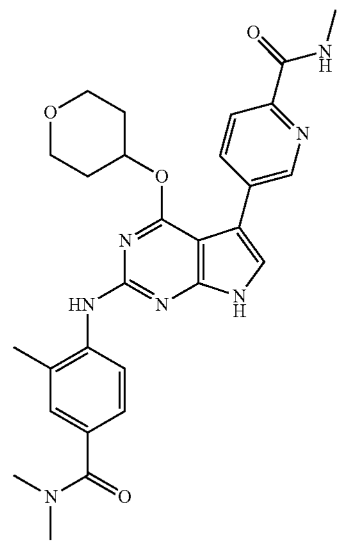 | 5-(2-(4-(dimethylcarbamoyl)-2-methylphenylamino)-4-(tetrahydro-2H-pyran-4-yloxy)-7H-pyrrolo[2,3-d]pyrimidin-5-yl)-N-methylpicolinamide | 530 | D |
| 160 | 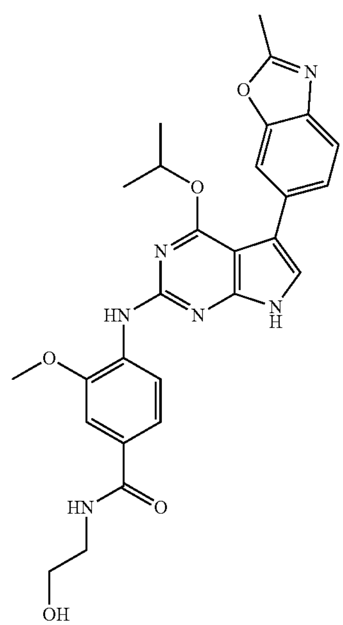 [SMILES: COc1cc(C(=O)NCCO)ccc1Nc1nc(OC(C)C)c2c(-c3ccc4nc(C)oc4c3)c[nH]c2n1] | N-(2-hydroxyethyl)-4-(4-isopropoxy-5-(2-methylbenzo[d]oxazol-6-yl)-7H-pyrrolo[2,3-d]pyrimidin-2-ylamino)-3-methoxybenzamide | 516.9 | D |

TABLE 1-continued

| Cmpd No. | Structure | Name | Obs. MH+ | Act. Level |
|---|---|---|---|---|
| 161 | 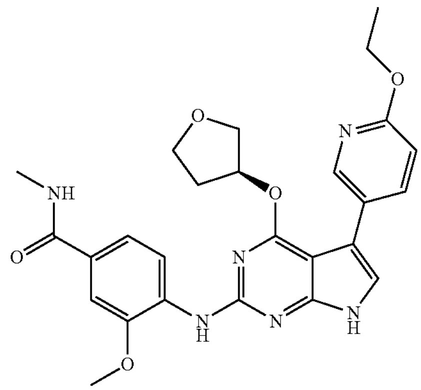 [SMILES: CCOc1ccc(-c2c[nH]c3nc(Nc4ccc(C(=O)NC)cc4OC)nc(O[C@H]4CCOC4)c23)cn1] | (S)-4-(5-(6-ethoxypyridin-3-yl)-4-(tetrahydrofuran-3-yloxy)-7H-pyrrolo[2,3-d]pyrimidin-2-ylamino)-3-methoxy-N-methylbenzamide | 505.2 | C |
| 162 | 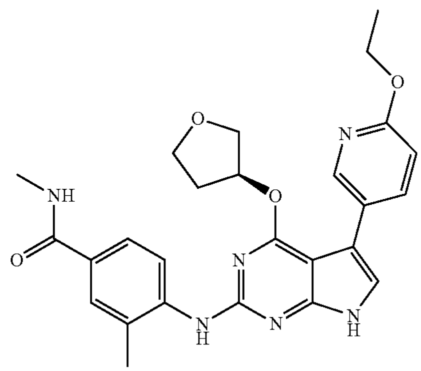 [SMILES: CCOc1ccc(-c2c[nH]c3nc(Nc4ccc(C(=O)NC)cc4C)nc(O[C@H]4CCOC4)c23)cn1] | (S)-4-(5-(6-ethoxypyridin-3-yl)-4-(tetrahydrofuran-3-yloxy)-7H-pyrrolo[2,3-d]pyrimidin-2-ylamino)-N,3-dimethylbenzamide | 489.2 | C |
| 163 | 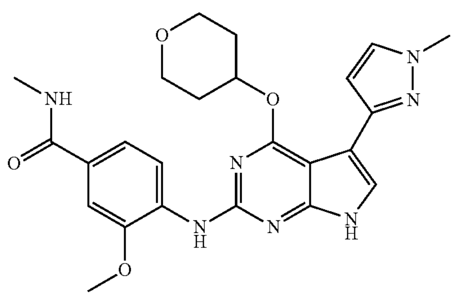 [SMILES: CNC(=O)c1ccc(Nc2nc(OC3CCOCC3)c3c(-c4ccn(C)n4)c[nH]c3n2)c(OC)c1] | 3-methoxy-N-methyl-4-(5-(1-methyl-1H-pyrazol-3-yl)-4-(tetrahydro-2H-pyran-4-yloxy)-7H-pyrrolo[2,3-d]pyrimidin-2-ylamino)benzamide | 478.1 | D |
| 164 | 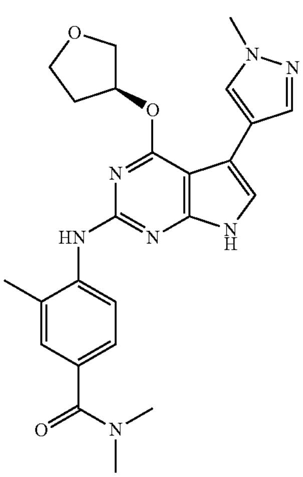 [SMILES: Cc1cc(C(=O)N(C)C)ccc1Nc1nc(O[C@H]2CCOC2)c2c(-c3cnn(C)c3)c[nH]c2n1] | (S)-N,N,3-trimethyl-4-(5-(1-methyl-1H-pyrazol-4-yl)-4-(tetrahydrofuran-3-yloxy)-7H-pyrrolo[2,3-d]pyrimidin-2-ylamino)benzamide | 462.05 | D |

TABLE 1-continued

| Cmpd No. | Structure | Name | Obs. MH+ | Act. Level |
|---|---|---|---|---|
| 165 | 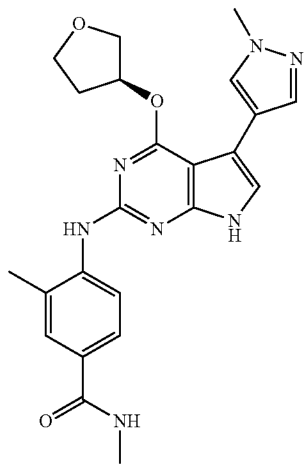 [SMILES: CNC(=O)c1ccc(Nc2nc(O[C@H]3CCOC3)c3c(-c4cnn(C)c4)c[nH]c3n2)c(C)c1] | (S)-N,3-dimethyl-4-(5-(1-methyl-1H-pyrazol-4-yl)-4-(tetrahydrofuran-3-yloxy)-7H-pyrrolo[2,3-d]pyrimidin-2-ylamino)benzamide | 448.05 | D |
| 166 | 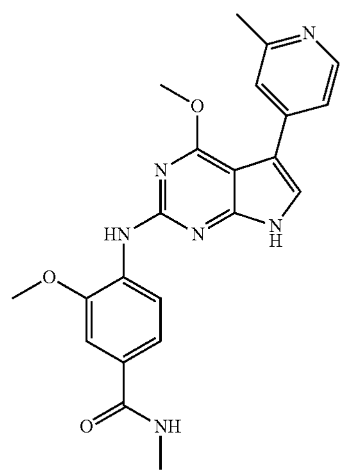 [SMILES: CNC(=O)c1ccc(Nc2nc(OC)c3c(-c4ccnc(C)c4)c[nH]c3n2)c(OC)c1] | 3-methoxy-4-(4-methoxy-5-(2-methylpyridin-4-yl)-7H-pyrrolo[2,3-d]pyrimidin-2-ylamino)-N-methylbenzamide | 419.05 | D |
| 167 | 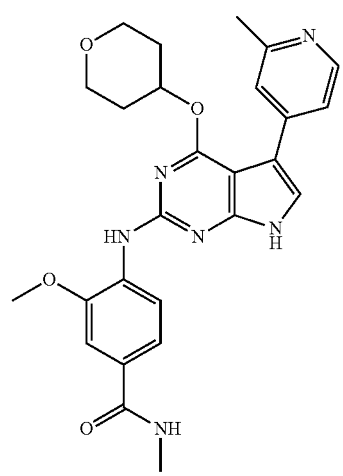 [SMILES: CNC(=O)c1ccc(Nc2nc(OC3CCOCC3)c3c(-c4ccnc(C)c4)c[nH]c3n2)c(OC)c1] | 3-methoxy-N-methyl-4-(5-(2-methylpyridin-4-yl)-4-(tetrahydro-2H-pyran-4-yloxy)-7H-pyrrolo[2,3-d]pyrimidin-2-ylamino)benzamide | 489.1 | D |

TABLE 1-continued

| Cmpd No. | Structure | Name | Obs. MH+ | Act. Level |
|---|---|---|---|---|
| 168 | 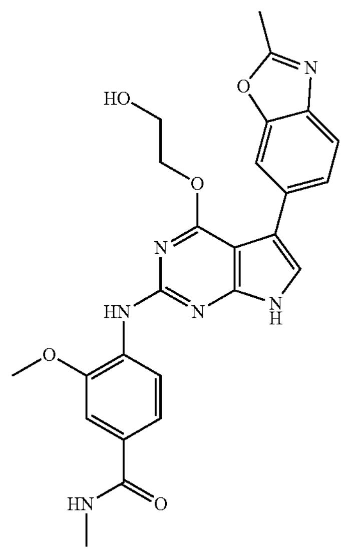 [SMILES: CNC(=O)c1ccc(Nc2nc(OCCO)c3c(-c4ccc5nc(C)oc5c4)c[nH]c3n2)c(OC)c1] | 4-(4-(2-hydroxyethoxy)-5-(2-methylbenzo[d]oxazol-6-yl)-7H-pyrrolo[2,3-d]pyrimidin-2-ylamino)-3-methoxy-N-methylbenzamide | 488.9 | D |
| 169 | 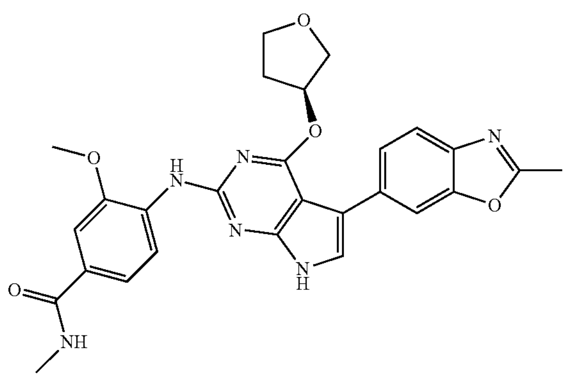 [SMILES: CNC(=O)c1ccc(Nc2nc(O[C@H]3CCOC3)c3c(-c4ccc5nc(C)oc5c4)c[nH]c3n2)c(OC)c1] | (S)-3-methoxy-N-methyl-4-(5-(2-methylbenzo[d]oxazol-6-yl)-4-(tetrahydrofuran-3-yloxy)-7H-pyrrolo[2,3-d]pyrimidin-2-ylamino)benzamide | 515 | D |
| 170 | 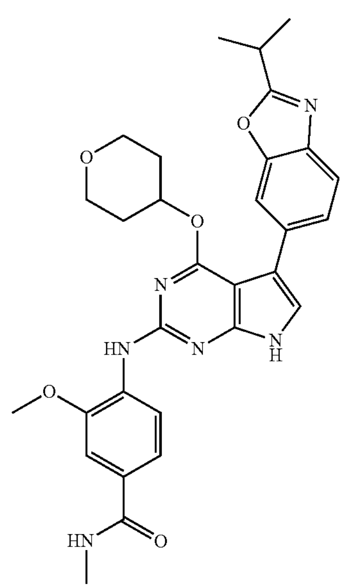 [SMILES: CNC(=O)c1ccc(Nc2nc(OC3CCOCC3)c3c(-c4ccc5nc(C(C)C)oc5c4)c[nH]c3n2)c(OC)c1] | 4-(5-(2-isopropylbenzo[d]oxazol-6-yl)-4-(tetrahydro-2H-pyran-4-yloxy)-7H-pyrrolo[2,3-d]pyrimidin-2-ylamino)-3-methoxy-N-methylbenzamide | 557.6 | C |

TABLE 1-continued

| Cmpd No. | Structure | Name | Obs. MH+ | Act. Level |
|---|---|---|---|---|
| 171 | 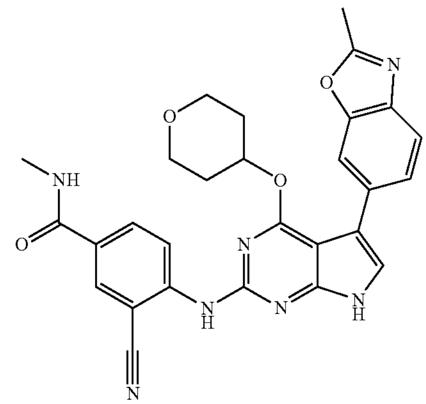 [SMILES: CNC(=O)c1ccc(Nc2nc(OC3CCOCC3)c3c(-c4ccc5nc(C)oc5c4)c[nH]c3n2)c(C#N)c1] | 3-cyano-N-methyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide | 524.2 | D |
| 172 | 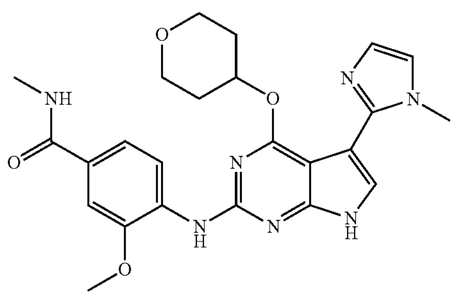 [SMILES: CNC(=O)c1ccc(Nc2nc(OC3CCOCC3)c3c(-c4nccn4C)c[nH]c3n2)c(OC)c1] | 3-methoxy-N-methyl-4-(5-(1-methyl-1H-imidazol-2-yl)-4-(tetrahydro-2H-pyran-4-yloxy)-7H-pyrrolo[2,3-d]pyrimidin-2-ylamino)benzamide | 478.1 | A |
| 173 | 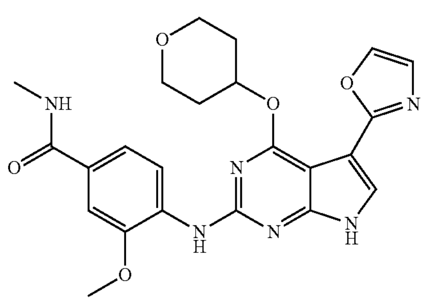 [SMILES: CNC(=O)c1ccc(Nc2nc(OC3CCOCC3)c3c(-c4ncco4)c[nH]c3n2)c(OC)c1] | 3-methoxy-N-methyl-4-(5-(oxazol-2-yl)-4-(tetrahydro-2H-pyran-4-yloxy)-7H-pyrrolo[2,3-d]pyrimidin-2-ylamino)benzamide | 465.1 | B |
| 174 | 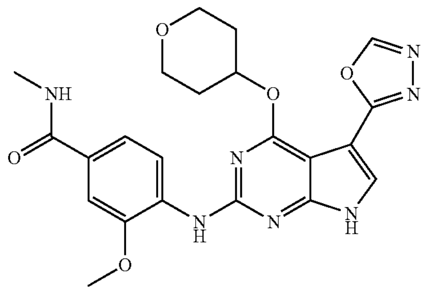 [SMILES: CNC(=O)c1ccc(Nc2nc(OC3CCOCC3)c3c(-c4nnco4)c[nH]c3n2)c(OC)c1] | 4-(5-(1,3,4-oxadiazol-2-yl)-4-(tetrahydro-2H-pyran-4-yloxy)-7H-pyrrolo[2,3-d]pyrimidin-2-ylamino)-3-methoxy-N-methylbenzamide | 466.2 | B |

| Cmpd No. | Structure | Name | Obs. MH+ | Act. Level |
|---|---|---|---|---|
| 175 | 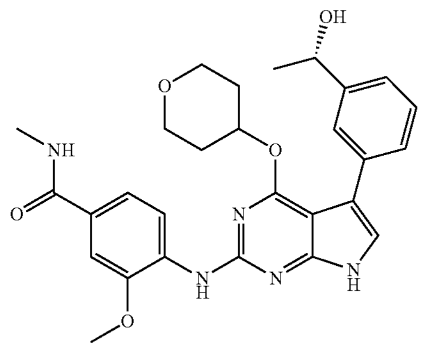 [SMILES: CNC(=O)c1ccc(Nc2nc(OC3CCOCC3)c3c(-c4cccc([C@H](C)O)c4)c[nH]c3n2)c(OC)c1] | (S)-4-(5-(3-(1-hydroxyethyl)phenyl)-4-(tetrahydro-2H-pyran-4-yloxy)-7H-pyrrolo[2,3-d]pyrimidin-2-ylamino)-3-methoxy-N-methylbenzamide | 518.2 | C |
| 176 | 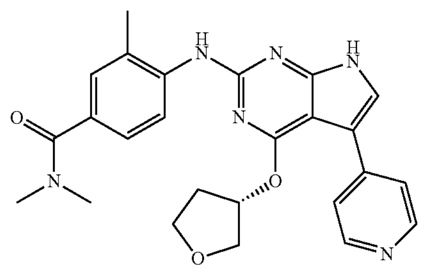 [SMILES: Cc1cc(C(=O)N(C)C)ccc1Nc1nc(O[C@H]2CCOC2)c2c(-c3ccncc3)c[nH]c2n1] | (S)-N,N,3-trimethyl-4-(5-(pyridin-4-yl)-4-(tetrahydrofuran-3-yloxy)-7H-pyrrolo[2,3-d]pyrimidin-2-ylamino)benzamide | 549.1 | C |
| 177 | 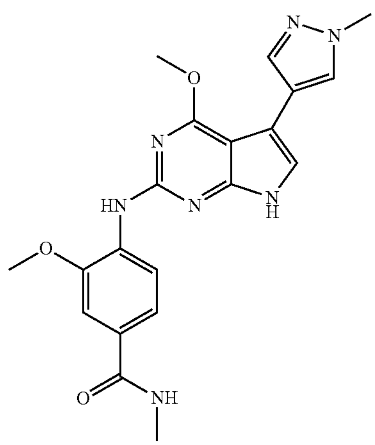 | 3-methoxy-4-(4-methoxy-5-(1-methyl-1H-pyrazol-4-yl)-7H-pyrrolo[2,3-d]pyrimidin-2-ylamino)-N-methylbenzamide | 408.05 | C |
| 178 | 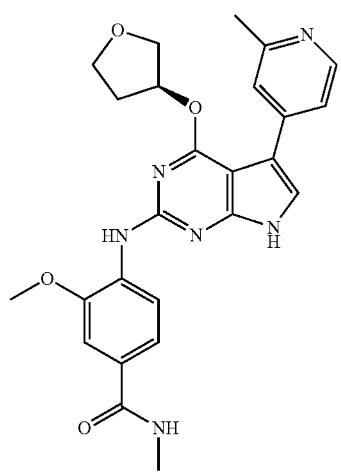 [SMILES: CNC(=O)c1ccc(Nc2nc(O[C@H]3CCOC3)c3c(-c4ccnc(C)c4)c[nH]c3n2)c(OC)c1] | (S)-3-methoxy-N-methyl-4-(5-(2-methylpyridin-4-yl)-4-(tetrahydrofuran-3-yloxy)-7H-pyrrolo[2,3-d]pyrimidin-2-ylamino)benzamide | 475.1 | D |

TABLE 1-continued

| Cmpd No. | Structure | Name | Obs. MH+ | Act. Level |
|---|---|---|---|---|
| 179 | 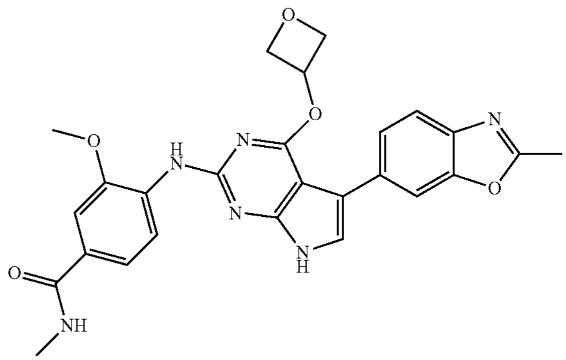 [SMILES: CNC(=O)c1ccc(Nc2nc(OC3COC3)c3c(-c4ccc5nc(C)oc5c4)c[nH]c3n2)c(OC)c1] | 3-methoxy-N-methyl-4-(5-(2-methylbenzo[d]oxazol-6-yl)-4-(oxetan-3-yloxy)-7H-pyrrolo[2,3-d]pyrimidin-2-ylamino)benzamide | 500.9 | D |
| 180 | 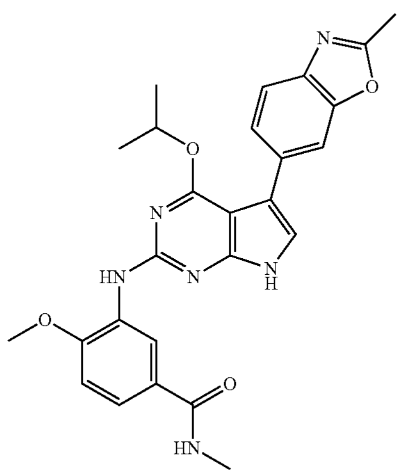 | 3-(4-isopropoxy-5-(2-methylbenzo[d]oxazol-6-yl)-7H-pyrrolo[2,3-d]pyrimidin-2-ylamino)-4-methoxy-N-methylbenzamide | 487.2 | C |
| 181 | 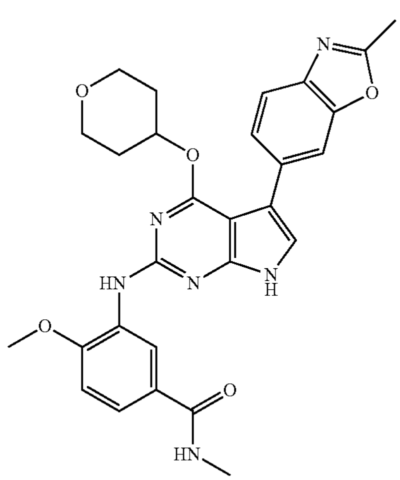 | 4-methoxy-N-methyl-3-(5-(2-methylbenzo[d]oxazol-6-yl)-4-(tetrahydro-2H-pyran-4-yloxy)-7H-pyrrolo[2,3-d]pyrimidin-2-ylamino)benzamide | 529.2 | C |

TABLE 1-continued

| Cmpd No. | Structure | Name | Obs. MH+ | Act. Level |
|---|---|---|---|---|
| 182 | 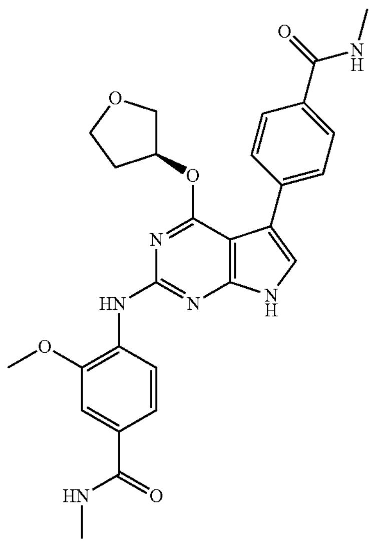 | (S)-3-methoxy-N-methyl-4-(5-(4-(methylcarbamoyl)phenyl)-4-(tetrahydrofuran-3-yloxy)-7H-pyrrolo[2,3-d]pyrimidin-2-ylamino)benzamide | 517.2 | D |
| 183 | 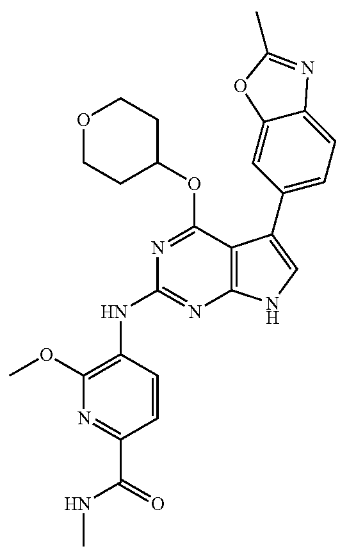 | 6-methoxy-N-methyl-5-(5-(2-methylbenzo[d]oxazol-6-yl)-4-(tetrahydro-2H-pyran-4-yloxy)-7H-pyrrolo[2,3-d]pyrimidin-2-ylamino)picolinamide | 530.6 | C |
| 184 | 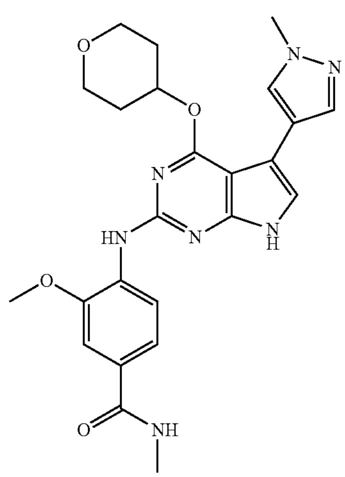 [SMILES: CNC(=O)c1ccc(Nc2nc(OC3CCOCC3)c3c(-c4cnn(C)c4)c[nH]c3n2)c(OC)c1] | 3-methoxy-N-methyl-4-(5-(1-methyl-1H-pyrazol-4-yl)-4-(tetrahydro-2H-pyran-4-yloxy)-7H-pyrrolo[2,3-d]pyrimidin-2-ylamino)benzamide | 478.05 | D |

TABLE 1-continued

| Cmpd No. | Structure | Name | Obs. MH+ | Act. Level |
|---|---|---|---|---|
| 185 | 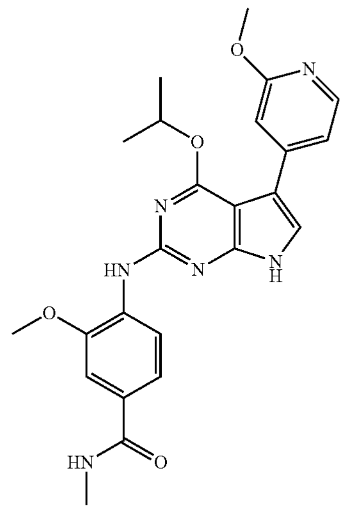 [SMILES: CNC(=O)c1ccc(Nc2nc(OC(C)C)c3c(-c4ccnc(OC)c4)c[nH]c3n2)c(OC)c1] | 4-(4-isopropoxy-5-(2-methoxypyridin-4-yl)-7H-pyrrolo[2,3-d]pyrimidin-2-ylamino)-3-methoxy-N-methylbenzamide | 463.2 | D |
| 186 | 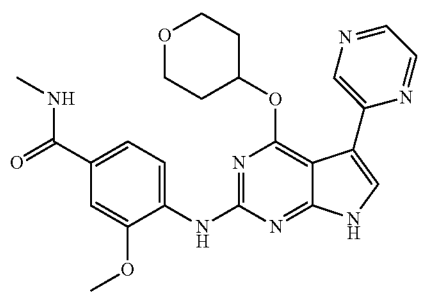 [SMILES: CNC(=O)c1ccc(Nc2nc(OC3CCOCC3)c3c(-c4cnccn4)c[nH]c3n2)c(OC)c1] | 3-methoxy-N-methyl-4-(5-(pyrazin-2-yl)-4-(tetrahydro-2H-pyran-4-yloxy)-7H-pyrrolo[2,3-d]pyrimidin-2-ylamino)benzamide | 476.1 | C |
| 187 | 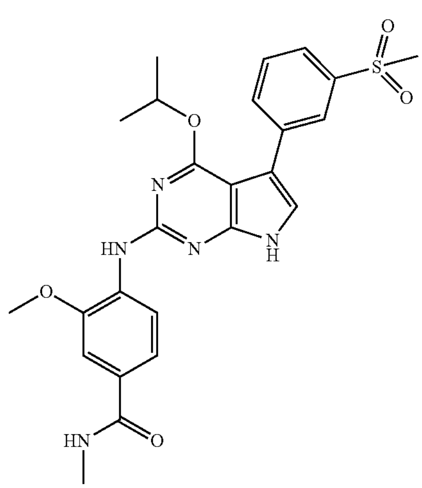 | 4-(4-isopropoxy-5-(3-(methylsulfonyl)phenyl)-7H-pyrrolo[2,3-d]pyrimidin-2-ylamino)-3-methoxy-N-methylbenzamide | 510.2 | C |

TABLE 1-continued

| Cmpd No. | Structure | Name | Obs. MH+ | Act. Level |
|---|---|---|---|---|
| 188 | 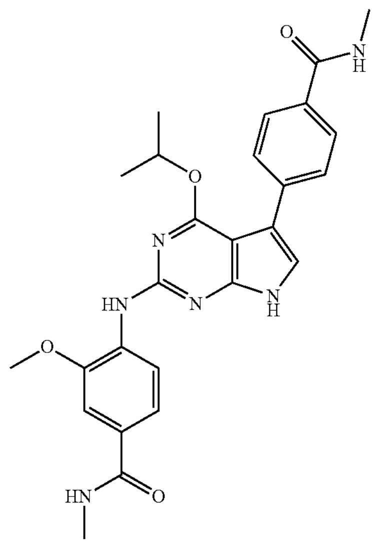 | 4-(4-isopropoxy-5-(4-(methylcarbamoyl)phenyl)-7H-pyrrolo[2,3-d]pyrimidin-2-ylamino)-3-methoxy-N-methylbenzamide | 489.2 | D |
| 189 | 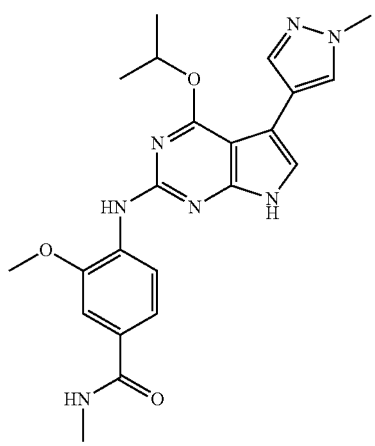 | 4-(4-isopropoxy-5-(1-methyl-1H-pyrazol-4-yl)-7H-pyrrolo[2,3-d]pyrimidin-2-ylamino)-3-methoxy-N-methylbenzamide | 436.2 | D |
| 190 | 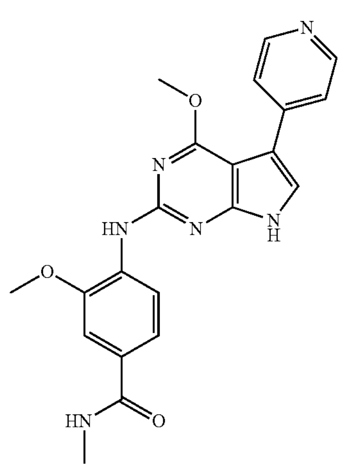 | 3-methoxy-4-(4-methoxy-5-(pyridin-4-yl)-7H-pyrrolo[2,3-d]pyrimidin-2-ylamino)-N-methylbenzamide | 405.1 | D |

TABLE 1-continued

| Cmpd No. | Structure | Name | Obs. MH+ | Act. Level |
|---|---|---|---|---|
| 191 | 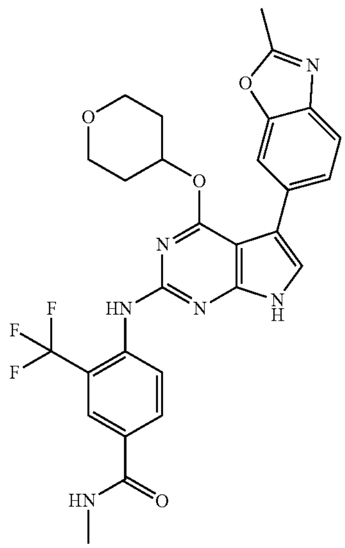 [SMILES: CNC(=O)c1ccc(Nc2nc(OC3CCOCC3)c3c(-c4ccc5nc(C)oc5c4)c[nH]c3n2)c(C(F)(F)F)c1] | N-methyl-4-(5-(2-methylbenzo[d]oxazol-6-yl)-4-(tetrahydro-2H-pyran-4-yloxy)-7H-pyrrolo[2,3-d]pyrimidin-2-ylamino)-3-(trifluoromethyl)benzamide | 566.7 | D |
| 192 | 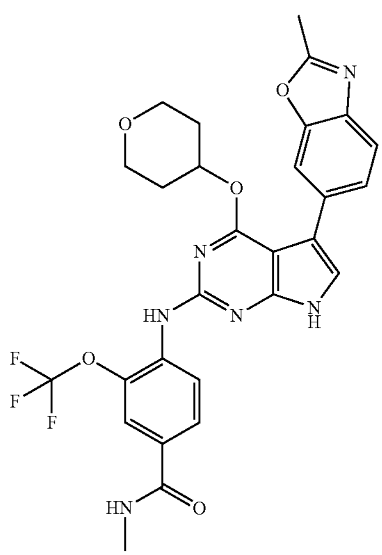 [SMILES: CNC(=O)c1ccc(Nc2nc(OC3CCOCC3)c3c(-c4ccc5nc(C)oc5c4)c[nH]c3n2)c(OC(F)(F)F)c1] | N-methyl-4-(5-(2-methylbenzo[d]oxazol-6-yl)-4-(tetrahydro-2H-pyran-4-yloxy)-7H-pyrrolo[2,3-d]pyrimidin-2-ylamino)-3-(trifluoromethoxy)benzamide | 582.7 | C |

TABLE 1-continued

| Cmpd No. | Structure | Name | Obs. MH+ | Act. Level |
|---|---|---|---|---|
| 193 | 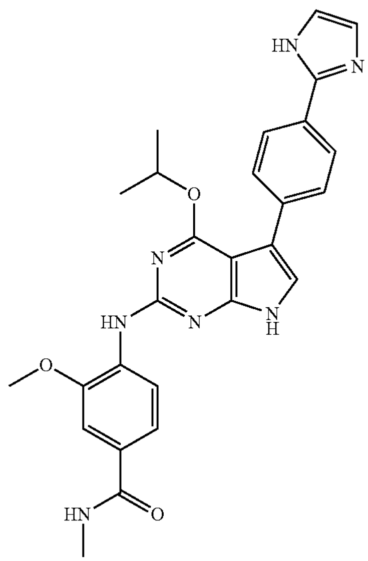 [SMILES: CNC(=O)c1ccc(Nc2nc(OC(C)C)c3c(-c4ccc(-c5ncc[nH]5)cc4)c[nH]c3n2)c(OC)c1] | 4-(5-(4-(1H-imidazol-2-yl)phenyl)-4-isopropoxy-7H-pyrrolo[2,3-d]pyrimidin-2-ylamino)-3-methoxy-N-methylbenzamide | 498.2 | D |
| 194 | 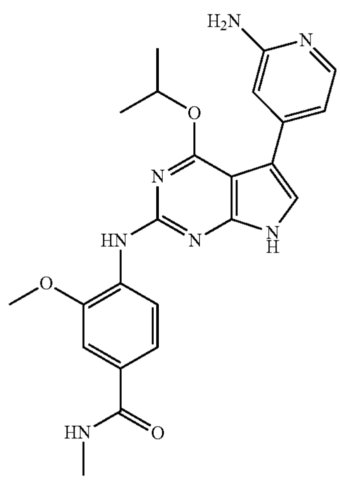 [SMILES: CNC(=O)c1ccc(Nc2nc(OC(C)C)c3c(-c4ccnc(N)c4)c[nH]c3n2)c(OC)c1] | 4-(5-(2-aminopyridin-4-yl)-4-isopropoxy-7H-pyrrolo[2,3-d]pyrimidin-2-ylamino)-3-methoxy-N-methylbenzamide | 448.2 | D |
| 195 | 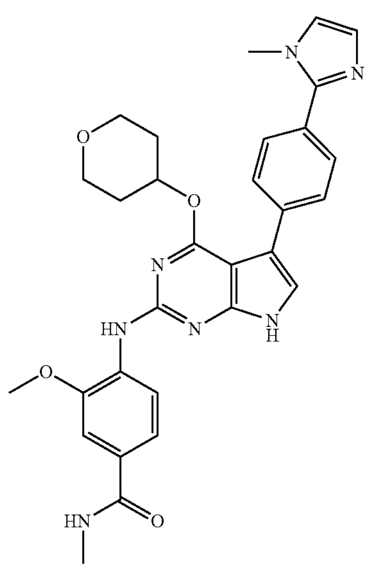 [SMILES: CNC(=O)c1ccc(Nc2nc(OC3CCOCC3)c3c(-c4ccc(-c5nccn5C)cc4)c[nH]c3n2)c(OC)c1] | 3-methoxy-N-methyl-4-(5-(4-(1-methyl-1H-imidazol-2-yl)phenyl)-4-(tetrahydro-2H-pyran-4-yloxy)-7H-pyrrolo[2,3-d]pyrimidin-2-ylamino)benzamide | 554.3 | A |

TABLE 1-continued

| Cmpd No. | Structure | Name | Obs. MH+ | Act. Level |
|---|---|---|---|---|
| 196 | 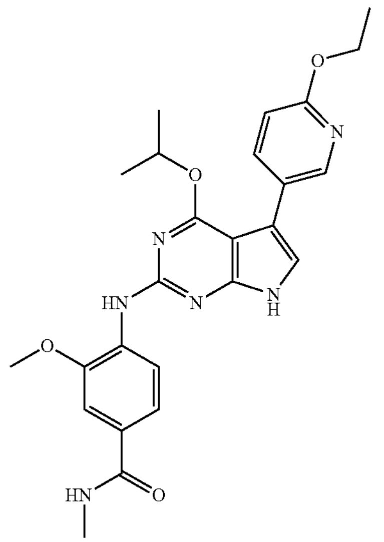 [SMILES: CCOc1ccc(-c2c[nH]c3nc(Nc4ccc(C(=O)NC)cc4OC)nc(OC(C)C)c23)cn1] | 4-(5-(6-ethoxypyridin-3-yl)-4-isopropoxy-7H-pyrrolo[2,3-d]pyrimidin-2-ylamino)-3-methoxy-N-methylbenzamide | 477.2 | C |
| 197 | 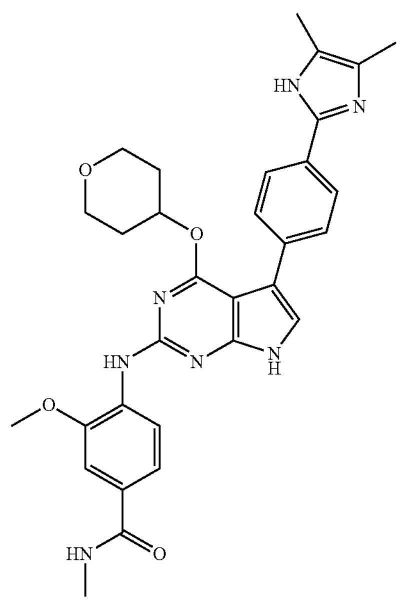 | 4-(5-(4-(4,5-dimethyl-1H-imidazol-2-yl)phenyl)-4-(tetrahydro-2H-pyran-4-yloxy)-7H-pyrrolo[2,3-d]pyrimidin-2-ylamino)-3-methoxy-N-methylbenzamide | 568.3 | C |
| 198 | 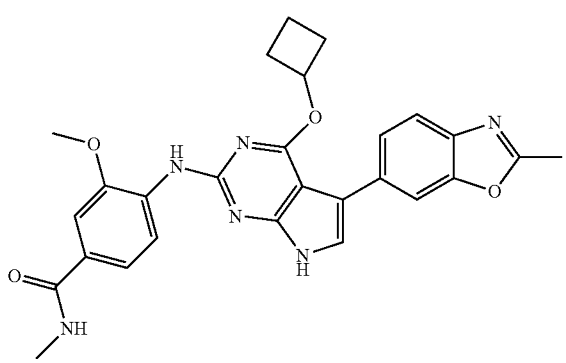 [SMILES: CNC(=O)c1ccc(Nc2nc(OC3CCC3)c3c(-c4ccc5nc(C)oc5c4)c[nH]c3n2)c(OC)c1] | 4-(4-cyclobutoxy-5-(2-methylbenzo[d]oxazol-6-yl)-7H-pyrrolo[2,3-d]pyrimidin-2-ylamino)-3-methoxy-N-methylbenzamide | 499.5 | D |

TABLE 1-continued

| Cmpd No. | Structure | Name | Obs. MH+ | Act. Level |
|---|---|---|---|---|
| 199 | 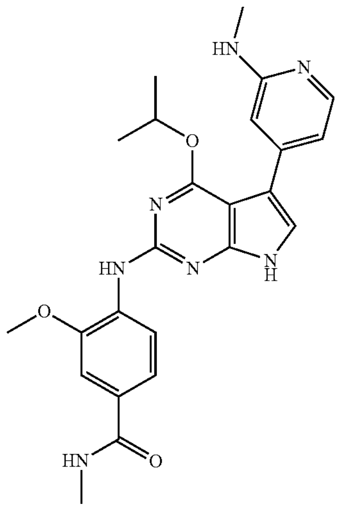 [SMILES: CNC(=O)c1ccc(Nc2nc(OC(C)C)c3c(-c4ccnc(NC)c4)c[nH]c3n2)c(OC)c1] | 4-(4-isopropoxy-5-(2-(methylamino)pyridin-4-yl)-7H-pyrrolo[2,3-d]pyrimidin-2-ylamino)-3-methoxy-N-methylbenzamide | 462.2 | D |
| 200 | 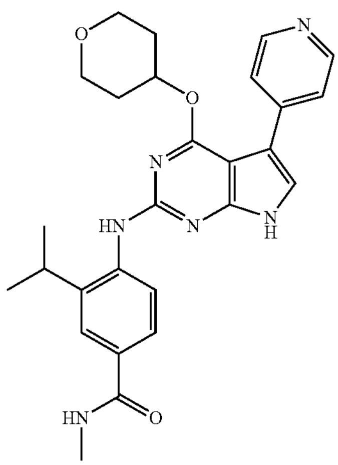 [SMILES: CNC(=O)c1ccc(Nc2nc(OC3CCOCC3)c3c(-c4ccncc4)c[nH]c3n2)c(C(C)C)c1] | 3-isopropyl-N-methyl-4-(5-(pyridin-4-yl)-4-(tetrahydro-2H-pyran-4-yloxy)-7H-pyrrolo[2,3-d]pyrimidin-2-ylamino)benzamide | 487.2 | C |
| 201 | 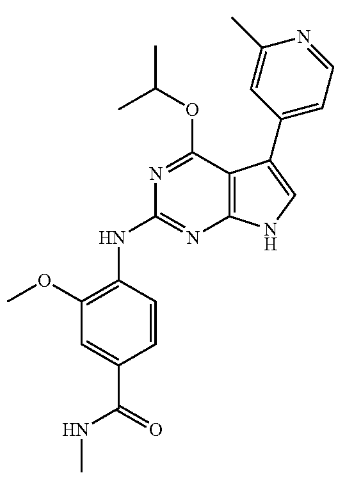 [SMILES: CNC(=O)c1ccc(Nc2nc(OC(C)C)c3c(-c4ccnc(C)c4)c[nH]c3n2)c(OC)c1] | 4-(4-isopropoxy-5-(2-methylpyridin-4-yl)-7H-pyrrolo[2,3-d]pyrimidin-2-ylamino)-3-methoxy-N-methylbenzamide | 447.2 | D |

| Cmpd No. | Structure | Name | Obs. MH+ | Act. Level |
|---|---|---|---|---|
| 202 | 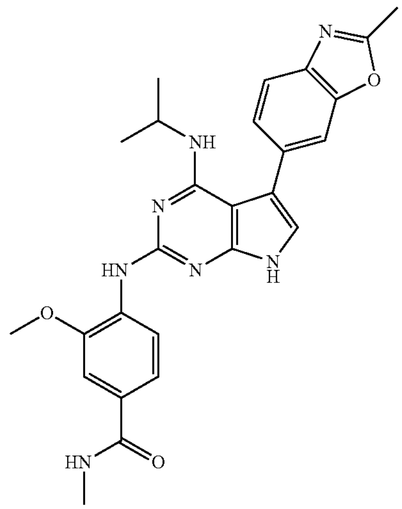 | 4-(4-(isopropylamino)-5-(2-methylbenzo[d]oxazol-6-yl)-7H-pyrrolo[2,3-d]pyrimidin-2-ylamino)-3-methoxy-N-methylbenzamide | 486.2 | D |
| 203 | 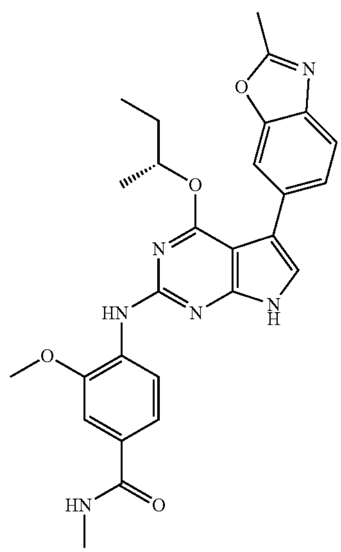 [SMILES: CC[C@@H](C)Oc1nc(Nc2ccc(C(=O)NC)cc2OC)nc2[nH]cc(-c3ccc4nc(C)oc4c3)c12] | (R)-4-(4-sec-butoxy-5-(2-methylbenzo[d]oxazol-6-yl)-7H-pyrrolo[2,3-d]pyrimidin-2-ylamino)-3-methoxy-N-methylbenzamide | 500.9 | C |
| 204 | 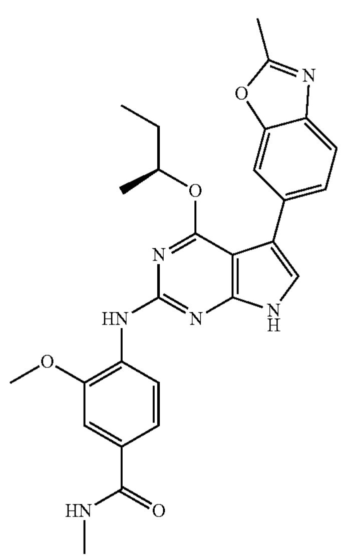 [SMILES: CC[C@H](C)Oc1nc(Nc2ccc(C(=O)NC)cc2OC)nc2[nH]cc(-c3ccc4nc(C)oc4c3)c12] | (S)-4-(4-sec-butoxy-5-(2-methylbenzo[d]oxazol-6-yl)-7H-pyrrolo[2,3-d]pyrimidin-2-ylamino)-3-methoxy-N-methylbenzamide | 500.9 | C |

TABLE 1-continued

| Cmpd No. | Structure | Name | Obs. MH+ | Act. Level |
|---|---|---|---|---|
| 205 | 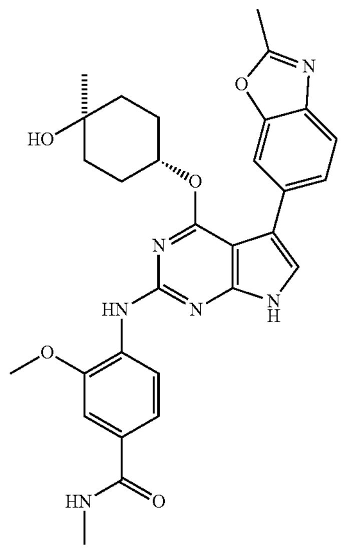 [SMILES: CNC(=O)c1ccc(Nc2nc(O[C@H]3CC[C@](C)(O)CC3)c3c(-c4ccc5nc(C)oc5c4)c[nH]c3n2)c(OC)c1] | 4-(4-((1r,4r)-4-hydroxy-4-methylcyclohexyloxy)-5-(2-methylbenzo[d]oxazol-6-yl)-7H-pyrrolo[2,3-d]pyrimidin-2-ylamino)-3-methoxy-N-methylbenzamide | 557.2 | D |
| 206 | 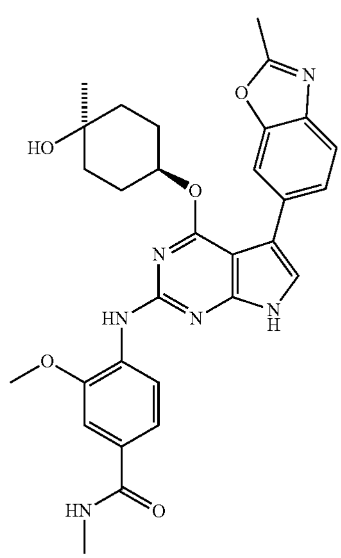 [SMILES: CNC(=O)c1ccc(Nc2nc(O[C@H]3CC[C@@](C)(O)CC3)c3c(-c4ccc5nc(C)oc5c4)c[nH]c3n2)c(OC)c1] | 4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-3-methoxy-N-methylbenzamide | 557.3 | D |

TABLE 1-continued

| Cmpd No. | Structure | Name | Obs. MH+ | Act. Level |
|---|---|---|---|---|
| 207 | 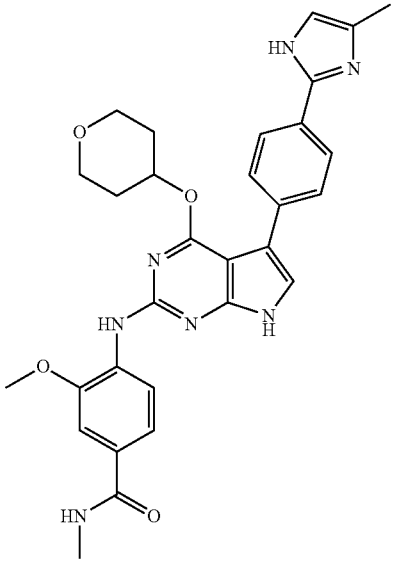 | 3-methoxy-N-methyl-4-(5-(4-(4-methyl-1H-imidazol-2-yl)phenyl)-4-(tetrahydro-2H-pyran-4-yloxy)-7H-pyrrolo[2,3-d]pyrimidin-2-ylamino)benzamide | 554.2 | D |
| 208 | 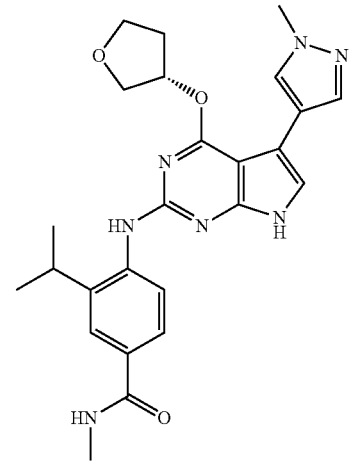 [SMILES: CNC(=O)c1ccc(Nc2nc(O[C@H]3CCOC3)c3c(-c4cnn(C)c4)c[nH]c3n2)c(C(C)C)c1] | (S)-3-isopropyl-N-methyl-4-(5-(1-methyl-1H-pyrazol-4-yl)-4-(tetrahydrofuran-3-yloxy)-7H-pyrrolo[2,3-d]pyrimidin-2-ylamino)benzamide | 476.2 | C |
| 209 | 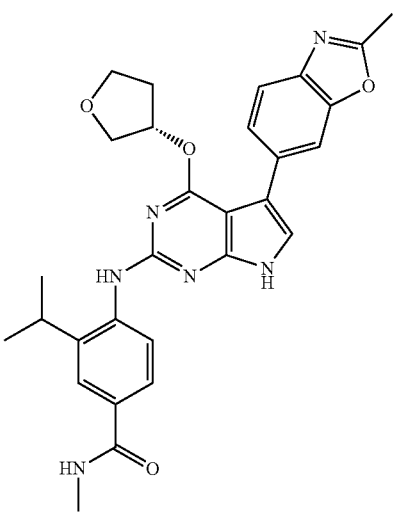 [SMILES: CNC(=O)c1ccc(Nc2nc(O[C@H]3CCOC3)c3c(-c4ccc5nc(C)oc5c4)c[nH]c3n2)c(C(C)C)c1] | (S)-3-isopropyl-N-methyl-4-(5-(2-methylbenzo[d]oxazol-6-yl)-4-(tetrahydrofuran-3-yloxy)-7H-pyrrolo[2,3-d]pyrimidin-2-ylamino)benzamide | 527.3 | A |

TABLE 1-continued

| Cmpd No. | Structure | Name | Obs. MH+ | Act. Level |
|---|---|---|---|---|
| 210 | 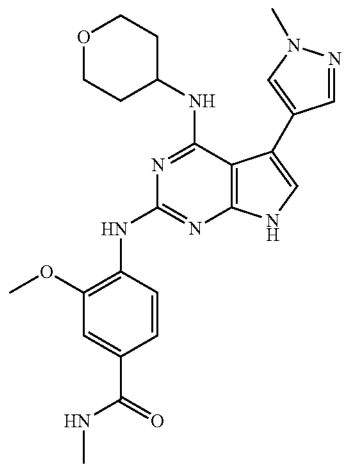 [SMILES: CNC(=O)c1ccc(Nc2nc(NC3CCOCC3)c3c(-c4cnn(C)c4)c[nH]c3n2)c(OC)c1] | 3-methoxy-N-methyl-4-(5-(1-methyl-1H-pyrazol-4-yl)-4-(tetrahydro-2H-pyran-4-ylamino)-7H-pyrrolo[2,3-d]pyrimidin-2-ylamino)benzamide | 77.2 | |
| 211 | 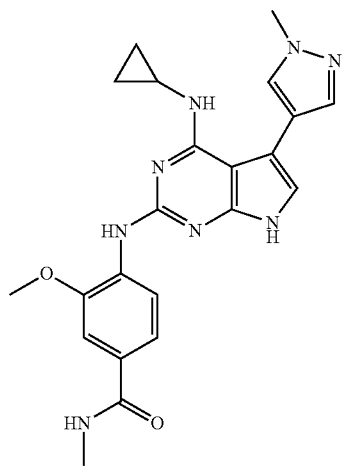 [SMILES: CNC(=O)c1ccc(Nc2nc(NC3CC3)c3c(-c4cnn(C)c4)c[nH]c3n2)c(OC)c1] | 4-(4-(cyclopropylamino)-5-(1-methyl-1H-pyrazol-4-yl)-7H-pyrrolo[2,3-d]pyrimidin-2-ylamino)-3-methoxy-N-methylbenzamide | 433.2 | C |
| 212 | 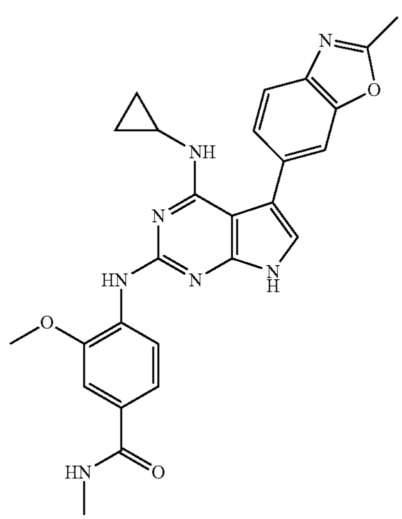 | 4-(4-(cyclopropylamino)-5-(2-methylbenzo[d]oxazol-6-yl)-7H-pyrrolo[2,3-d]pyrimidin-2-ylamino)-3-methoxy-N-methylbenzamide | 484.2 | C |

TABLE 1-continued

| Cmpd No. | Structure | Name | Obs. MH+ | Act. Level |
|---|---|---|---|---|
| 213 | 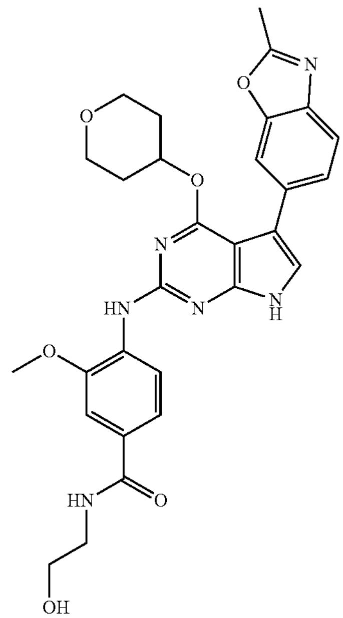 [SMILES: COc1cc(C(=O)NCCO)ccc1Nc1nc(OC2CCOCC2)c2c(-c3ccc4nc(C)oc4c3)c[nH]c2n1] | N-(2-hydroxyethyl)-3-methoxy-4-(5-(2-methylbenzo[d]oxazol-6-yl)-4-(tetrahydro-2H-pyran-4-yloxy)-7H-pyrrolo[2,3-d]pyrimidin-2-ylamino)benzamide | 558.9 | D |
| 214 | 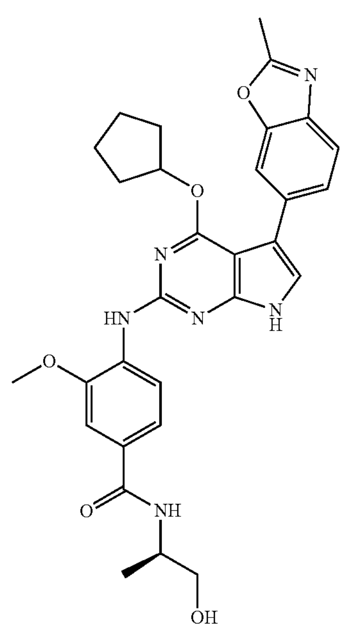 [SMILES: COc1cc(C(=O)N[C@H](C)CO)ccc1Nc1nc(OC2CCCC2)c2c(-c3ccc4nc(C)oc4c3)c[nH]c2n1] | (R)-4-(4-(cyclopentyloxy)-5-(2-methylbenzo[d]oxazol-6-yl)-7H-pyrrolo[2,3-d]pyrimidin-2-ylamino)-N-(1-hydroxypropan-2-yl)-3-methoxybenzamide | 557.6 | D |

| Cmpd No. | Structure | Name | Obs. MH+ | Act. Level |
|---|---|---|---|---|
| 215 | 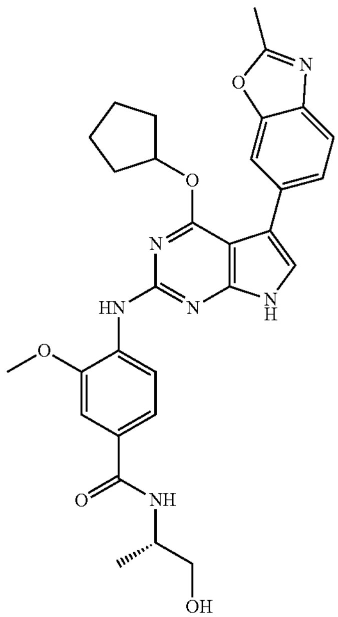 [SMILES: COc1cc(C(=O)N[C@@H](C)CO)ccc1Nc1nc(OC2CCCC2)c2c(-c3ccc4nc(C)oc4c3)c[nH]c2n1] | (S)-4-(4-(cyclopentyloxy)-5-(2-methylbenzo[d]oxazol-6-yl)-7H-pyrrolo[2,3-d]pyrimidin-2-ylamino)-N-(1-hydroxypropan-2-yl)-3-methoxybenzamide | 557.6 | D |
| 216 | 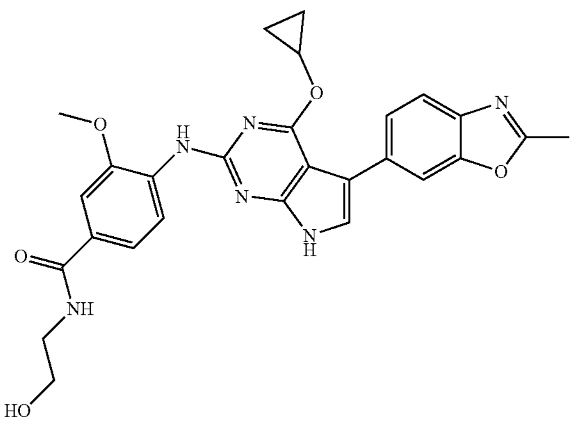 [SMILES: COc1cc(C(=O)NCCO)ccc1Nc1nc(OC2CC2)c2c(-c3ccc4nc(C)oc4c3)c[nH]c2n1] | 4-(4-cyclopropoxy-5-(2-methylbenzo[d]oxazol-6-yl)-7H-pyrrolo[2,3-d]pyrimidin-2-ylamino)-N-(2-hydroxyethyl)-3-methoxybenzamide | 515 | D |
| 217 | 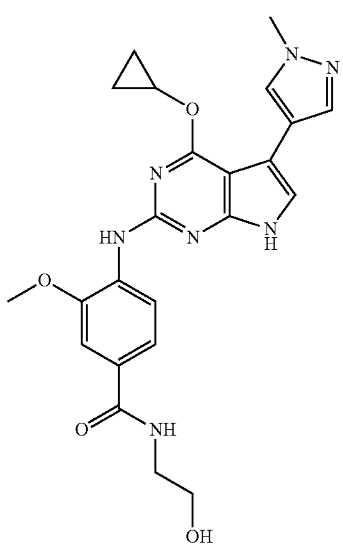 [SMILES: COc1cc(C(=O)NCCO)ccc1Nc1nc(OC2CC2)c2c(-c3cnn(C)c3)c[nH]c2n1] | 4-(4-cyclopropoxy-5-(1-methyl-1H-pyrazol-4-yl)-7H-pyrrolo[2,3-d]pyrimidin-2-ylamino)-N-(2-hydroxyethyl)-3-methoxybenzamide | 464 | C |

TABLE 1-continued

| Cmpd No. | Structure | Name | Obs. MH+ | Act. Level |
|---|---|---|---|---|
| 218 | 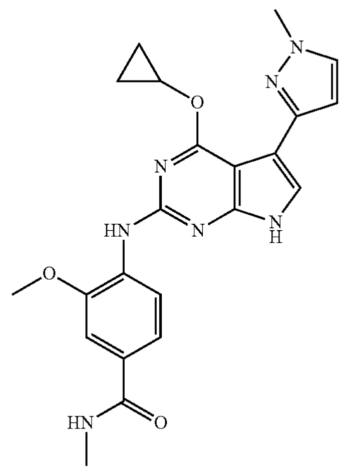 [SMILES: CNC(=O)c1ccc(Nc2nc(OC3CC3)c3c(-c4ccn(C)n4)c[nH]c3n2)c(OC)c1] | 4-(4-cyclopropoxy-5-(1-methyl-1H-pyrazol-3-yl)-7H-pyrrolo[2,3-d]pyrimidin-2-ylamino)-3-methoxy-N-methylbenzamide | 434 | A |
| 219 | 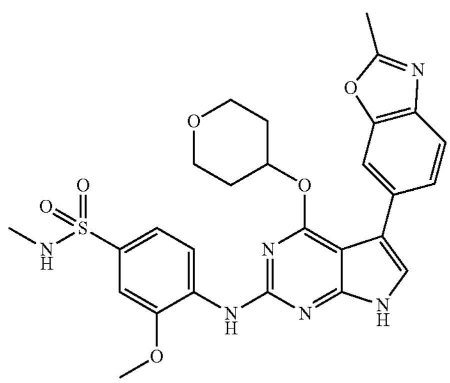 [SMILES: CNS(=O)(=O)c1ccc(Nc2nc(OC3CCOCC3)c3c(-c4ccc5nc(C)oc5c4)c[nH]c3n2)c(OC)c1] | 3-methoxy-N-methyl-4-(5-(2-methylbenzo[d]oxazol-6-yl)-4-(tetrahydro-2H-pyran-4-yloxy)-7H-pyrrolo[2,3-d]pyrimidin-2-ylamino)benzenesulfonamide | 565.2 | C |
| 220 | 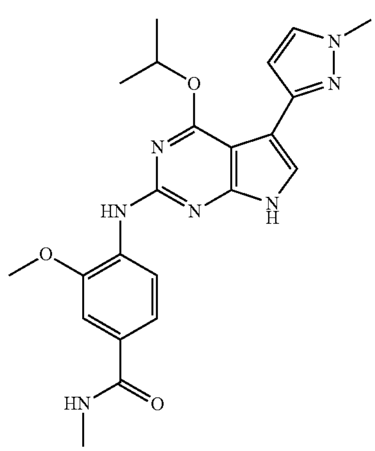 | 4-(4-isopropoxy-5-(1-methyl-1H-pyrazol-3-yl)-7H-pyrrolo[2,3-d]pyrimidin-2-ylamino)-3-methoxy-N-methylbenzamide | 436.2 | A |

TABLE 1-continued

| Cmpd No. | Structure | Name | Obs. MH+ | Act. Level |
|---|---|---|---|---|
| 221 | 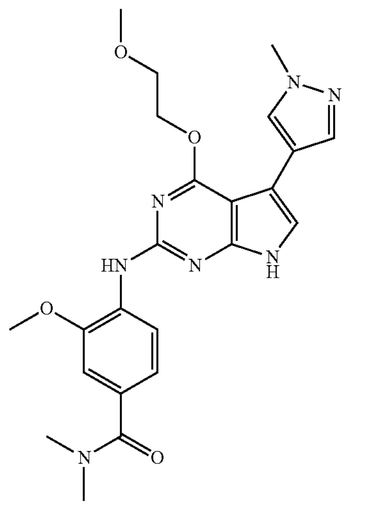 [SMILES: COCCOc1nc(Nc2ccc(C(=O)N(C)C)cc2OC)nc2[nH]cc(-c3cnn(C)c3)c12] | 3-methoxy-4-(4-(2-methoxyethoxy)-5-(1-methyl-1H-pyrazol-4-yl)-7H-pyrrolo[2,3-d]pyrimidin-2-ylamino)-N,N-dimethylbenzamide | 466.3 | D |
| 222 | 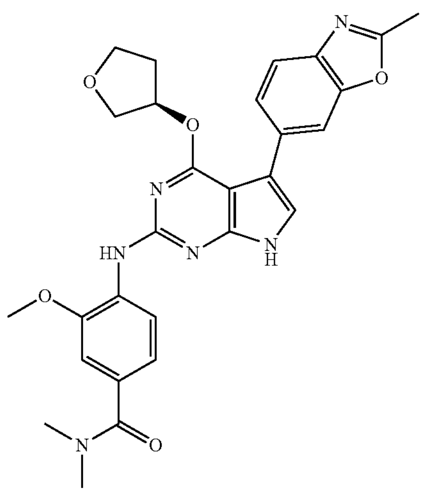 | (R)-3-methoxy-N,N-dimethyl-4-(5-(2-methylbenzo[d]oxazol-6-yl)-4-(tetrahydrofuran-3-yloxy)-7H-pyrrolo[2,3-d]pyrimidin-2-ylamino)benzamide | 529.3 | D |
| 223 | 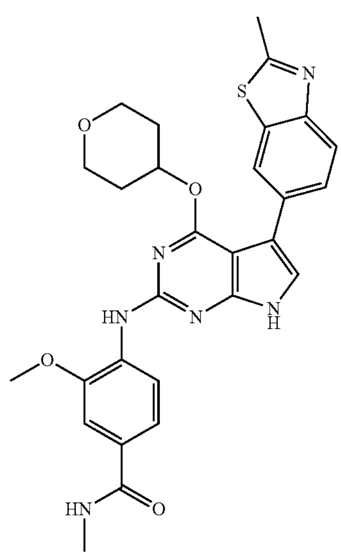 [SMILES: CNC(=O)c1ccc(Nc2nc(OC3CCOCC3)c3c(-c4ccc5nc(C)sc5c4)c[nH]c3n2)c(OC)c1] | 3-methoxy-N-methyl-4-(5-(2-methylbenzo[d]thiazol-6-yl)-4-(tetrahydro-2H-pyran-4-yloxy)-7H-pyrrolo[2,3-d]pyrimidin-2-ylamino)benzamide | 545.5 | D |

TABLE 1-continued

| Cmpd No. | Structure | Name | Obs. MH$^+$ | Act. Level |
|---|---|---|---|---|
| 224 | 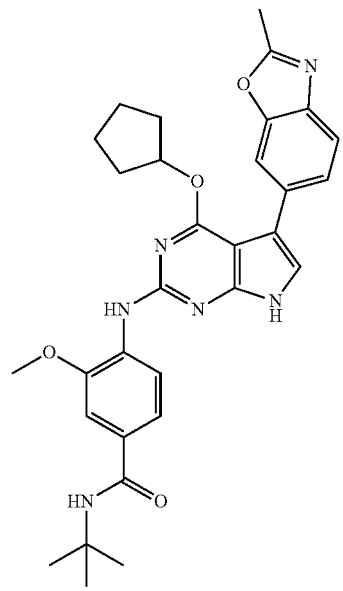 [SMILES: COc1cc(C(=O)NC(C)(C)C)ccc1Nc1nc(OC2CCCC2)c2c(-c3ccc4nc(C)oc4c3)c[nH]c2n1] | N-tert-butyl-4-(4-(cyclopentyloxy)-5-(2-methylbenzo[d]oxazol-6-yl)-7H-pyrrolo[2,3-d]pyrimidin-2-ylamino)-3-methoxybenzamide | 555.3 | C |
| 225 | 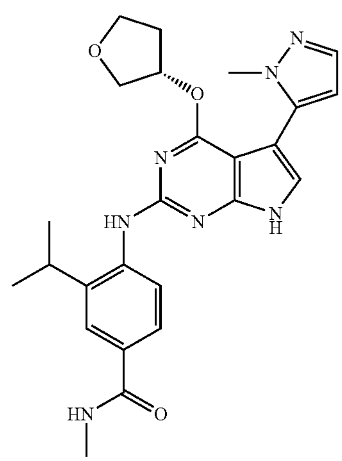 [SMILES: CNC(=O)c1ccc(Nc2nc(O[C@H]3CCOC3)c3c(-c4ccnn4C)c[nH]c3n2)c(C(C)C)c1] | (S)-3-isopropyl-N-methyl-4-(5-(1-methyl-1H-pyrazol-5-yl)-4-(tetrahydrofuran-3-yloxy)-7H-pyrrolo[2,3-d]pyrimidin-2-ylamino)benzamide | 476.3 | A |
| 226 | 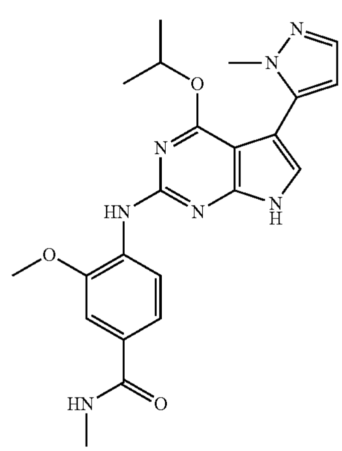 [SMILES: CNC(=O)c1ccc(Nc2nc(OC(C)C)c3c(-c4ccnn4C)c[nH]c3n2)c(OC)c1] | 4-(4-isopropoxy-5-(1-methyl-1H-pyrazol-5-yl)-7H-pyrrolo[2,3-d]pyrimidin-2-ylamino)-3-methoxy-N-methylbenzamide | 436.2 | A |

TABLE 1-continued

| Cmpd No. | Structure | Name | Obs. MH+ | Act. Level |
|---|---|---|---|---|
| 227 | 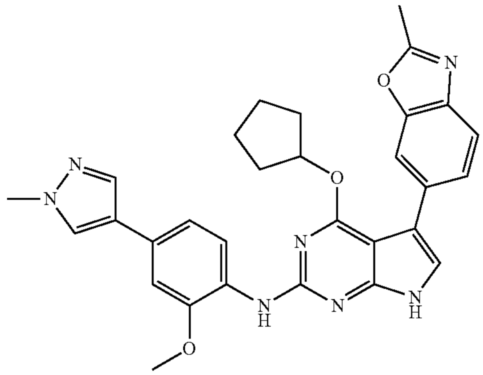 [SMILES: COc1cc(-c2cnn(C)c2)ccc1Nc1nc(OC2CCCC2)c2c(-c3ccc4nc(C)oc4c3)c[nH]c2n1] | 4-(cyclopentyloxy)-N-(2-methoxy-4-(1-methyl-1H-pyrazol-4-yl)phenyl)-5-(2-methylbenzo[d]oxazol-6-yl)-7H-pyrrolo[2,3-d]pyrimidin-2-amine | 536.3 | C |
| 228 | 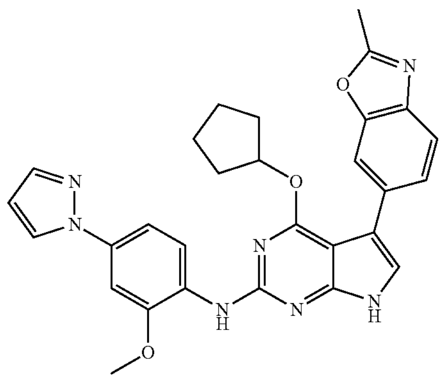 [SMILES: COc1cc(-n2cccn2)ccc1Nc1nc(OC2CCCC2)c2c(-c3ccc4nc(C)oc4c3)c[nH]c2n1] | 4-(cyclopentyloxy)-N-(2-methoxy-4-(1H-pyrazol-1-yl)phenyl)-5-(2-methylbenzo[d]oxazol-6-yl)-7H-pyrrolo[2,3-d]pyrimidin-2-amine | 522.2 | C |
| 229 | 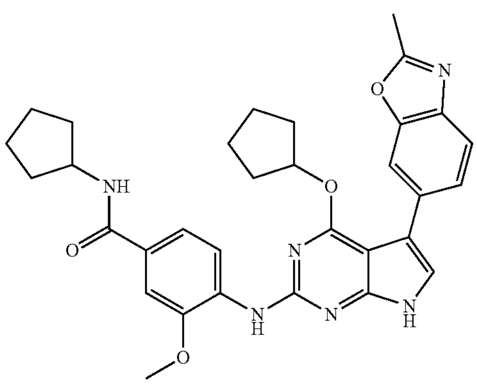 [SMILES: COc1cc(C(=O)NC2CCCC2)ccc1Nc1nc(OC2CCCC2)c2c(-c3ccc4nc(C)oc4c3)c[nH]c2n1] | N-cyclopentyl-4-(4-(cyclopentyloxy)-5-(2-methylbenzo[d]oxazol-6-yl)-7H-pyrrolo[2,3-d]pyrimidin-2-ylamino)-3-methoxybenzamide | 567.3 | B |
| 230 | 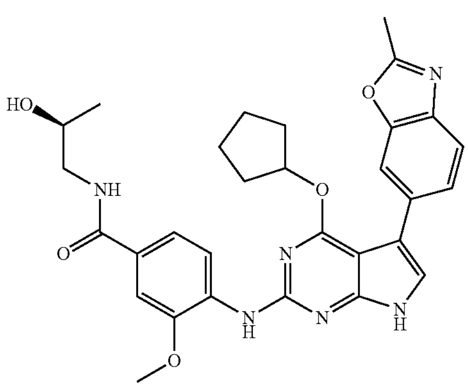 [SMILES: COc1cc(C(=O)NC[C@H](C)O)ccc1Nc1nc(OC2CCCC2)c2c(-c3ccc4nc(C)oc4c3)c[nH]c2n1] | (R)-4-(4-(cyclopentyloxy)-5-(2-methylbenzo[d]oxazol-6-yl)-7H-pyrrolo[2,3-d]pyrimidin-2-ylamino)-N-(2-hydroxypropyl)-3-methoxybenzamide | 557.3 | C |

| Cmpd No. | Structure | Name | Obs. MH+ | Act. Level |
|---|---|---|---|---|
| 231 | 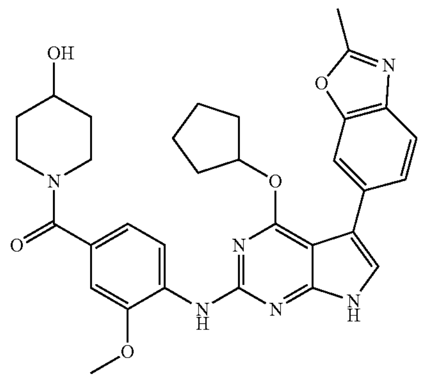 [SMILES: COc1cc(C(=O)N2CCC(O)CC2)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)(4-hydroxypiperidin-1-yl)methanone | 583.3 | D |
| 232 | 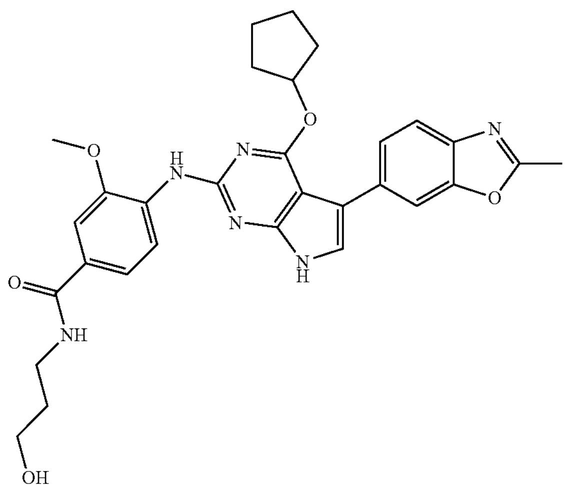 [SMILES: COc1cc(C(=O)NCCCO)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-(3-hydroxypropyl)-3-methoxybenzamide | 557.3 | D |
| 233 | 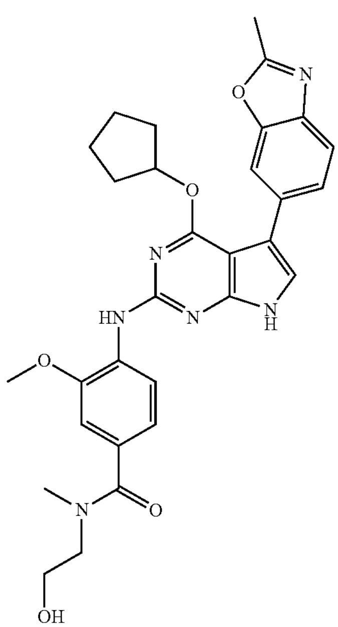 [SMILES: COc1cc(C(=O)N(C)CCO)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-(2-hydroxyethyl)-3-methoxy-N-methylbenzamide | 557.5 | D |

TABLE 1-continued

| Cmpd No. | Structure | Name | Obs. MH+ | Act. Level |
|---|---|---|---|---|
| 234 | 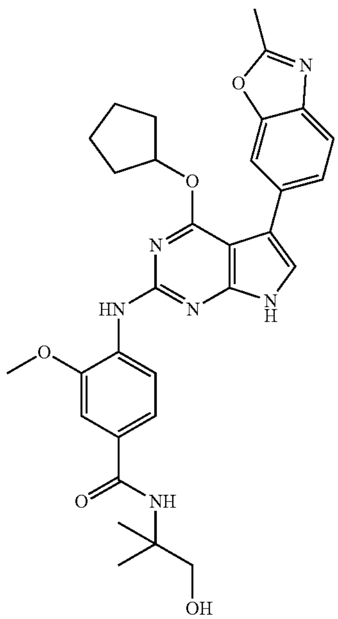 [SMILES: COc1cc(C(=O)NC(C)(C)CO)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-(1-hydroxy-2-methylpropan-2-yl)-3-methoxybenzamide | 571.6 | C |
| 235 | 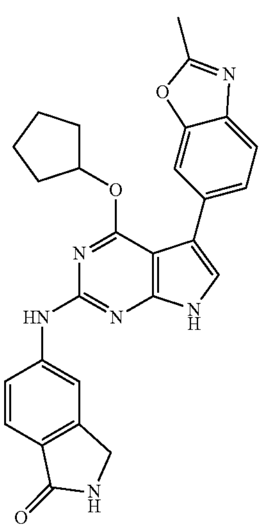 [SMILES: Cc1nc2ccc(-c3c[nH]c4nc(Nc5ccc6c(c5)CNC6=O)nc(OC5CCCC5)c34)cc2o1] | 5-(4-(cyclopentyloxy)-5-(2-methylbenzo[d]oxazol-6-yl)-7H-pyrrolo[2,3-d]pyrimidin-2-ylamino)isoindolin-1-one | 481 | D |

TABLE 1-continued

| Cmpd No. | Structure | Name | Obs. MH+ | Act. Level |
|---|---|---|---|---|
| 236 | 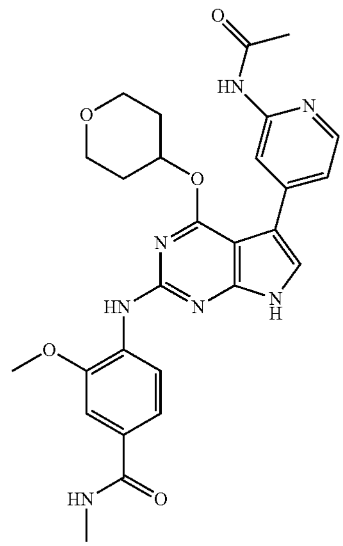 [SMILES: CNC(=O)c1ccc(Nc2nc(OC3CCOCC3)c3c(-c4ccnc(NC(C)=O)c4)c[nH]c3n2)c(OC)c1] | 4-(5-(2-acetamidopyridin-4-yl)-4-(tetrahydro-2H-pyran-4-yloxy)-7H-pyrrolo[2,3-d]pyrimidin-2-ylamino)-3-methoxy-N-methylbenzamide | 532 | D |
| 237 | 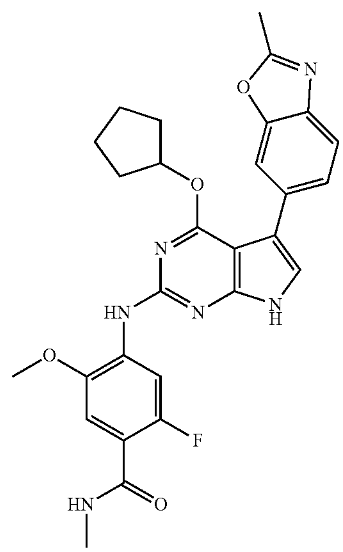 [SMILES: CNC(=O)c1cc(OC)c(Nc2nc(OC3CCCC3)c3c(-c4ccc5nc(C)oc5c4)c[nH]c3n2)cc1F] | 4-(4-(cyclopentyloxy)-5-(2-methylbenzo[d]oxazol-6-yl)-7H-pyrrolo[2,3-d]pyrimidin-2-ylamino)-2-fluoro-5-methoxy-N-methylbenzamide | 530.9 | C |
| 238 | 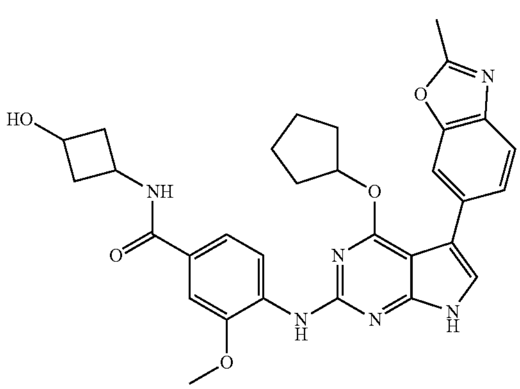 [SMILES: COc1cc(C(=O)NC2CC(O)C2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-((1s,3s)-3-hydroxycyclobutyl)-3-methoxybenzamide | 569.3 | D |

TABLE 1-continued

| Cmpd No. | Structure | Name | Obs. MH+ | Act. Level |
|---|---|---|---|---|
| 239 | 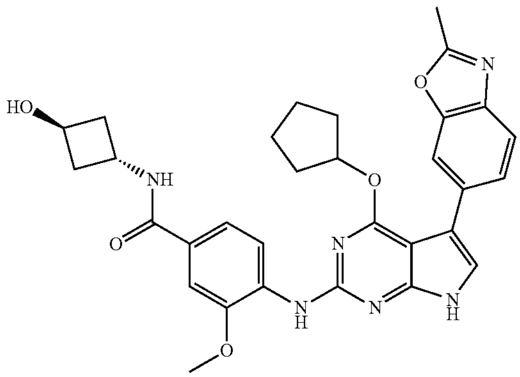 [SMILES: COc1cc(C(=O)N[C@H]2C[C@H](O)C2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-((1r,3r)-3-hydroxycyclobutyl)-3-methoxybenzamide | 569.3 | D |
| 240 | 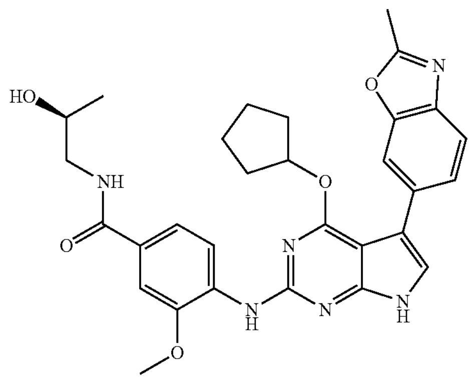 [SMILES: COc1cc(C(=O)NC[C@H](C)O)ccc1Nc1nc(OC2CCCC2)c2c(-c3ccc4nc(C)oc4c3)c[nH]c2n1] | (S)-4-(4-(cyclopentyloxy)-5-(2-methylbenzo[d]oxazol-6-yl)-7H-pyrrolo[2,3-d]pyrimidin-2-ylamino)-N-(2-hydroxypropyl)-3-methoxybenzamide | 557.3 | C |
| 241 | 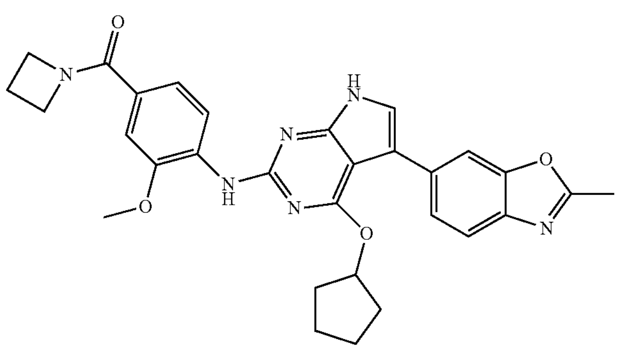 [SMILES: COc1cc(C(=O)N2CCC2)ccc1Nc1nc(OC2CCCC2)c2c(-c3ccc4nc(C)oc4c3)c[nH]c2n1] | azetidin-1-yl(4-(4-(cyclopentyloxy)-5-(2-methylbenzo[d]oxazol-6-yl)-7H-pyrrolo[2,3-d]pyrimidin-2-ylamino)-3-methoxyphenyl)methanone | 539.3 | D |
| 242 | 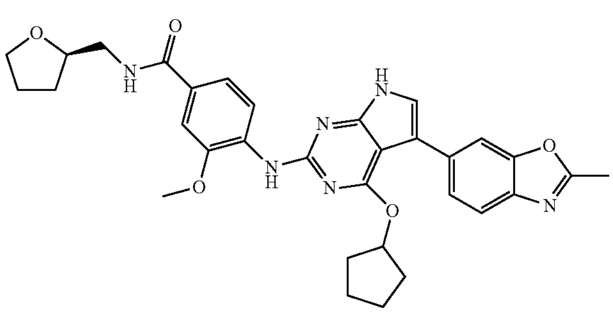 [SMILES: COc1cc(C(=O)NC[C@H]2CCCO2)ccc1Nc1nc(OC2CCCC2)c2c(-c3ccc4nc(C)oc4c3)c[nH]c2n1] | (R)-4-(4-(cyclopentyloxy)-5-(2-methylbenzo[d]oxazol-6-yl)-7H-pyrrolo[2,3-d]pyrimidin-2-ylamino)-3-methoxy-N-((tetrahydrofuran-2-yl)methyl)benzamide | 583.3 | C |

TABLE 1-continued

| Cmpd No. | Structure | Name | Obs. MH+ | Act. Level |
|---|---|---|---|---|
| 243 | 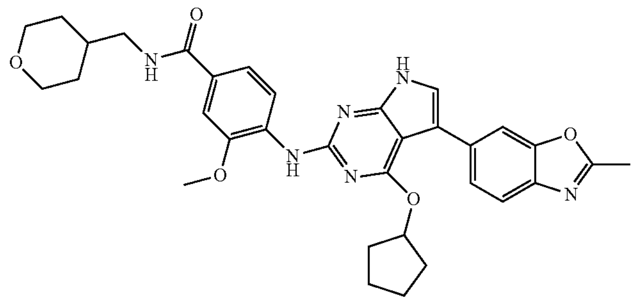 [SMILES: COc1cc(C(=O)NCC2CCOCC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-((tetrahydro-2H-pyran-4-yl)methyl)benzamide | 597.4 | C |
| 244 | 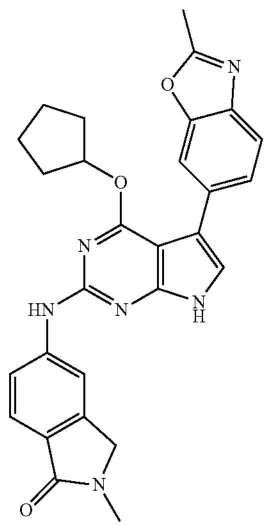 [SMILES: Cc1nc2ccc(-c3c[nH]c4nc(Nc5ccc6c(c5)CN(C)C6=O)nc(OC5CCCC5)c34)cc2o1] | 5-(4-(cyclopentyloxy)-5-(2-methylbenzo[d]oxazol-6-yl)-7H-pyrrolo[2,3-d]pyrimidin-2-ylamino)-2-methylisoindolin-1-one | 495.5 | D |
| 245 | 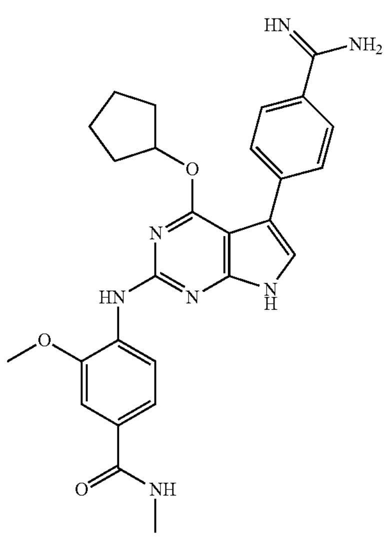 [SMILES: CNC(=O)c1ccc(Nc2nc(OC3CCCC3)c3c(-c4ccc(C(=N)N)cc4)c[nH]c3n2)c(OC)c1] | 4-(5-(4-carbamimidoylphenyl)-4-(cyclopentyloxy)-7H-pyrrolo[2,3-d]pyrimidin-2-ylamino)-3-methoxy-N-methylbenzamide | 500 | A |

| Cmpd No. | Structure | Name | Obs. MH+ | Act. Level |
|---|---|---|---|---|
| 246 | 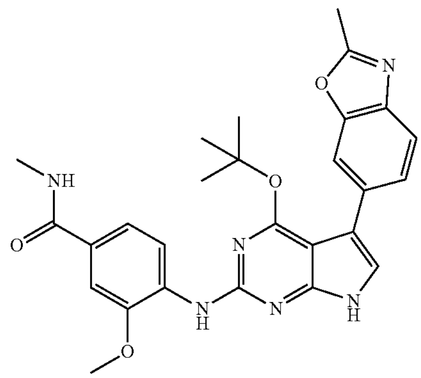 [SMILES: CNC(=O)c1ccc(Nc2nc(OC(C)(C)C)c3c(-c4ccc5nc(C)oc5c4)c[nH]c3n2)c(OC)c1] | 4-(4-tert-butoxy-5-(2-methylbenzo[d]oxazol-6-yl)-7H-pyrrolo[2,3-d]pyrimidin-2-ylamino)-3-methoxy-N-methylbenzamide | 501.3 | D |
| 247 | 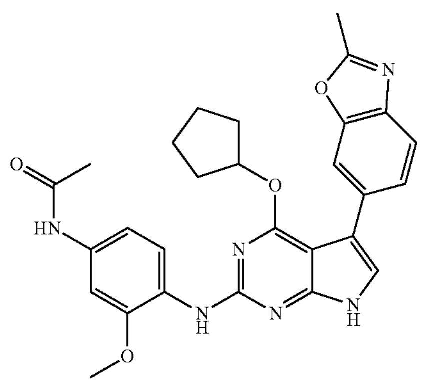 [SMILES: COc1cc(NC(C)=O)ccc1Nc1nc(OC2CCCC2)c2c(-c3ccc4nc(C)oc4c3)c[nH]c2n1] | N-(4-(4-(cyclopentyloxy)-5-(2-methylbenzo[d]oxazol-6-yl)-7H-pyrrolo[2,3-d]pyrimidin-2-ylamino)-3-methoxyphenyl)acetamide | 513.3 | C |
| 248 | 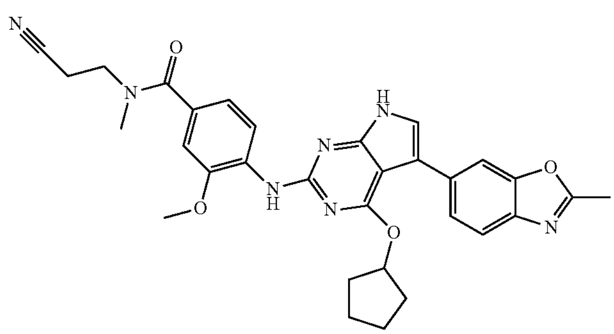 [SMILES: COc1cc(C(=O)N(C)CCC#N)ccc1Nc1nc(OC2CCCC2)c2c(-c3ccc4nc(C)oc4c3)c[nH]c2n1] | N-(2-cyanoethyl)-4-(4-(cyclopentyloxy)-5-(2-methylbenzo[d]oxazol-6-yl)-7H-pyrrolo[2,3-d]pyrimidin-2-ylamino)-3-methoxy-N-methylbenzamide | 566.3 | D |
| 249 | 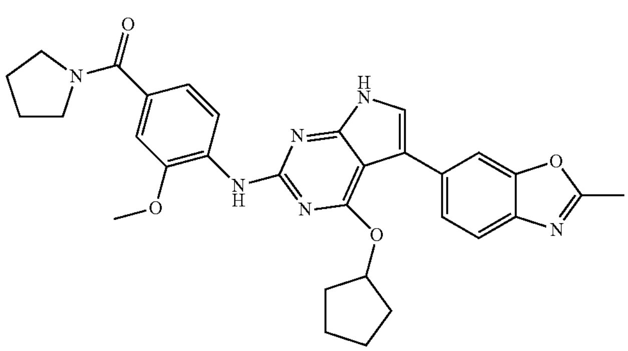 [SMILES: COc1cc(C(=O)N2CCCC2)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)(pyrrolidin-1-yl)methanone | 553.3 | C |

TABLE 1-continued

| Cmpd No. | Structure | Name | Obs. MH+ | Act. Level |
|---|---|---|---|---|
| 250 | 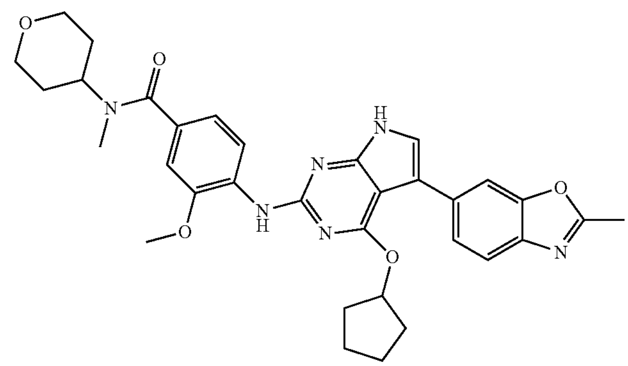 [SMILES: COc1cc(C(=O)N(C)C2CCOCC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-methyl-N-(tetrahydro-2H-pyran-4-yl)benzamide | 597.4 | C |
| 251 | 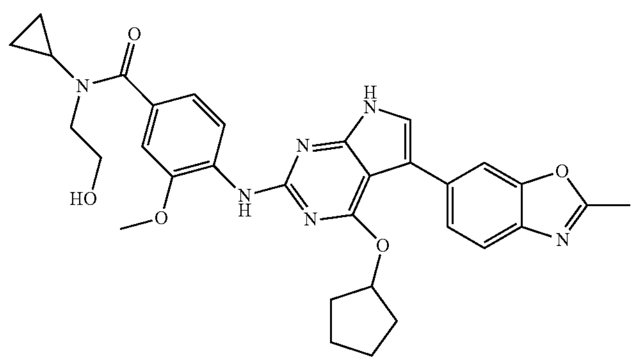 [SMILES: COc1cc(C(=O)N(CCO)C2CC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-cyclopropyl-N-(2-hydroxyethyl)-3-methoxybenzamide | 583.3 | C |
| 252 | 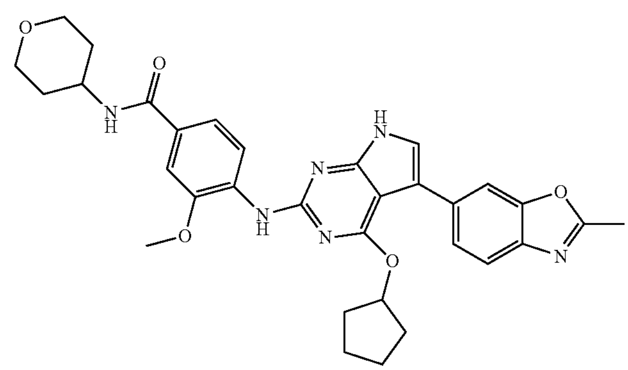 [SMILES: COc1cc(C(=O)NC2CCOCC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-(tetrahydro-2H-pyran-4-yl)benzamide | 583.3 | C |
| 253 | 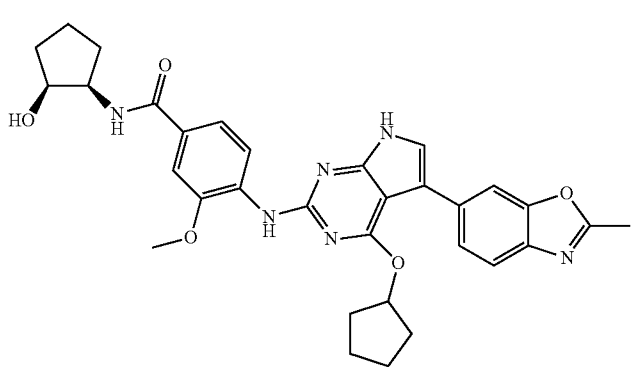 [SMILES: COc1cc(C(=O)N[C@@H]2CCC[C@@H]2O)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-((1R,2S)-2-hydroxycyclopentyl)-3-methoxybenzamide | 583.3 | C |

| Cmpd No. | Structure | Name | Obs. MH+ | Act. Level |
|---|---|---|---|---|
| 254 | 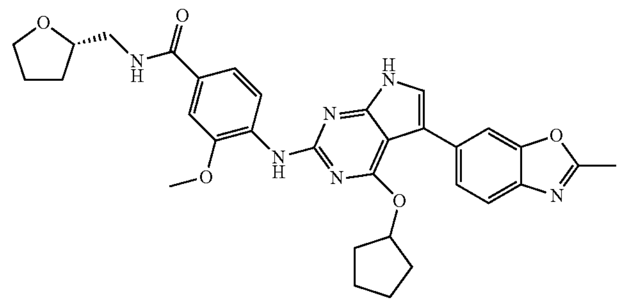 [SMILES: COc1cc(C(=O)NC[C@@H]2CCCO2)ccc1Nc1nc(OC2CCCC2)c2c(-c3ccc4nc(C)oc4c3)c[nH]c2n1] | (S)-4-(4-(cyclopentyloxy)-5-(2-methylbenzo[d]oxazol-6-yl)-7H-pyrrolo[2,3-d]pyrimidin-2-ylamino)-3-methoxy-N-((tetrahydrofuran-2-yl)methyl)benzamide | 583.3 | C |
| 255 | 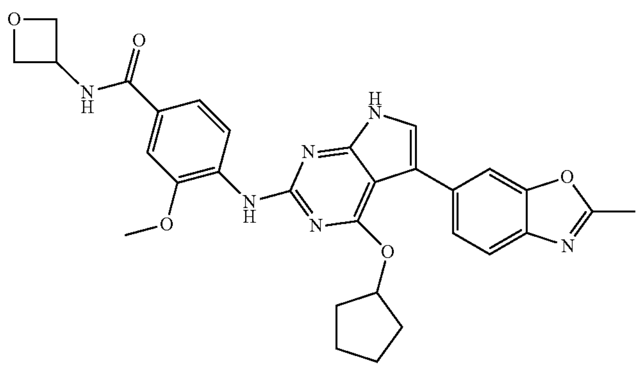 [SMILES: COc1cc(C(=O)NC2COC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-(oxetan-3-yl)benzamide | 555.3 | C |
| 256 | 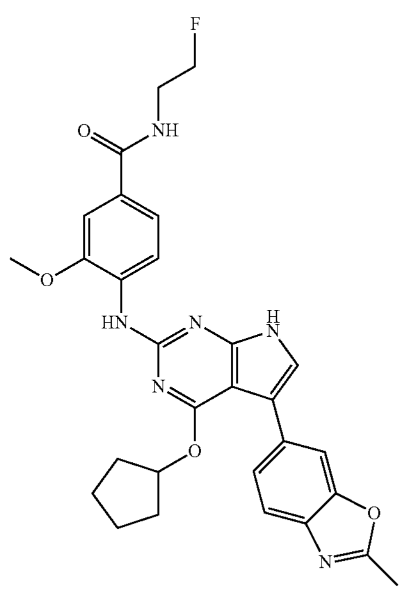 | 4-(4-(cyclopentyloxy)-5-(2-methylbenzo[d]oxazol-6-yl)-7H-pyrrolo[2,3-d]pyrimidin-2-ylamino)-N-(2-fluoroethyl)-3-methoxybenzamide | 545.3 | C |

TABLE 1-continued

| Cmpd No. | Structure | Name | Obs. MH+ | Act. Level |
|---|---|---|---|---|
| 257 | 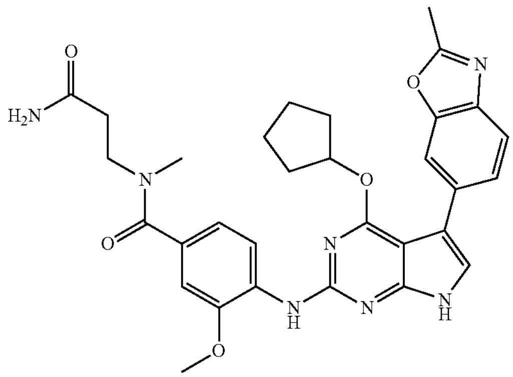 [SMILES: COc1cc(C(=O)N(C)CCC(N)=O)ccc1Nc1nc(OC2CCCC2)c2c(-c3ccc4nc(C)oc4c3)c[nH]c2n1] | N-(3-amino-3-oxopropyl)-4-(4-(cyclopentyloxy)-5-(2-methylbenzo[d]oxazol-6-yl)-7H-pyrrolo[2,3-d]pyrimidin-2-ylamino)-3-methoxy-N-methylbenzamide | 584.3 | D |
| 258 | 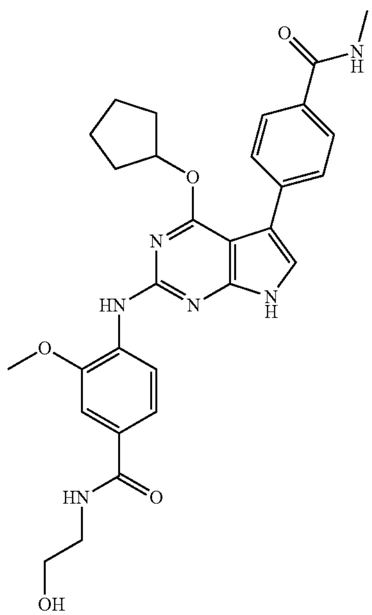 | 4-(4-(cyclopentyloxy)-5-(4-(methylcarbamoyl)phenyl)-7H-pyrrolo[2,3-d]pyrimidin-2-ylamino)-N-(2-hydroxyethyl)-3-methoxybenzamide | 545 | D |
| 259 | 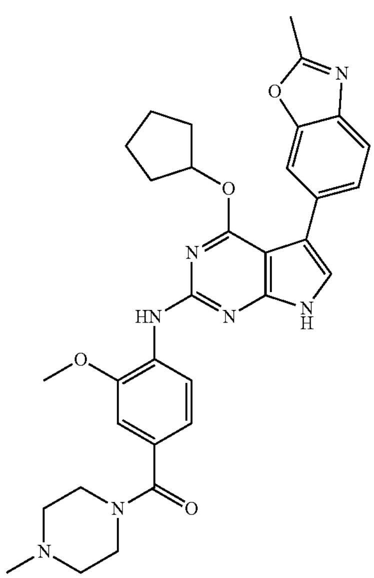 [SMILES: COc1cc(C(=O)N2CCN(C)CC2)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)(4-methylpiperazin-1-yl)methanone | 582 | D |

TABLE 1-continued

| Cmpd No. | Structure | Name | Obs. MH+ | Act. Level |
|---|---|---|---|---|
| 260 | 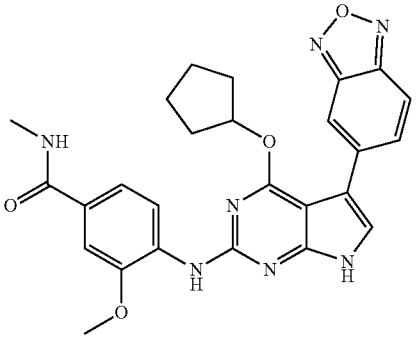 [SMILES: CNC(=O)c1ccc(Nc2nc(OC3CCCC3)c3c(-c4ccc5nonc5c4)c[nH]c3n2)c(OC)c1] | 4-(5-(benzo[c][1,2,5]oxadiazol-5-yl)-4-(cyclopentyloxy)-7H-pyrrolo[2,3-d]pyrimidin-2-ylamino)-3-methoxy-N-methylbenzamide | 500.2 | A |
| 261 | 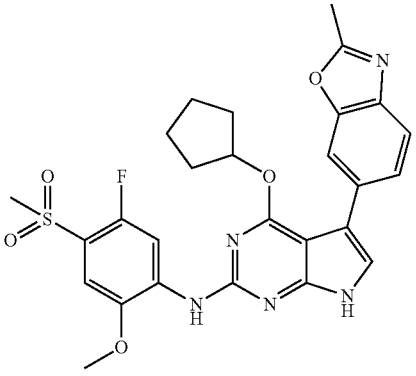 [SMILES: COc1cc(S(C)(=O)=O)c(F)cc1Nc1nc(OC2CCCC2)c2c(-c3ccc4nc(C)oc4c3)c[nH]c2n1] | 4-(cyclopentyloxy)-N-(5-fluoro-2-methoxy-4-(methylsulfonyl)phenyl)-5-(2-methylbenzo[d]oxazol-6-yl)-7H-pyrrolo[2,3-d]pyrimidin-2-amine | 552.2 | C |
| 262 | 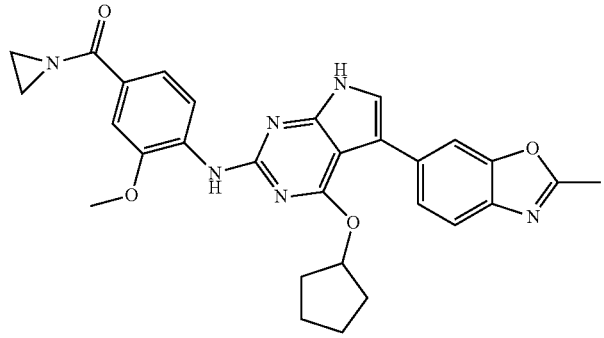 [SMILES: COc1cc(C(=O)N2CC2)ccc1Nc1nc(OC2CCCC2)c2c(-c3ccc4nc(C)oc4c3)c[nH]c2n1] | aziridin-1-yl(4-(4-(cyclopentyloxy)-5-(2-methylbenzo[d]oxazol-6-yl)-7H-pyrrolo[2,3-d]pyrimidin-2-ylamino)-3-methoxyphenyl)methanone | 525.3 | C |
| 263 | 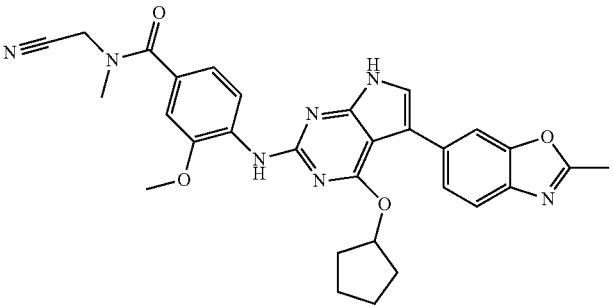 [SMILES: COc1cc(C(=O)N(C)CC#N)ccc1Nc1nc(OC2CCCC2)c2c(-c3ccc4nc(C)oc4c3)c[nH]c2n1] | N-(cyanomethyl)-4-(4-(cyclopentyloxy)-5-(2-methylbenzo[d]oxazol-6-yl)-7H-pyrrolo[2,3-d]pyrimidin-2-ylamino)-3-methoxy-N-methylbenzamide | 552.2 | D |

| Cmpd No. | Structure | Name | Obs. MH+ | Act. Level |
|---|---|---|---|---|
| 264 | 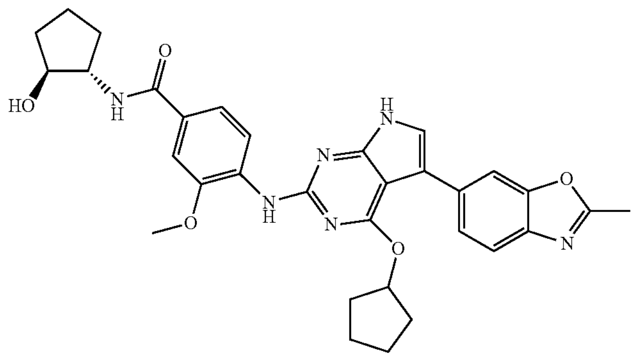 [SMILES: COc1cc(C(=O)N[C@H]2CCC[C@@H]2O)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-((1S,2R)-2-hydroxycyclopentyl)-3-methoxybenzamide | 583.3 | C |
| 265 | 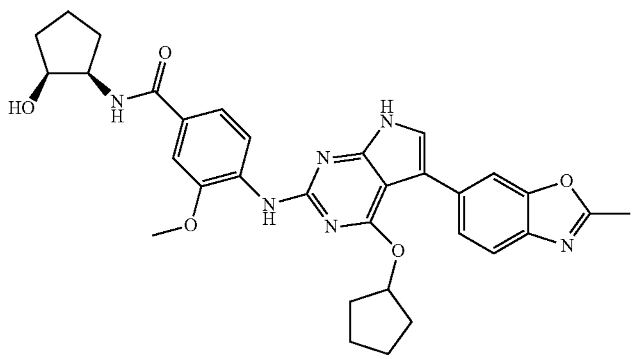 [SMILES: COc1cc(C(=O)N[C@@H]2CCC[C@@H]2O)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-((1S,2S)-2-hydroxycyclopentyl)-3-methoxybenzamide | 583.3 | C |
| 266 | 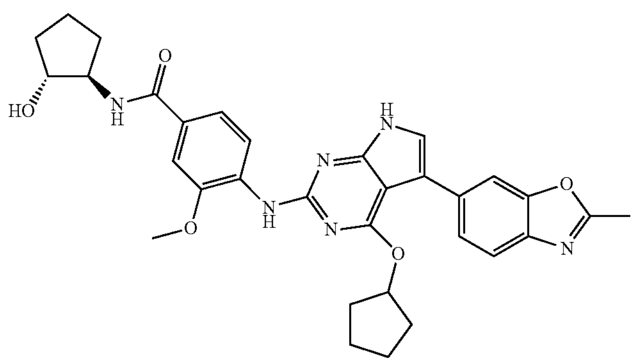 [SMILES: COc1cc(C(=O)N[C@@H]2CCC[C@H]2O)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-((1R,2S)-2-hydroxycyclopentyl)-3-methoxybenzamide | 583.3 | C |
| 267 | 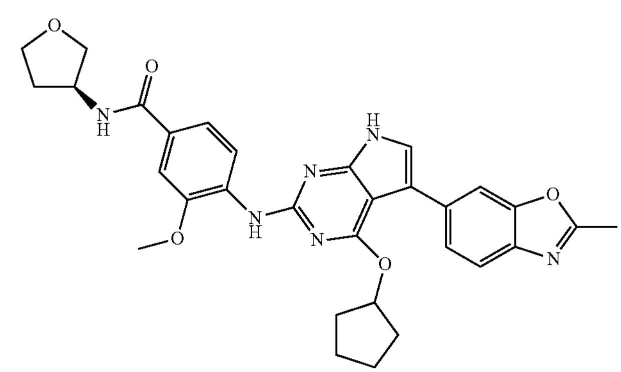 [SMILES: COc1cc(C(=O)N[C@H]2CCOC2)ccc1Nc1nc(OC2CCCC2)c2c(-c3ccc4nc(C)oc4c3)c[nH]c2n1] | (S)-4-(4-(cyclopentyloxy)-5-(2-methylbenzo[d]oxazol-6-yl)-7H-pyrrolo[2,3-d]pyrimidin-2-ylamino)-3-methoxy-N-(tetrahydrofuran-3-yl)benzamide | 569.3 | C |

TABLE 1-continued

| Cmpd No. | Structure | Name | Obs. MH+ | Act. Level |
|---|---|---|---|---|
| 268 | 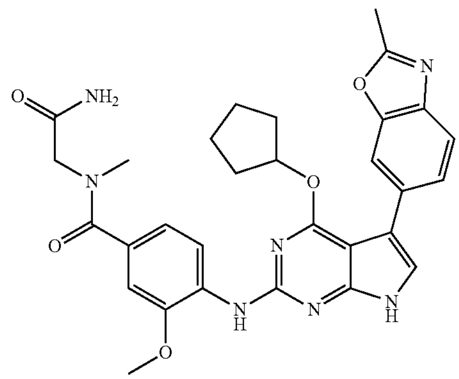 [SMILES: COc1cc(C(=O)N(C)CC(N)=O)ccc1Nc1nc(OC2CCCC2)c2c(-c3ccc4nc(C)oc4c3)c[nH]c2n1] | N-(2-amino-2-oxoethyl)-4-(4-(cyclopentyloxy)-5-(2-methylbenzo[d]oxazol-6-yl)-7H-pyrrolo[2,3-d]pyrimidin-2-ylamino)-3-methoxy-N-methylbenzamide | 570.3 | D |
| 269 | 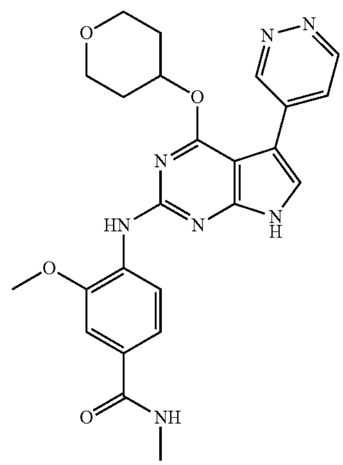 [SMILES: CNC(=O)c1ccc(Nc2nc(OC3CCOCC3)c3c(-c4ccnnc4)c[nH]c3n2)c(OC)c1] | 3-methoxy-N-methyl-4-(5-(pyridazin-4-yl)-4-(tetrahydro-2H-pyran-4-yloxy)-7H-pyrrolo[2,3-d]pyrimidin-2-ylamino)benzamide | 476 | B |
| 270 | 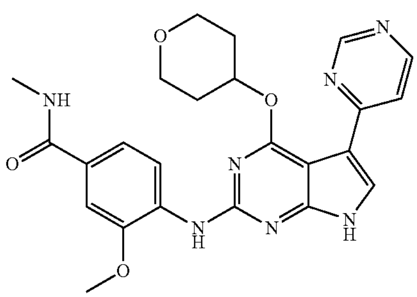 [SMILES: CNC(=O)c1ccc(Nc2nc(OC3CCOCC3)c3c(-c4ccncn4)c[nH]c3n2)c(OC)c1] | 3-methoxy-N-methyl-4-(5-(pyrimidin-4-yl)-4-(tetrahydro-2H-pyran-4-yloxy)-7H-pyrrolo[2,3-d]pyrimidin-2-ylamino)benzamide | 476.2 | C |
| 271 | 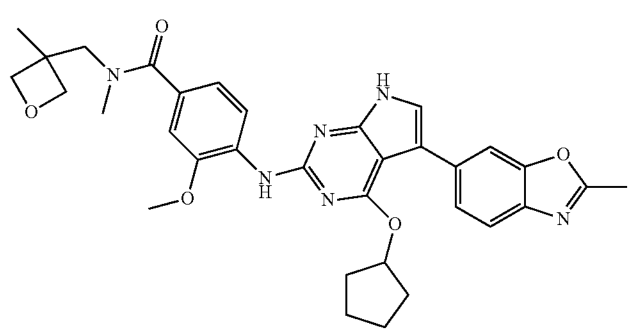 [SMILES: COc1cc(C(=O)N(C)CC2(C)COC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-methyl-N-((3-methyloxetan-3-yl)methyl)benzamide | 597.4 | D |

TABLE 1-continued

| Cmpd No. | Structure | Name | Obs. MH+ | Act. Level |
|---|---|---|---|---|
| 272 | 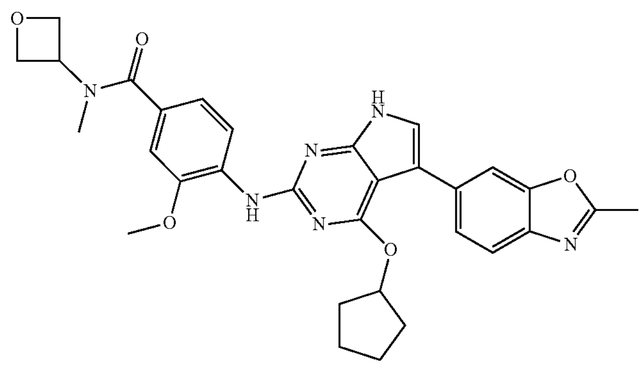 [SMILES: COc1cc(C(=O)N(C)C2COC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-methyl-N-(oxetan-3-yl)benzamide | 569.3 | D |
| 273 | 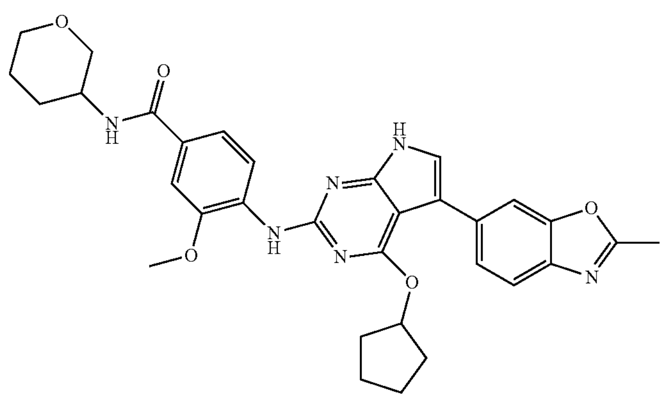 [SMILES: COc1cc(C(=O)NC2CCCOC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-(tetrahydro-2H-pyran-3-yl)benzamide | 583.3 | D |
| 274 | 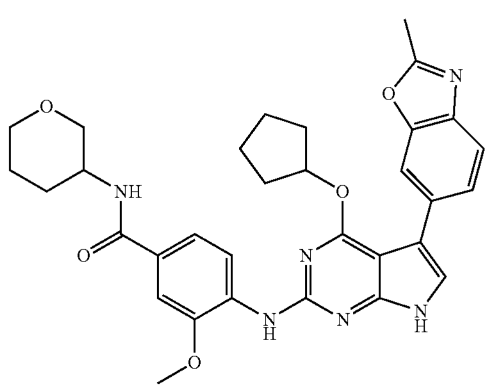 [SMILES: COc1cc(C(=O)NC2CCCOC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-(tetrahydro-2H-pyran-3-yl)benzamide | 583.4 | D |

TABLE 1-continued

| Cmpd No. | Structure | Name | Obs. MH+ | Act. Level |
|---|---|---|---|---|
| 275 | 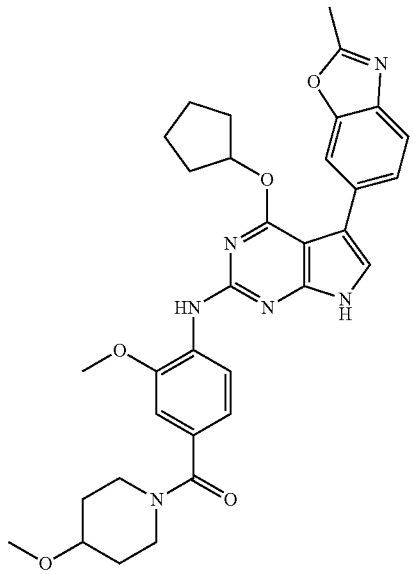 [SMILES: COc1cc(C(=O)N2CCC(OC)CC2)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)(4-methoxypiperidin-1-yl)methanone | 597.5 | D |
| 276 | 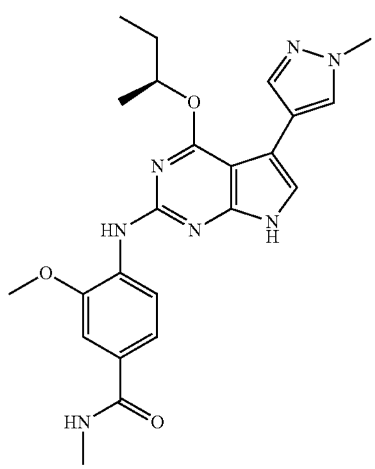 | (S)-4-(4-sec-butoxy-5-(1-methyl-1H-pyrazol-4-yl)-7H-pyrrolo[2,3-d]pyrimidin-2-ylamino)-3-methoxy-N-methylbenzamide | 450 | D |
| 277 | 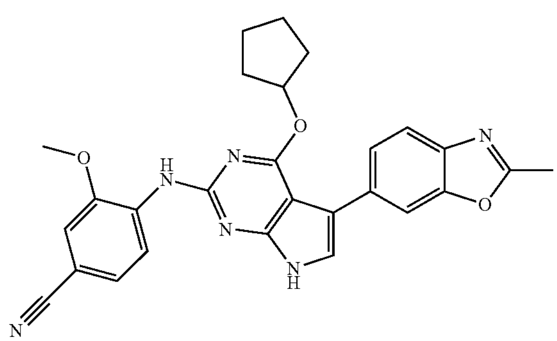 [SMILES: COc1cc(C#N)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxybenzonitrile | 481 | C |

TABLE 1-continued

| Cmpd No. | Structure | Name | Obs. MH+ | Act. Level |
|---|---|---|---|---|
| 278 | 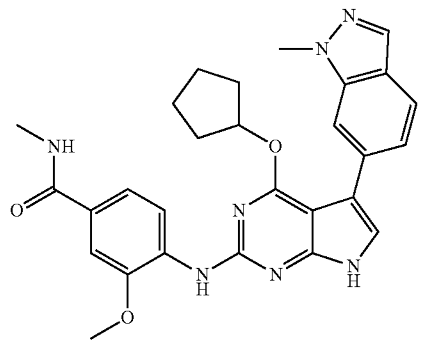 [SMILES: CNC(=O)c1ccc(Nc2nc(OC3CCCC3)c3c(-c4ccc5cnn(C)c5c4)c[nH]c3n2)c(OC)c1] | 4-(4-(cyclopentyloxy)-5-(1-methyl-1H-indazol-6-yl)-7H-pyrrolo[2,3-d]pyrimidin-2-ylamino)-3-methoxy-N-methylbenzamide | 512.3 | B |
| 279 | 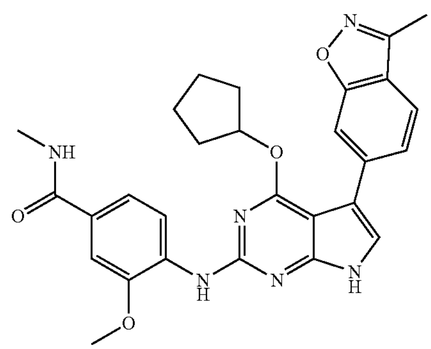 [SMILES: CNC(=O)c1ccc(Nc2nc(OC3CCCC3)c3c(-c4ccc5c(C)noc5c4)c[nH]c3n2)c(OC)c1] | 4-(4-(cyclopentyloxy)-5-(3-methylbenzo[d]isoxazol-6-yl)-7H-pyrrolo[2,3-d]pyrimidin-2-ylamino)-3-methoxy-N-methylbenzamide | 513.3 | D |
| 280 | 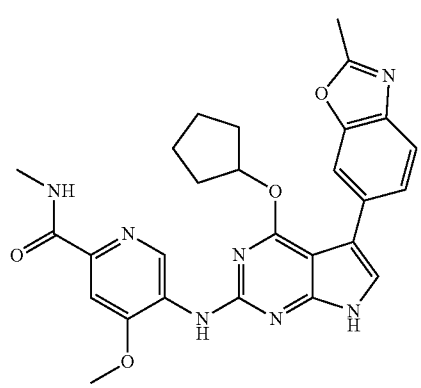 [SMILES: CNC(=O)c1cc(OC)c(Nc2nc(OC3CCCC3)c3c(-c4ccc5nc(C)oc5c4)c[nH]c3n2)cn1] | 5-(4-(cyclopentyloxy)-5-(2-methylbenzo[d]oxazol-6-yl)-7H-pyrrolo[2,3-d]pyrimidin-2-ylamino)-4-methoxy-N-methylpicolinamide | 514.3 | D |

TABLE 1-continued

| Cmpd No. | Structure | Name | Obs. MH+ | Act. Level |
|---|---|---|---|---|
| 281 | 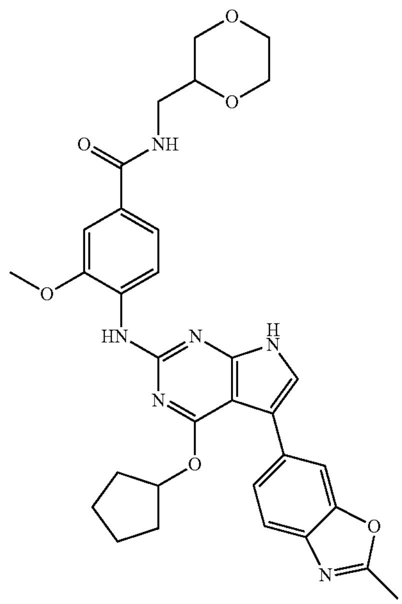 | N-((1,4-dioxan-2-yl)methyl)-4-(4-(cyclopentyloxy)-5-(2-methylbenzo[d]oxazol-6-yl)-7H-pyrrolo[2,3-d]pyrimidin-2-ylamino)-3-methoxybenzamide | 599.3 | C |
| 282 | 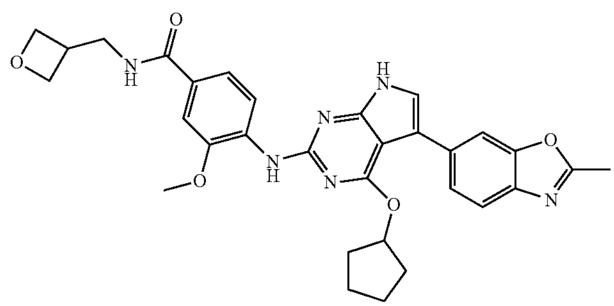 [SMILES: COc1cc(C(=O)NCC2COC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-(oxetan-3-ylmethyl)benzamide | 569.3 | C |
| 283 | 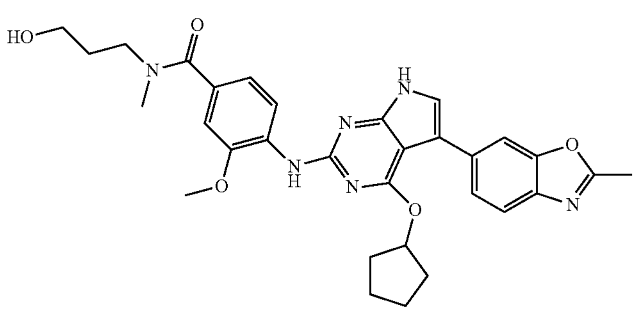 [SMILES: COc1cc(C(=O)N(C)CCCO)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-(3-hydroxypropyl)-3-methoxy-N-methylbenzamide | 571.3 | D |
| 284 | 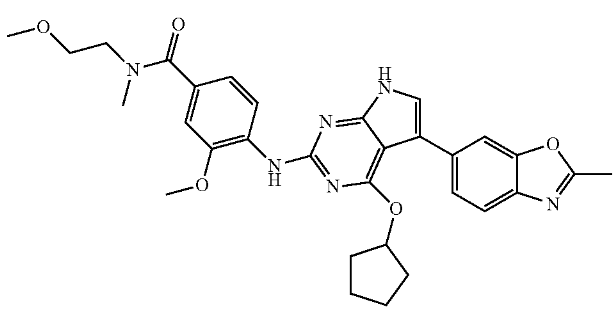 | 4-(4-(cyclopentyloxy)-5-(2-methylbenzo[d]oxazol-6-yl)-7H-pyrrolo[2,3-d]pyrimidin-2-ylamino)-3-methoxy-N-(2-methoxyethyl)-N-methylbenzamide | 571.3 | D |

TABLE 1-continued

| Cmpd No. | Structure | Name | Obs. MH+ | Act. Level |
|---|---|---|---|---|
| 285 | 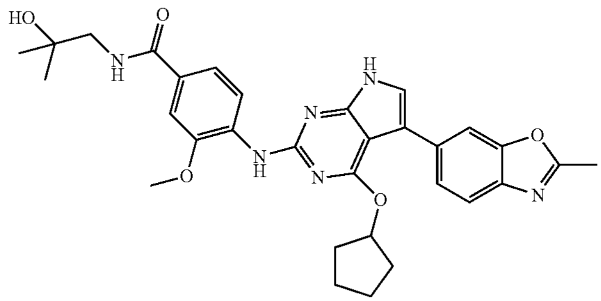 [SMILES: COc1cc(C(=O)NCC(C)(C)O)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-(2-hydroxy-2-methylpropyl)-3-methoxybenzamide | 571.3 | C |
| 286 | 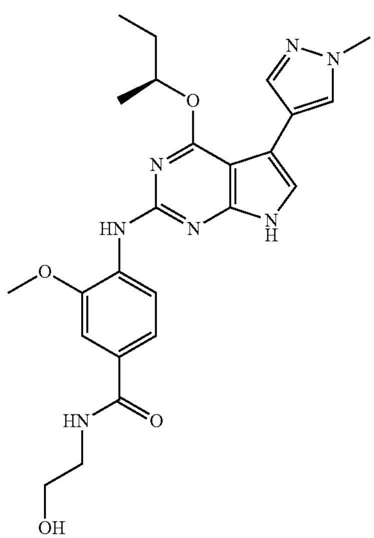 | (S)-4-(4-sec-butoxy-5-(1-methyl-1H-pyrazol-4-yl)-7H-pyrrolo[2,3-d]pyrimidin-2-ylamino)-N-(2-hydroxyethyl)-3-methoxybenzamide | 480 | C |
| 287 | 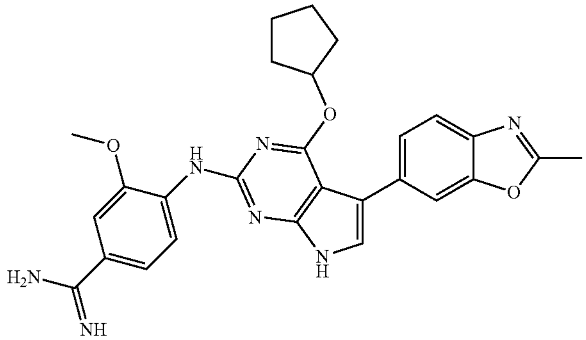 [SMILES: COc1cc(C(=N)N)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxybenzimidamide | 498 | A |

TABLE 1-continued

| Cmpd No. | Structure | Name | Obs. MH+ | Act. Level |
|---|---|---|---|---|
| 288 | 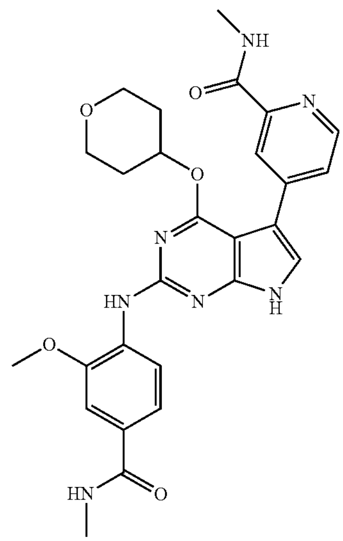 [SMILES: CNC(=O)c1ccc(Nc2nc(OC3CCOCC3)c3c(-c4ccnc(C(=O)NC)c4)c[nH]c3n2)c(OC)c1] | 4-(2-(2-methoxy-4-(methylcarbamoyl)phenylamino)-4-(tetrahydro-2H-pyran-4-yloxy)-7H-pyrrolo[2,3-d]pyrimidin-5-yl)-N-methylpicolinamide | 531.9 | C |
| 289 | 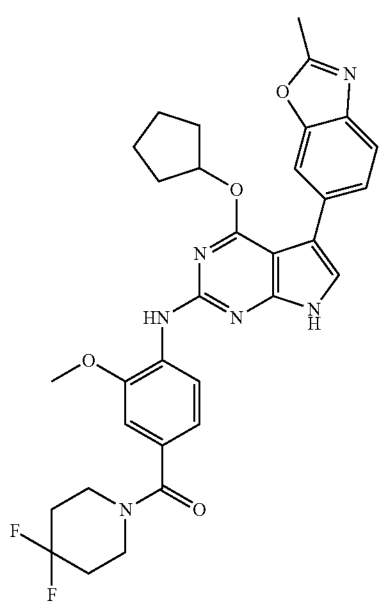 [SMILES: COc1cc(C(=O)N2CCC(F)(F)CC2)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)(4,4-difluoropiperidin-1-yl)methanone | 602.8 | C |

TABLE 1-continued

| Cmpd No. | Structure | Name | Obs. MH+ | Act. Level |
|---|---|---|---|---|
| 290 | 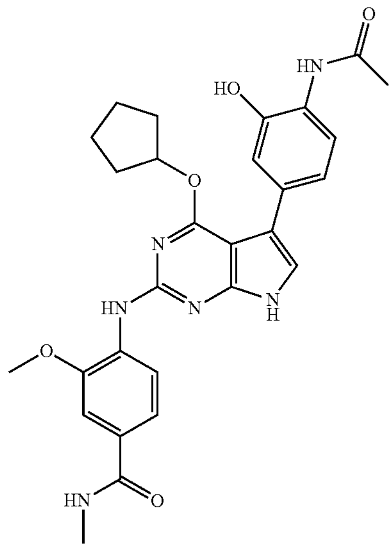 [SMILES: CNC(=O)c1ccc(Nc2nc(OC3CCCC3)c3c(-c4ccc(NC(C)=O)c(O)c4)c[nH]c3n2)c(OC)c1] | 4-(5-(4-acetamido-3-hydroxyphenyl)-4-(cyclopentyloxy)-7H-pyrrolo[2,3-d]pyrimidin-2-ylamino)-3-methoxy-N-methylbenzamide | 531 | C |
| 291 | 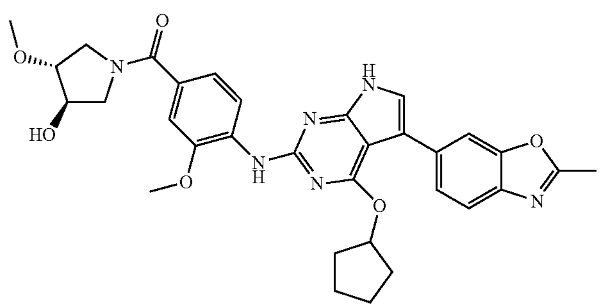 | (4-(4-(cyclopentyloxy)-5-(2-methylbenzo[d]oxazol-6-yl)-7H-pyrrolo[2,3-d]pyrimidin-2-ylamino)-3-methoxyphenyl)((3R,4R)-3-hydroxy-4-methoxypyrrolidin-1-yl)methanone | 599.4 | D |
| 292 | 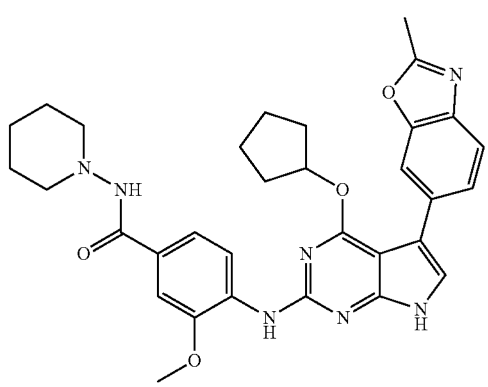 [SMILES: COc1cc(C(=O)NN2CCCCC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-(piperidin-1-yl)benzamide | 582.4 | C |

TABLE 1-continued

| Cmpd No. | Structure | Name | Obs. MH+ | Act. Level |
|---|---|---|---|---|
| 293 | 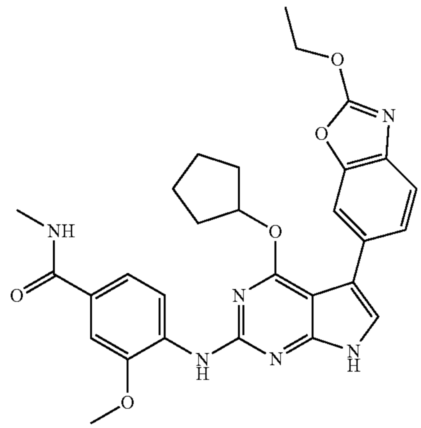 [SMILES: CCOc1nc2ccc(-c3c[nH]c4nc(Nc5ccc(C(=O)NC)cc5OC)nc(OC5CCCC5)c34)cc2o1] | 4-(4-(cyclopentyloxy)-5-(2-ethoxybenzo[d]oxazol-6-yl)-7H-pyrrolo[2,3-d]pyrimidin-2-ylamino)-3-methoxy-N-methylbenzamide | 543.3 | C |
| 294 | 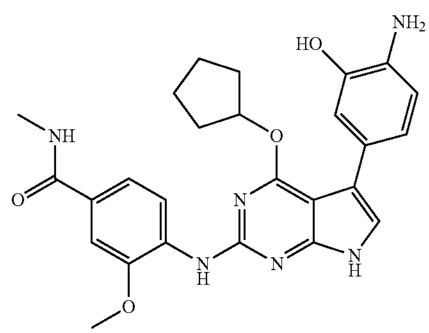 [SMILES: CNC(=O)c1ccc(Nc2nc(OC3CCCC3)c3c(-c4ccc(N)c(O)c4)c[nH]c3n2)c(OC)c1] | 4-(5-(4-amino-3-hydroxyphenyl)-4-(cyclopentyloxy)-7H-pyrrolo[2,3-d]pyrimidin-2-ylamino)-3-methoxy-N-methylbenzamide | 489.2 | C |
| 295 | 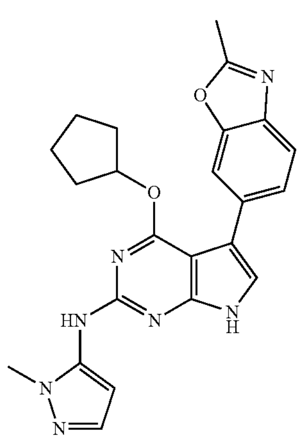 [SMILES: Cc1nc2ccc(-c3c[nH]c4nc(Nc5ccnn5C)nc(OC5CCCC5)c34)cc2o1] | 4-(cyclopentyloxy)-N-(1-methyl-1H-pyrazol-5-yl)-5-(2-methylbenzo[d]oxazol-6-yl)-7H-pyrrolo[2,3-d]pyrimidin-2-amine | 429.9 | C |

| Cmpd No. | Structure | Name | Obs. MH+ | Act. Level |
|---|---|---|---|---|
| 296 | 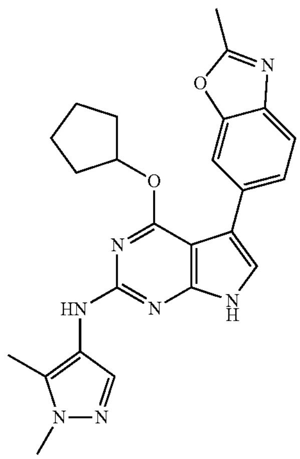 [SMILES: Cc1nc2ccc(-c3c[nH]c4nc(Nc5cnn(C)c5C)nc(OC5CCCC5)c34)cc2o1] | 4-(cyclopentyloxy)-N-(1,5-dimethyl-1H-pyrazol-4-yl)-5-(2-methylbenzo[d]oxazol-6-yl)-7H-pyrrolo[2,3-d]pyrimidin-2-amine | 444 | D |
| 297 | 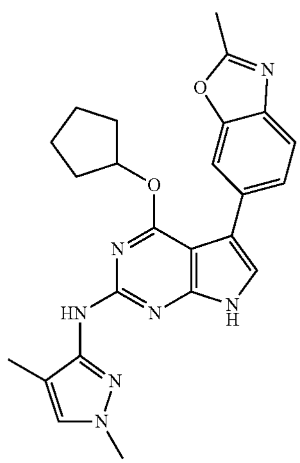 [SMILES: Cc1nc2ccc(-c3c[nH]c4nc(Nc5nn(C)cc5C)nc(OC5CCCC5)c34)cc2o1] | 4-(cyclopentyloxy)-N-(1,4-dimethyl-1H-pyrazol-3-yl)-5-(2-methylbenzo[d]oxazol-6-yl)-7H-pyrrolo[2,3-d]pyrimidin-2-amine | 444 | |
| 298 | 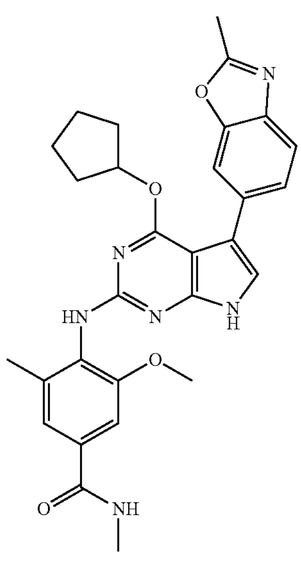 [SMILES: CNC(=O)c1cc(C)c(Nc2nc(OC3CCCC3)c3c(-c4ccc5nc(C)oc5c4)c[nH]c3n2)c(OC)c1] | 4-(4-(cyclopentyloxy)-5-(2-methylbenzo[d]oxazol-6-yl)-7H-pyrrolo[2,3-d]pyrimidin-2-ylamino)-3-methoxy-N,5-dimethylbenzamide | 527.2 | A |

TABLE 1-continued

| Cmpd No. | Structure | Name | Obs. MH+ | Act. Level |
|---|---|---|---|---|
| 299 | 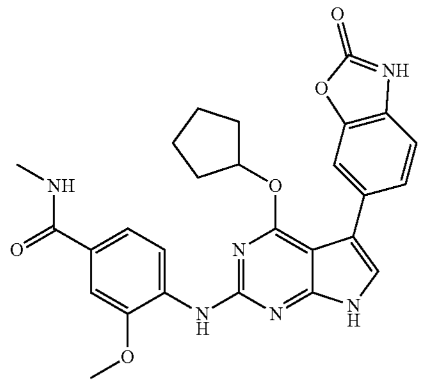 | 4-(4-(cyclopentyloxy)-5-(2-oxo-2,3-dihydrobenzo[d]oxazol-6-yl)-7H-pyrrolo[2,3-d]pyrimidin-2-ylamino)-3-methoxy-N-methylbenzamide | 515.2 | C |
| 300 | 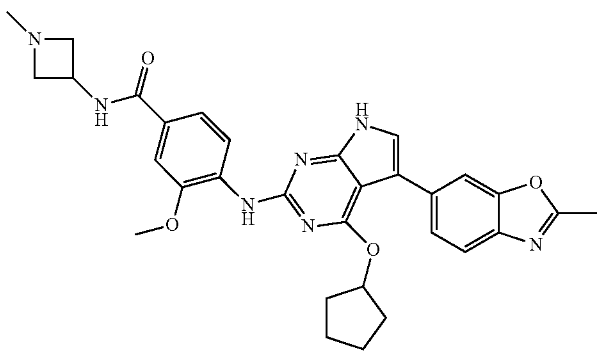 | 4-(4-(cyclopentyloxy)-5-(2-methylbenzo[d]oxazol-6-yl)-7H-pyrrolo[2,3-d]pyrimidin-2-ylamino)-3-methoxy-N-(1-methylazetidin-3-yl)benzamide | 568.3 | C |
| 301 | 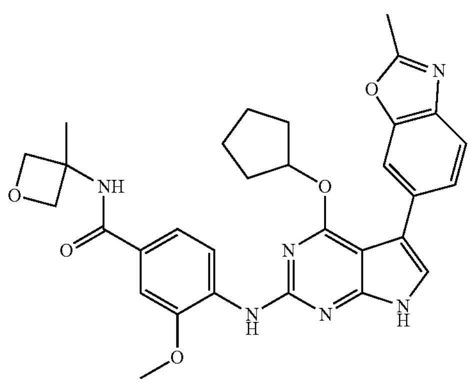 [SMILES: COc1cc(C(=O)NC2(C)COC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-(3-methyloxetan-3-yl)benzamide | 569.3 | C |
| 302 | 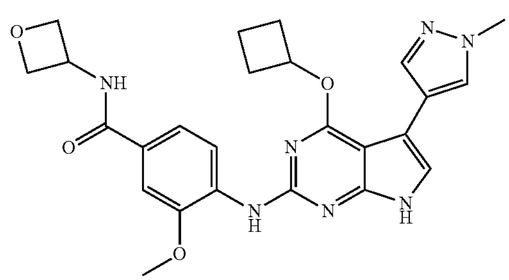 [SMILES: COc1cc(C(=O)NC2COC2)ccc1Nc1nc(OC2CCC2)c2c(-c3cnn(C)c3)c[nH]c2n1] | 4-(4-cyclobutoxy-5-(1-methyl-1H-pyrazol-4-yl)-7H-pyrrolo[2,3-d]pyrimidin-2-ylamino)-3-methoxy-N-(oxetan-3-yl)benzamide | 490.3 | C |

TABLE 1-continued

| Cmpd No. | Structure | Name | Obs. MH+ | Act. Level |
|---|---|---|---|---|
| 303 | 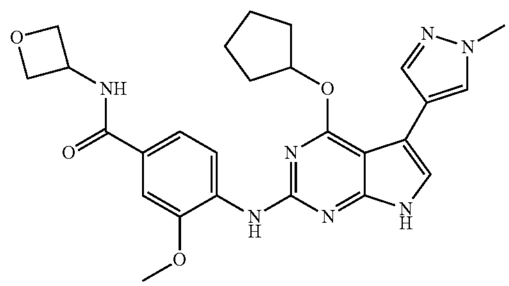 [SMILES: COc1cc(C(=O)NC2COC2)ccc1Nc1nc(OC2CCCC2)c2c(-c3cnn(C)c3)c[nH]c2n1] | 4-(4-(cyclopentyloxy)-5-(1-methyl-1H-pyrazol-4-yl)-7H-pyrrolo[2,3-d]pyrimidin-2-ylamino)-3-methoxy-N-(oxetan-3-yl)benzamide | 504.3 | D |
| 304 | 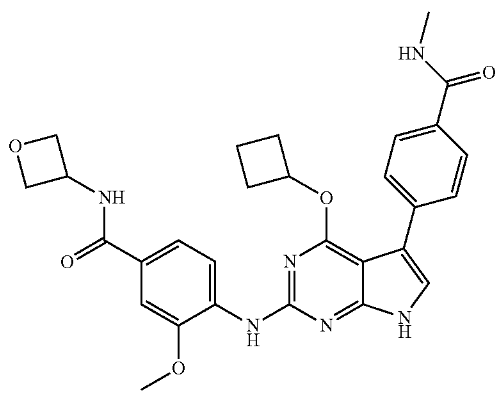 [SMILES: CNC(=O)c1ccc(-c2c[nH]c3nc(Nc4ccc(C(=O)NC5COC5)cc4OC)nc(OC4CCC4)c23)cc1] | 4-(4-cyclobutoxy-5-(4-(methylcarbamoyl)phenyl)-7H-pyrrolo[2,3-d]pyrimidin-2-ylamino)-3-methoxy-N-(oxetan-3-yl)benzamide | 543.3 | D |
| 305 | 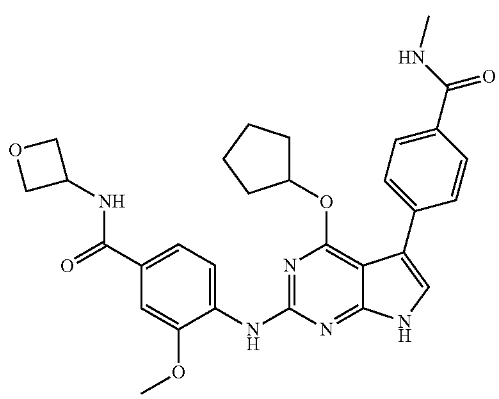 [SMILES: CNC(=O)c1ccc(-c2c[nH]c3nc(Nc4ccc(C(=O)NC5COC5)cc4OC)nc(OC4CCCC4)c23)cc1] | 4-(4-(cyclopentyloxy)-5-(4-(methylcarbamoyl)phenyl)-7H-pyrrolo[2,3-d]pyrimidin-2-ylamino)-3-methoxy-N-(oxetan-3-yl)benzamide | 557.3 | D |
| 306 | 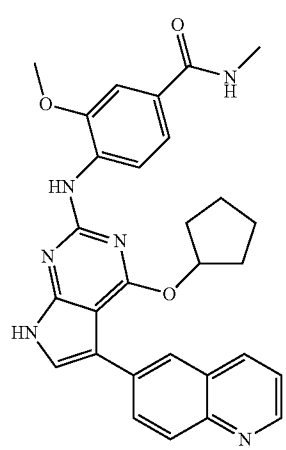 [SMILES: CNC(=O)c1ccc(Nc2nc(OC3CCCC3)c3c(-c4ccc5ncccc5c4)c[nH]c3n2)c(OC)c1] | 4-(4-(cyclopentyloxy)-5-(quinolin-6-yl)-7H-pyrrolo[2,3-d]pyrimidin-2-ylamino)-3-methoxy-N-methylbenzamide | 509.3 | D |

TABLE 1-continued

| Cmpd No. | Structure | Name | Obs. MH+ | Act. Level |
|---|---|---|---|---|
| 307 | 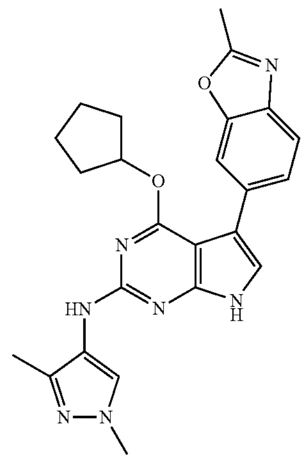 [SMILES: Cc1nc2ccc(-c3c[nH]c4nc(Nc5cn(C)nc5C)nc(OC5CCCC5)c34)cc2o1] | 4-(cyclopentyloxy)-N-(1,3-dimethyl-1H-pyrazol-4-yl)-5-(2-methylbenzo[d]oxazol-6-yl)-7H-pyrrolo[2,3-d]pyrimidin-2-amine | 444 | D |
| 308 | 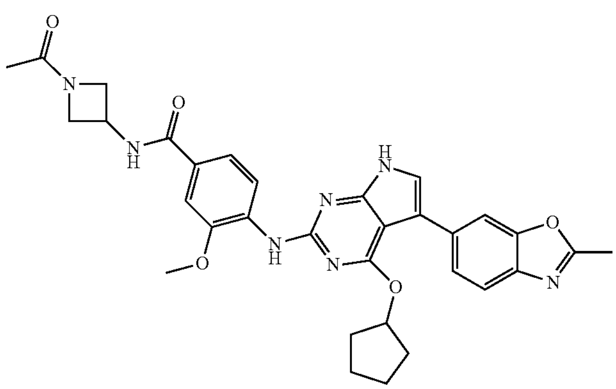 [SMILES: COc1cc(C(=O)NC2CN(C(C)=O)C2)ccc1Nc1nc(OC2CCCC2)c2c(-c3ccc4nc(C)oc4c3)c[nH]c2n1] | N-(1-acetylazetidin-3-yl)-4-(4-(cyclopentyloxy)-5-(2-methylbenzo[d]oxazol-6-yl)-7H-pyrrolo[2,3-d]pyrimidin-2-ylamino)-3-methoxybenzamide | 596.3 | C |
| 309 | 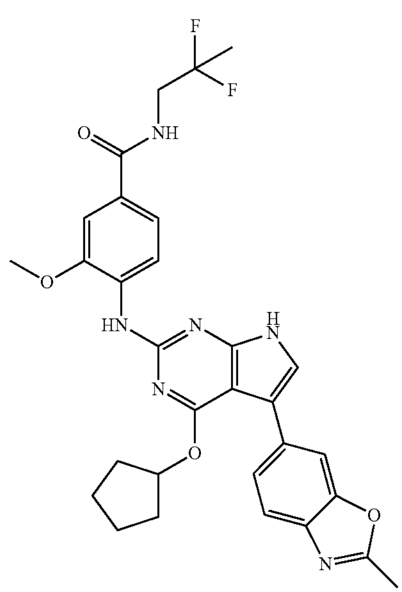 | 4-(4-(cyclopentyloxy)-5-(2-methylbenzo[d]oxazol-6-yl)-7H-pyrrolo[2,3-d]pyrimidin-2-ylamino)-N-(2,2-difluoropropyl)-3-methoxybenzamide | 577.3 | C |

TABLE 1-continued

| Cmpd No. | Structure | Name | Obs. MH+ | Act. Level |
|---|---|---|---|---|
| 310 | 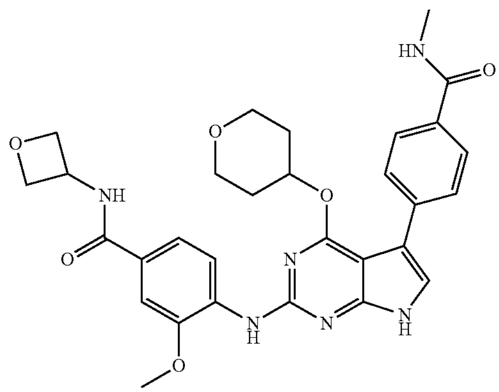 [SMILES: CNC(=O)c1ccc(-c2c[nH]c3nc(Nc4ccc(C(=O)NC5COC5)cc4OC)nc(OC4CCOCC4)c23)cc1] | 3-methoxy-4-(5-(4-(methylcarbamoyl)phenyl)-4-(tetrahydro-2H-pyran-4-yloxy)-7H-pyrrolo[2,3-d]pyrimidin-2-ylamino)-N-(oxetan-3-yl)benzamide | 573.3 | D |
| 311 | 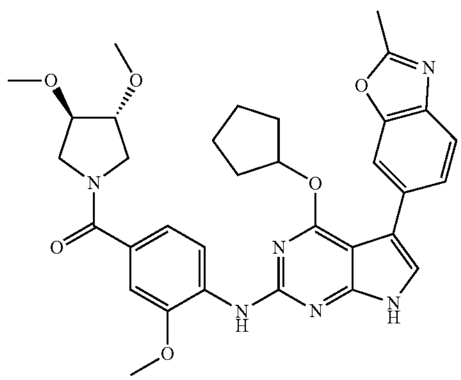 [SMILES: COc1cc(C(=O)N2C[C@@H](OC)[C@H](OC)C2)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)((3R,4R)-3,4-dimethoxypyrrolidin-1-yl)methanone | 613.4 | D |
| 312 | 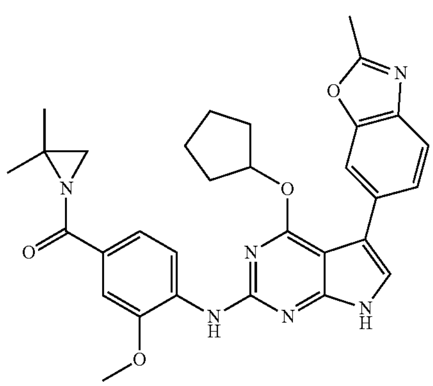 [SMILES: COc1cc(C(=O)N2CC2(C)C)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)(2,2-dimethylaziridin-1-yl)methanone | 553.3 | B |
| 313 | 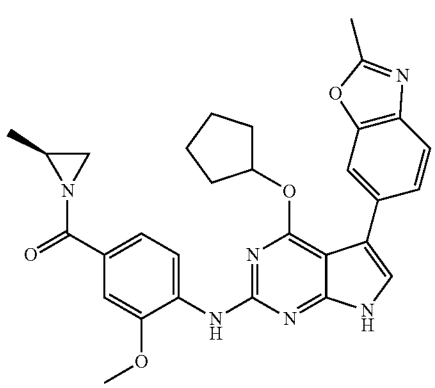 [SMILES: COc1cc(C(=O)N2C[C@@H]2C)ccc1Nc1nc(OC2CCCC2)c2c(-c3ccc4nc(C)oc4c3)c[nH]c2n1] | (S)-(4-(4-(cyclopentyloxy)-5-(2-methylbenzo[d]oxazol-6-yl)-7H-pyrrolo[2,3-d]pyrimidin-2-ylamino)-3-methoxyphenyl)(2-methylaziridin-1-yl)methanone | 539.3 | B |

TABLE 1-continued

| Cmpd No. | Structure | Name | Obs. MH+ | Act. Level |
|---|---|---|---|---|
| 314 | 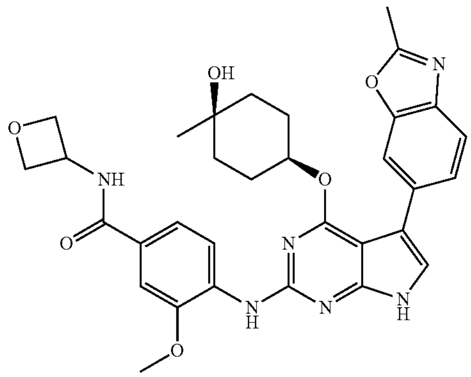 [SMILES: COc1cc(C(=O)NC2COC2)ccc1Nc1nc(O[C@H]2CC[C@@](C)(O)CC2)c2c(-c3ccc4nc(C)oc4c3)c[nH]c2n1] | 4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-3-methoxy-N-(oxetan-3-yl)benzamide | 599.3 | D |
| 315 | 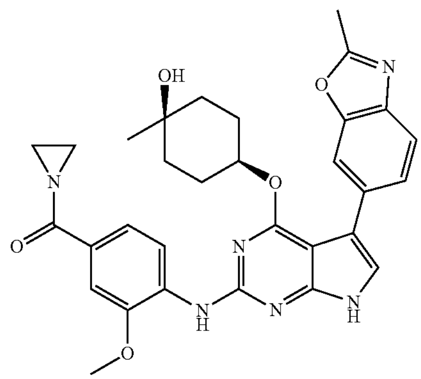 [SMILES: COc1cc(C(=O)N2CC2)ccc1Nc1nc(O[C@H]2CC[C@@](C)(O)CC2)c2c(-c3ccc4nc(C)oc4c3)c[nH]c2n1] | aziridin-1-yl(4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-3-methoxyphenyl)methanone | 569.3 | D |
| 316 | 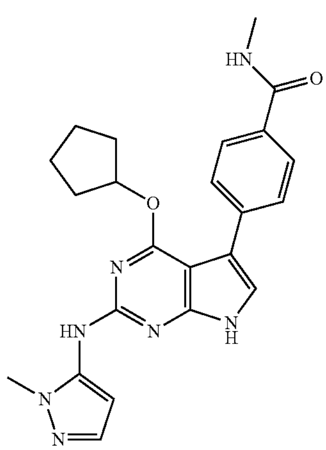 [SMILES: CNC(=O)c1ccc(-c2c[nH]c3nc(Nc4ccnn4C)nc(OC4CCCC4)c23)cc1] | 4-(4-(cyclopentyloxy)-2-(1-methyl-1H-pyrazol-5-ylamino)-7H-pyrrolo[2,3-d]pyrimidin-5-yl)-N-methylbenzamide | 432 | D |

TABLE 1-continued

| Cmpd No. | Structure | Name | Obs. MH+ | Act. Level |
|---|---|---|---|---|
| 317 | 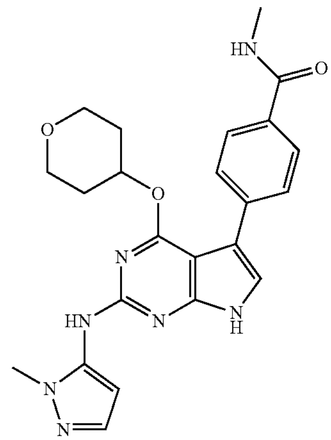 [SMILES: CNC(=O)c1ccc(-c2c[nH]c3nc(Nc4ccnn4C)nc(OC4CCOCC4)c23)cc1] | N-methyl-4-(2-(1-methyl-1H-pyrazol-5-ylamino)-4-(tetrahydro-2H-pyran-4-yloxy)-7H-pyrrolo[2,3-d]pyrimidin-5-yl)benzamide | 447.9 | B |
| 318 | 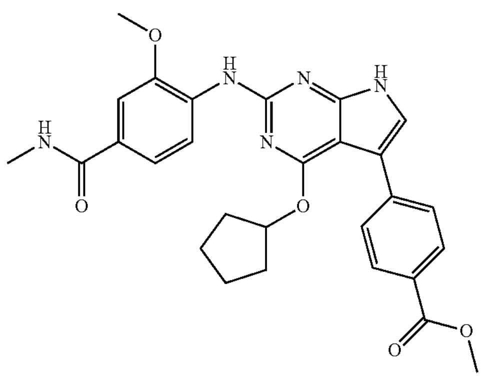 | methyl 4-(4-(cyclopentyloxy)-2-(2-methoxy-4-(methylcarbamoyl)phenylamino)-7H-pyrrolo[2,3-d]pyrimidin-5-yl)benzoate | 516.2 | A |
| 319 | 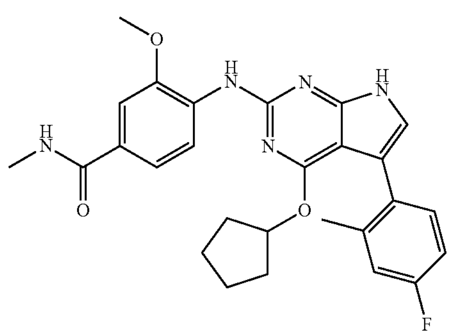 [SMILES: CNC(=O)c1ccc(Nc2nc(OC3CCCC3)c3c(-c4ccc(F)cc4C)c[nH]c3n2)c(OC)c1] | 4-(4-(cyclopentyloxy)-5-(4-fluoro-2-methylphenyl)-7H-pyrrolo[2,3-d]pyrimidin-2-ylamino)-3-methoxy-N-methylbenzamide | 490.2 | A |
| 320 | 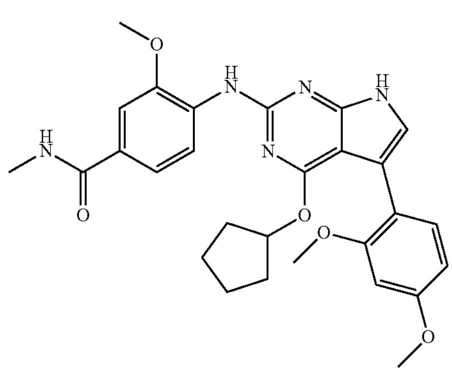 [SMILES: CNC(=O)c1ccc(Nc2nc(OC3CCCC3)c3c(-c4ccc(OC)cc4OC)c[nH]c3n2)c(OC)c1] | 4-(4-(cyclopentyloxy)-5-(2,4-dimethoxyphenyl)-7H-pyrrolo[2,3-d]pyrimidin-2-ylamino)-3-methoxy-N-methylbenzamide | 518.4 | A |

TABLE 1-continued

| Cmpd No. | Structure | Name | Obs. MH+ | Act. Level |
|---|---|---|---|---|
| 321 | 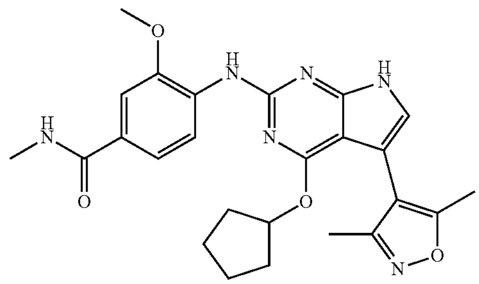 | 4-(4-(cyclopentyloxy)-5-(3,5-dimethylisoxazol-4-yl)-7H-pyrrolo[2,3-d]pyrimidin-2-ylamino)-3-methoxy-N-methylbenzamide | 477.4 | A |
| 322 | 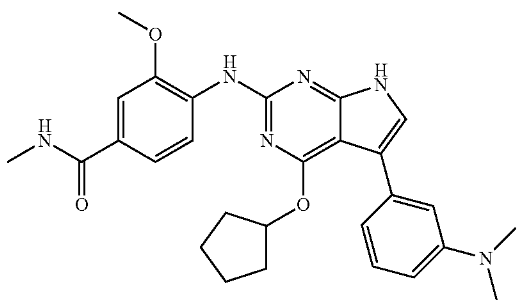 | 4-(4-(cyclopentyloxy)-5-(3-(dimethylamino)phenyl)-7H-pyrrolo[2,3-d]pyrimidin-2-ylamino)-3-methoxy-N-methylbenzamide | 501.4 | B |
| 323 | 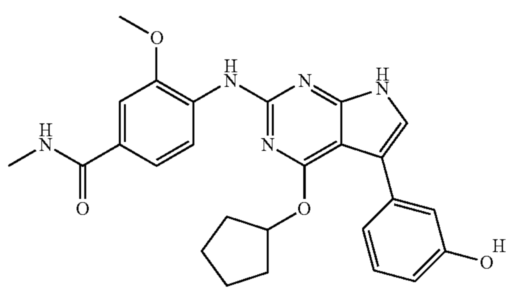 | 4-(4-(cyclopentyloxy)-5-(3-hydroxyphenyl)-7H-pyrrolo[2,3-d]pyrimidin-2-ylamino)-3-methoxy-N-methylbenzamide | 474.2 | D |
| 324 | 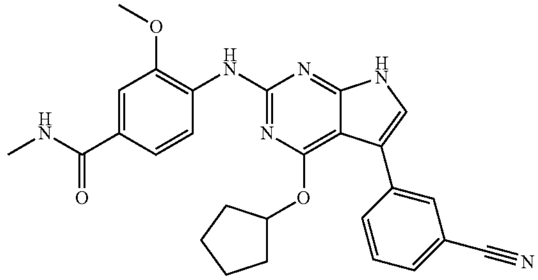 [SMILES: CNC(=O)c1ccc(Nc2nc(OC3CCCC3)c3c(-c4cccc(C#N)c4)c[nH]c3n2)c(OC)c1] | 4-(5-(3-cyanophenyl)-4-(cyclopentyloxy)-7H-pyrrolo[2,3-d]pyrimidin-2-ylamino)-3-methoxy-N-methylbenzamide | 483.2 | A |

| Cmpd No. | Structure | Name | Obs. MH+ | Act. Level |
|---|---|---|---|---|
| 325 | 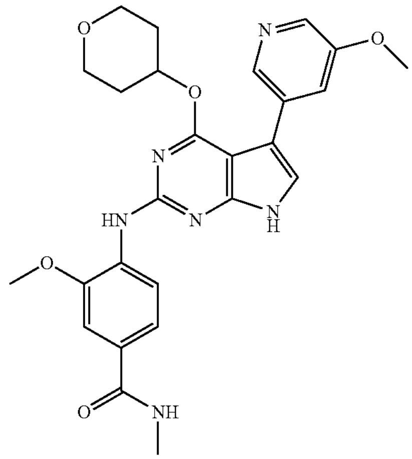 | 3-methoxy-4-(5-(5-methoxypyridin-3-yl)-4-(tetrahydro-2H-pyran-4-yloxy)-7H-pyrrolo[2,3-d]pyrimidin-2-ylamino)-N-methylbenzamide | 504.95 | C |
| 326 | 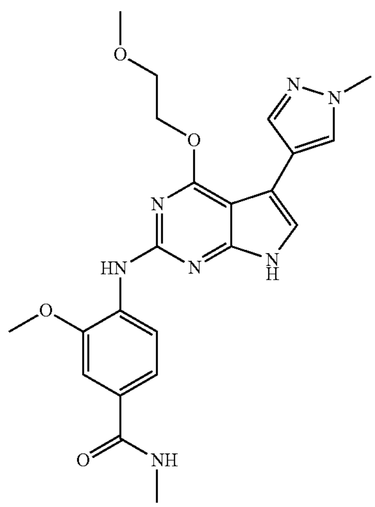 | 3-methoxy-4-(4-(2-methoxyethoxy)-5-(1-methyl-1H-pyrazol-4-yl)-7H-pyrrolo[2,3-d]pyrimidin-2-ylamino)-N-methylbenzamide | 451.95 | D |
| 327 | 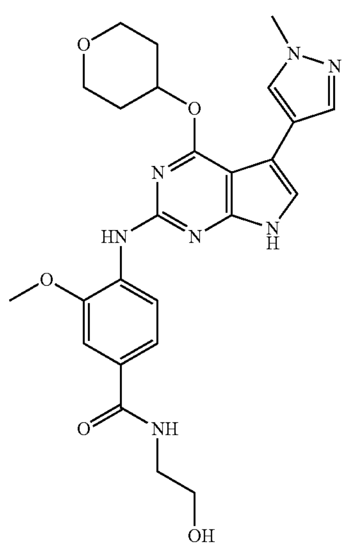 [SMILES: COc1cc(C(=O)NCCO)ccc1Nc1nc(OC2CCOCC2)c2c(-c3cnn(C)c3)c[nH]c2n1] | N-(2-hydroxyethyl)-3-methoxy-4-(5-(1-methyl-1H-pyrazol-4-yl)-4-(tetrahydro-2H-pyran-4-yloxy)-7H-pyrrolo[2,3-d]pyrimidin-2-ylamino)benzamide | 508.1 | C |

| Cmpd No. | Structure | Name | Obs. MH+ | Act. Level |
|---|---|---|---|---|
| 328 | 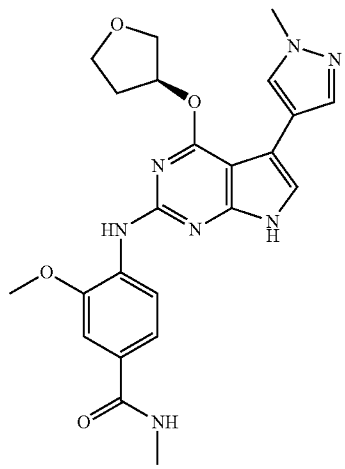 [SMILES: CNC(=O)c1ccc(Nc2nc(O[C@H]3CCOC3)c3c(-c4cnn(C)c4)c[nH]c3n2)c(OC)c1] | (S)-3-methoxy-N-methyl-4-(5-(1-methyl-1H-pyrazol-4-yl)-4-(tetrahydrofuran-3-yloxy)-7H-pyrrolo[2,3-d]pyrimidin-2-ylamino)benzamide | 464.1 | D |
| 329 | 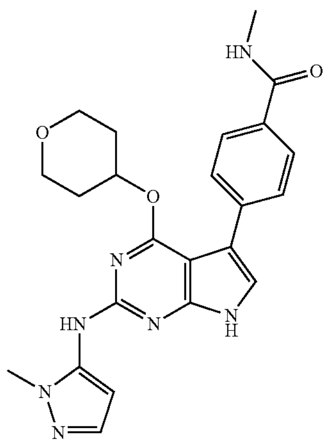 [SMILES: CNC(=O)c1ccc(-c2c[nH]c3nc(Nc4ccnn4C)nc(OC4CCOCC4)c23)cc1] | N-methyl-4-(2-(1-methyl-1H-pyrazol-5-ylamino)-4-(tetrahydro-2H-pyran-4-yloxy)-7H-pyrrolo[2,3-d]pyrimidin-5-yl)benzamide | 448.3 | B |
| 330 | 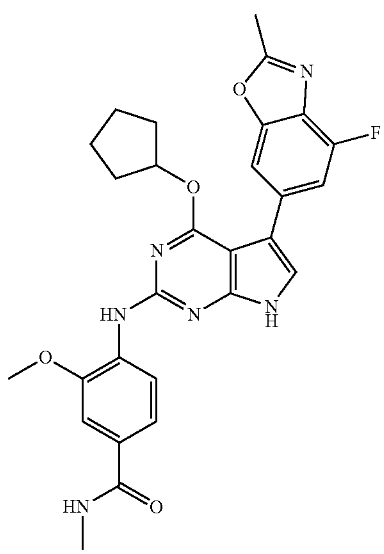 [SMILES: CNC(=O)c1ccc(Nc2nc(OC3CCCC3)c3c(-c4cc(F)c5nc(C)oc5c4)c[nH]c3n2)c(OC)c1] | 4-(4-(cyclopentyloxy)-5-(4-fluoro-2-methylbenzo[d]oxazol-6-yl)-7H-pyrrolo[2,3-d]pyrimidin-2-ylamino)-3-methoxy-N-methylbenzamide | 531.3 | C |

TABLE 1-continued
| Cmpd No. | Structure | Name | Obs. MH+ | Act. Level |
|---|---|---|---|---|
| 331 | 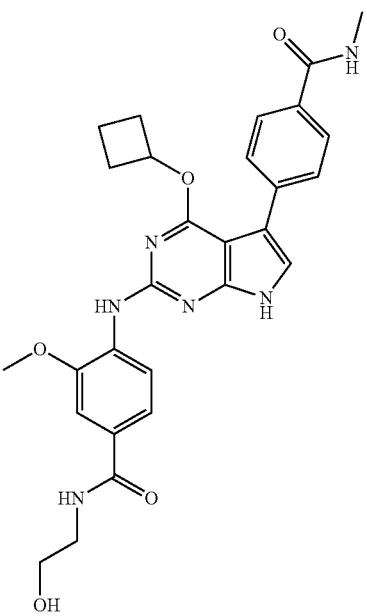 | 4-(4-cyclobutoxy-5-(4-(methylcarbamoyl)phenyl)-7H-pyrrolo[2,3-d]pyrimidin-2-ylamino)-N-(2-hydroxyethyl)-3-methoxybenzamide | 531.3 | C |
| 332 | 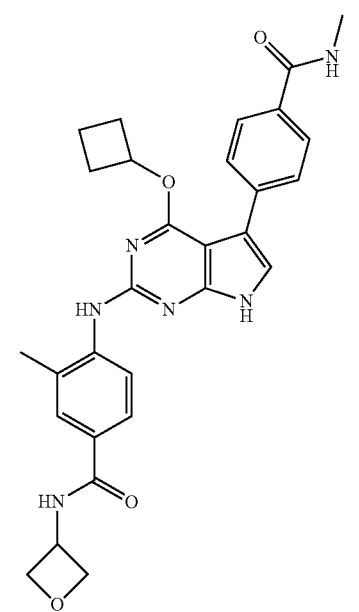 | 4-(4-cyclobutoxy-5-(4-(methylcarbamoyl)phenyl)-7H-pyrrolo[2,3-d]pyrimidin-2-ylamino)-3-methyl-N-(oxetan-3-yl)benzamide | 527.4 | D |

| Cmpd No. | Structure | Name | Obs. MH+ | Act. Level |
|---|---|---|---|---|
| 333 | 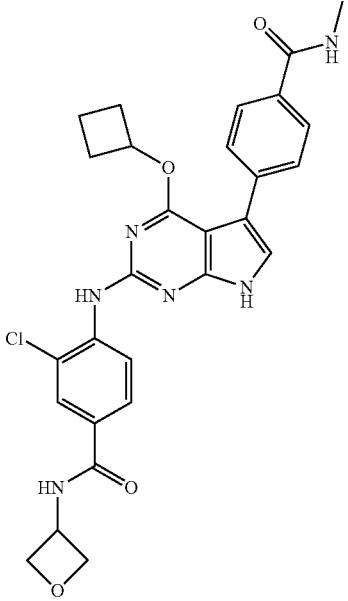 [SMILES: CNC(=O)c1ccc(-c2c[nH]c3nc(Nc4ccc(C(=O)NC5COC5)cc4Cl)nc(OC4CCC4)c23)cc1] | 3-chloro-4-(4-cyclobutoxy-5-(4-(methylcarbamoyl)phenyl)-7H-pyrrolo[2,3-d]pyrimidin-2-ylamino)-N-(oxetan-3-yl)benzamide | 547.2 | D |
| 334 | 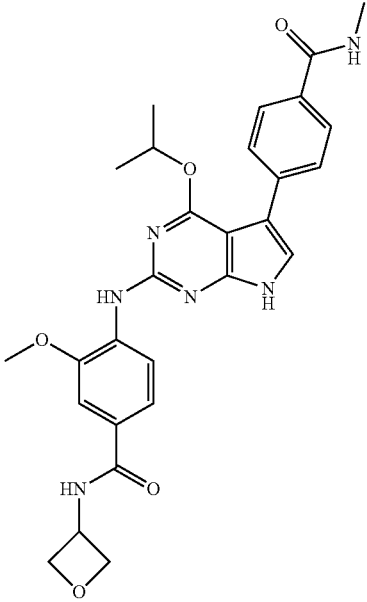 | 4-(4-isopropoxy-5-(4-(methylcarbamoyl)phenyl)-7H-pyrrolo[2,3-d]pyrimidin-2-ylamino)-3-methoxy-N-(oxetan-3-yl)benzamide | 531 | D |

TABLE 1-continued

| Cmpd No. | Structure | Name | Obs. MH+ | Act. Level |
|---|---|---|---|---|
| 335 | 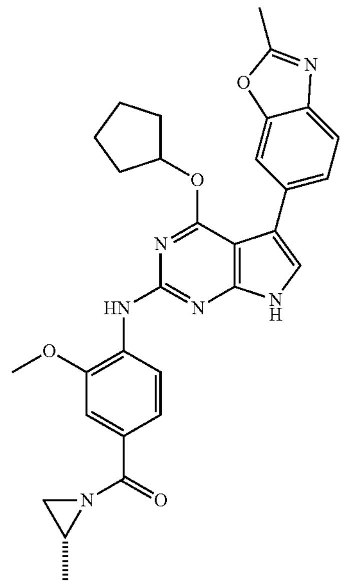 [SMILES: COc1cc(C(=O)N2C[C@H]2C)ccc1Nc1nc(OC2CCCC2)c2c(-c3ccc4nc(C)oc4c3)c[nH]c2n1] | (R)-(4-(4-(cyclopentyloxy)-5-(2-methylbenzo[d]oxazol-6-yl)-7H-pyrrolo[2,3-d]pyrimidin-2-ylamino)-3-methoxyphenyl)(2-methylaziridin-1-yl)methanone | 539.3 | B |
| 336 | 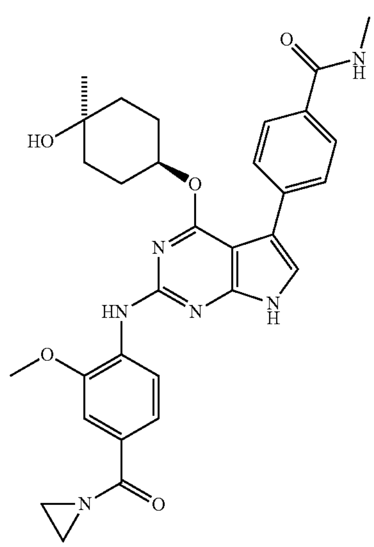 | 4-(2-(4-(aziridine-1-carbonyl)-2-methoxyphenylamino)-4-((1s,4s)-4-hydroxy-4-methylcyclohexyloxy)-7H-pyrrolo[2,3-d]pyrimidin-5-yl)-N-methylbenzamide | 571.3 | D |

TABLE 1-continued

| Cmpd No. | Structure | Name | Obs. MH+ | Act. Level |
|---|---|---|---|---|
| 337 | 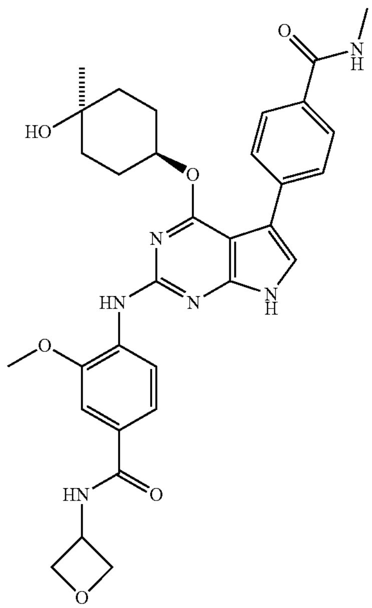 | 4-(4-((1s,4s)-4-hydroxy-4-methylcyclohexyloxy)-5-(4-(methylcarbamoyl)phenyl)-7H-pyrrolo[2,3-d]pyrimidin-2-ylamino)-3-methoxy-N-(oxetan-3-yl)benzamide | 601.4 | D |
| 338 | 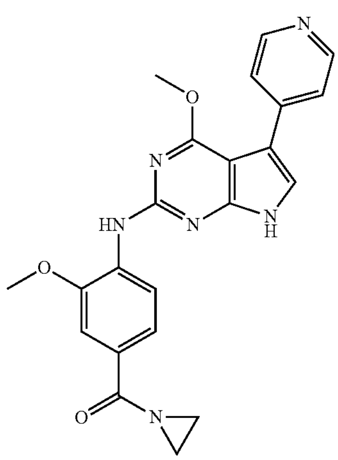 [SMILES: COc1cc(C(=O)N2CC2)ccc1Nc1nc(OC)c2c(-c3ccncc3)c[nH]c2n1] | aziridin-1-yl(3-methoxy-4-(4-methoxy-5-(pyridin-4-yl)-7H-pyrrolo[2,3-d]pyrimidin-2-ylamino)phenyl)methanone | 417.2 | B |

TABLE 1-continued
| Cmpd No. | Structure | Name | Obs. MH$^+$ | Act. Level |
|---|---|---|---|---|
| 339 | 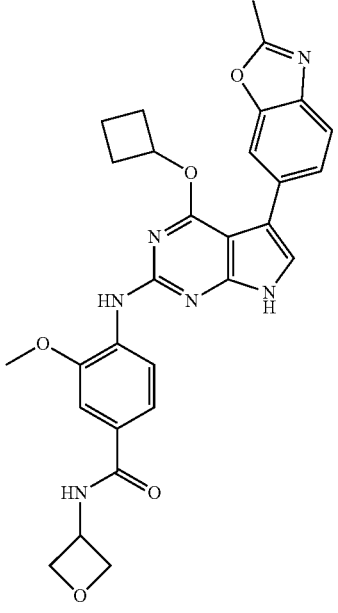 [SMILES: COc1cc(C(=O)NC2COC2)ccc1Nc1nc(OC2CCC2)c2c(-c3ccc4nc(C)oc4c3)c[nH]c2n1] | 4-(4-cyclobutoxy-5-(2-methylbenzo[d]oxazol-6-yl)-7H-pyrrolo[2,3-d]pyrimidin-2-ylamino)-3-methoxy-N-(oxetan-3-yl)benzamide | 541.3 | C |
| 340 | 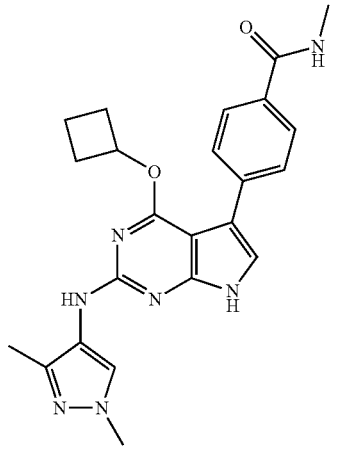 | 4-(4-cyclobutoxy-2-(1,3-dimethyl-1H-pyrazol-4-ylamino)-7H-pyrrolo[2,3-d]pyrimidin-5-yl)-N-methylbenzamide | 432.5 | D |

TABLE 1-continued

| Cmpd No. | Structure | Name | Obs. MH+ | Act. Level |
|---|---|---|---|---|
| 341 | 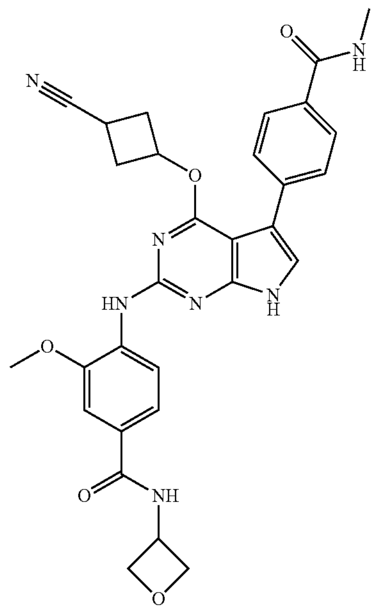 | 4-(4-(3-cyanocyclobutoxy)-5-(4-(methylcarbamoyl)phenyl)-7H-pyrrolo[2,3-d]pyrimidin-2-ylamino)-3-methoxy-N-(oxetan-3-yl)benzamide | 567.9 | D |
| 342 | 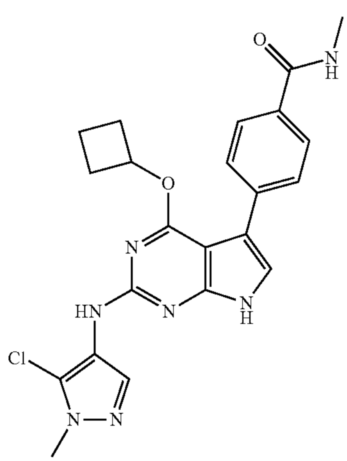 [SMILES: CNC(=O)c1ccc(-c2c[nH]c3nc(Nc4cnn(C)c4Cl)nc(OC4CCC4)c23)cc1] | 4-(2-(5-chloro-1-methyl-1H-pyrazol-4-ylamino)-4-cyclobutoxy-7H-pyrrolo[2,3-d]pyrimidin-5-yl)-N-methylbenzamide | 52.2 | |

TABLE 1-continued
| Cmpd No. | Structure | Name | Obs. MH+ | Act. Level |
|---|---|---|---|---|
| 343 | 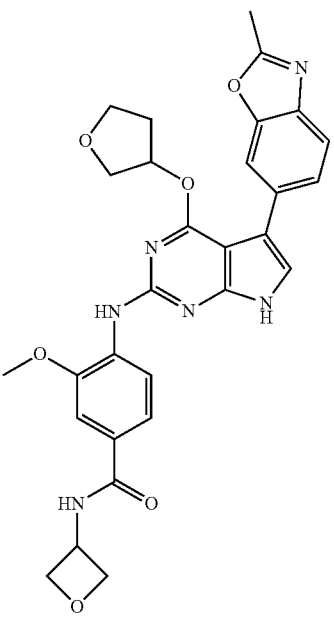 [SMILES: COc1cc(C(=O)NC2COC2)ccc1Nc1nc(OC2CCOC2)c2c(-c3ccc4nc(C)oc4c3)c[nH]c2n1] | (S)-3-methoxy-4-(5-(2-methylbenzo[d]oxazol-6-yl)-4-(tetrahydrofuran-3-yloxy)-7H-pyrrolo[2,3-d]pyrimidin-2-ylamino)-N-(oxetan-3-yl)benzamide | 557.1 | D |
| 344 | 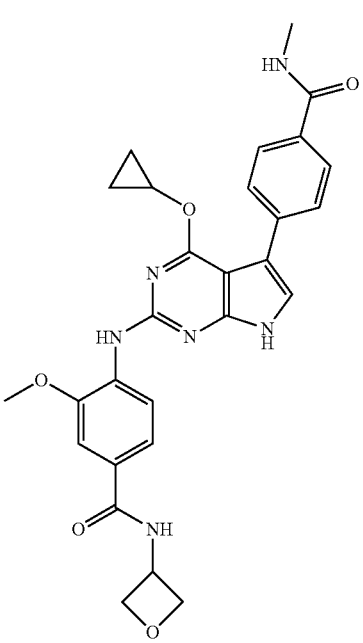 [SMILES: CNC(=O)c1ccc(-c2c[nH]c3nc(Nc4ccc(C(=O)NC5COC5)cc4OC)nc(OC4CC4)c23)cc1] | 4-(4-cyclopropoxy-5-(4-(methylcarbamoyl)phenyl)-7H-pyrrolo[2,3-d]pyrimidin-2-ylamino)-3-methoxy-N-(oxetan-3-yl)benzamide | 529.1 | C |

TABLE 1-continued
| Cmpd No. | Structure | Name | Obs. MH+ | Act. Level |
|---|---|---|---|---|
| 345 | 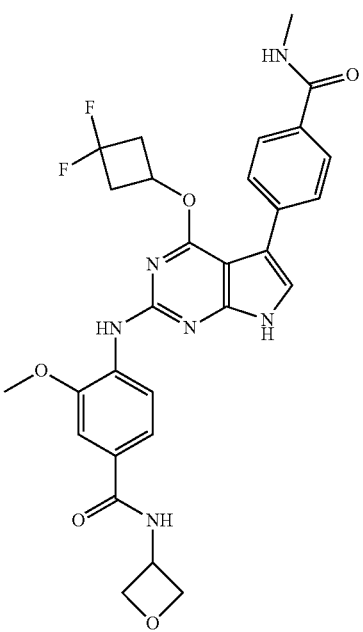 [SMILES: CNC(=O)c1ccc(-c2c[nH]c3nc(Nc4ccc(C(=O)NC5COC5)cc4OC)nc(OC4CC(F)(F)C4)c23)cc1] | 4-(4-(3,3-difluorocyclobutoxy)-5-(4-(methylcarbamoyl)phenyl)-7H-pyrrolo[2,3-d]pyrimidin-2-ylamino)-3-methoxy-N-(oxetan-3-yl)benzamide | 579 | D |
| 346 | 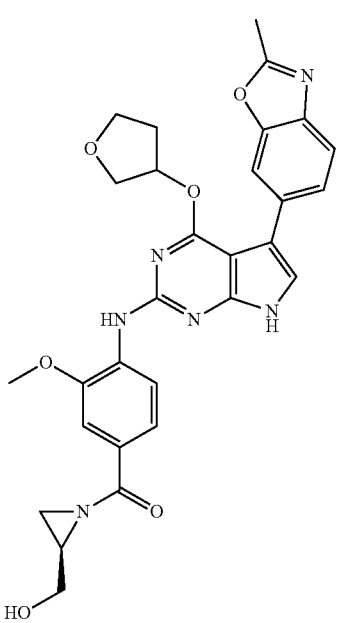 [SMILES: COc1cc(C(=O)N2C[C@@H]2CO)ccc1Nc1nc(OC2CCOC2)c2c(-c3ccc4nc(C)oc4c3)c[nH]c2n1] | (R)-(4-(4-(cyclopentyloxy)-5-(2-methylbenzo[d]oxazol-6-yl)-7H-pyrrolo[2,3-d]pyrimidin-2-ylamino)-3-methoxyphenyl)(2-(hydroxymethyl)aziridin-1-yl)methanone | 555.3 | C |

TABLE 1-continued

| Cmpd No. | Structure | Name | Obs. MH+ | Act. Level |
|---|---|---|---|---|
| 347 | 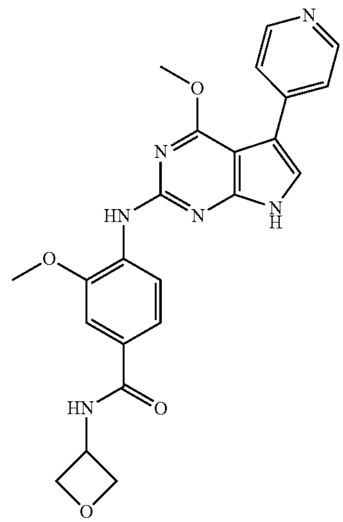 [SMILES: COc1cc(C(=O)NC2COC2)ccc1Nc1nc(OC)c2c(-c3ccncc3)c[nH]c2n1] | 3-methoxy-4-(4-methoxy-5-(pyridin-4-yl)-7H-pyrrolo[2,3-d]pyrimidin-2-ylamino)-N-(oxetan-3-yl)benzamide | 447.2 | C |
| 348 | 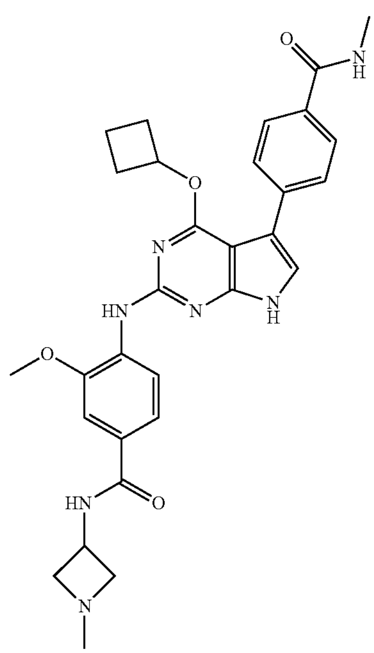 | 4-(4-cyclobutoxy-5-(4-(methylcarbamoyl)phenyl)-7H-pyrrolo[2,3-d]pyrimidin-2-ylamino)-3-methoxy-N-(1-methylazetidin-3-yl)benzamide | 556.3 | C |

TABLE 1-continued

| Cmpd No. | Structure | Name | Obs. MH+ | Act. Level |
|---|---|---|---|---|
| 349 | 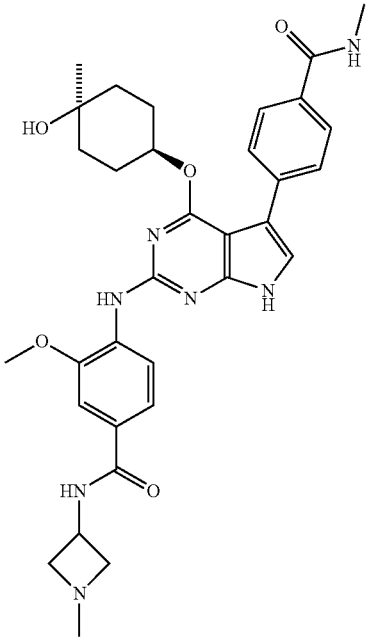 | 4-(4-((1s,4s)-4-hydroxy-4-methylcyclohexyloxy)-5-(4-(methylcarbamoyl)phenyl)-7H-pyrrolo[2,3-d]pyrimidin-2-ylamino)-3-methoxy-N-(1-methylazetidin-3-yl)benzamide | 614.4 | C |
| 350 | 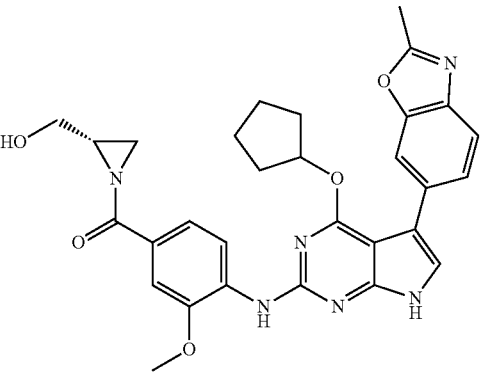 [SMILES: COc1cc(C(=O)N2C[C@H]2CO)ccc1Nc1nc(OC2CCCC2)c2c(-c3ccc4nc(C)oc4c3)c[nH]c2n1] | (S)-(4-(4-(cyclopentyloxy)-5-(2-methylbenzo[d]oxazol-6-yl)-7H-pyrrolo[2,3-d]pyrimidin-2-ylamino)-3-methoxyphenyl)(2-(hydroxymethyl)aziridin-1-yl)methanone | 555.3 | C |
| 351 | 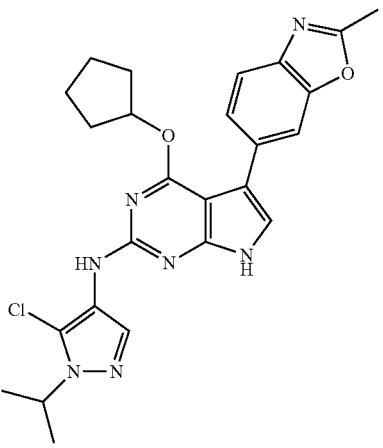 [SMILES: Cc1nc2ccc(-c3c[nH]c4nc(Nc5cnn(C(C)C)c5Cl)nc(OC5CCCC5)c34)cc2o1] | N-(5-chloro-1-isopropyl-1H-pyrazol-4-yl)-4-(cyclopentyloxy)-5-(2-methylbenzo[d]oxazol-6-yl)-7H-pyrrolo[2,3-d]pyrimidin-2-amine | 492.2 | C |

TABLE 1-continued

| Cmpd No. | Structure | Name | Obs. MH+ | Act. Level |
|---|---|---|---|---|
| 352 | 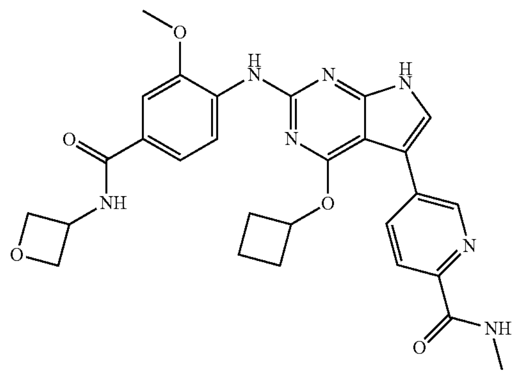 [SMILES: CNC(=O)c1ccc(-c2c[nH]c3nc(Nc4ccc(C(=O)NC5COC5)cc4OC)nc(OC4CCC4)c23)cn1] | 5-(4-cyclobutoxy-2-(2-methoxy-4-(oxetan-3-ylcarbamoyl)phenylamino)-7H-pyrrolo[2,3-d]pyrimidin-5-yl)-N-methylpicolinamide | 544.3 | A |
| 353 | 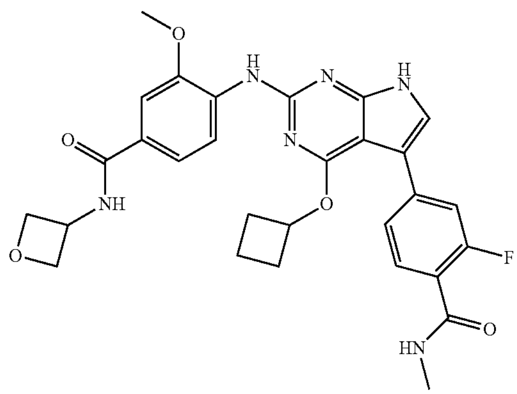 [SMILES: CNC(=O)c1ccc(-c2c[nH]c3nc(Nc4ccc(C(=O)NC5COC5)cc4OC)nc(OC4CCC4)c23)cc1F] | 4-(4-cyclobutoxy-2-(2-methoxy-4-(oxetan-3-ylcarbamoyl)phenylamino)-7H-pyrrolo[2,3-d]pyrimidin-5-yl)-2-fluoro-N-methylbenzamide | 561.3 | A |
| 354 | 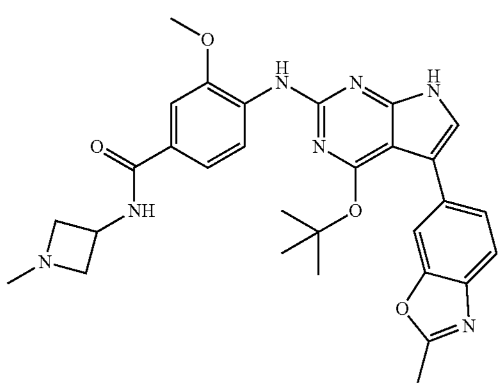 [SMILES: COc1cc(C(=O)NC2CN(C)C2)ccc1Nc1nc(OC(C)(C)C)c2c(-c3ccc4nc(C)oc4c3)c[nH]c2n1] | 4-(4-tert-butoxy-5-(2-methylbenzo[d]oxazol-6-yl)-7H-pyrrolo[2,3-d]pyrimidin-2-ylamino)-3-methoxy-N-(1-methylazetidin-3-yl)benzamide | 556.3 | D |
| 355 | 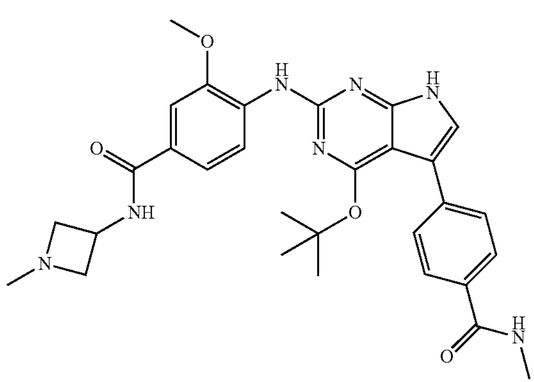 | 4-(4-tert-butoxy-5-(4-(methylcarbamoyl)phenyl)-7H-pyrrolo[2,3-d]pyrimidin-2-ylamino)-3-methoxy-N-(1-methylazetidin-3-yl)benzamide | 558.4 | D |

TABLE 1-continued

| Cmpd No. | Structure | Name | Obs. MH+ | Act. Level |
|---|---|---|---|---|
| 356 | 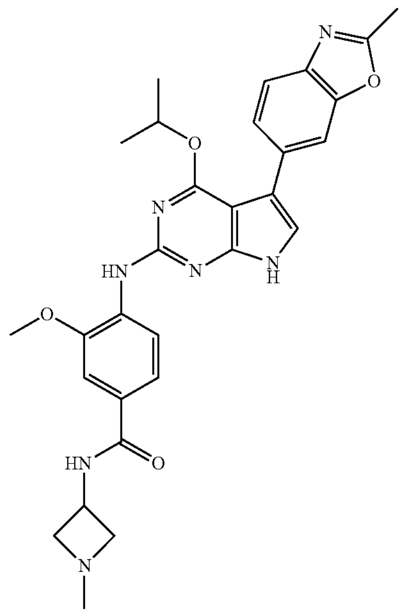 | 4-(4-isopropoxy-5-(2-methylbenzo[d]oxazol-6-yl)-7H-pyrrolo[2,3-d]pyrimidin-2-ylamino)-3-methoxy-N-(1-methylazetidin-3-yl)benzamide | 542.3 | D |
| 357 | 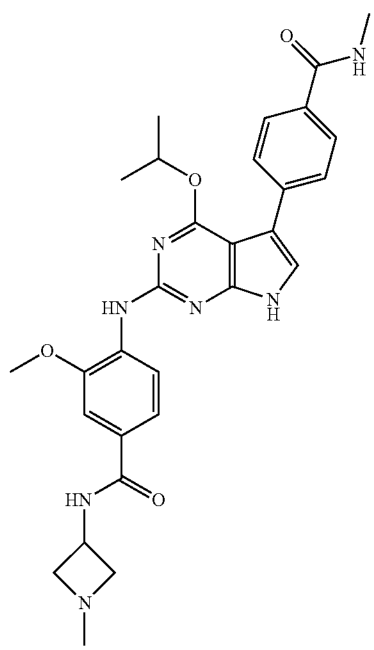 | 4-(4-isopropoxy-5-(4-(methylcarbamoyl)phenyl)-7H-pyrrolo[2,3-d]pyrimidin-2-ylamino)-3-methoxy-N-(1-methylazetidin-3-yl)benzamide | 544.3 | D |

TABLE 1-continued

| Cmpd No. | Structure | Name | Obs. MH+ | Act. Level |
|---|---|---|---|---|
| 358 | 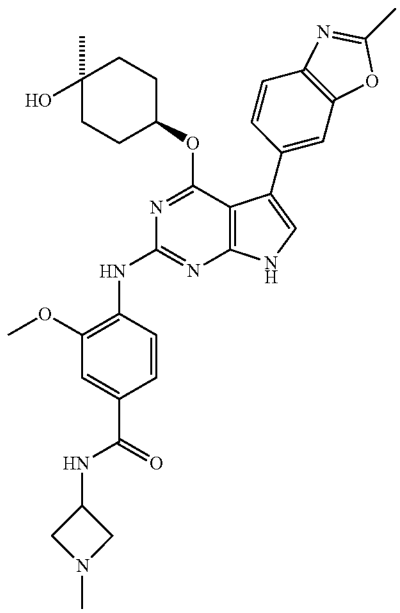 | 4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-3-methoxy-N-(1-methylazetidin-3-yl)benzamide | 612.4 | C |
| 359 | 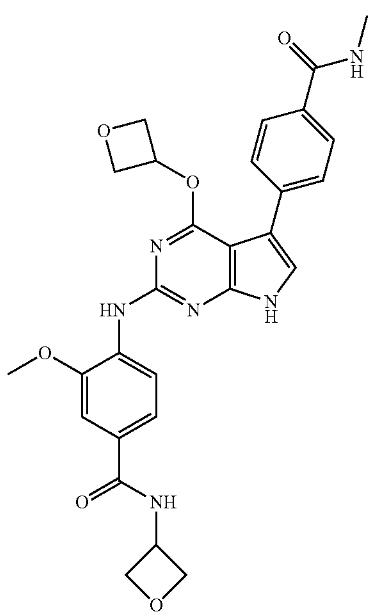 | 3-methoxy-4-(5-(4-(methylcarbamoyl)phenyl)-4-(oxetan-3-yloxy)-7H-pyrrolo[2,3-d]pyrimidin-2-ylamino)-N-(oxetan-3-yl)benzamide | 545.3 | C |

TABLE 1-continued

| Cmpd No. | Structure | Name | Obs. MH+ | Act. Level |
|---|---|---|---|---|
| 360 | 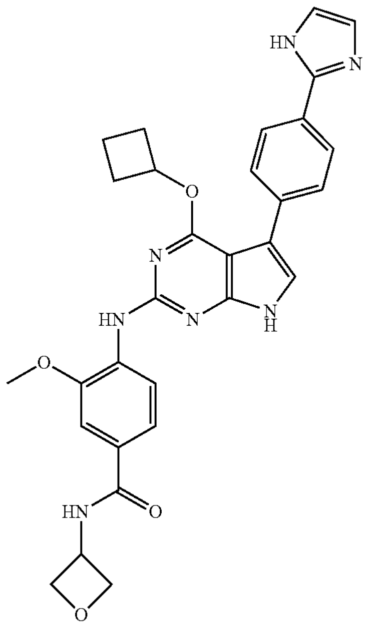 [SMILES: COc1cc(C(=O)NC2COC2)ccc1Nc1nc(OC2CCC2)c2c(-c3ccc(-c4ncc[nH]4)cc3)c[nH]c2n1] | 4-(5-(4-(1H-imidazol-2-yl)phenyl)-4-cyclobutoxy-7H-pyrrolo[2,3-d]pyrimidin-2-ylamino)-3-methoxy-N-(oxetan-3-yl)benzamide | 552.3 | D |
| 361 | 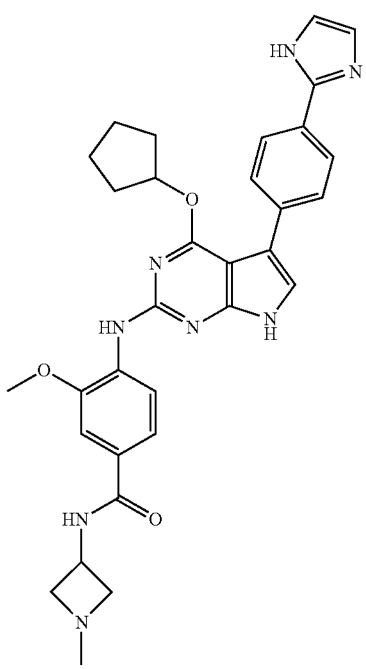 [SMILES: COc1cc(C(=O)NC2CN(C)C2)ccc1Nc1nc(OC2CCCC2)c2c(-c3ccc(-c4ncc[nH]4)cc3)c[nH]c2n1] | 4-(5-(4-(1H-imidazol-2-yl)phenyl)-4-(cyclopentyloxy)-7H-pyrrolo[2,3-d]pyrimidin-2-ylamino)-3-methoxy-N-(1-methylazetidin-3-yl)benzamide | 579.4 | C |

TABLE 1-continued

| Cmpd No. | Structure | Name | Obs. MH+ | Act. Level |
|---|---|---|---|---|
| 362 | 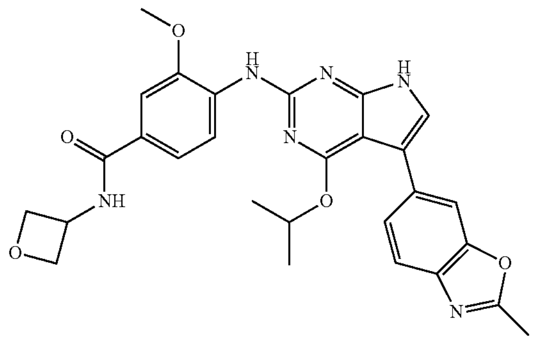 [SMILES: COc1cc(C(=O)NC2COC2)ccc1Nc1nc(OC(C)C)c2c(-c3ccc4nc(C)oc4c3)c[nH]c2n1] | 4-(4-isopropoxy-5-(2-methylbenzo[d]oxazol-6-yl)-7H-pyrrolo[2,3-d]pyrimidin-2-ylamino)-3-methoxy-N-(oxetan-3-yl)benzamide | 529.3 | C |
| 363 | 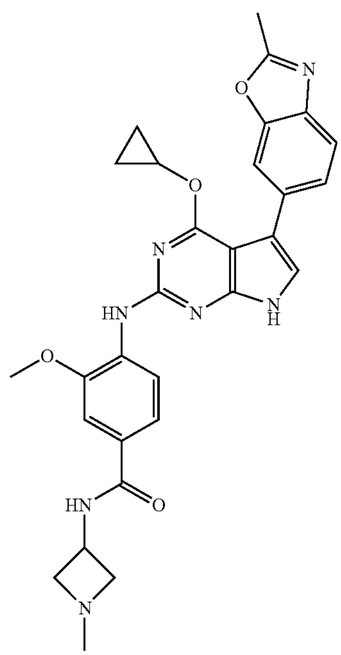 [SMILES: COc1cc(C(=O)NC2CN(C)C2)ccc1Nc1nc(OC2CC2)c2c(-c3ccc4nc(C)oc4c3)c[nH]c2n1] | 4-(4-cyclopropoxy-5-(2-methylbenzo[d]oxazol-6-yl)-7H-pyrrolo[2,3-d]pyrimidin-2-ylamino)-3-methoxy-N-(1-methylazetidin-3-yl)benzamide | 540.3 | D |

TABLE 1-continued
| Cmpd No. | Structure | Name | Obs. MH+ | Act. Level |
|---|---|---|---|---|
| 364 | 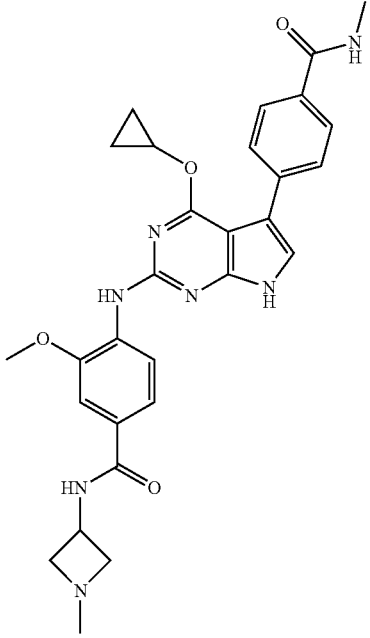 | 4-(4-cyclopropoxy-5-(4-(methylcarbamoyl)phenyl)-7H-pyrrolo[2,3-d]pyrimidin-2-ylamino)-3-methoxy-N-(1-methylazetidin-3-yl)benzamide | 542.3 | C |
| 365 | 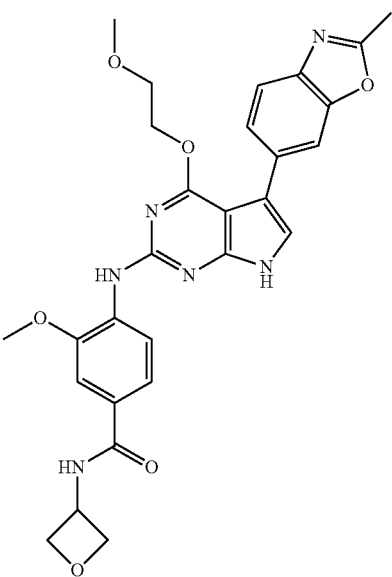 | 3-methoxy-4-(4-(2-methoxyethoxy)-5-(2-methylbenzo[d]oxazol-6-yl)-7H-pyrrolo[2,3-d]pyrimidin-2-ylamino)-N-(oxetan-3-yl)benzamide | 545.3 | D |

TABLE 1-continued

| Cmpd No. | Structure | Name | Obs. MH+ | Act. Level |
|---|---|---|---|---|
| 366 | 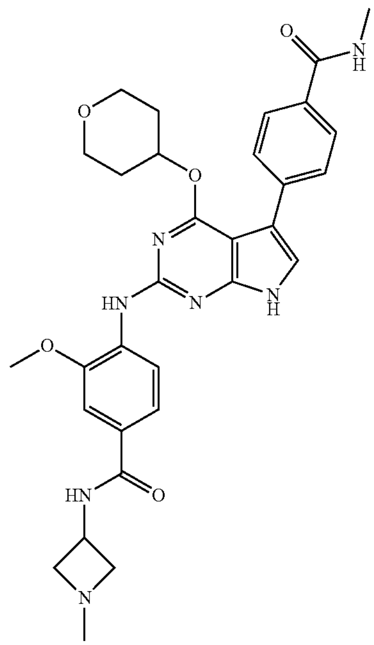 | 3-methoxy-N-(1-methyl-azetidin-3-yl)-4-(5-(4-(methylcarbamoyl)phenyl)-4-(tetrahydro-2H-pyran-4-yloxy)-7H-pyrrolo[2,3-d]pyrimidin-2-ylamino)benzamide | 586.4 | C |
| 367 | 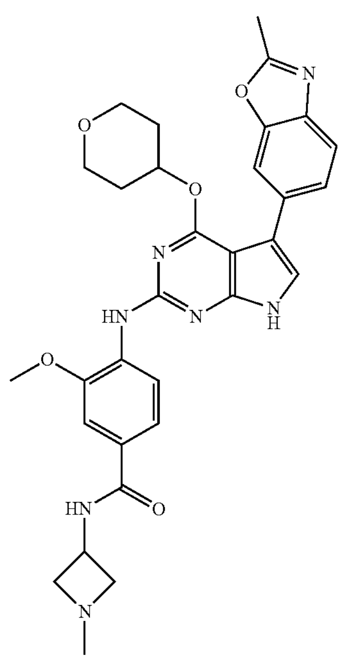 [SMILES: COc1cc(C(=O)NC2CN(C)C2)ccc1Nc1nc(OC2CCOCC2)c2c(-c3ccc4nc(C)oc4c3)c[nH]c2n1] | 3-methoxy-N-(1-methylazetidin-3-yl)-4-(5-(2-methylbenzo[d]oxazol-6-yl)-4-(tetrahydro-2H-pyran-4-yloxy)-7H-pyrrolo[2,3-d]pyrimidin-2-ylamino)benzamide | 584.4 | C |

TABLE 1-continued
| Cmpd No. | Structure | Name | Obs. MH+ | Act. Level |
|---|---|---|---|---|
| 368 | 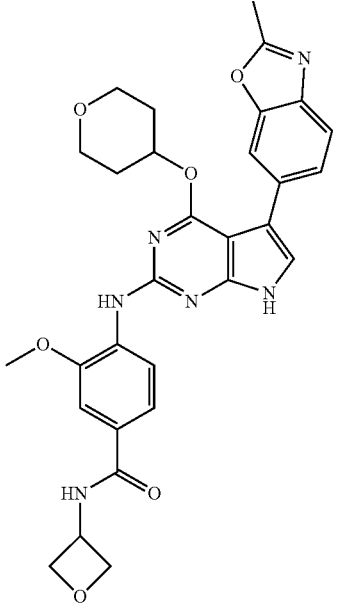 [SMILES: COc1cc(C(=O)NC2COC2)ccc1Nc1nc(OC2CCOCC2)c2c(-c3ccc4nc(C)oc4c3)c[nH]c2n1] | 3-methoxy-4-(5-(2-methylbenzo[d]oxazol-6-yl)-4-(tetrahydro-2H-pyran-4-yloxy)-7H-pyrrolo[2,3-d]pyrimidin-2-ylamino)-N-(oxetan-3-yl)benzamide | 571.3 | D |
| 369 | 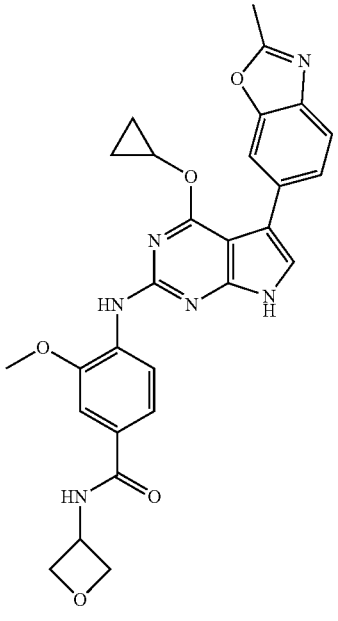 [SMILES: COc1cc(C(=O)NC2COC2)ccc1Nc1nc(OC2CC2)c2c(-c3ccc4nc(C)oc4c3)c[nH]c2n1] | 4-(4-cyclopropoxy-5-(2-methylbenzo[d]oxazol-6-yl)-7H-pyrrolo[2,3-d]pyrimidin-2-ylamino)-3-methoxy-N-(oxetan-3-yl)benzamide | 527.3 | C |

TABLE 1-continued

| Cmpd No. | Structure | Name | Obs. MH+ | Act. Level |
|---|---|---|---|---|
| 370 | 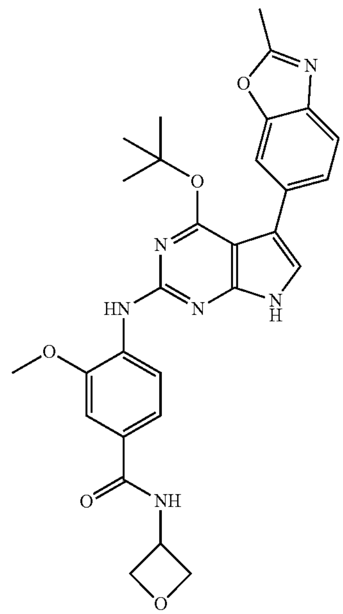 [SMILES: COc1cc(C(=O)NC2COC2)ccc1Nc1nc(OC(C)(C)C)c2c(-c3ccc4nc(C)oc4c3)c[nH]c2n1] | 4-(4-tert-butoxy-5-(2-methylbenzo[d]oxazol-6-yl)-7H-pyrrolo[2,3-d]pyrimidin-2-ylamino)-3-methoxy-N-(oxetan-3-yl)benzamide | 543.3 | D |
| 371 | 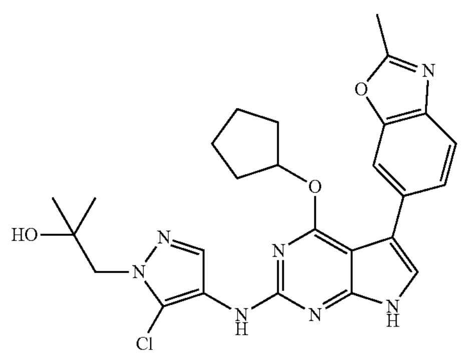 [SMILES: Cc1nc2ccc(-c3c[nH]c4nc(Nc5cnn(CC(C)(C)O)c5Cl)nc(OC5CCCC5)c34)cc2o1] | 1-(5-chloro-4-(4-(cyclopentyloxy)-5-(2-methylbenzo[d]oxazol-6-yl)-7H-pyrrolo[2,3-d]pyrimidin-2-ylamino)-1H-pyrazol-1-yl)-2-methylpropan-2-ol | 522.3 | D |
| 372 | 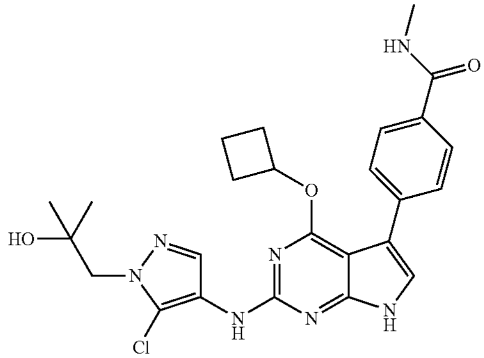 [SMILES: CNC(=O)c1ccc(-c2c[nH]c3nc(Nc4cnn(CC(C)(C)O)c4Cl)nc(OC4CCC4)c23)cc1] | 4-(2-(5-chloro-1-(2-hydroxy-2-methylpropyl)-1H-pyrazol-4-ylamino)-4-cyclobutoxy-7H-pyrrolo[2,3-d]pyrimidin-5-yl)-N-methylbenzamide | 510.3 | D |

TABLE 1-continued

| Cmpd No. | Structure | Name | Obs. MH+ | Act. Level |
|---|---|---|---|---|
| 373 | 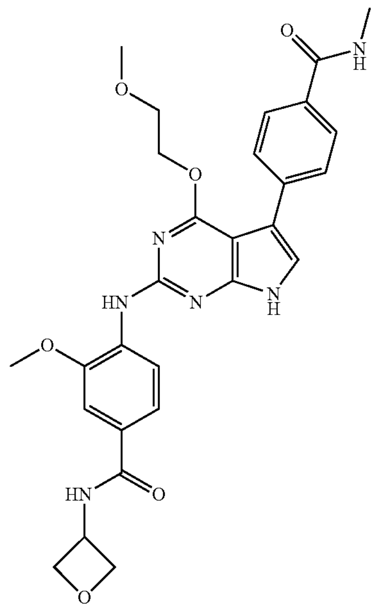 | 3-methoxy-4-(4-(2-methoxyethoxy)-5-(4-(methylcarbamoyl)phenyl)-7H-pyrrolo[2,3-d]pyrimidin-2-ylamino)-N-(oxetan-3-yl)benzamide | 547.3 | C |
| 374 | 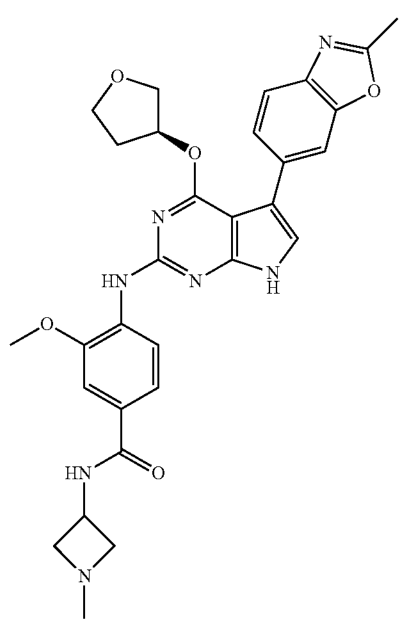 | (S)-3-methoxy-N-(1-methylazetidin-3-yl)-4-(5-(2-methylbenzo[d]oxazol-6-yl)-4-(tetrahydrofuran-3-yloxy)-7H-pyrrolo[2,3-d]pyrimidin-2-ylamino)benzamide | 570.3 | D |

TABLE 1-continued

| Cmpd No. | Structure | Name | Obs. MH+ | Act. Level |
|---|---|---|---|---|
| 375 | 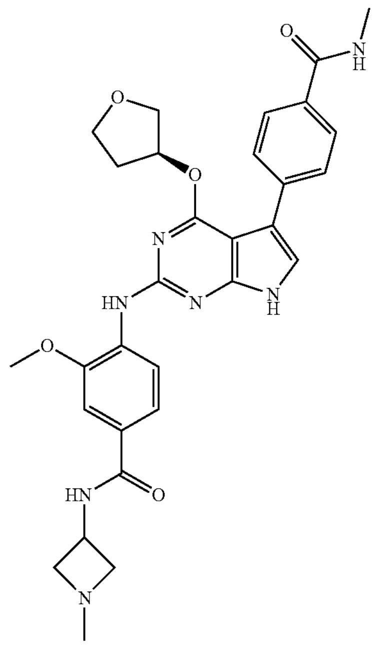 | (S)-3-methoxy-N-(1-methylazetidin-3-yl)-4-(5-(4-(methylcarbamoyl)phenyl)-4-(tetrahydrofuran-3-yloxy)-7H-pyrrolo[2,3-d]pyrimidin-2-ylamino)benzamide | 572.3 | B |
| 376 | 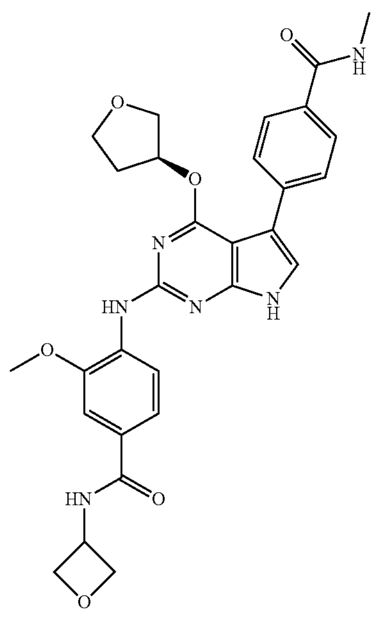 | (S)-3-methoxy-4-(5-(4-(methylcarbamoyl)phenyl)-4-(tetrahydrofuran-3-yloxy)-7H-pyrrolo[2,3-d]pyrimidin-2-ylamino)-N-(oxetan-3-yl)benzamide | 559.3 | D |
| 377 | 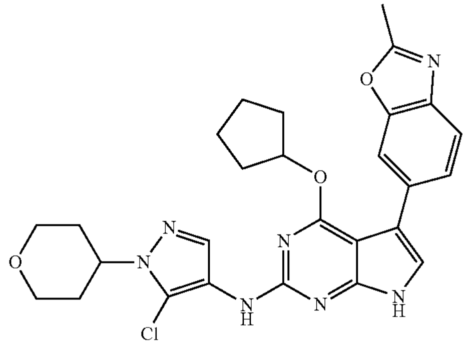 [SMILES: Cc1nc2ccc(-c3c[nH]c4nc(Nc5cnn(C6CCOCC6)c5Cl)nc(OC5CCCC5)c34)cc2o1] | N-(5-chloro-1-(tetrahydro-2H-pyran-4-yl)-1H-pyrazol-4-yl)-4-(cyclopentyloxy)-5-(2-methylbenzo[d]oxazol-6-yl)-7H-pyrrolo[2,3-d]pyrimidin-2-amine | 534.3 | D |

TABLE 1-continued

| Cmpd No. | Structure | Name | Obs. MH+ | Act. Level |
|---|---|---|---|---|
| 378 | 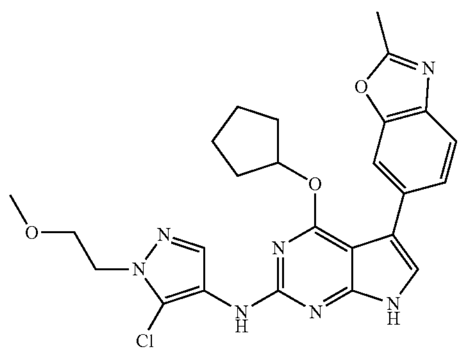 [SMILES: COCCn1ncc(Nc2nc(OC3CCCC3)c3c(-c4ccc5nc(C)oc5c4)c[nH]c3n2)c1Cl] | N-(5-chloro-1-(2-methoxyethyl)-1H-pyrazol-4-yl)-4-(cyclopentyloxy)-5-(2-methylbenzo[d]oxazol-6-yl)-7H-pyrrolo[2,3-d]pyrimidin-2-amine | 508.2 | D |
| 379 | 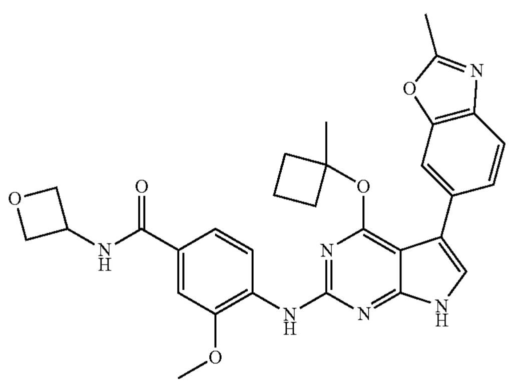 [SMILES: COc1cc(C(=O)NC2COC2)ccc1Nc1nc(OC2(C)CCC2)c2c(-c3ccc4nc(C)oc4c3)c[nH]c2n1] | 3-methoxy-4-(5-(2-methylbenzo[d]oxazol-6-yl)-4-(1-methylcyclobutoxy)-7H-pyrrolo[2,3-d]pyrimidin-2-ylamino)-N-(oxetan-3-yl)benzamide | 555.3 | D |
| 380 | 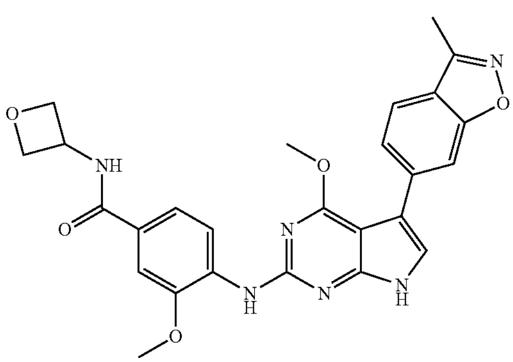 [SMILES: COc1cc(C(=O)NC2COC2)ccc1Nc1nc(OC)c2c(-c3ccc4c(C)noc4c3)c[nH]c2n1] | 3-methoxy-4-(4-methoxy-5-(3-methylbenzo[d]isoxazol-6-yl)-7H-pyrrolo[2,3-d]pyrimidin-2-ylamino)-N-(oxetan-3-yl)benzamide | 501.2 | C |
| 381 | 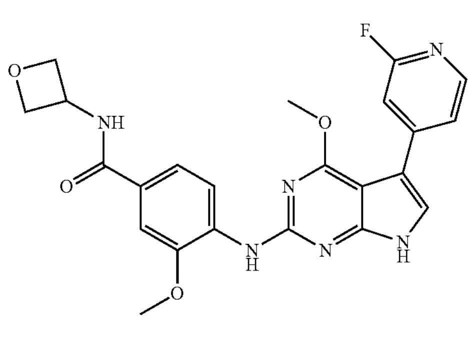 | 4-(5-(2-fluoropyridin-4-yl)-4-methoxy-7H-pyrrolo[2,3-d]pyrimidin-2-ylamino)-3-methoxy-N-(oxetan-3-yl)benzamide | 465.2 | C |

TABLE 1-continued

| Cmpd No. | Structure | Name | Obs. MH+ | Act. Level |
|---|---|---|---|---|
| 382 | 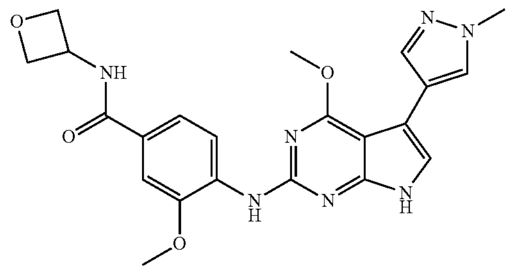 [SMILES: COc1cc(C(=O)NC2COC2)ccc1Nc1nc(OC)c2c(-c3cnn(C)c3)c[nH]c2n1] | 3-methoxy-4-(4-methoxy-5-(1-methyl-1H-pyrazol-4-yl)-7H-pyrrolo[2,3-d]pyrimidin-2-ylamino)-N-(oxetan-3-yl)benzamide | 450.2 | C |
| 383 | 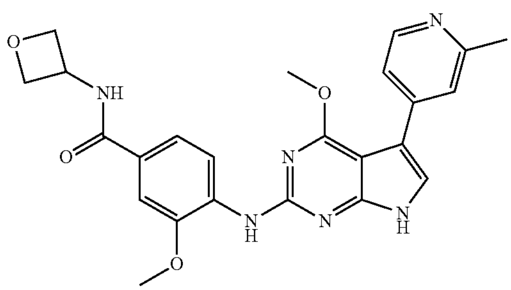 [SMILES: COc1cc(C(=O)NC2COC2)ccc1Nc1nc(OC)c2c(-c3ccnc(C)c3)c[nH]c2n1] | 3-methoxy-4-(4-methoxy-5-(2-methylpyridin-4-yl)-7H-pyrrolo[2,3-d]pyrimidin-2-ylamino)-N-(oxetan-3-yl)benzamide | 461.2 | D |
| 384 | 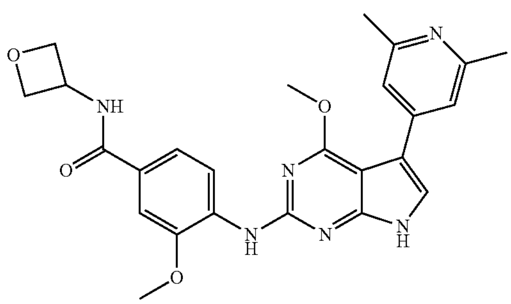 [SMILES: COc1cc(C(=O)NC2COC2)ccc1Nc1nc(OC)c2c(-c3cc(C)nc(C)c3)c[nH]c2n1] | 4-(5-(2,6-dimethylpyridin-4-yl)-4-methoxy-7H-pyrrolo[2,3-d]pyrimidin-2-ylamino)-3-methoxy-N-(oxetan-3-yl)benzamide | 475.2 | D |
| 385 | 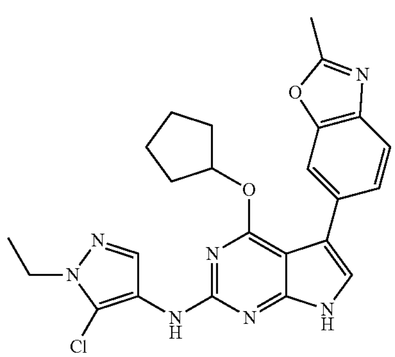 [SMILES: CCn1ncc(Nc2nc(OC3CCCC3)c3c(-c4ccc5nc(C)oc5c4)c[nH]c3n2)c1Cl] | N-(5-chloro-1-ethyl-1H-pyrazol-4-yl)-4-(cyclopentyloxy)-5-(2-methylbenzo[d]oxazol-6-yl)-7H-pyrrolo[2,3-d]pyrimidin-2-amine | 478.2 | C |

TABLE 1-continued

| Cmpd No. | Structure | Name | Obs. MH+ | Act. Level |
|---|---|---|---|---|
| 386 | 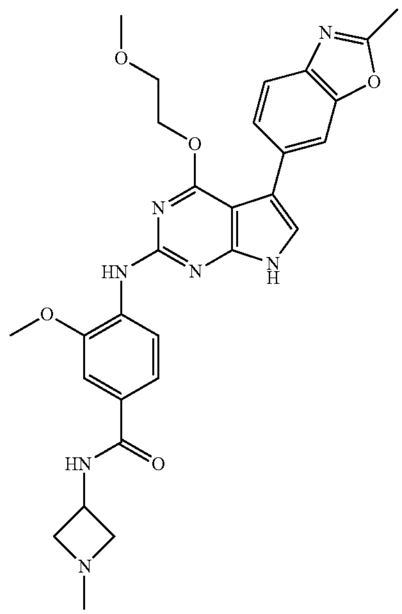 | 3-methoxy-4-(4-(2-methoxyethoxy)-5-(2-methylbenzo[d]oxazol-6-yl)-7H-pyrrolo[2,3-d]pyrimidin-2-ylamino)-N-(1-methylazetidin-3-yl)benzamide | 558.3 | A |
| 387 | 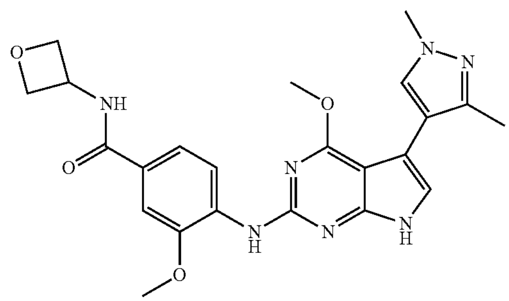 [SMILES: COc1cc(C(=O)NC2COC2)ccc1Nc1nc(OC)c2c(-c3cn(C)nc3C)c[nH]c2n1] | 4-(5-(1,3-dimethyl-1H-pyrazol-4-yl)-4-methoxy-7H-pyrrolo[2,3-d]pyrimidin-2-ylamino)-3-methoxy-N-(oxetan-3-yl)benzamide | 464.3 | A |
| 388 | 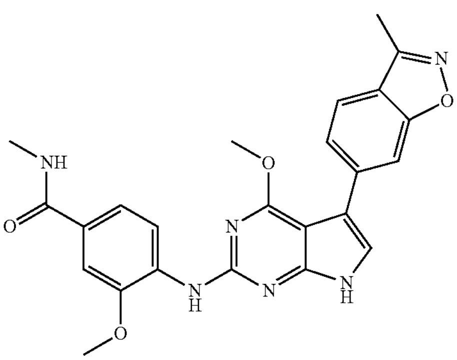 [SMILES: CNC(=O)c1ccc(Nc2nc(OC)c3c(-c4ccc5c(C)noc5c4)c[nH]c3n2)c(OC)c1] | 3-methoxy-4-(4-methoxy-5-(3-methylbenzo[d]isoxazol-6-yl)-7H-pyrrolo[2,3-d]pyrimidin-2-ylamino)-N-methylbenzamide | 457.2 | C |
| 389 | 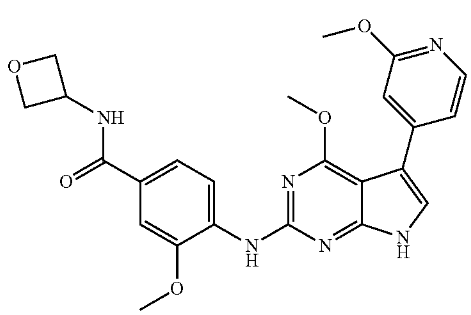 [SMILES: COc1cc(-c2c[nH]c3nc(Nc4ccc(C(=O)NC5COC5)cc4OC)nc(OC)c23)ccn1] | 3-methoxy-4-(4-methoxy-5-(2-methoxypyridin-4-yl)-7H-pyrrolo[2,3-d]pyrimidin-2-ylamino)-N-(oxetan-3-yl)benzamide | 477.3 | D |

TABLE 1-continued

| Cmpd No. | Structure | Name | Obs. MH+ | Act. Level |
|---|---|---|---|---|
| 390 | 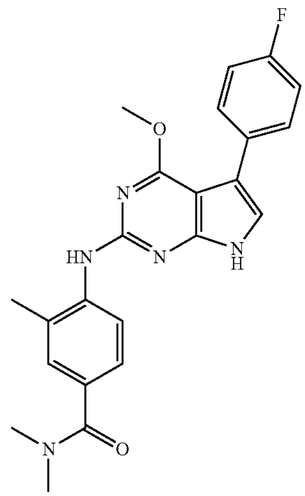 [SMILES: COc1nc(Nc2ccc(C(=O)N(C)C)cc2C)nc2[nH]cc(-c3ccc(F)cc3)c12] | 4-(5-(4-fluorophenyl)-4-methoxy-7H-pyrrolo[2,3-d]pyrimidin-2-ylamino)-N,N,3-trimethylbenzamide | 420.3 | A |
| 391 | 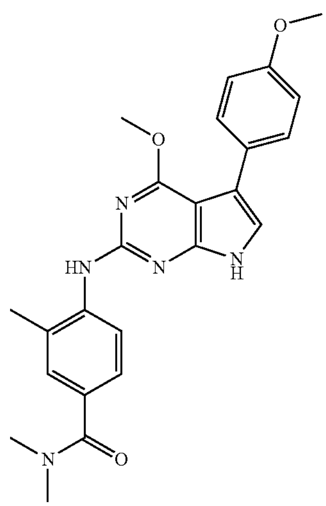 | 4-(4-methoxy-5-(4-methoxyphenyl)-7H-pyrrolo[2,3-d]pyrimidin-2-ylamino)-N,N,3-trimethylbenzamide | 432.2 | C |
| 392 | 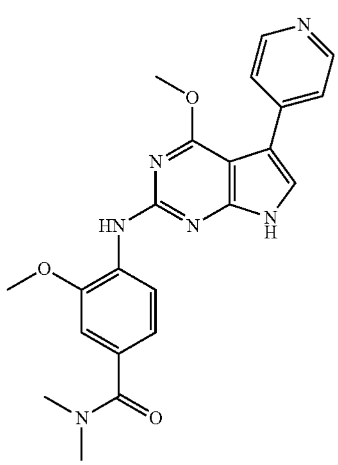 [SMILES: COc1cc(C(=O)N(C)C)ccc1Nc1nc(OC)c2c(-c3ccncc3)c[nH]c2n1] | 3-methoxy-4-(4-methoxy-5-(pyridin-4-yl)-7H-pyrrolo[2,3-d]pyrimidin-2-ylamino)-N,N-dimethylbenzamide | 419.1 | D |

TABLE 1-continued

| Cmpd No. | Structure | Name | Obs. MH+ | Act. Level |
|---|---|---|---|---|
| 393 | 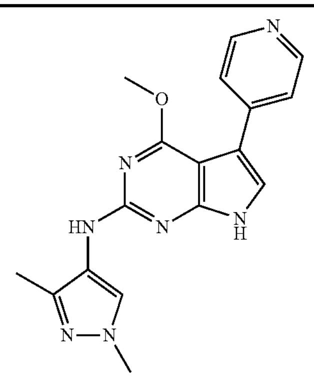 | N-(1,3-dimethyl-1H-pyrazol-4-yl)-4-methoxy-5-(pyridin-4-yl)-7H-pyrrolo[2,3-d]pyrimidin-2-amine | 336.1 | C |
| 394 | 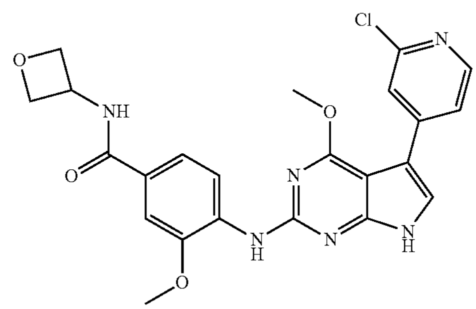 [SMILES: COc1cc(C(=O)NC2COC2)ccc1Nc1nc(OC)c2c(-c3ccnc(Cl)c3)c[nH]c2n1] | 4-(5-(2-chloropyridin-4-yl)-4-methoxy-7H-pyrrolo[2,3-d]pyrimidin-2-ylamino)-3-methoxy-N-(oxetan-3-yl)benzamide | 481.2 | C |
| 395 | 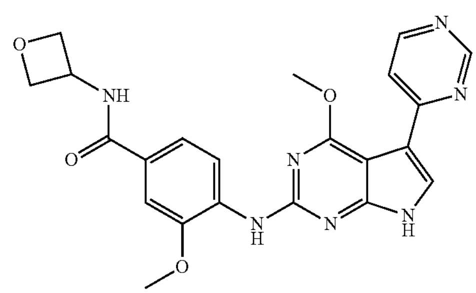 [SMILES: COc1cc(C(=O)NC2COC2)ccc1Nc1nc(OC)c2c(-c3ccncn3)c[nH]c2n1] | 3-methoxy-4-(4-methoxy-5-(pyrimidin-4-yl)-7H-pyrrolo[2,3-d]pyrimidin-2-ylamino)-N-(oxetan-3-yl)benzamide | 448.2 | A |
| 396 | 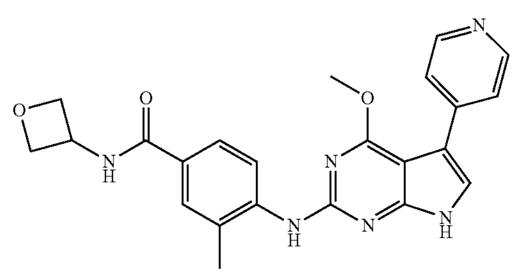 [SMILES: COc1nc(Nc2ccc(C(=O)NC3COC3)cc2C)nc2[nH]cc(-c3ccncc3)c12] | 4-(4-methoxy-5-(pyridin-4-yl)-7H-pyrrolo[2,3-d]pyrimidin-2-ylamino)-3-methyl-N-(oxetan-3-yl)benzamide | 431.2 | C |
| 397 | 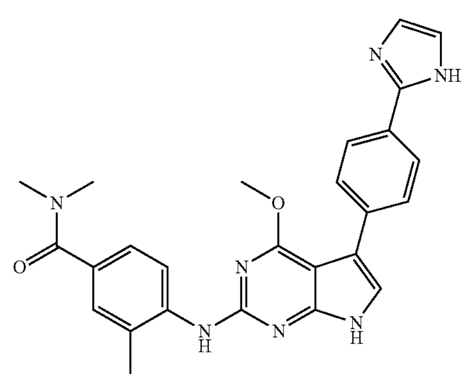 [SMILES: COc1nc(Nc2ccc(C(=O)N(C)C)cc2C)nc2[nH]cc(-c3ccc(-c4ncc[nH]4)cc3)c12] | 4-(5-(4-(1H-imidazol-2-yl)phenyl)-4-methoxy-7H-pyrrolo[2,3-d]pyrimidin-2-ylamino)-N,N,3-trimethylbenzamide | 468.3 | D |

TABLE 1-continued

| Cmpd No. | Structure | Name | Obs. MH+ | Act. Level |
|---|---|---|---|---|
| 398 | 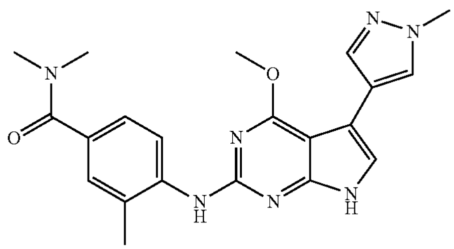 [SMILES: COc1nc(Nc2ccc(C(=O)N(C)C)cc2C)nc2[nH]cc(-c3cnn(C)c3)c12] | 4-(4-methoxy-5-(1-methyl-1H-pyrazol-4-yl)-7H-pyrrolo[2,3-d]pyrimidin-2-ylamino)-N,N,3-trimethylbenzamide | 406.2 | B |
| 399 | 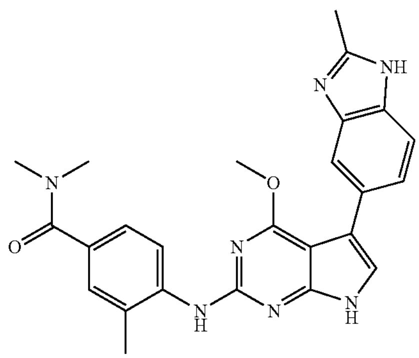 [SMILES: COc1nc(Nc2ccc(C(=O)N(C)C)cc2C)nc2[nH]cc(-c3ccc4[nH]c(C)nc4c3)c12] | 4-(4-methoxy-5-(2-methyl-1H-benzo[d]imidazol-5-yl)-7H-pyrrolo[2,3-d]pyrimidin-2-ylamino)-N,N,3-trimethylbenzamide | 456.3 | D |
| 400 | 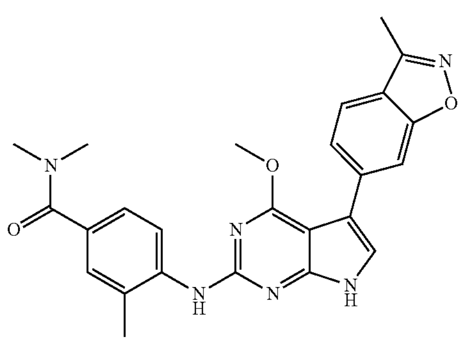 [SMILES: COc1nc(Nc2ccc(C(=O)N(C)C)cc2C)nc2[nH]cc(-c3ccc4c(C)noc4c3)c12] | 4-(4-methoxy-5-(3-methylbenzo[d]isoxazol-6-yl)-7H-pyrrolo[2,3-d]pyrimidin-2-ylamino)-N,N,3-trimethylbenzamide | 457.2 | D |
| 401 | 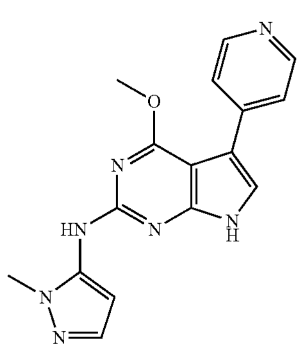 [SMILES: COc1nc(Nc2ccnn2C)nc2[nH]cc(-c3ccncc3)c12] | 4-methoxy-N-(1-methyl-1H-pyrazol-5-yl)-5-(pyridin-4-yl)-7H-pyrrolo[2,3-d]pyrimidin-2-amine | 322 | A |

TABLE 1-continued

| Cmpd No. | Structure | Name | Obs. MH+ | Act. Level |
|---|---|---|---|---|
| 402 | 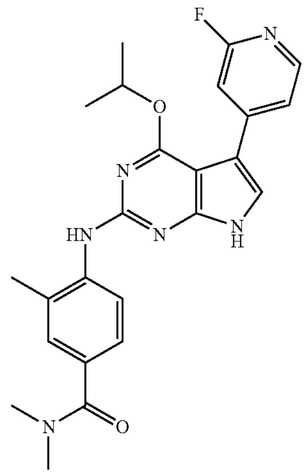 [SMILES: Cc1cc(C(=O)N(C)C)ccc1Nc1nc(OC(C)C)c2c(-c3ccnc(F)c3)c[nH]c2n1] | 4-(5-(2-fluoropyridin-4-yl)-4-isopropoxy-7H-pyrrolo[2,3-d]pyrimidin-2-ylamino)-N,N,3-trimethylbenzamide | 449.2 | D |
| 403 | 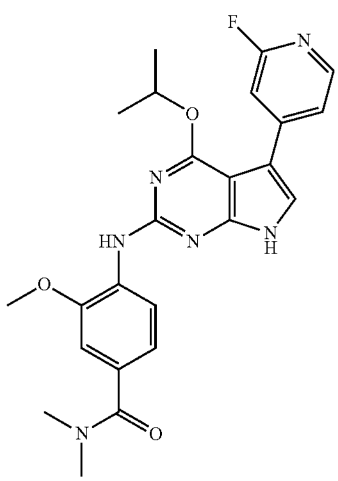 [SMILES: COc1cc(C(=O)N(C)C)ccc1Nc1nc(OC(C)C)c2c(-c3ccnc(F)c3)c[nH]c2n1] | 4-(5-(2-fluoropyridin-4-yl)-4-isopropoxy-7H-pyrrolo[2,3-d]pyrimidin-2-ylamino)-3-methoxy-N,N-dimethylbenzamide | 465.2 | D |
| 404 | 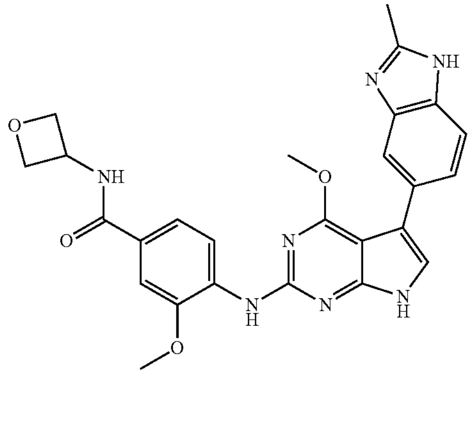 [SMILES: COc1cc(C(=O)NC2COC2)ccc1Nc1nc(OC)c2c(-c3ccc4[nH]c(C)nc4c3)c[nH]c2n1] | 3-methoxy-4-(4-methoxy-5-(2-methyl-1H-benzo[d]imidazol-5-yl)-7H-pyrrolo[2,3-d]pyrimidin-2-ylamino)-N-(oxetan-3-yl)benzamide | 500.2 | C |

TABLE 1-continued

| Cmpd No. | Structure | Name | Obs. MH+ | Act. Level |
|---|---|---|---|---|
| 405 | 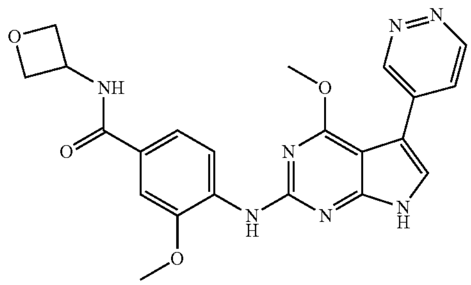 [SMILES: COc1cc(C(=O)NC2COC2)ccc1Nc1nc(OC)c2c(-c3ccnnc3)c[nH]c2n1] | 3-methoxy-4-(4-methoxy-5-(pyridazin-4-yl)-7H-pyrrolo[2,3-d]pyrimidin-2-ylamino)-N-(oxetan-3-yl)benzamide | 448.2 | B |
| 406 | 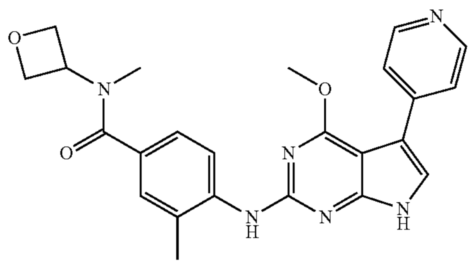 [SMILES: COc1nc(Nc2ccc(C(=O)N(C)C3COC3)cc2C)nc2[nH]cc(-c3ccncc3)c12] | 4-(4-methoxy-5-(pyridin-4-yl)-7H-pyrrolo[2,3-d]pyrimidin-2-ylamino)-N,3-dimethyl-N-(oxetan-3-yl)benzamide | 445.2 | C |
| 407 | 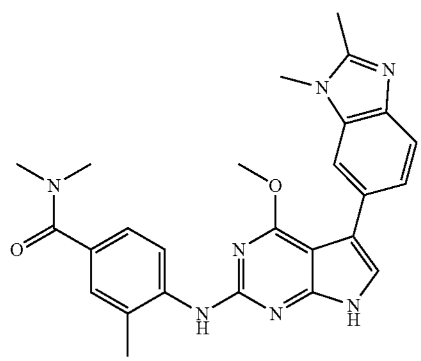 [SMILES: COc1nc(Nc2ccc(C(=O)N(C)C)cc2C)nc2[nH]cc(-c3ccc4nc(C)n(C)c4c3)c12] | 4-(5-(1,2-dimethyl-1H-benzo[d]imidazol-6-yl)-4-methoxy-7H-pyrrolo[2,3-d]pyrimidin-2-ylamino)-N,N,3-trimethylbenzamide | 470.3 | C |
| 408 | 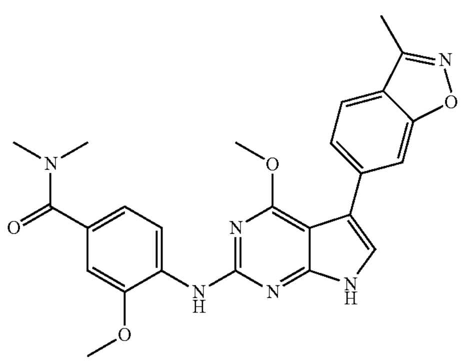 [SMILES: COc1cc(C(=O)N(C)C)ccc1Nc1nc(OC)c2c(-c3ccc4c(C)noc4c3)c[nH]c2n1] | 3-methoxy-4-(4-methoxy-5-(3-methylbenzo[d]isoxazol-6-yl)-7H-pyrrolo[2,3-d]pyrimidin-2-ylamino)-N,N-dimethylbenzamide | 473.2 | C |
| 409 | 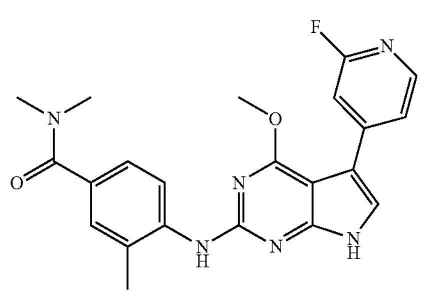 [SMILES: COc1nc(Nc2ccc(C(=O)N(C)C)cc2C)nc2[nH]cc(-c3ccnc(F)c3)c12] | 4-(5-(2-fluoropyridin-4-yl)-4-methoxy-7H-pyrrolo[2,3-d]pyrimidin-2-ylamino)-N,N,3-trimethylbenzamide | 421.2 | B |

TABLE 1-continued

| Cmpd No. | Structure | Name | Obs. MH+ | Act. Level |
|---|---|---|---|---|
| 410 | 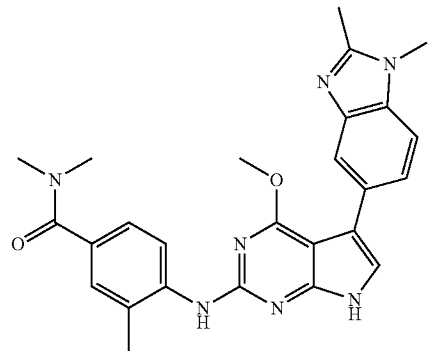 [SMILES: COc1nc(Nc2ccc(C(=O)N(C)C)cc2C)nc2[nH]cc(-c3ccc4c(c3)nc(C)n4C)c12] | 4-(5-(1,2-dimethyl-1H-benzo[d]imidazol-5-yl)-4-methoxy-7H-pyrrolo[2,3-d]pyrimidin-2-ylamino)-N,N,3-trimethylbenzamide | 470.3 | A |
| 411 | 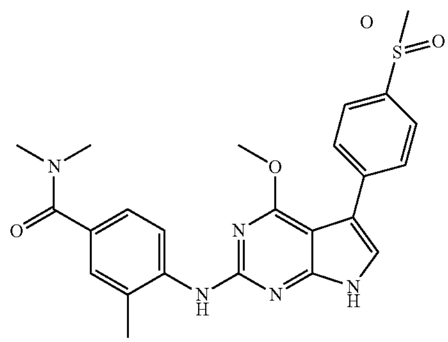 | 4-(4-methoxy-5-(4-(methylsulfonyl)phenyl)-7H-pyrrolo[2,3-d]pyrimidin-2-ylamino)-N,N,3-trimethylbenzamide | 480.2 | A |
| 412 | 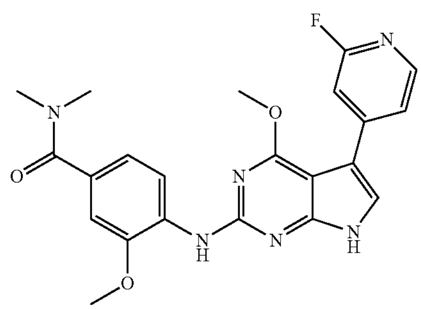 [SMILES: COc1cc(C(=O)N(C)C)ccc1Nc1nc(OC)c2c(-c3ccnc(F)c3)c[nH]c2n1] | 4-(5-(2-fluoropyridin-4-yl)-4-methoxy-7H-pyrrolo[2,3-d]pyrimidin-2-ylamino)-3-methoxy-N,N-dimethylbenzamide | 437.2 | B |
| 413 | 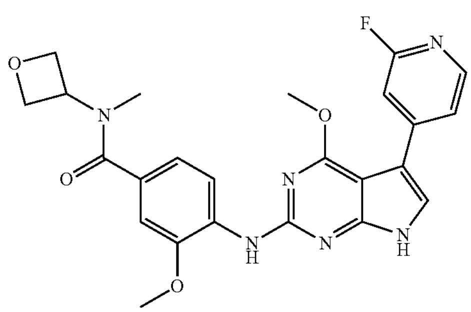 [SMILES: COc1cc(C(=O)N(C)C2COC2)ccc1Nc1nc(OC)c2c(-c3ccnc(F)c3)c[nH]c2n1] | 4-(5-(2-fluoropyridin-4-yl)-4-methoxy-7H-pyrrolo[2,3-d]pyrimidin-2-ylamino)-3-methoxy-N-methyl-N-(oxetan-3-yl)benzamide | 479.3 | C |
| 414 | 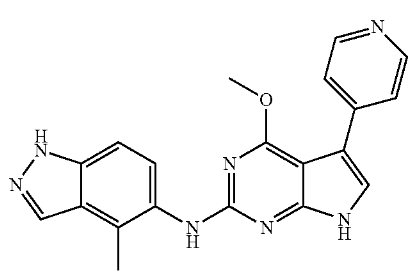 [SMILES: COc1nc(Nc2ccc3[nH]ncc3c2C)nc2[nH]cc(-c3ccncc3)c12] | 4-methoxy-N-(4-methyl-1H-indazol-5-yl)-5-(pyridin-4-yl)-7H-pyrrolo[2,3-d]pyrimidin-2-amine | 372.2 | A |

TABLE 1-continued

| Cmpd No. | Structure | Name | Obs. MH$^+$ | Act. Level |
|---|---|---|---|---|
| 415 | 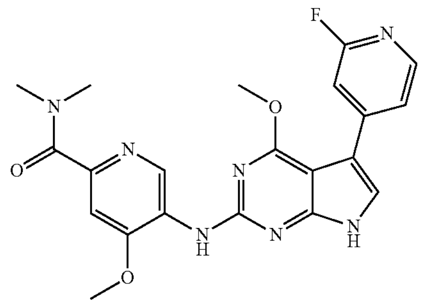 [SMILES: COc1cc(C(=O)N(C)C)ncc1Nc1nc(OC)c2c(-c3ccnc(F)c3)c[nH]c2n1] | 5-(5-(2-fluoropyridin-4-yl)-4-methoxy-7H-pyrrolo[2,3-d]pyrimidin-2-ylamino)-4-methoxy-N,N-dimethylpicolinamide | 438.2 | B |
| 416 | 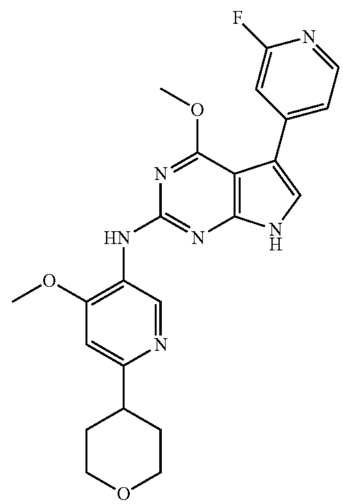 [SMILES: COc1cc(C2CCOCC2)ncc1Nc1nc(OC)c2c(-c3ccnc(F)c3)c[nH]c2n1] | 5-(2-fluoropyridin-4-yl)-4-methoxy-N-(4-methoxy-6-(tetrahydro-2H-pyran-4-yl)pyridin-3-yl)-7H-pyrrolo[2,3-d]pyrimidin-2-amine | 451.2 | A |
| 417 | 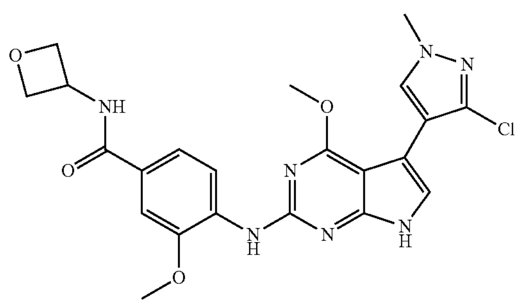 [SMILES: COc1cc(C(=O)NC2COC2)ccc1Nc1nc(OC)c2c(-c3cn(C)nc3Cl)c[nH]c2n1] | 4-(5-(3-chloro-1-methyl-1H-pyrazol-4-yl)-4-methoxy-7H-pyrrolo[2,3-d]pyrimidin-2-ylamino)-3-methoxy-N-(oxetan-3-yl)benzamide | 484.2 | A |
| 418 | 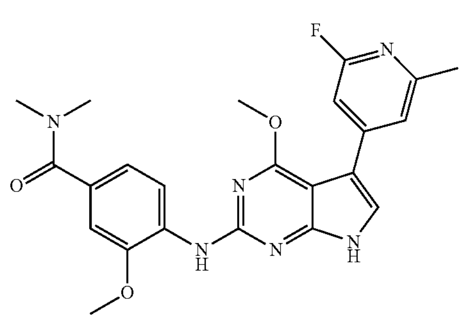 [SMILES: COc1cc(C(=O)N(C)C)ccc1Nc1nc(OC)c2c(-c3cc(C)nc(F)c3)c[nH]c2n1] | 4-(5-(2-fluoro-6-methylpyridin-yl)-4-methoxy-7H-pyrrolo[2,3-d]pyrimidin-2-ylamino)-3-methoxy-N,N-dimethylbenzamide | 451.2 | D |

TABLE 1-continued

| Cmpd No. | Structure | Name | Obs. MH+ | Act. Level |
|---|---|---|---|---|
| 419 | 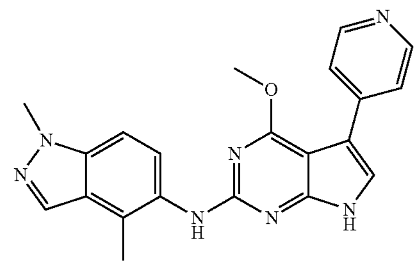 [SMILES: COc1nc(Nc2ccc3c(cnn3C)c2C)nc2[nH]cc(-c3ccncc3)c12] | N-(1,4-dimethyl-1H-indazol-5-yl)-4-methoxy-5-(pyridin-4-yl)-7H-pyrrolo[2,3-d]pyrimidin-2-amine | 386.2 | C |
| 420 | 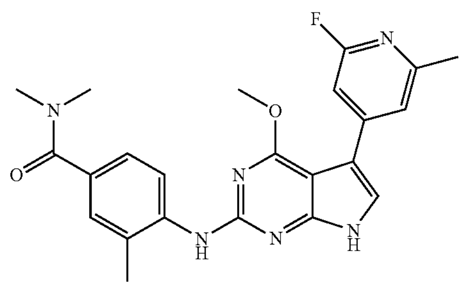 [SMILES: COc1nc(Nc2ccc(C(=O)N(C)C)cc2C)nc2[nH]cc(-c3cc(C)nc(F)c3)c12] | 4-(5-(2-fluoro-6-methylpyridin-4-yl)-4-methoxy-7H-pyrrolo[2,3-d]pyrimidin-2-ylamino)-N,N,3-trimethylbenzamide | 435.3 | D |
| 421 | 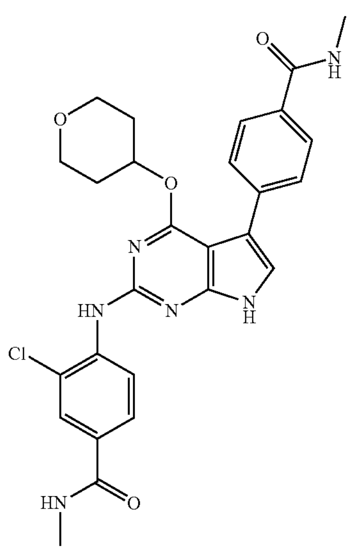 [SMILES: CNC(=O)c1ccc(-c2c[nH]c3nc(Nc4ccc(C(=O)NC)cc4Cl)nc(OC4CCOCC4)c23)cc1] | 3-chloro-N-methyl-4-(5-(4-(methylcarbamoyl)phenyl)-4-(tetrahydro-2H-pyran-4-yloxy)-7H-pyrrolo[2,3-d]pyrimidin-2-ylamino)benzamide | 535.2 | D |

TABLE 1-continued
| Cmpd No. | Structure | Name | Obs. MH+ | Act. Level |
|---|---|---|---|---|
| 422 | 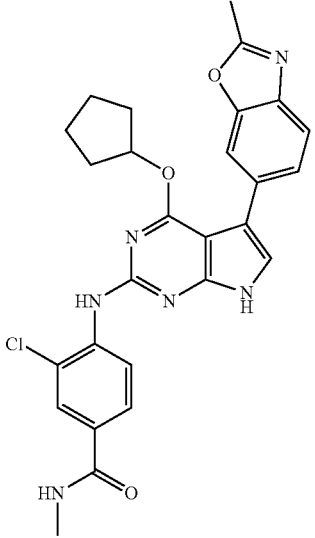 [SMILES: CNC(=O)c1ccc(Nc2nc(OC3CCCC3)c3c(-c4ccc5nc(C)oc5c4)c[nH]c3n2)c(Cl)c1] | 3-chloro-4-(4-(cyclopentyloxy)-5-(2-methylbenzo[d]oxazol-6-yl)-7H-pyrrolo[2,3-d]pyrimidin-2-ylamino)-N-methylbenzamide | 517.6 | D |
| 423 | 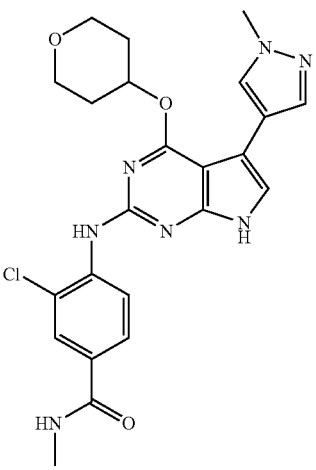 [SMILES: CNC(=O)c1ccc(Nc2nc(OC3CCOCC3)c3c(-c4cnn(C)c4)c[nH]c3n2)c(Cl)c1] | 3-chloro-N-methyl-4-(5-(1-methyl-1H-pyrazol-4-yl)-4-(tetrahydro-2H-pyran-4-yloxy)-7H-pyrrolo[2,3-d]pyrimidin-2-ylamino)benzamide | 482.1 | D |
| 424 | 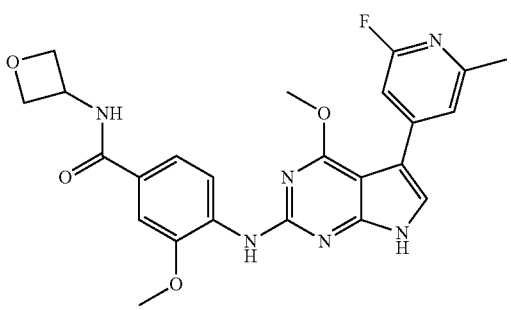 | 4-(5-(2-fluoro-6-methylpyridin-yl)-4-methoxy-7H-pyrrolo[2,3-d]pyrimidin-2-ylamino)-3-methoxy-N-(oxetan-3-yl)benzamide | 479.2 | C |

TABLE 1-continued

| Cmpd No. | Structure | Name | Obs. MH+ | Act. Level |
|---|---|---|---|---|
| 425 | 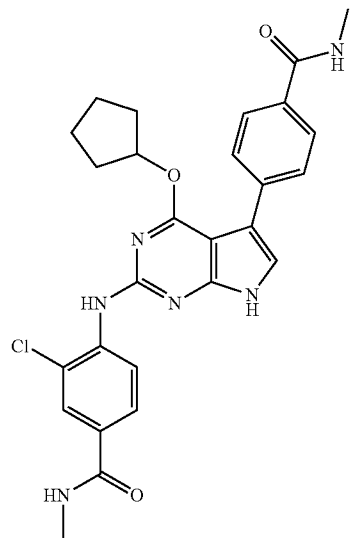 [SMILES: CNC(=O)c1ccc(-c2c[nH]c3nc(Nc4ccc(C(=O)NC)cc4Cl)nc(OC4CCCC4)c23)cc1] | 3-chloro-4-(4-(cyclopentyloxy)-5-(4-(methylcarbamoyl)phenyl)-7H-pyrrolo[2,3-d]pyrimidin-2-ylamino)-N-methylbenzamide | 519.2 | D |
| 426 | 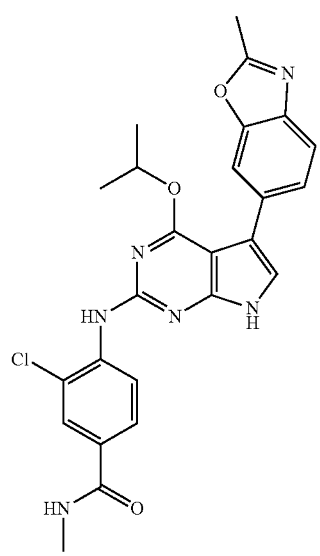 [SMILES: CNC(=O)c1ccc(Nc2nc(OC(C)C)c3c(-c4ccc5nc(C)oc5c4)c[nH]c3n2)c(Cl)c1] | 3-chloro-4-(4-isopropoxy-5-(2-methylbenzo[d]oxazol-6-yl)-7H-pyrrolo[2,3-d]pyrimidin-2-ylamino)-N-methylbenzamide | 491.3 | D |

| Cmpd No. | Structure | Name | Obs. MH+ | Act. Level |
|---|---|---|---|---|
| 427 | 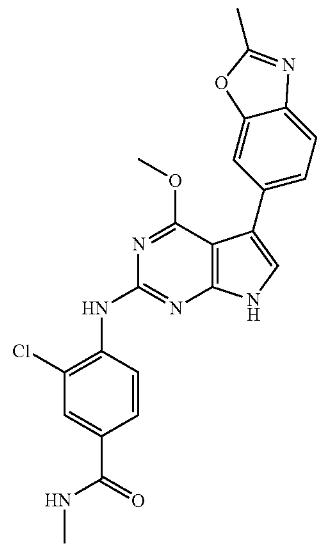 [SMILES: CNC(=O)c1ccc(Nc2nc(OC)c3c(-c4ccc5nc(C)oc5c4)c[nH]c3n2)c(Cl)c1] | 3-chloro-4-(4-methoxy-5-(2-methylbenzo[d]oxazol-6-yl)-7H-pyrrolo[2,3-d]pyrimidin-2-ylamino)-N-methylbenzamide | 463.1 | D |
| 428 | 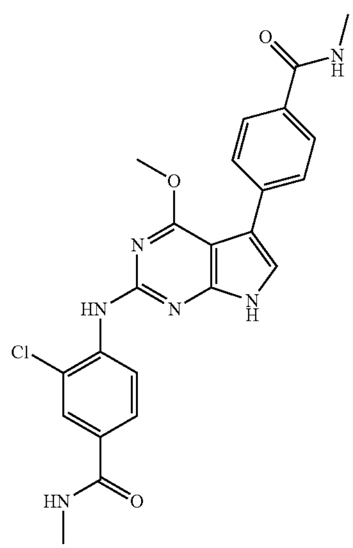 [SMILES: CNC(=O)c1ccc(-c2c[nH]c3nc(Nc4ccc(C(=O)NC)cc4Cl)nc(OC)c23)cc1] | 3-chloro-4-(4-methoxy-5-(4-(methylcarbamoyl)phenyl)-7H-pyrrolo[2,3-d]pyrimidin-2-ylamino)-N-methylbenzamide | 465.1 | D |
| 429 | 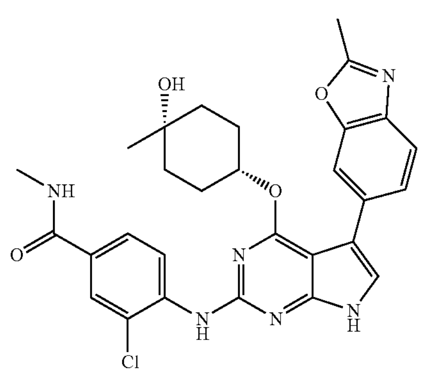 [SMILES: CNC(=O)c1ccc(Nc2nc(O[C@H]3CC[C@@](C)(O)CC3)c3c(-c4ccc5nc(C)oc5c4)c[nH]c3n2)c(Cl)c1] | 3-chloro-4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-N-methylbenzamide | 561.3 | D |

TABLE 1-continued
| Cmpd No. | Structure | Name | Obs. MH+ | Act. Level |
|---|---|---|---|---|
| 430 | 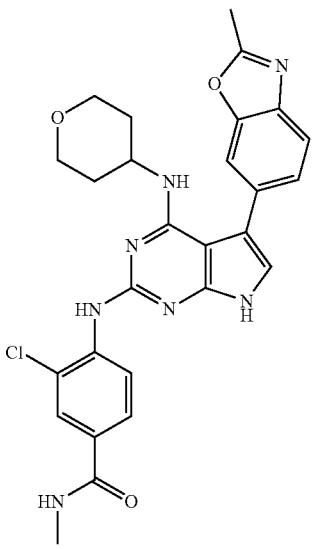 [SMILES: CNC(=O)c1ccc(Nc2nc(NC3CCOCC3)c3c(-c4ccc5nc(C)oc5c4)c[nH]c3n2)c(Cl)c1] | 3-chloro-N-methyl-4-(5-(2-methylbenzo[d]oxazol-6-yl)-4-(tetrahydro-2H-pyran-4-ylamino)-7H-pyrrolo[2,3-d]pyrimidin-2-ylamino)benzamide | 532.2 | D |
| 431 | 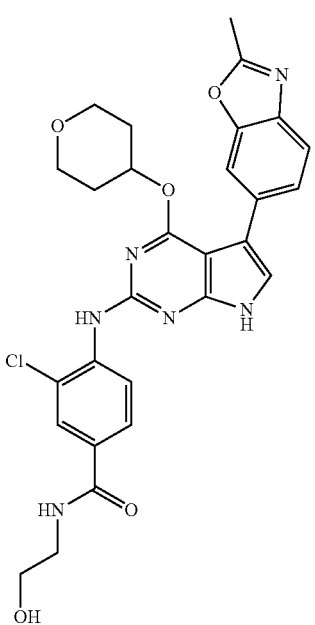 [SMILES: Cc1nc2ccc(-c3c[nH]c4nc(Nc5ccc(C(=O)NCCO)cc5Cl)nc(OC5CCOCC5)c34)cc2o1] | 3-chloro-N-(2-hydroxyethyl)-4-(5-(2-methylbenzo[d]oxazol-6-yl)-4-(tetrahydro-2H-pyran-4-yloxy)-7H-pyrrolo[2,3-d]pyrimidin-2-ylamino)benzamide | 563.1 | D |

TABLE 1-continued

| Cmpd No. | Structure | Name | Obs. MH+ | Act. Level |
|---|---|---|---|---|
| 432 | 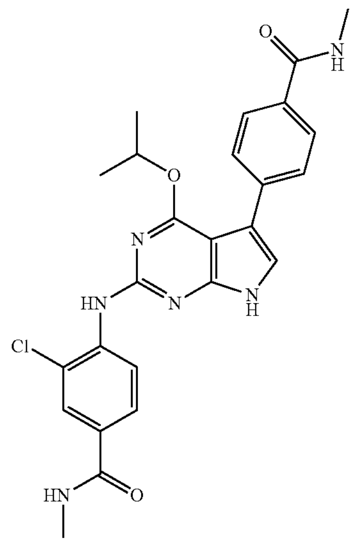 [SMILES: CNC(=O)c1ccc(-c2c[nH]c3nc(Nc4ccc(C(=O)NC)cc4Cl)nc(OC(C)C)c23)cc1] | 3-chloro-4-(4-isopropoxy-5-(4-(methylcarbamoyl)phenyl)-7H-pyrrolo[2,3-d]pyrimidin-2-ylamino)-N-methylbenzamide | 493.2 | D |
| 433 | 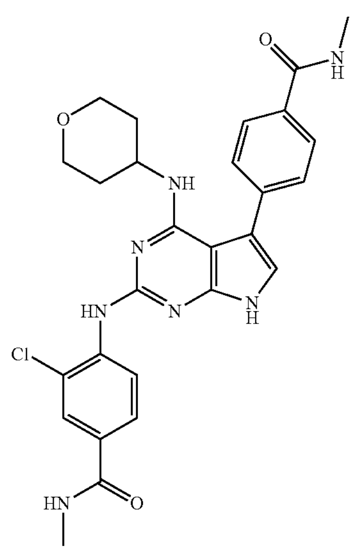 [SMILES: CNC(=O)c1ccc(-c2c[nH]c3nc(Nc4ccc(C(=O)NC)cc4Cl)nc(NC4CCOCC4)c23)cc1] | 3-chloro-N-methyl-4-(5-(4-(methylcarbamoyl)phenyl)-4-(tetrahydro-2H-pyran-4-ylamino)-7H-pyrrolo[2,3-d]pyrimidin-2-ylamino)benzamide | 534.4 | D |

| Cmpd No. | Structure | Name | Obs. MH+ | Act. Level |
|---|---|---|---|---|
| 434 | 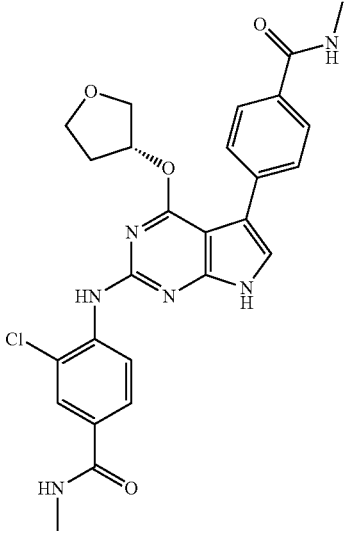 [SMILES: CNC(=O)c1ccc(-c2c[nH]c3nc(Nc4ccc(C(=O)NC)cc4Cl)nc(O[C@@H]4CCOC4)c23)cc1] | (R)-3-chloro-N-methyl-4-(5-(4-(methylcarbamoyl)phenyl)-4-(tetrahydrofuran-3-yloxy)-7H-pyrrolo[2,3-d]pyrimidin-2-ylamino)benzamide | 521.2 | D |
| 435 | 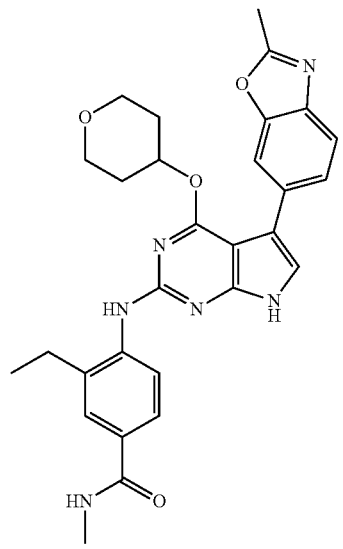 | 3-ethyl-N-methyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide | 527.2 | D |

TABLE 1-continued

| Cmpd No. | Structure | Name | Obs. MH+ | Act. Level |
|---|---|---|---|---|
| 436 | 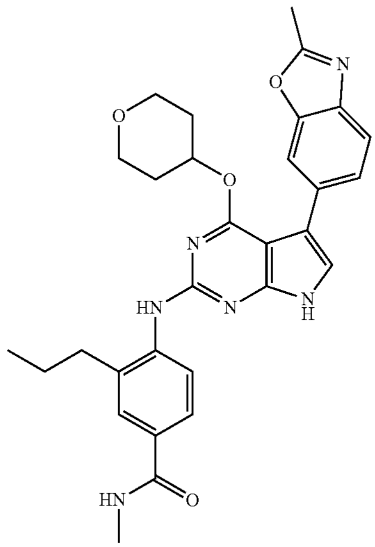 [SMILES: CCCc1cc(C(=O)NC)ccc1Nc1nc(OC2CCOCC2)c2c(-c3ccc4nc(C)oc4c3)c[nH]c2n1] | N-methyl-4-(5-(2-methylbenzo[d]oxazol-6-yl)-4-(tetrahydro-2H-pyran-4-yloxy)-7H-pyrrolo[2,3-d]pyrimidin-2-ylamino)-3-propylbenzamide | 541.2 | D |
| 437 | 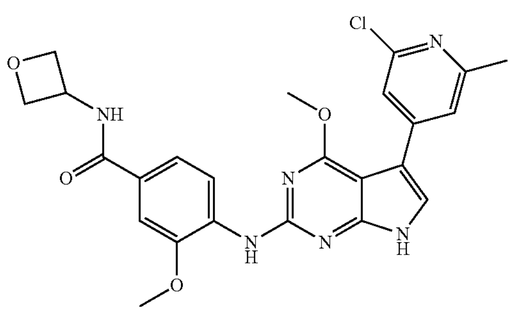 | 4-(5-(2-chloro-6-methylpyridin-4-yl)-4-methoxy-7H-pyrrolo[2,3-d]pyrimidin-2-ylamino)-3-methoxy-N-(oxetan-3-yl)benzamide | 495.2 | D |
| 438 | 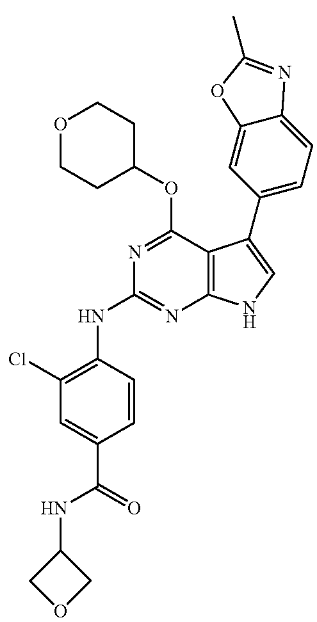 [SMILES: Cc1nc2ccc(-c3c[nH]c4nc(Nc5ccc(C(=O)NC6COC6)cc5Cl)nc(OC5CCOCC5)c34)cc2o1] | 3-chloro-4-(5-(2-methylbenzo[d]oxazol-6-yl)-4-(tetrahydro-2H-pyran-4-yloxy)-7H-pyrrolo[2,3-d]pyrimidin-2-ylamino)-N-(oxetan-3-yl)benzamide | 575.1 | D |

What is claimed is:

1. A compound of formula (I):

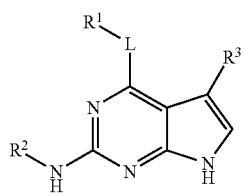

and pharmaceutically acceptable salts, tautomers, stereoisomers, enantiomers, and isotopologues thereof,
wherein:
$R^1$ is substituted or unsubstituted $C_{1-8}$ alkyl, substituted or unsubstituted $C_{3-8}$ cycloalkyl, or substituted or unsubstituted non-aromatic heterocyclyl;
$R^2$ is substituted or unsubstituted aryl, or substituted or unsubstituted heteroaryl;
$R^3$ is substituted or unsubstituted heterocyclyl or substituted or unsubstituted aryl, and
L is NH or O;
provided
$R^3$ is not pyridyl when L is NH or when $R^2$ is pyrazolyl; and
the compound is not
N-methyl-N-[trans-3-[[5-(1-methyl-1H-pyrazol-4-yl)-2-[(1-methyl-1H-pyrazol-4-yl)amino]-7H-pyrrolo[2,3-d]pyrimidin-4-yl]oxy]cyclobutyl]-2-propenamide; or
N-methyl-N-[trans-3-[[5-(1-methyl-1H-pyrazol-3-yl)-2-[(1-methyl-1H-pyrazol-4-yl)amino]-7H-pyrrolo[2,3-d]pyrimidin-4-yl]oxy]cyclobutyl]-2-propenamide.

2. The compound of claim 1, wherein L is O.

3. The compound of claim 1, wherein $R^1$ is substituted or unsubstituted alkyl.

4. The compound of claim 1, wherein $R^1$ is substituted or unsubstituted methyl, ethyl, propyl, isopropyl, n-butyl, sec-butyl, tert-butyl, n-pentyl, sec-pentyl, tert-pentyl, or 2,2-dimethylpropyl.

5. The compound of claim 1, wherein $R^1$ is substituted or unsubstituted methyl, ethyl, isopropyl, sec-butyl, t-butyl, or 2,2-dimethylpropyl.

6. The compound of claim 3, wherein the alkyl is substituted with one or more —OR or —$NR_2$, wherein each R is independently —H or substituted or unsubstituted ($C_{1-4}$) alkyl.

7. The compound of claim 1, wherein $R^1$ is substituted or unsubstituted $C_{3-8}$ cycloalkyl.

8. The compound of claim 1, wherein $R^1$ is substituted or unsubstituted cyclopropyl, cyclobutyl, cyclopentyl, cyclohexyl, or cycloheptyl.

9. The compound of claim 7, wherein the cycloalkyl is substituted with one or more —CN, halogen, —OR or a substituted or unsubstituted $C_{1-3}$ alkyl, wherein each R is independently —H or substituted or unsubstituted ($C_{1-4}$) alkyl.

10. The compound of claim 1, wherein $R^1$ is substituted or unsubstituted non-aromatic heterocyclyl.

11. The compound of claim 1, wherein $R^1$ is substituted or unsubstituted oxetanyl, tetrahydrofuranyl, tetrahydropyranyl, or piperidinyl.

12. The compound of claim 1, wherein $R^1$ is substituted or unsubstituted $C_{1-8}$ alkyl,

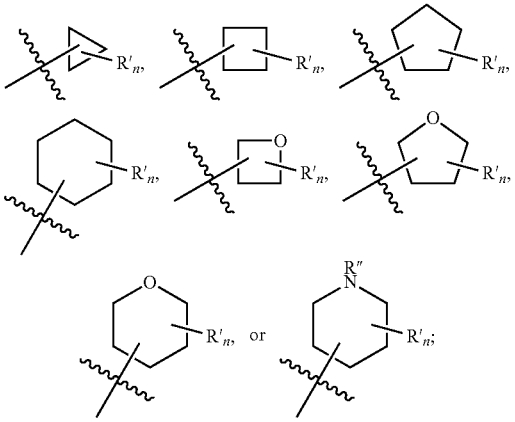

wherein
each R' is independently —CN, halogen, —OR or $C_{1-3}$ alkyl;
R" is —H or $C_{1-3}$ alkyl;
each R is independently —H or substituted or unsubstituted ($C_{1-4}$)alkyl; and
n is 0-2.

13. The compound of claim 1, wherein $R^2$ is substituted phenyl.

14. The compound of claim 13, wherein $R^2$ is phenyl, substituted with one or more substituted or unsubstituted $C_{1-6}$ alkyl, halogen, —CN, —$OR^5$, —C(=O)$NR^5{}_2$, —C(=O)(substituted or unsubstituted heterocyclyl), —C(=O)(substituted or unsubstituted heterocyclylalkyl), —NHC(=O)$R^5$, —$SO_2NR^5{}_2$, or substituted or unsubstituted heteroaryl, wherein each $R^5$ is independently —H, substituted or unsubstituted alkyl, substituted or unsubstituted cycloalkyl, substituted or unsubstituted heterocyclyl, or substituted or unsubstituted heterocyclylalkyl.

15. The compound of claim 13, wherein $R^2$ is phenyl, substituted with one or more —($C_{1-3}$ alkyl), —($C_{1-3}$ alkyl)$NR_2$, —$CF_3$, —F, —CN, —$OCH_3$, —$OCF_3$, —C(=O)$NR_2$, —C(=O)NR(substituted or unsubstituted cycloalkyl), —C(=O)NR$(CH_2)_{0-2}CR_2(CH_2)_{0-2}$OR, —C(=O)NR$(CH_2)_{0-2}CR_2(CH_2)_{0-2}NR_2$, —C(=O)NR$(CH_2)_{0-2}CR_2(CH_2)_{0-2}$C(=O)$NR_2$, —C(=O)N(substituted or unsubstituted cycloalkyl)$(CH_2)_{0-2}$OR, —C(=O)NR$(CH_2)_{0-3}$(substituted or unsubstituted heterocyclyl), —C(=O)$(CH_2)_{0-3}$(substituted or unsubstituted heterocyclyl), —C(=NR)$NR_2$, —NRC(=O)R, —$SO_2NR_2$, —$SO_2R$, or substituted or unsubstituted heterocyclyl, wherein each R is independently —H or substituted or unsubstituted ($C_{1-4}$)alkyl.

16. The compound of claim 15, wherein each R is independently —H or —$CH_3$.

17. The compound of claim 13, wherein $R^2$ is phenyl, substituted with one or more —$CH_3$, —$CH_2CH_3$, —$CH_2CH_2CH_3$, —$CH(CH_3)_2$, —$CH_2NH_2$, —$CF_3$, —Cl, —F, —CN, —$OCH_3$, —$OCF_3$, —C(=O)$NH_2$, —C(=O)$NHCH_3$, —C(=O)N$(CH_3)_2$, —C(=O)NHC$(CH_3)_3$, —C(=O)$NHCH_2CH_2F$, —C(=O)$NHCH_2CHF_2$, —C(=O)$NHCH_2CF_3$, —C(=O)$NHCH_2CF_2CH_3$, —C(=O)$NHCH_2CN$, —C(=O)N$(CH_3)CH_2CN$, —C(=O)$NHCH_2CH_2CN$, —C(=O)N$(CH_3)CH_2CH_2CN$, —C(=O)NH-cyclobutyl, —C(=O)NH-(hydroxy-cyclobutyl), —C(=O)NH-cyclopentyl, —C(=O)NH-(hydroxy-cyclopentyl), —C(=O)NHCH₂CH₂OH, —C(=O)NHCH₂CH₂OCH₃, —C(=O)N(CH₃)CH₂CH₂OH, —C(=O)N(CH₃)CH₂CH₂OCH₃, —C(=O)NHCH₂CH₂CH₂OH, —C(=O)NHCH₂CH₂CH₂OH, —C(=O)N(CH₃)CH₂CH₂CH₂OCH₃, —C(=O)NHCH₂CH(CH₃)OH, —C(=O)NHCH₂C(CH₃)₂OH, —C(=O)NHCH(CH₃)CH₂OH, —C(=O)NHC(CH₃)₂CH₂OH, —C(=O)NHCH₂CH₂NH₂, —C(=O)NHCH₂CH₂NH(CH₃), —C(=O)NHCH₂CH₂N(CH₃)₂, —C(=O)NHCH₂C(=O)NH₂, —C(=O)N(CH₃)CH₂C(=O)NH₂, —C(=O)NHCH₂CH₂C(=O)NH₂, —C(=O)N(CH₃)CH₂CH₂C(=O)NH₂, —C(=O)N(cyclopropyl)CH₂CH₂OH, —C(=O)NH-oxetanyl, —C(=O)N(CH₃)-oxetanyl, —C(=O)NH-(methyl-oxetanyl), —C(=O)NH-azetidinyl, —C(=O)NH-(methylazetidinyl), —C(=O)NH-(1-acetylazetidinyl), —C(=O)NH-pyrrolidyl, —C(=O)NH-piperidyl, —C(=O)NH-tetrahydrofuranyl, —C(=O)N(CH₃)-tetrahydrofuranyl, —C(=O)NH-tetrahydropyranyl, —C(=O)N(CH₃)-tetrahydropyranyl, —C(=O)NHCH₂-oxetanyl, —C(=O)N(CH₃)CH₂-oxetanyl, —C(=O)NHCH₂-(methyl-oxetanyl), —C(=O)N(CH₃)CH₂-(methyl-oxetanyl), —C(=O)NHCH₂-tetrahydrofuranyl, —C(=O)NHCH₂-tetrahydropyranyl, —C(=O)NHCH₂-dioxanyl, —C(=O)aziridinyl, —C(=O)(methyl-aziridinyl), —C(=O)(dimethyl-aziridinyl), —C(=O)(hydroxymethyl-aziridinyl), —C(=O)azetidinyl, —C(=O)pyrrolidinyl, —C(=O)(hydroxyl-pyrrolidinyl), —C(=O)(hydroxyl, methoxypyrrolidinyl), —C(=O)(dimethoxypyrrolidinyl), —C(=O)morpholinyl, —C(=O)piperazinyl, —C(=O)(methylpiperazinyl), —C(=O)(hydroxy-piperidyl), —C(=O)(fluoropiperidinyl), —(C=O)(methoxy-piperidyl), —C(=NH)NH₂, —NHC(=O)CH₃, —SO₂NHCH₃, —SO₂CH₃, or substituted or unsubstituted pyrazolyl.

18. The compound of claim 13, wherein R² is phenyl, substituted with one or more —CH₃, —CH₂CH₃, —CH₂CH₂CH₃, —CH(CH₃)₂, —CH₂NH₂, —CF₃, —Cl, —F, —CN, —OCH₃, —OCF₃, —C(=O)NH₂, —C(=O)NHCH₃, —C(=O)N(CH₃)₂, —C(=O)NHC(CH₃)₃, —C(=O)NHCH₂CH₂F, —C(=O)NHCH₂CF₂CH₃, —C(=O)N(CH₃)CH₂CN, —C(=O)N(CH₃)CH₂CH₂CN, —C(=O)NH-(3-hydroxy-cyclobutyl), —C(=O)NH-cyclopentyl, —C(=O)NH-(2-hydroxycyclopentyl), —C(=O)NHCH₂CH₂OH, —C(=O)NHCH₂CH₂OCH₃, —C(=O)N(CH₃)CH₂CH₂OH, —C(=O)N(CH₃)CH₂CH₂OCH₃, —C(=O)NHCH₂CH₂CH₂OH, —C(=O)N(CH₃)CH₂CH₂CH₂OH, —C(=O)NHCH₂CH(CH₃)OH, —C(=O)NHCH₂C(CH₃)₂OH, —C(=O)NHCH(CH₃)CH₂OH, —C(=O)NHC(CH₃)₂CH₂OH, —C(=O)NHCH₂CH₂NH₂, —C(=O)NHCH₂CH₂NH(CH₃), —C(=O)NHCH₂CH₂N(CH₃)₂, —C(=O)N(CH₃)CH₂C(=O)NH₂, —C(=O)N(CH₃)CH₂CH₂C(=O)NH₂, —C(=O)N(cyclopropyl)CH₂CH₂OH, —C(=O)NH-oxetanyl, —C(=O)N(CH₃)-oxetanyl, —C(=O)NH-(3-methyl-oxetanyl), —C(=O)NH-(1-methylazetidinyl), —C(=O)NH-(1-acetylazetidinyl), —C(=O)NH-piperidyl, —C(=O)NH-tetrahydrofuranyl, —C(=O)NH-tetrahydropyranyl, —C(=O)N(CH₃)-tetrahydropyranyl, —C(=O)NHCH₂-oxetanyl, —C(=O)N(CH₃)CH₂-(3-methyl-oxetanyl), —C(=O)NHCH₂-tetrahydrofuranyl, —C(=O)NHCH₂-tetrahydropyranyl, —C(=O)NHCH₂-dioxanyl, —C(=O)aziridinyl, —C(=O)(2-methyl-aziridinyl), —C(=O)(2,2-dimethyl-aziridinyl), —C(=O)(2-(hydroxymethyl)aziridinyl), —C(=O)azetidinyl, —C(=O)pyrrolidinyl, —C(=O)(3-hydroxy-4-methoxypyrrolidinyl), —C(=O)(3,4-dimethoxypyrrolidinyl), —C(=O)morpholinyl, —C(=O)piperazinyl, —C(=O)(4-methylpiperazinyl), —C(=O)(4-hydroxy-piperidyl), —C(=O)(4,4-difluoropiperidinyl), —(C=O)(4-methoxy-piperidyl), —C(=NH)NH₂, —NHC(=O)CH₃, —SO₂NHCH₃, —SO₂CH₃, or substituted or unsubstituted pyrazolyl.

19. The compound of claim 1, wherein R² is substituted or unsubstituted pyrazolyl, substituted or unsubstituted pyridyl, substituted or unsubstituted indazolyl or substituted or unsubstituted isoindolinone.

20. The compound of claim 19, wherein R² is substituted with one or more halogen, substituted or unsubstituted (C₁₋₄)alkyl, —OR, —C(=O)NR₂, or substituted or unsubstituted heterocyclyl, wherein each R is independently —H or substituted or unsubstituted (C₁₋₄)alkyl.

21. The compound of claim 1, wherein R³ is substituted or unsubstituted heterocyclyl.

22. The compound of claim 21, wherein the heterocyclyl is substituted or unsubstituted pyrazolyl, oxazolyl, isoxazolyl, oxadiazolyl, pyridyl, pyridazinyl, pyrimidyl, pyrazinyl, benztriazolyl, indazolyl, indolyl, benzoxazolyl, benzisoxazolyl, benzthiazolyl, benzoxazolonyl, benzoxadiazolyl, benzimidazolyl, or quinolyl.

23. The compound of claim 21, wherein the heterocyclyl is substituted with one or more substituents selected from substituted or unsubstituted (C₁₋₄)alkyl, halogen, —OR, —CN, —NR₂, —C(=O)NR₂, —NRC(=O)R, or substituted or unsubstituted triazolyl, wherein each R is independently —H or substituted or unsubstituted (C₁₋₄)alkyl.

24. The compound of claim 21, wherein the heterocyclyl is substituted with one or more substituents selected from —CH₃, —CH(CH₃)₂, —F, —Cl, —OH, —OCH₃, —OCH₂CH₃, —CN, —NH₂, —NHCH₃, —N(CH₃)₂, —C(=O)NH(CH₃), —NHC(=O)CH₃, or substituted or unsubstituted triazolyl.

25. The compound of claim 1, wherein R³ is substituted or unsubstituted aryl.

26. The compound of claim 1, wherein R³ is substituted or unsubstituted phenyl.

27. The compound of claim 26, wherein the phenyl is substituted with one or more substituents selected from substituted or unsubstituted C₁₋₄ alkyl, halogen, —CN, —OR, —NR₂, —NRSO₂R', —NR(C=O)NR₂, —NR(C=O)R', —COOR, —(C=O)NR₂, —C(=N)NR₂, —SO₂R', or substituted or unsubstituted heteroaryl, wherein each R is independently —H or substituted or unsubstituted (C₁₋₄)alkyl, and R' is C₁₋₃ alkyl.

28. The compound of claim 26, wherein the phenyl is substituted with one or more substituents selected from —CH₃, —CH₂OH, —CH(OH)CH₃, —C(CH₃)₂OH, —CN, —F, —Cl, —OH, —OCH₃, —NH₂, —N(CH₃)₂, —NHSO₂CH₃, —NH(C=O)NH₂, —NH(C=O)CH₃, —COOCH₃, —(C=O)NHCH₃, —C(=NH)NH₂, —SO₂CH₃, substituted or unsubstituted triazolyl, substituted or unsubstituted pyrazolyl, or substituted or unsubstituted imidazolyl.

29. A compound, wherein the compound is

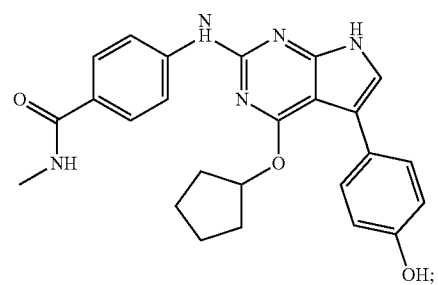

373
-continued
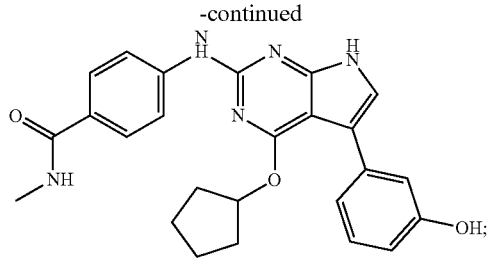
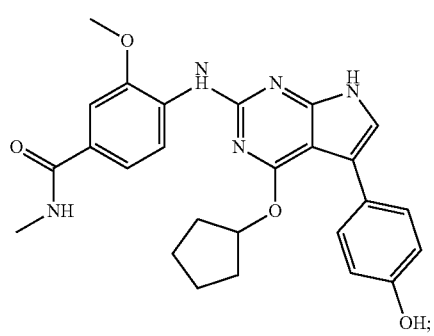
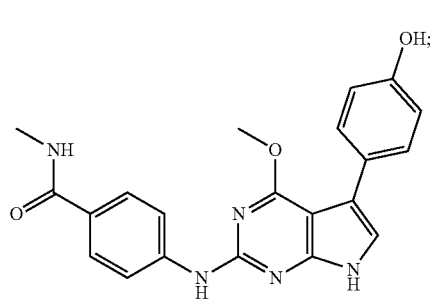
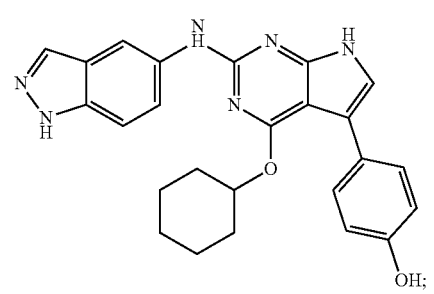
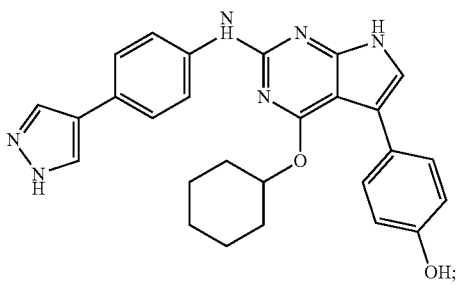
374
-continued
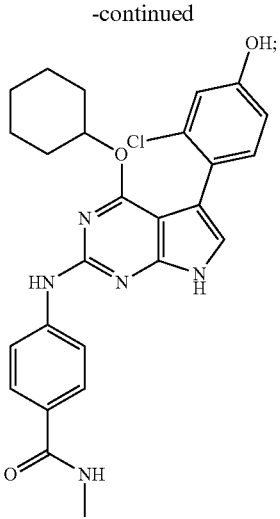
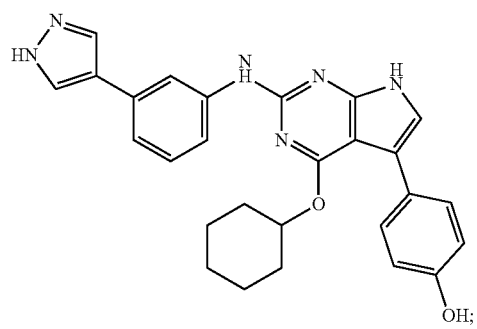
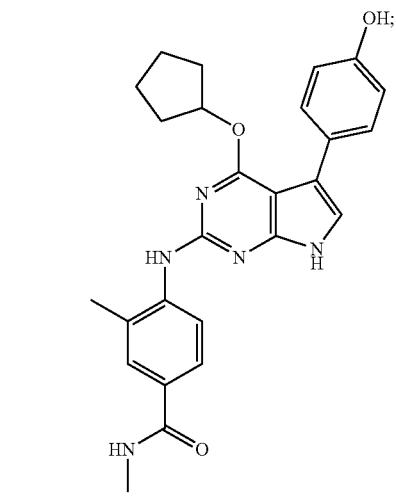

375
-continued
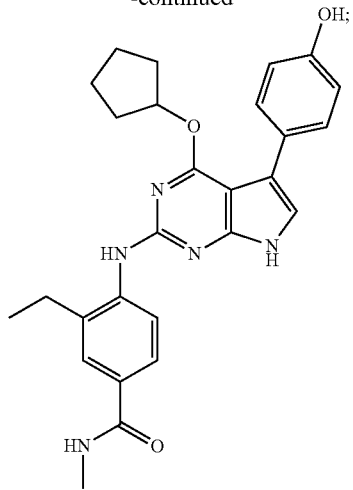
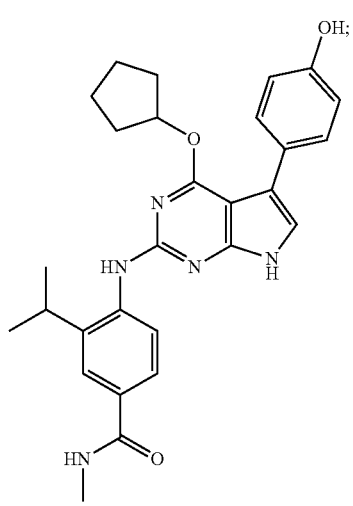
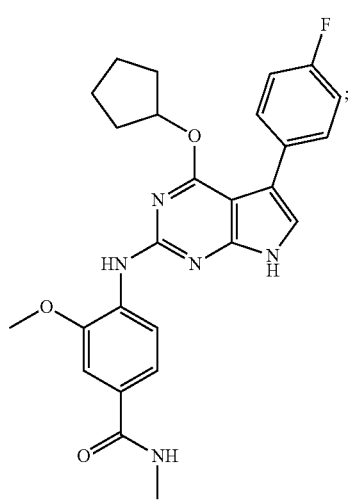
376
-continued
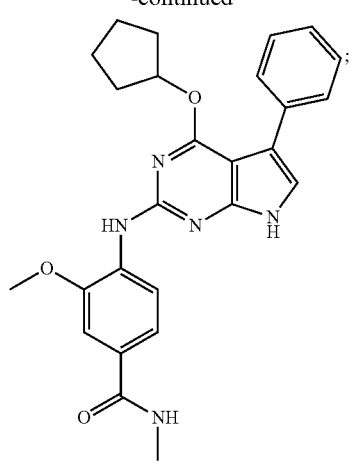
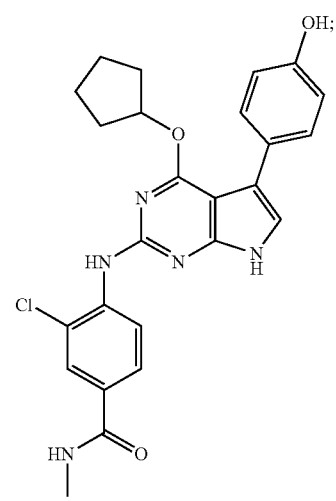
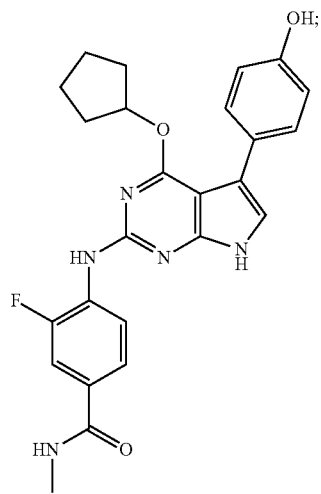

377
-continued
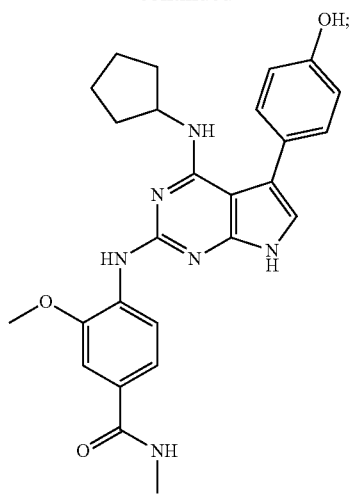
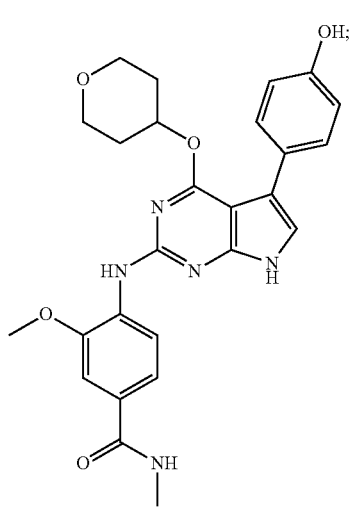
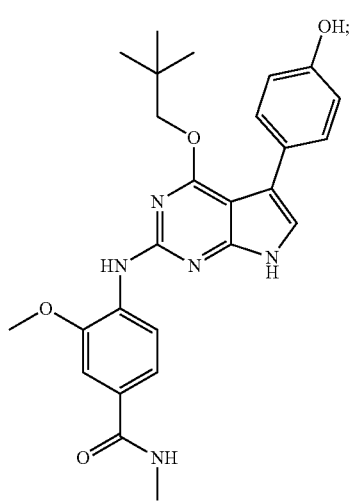
378
-continued
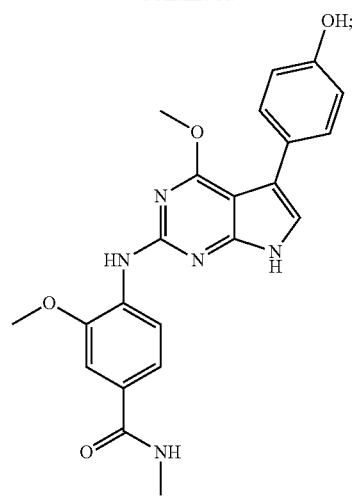
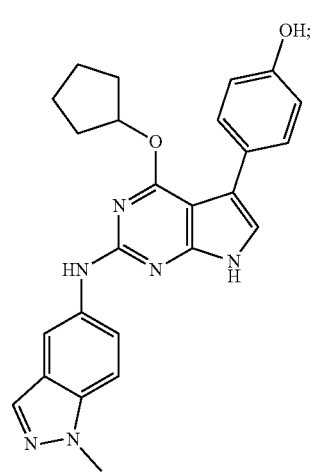
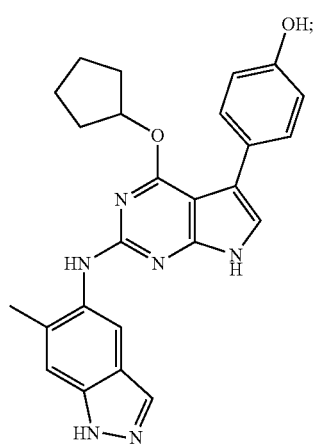

379
-continued
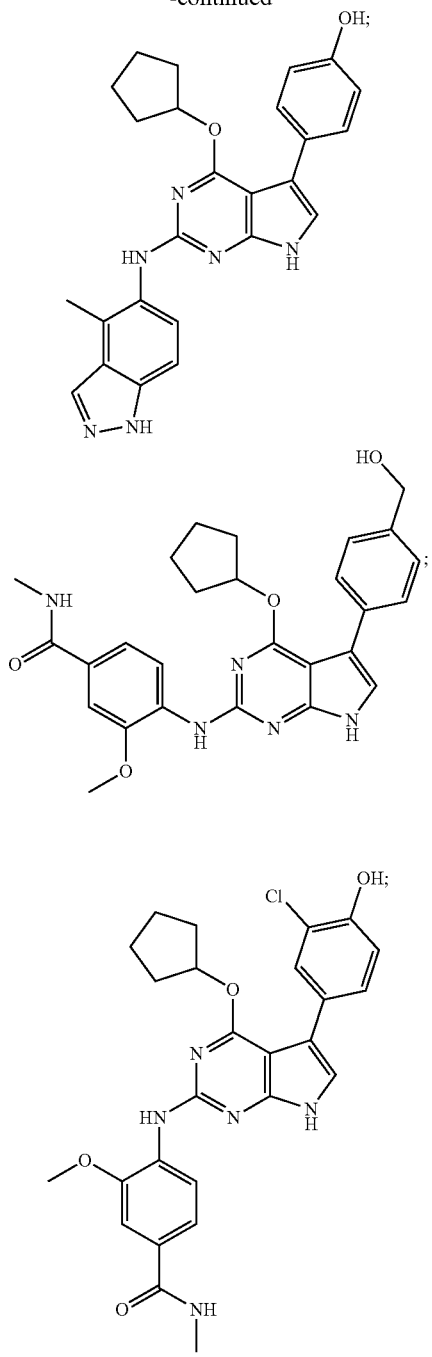
380
-continued
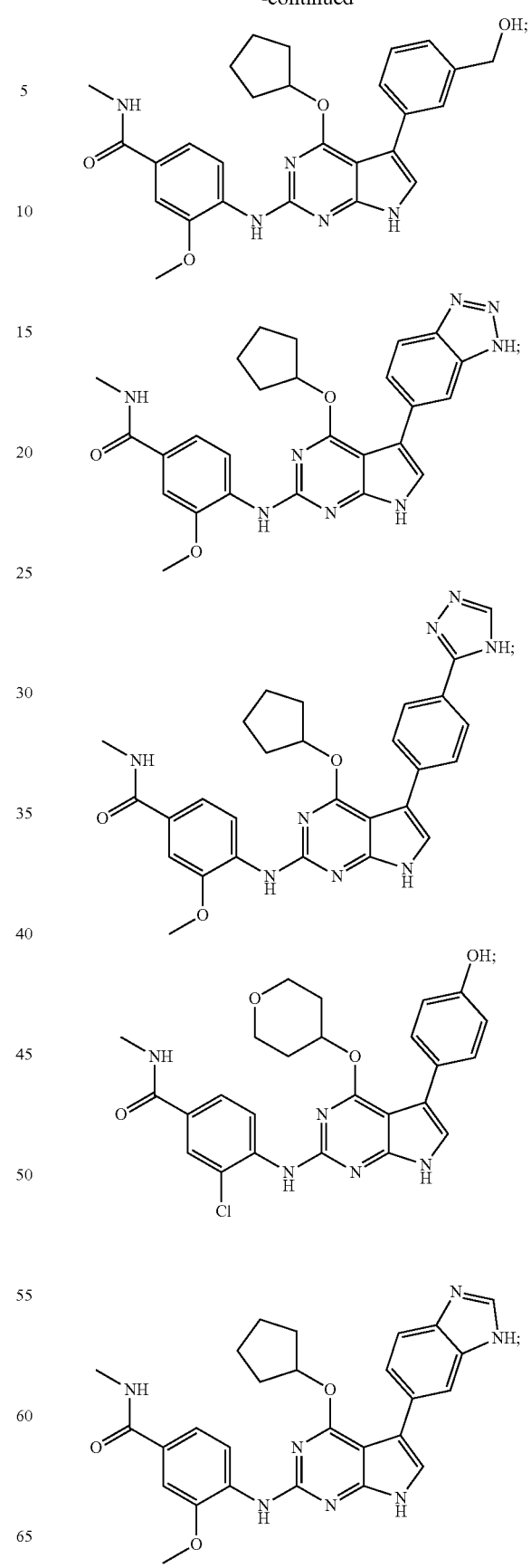

381
-continued
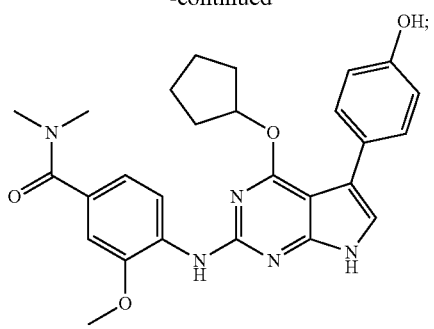
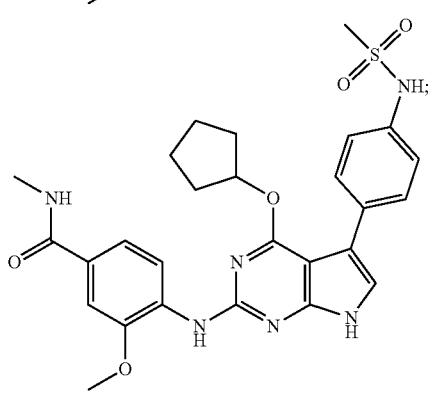
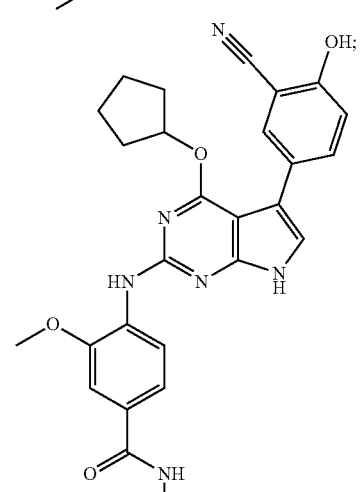
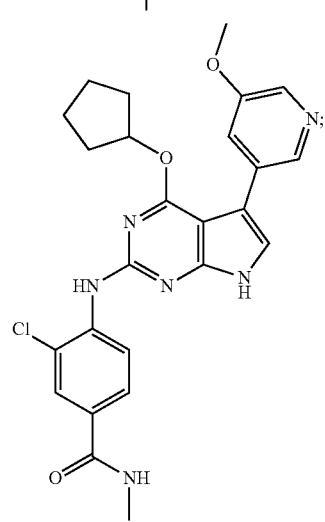
382
-continued
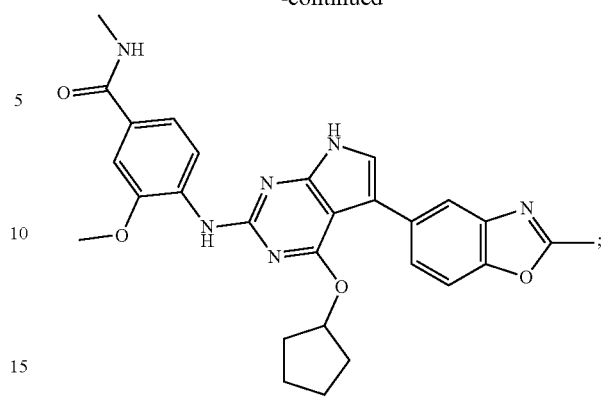
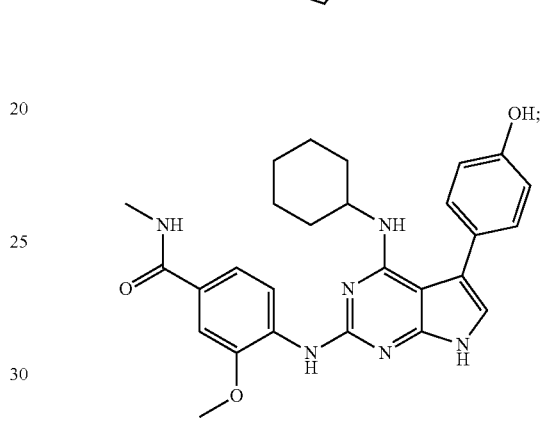
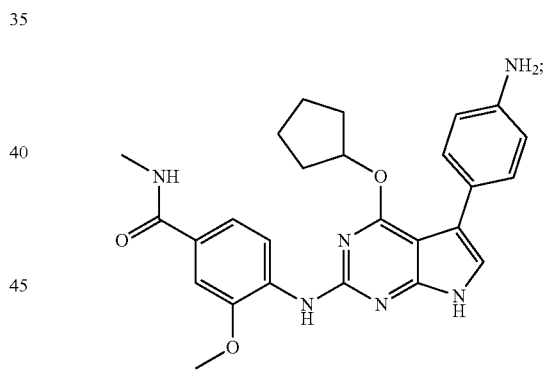
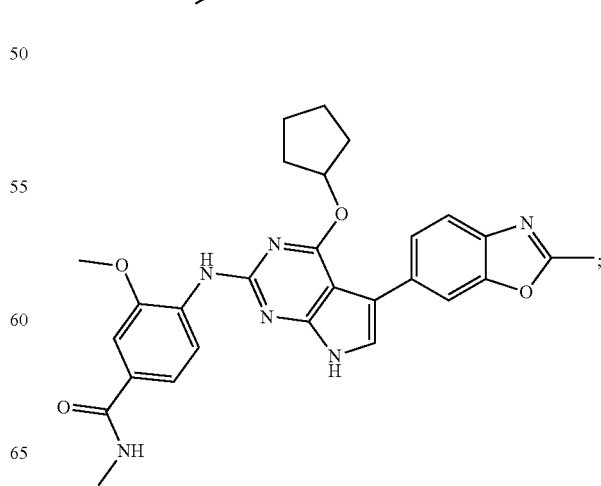

383
-continued
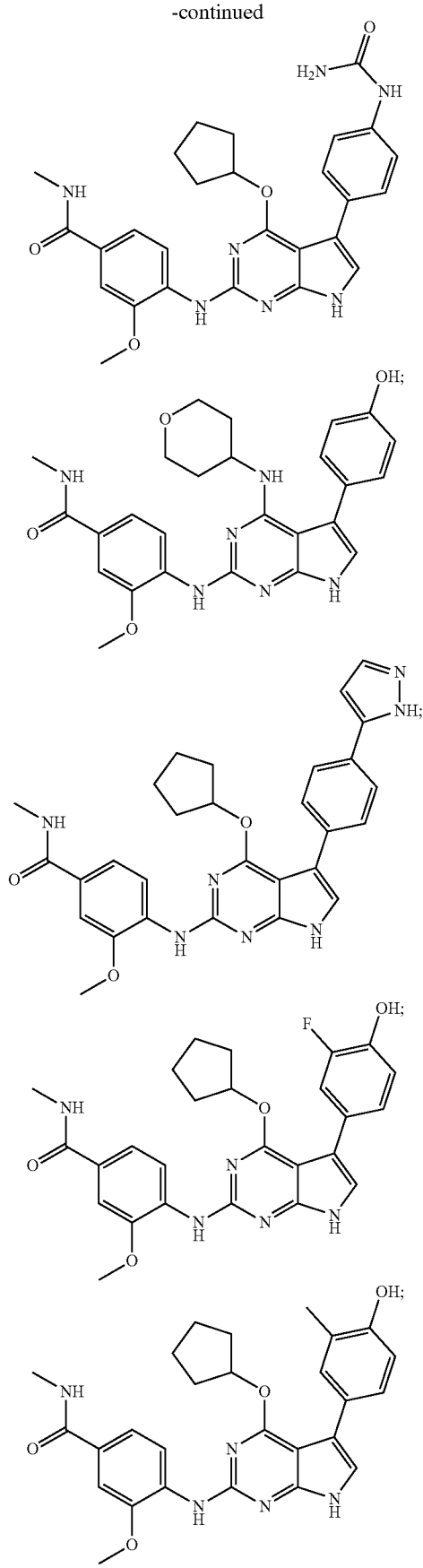
384
-continued
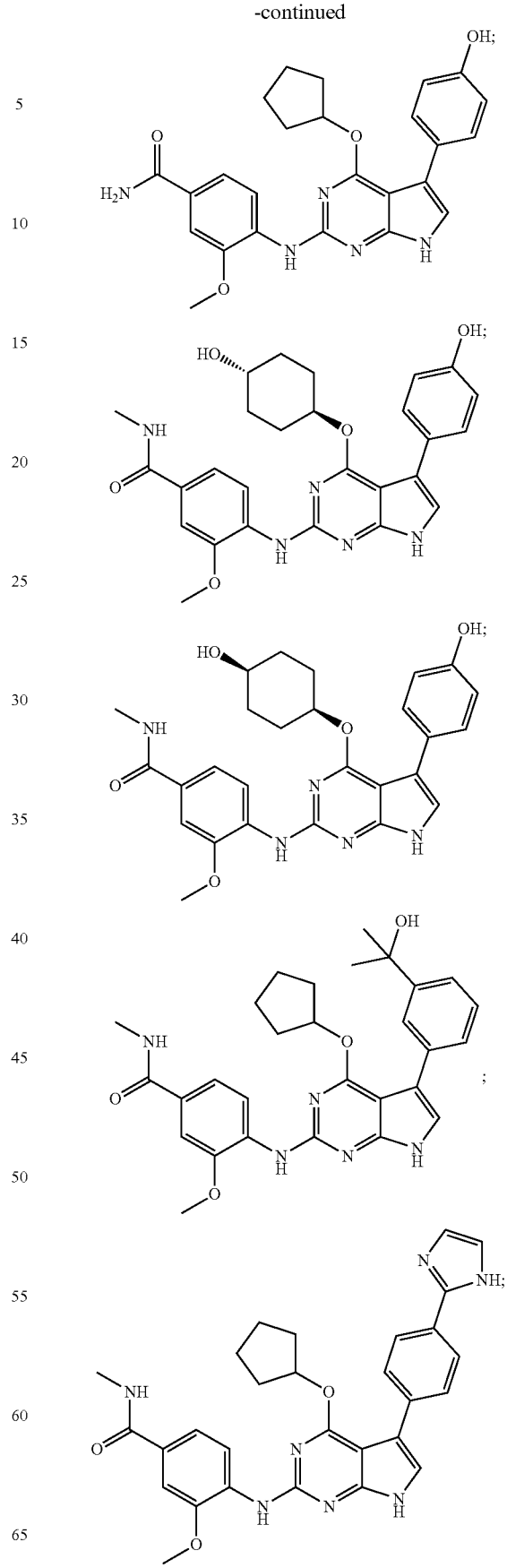

385
-continued
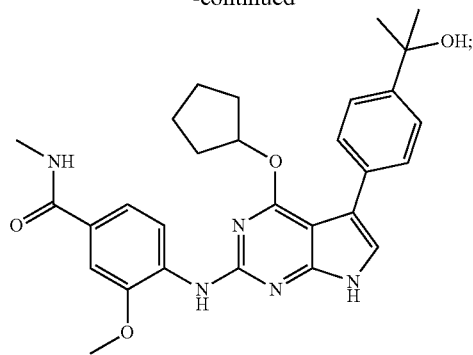
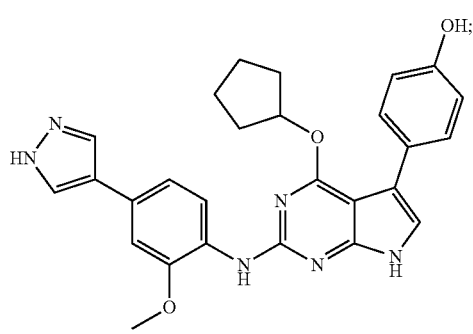
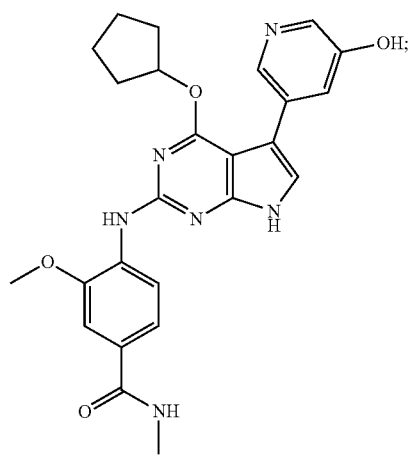
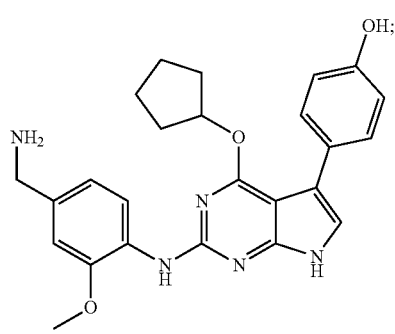
386
-continued
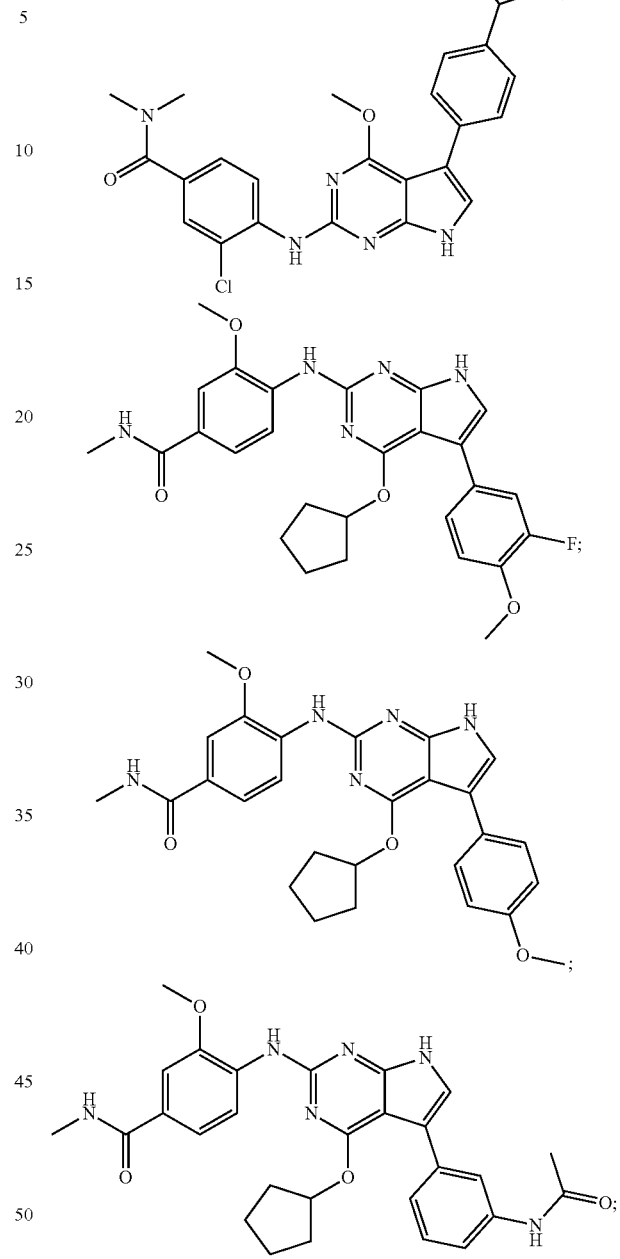
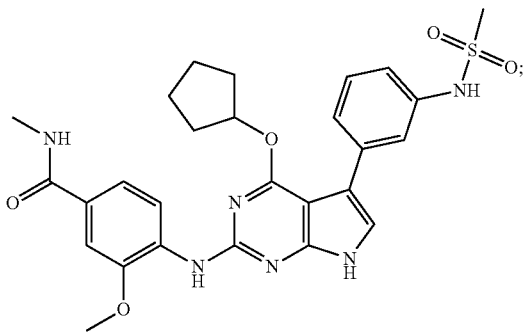

387
-continued
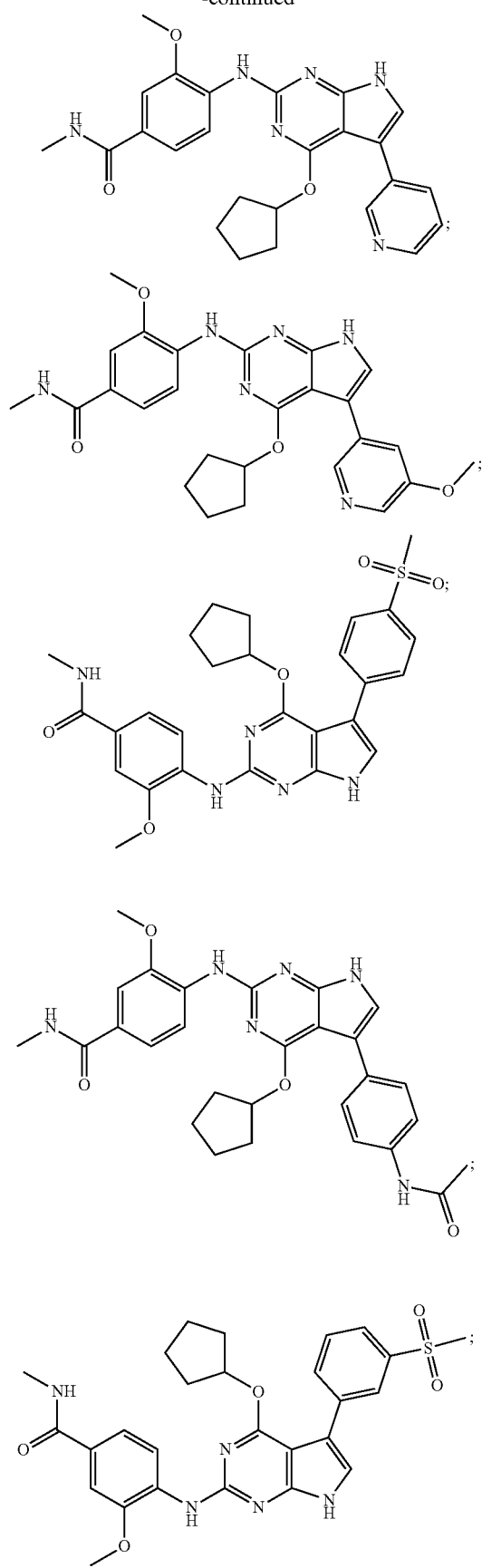
388
-continued
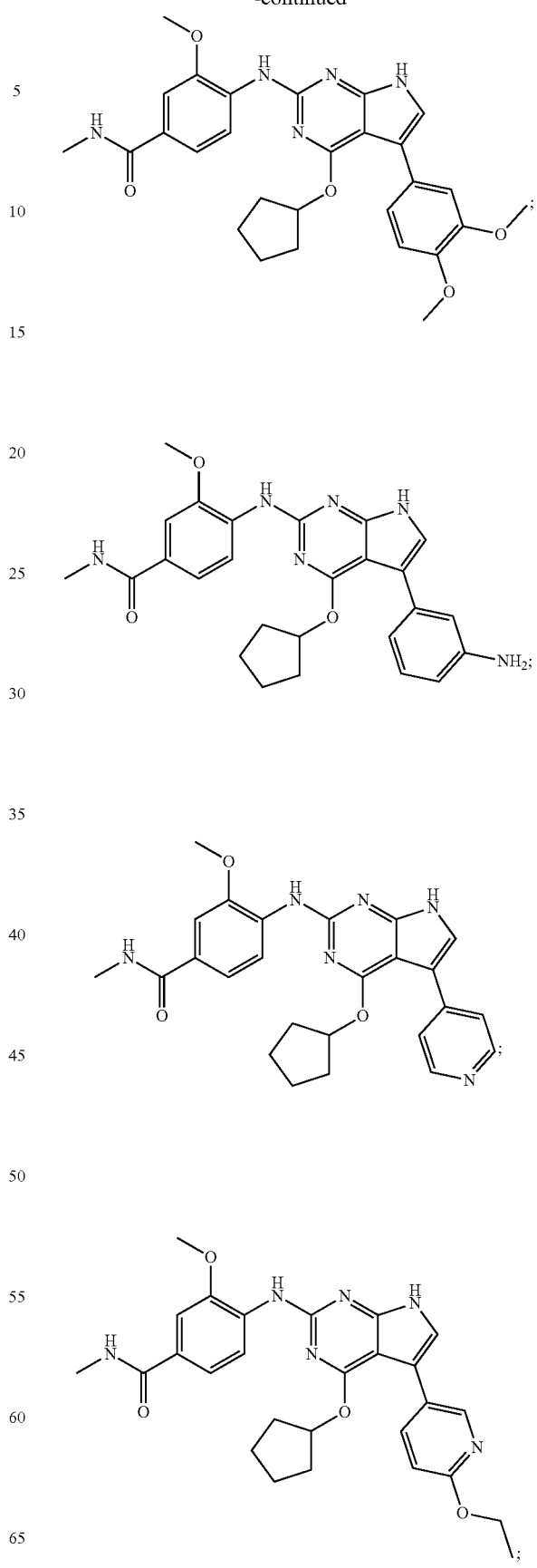

389
-continued
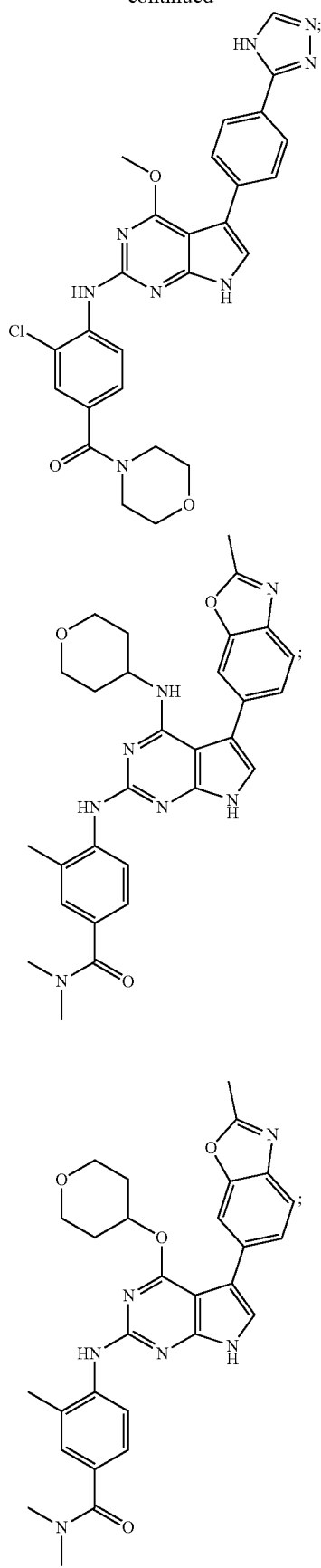
390
-continued
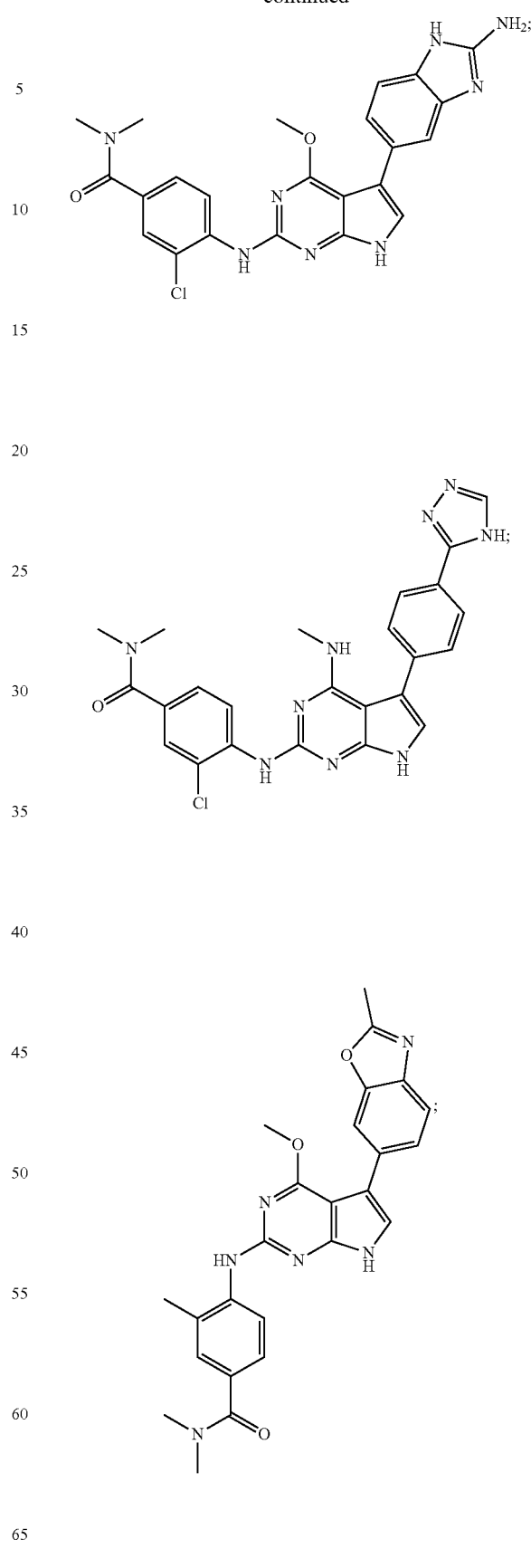

391
-continued
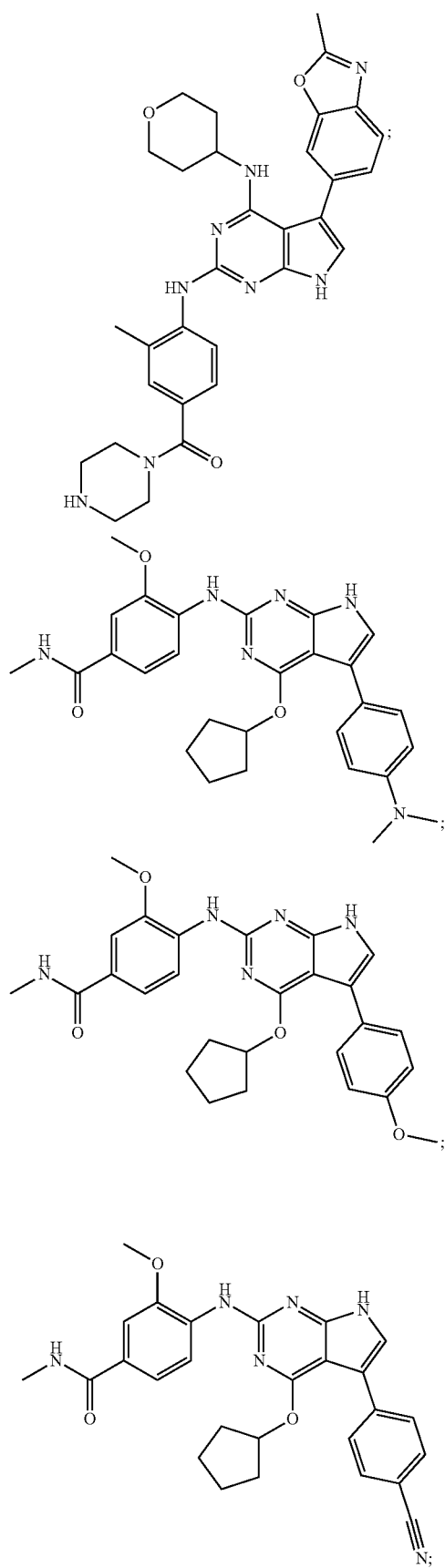
392
-continued
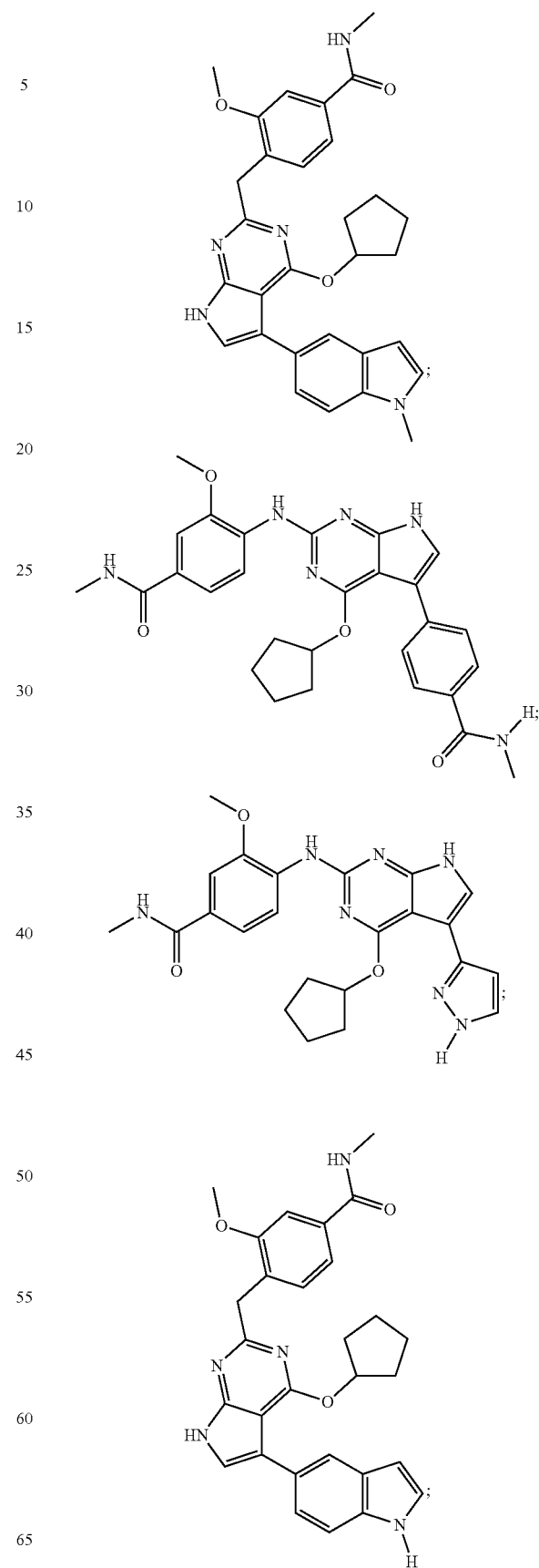

393
-continued
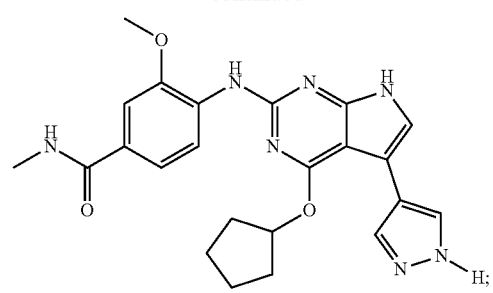
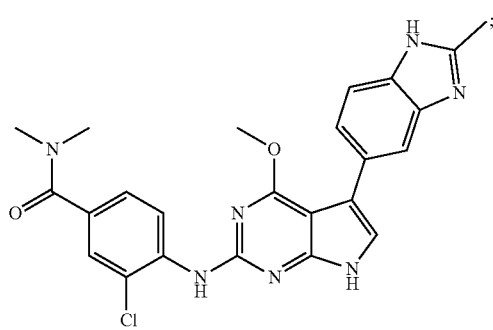
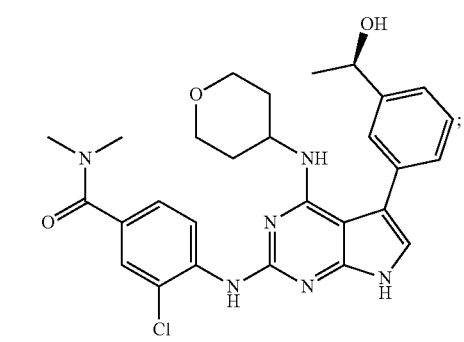
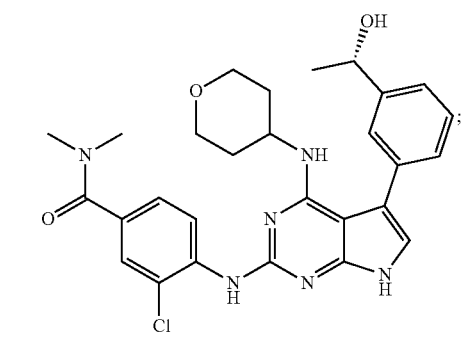
394
-continued
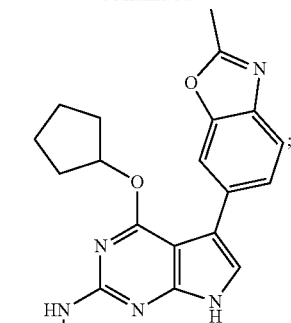
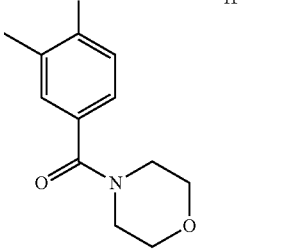
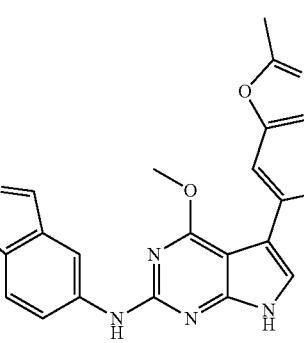
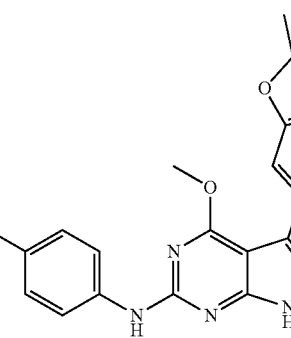
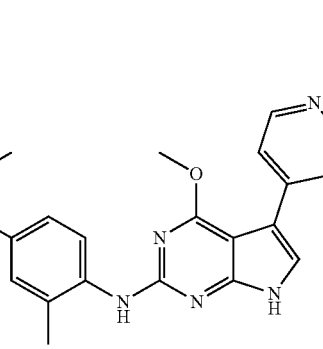

395
-continued
396
-continued
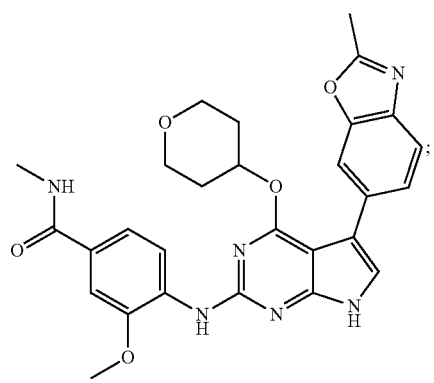
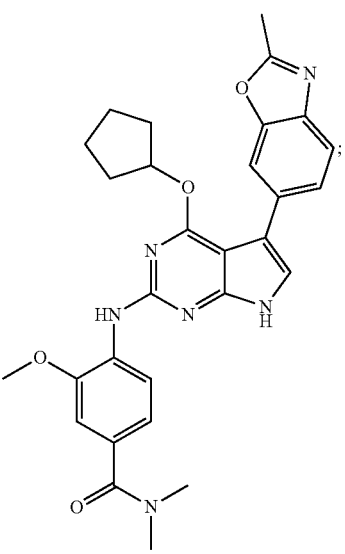
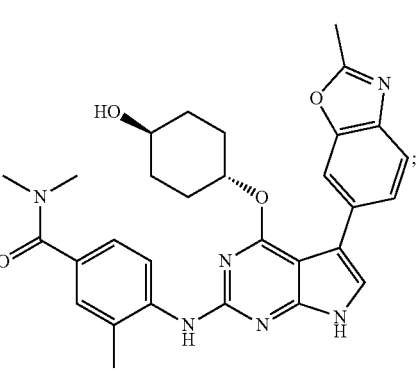
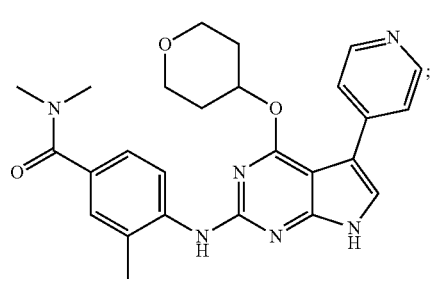
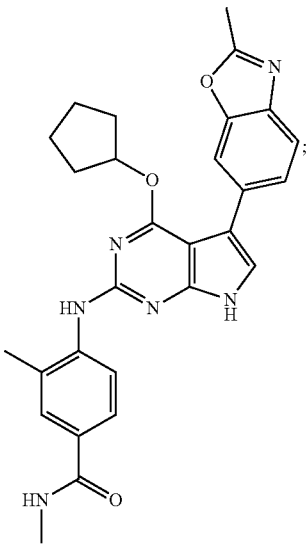
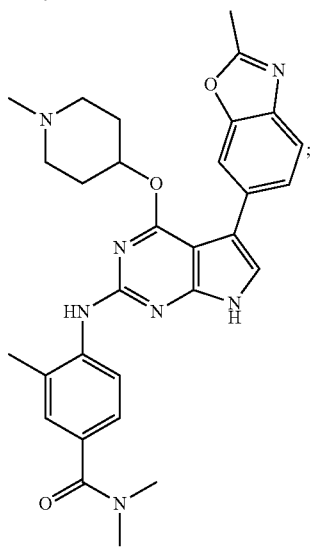
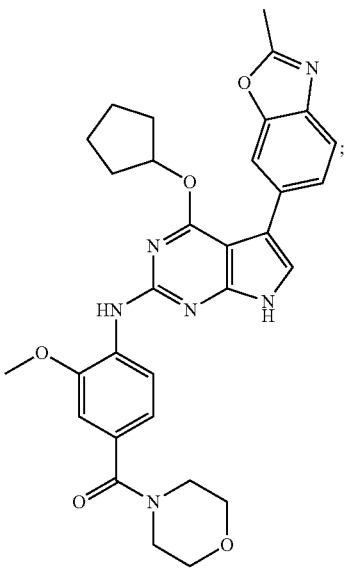

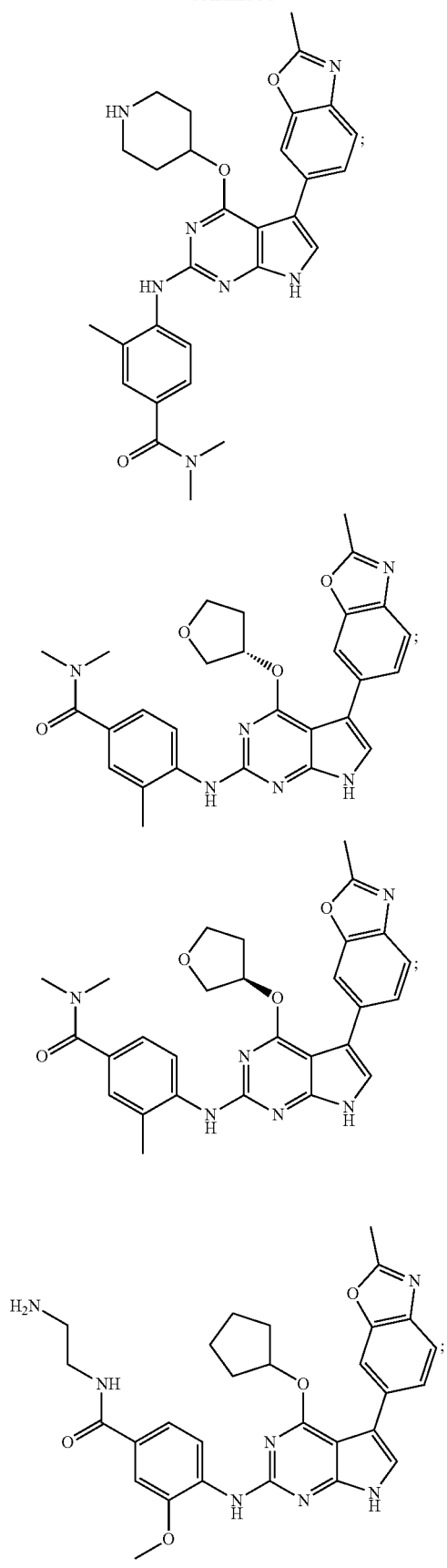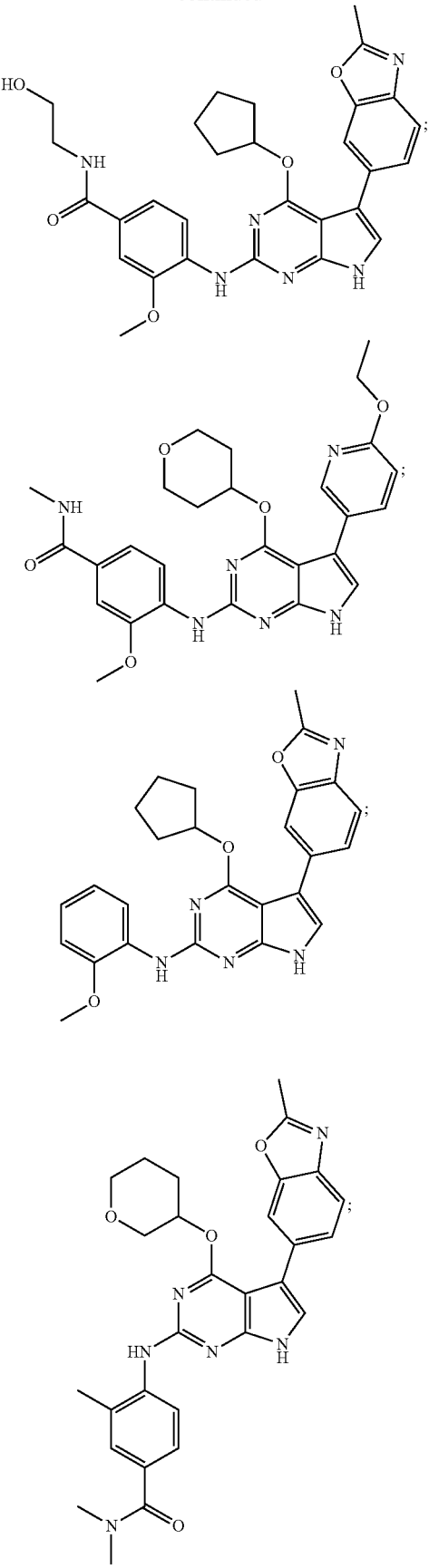

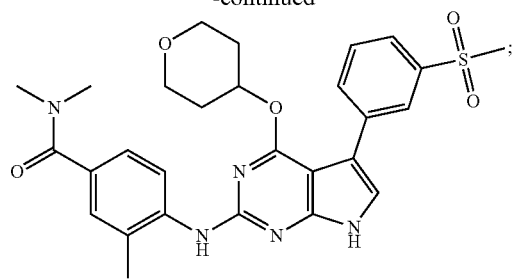
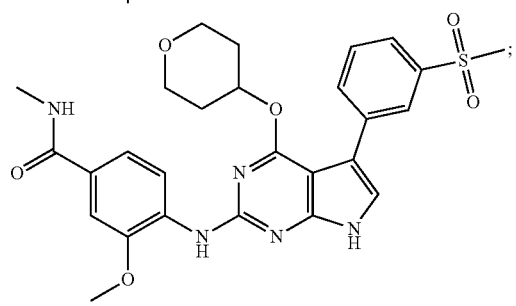
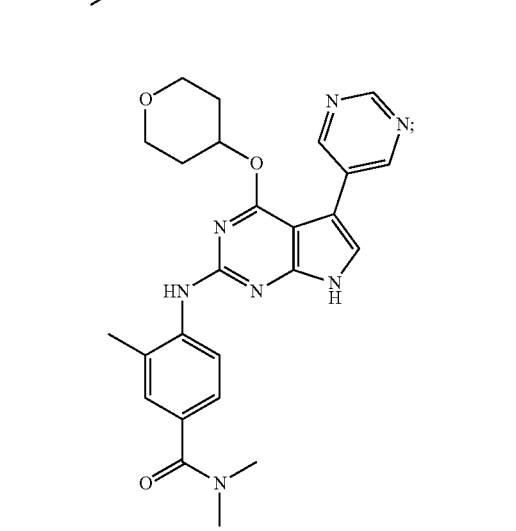
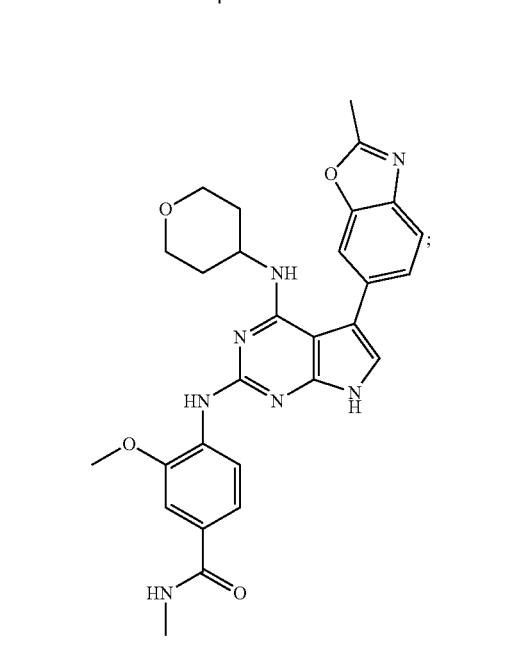
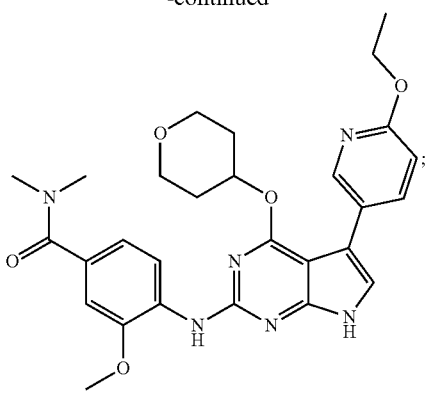
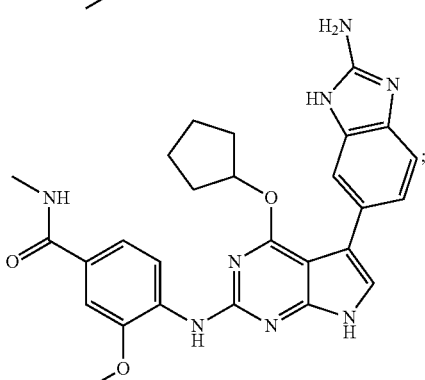
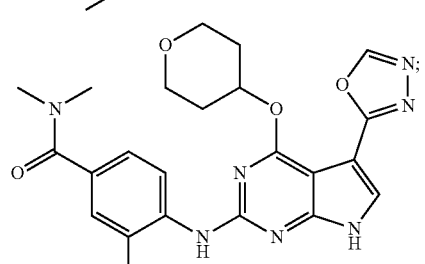
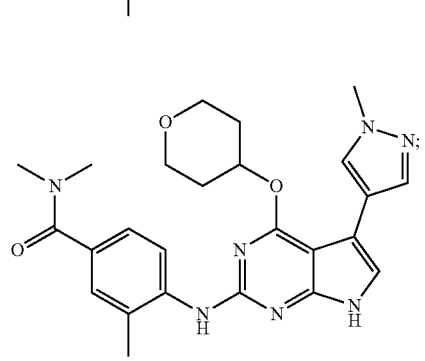
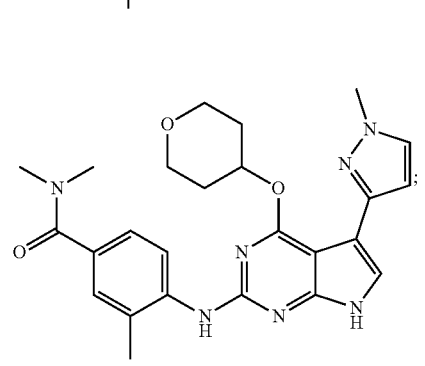

401
-continued
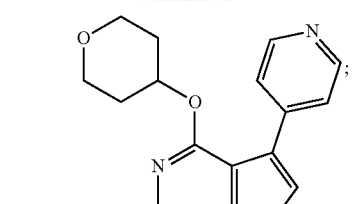
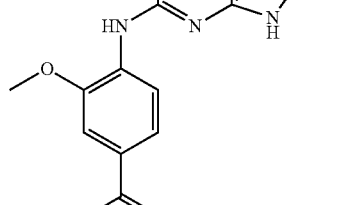
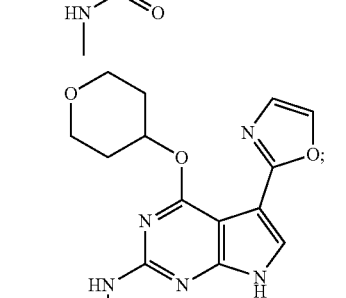
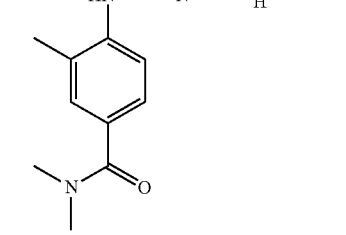
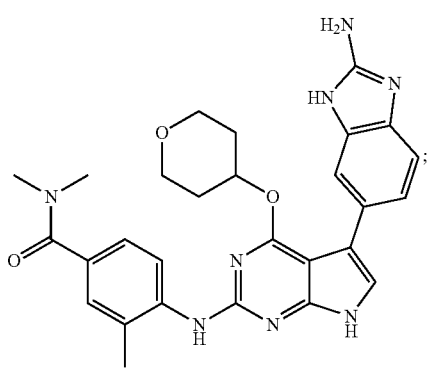
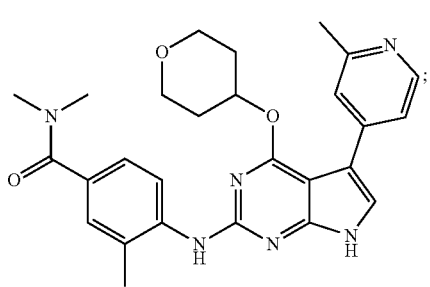
402
-continued
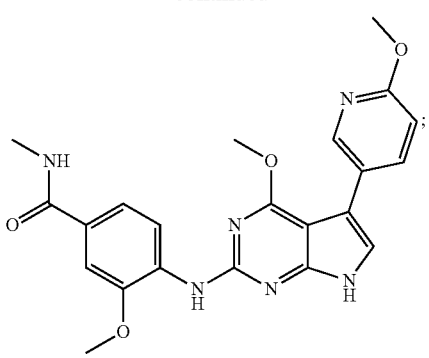
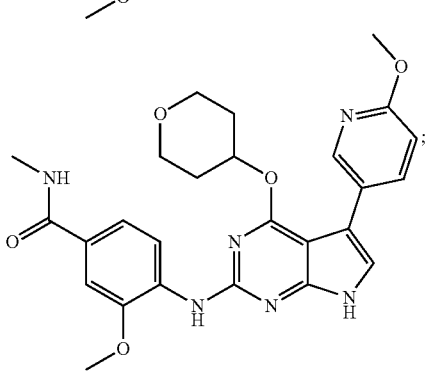
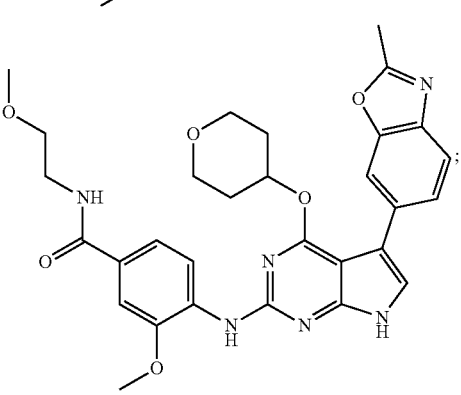
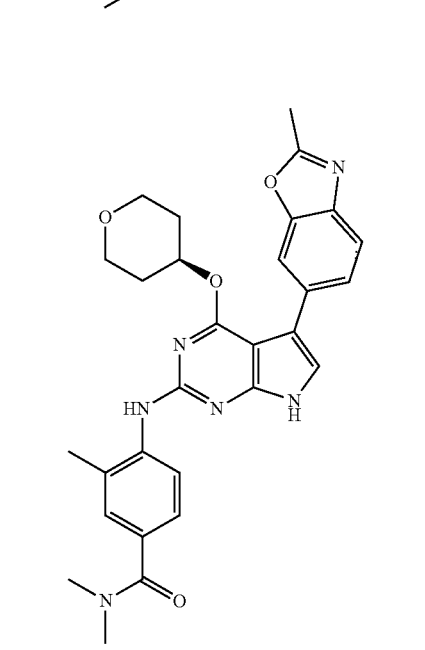

403
-continued
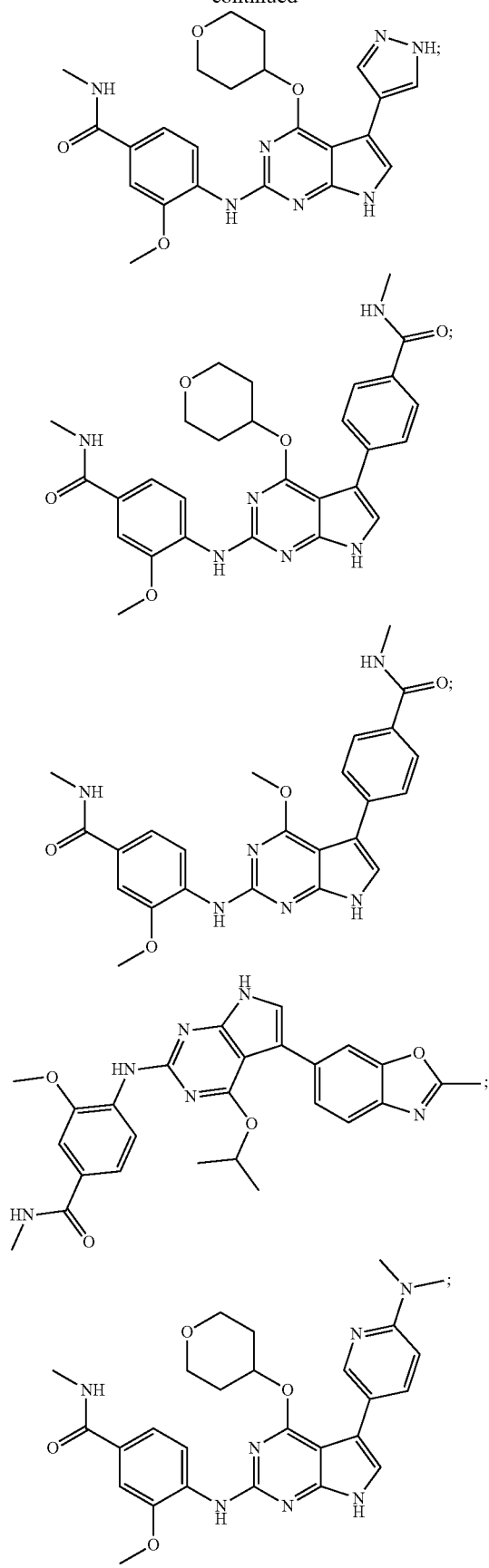
404
-continued
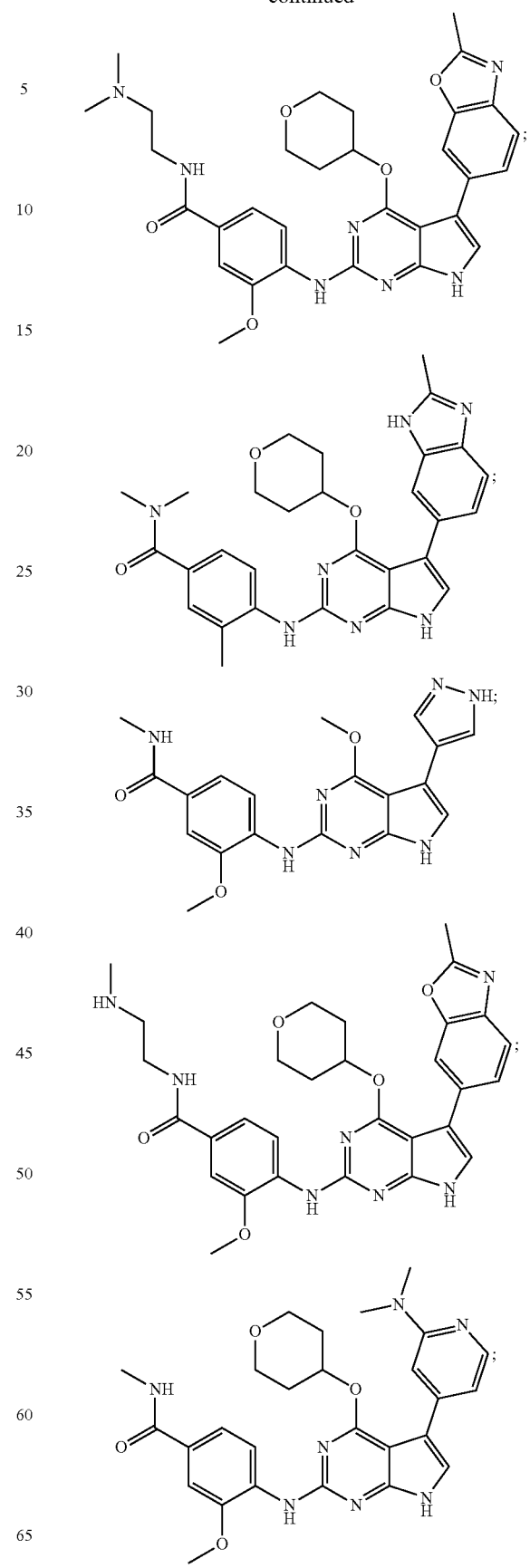

405
-continued
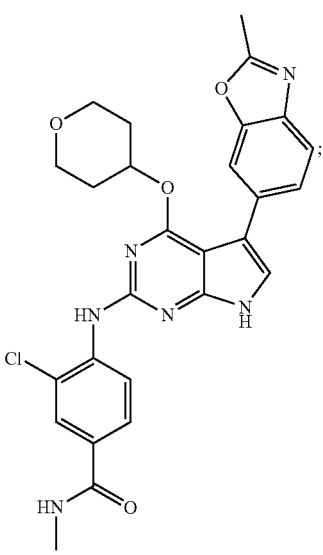
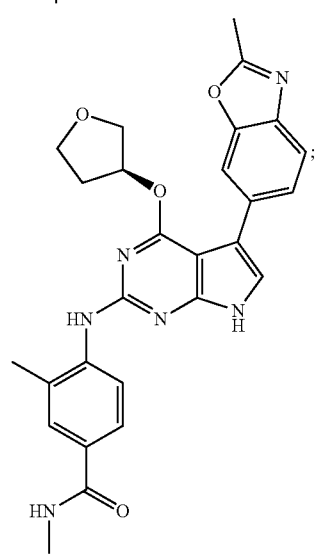
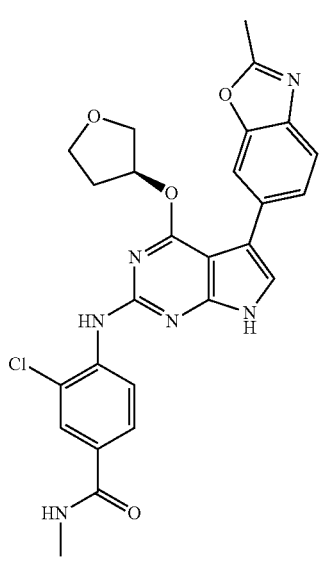
406
-continued
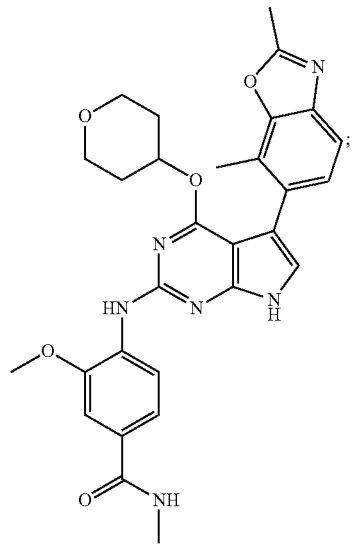
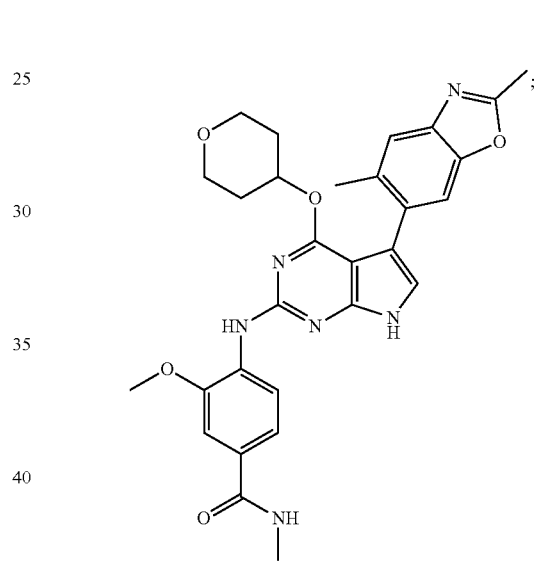
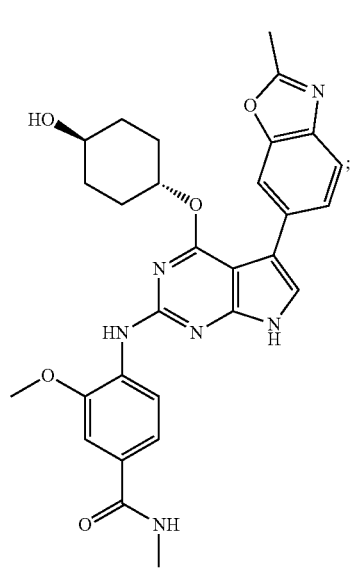

407
-continued
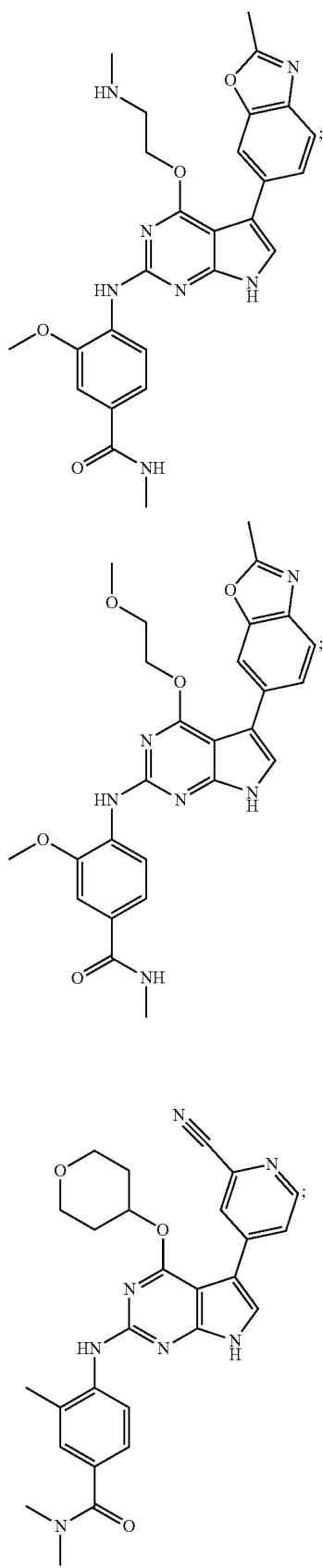
408
-continued
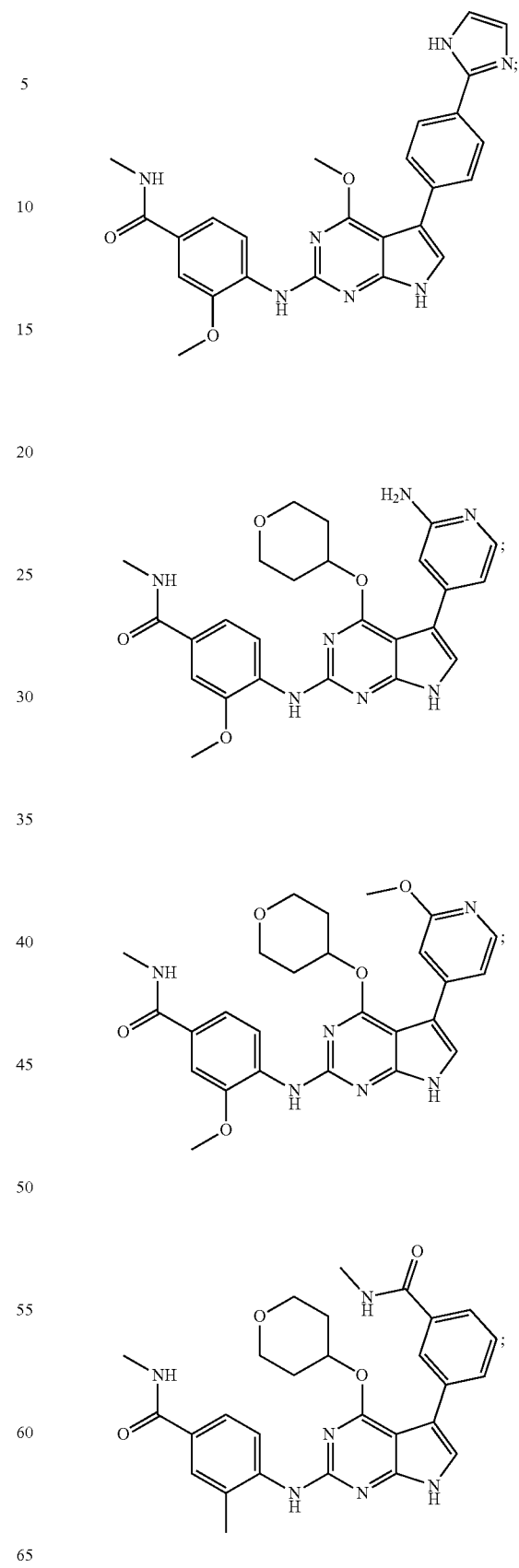

409
-continued
410
-continued
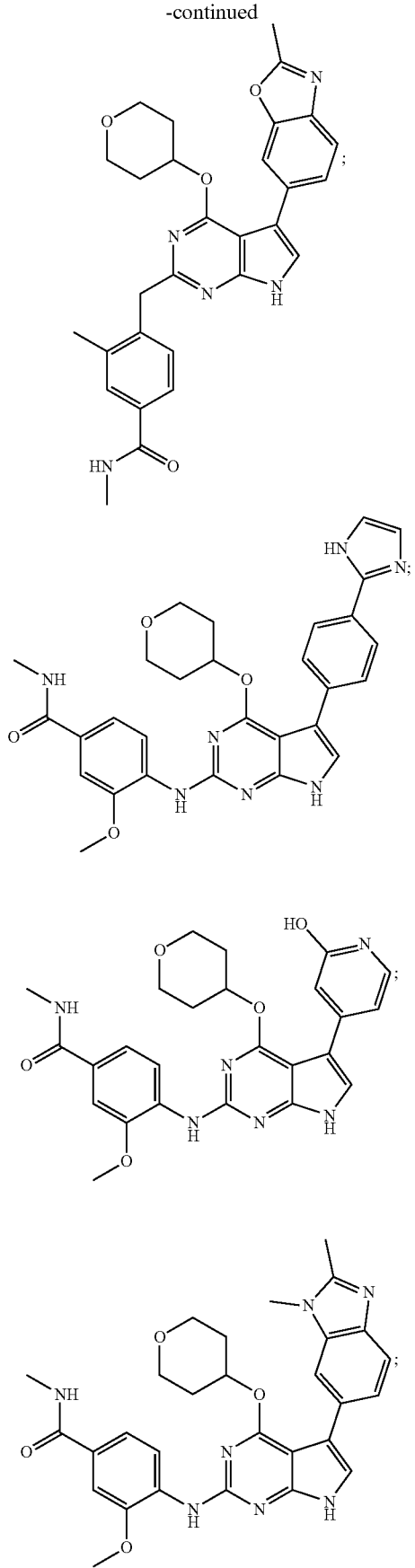
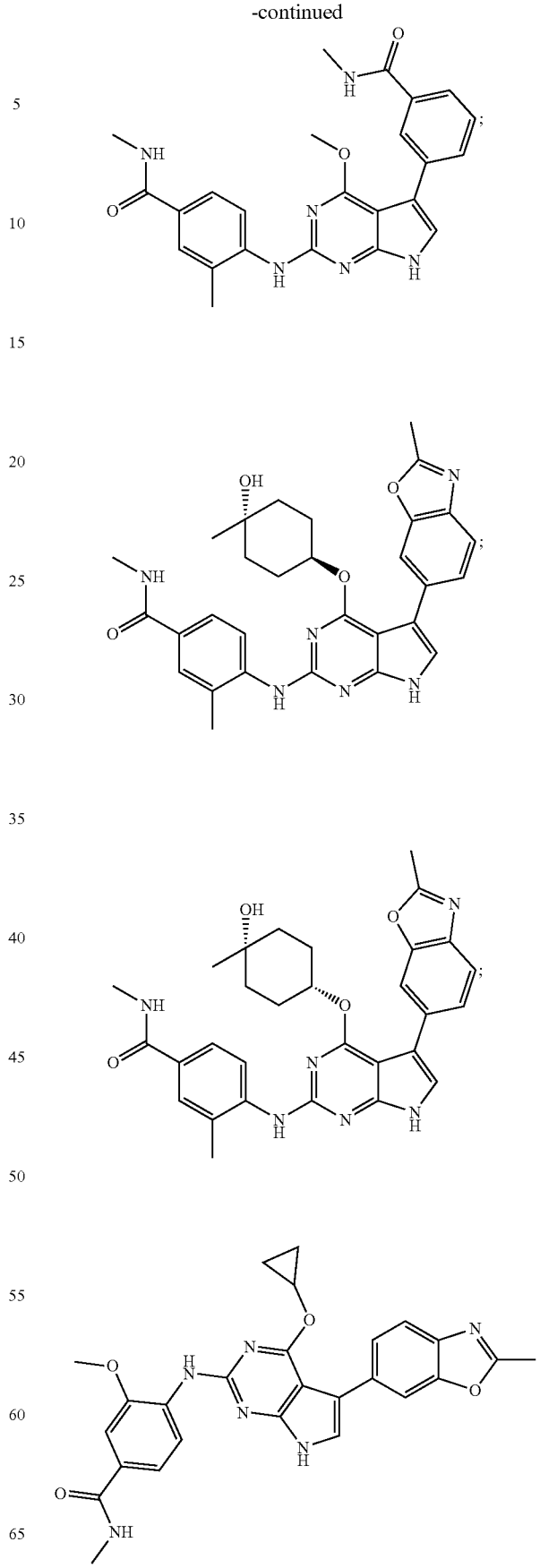

411
-continued
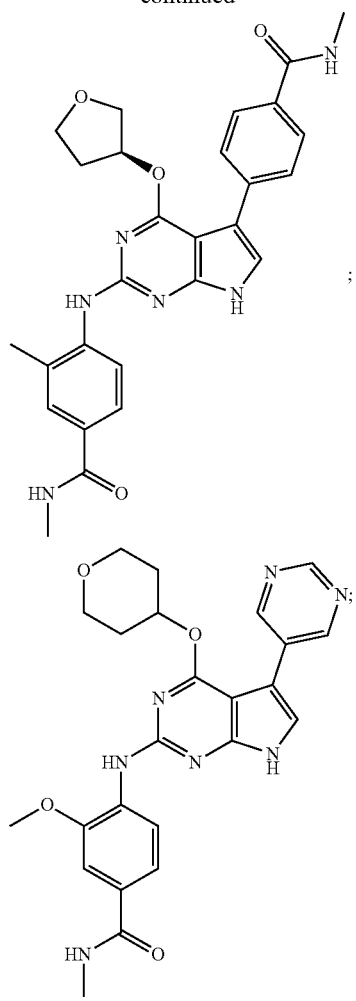
412
-continued
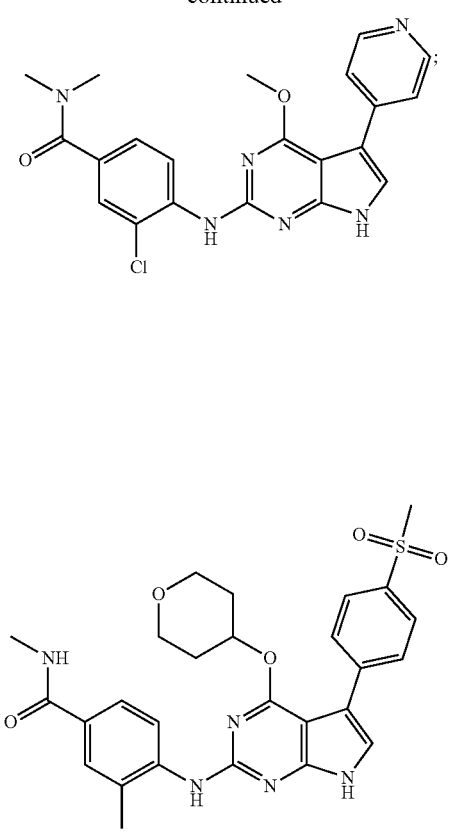
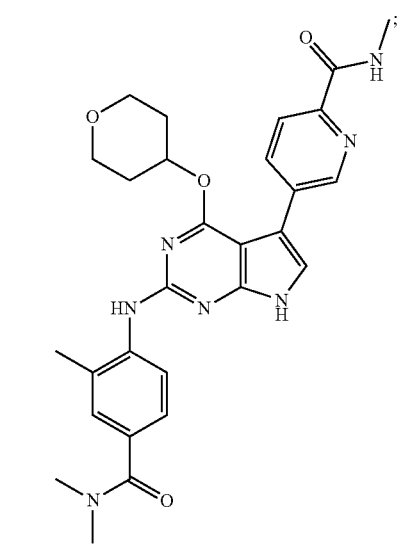

413
-continued
414
-continued
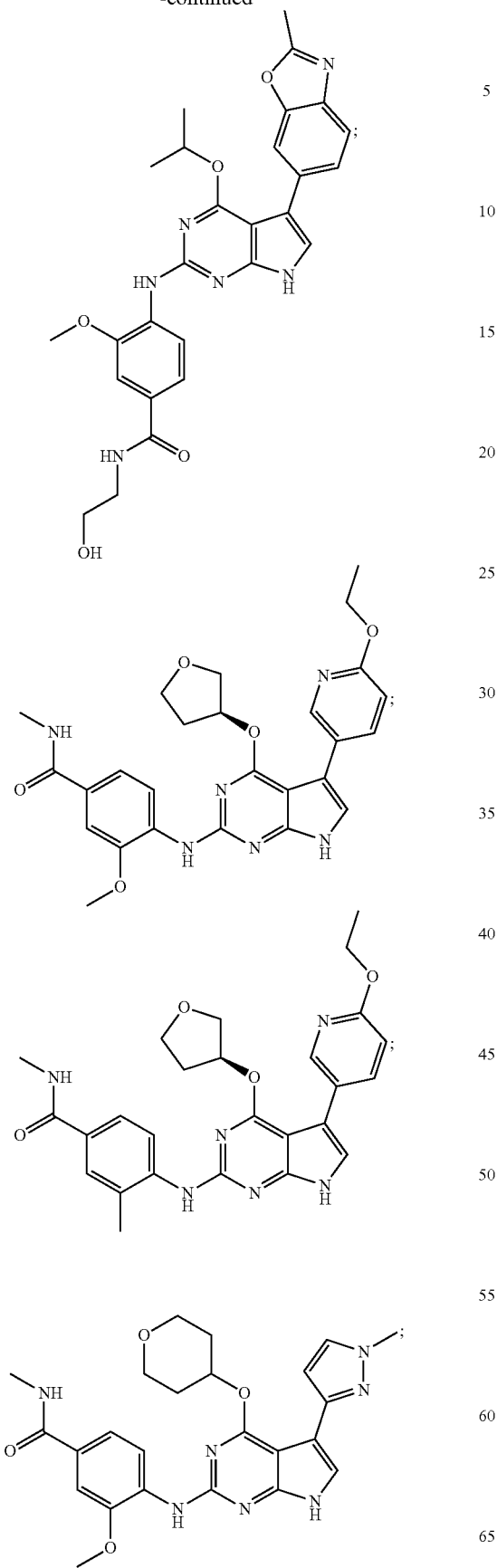
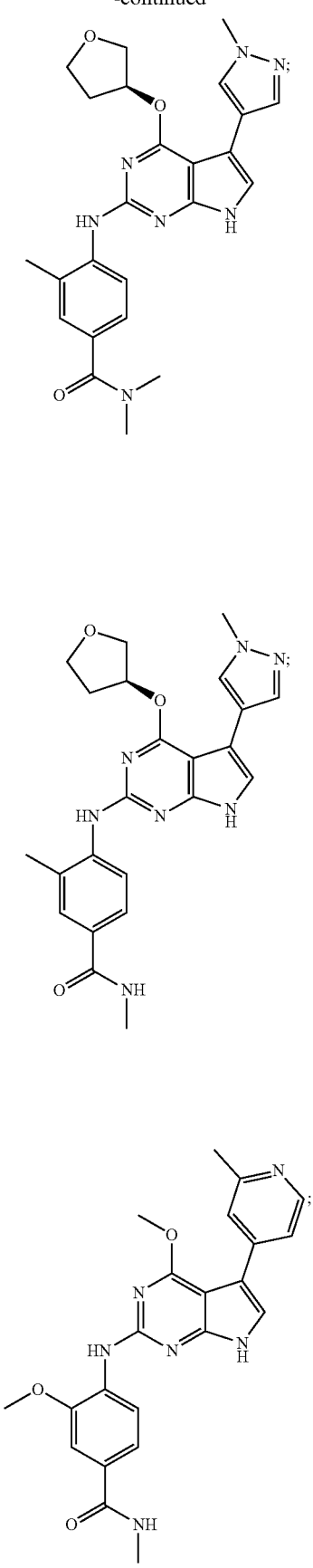

415
-continued
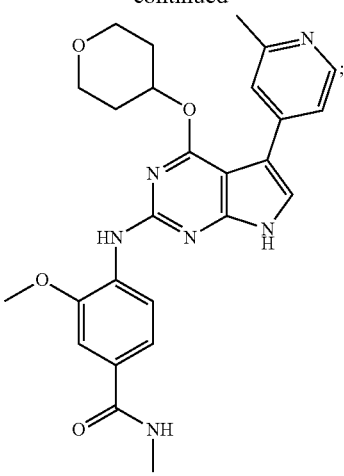
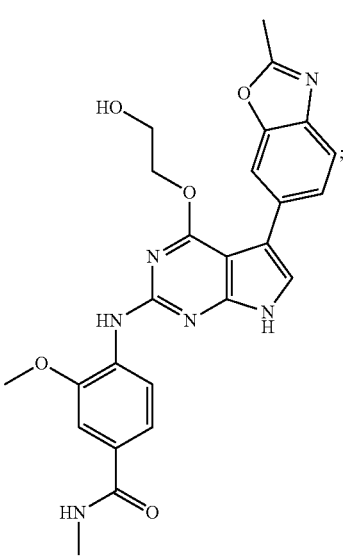
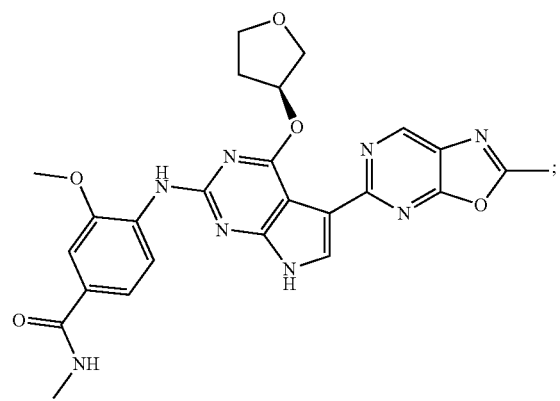
416
-continued
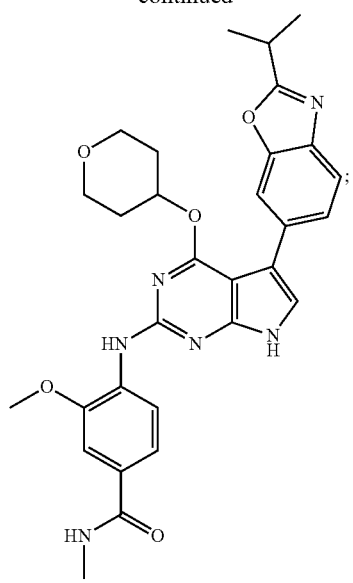
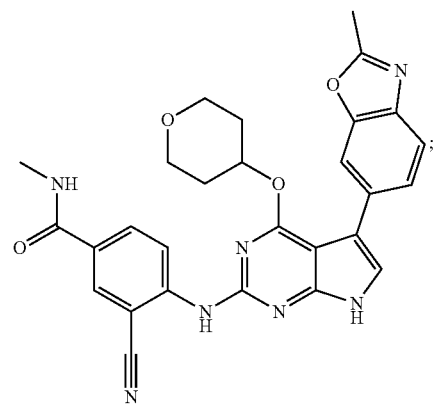
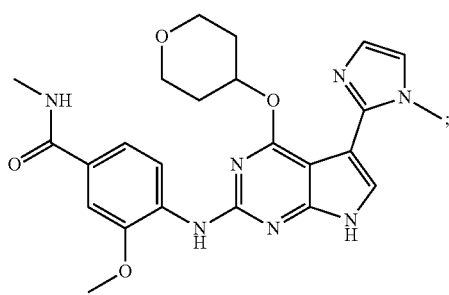
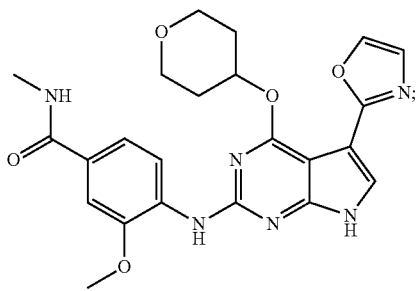

417
-continued
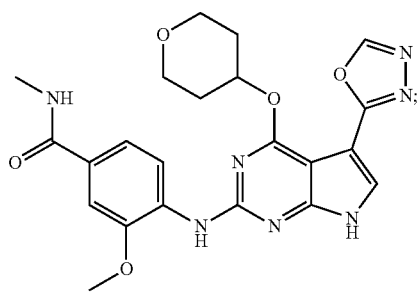
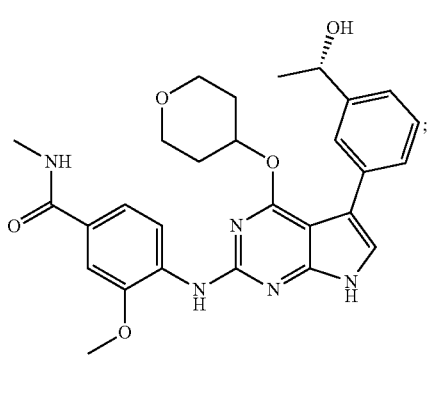
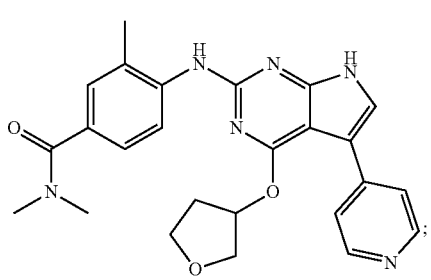
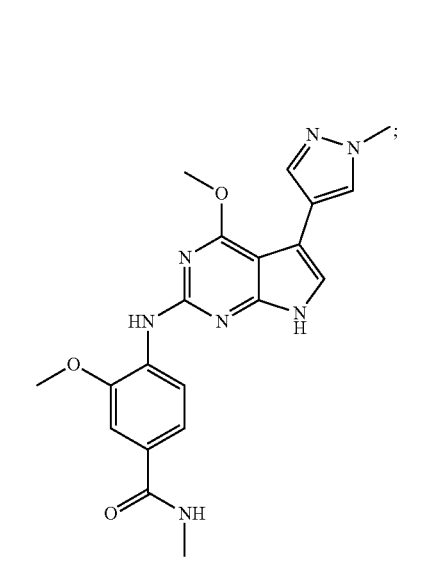
418
-continued
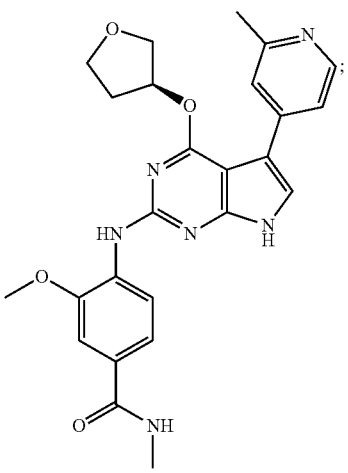
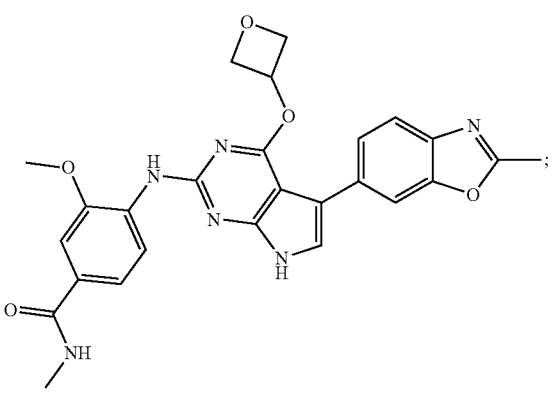
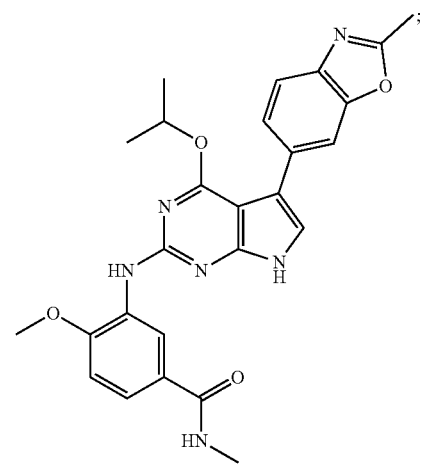

419
-continued
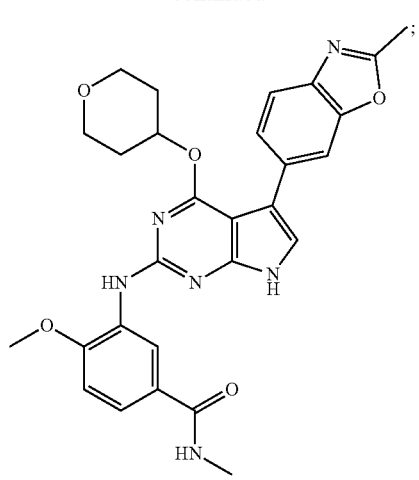
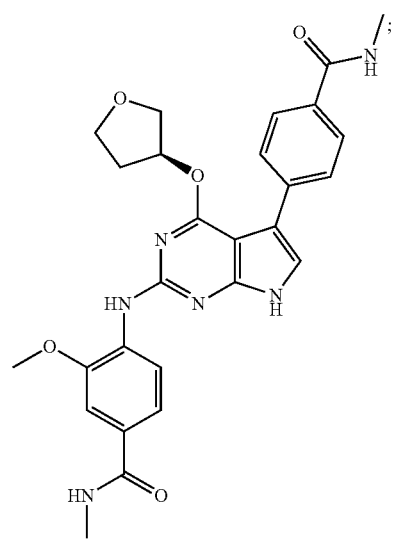
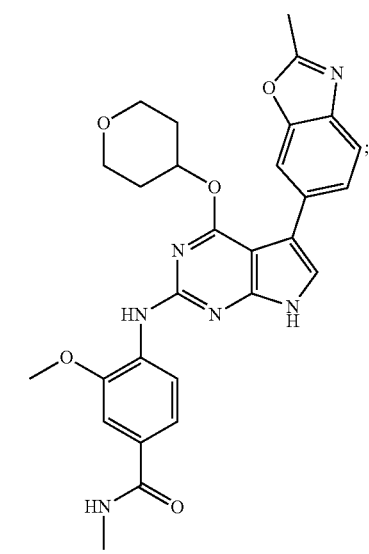
420
-continued
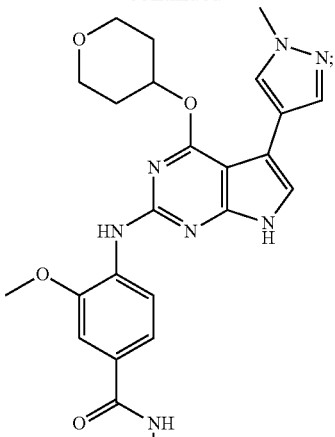
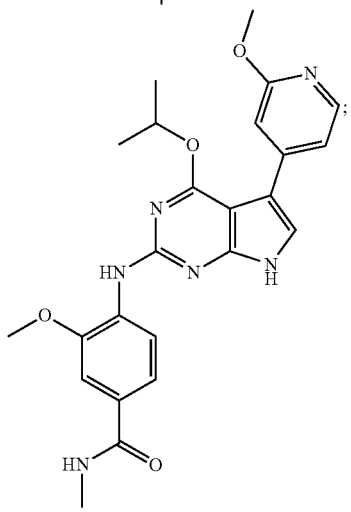
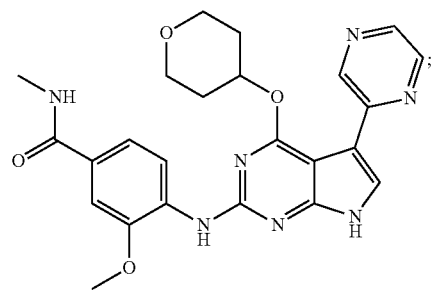
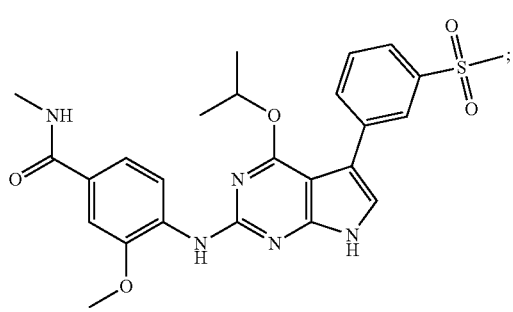

421
-continued
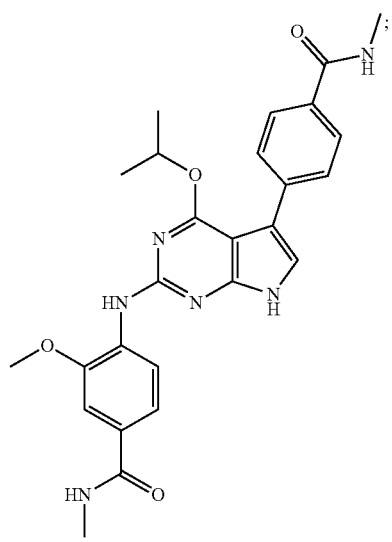
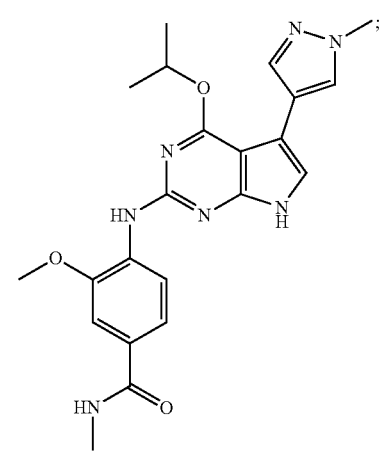
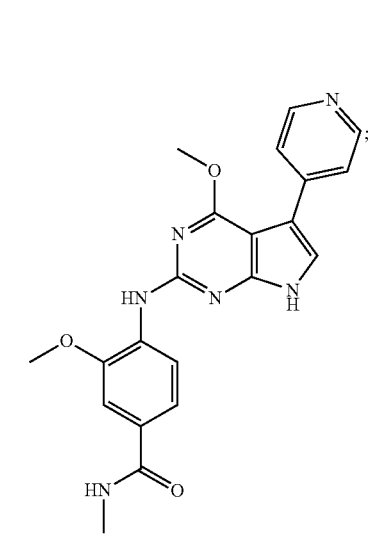
422
-continued
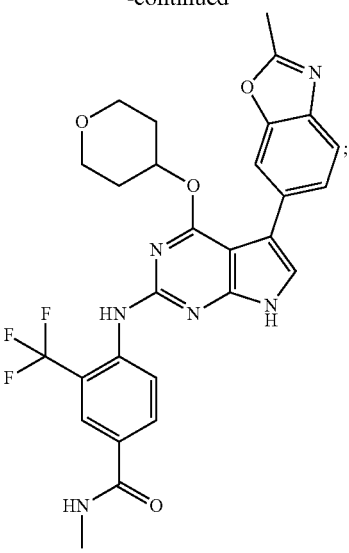
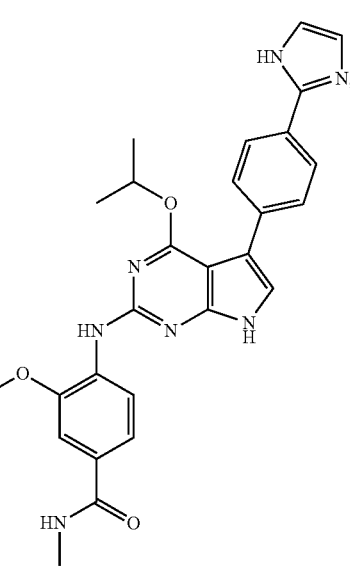
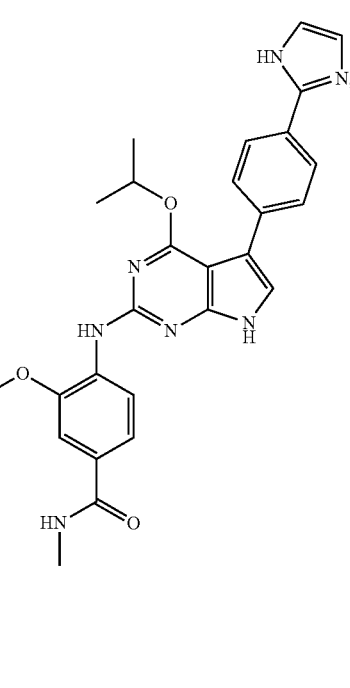

423
-continued
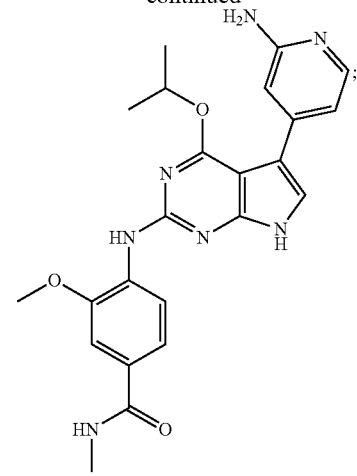
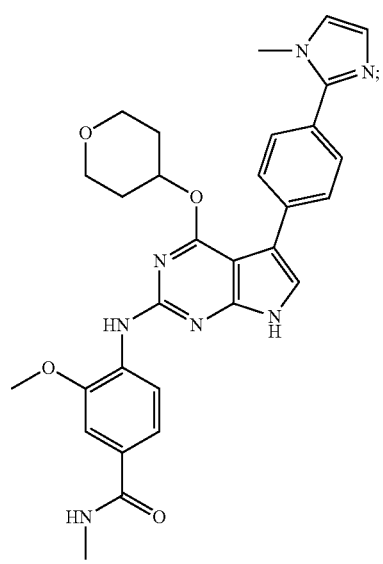
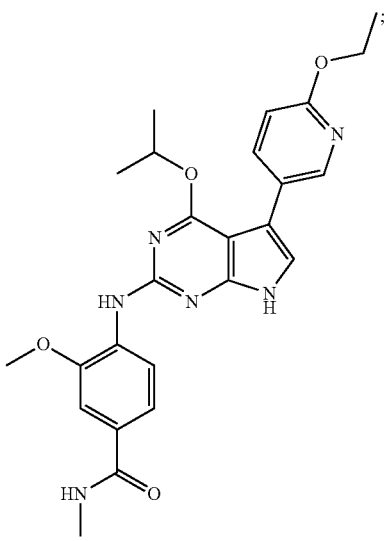
424
-continued
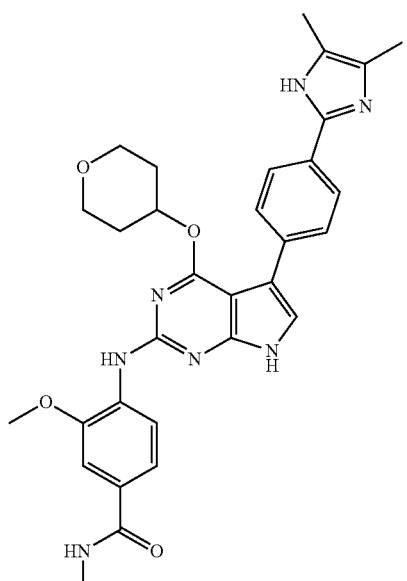
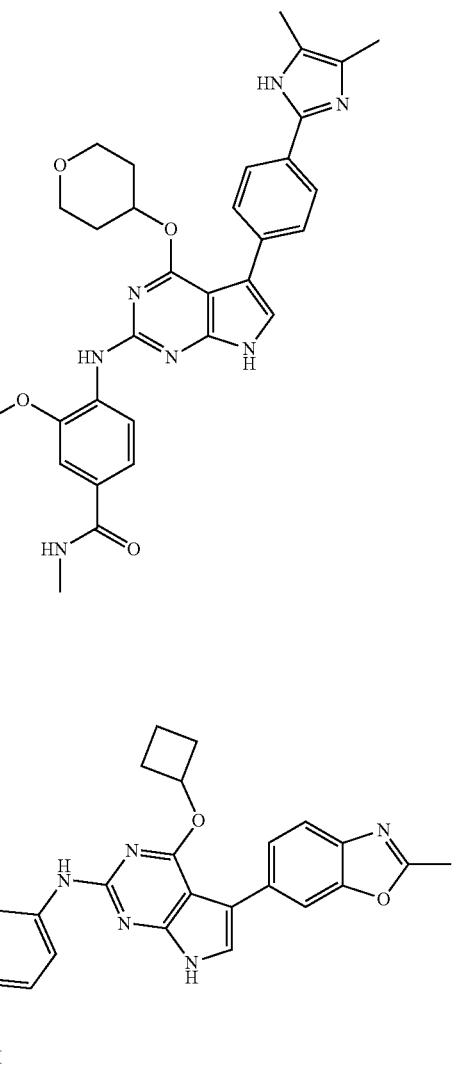
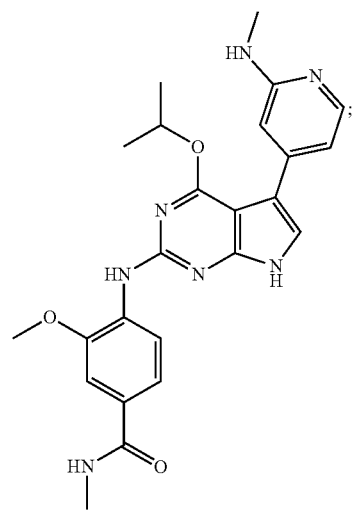

425
-continued
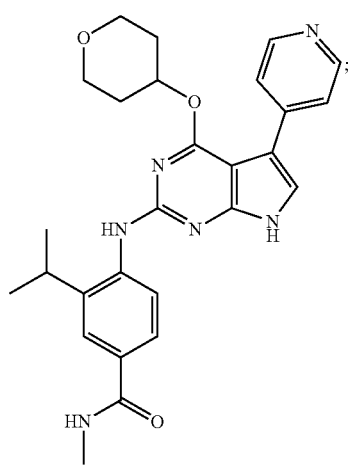
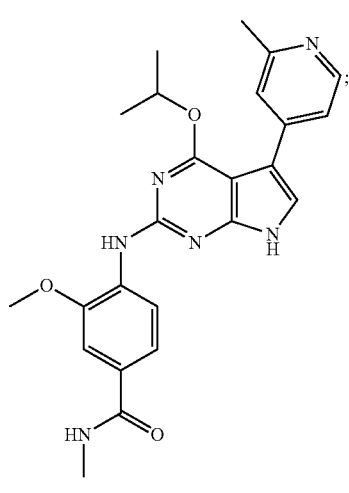
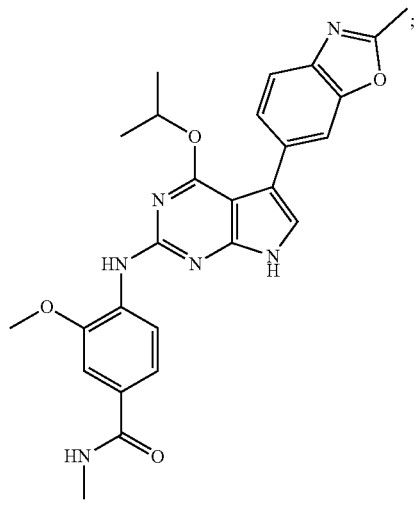
426
-continued
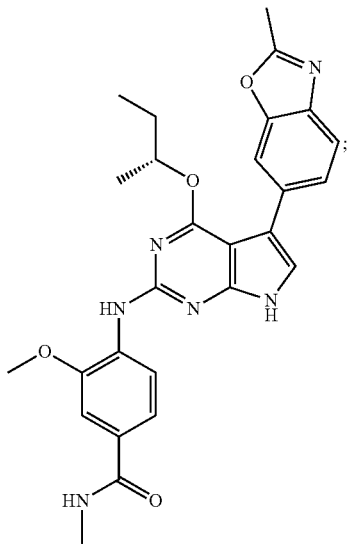
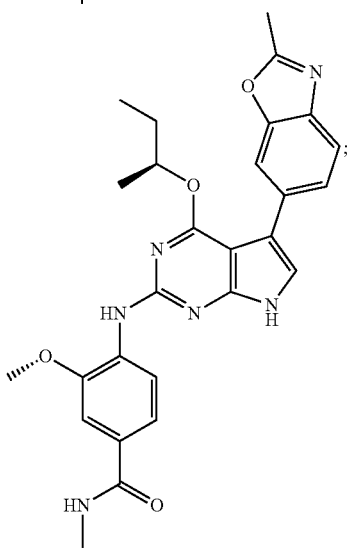
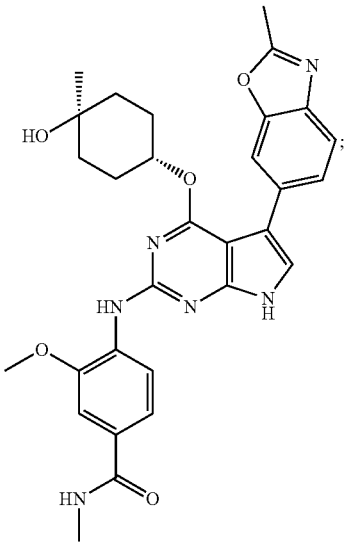

427
-continued
428
-continued
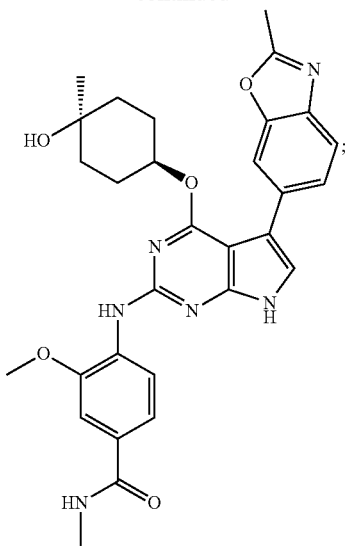
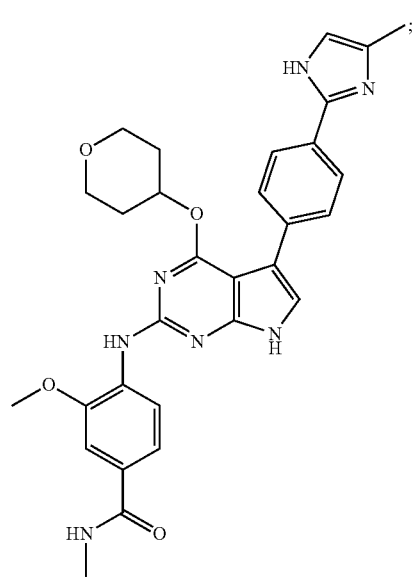
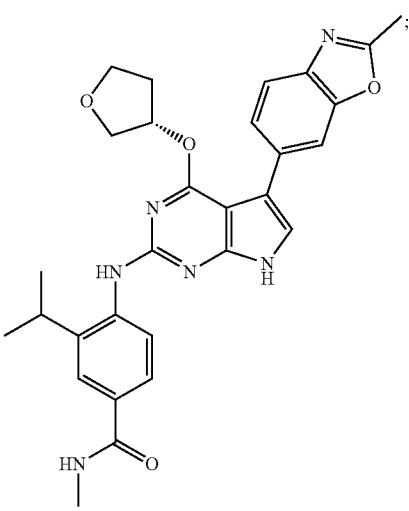
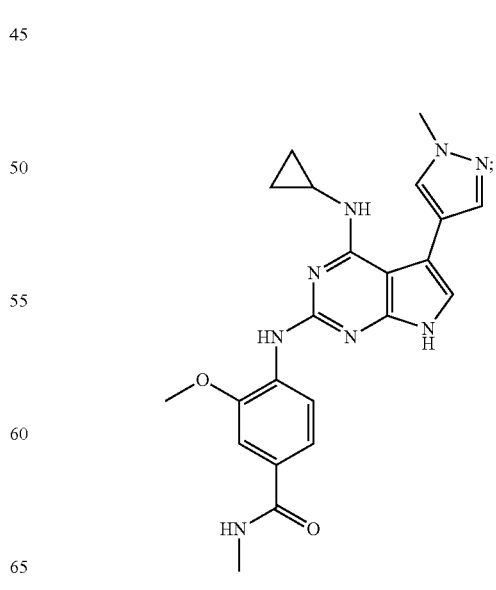

429
-continued
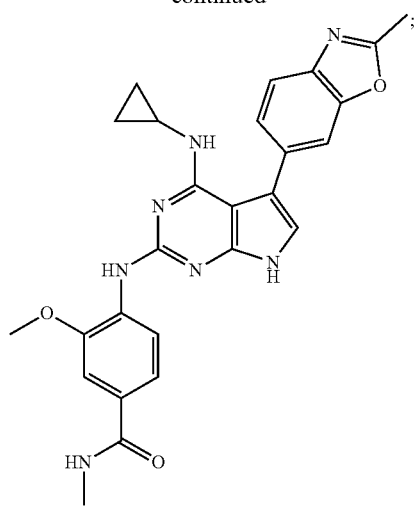
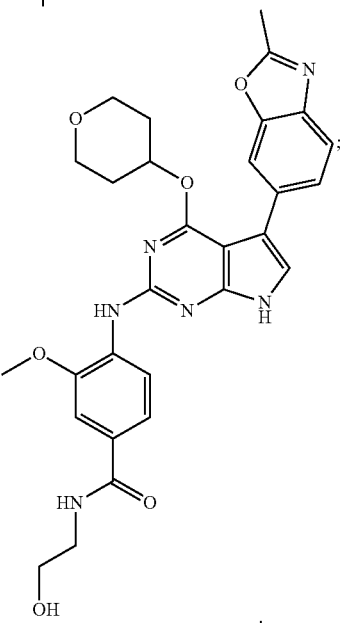
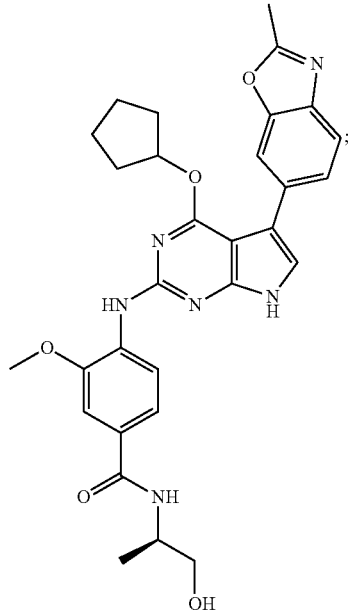
430
-continued
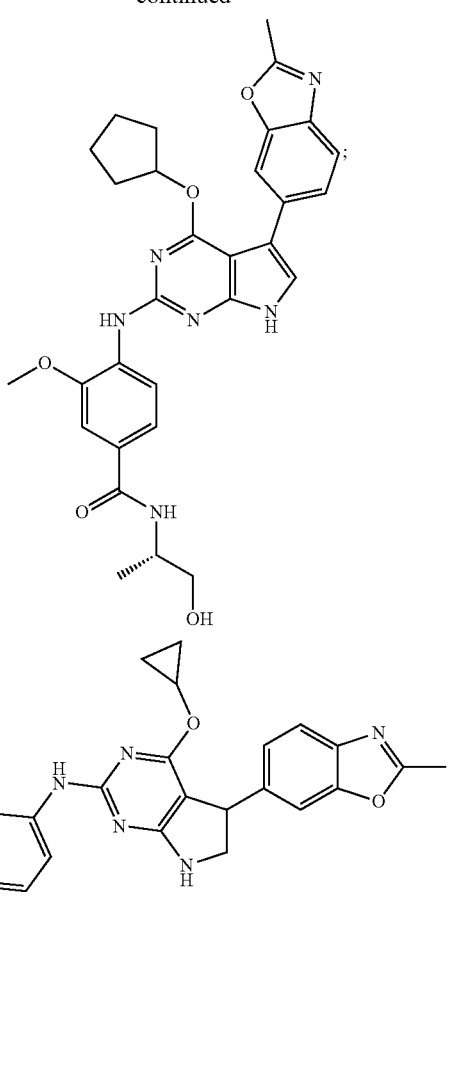
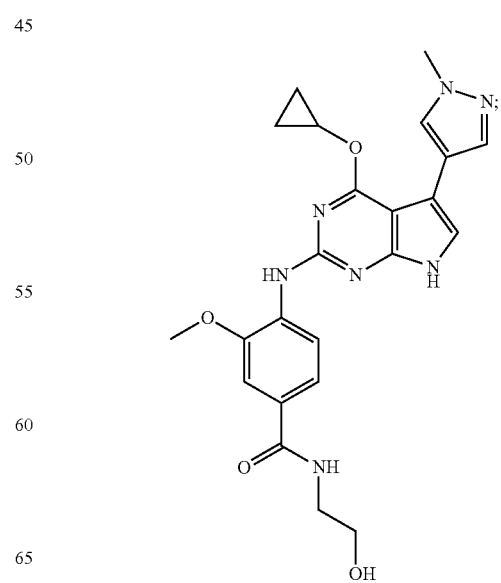

431
-continued
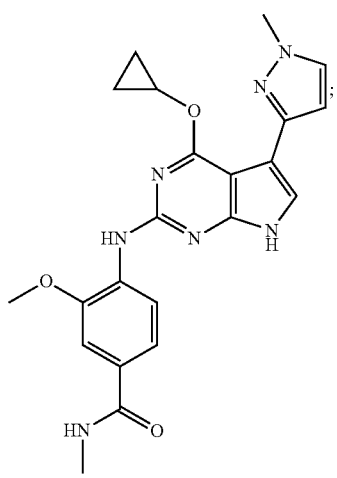
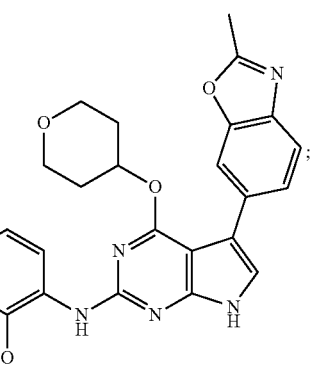
432
-continued
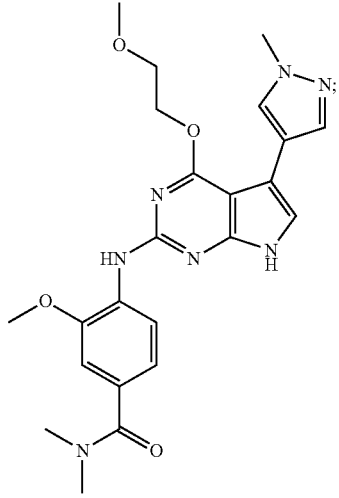
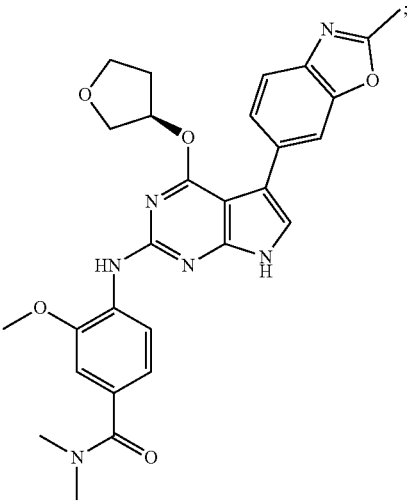
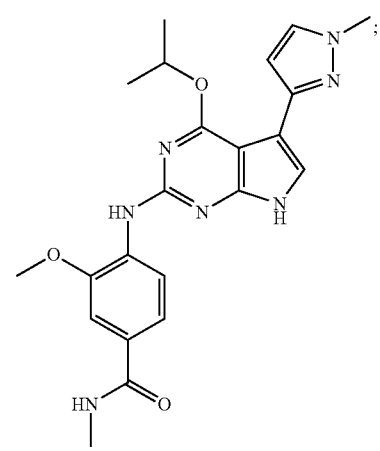
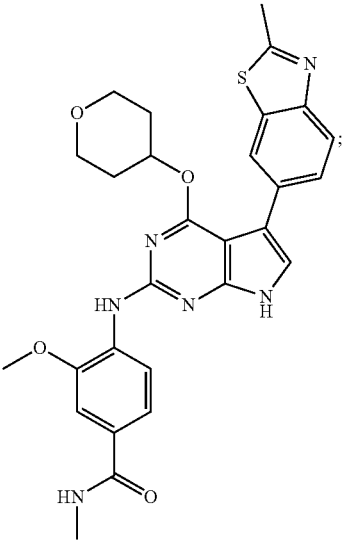

433
-continued
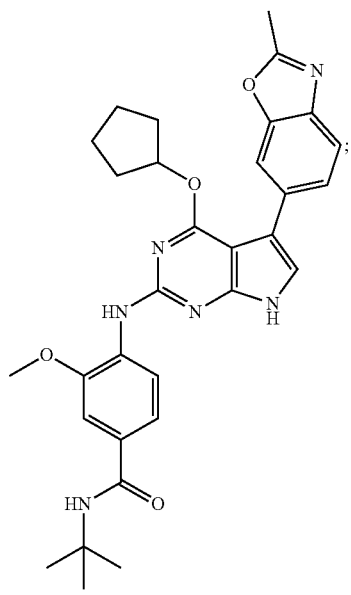
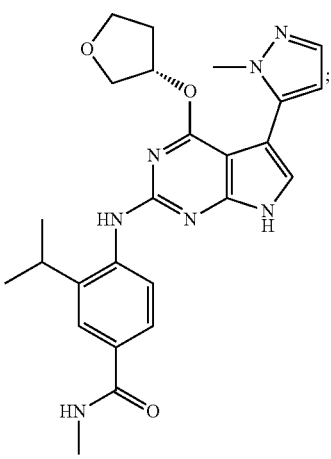
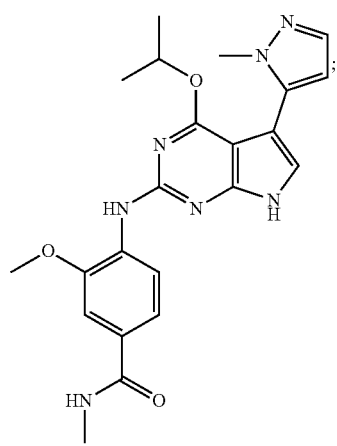
434
-continued
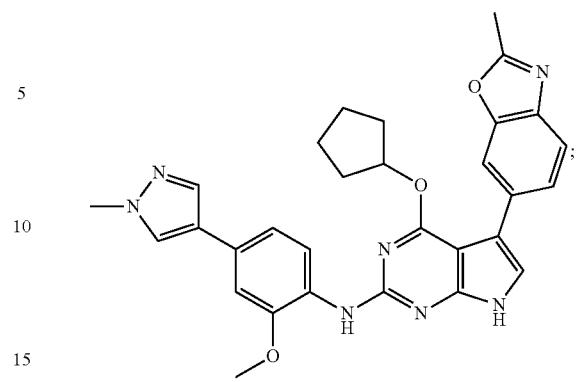
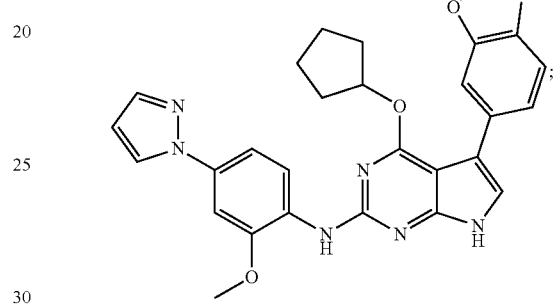
end 54
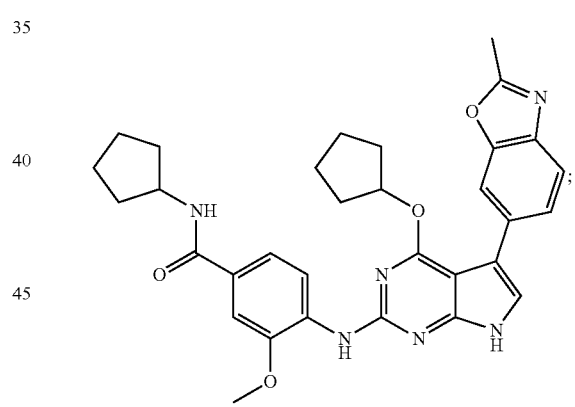
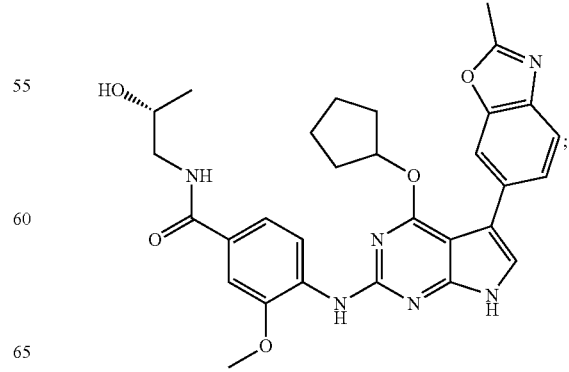

435
-continued
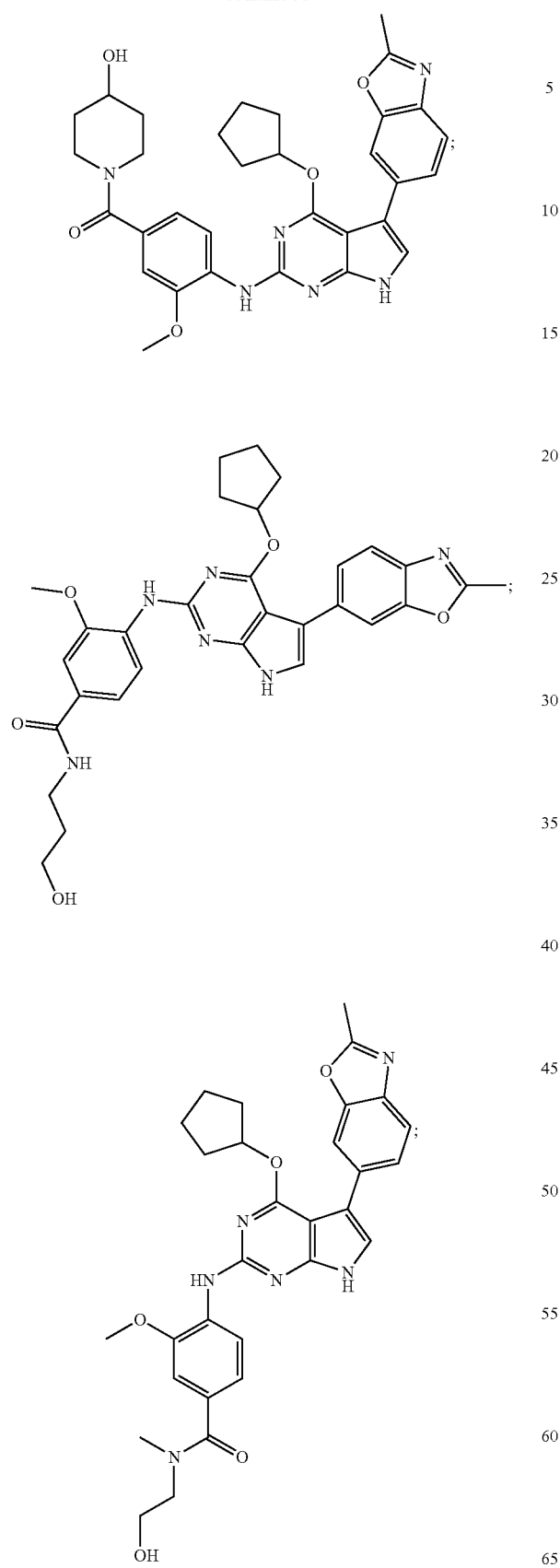
436
-continued
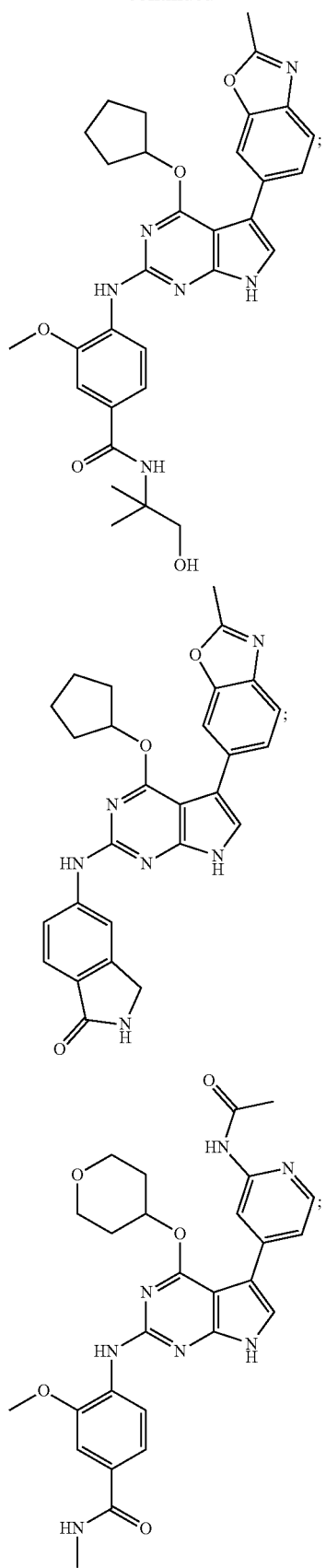

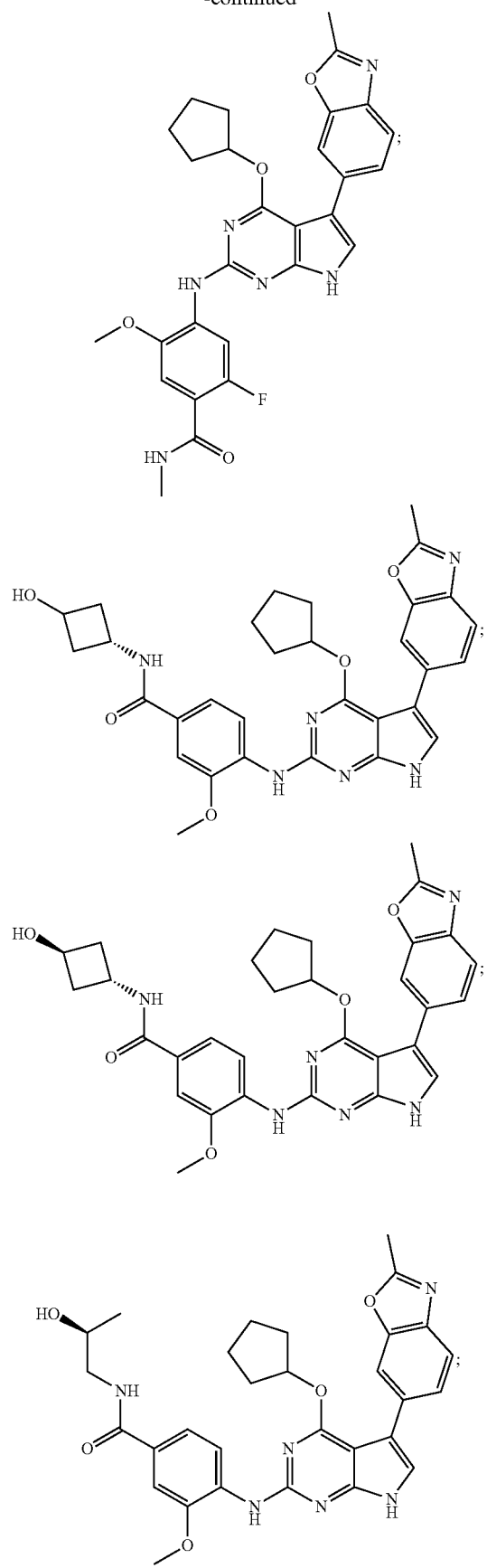
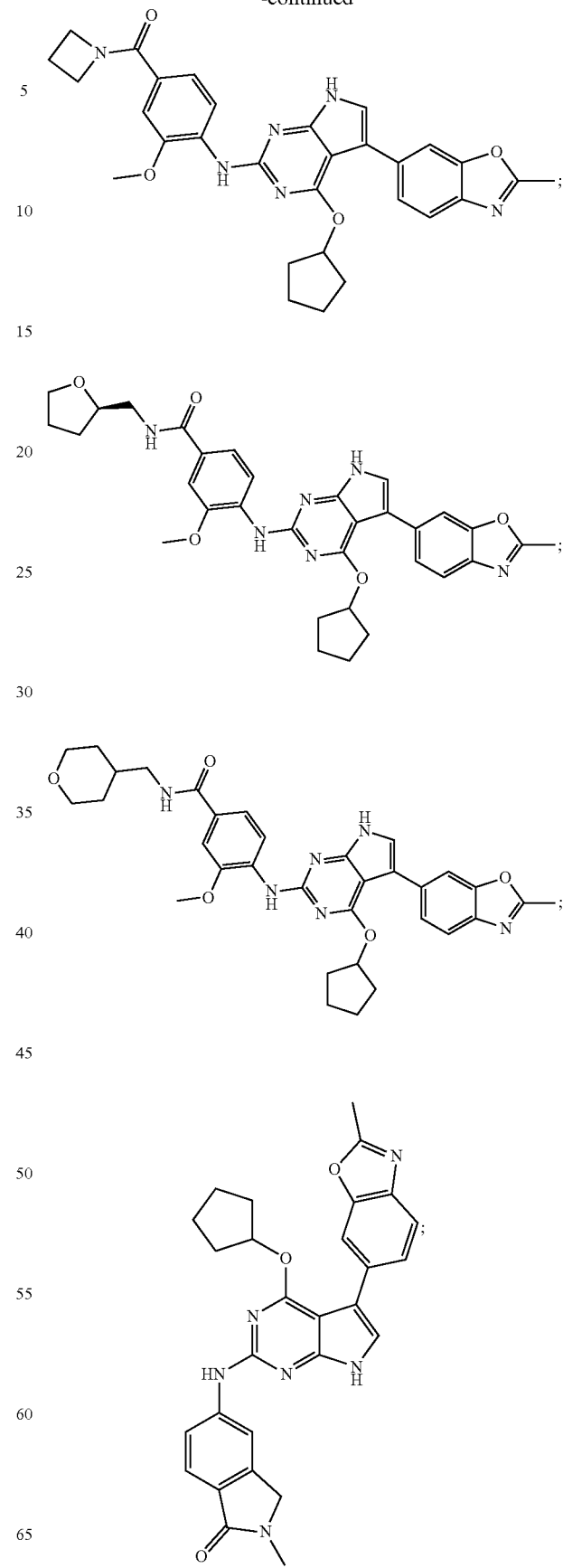

439
-continued
440
-continued
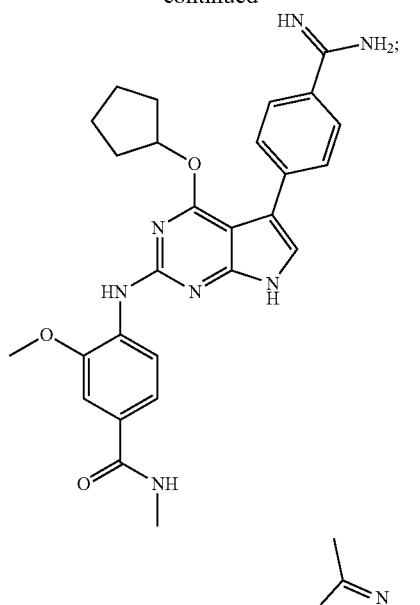
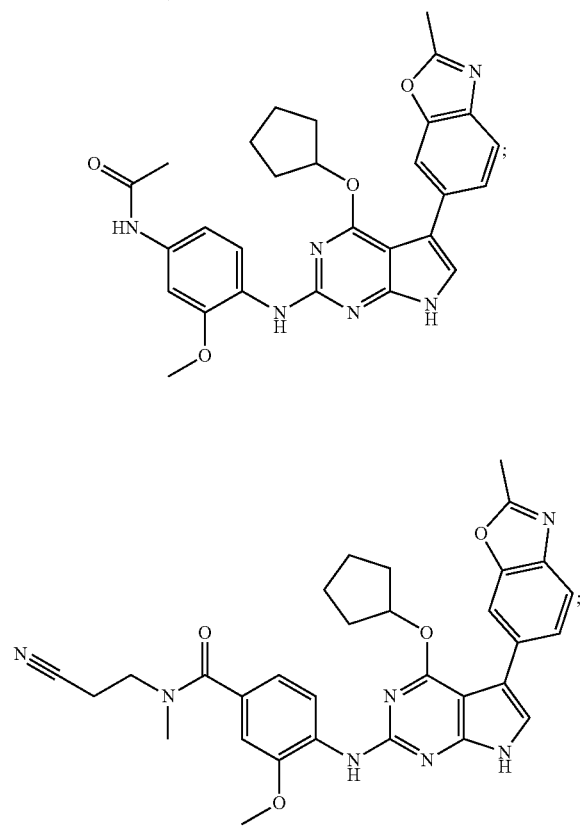
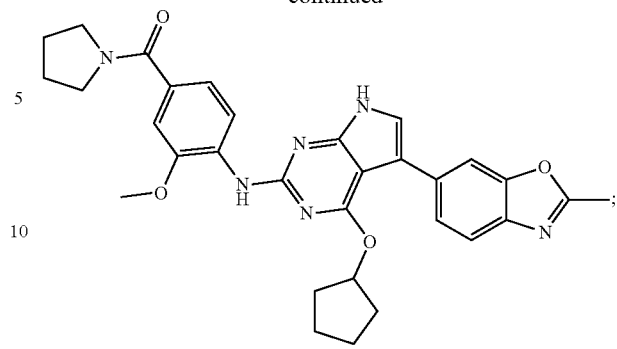
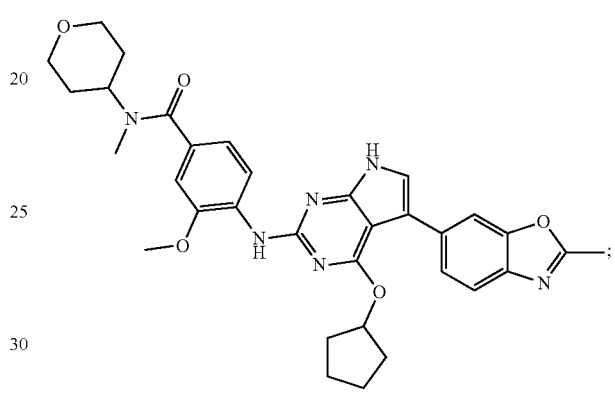
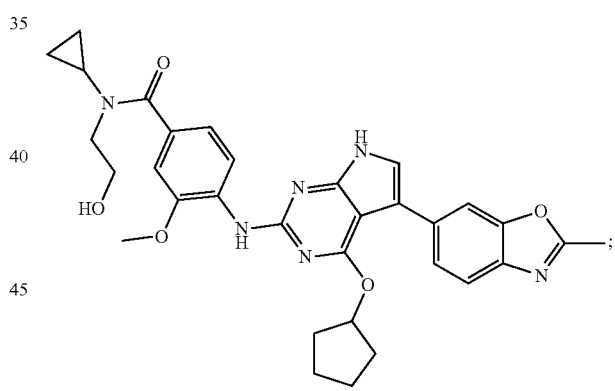

441
-continued
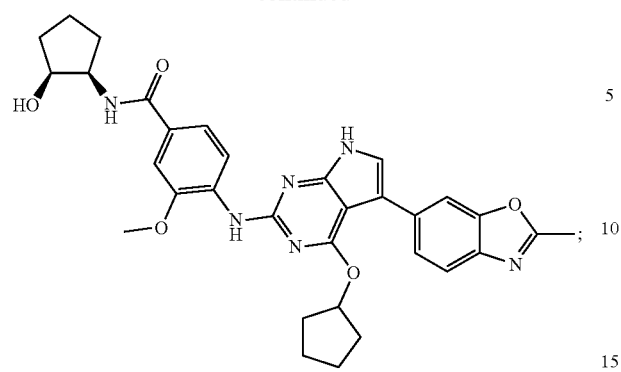
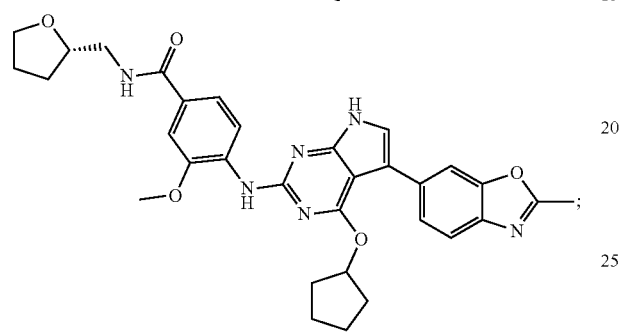
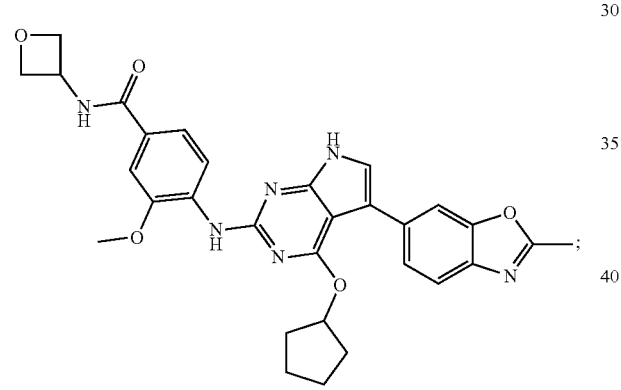
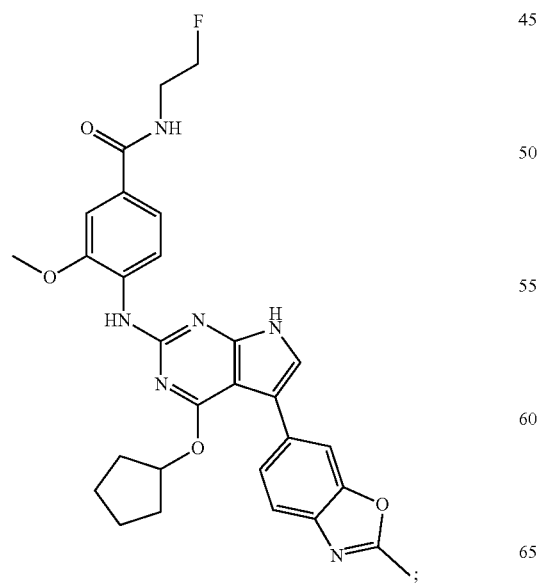
442
-continued
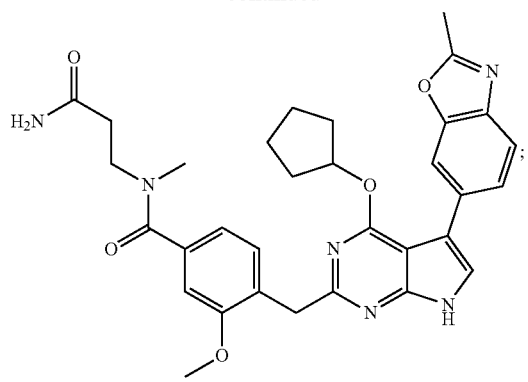
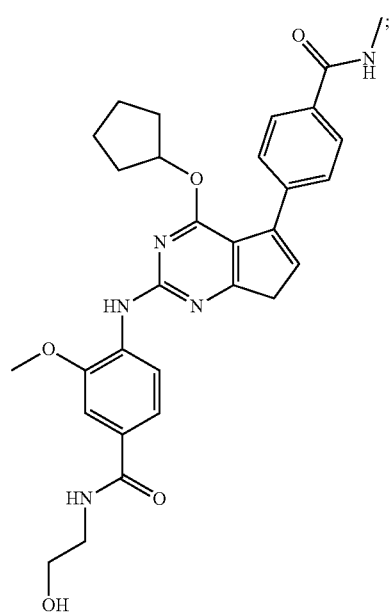
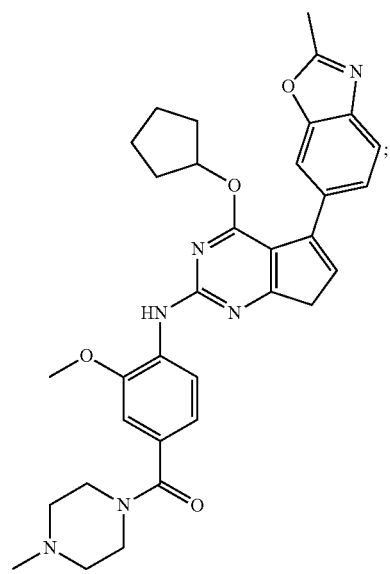

443
-continued
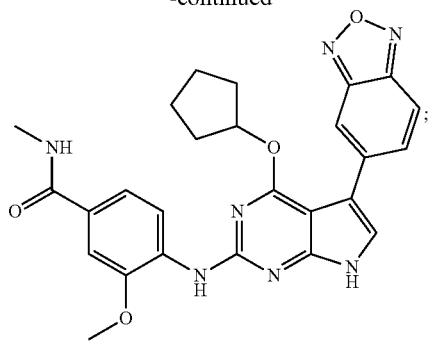
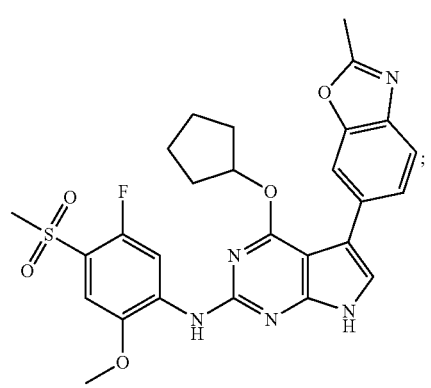
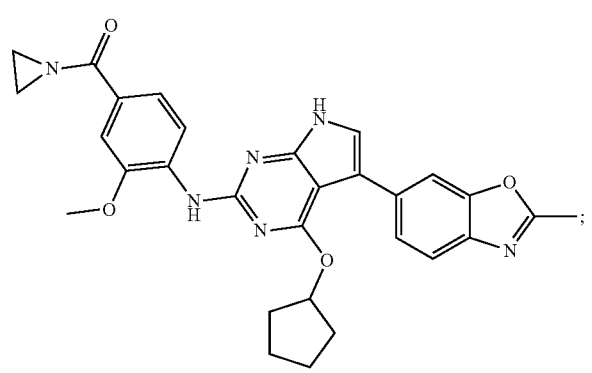
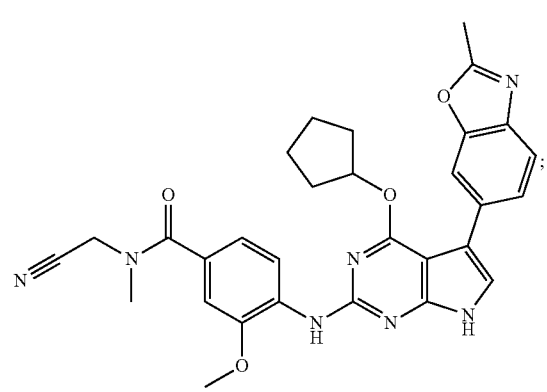
444
-continued
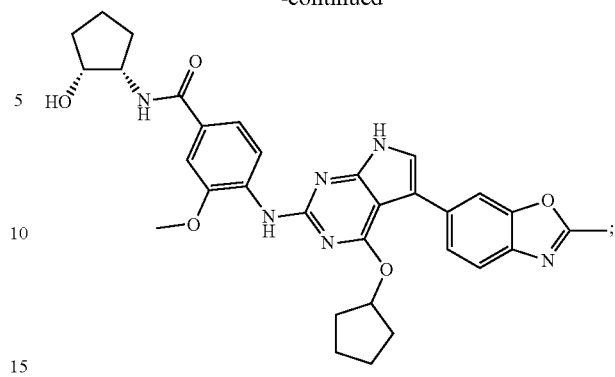
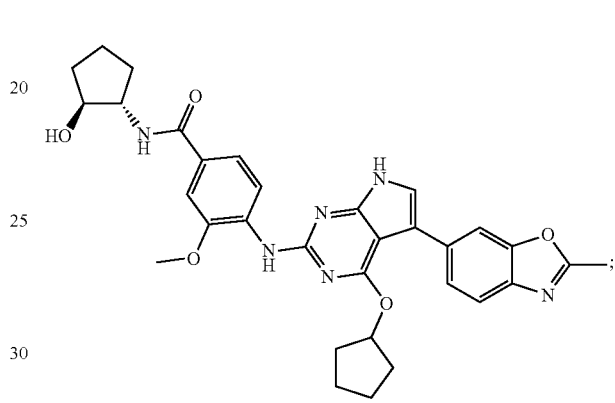
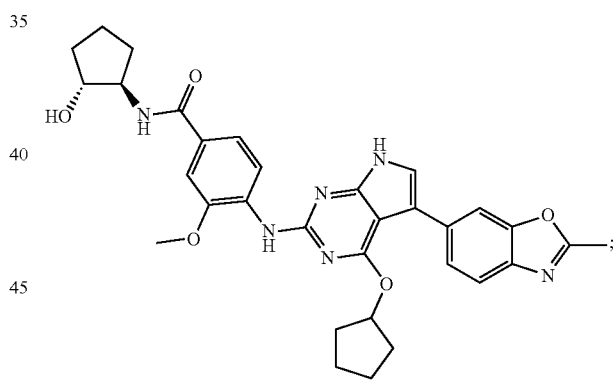
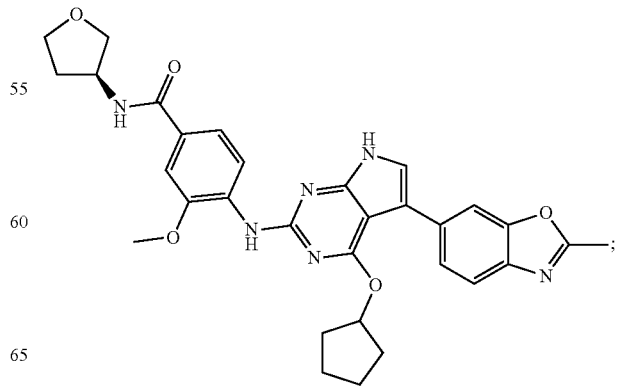

445
-continued
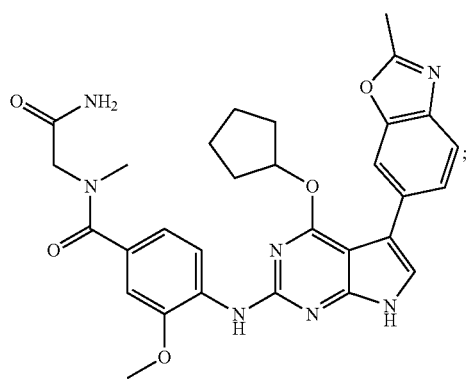
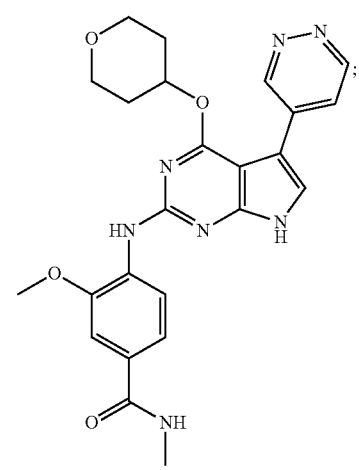
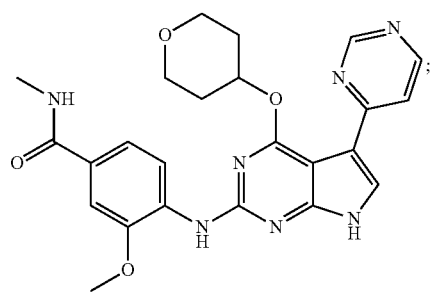
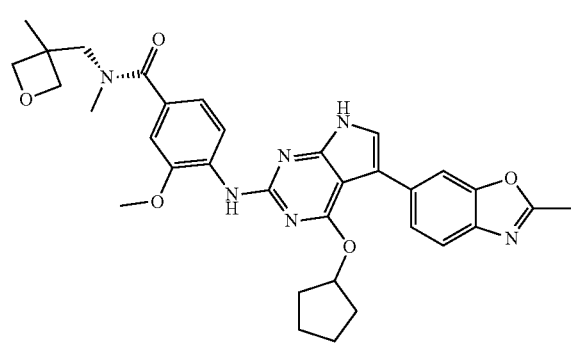
446
-continued
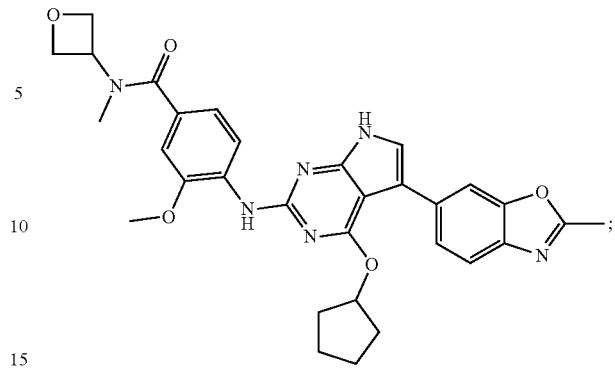
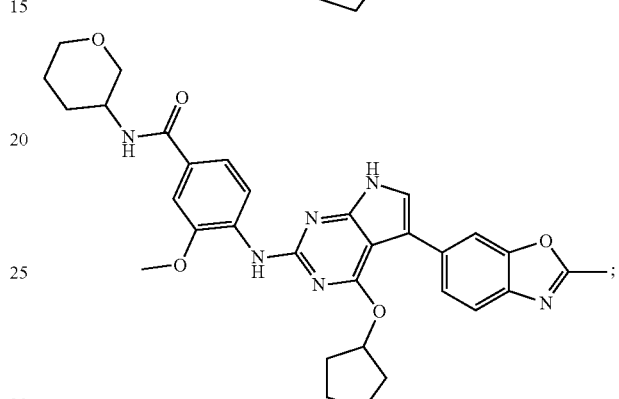
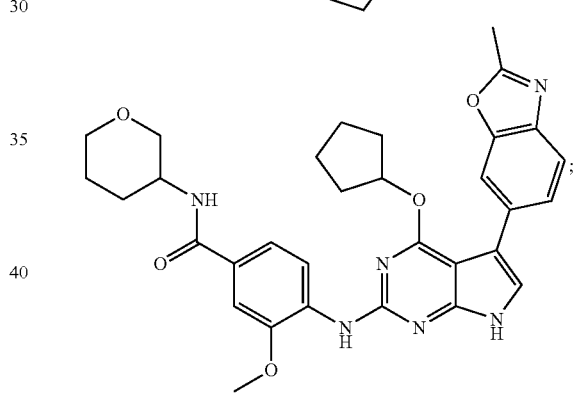
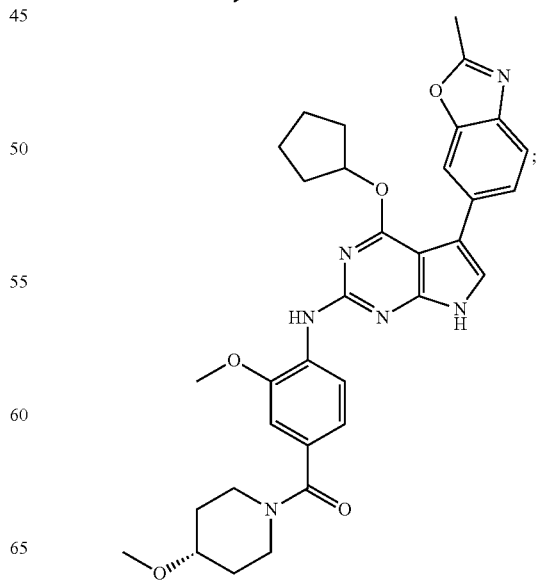

447
-continued
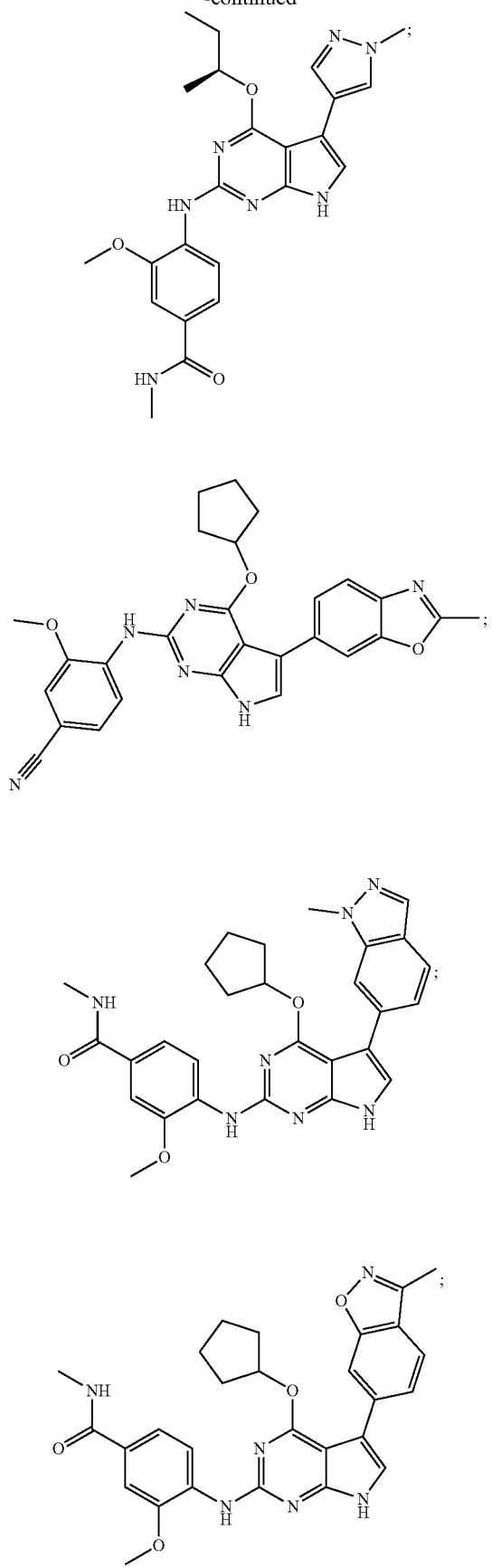
448
-continued
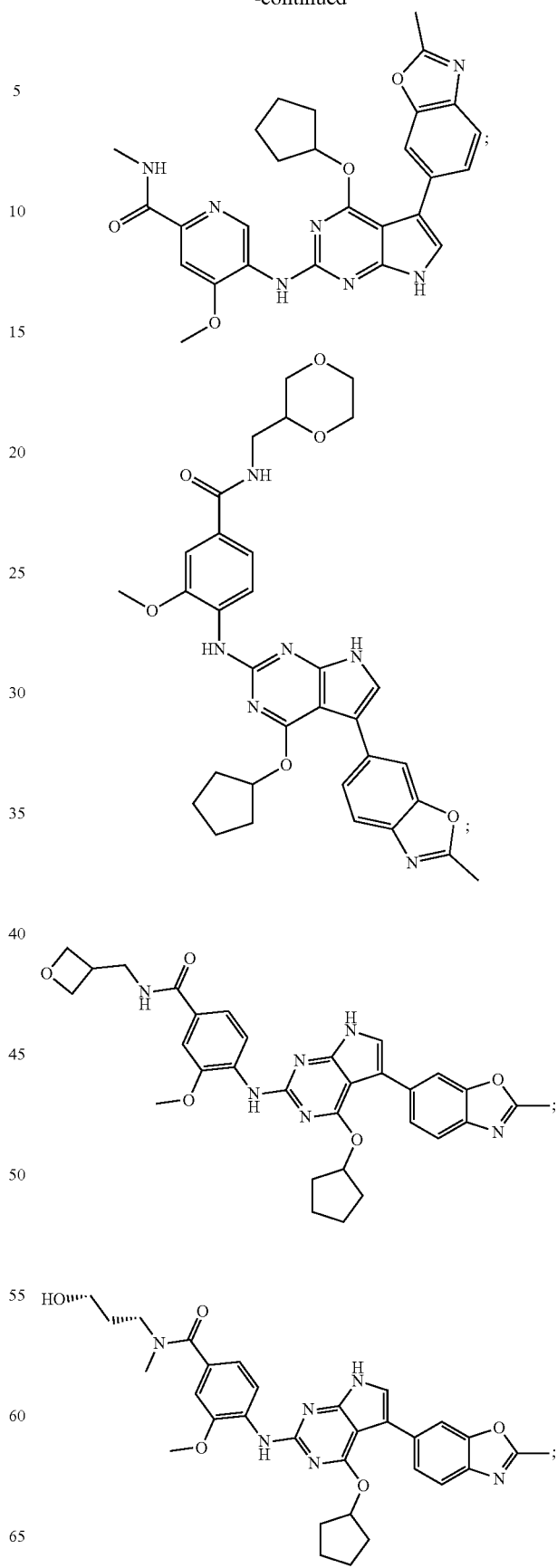

449
-continued
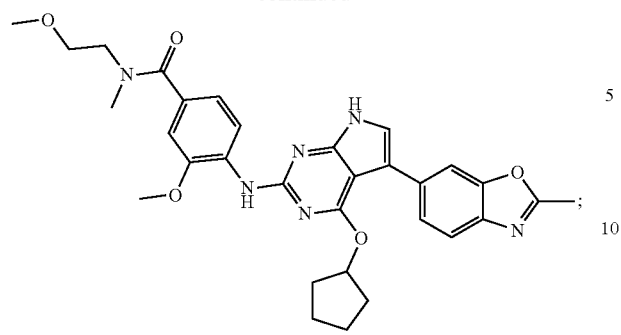
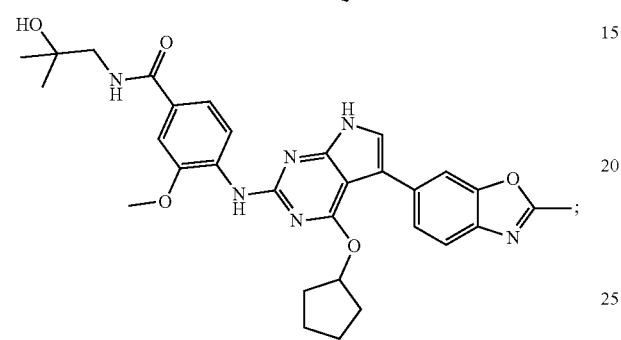
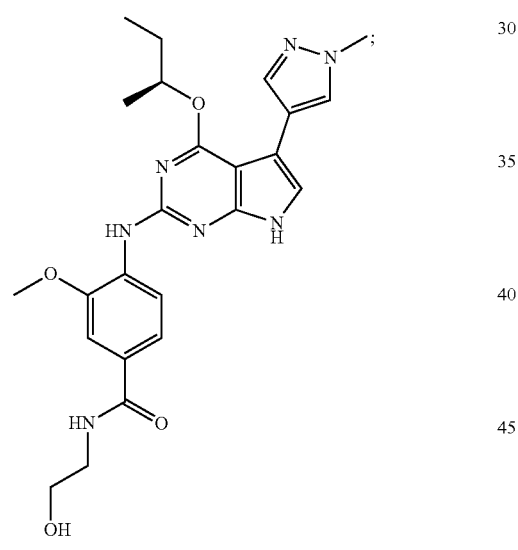
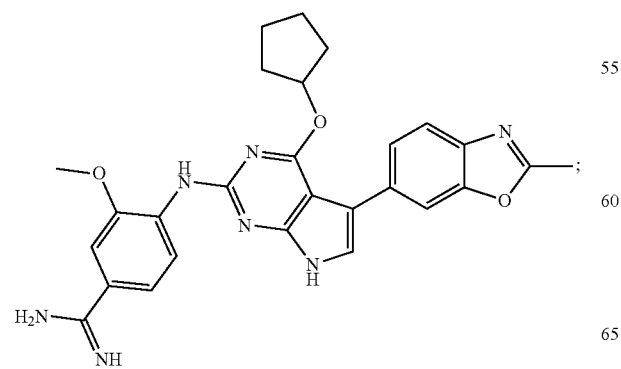
450
-continued
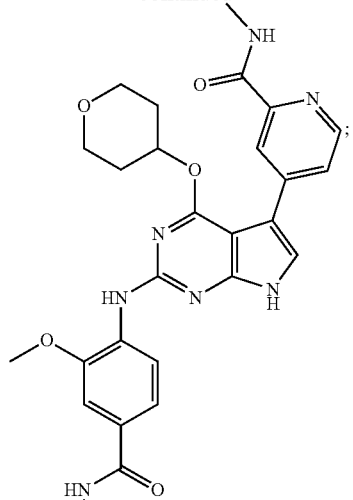
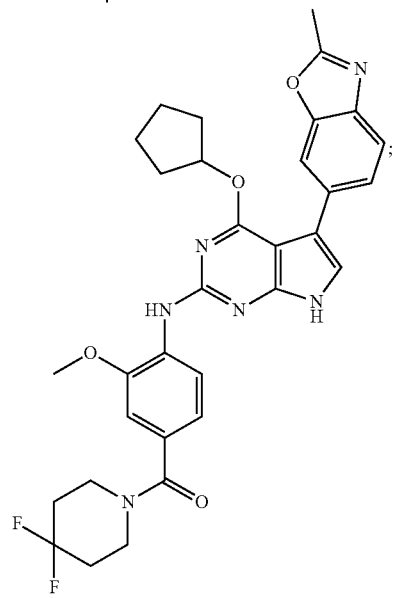
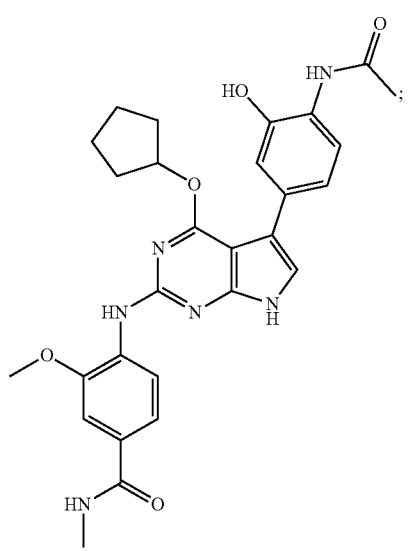

451
-continued
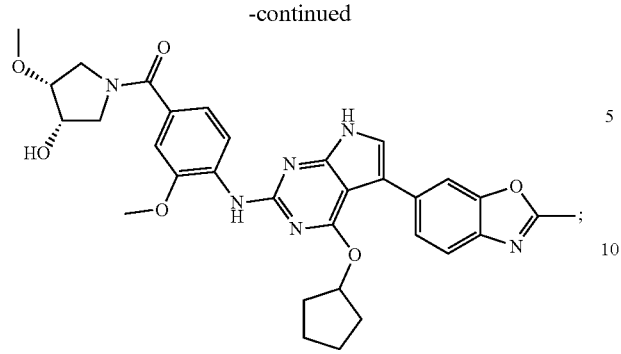
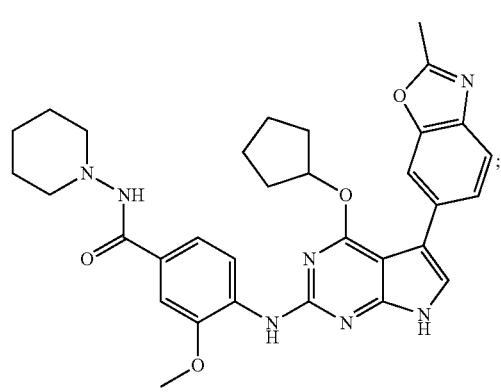
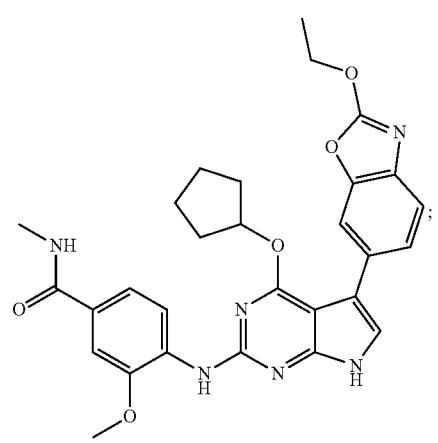
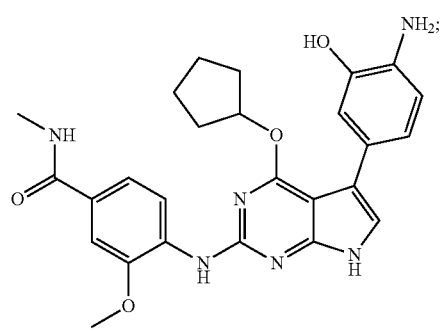
452
-continued
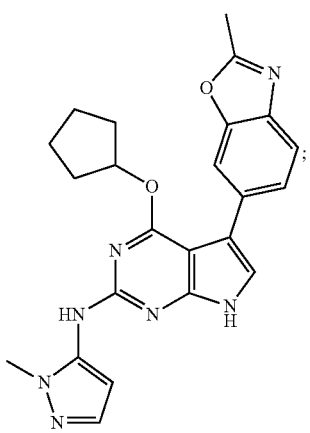
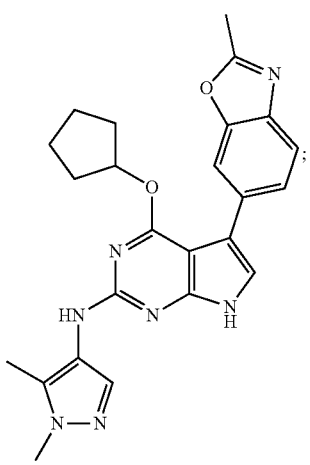
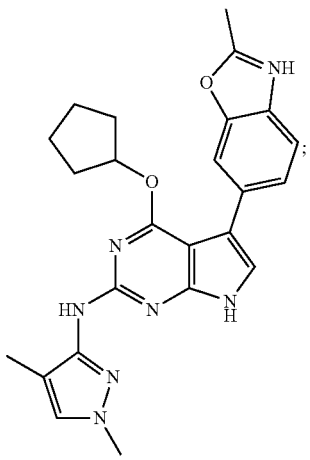

453
-continued
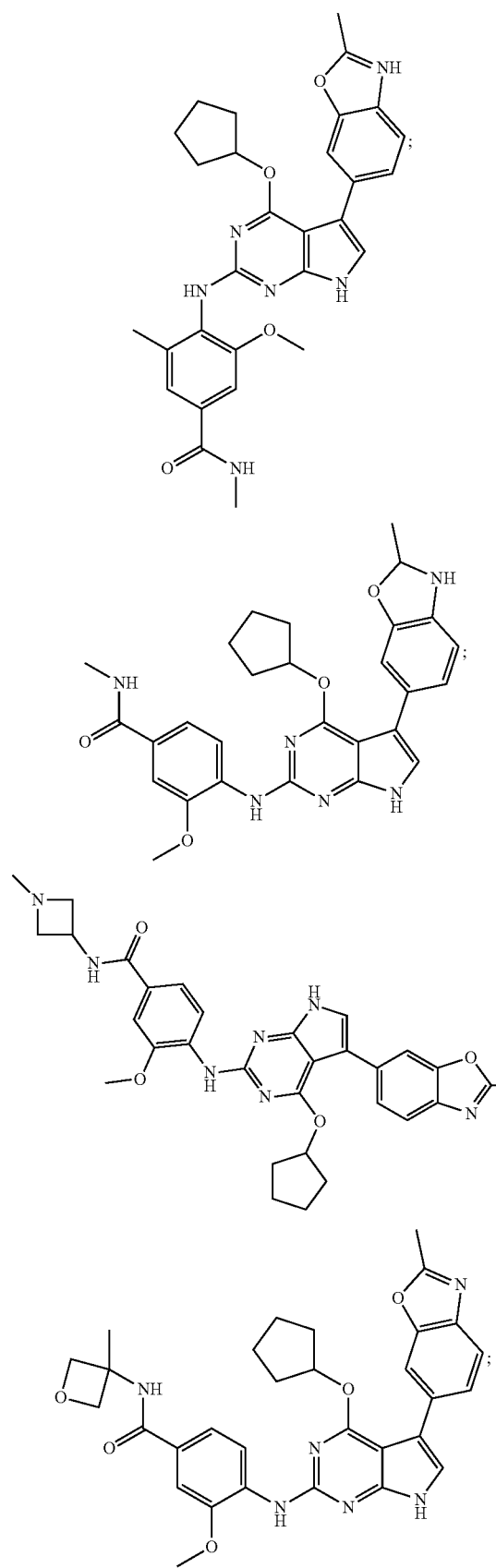
454
-continued
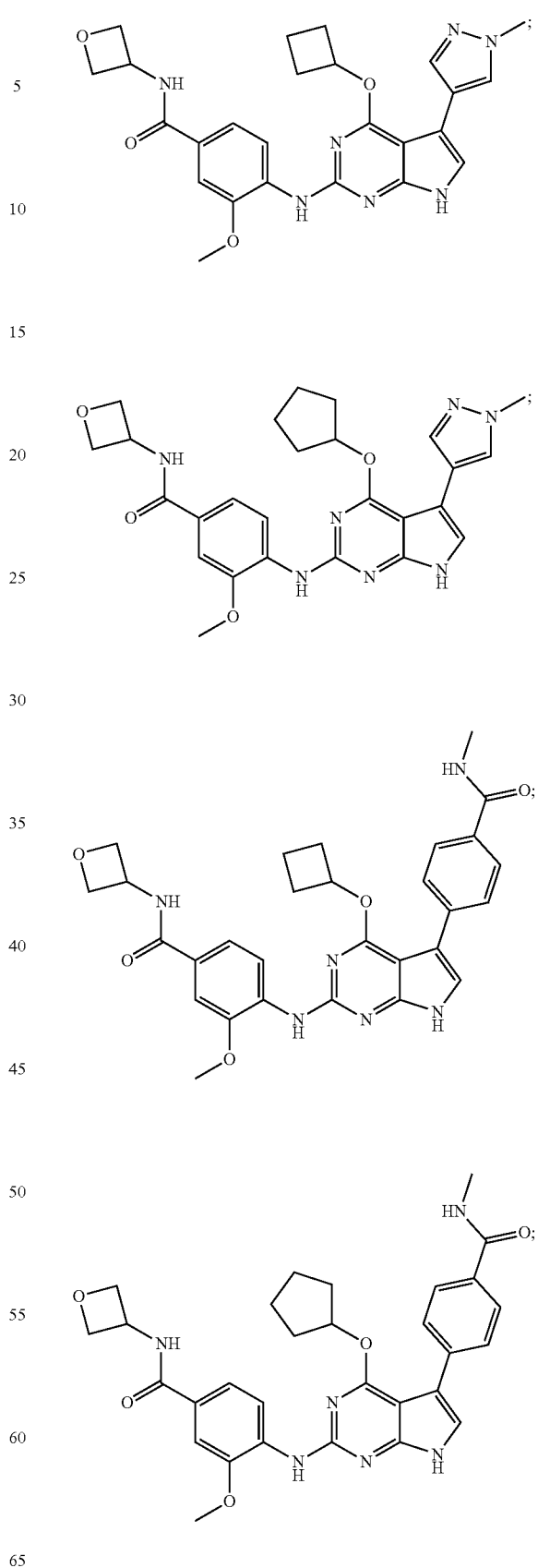

455
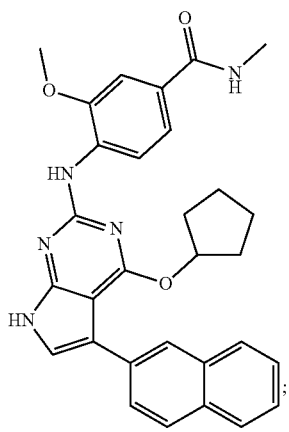
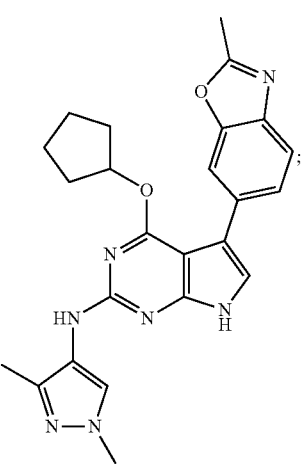
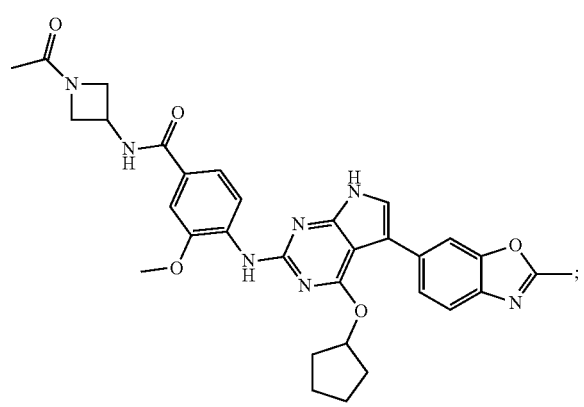
456
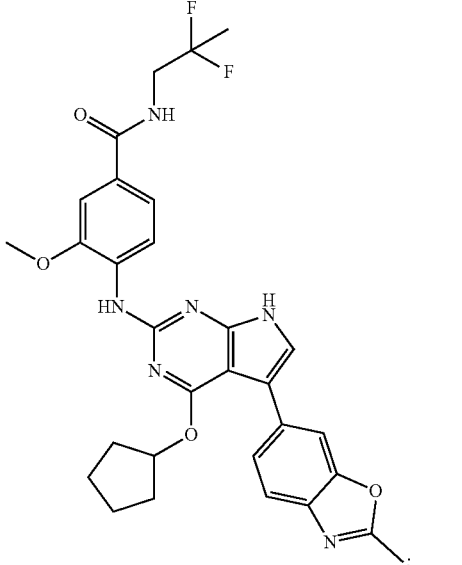

457
-continued
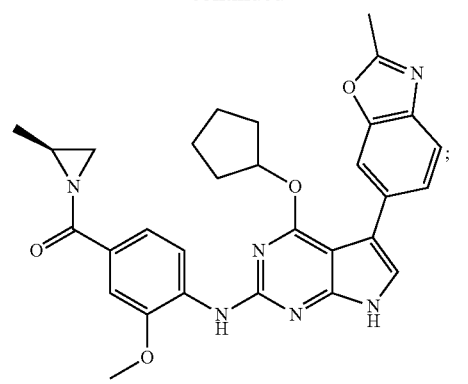
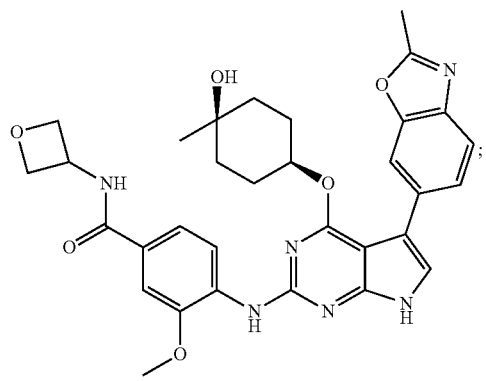
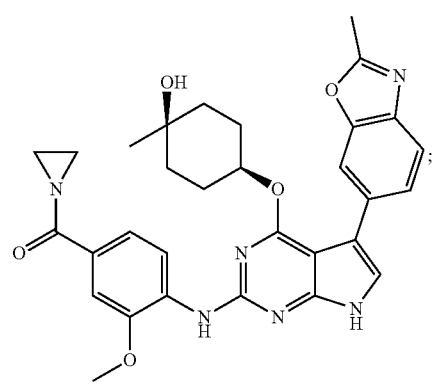
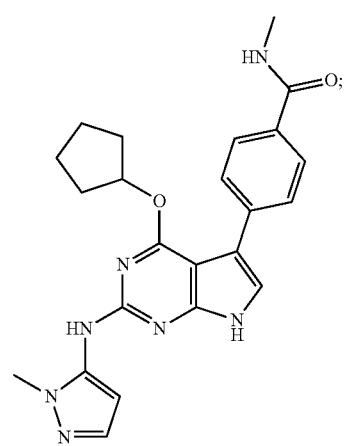
458
-continued
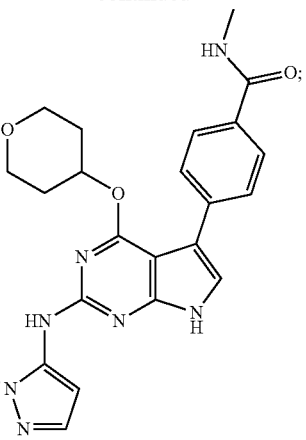
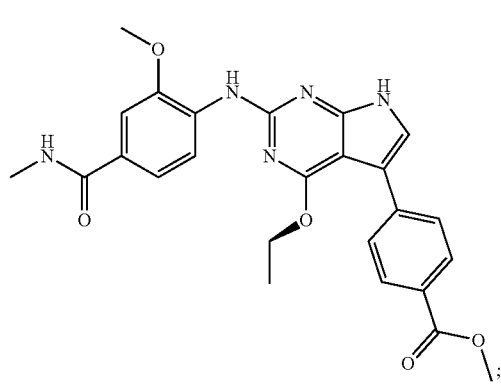
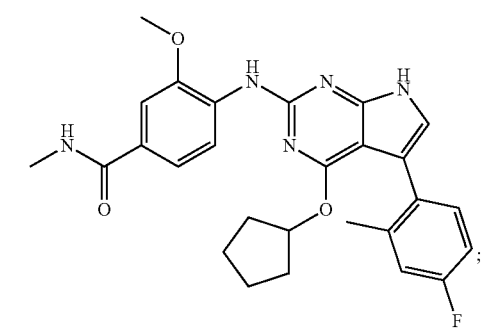
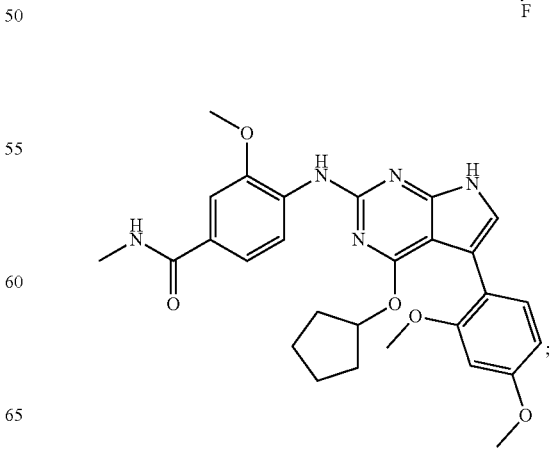

459
-continued
460
-continued
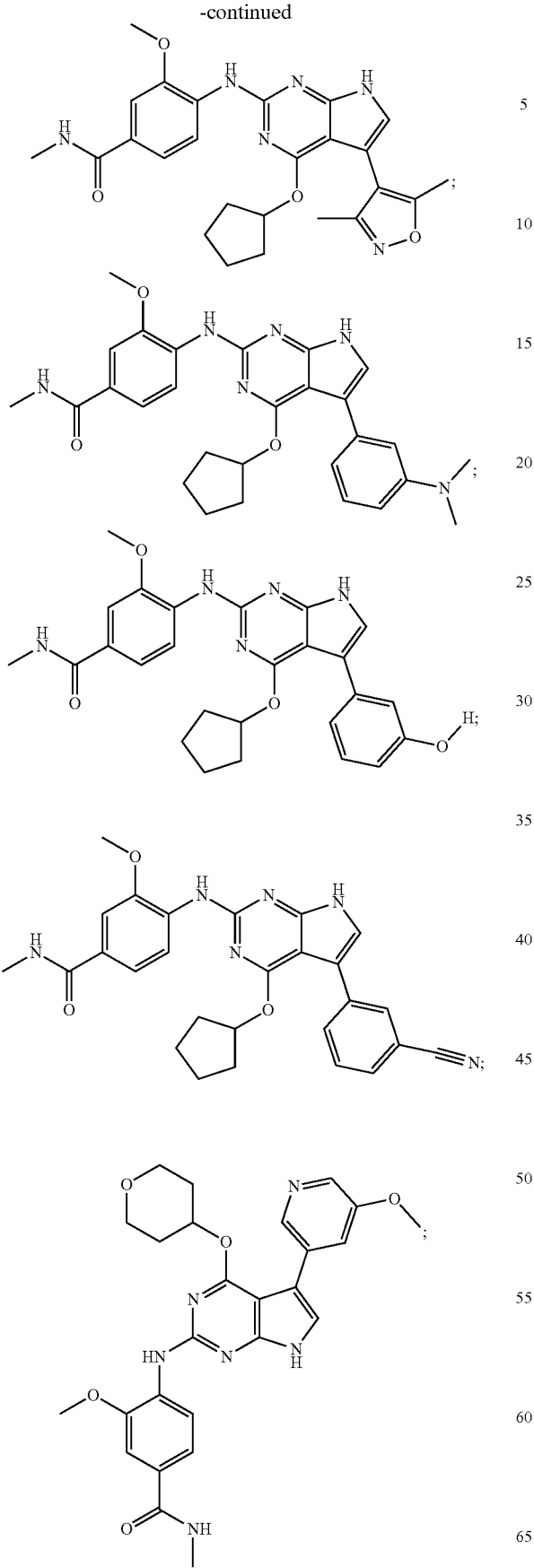
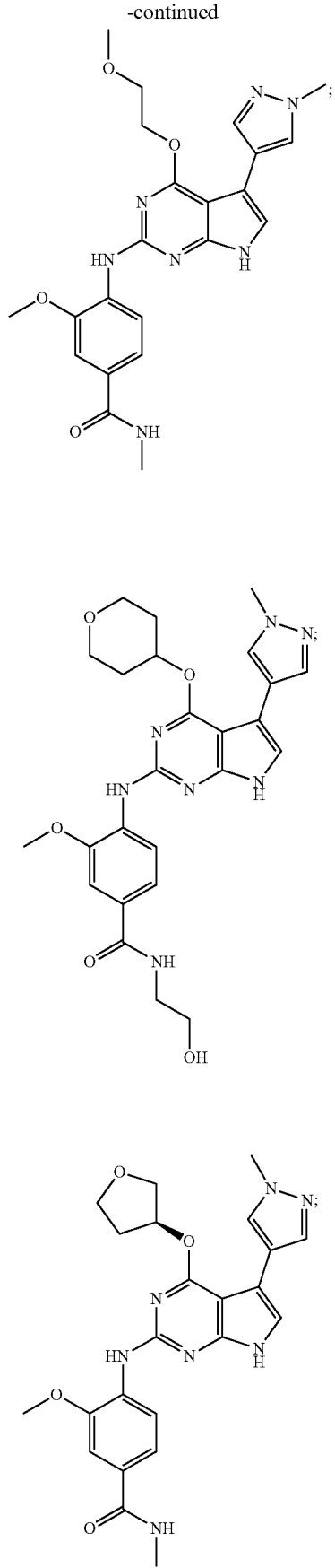

461
-continued
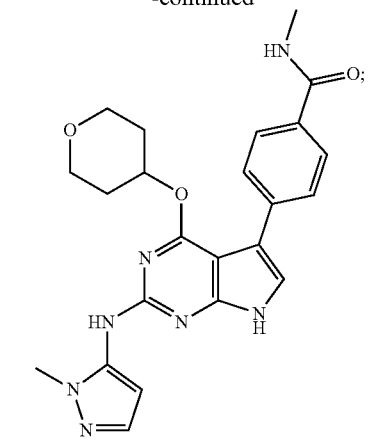
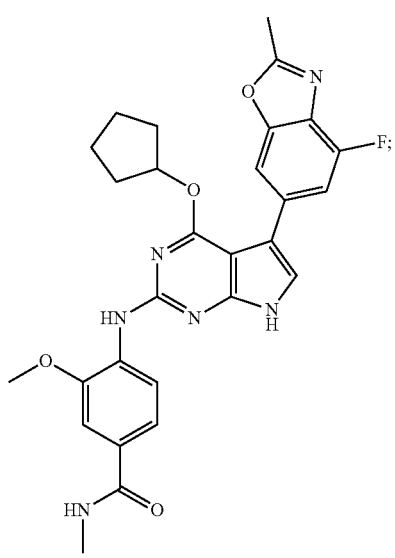
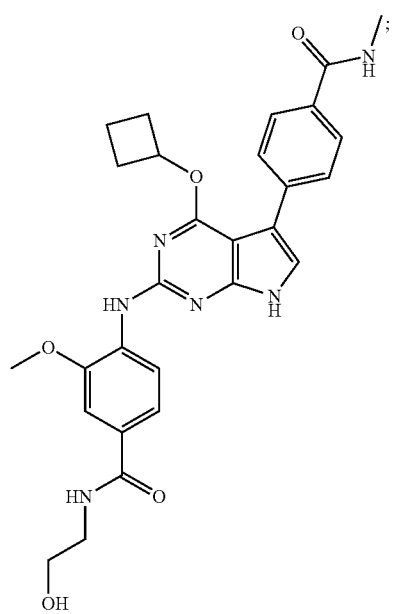
462
-continued
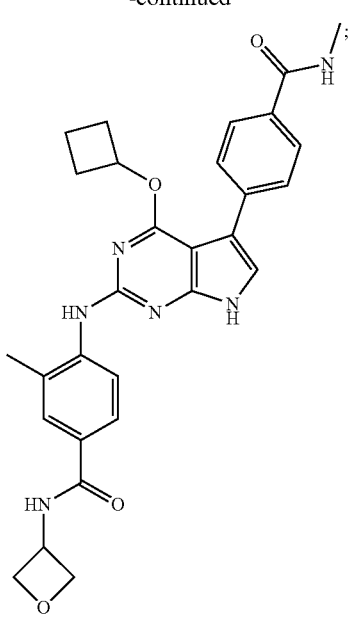
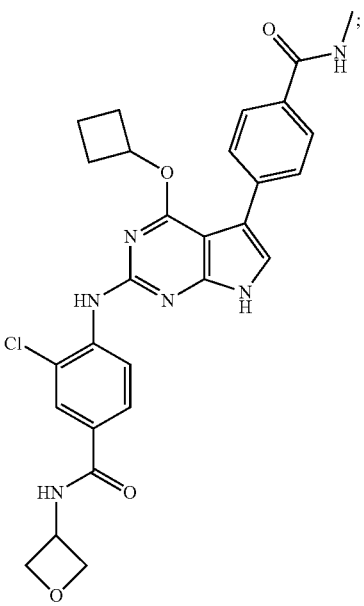

463
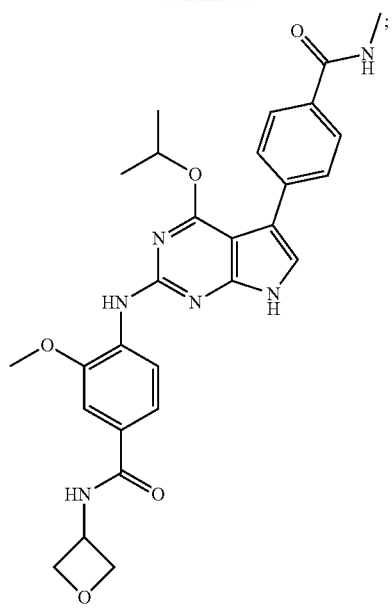
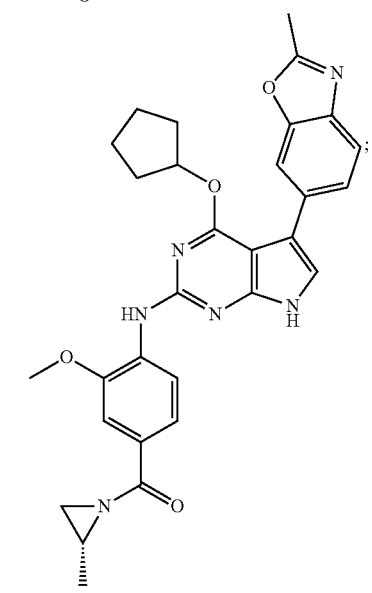
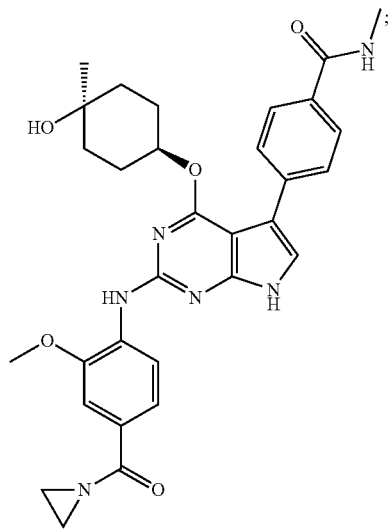
464
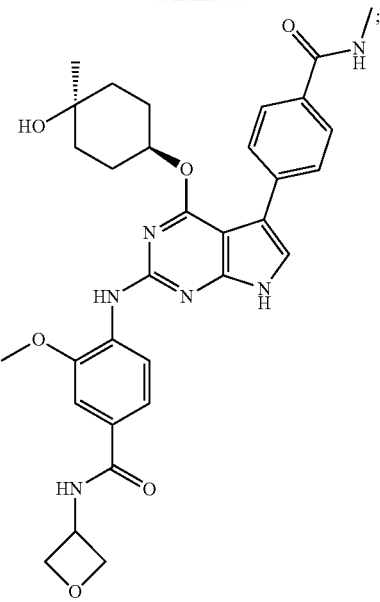
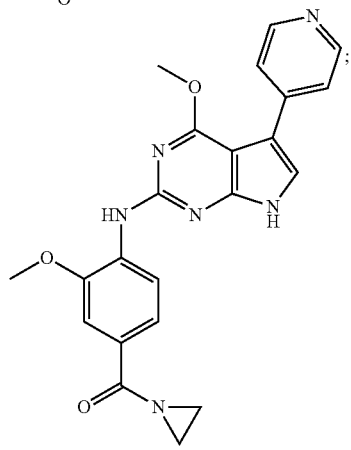
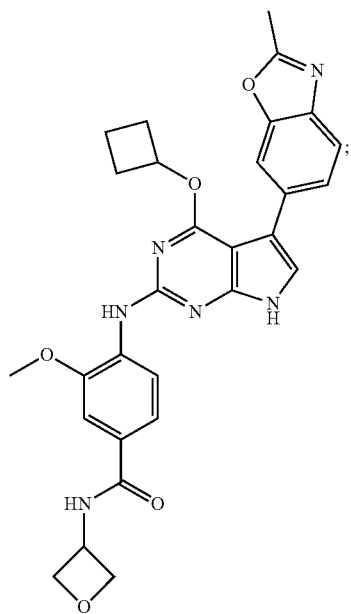

465
-continued
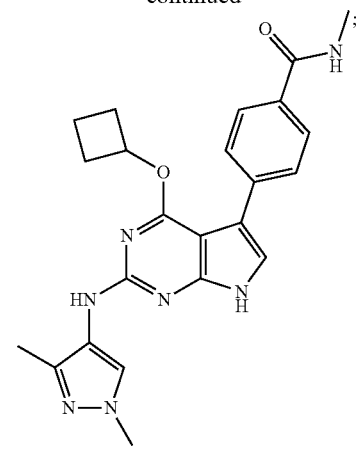
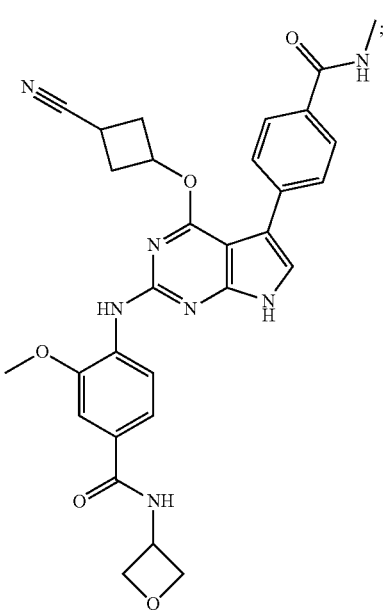
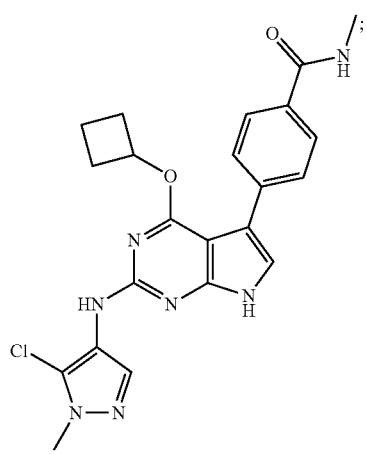
466
-continued
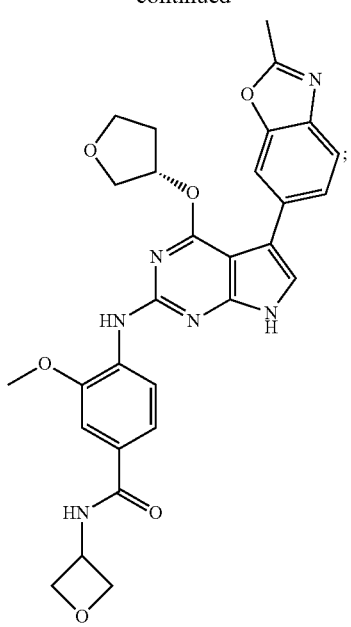
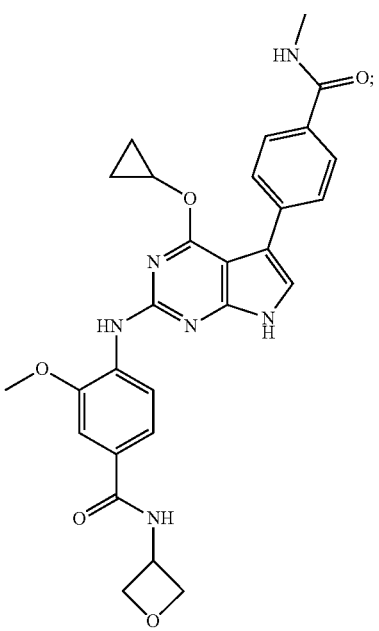

467
-continued
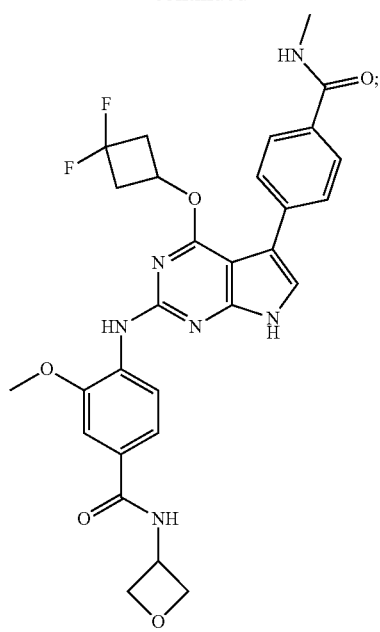
468
-continued
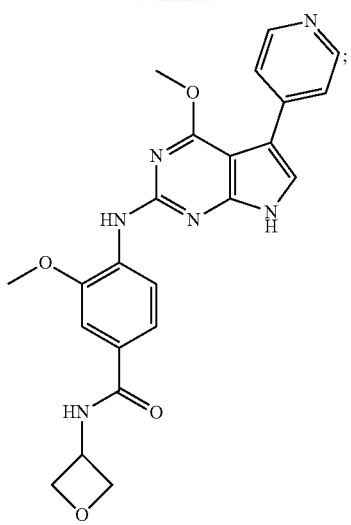
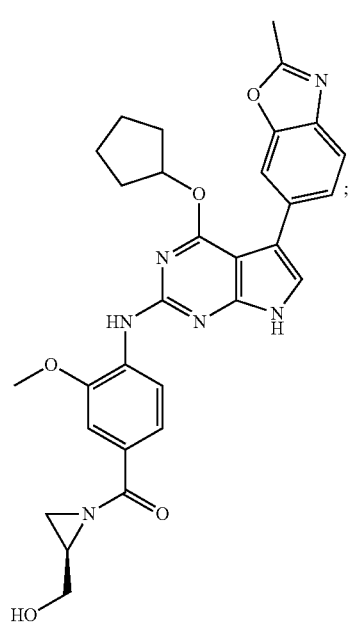

469
-continued
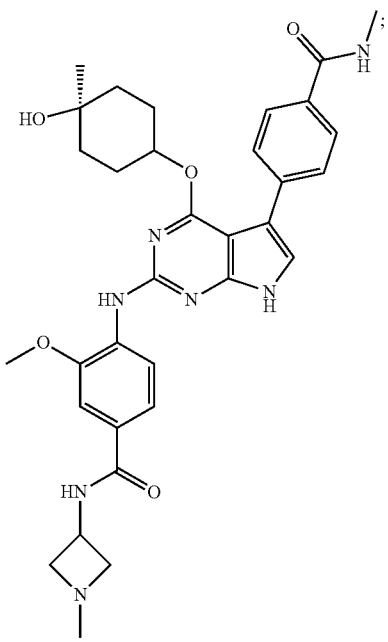
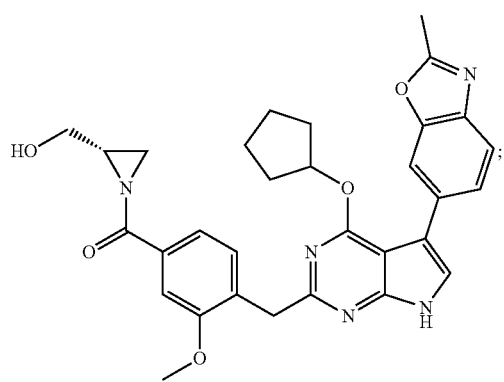
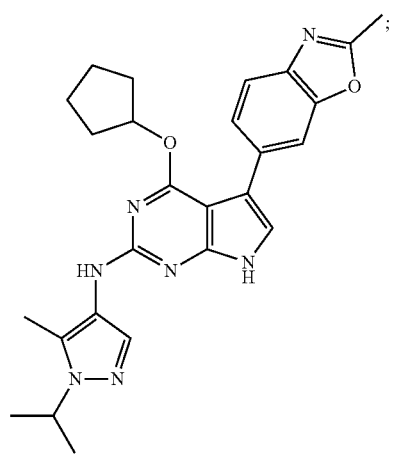
470
-continued
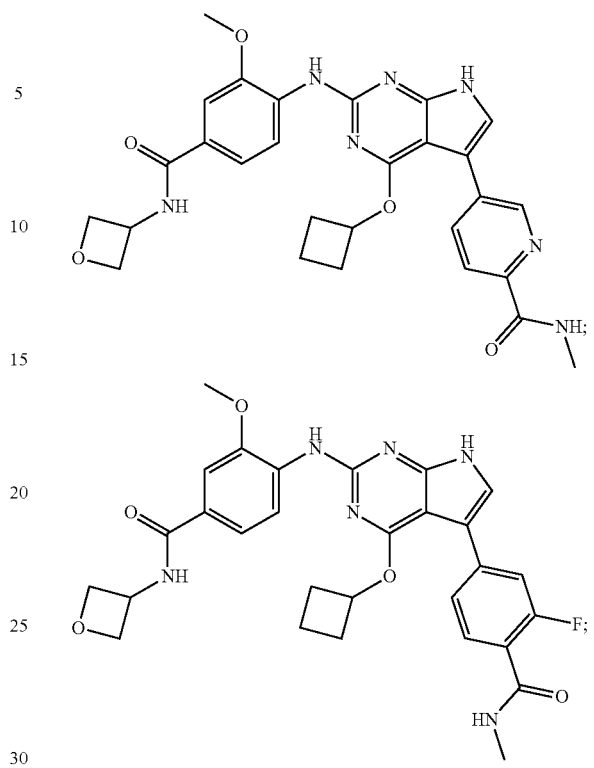
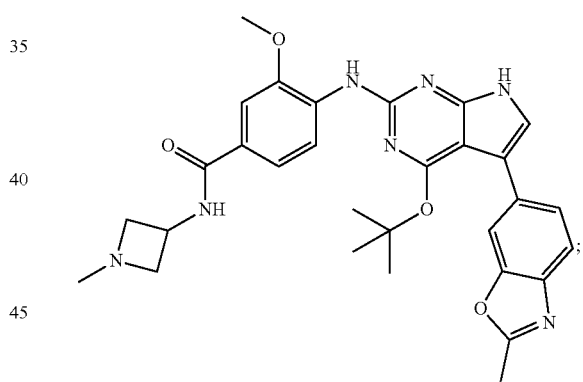

471
-continued
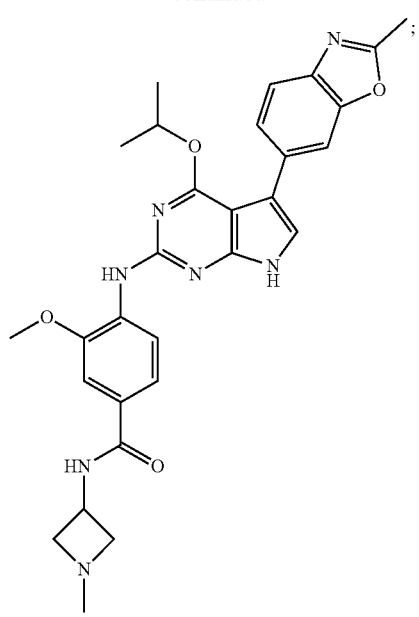
472
-continued
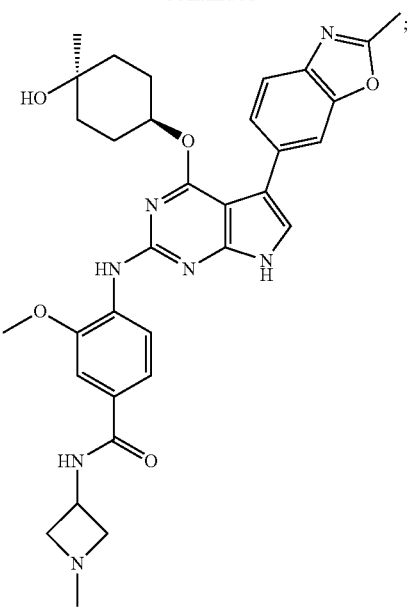
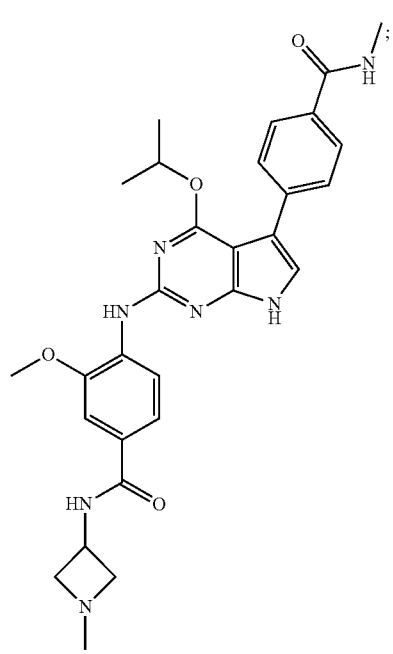
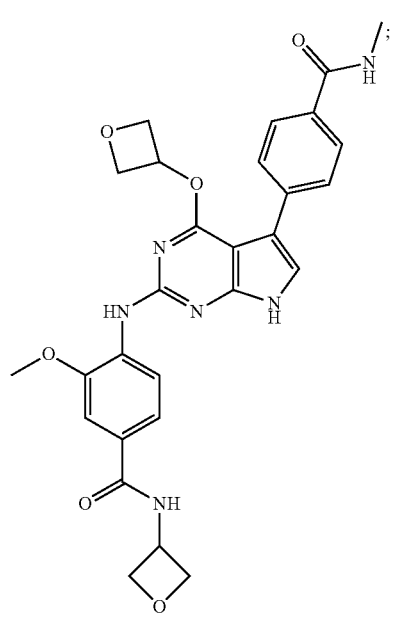

473
-continued
474
-continued
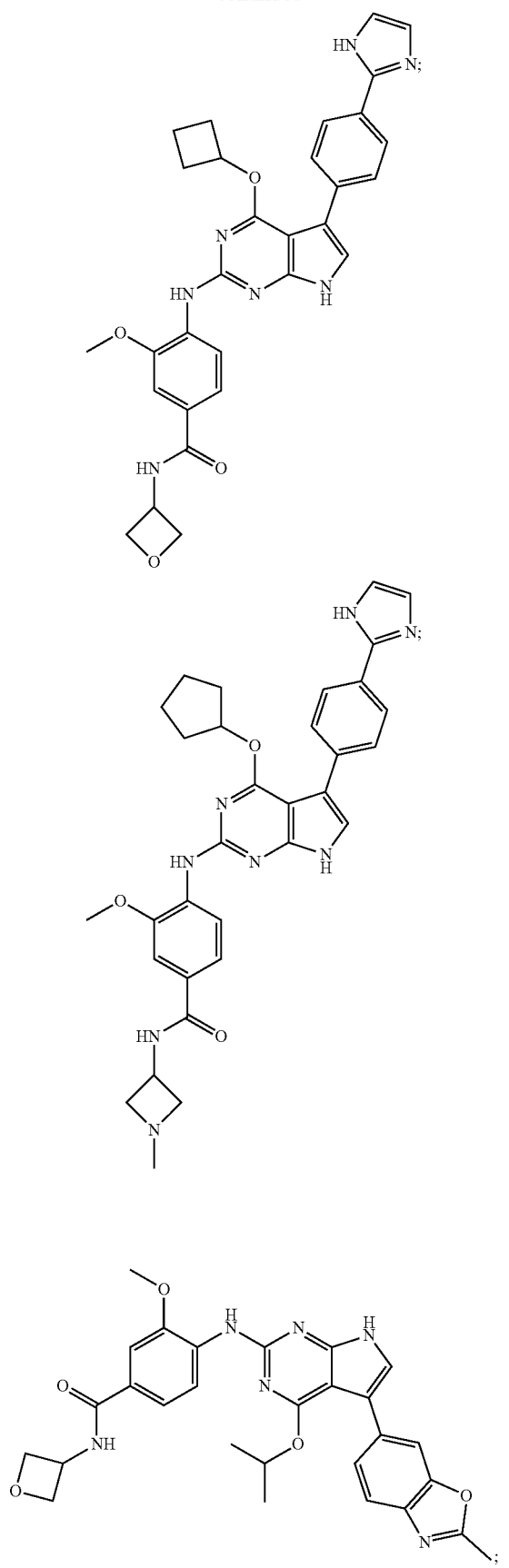

475
-continued
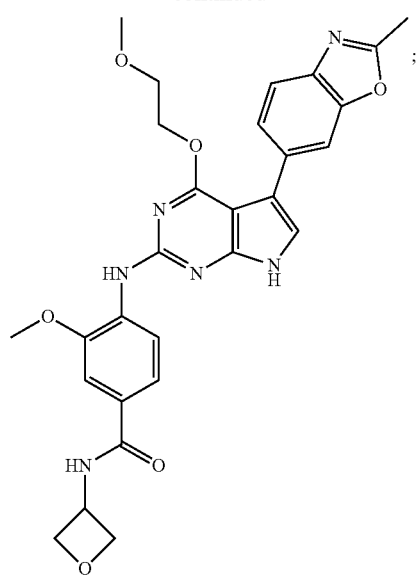
476
-continued
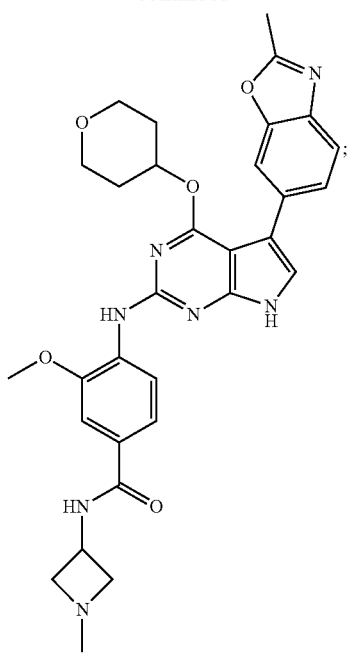
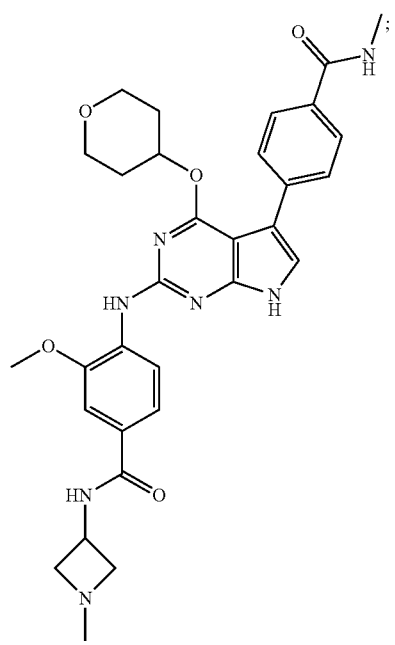
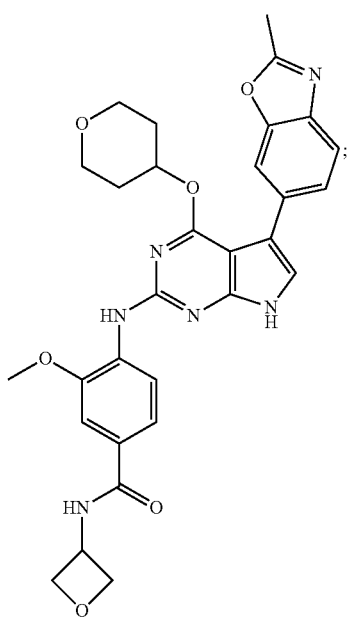

477
-continued
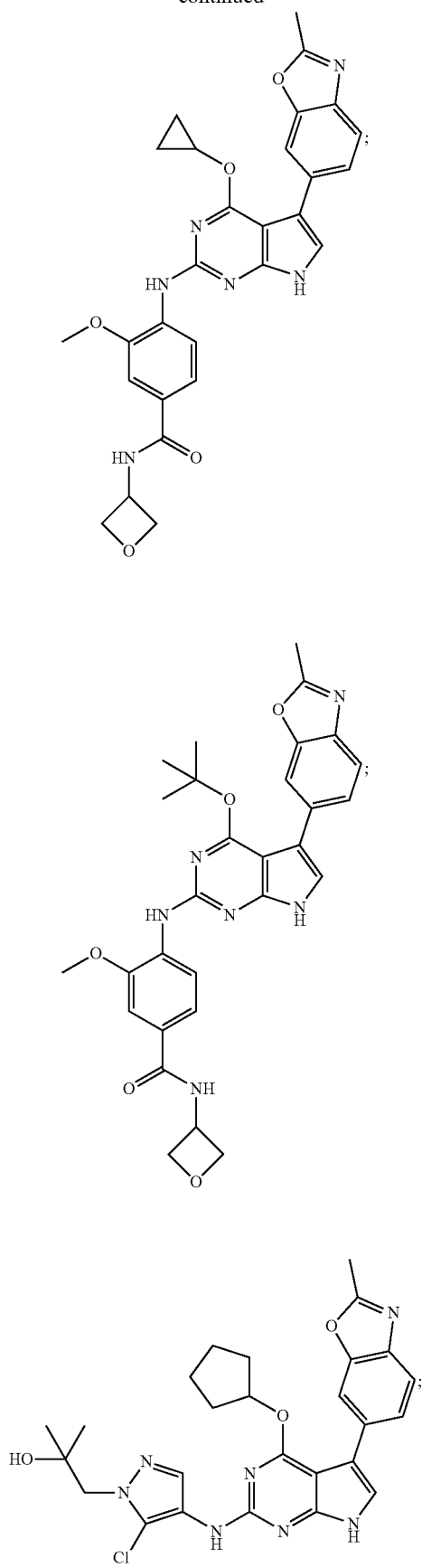
478
-continued
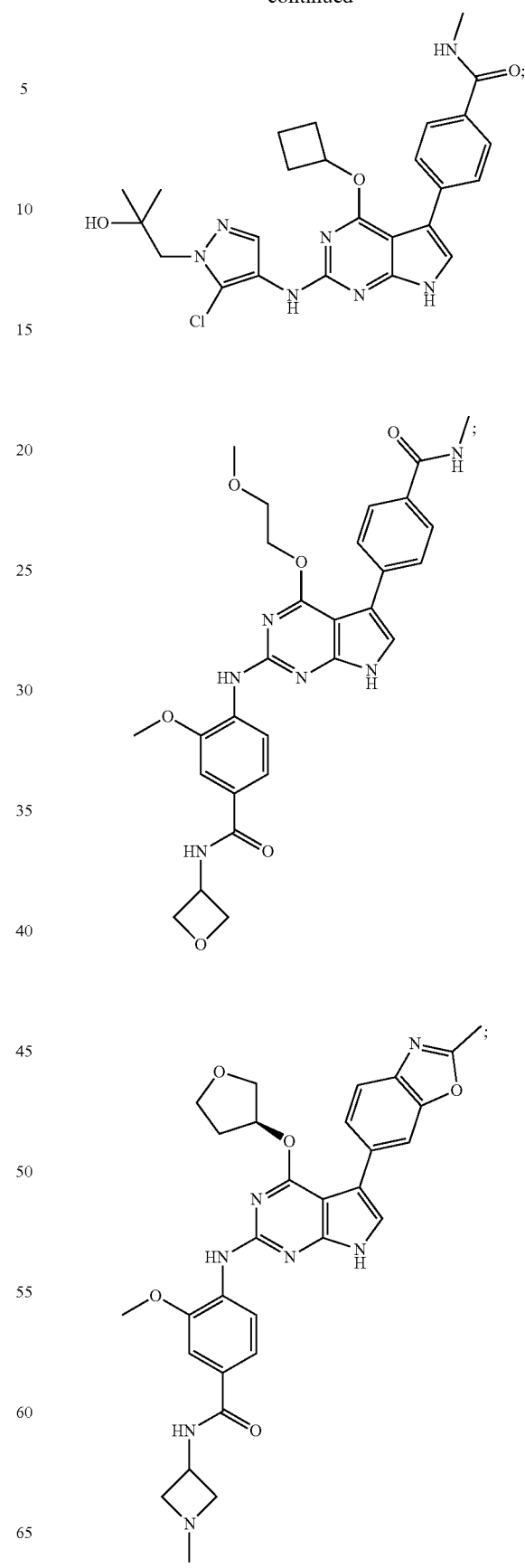

479
-continued
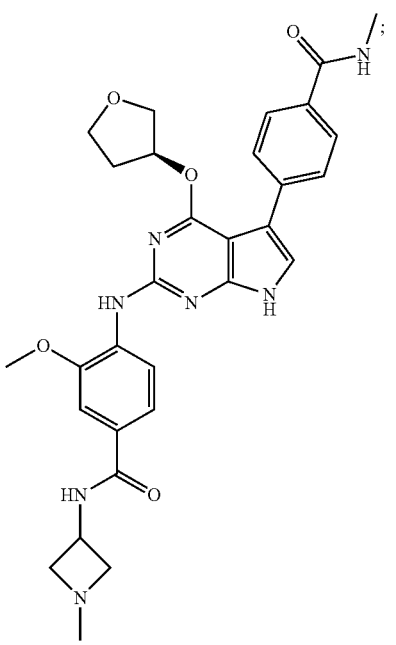
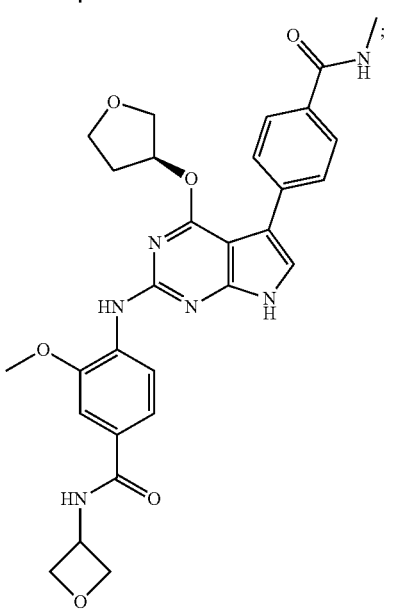
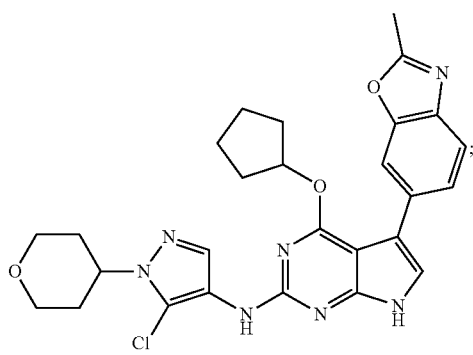
480
-continued
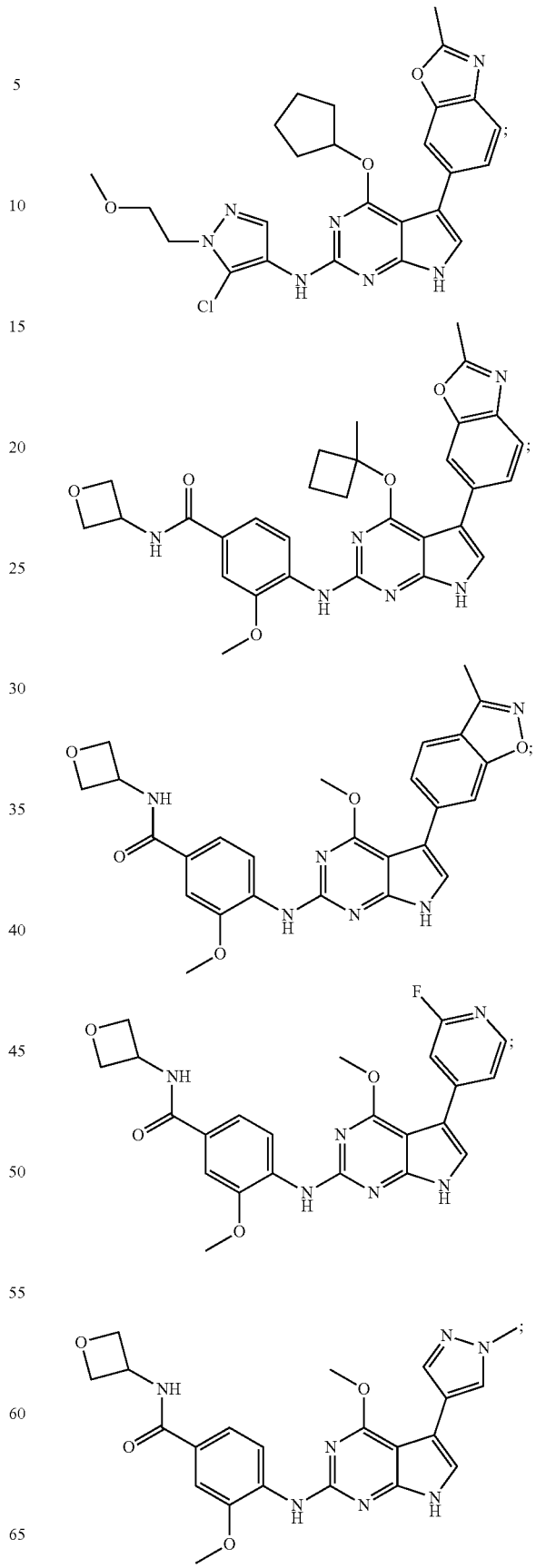

481
-continued
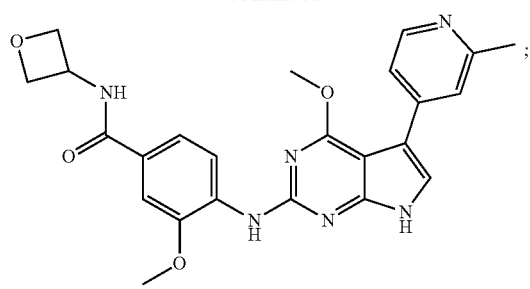
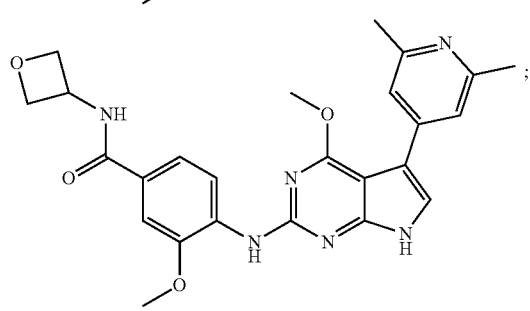
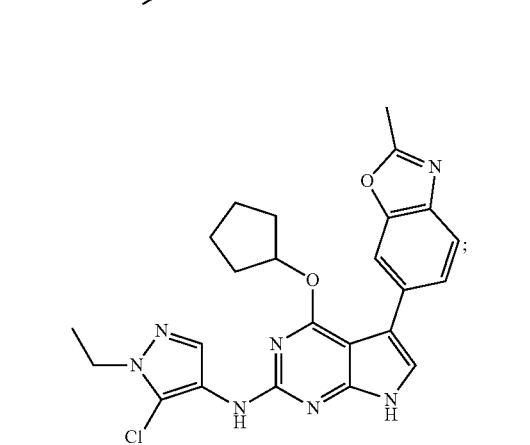
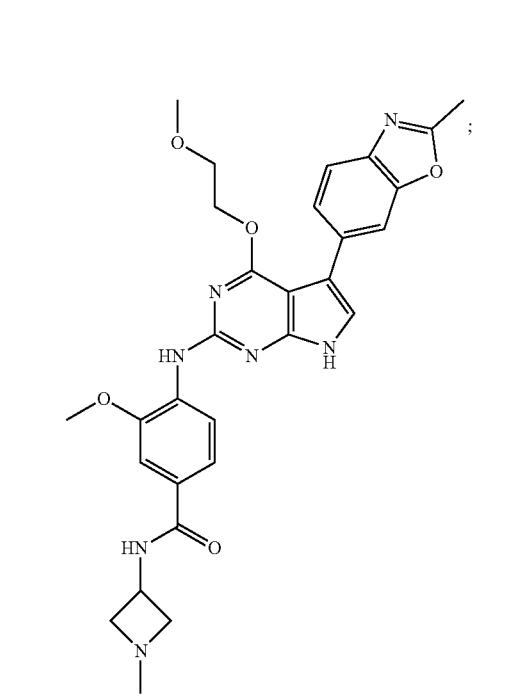
482
-continued
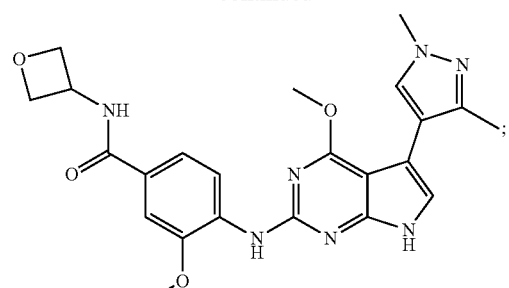
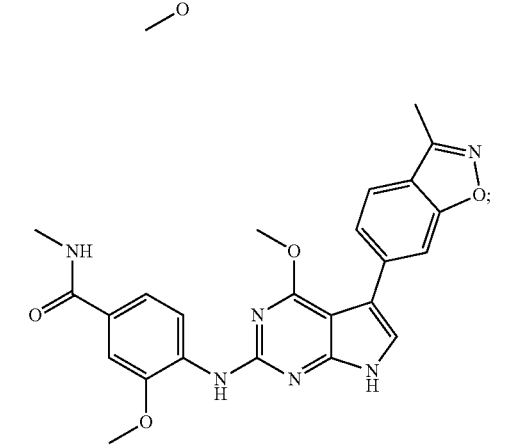
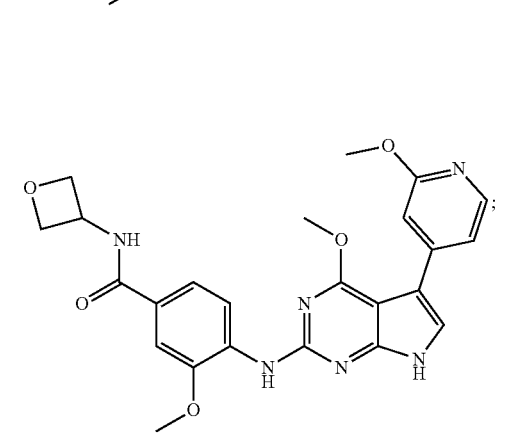
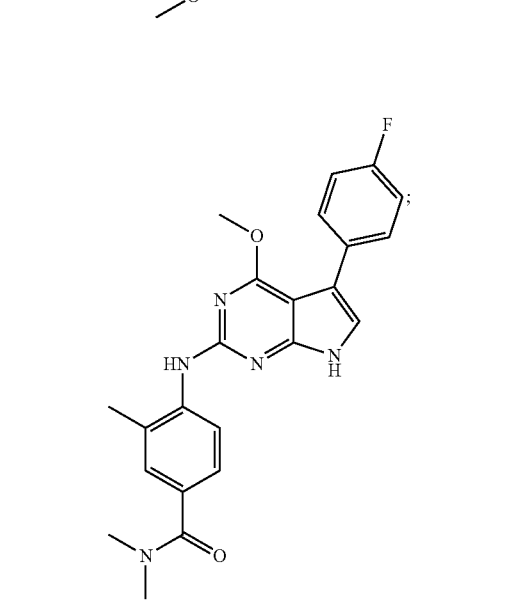

483
-continued
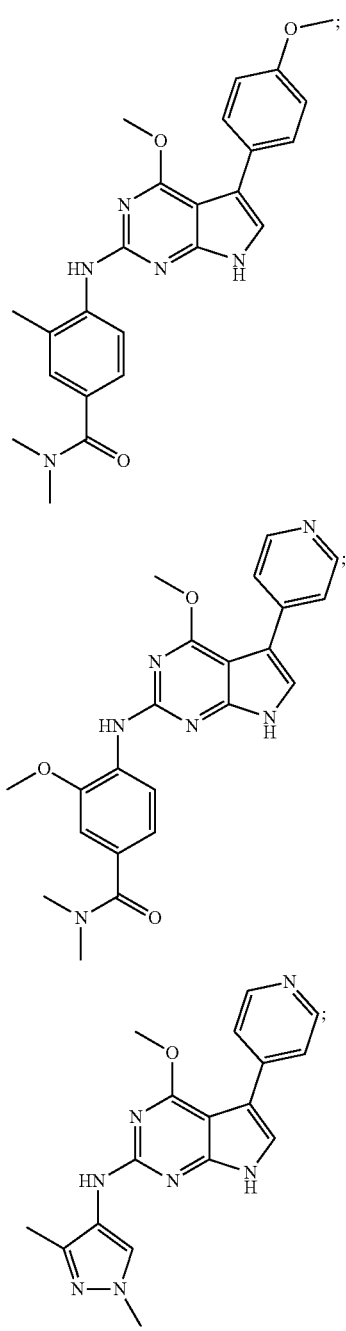
484
-continued
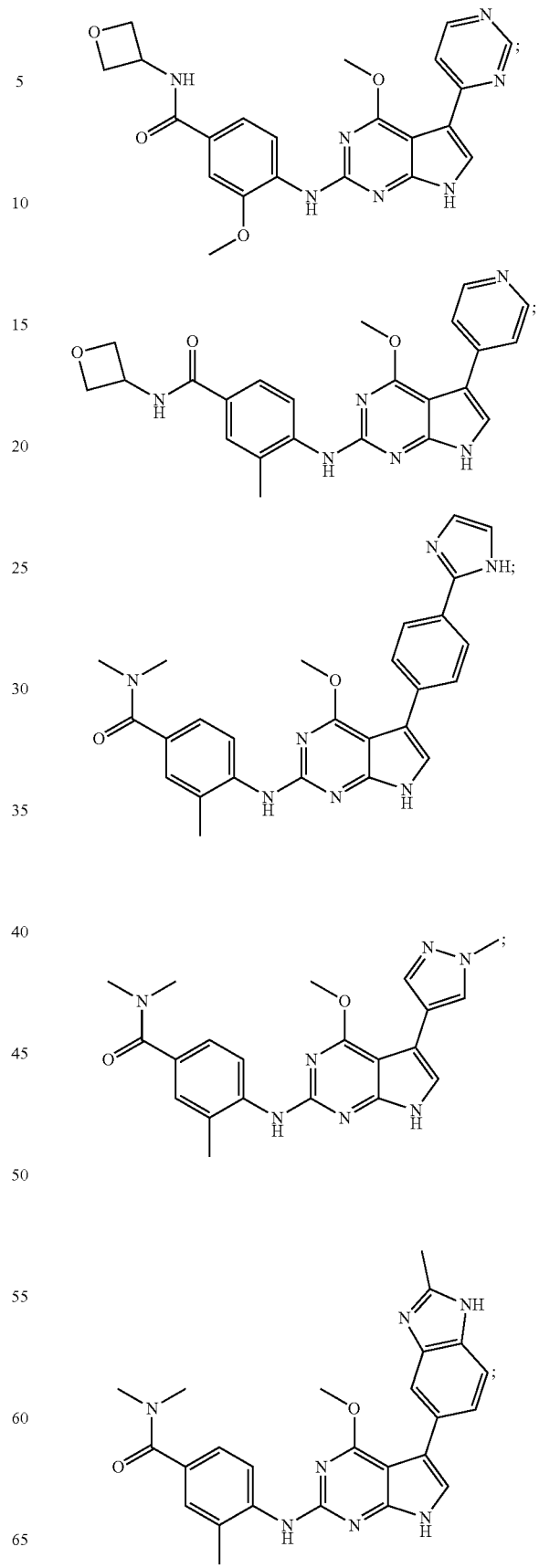

485
-continued
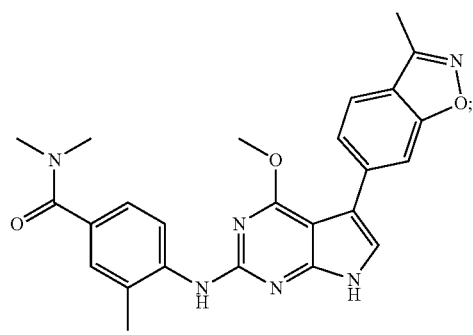
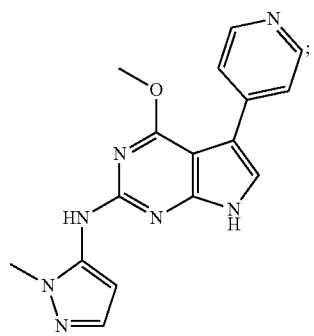
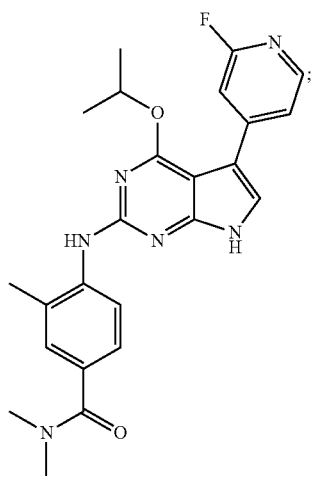
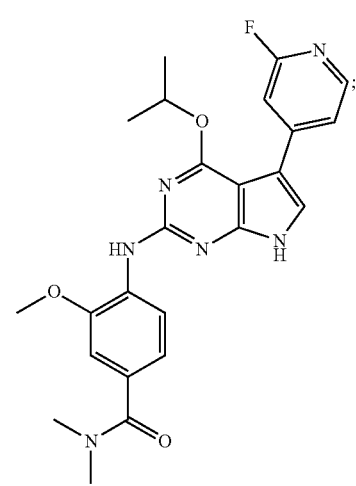
486
-continued
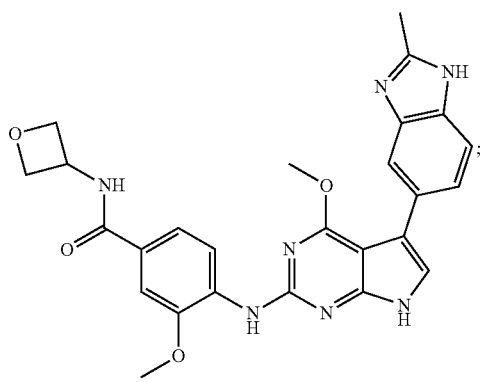
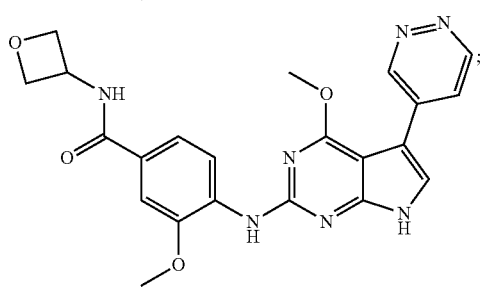
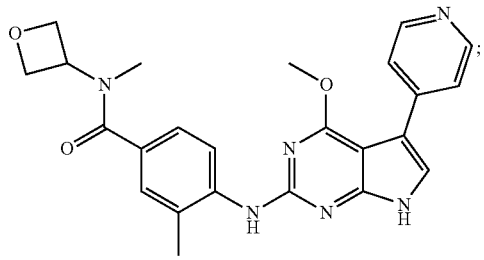
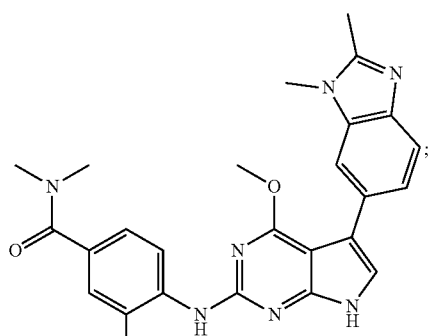
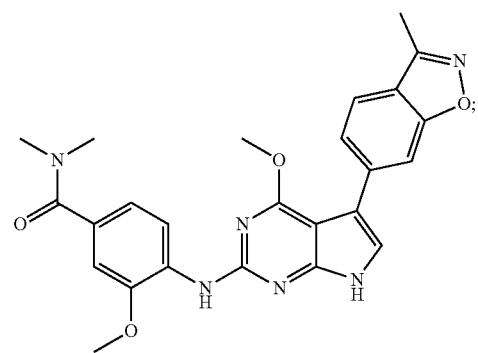

487
-continued
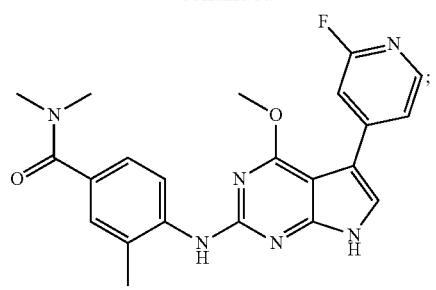
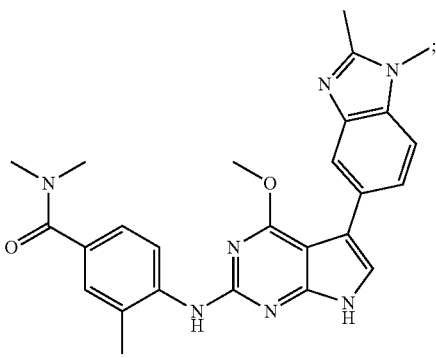
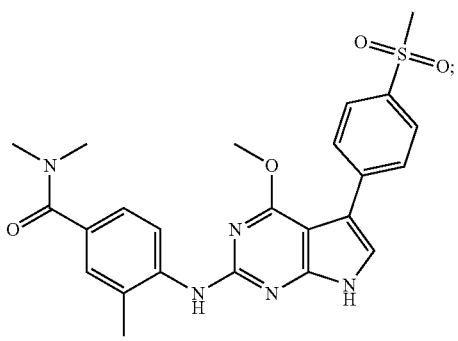
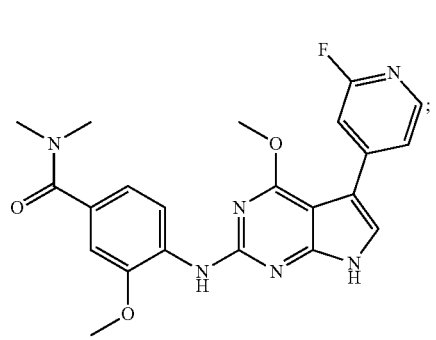
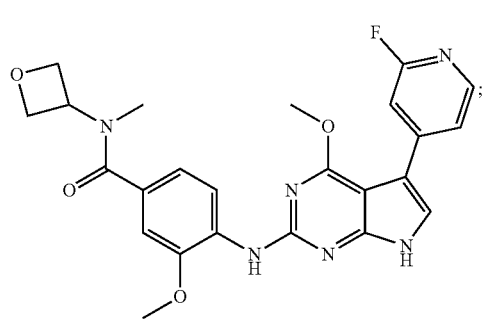
488
-continued
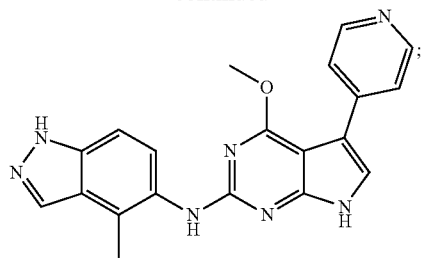
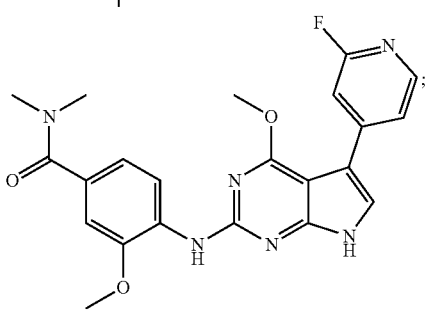
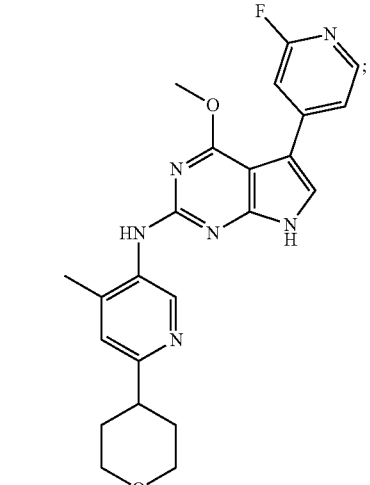
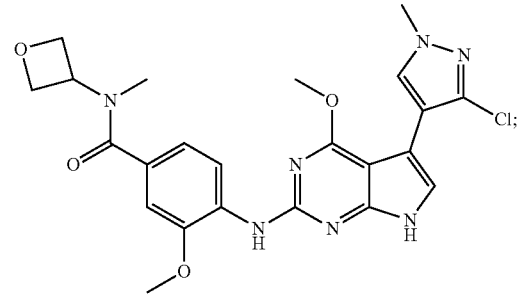
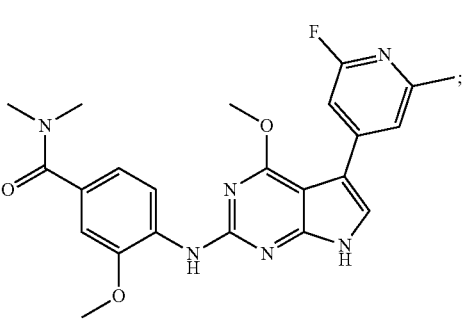

489
-continued
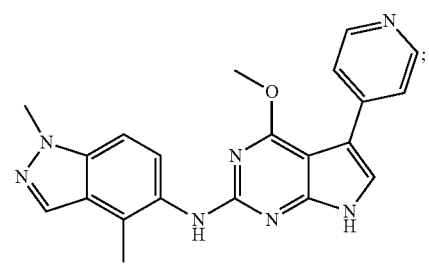
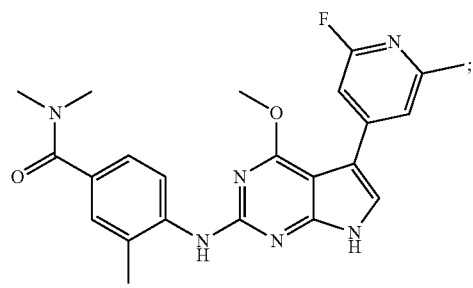
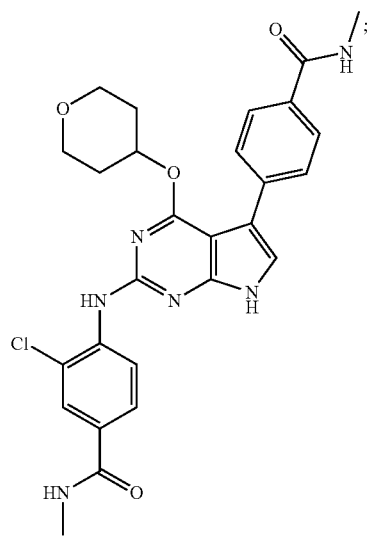
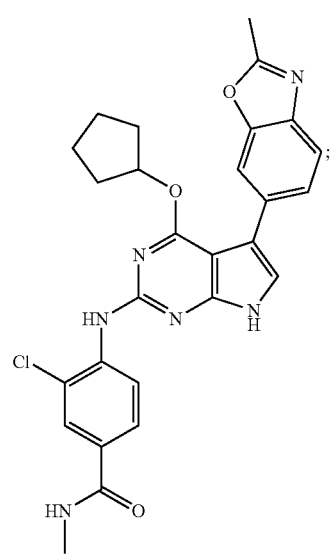
490
-continued
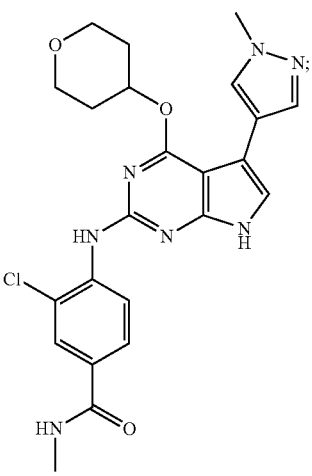
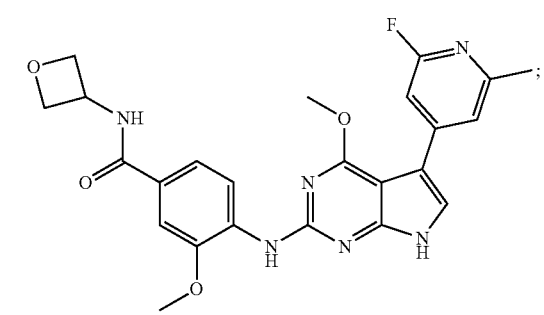
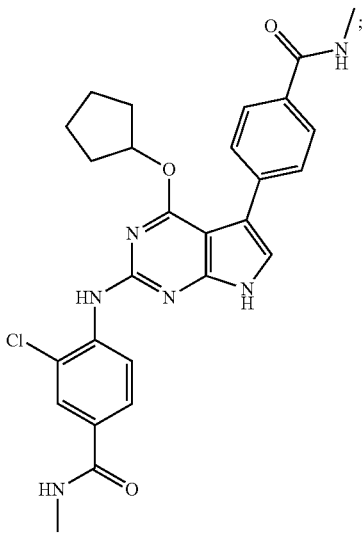

491
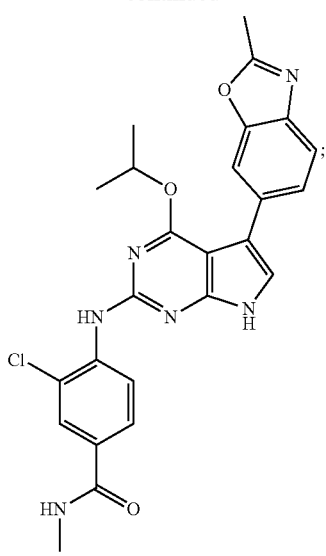
492
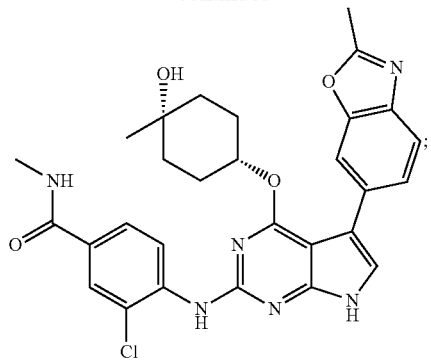
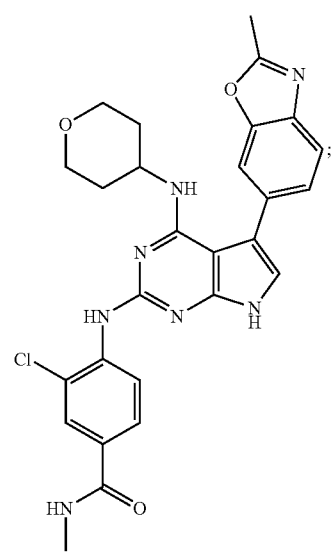
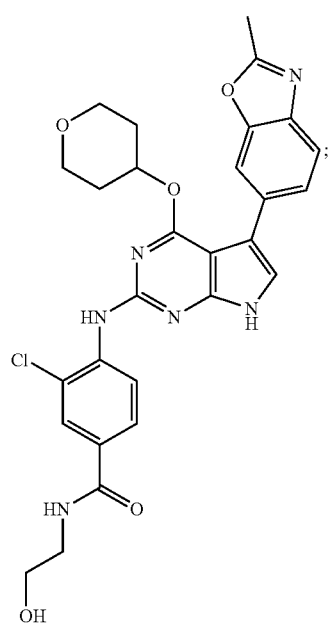 [SMILES: Cc1nc2ccc(-c3c[nH]c4nc(Nc5ccc(C(=O)NC6COC6)cc5Cl)nc(OC5CCOCC5)c34)cc2o1]

493
-continued
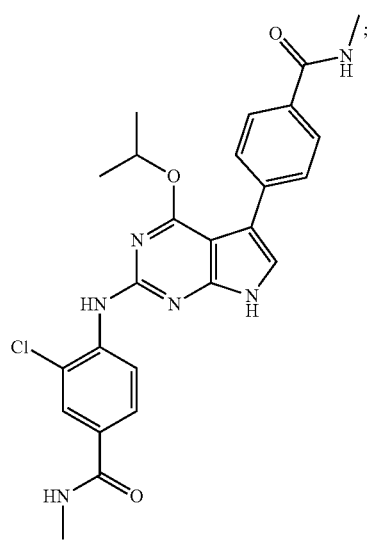
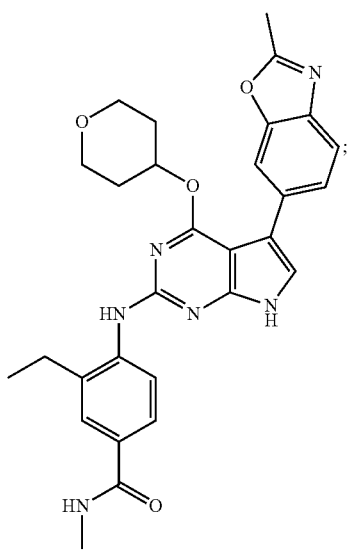
494
-continued
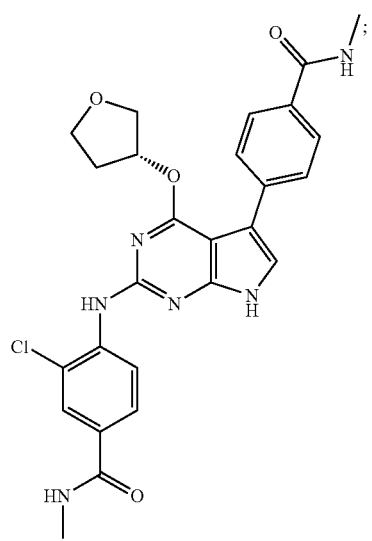
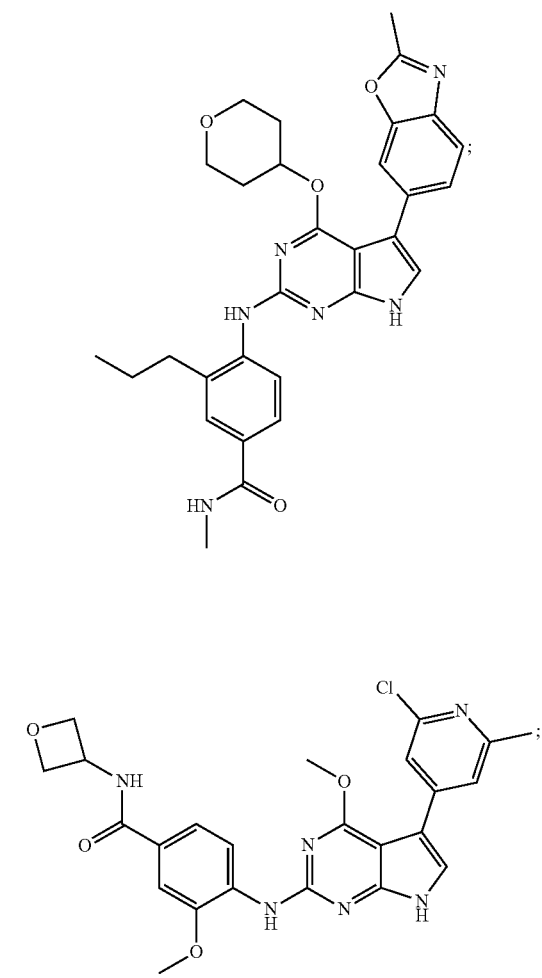

-continued

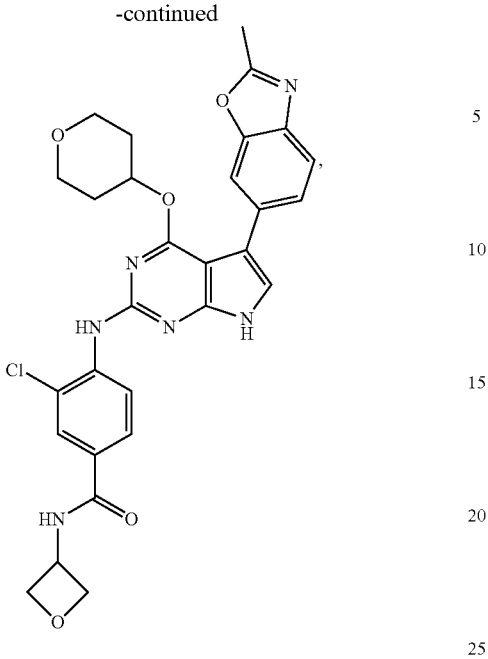

, or a pharmaceutically acceptable salt, tautomer, stereoisomer, enantiomer, or isotopologue thereof.

30. The compound of claim 1 or claim 29, wherein the compound at a concentration of 10 µM inhibits triple negative breast cancer cell proliferation by at least about 50%.

31. A pharmaceutical composition comprising an effective amount of a compound of claim 1 or claim 29, or a pharmaceutically acceptable salt, tautomer, stereoisomer, enantiomer, or isotopologue thereof, and a pharmaceutically acceptable carrier, excipient or vehicle.

32. A method for the treatment of breast cancer, the methods comprising administering to a subject in need thereof an effective amount of a compound of claim 1 or claim 29.

\* \* \* \* \*